(12) United States Patent
Cai et al.

(10) Patent No.: US 10,894,795 B2
(45) Date of Patent: Jan. 19, 2021

(54) PHOSPHOINOSITIDE 3-KINASE INHIBITORS WITH A ZINC BINDING MOIETY

(71) Applicant: Curis, Inc., Lexington, MA (US)

(72) Inventors: Xiong Cai, Bedford, MA (US); Haixiao Zhai, Bedford, MA (US); Chengjung Lai, Belmont, MA (US); Changgeng Qian, Wayland, MA (US)

(73) Assignee: Curis, Inc., Lexington, MA (US)

( * ) Notice: Subject to any disclaimer, the term of this patent is extended or adjusted under 35 U.S.C. 154(b) by 0 days.

(21) Appl. No.: 15/930,103

(22) Filed: May 12, 2020

(65) Prior Publication Data

US 2020/0339593 A1    Oct. 29, 2020

Related U.S. Application Data

(63) Continuation of application No. 16/425,316, filed on May 29, 2019, now Pat. No. 10,676,482, which is a continuation of application No. 15/637,448, filed on Jun. 29, 2017, now Pat. No. 10,336,770, which is a continuation of application No. 14/539,327, filed on Nov. 12, 2014, now Pat. No. 9,725,461, which is a continuation of application No. 13/892,373, filed on May 13, 2013, now Pat. No. 8,906,909, which is a continuation of application No. 13/078,769, filed on Apr. 1, 2011, now Pat. No. 8,461,157, which is a continuation-in-part of application No. 12/684,594, filed on Jan. 8, 2010, now Pat. No. 8,367,663.

(60) Provisional application No. 61/143,271, filed on Jan. 8, 2009, provisional application No. 61/172,580, filed on Apr. 24, 2009.

(51) Int. Cl.
| | | |
|---|---|---|
| *C07D 495/04* | (2006.01) | |
| *C07D 413/14* | (2006.01) | |
| *C07D 491/04* | (2006.01) | |
| *A61K 31/535* | (2006.01) | |

(52) U.S. Cl.
CPC .......... *C07D 495/04* (2013.01); *A61K 31/535* (2013.01); *C07D 413/14* (2013.01); *C07D 491/04* (2013.01)

(58) Field of Classification Search
CPC .. C07D 495/04; C07D 413/14; C07D 491/04; A61K 31/535
See application file for complete search history.

(56) References Cited

U.S. PATENT DOCUMENTS

| | | |
|---|---|---|
| 5,502,187 A | 3/1996 | Ayer et al. |
| 6,087,367 A | 7/2000 | Breslow et al. |
| 6,608,053 B2 | 8/2003 | Hayakawa et al. |
| 6,777,217 B1 | 8/2004 | Schreiber et al. |
| 7,300,935 B2 | 11/2007 | Cho et al. |
| 8,367,663 B2 | 2/2013 | Cai et al. |
| 8,461,157 B2 | 6/2013 | Cai et al. |
| 8,710,219 B2 | 4/2014 | Cai et al. |
| 8,906,909 B2 | 12/2014 | Cai et al. |
| 9,249,156 B2 | 2/2016 | Cai et al. |
| 9,657,032 B2 | 5/2017 | Qian et al. |
| 9,725,461 B2 | 8/2017 | Cai et al. |
| 10,336,770 B2 | 7/2019 | Cai et al. |
| 10,676,482 B2 | 6/2020 | Cai et al. |
| 2006/0160829 A1 | 7/2006 | Cho et al. |
| 2007/0249587 A1 | 10/2007 | Yonetoku et al. |
| 2008/0076768 A1 | 3/2008 | Chuckowree et al. |
| 2008/0076774 A1 | 3/2008 | Anand et al. |
| 2008/0125440 A1 | 5/2008 | Cai et al. |
| 2008/0125478 A1 | 5/2008 | Cai et al. |
| 2008/0139590 A1 | 6/2008 | Qian et al. |
| 2008/0161320 A1 | 7/2008 | Cai et al. |
| 2008/0194578 A1 | 8/2008 | Qian et al. |
| 2008/0221132 A1 | 9/2008 | Cai et al. |
| 2008/0234332 A1 | 9/2008 | Cai et al. |
| 2008/0242665 A1 | 10/2008 | Bayliss et al. |
| 2008/0269210 A1 | 10/2008 | Castanedo et al. |
| 2009/0076044 A1 | 3/2009 | Qian et al. |
| 2009/0093507 A1 | 4/2009 | Qian et al. |
| 2010/0233164 A1 | 9/2010 | Ebens, Jr. et al. |
| 2010/0292468 A1 | 11/2010 | Babu et al. |
| 2011/0086837 A1 | 4/2011 | Belvin et al. |
| 2013/0090335 A1 | 4/2013 | Cai et al. |
| 2013/0102595 A1 | 4/2013 | Bao et al. |

FOREIGN PATENT DOCUMENTS

| | | |
|---|---|---|
| EP | 1277738 A1 | 1/2003 |
| WO | 03075929 A1 | 9/2003 |
| WO | 03076395 A1 | 9/2003 |

(Continued)

OTHER PUBLICATIONS

"PI3 Kinase Signaling in Disease", Curis News Release. Curis Presents Preclinical Data for CU-903 at Keystone Symposia Event, Drugs.com, <http://www.drugs.com/clinical_trials/curis-presents-preclinical-data-cu-903-keystone-symposiaevent-8220-pi3-kinase-signaling-8221-7094, 2009, 1-2.

(Continued)

*Primary Examiner* — Rebecca L Anderson

(74) *Attorney, Agent, or Firm* — Elmore Patent Law Group, P.C.; Edgar W. Harlan; Carolyn S. Elmore

(57) ABSTRACT

The instant application relates to deazapurines, thienopyrimidines and furopyrimidines with zinc-binding moiety based derivatives and their use in the treatment of phosphoinositide 3-kinase related diseases and disorders such as cancer. The instant application further relates to the the treatment of histone deacetylase related disorders and diseases related to both histone deacetylase and phosphoinositide 3-kinase.

8 Claims, No Drawings

(56) References Cited

FOREIGN PATENT DOCUMENTS

| | | |
|---|---|---|
| WO | 03076400 A1 | 9/2003 |
| WO | 03076401 A1 | 9/2003 |
| WO | 03076421 A1 | 9/2003 |
| WO | 03076422 A1 | 9/2003 |
| WO | 2004017950 A2 | 3/2004 |
| WO | 2006046031 A1 | 5/2006 |
| WO | 2006046035 A1 | 5/2006 |
| WO | 2006046040 A1 | 5/2006 |
| WO | 2006082428 A2 | 8/2006 |
| WO | 2006122926 A1 | 11/2006 |
| WO | 2007082873 A1 | 7/2007 |
| WO | 2007082874 A1 | 7/2007 |
| WO | 2007082880 A1 | 7/2007 |
| WO | 2007122410 A1 | 11/2007 |
| WO | 2007127175 A2 | 11/2007 |
| WO | 2007127183 A1 | 11/2007 |
| WO | 2007129161 A2 | 11/2007 |
| WO | 2007131364 A1 | 11/2007 |
| WO | 2008033743 A1 | 3/2008 |
| WO | 2008033744 A2 | 3/2008 |
| WO | 2008033745 A2 | 3/2008 |
| WO | 2008033746 A2 | 3/2008 |
| WO | 2008033747 A2 | 3/2008 |
| WO | 2008033748 A2 | 3/2008 |
| WO | 2008033749 A2 | 3/2008 |
| WO | 2008055068 A2 | 5/2008 |
| WO | 2008070740 A1 | 6/2008 |
| WO | 2008073785 A2 | 6/2008 |
| WO | 2008100985 A2 | 8/2008 |
| WO | 2009036020 A1 | 3/2009 |
| WO | 2009036057 A1 | 3/2009 |
| WO | 2009036066 A1 | 3/2009 |
| WO | 2009036082 A2 | 3/2009 |
| WO | 2009042646 A1 | 4/2009 |
| WO | 2009052145 A1 | 4/2009 |
| WO | 2009055730 A1 | 4/2009 |
| WO | 2009058895 A1 | 5/2009 |
| WO | 2009086012 A1 | 7/2009 |
| WO | 2009155659 A1 | 12/2009 |
| WO | 2010008847 A2 | 1/2010 |
| WO | 2010105008 A2 | 9/2010 |
| WO | 2011054620 A1 | 5/2011 |
| WO | 2011130628 A1 | 10/2011 |

OTHER PUBLICATIONS

Belvin, M. et al., "PI3K inhibition rescues resistance to EGFR inhibitors in K-Ras mutant and ErbB3 expressing NSCLC cells", Poster No. 4004, AACR Apr. 2008, Poster Section 29, Board 2.

Butler, L. M. et al., "Suberoylanilide Hydroxamic Acid, an Inhibitor of Histone Deacetylase, Suppresses the Growth of Prostate Cancer Cells in Vitro and in Vivo", Cancer Research, 60, 2000, 5165-5170.

Chaussade, C. et al., "Evidence for functional redundancy of class IA PI3K isoforms in insulin signalling", Biochem. J., 404, 2007, 449-458.

Curtin, M. et al., "Histone Deacetylase Inhibitors: The Abbott Experience", Current Medicinal Chemistry, 10, 2003, 2373-2392.

Denlinger, C. E. et al., "Inhibition of phosphatidylinositol 3-kinase/Akt and histone deacetylase activity induces apoptosis in non-small cell lung cancer in vitro and in vivo", J Thorac Cardiovasc Surg, 130, 2005, 1422-9.

Engelman, J. A. et al., "Targeting PI3K signalling in cancer: opportunities, challenges and limitations", Nature Reviews Cancer, 9, 2009, 550-562.

Fan, Q-W et al., "A Dual Phosphoinositide-3-Kinase α/mTOR Inhibitor Cooperates with Blockade of Epidermal Growth Factor Receptor in PTEN-Mutant Glioma", Cancer Res., 67(17), 2007, 7960-7965.

Fan, Q-W et al., "A dual PI3 kinase/mTOR inhibitor reveals emergent efficacy in glioma", Cancer Cell, 9, 2006, 341-349.

Hayakawa, M. et al., "Synthesis and biological evaluation of 4-morpholino-2-phenylquinazolines and related derivatives as novel PI3 kinase p110α inhibitors", Bioorganic & Medicinal Chemistry, 14, 2006, 6847-6858.

Hayakawa, M. et al., "Synthesis and biological evaluation of imidazo[1,2-a]pyridine derivatives as novel PI3 kinase p110α inhibitors", Bioorganic & Medicinal Chemistry, 15, 2007, 403-412.

Kulp, S. K. "Antitumor Effects of a Novel Phenylbutyrate-Based Histone Deacetylase Inhibitor, (S)-HDAC-42, in Prostate Cancer", Clinical Cancer Research, 12(17), 2006, 5199-5206.

Lea, M. A. et al., "Induction of Differentiation of Colon Cancer Cells by Combined Inhibition of Kinases and Histone Deacetylase", Anticancer Research, 27, 2007, 741-748.

Mayo, M. W. et al., "Ineffectiveness of Histone Deacetylase Inhibitors to Induce Apoptosis Involves the Transcriptional Activation of NF-κB through the Akt Pathway", The Journal of Biological Chemistry, 278(21), 2003, 18980-18989.

Minucci, S. et al., Histone deacetylase inhibitors and the promise of epigenetic (and more) treatments for cancer, Nature, 6, 2006, 38-51.

Ozaki, K-I et al., "Blockade of the ERK or PI3K-Akt signaling pathway enhances the cytotoxicity of histone deacetylase inhibitors in tumor cells resistant to gefitinib or imatinib", Biochemical and biophysical research communications, 391(4), 2010, 1610-1615.

Suzuki, T. et al., "Novel Histone Deacetylase Inhibitors: Design, Synthesis, Enzyme Inhibition, and Binding Mode Study of SAHA-Based Non-hydroxamates", Bioorganic & Medicinal Chemistry Letters, 13, 2003, 4321-4326.

Wang, Q. et al., "Augmentation of Sodium Butyrate-induced Apoptosis by Phosphatidylinositol 3'-Kinase Inhibition in the KM20 Human Colon Cancer Cell Line", Clin Cancer Res, 8, 2002, 1940-1947.

Wegener, D. et al., "Identification of novel small-molecule histone deacetylase inhibitors by medium-throughput screening using a fluorigenic assay", Biochem. Journal, 413, 2008, 143-150.

Wozniak, M. B. et al., "Vorinostat interferes with the signaling transduction pathway of T-cell receptor and synergizes with phosphoinositide-3 kinase inhibitors in cutaneous T-cell lymphoma", Haematologica, 95(4), 2010, 613-621.

Yaguchi, S. I. et al., "Antitumor Activity of ZSTK474, a New Phosphatidylinositol 3-Kinase Inhibitor", Journal of the National Cancer Institute, 98(8), 2006, 545-556.

PHOSPHOINOSITIDE 3-KINASE INHIBITORS WITH A ZINC BINDING MOIETY

RELATED APPLICATIONS

This application is a continuation of U.S. application Ser. No. 16/425,316, filed on May 29, 2019, which is a continuation of U.S. application Ser. No. 15/637,448 (now U.S. Pat. No. 10,336,770), filed on Jun. 29, 2017, which is a continuation of U.S. application Ser. No. 14/539,327 (now U.S. Pat. No. 9,725,461), filed on Nov. 12, 2014, which is a continuation of U.S. application Ser. No. 13/892,373 (now U.S. Pat. No. 8,906,909), filed May 13, 2013, which is a continuation of U.S. application Ser. No. 13/078,769 (now U.S. Pat. No. 8,461,157), filed Apr. 1, 2011, which is a continuation-in-part of U.S. application Ser. No. 12/684,594 (now U.S. Pat. No. 8,367,663), filed Jan. 8, 2010, which claims the benefit of U.S. Provisional Applications No. 61/143,271, filed Jan. 8, 2009, and 61/172,580, filed Apr. 24, 2009. The entire teachings of the above applications are incorporated herein by reference.

BACKGROUND OF THE INVENTION

Phosphoinositides (PIs), which are phosphorylated derivatives of phosphatidylinositol, are essential in eukaryotic cells, regulating nuclear processes, cytoskeletal dynamics, signalling and membrane trafficking. Among the enzymes involved in PI metabolism, PI3-kinases (PI3K) have attracted special attention because of their oncogenic properties and potential as drug targets. PI3-kinases phosphorylate phosphatidylinositols or PIs at the 3-position of the inositol ring. (Lindmo et al. *Journal of Cell Science* 119, 605-614, 2006). The 3-phosphorylated phospholipids generated by PI3K activity bind to the pleckstrin homology (PH) domain of protein kinase B (PKB), causing translocation of PKB to the cell membrane and subsequent phosphorylation of PKB. Phosphorylated PKB inhibits apoptosis-inducing proteins such as FKHR, Bad, and caspases, and is thought to play an important role in cancer progression. The PI3Ks are divided into classes I-III, and class I is further subclassified into classes Ia and Ib. Among these isoforms, class Ia enzymes are thought to play the most important role in cell proliferation in response to growth factor-tyrosine kinase pathway activation (Hayakawa et al., *Bioorganic & Medicinal Chemistry* 14, 6847-6858, 2006). Three frequent mutations in cancer constitutively activate PI3Kα and, when expressed in cells, they drive the oncogenic transformation and chronic activation of downstream signalling by molecules such as PKB, S6K and 4E bp1 that is commonly seen in cancer cells. (Stephens et al., *Current Opinion in Pharmacology,* 5 (4) 357-365, 2005). As such, PI3-kinases are attractive targets for the treatment of proliferative diseases.

There are several known PI3-kinase inhibitors including Wortmannin and LY294002. Although wortmannin is a potent PI3K inhibitor with a low nanomolar $IC_{50}$ value, it has low in vivo anti-tumor activity. (Hayakawa et al, Bioorg Med Chem, 14(20), 6847-6858 (2006)). Recently, a group of morpholine substituted quinazoline, pyridopyrimidine and thienopyrimidine compounds have been reported to be effective in inhibiting PI3kinase p110α. (Hayakawa, 6847-6858). Oral dosage of a morpholine substituted thienopyrimidine compound (GDC-0941) has shown tumor suppression in glioblastoma xenografts in vivo. (Folkes et al., *Journal of Medicinal Chemistry,* 51, 5522-5532, 2008). The following publications disclose a series of thienopyrimidine, pyridopyrimidine and quinazoline based PI3-Kinase inhibitors: WO 2008/073785; WO 2008/070740; WO 2007/127183; U.S. Patent Publication 20080242665.

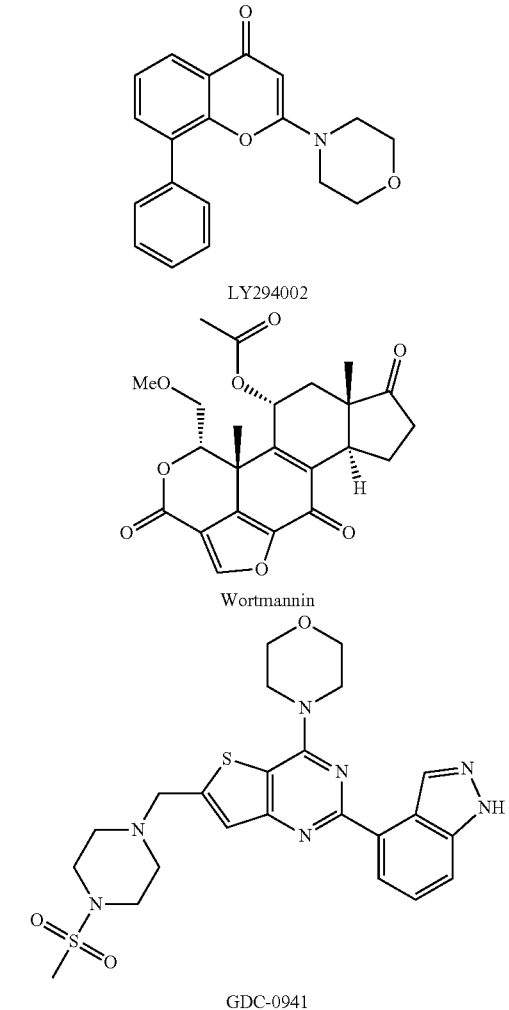

LY294002

Wortmannin

GDC-0941

Histone acetylation is a reversible modification, with deacetylation being catalyzed by a family of enzymes termed histone deacetylases (HDACs). HDAC's are represented by 18 genes in humans and are divided into four distinct classes (*J Mol Biol,* 2004, 338:1, 17-31). In mammalians class I HDAC's (HDAC1-3, and HDAC8) are related to yeast RPD3 HDAC, class 2 (HDAC4-7, HDAC9 and HDAC10) related to yeast HDA1, class 4 (HDAC11), and class 3 (a distinct class encompassing the sirtuins which are related to yeast Sir2).

Csordas, *Biochem. J.,* 1990, 286: 23-38 teaches that histones are subject to post-translational acetylation of the, ε-amino groups of N-terminal lysine residues, a reaction that is catalyzed by histone acetyl transferase (HAT1). Acetylation neutralizes the positive charge of the lysine side chain, and is thought to impact chromatin structure. Indeed, access of transcription factors to chromatin templates is enhanced by histone hyperacetylation, and enrichment in underacetylated histone H4 has been found in transcriptionally silent regions of the genome (Taunton et al., Science, 1996, 272:408-411). In the case of tumor suppressor genes, transcriptional silencing due to histone modification can lead to oncogenic transformation and cancer.

Several classes of HDAC inhibitors currently are being evaluated by clinical investigators. Examples include hydroxamic acid derivatives, Suberoylanilide hydroxamic acid (SAHA), PXD101 and LAQ824, are currently in the clinical development. In the benzamide class of HDAC inhibitors, MS-275, MGCD0103 and CI-994 have reached clinical trials. Mourne et al. (Abstract #4725, AACR 2005), demonstrate that thiophenyl modification of benzamides significantly enhance HDAC inhibitory activity against HDAC1.

Mammalian Target of Rapamycin (mTOR) is a signaling protein which is downstream of multiple signaling pathways, including the PI3K/Akt pathway. Cell signaling through mTOR controls a variety of cellular responses, including responses to nutrients and growth factors. mTOR inhibitors are currently in clinical use for the prevention of transplant rejection. However, the ability of these compounds to shrink tumors suggests their potential use as anti-cancer agents. The effect of mTOR inhibitors on cancer cells may arise from inhibition of the PI3/Akt pathway. Inhibition of mTOR also lowers VEGF levels, resulting in an antiangiogenic effect that may also contribute to tumor shrinkage. Recent research suggests that the inhibition of multiple targets in the PI3K/Akt pathway provides improved anticancer activity. Thus, compounds which inhibit both PI3K and mTOR are desirable.

Certain cancers have been effectively treated with such a combinatorial approach; however, treatment regimes using a cocktail of cytotoxic drugs often are limited by dose limiting toxicities and drug-drug interactions. More recent advances with molecularly targeted drugs have provided new approaches to combination treatment for cancer, allowing multiple targeted agents to be used simultaneously, or combining these new therapies with standard chemotherapeutics or radiation to improve outcome without reaching dose limiting toxicities. However, the ability to use such combinations currently is limited to drugs that show compatible pharmacologic and pharmacodynamic properties. In addition, the regulatory requirements to demonstrate safety and efficacy of combination therapies can be more costly and lengthy than corresponding single agent trials. Once approved, combination strategies may also be associated with increased costs to patients, as well as decreased patient compliance owing to the more intricate dosing paradigms required.

SUMMARY OF THE INVENTION

The present invention relates to deazapurines, thienopyrimidines and furopyrimidines with zinc-binding moiety based derivatives and their use in the treatment of PI3K related diseases and disorders such as cancer. The compounds of the present invention may further act as HDAC or matrix metalloproteinase (MMP) inhibitors by virtue of their ability to bind zinc ions. Surprisingly these compounds are active at multiple therapeutic targets and are effective for treating disease. Moreover, in some cases it has even more surprisingly been found that the compounds have enhanced activity when compared to the activities of combinations of separate molecules individually having the PI3-Kinase and HDAC activity. In other words, the combination of PI3-kinases and HDAC inhibitors into a single molecule may provide a synergistic effect as compared to the PI3-kinases. In another embodiment, certain compounds of the present invention also inhibit mTor in addition to having PI3-Kinase and HDAC activity.

Moreover, the efficacy of single-agent PI3K pathway inhibitors is limited by the presence of primary/acquired genetic alterations and activation of multiple pro-survival and growth pathways (Engelman (2009) Nature Reviews Cancer, 9: 550-562). Inhibition of PI3K by single-agent PI3K pathway inhibitors can actually upregulate signaling of the RAF-MEK-ERK pathway by the release of negative feedback loops. The compounds of the invention, by virtue of their integrated PI3K/HDAC inhibitory activities, provide the potential to overcome the limitations in the treatment of cancers with single-target PI3K inhibitors. The compounds of the invention may disrupt cancer networks in in vivo and in vitro experiments, resulting from durable inhibition of the PI3K-AKT-mTOR pathway, the inhibition of the RAF-MEK-ERK pathway, and the downregulation of receptor tyrosine kinase (RTK) protein levels. In addition, the compounds of the invention may induce cell cycle arrest and apoptosis resulting from the upregulation of tumor suppressors p53 and p21. Accordingly, compounds of the invention have the potential to overcome primary and acquired drug resistance and may be more efficacious than mono-treatment with single-agent PI3K pathway inhibitors in clinical applications.

Accordingly, one aspect of the present invention provides a compound having the general formula (I):

Formula I

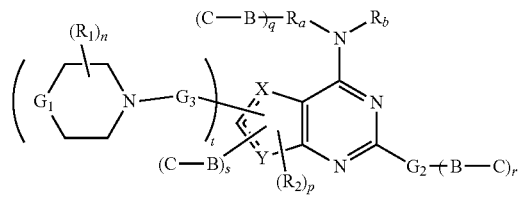

or a geometric isomer, enantiomer, diastereomer, racemate, pharmaceutically acceptable salt or prodrug thereof.

wherein ═══ represents a single or double bond;

q, r and s are independently 0 or 1, wherein at least one of q, r and s is 1; preferably, one of q, r and s is 1 and the rest are 0;

n is 0, 1, 2, 3 or 4;

p is 0, 1 or 2, preferably 0 or 1;

t is 0 or 1; preferably, when s is 1, t is 0;

X and Y are independently $CR_1$, $N(R_8)$, S or O; wherein when one of X and Y is $CR_1$, the other is $N(R_8)$, S or O; preferably X is S and Y is $CR_1$;

$G_1$ is $CR_1$, S, O, $NR_{10}$ or $NS(O)_2R_{10}$;

$G_2$ is substituted or unsubstituted aryl, substituted or unsubstituted heteroaryl or, substituted or unsubstituted heterocyclic;

$G_3$ is substituted or unsubstituted $C_1$-$C_8$ alkyl, substituted or unsubstituted $C_2$-$C_8$ alkenyl or substituted or unsubstituted $C_2$-$C_8$ alkynyl;

each $R_8$ is independently hydrogen, acyl, aliphatic or substituted aliphatic;

each $R_1$ and $R_2$ is absent or is independently selected from hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic;

$R_a$ is optionally substituted alkyl, optionally substituted aryl or optionally substituted heteroaryl;

$R_b$ is hydrogen, optionally substituted alkyl, optionally substituted aryl or optionally substituted heteroaryl;

or $R_a$ and $R_b$, together with the nitrogen atom to which they are attached, form an optionally substituted heterocyclic group;

$R_{10}$ is selected from hydrogen, hydroxy, amino, alkoxy, alkylamino, dialkylamino, sulfonyl, acyl, aliphatic, substituted aliphatic, aryl, substituted aryl, heteroaryl, substituted heteroaryl, heterocyclic, and substituted heterocyclic; preferably $R_{10}$ is hydrogen, acyl, aliphatic or substituted aliphatic;

B is a linker; and

C is selected from:

(a)

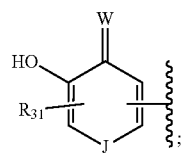

where W is O or S; J is O, NH or NCH$_3$; and $R_{31}$ is hydrogen or lower alkyl;

(b)

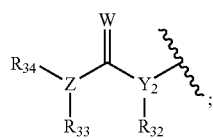

where W is O or S; $Y_2$ is absent, N, or CH; Z is N or CH; $R_{32}$ and $R_{34}$ are independently hydrogen, hydroxy, aliphatic group, provided that if $R_{32}$ and $R_{34}$ are both present, one of $R_{32}$ or $R_{34}$ must be hydroxy and if $Y_2$ is absent, $R_{34}$ must be hydroxy; and $R_{33}$ is hydrogen or aliphatic group;

(c)

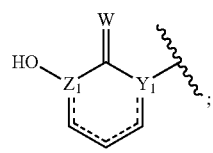

where W is O or S; $Y_1$ and $Z_1$ are independently N, C or CH; and (d)

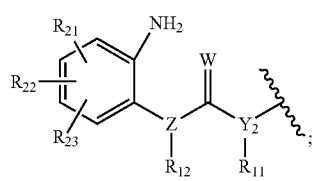

where Z, $Y_2$, and W are as previously defined; $R_{11}$ and $R_{12}$ are independently selected from hydrogen or aliphatic; $R_{21}$, $R_{22}$ and $R_{23}$ are independently selected from hydrogen, hydroxy, amino, halogen, alkoxy, alkylamino, dialkylamino, CF$_3$, CN, NO$_2$, sulfonyl, acyl, aliphatic, substituted aliphatic, aryl, substituted aryl, heteroaryl, substituted heteroaryl, heterocyclic, and substituted heterocyclic.

In another embodiment, each $R_1$ and $R_2$ is independently absent, hydrogen, hydroxy, amino, halogen, alkoxy, alkylamino, dialkylamino, CF$_3$, CN, NO$_2$, sulfonyl, acyl, aliphatic, substituted aliphatic, aryl, substituted aryl, heteroaryl, substituted heteroaryl, heterocyclic, and substituted heterocyclic; arylalkyl, substituted arylalkyl, heteroarylalkyl, substituted heteroarylalkyl, heterocyclylalkyl or substituted heterocyclylalkyl.

Another aspect of the invention provides methods of inhibiting PI3 kinase activity, by contacting a PI3 kinase with an effective inhibitory amount of a compound of Formula I, or a stereoisomer, geometric isomer, tautomer, solvate, metabolite, or pharmaceutically acceptable salt or prodrug thereof.

DETAILED DESCRIPTION OF THE INVENTION

In a first embodiment of the compounds of the present invention are compounds represented by formulae (I) as illustrated above, or its geometric isomers, enantiomers, diastereomers, racemates, pharmaceutically acceptable salts, prodrugs and solvates thereof.

In one embodiment, the compounds of the present invention are compounds represented by formula (II) or formula (III), or a geometric isomer, enantiomer, diastereomer, racemate, pharmaceutically acceptable salt, or prodrug thereof:

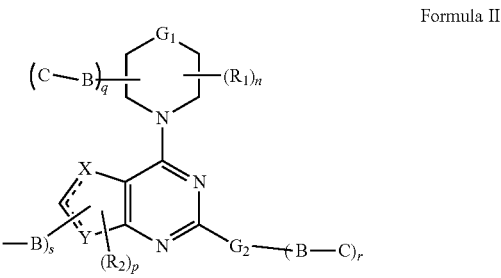

Formula II

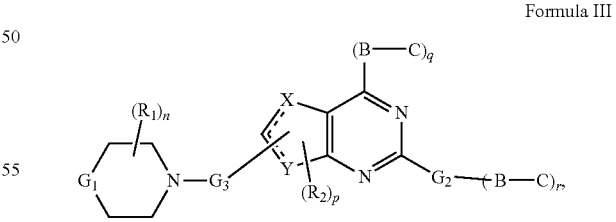

Formula III wherein ===== represents a single or double bond and $G_1$, $G_2$, $G_3$, $R_1$, $R_2$, X, Y, n, p, q, r, and C are as defined above. Preferably, in Formula (III), q is 1 and r is 0.

In another embodiment of the compounds of the present invention are compounds represented by formula (IV) and (V) as illustrated below, or its geometric isomers, enantiomers, diastereomers, racemates, pharmaceutically acceptable salts, and prodrugs thereof:

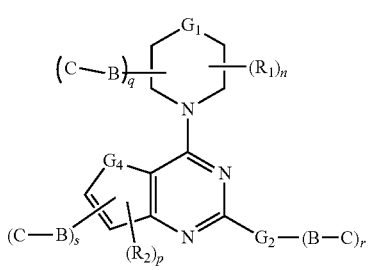

Formula IV

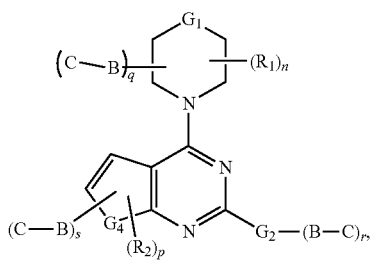

Formula V wherein ===== represents a single or double bond; $G_1$, $G_2$, $R_1$, $R_2$, $R_8$, n, p, q, r, s, B and C are as defined above; and $G_4$ is $NR_8$, S or O, preferably S. Preferably $G_1$ is O.

In another embodiment of the compounds of the present invention are compounds represented by formula (VI) or (VII) as illustrated below, and the geometric isomers, enantiomers, diastereomers, racemates, pharmaceutically acceptable salts, and prodrugs thereof:

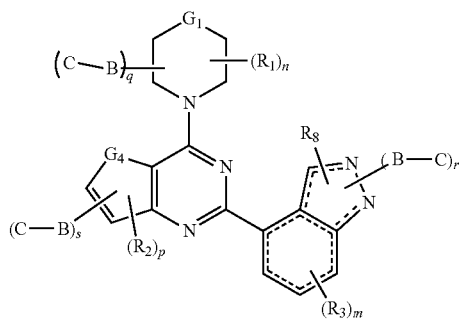

Formula VI

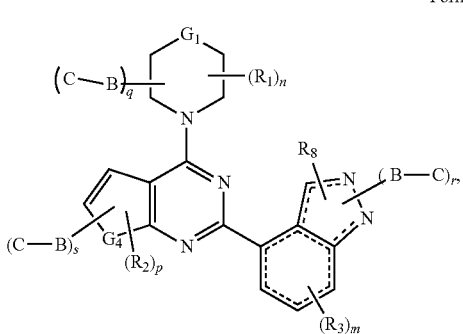

Formula VII wherein ===== represents single or double bond; $G_1$, $G_4$, $R_1$, $R_2$, $R_8$, n, p, q, r, s, B and C are as defined above; m is 0, 1, 2 or 3; m is 0, 1, 2 or 3; and $R_3$ is selected from absent, hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic.

In another embodiment of the compounds of the present invention are compounds represented by formula (VIII) and (IX) as illustrated below, or the geometric isomers, enantiomers, diastereomers, racemates, pharmaceutically acceptable salts, and prodrugs thereof:

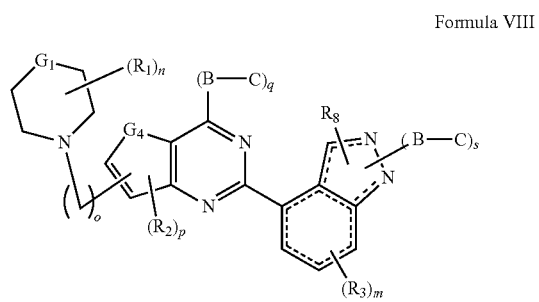

Formula VIII

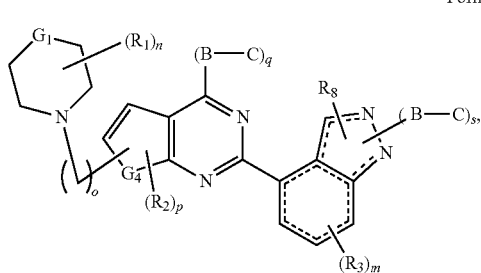

Formula IX wherein ===== represents a single or double bond; $G_1$, $G_4$, $R_1$, $R_2$, $R_3$, $R_8$, n, m, p, q, s, B and C are as defined above; and o is 1, 2, 3 or 4.

In preferred embodiments of the compounds of Formulas I, II, IV, V, VI and VII, q and r are 0 and s is 1. In another preferred embodiment q is 1 while r and s are 0. In another preferred embodiment q and s are 0 and r is 1.

In preferred embodiments of the compounds of Formula III, r is 0 and q is 1.

In preferred embodiments of the compounds of Formulas VIII and IX, q is 1 and s is 0.

In a preferred embodiment, B is a $C_1$-$C_8$ alkyl where one or more $CH_2$ can be optionally replaced by O, S, $SO_2$, $NR_8$ or —CONH—, C is —C(O)N(H)OH, and $G_1$ is —O. In another preferred embodiment, B is a $C_1$-$C_8$ alkyl where one or more $CH_2$ can be optionally replaced by O, S, $SO_2$, $NR_8$ or —CONH—, C is —C(O)N(H)OH, and $G_1$ is —NS(O)$_2$CH$_3$. In another preferred embodiment, B is an aryl, heteroaryl, $C_1$-$C_{10}$-alkylaryl, $C_1$-$C_{10}$-alkylheteroaryl group, $C_1$-$C_{10}$-alkylheterocyclylaryl, $C_1$-$C_{10}$-alkylheterocyclylheteroaryl, $C_1$-$C_{10}$-alkylheterocyclylaryl-$C_1$-$C_{10}$-alkyl, or $C_1$-$C_{10}$-alkylheterocyclylheteroaryl-$C_1$-$C_{10}$-alkyl group where one or more $CH_2$ can be optionally replaced by O, S, $SO_2$, $NR_8$ or —CONH—, and $G_1$ is —O or —NS(O)$_2$CH$_3$.

In another embodiment of the compounds of the present invention are compounds represented by formula (X) and (XI) as illustrated below, or the geometric isomers, enantiomers, diastereomers, racemates, pharmaceutically acceptable salts or prodrugs thereof:

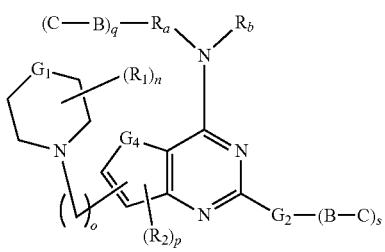

Formula X

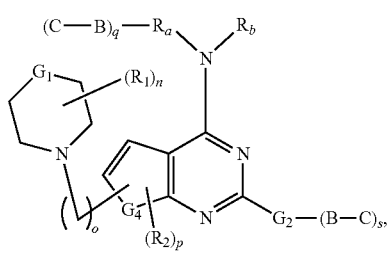

Formula XI wherein ===== represents a single or double bond; $G_1$, $G_2$, $G_4$, $R_a$, $R_b$, $R_1$, $R_2$, n, p, q, s, B and C are as defined above; and o is 1, 2, 3 or 4. In preferred embodiments, $G_2$ is optionally substituted phenyl, pyridyl, pyrimidyl, indolyl, indazolyl, pyridopyrrolyl, pyrrolyl, imidazolyl, pyrazolyl or benzimidazolyl.

In another embodiment of the compounds of the present invention are compounds represented by formula (XII) and (XIII) as illustrated below, or the geometric isomers, enantiomers, diastereomers, racemates, pharmaceutically acceptable salts or prodrugs thereof:

Formula XII

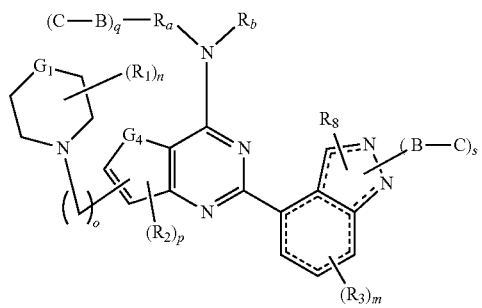

Formula XIII

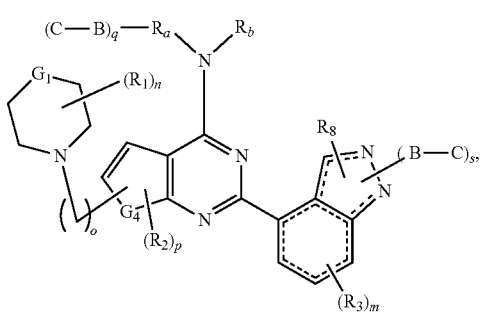

wherein ===== represents a single or double bond; $G_1$, $G_4$, $R_a$, $R_b$, $R_1$, $R_2$, $R_3$, $R_8$, n, p, q, r, s, B and C are as defined above; m is 0, 1, 2 or 3; and o is 1, 2, 3 or 4.

In a preferred embodiment of the compounds of Formulas X-XIII, q is 0 and s is 1. In another preferred embodiment, q is 1 and s is 0. In a preferred embodiment, B is a $C_1$-$C_8$ alkyl where one or more $CH_2$ can be optionally replaced by O, S, $SO_2$, $NR_8$ or —CONH—, C is —C(O)N(H)OH, and $G_1$ is —O. In another preferred embodiment, B is a $C_1$-$C_8$ alkyl where one or more $CH_2$ can be optionally replaced by O, S, $SO_2$, $NR_8$ or —CONH—, C is —C(O)N(H)OH, and $G_1$ is —NS(O)$_2$CH$_3$.

In another embodiment of the compounds of the present invention are compounds represented by formula XIV and XV as illustrated below, or its geometric isomers, enantiomers, diastereomers, racemates, pharmaceutically acceptable salts or prodrugs thereof:

Formula XIV

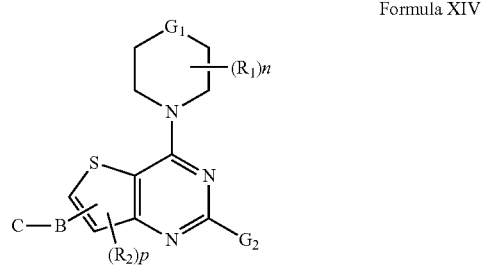

Formula XV

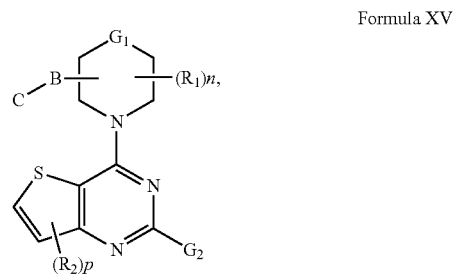

wherein $G_1$, $G_2$, n, p, B, C, $R_1$ and $R_2$ are as defined above. In preferred embodiments, $G_2$ is optionally substituted phenyl, pyridyl, pyrimidyl, indolyl, indazolyl, pyridopyrrolyl, pyrrolyl, imidazolyl, pyrazolyl or benzimidazolyl.

In another embodiment of the compounds of the present invention are compounds represented by formula XVI and XVII as illustrated below, or its geometric isomers, enantiomers, diastereomers, racemates, pharmaceutically acceptable salts or prodrugs thereof:

XVI

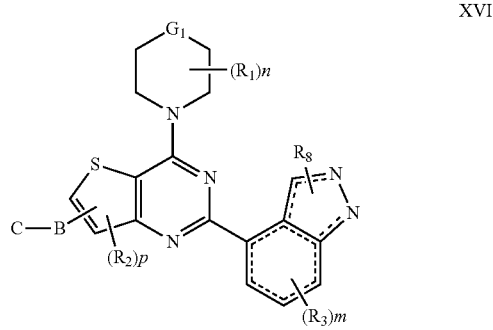

XVII

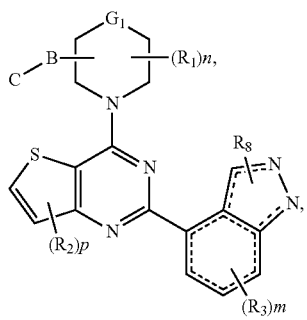

wherein $G_1$, n, m, p, B, C, $R_1$, $R_2$, $R_3$ and $R_8$ are as defined above.

A preferred embodiment of the compounds of Formulas IX-XVII is where B is a $C_1$-$C_8$ alkyl where one or more $CH_2$ can be optionally replaced by O, S, $SO_2$, $N(R_8)$, —CONH—, aryl, substituted aryl, heteroaryl, substituted heteroaryl, heterocyclic or substituted heterocyclic groups, C is —C(O)N(H)OH, and $G_1$ is O. Another preferred embodiment is where B is a $C_1$-$C_8$ alkyl where one or more $CH_2$ can be optionally replaced by O, S, $SO_2$, $NR_8$, —CONH—, aryl, substituted aryl, heteroaryl, substituted heteroaryl, heterocyclic or substituted heterocyclic groups, C is —C(O)N(H)OH, and $G_1$ is —NS(O)$_2$CH$_3$.

In another embodiment of the compounds of the present invention are compounds represented by formula XVIII or formula XIX, as illustrated below, or the geometric isomers, enantiomers, diastereomers, racemates, pharmaceutically acceptable salts, or prodrugs thereof:

XVIII

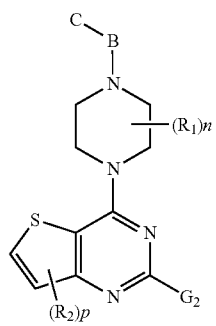

XIX

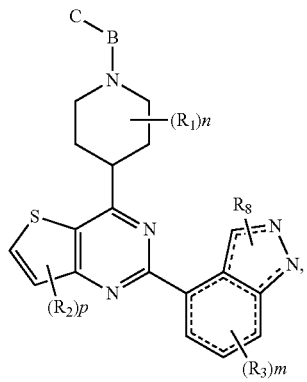

wherein n, m, p, B, C, $R_1$, $R_2$, $R_3$, and $R_8$ are as defined above.

In another embodiment of the compounds of the present invention are compounds represented by formula XX as illustrated below, or its geometric isomers, enantiomers, diastereomers, racemates, pharmaceutically acceptable salts, or prodrugs thereof:

Formula XX

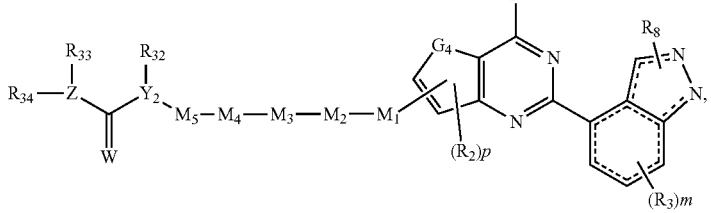

wherein n, p, $Y_2$, W, Z, $G_1$, $G_4$, $G_2$, $R_1$, $R_2$, $R_3$, $R_{32}$, $R_{33}$ and $R_{34}$ are as defined above; $M_1$ is absent, O, S, $NR_8$, $C_1$-$C_6$ alkyl, $C_2$-$C_6$ alkenyl, $C_2$-$C_6$ alkynyl, aryl, heteroaryl, heterocyclic, SO, $SO_2$ or C=O; $M_2$ is absent, $C_1$-$C_6$ alkyl, O, $NR_8$, heterocyclic, aryl, heteroaryl, or C=O; $M_3$ is absent, O, $NR_8$, S, SO, $SO_2$, CO, $C_1$-$C_6$ alkyl, $C_2$-$C_6$ alkenyl, $C_2$-$C_6$ alkynyl, aryl, heteroaryl, or heterocyclic; $M_4$ is absent, O, $NR_8$, heteroaryl, heterocyclic or aryl; and $M_5$ is absent, $C_1$-$C_8$ alkyl, $C_2$-$C_8$ alkenyl, $C_2$-$C_8$alkynyl, heteroaryl, heterocyclic or aryl. In preferred embodiments, $G_2$ is optionally substituted phenyl, pyridyl, pyrimidyl, indolyl, indazolyl, pyridopyrrolyl, pyrrolyl, imidazolyl, pyrazolyl or benzoimidazolyl. In more preferred embodiments, $G_2$ is optionally substituted phenyl, pyridyl, pyrimidyl, indazolyl, pyrrolyl or benzimidazolyl.

In another embodiment of the compounds of the present invention are compounds represented by formula (XXI) as illustrated below, or its geometric isomers, enantiomers, diastereomers, racemates, pharmaceutically acceptable salts, or prodrugs thereof:

Formula XXI wherein n, m, p, $Y_2$, W, Z, $G_1$, $G_4$, $R_1$, $R_2$, $R_3$, $R_8$, $R_{32}$, $R_{33}$, $R_{34}$ and $M_1$-$M_5$ are as defined above.

In another embodiment of the compounds of the present invention are compounds represented by formula (XXII) as illustrated below, or its geometric isomers, enantiomers, diastereomers, racemates, pharmaceutically acceptable salts, or prodrugs thereof:

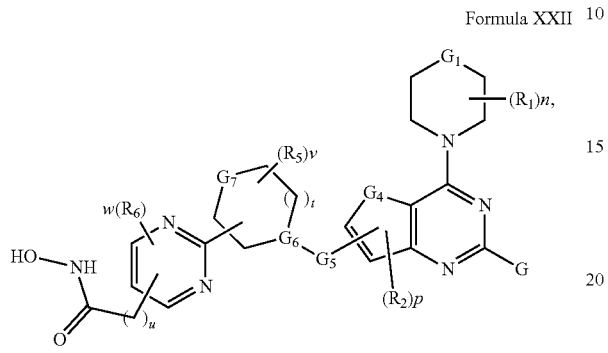

Formula XXII wherein $G_1$, $G_2$, $G_4$, n, p, $R_1$, $R_2$ and $R_3$ are as defined above; t, v and w are independently 0, 1, 2 or 3; u is 0, 1, 2, 3, 4, 5, 6, 7 or 8; $G_5$ is absent, $C_1$-$C_8$ alkyl or a $C_1$-$C_8$ alkyl interrupted by one or more O, S, S(O), $SO_2$, N($R_8$), or C(O); preferably $G_5$ is —N($R_8$)—$C_1$-$C_4$-alkyl, t is 1 and u is 0; $G_6$ is selected from $CR_1$ or $NR_8$, wherein $R_1$ and $R_8$ are as defined above;
$G_7$ is selected from —$CR_1$, —$NR_8$, S or O wherein $R_1$ and $R_8$ are as defined above; or
$G_7$ is selected from —$C(R_1)_2$, and —N; $R_5$ and $R_6$ are independently selected from absent, hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic. In preferred embodiments, $G_2$ is optionally substituted phenyl, pyridyl, pyrimidyl, indolyl, indazolyl, pyridopyrrolyl, pyrrolyl, imidazolyl, pyrazolyl or benzimidazolyl. In more preferred embodiments, $G_2$ is optionally substituted phenyl, pyridyl, pyrimidyl, indazolyl, pyrrolyl or benzimidazolyl. Preferably, when $G_7$ is $CR_1$ or N, the pyrimidine ring is directly bonded to $G_7$.

In another embodiment of the compounds of the present invention are compounds represented by Formula XXIII as illustrated below, or its geometric isomers, enantiomers, diastereomers, racemates, pharmaceutically acceptable salts, or prodrugs thereof:

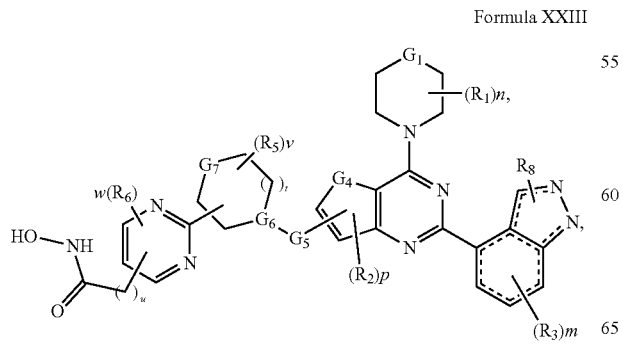

Formula XXIII wherein $G_1$, $G_4$, n, m, p, $R_1$, $R_2$, $R_3$, $R_8$, t, v, w, u, $G_5$, $G_6$, and $G_7$ are as defined above.

In another embodiment of the compounds of the present invention are compounds represented by formula (XXIV) as illustrated below, or the geometric isomers, enantiomers, diastereomers, racemates, pharmaceutically acceptable salts, or prodrugs thereof:

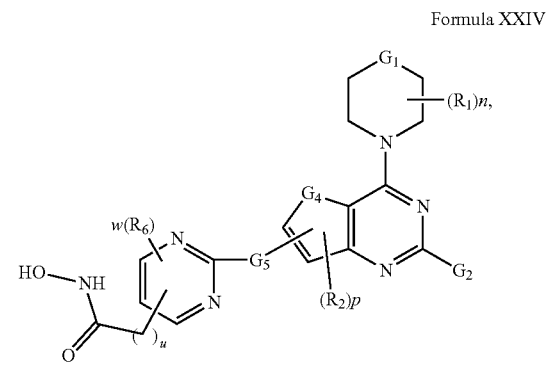

Formula XXIV wherein $G_1$, $G_2$, $G_4$, $G_5$, n, p, w, u, $R_1$, $R_2$, $R_3$ and $R_6$ are as defined above. In preferred embodiments, $G_2$ is optionally substituted phenyl, pyridyl, pyrimidyl, indolyl, indazolyl, pyridopyrrolyl, pyrrolyl, imidazolyl, pyrazolyl or benzimidazolyl. In more preferred embodiments, $G_1$ is O, $G_2$ is optionally substituted phenyl, pyridyl, pyrimidyl, indazolyl, pyrrolyl or benzimidazolyl, $G_5$ is —N($R_8$)—$C_1$-$C_4$-alkyl and u is 0.

In another embodiment of the compounds of the present invention are compounds represented by formula (XXV) as illustrated below, or the geometric isomers, enantiomers, diastereomers, racemates, pharmaceutically acceptable salts, and prodrugs thereof:

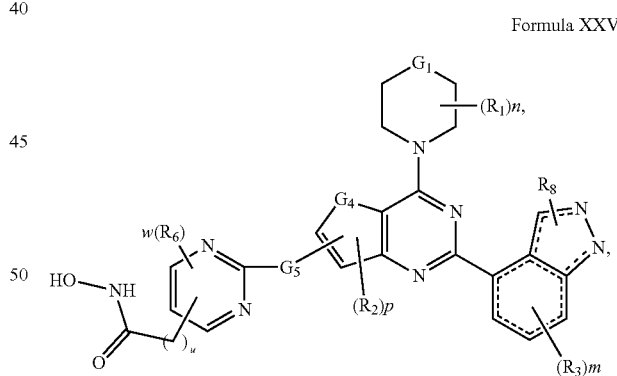

Formula XXV

In more preferred embodiments of the compounds of formulas I, II, III, IV, V, X, XI, XIV, XV, XVIII, XX, XXII and XXIV, $G_2$ is selected from the group:

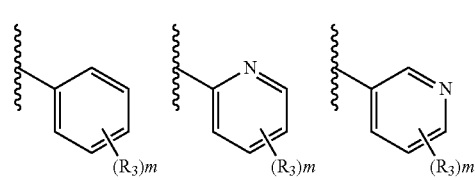

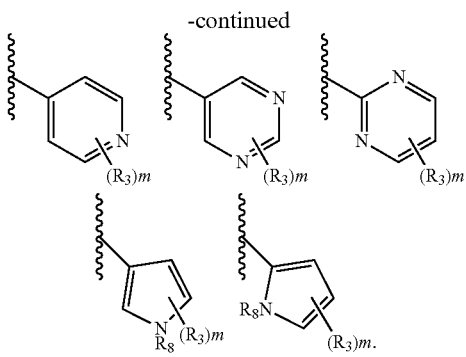

Preferably in these groups, m is 1 and $R_3$ is hydroxyl, hydroxymethyl, amino, acylamino, such as acetylamino, or methylamino. In another preferred embodiment, $G_2$ is selected from the groups shown below:

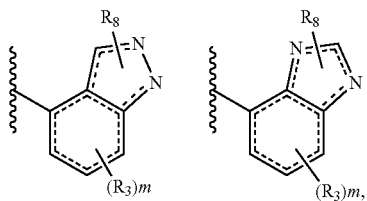

where $R_3$, $R_8$ and m are as defined above.

In certain preferred embodiments of the compounds of formulas I, II, III, IV, V, X, XI, XIV, XV, XVIII, XX, XXII and XXIV, $G_2$ is an optionally substituted monoaryl or monoheteroaryl group. In more preferred embodiments, $G_2$ is phenyl, pyridyl, pyrimidyl or pyrrolyl with one or more substituents including but not limited to hydroxyl, hydroxymethyl, amino and substituted amino; $G_1$ is O, $G_5$ is —N($R_8$)—$C_1$-$C_4$-alkyl. For example, $G_2$ can be phenyl, pyridyl, pyrimidyl or pyrrolyl substituted by a hydroxyl, hydroxymethyl, acetylamino, amino, or methylamino group. Such compounds have significant inhibitory activity toward PI3 kinase and HDAC and may also have significant inhibitory activity toward mTor.

The most preferred embodiment for C is:

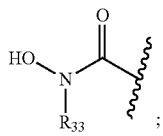

where $R_{33}$ is selected from hydrogen and lower alkyl.

In a preferred embodiment, the bivalent B is a direct bond or straight- or branched-, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylhererocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl, which one or more methylenes can be interrupted or terminated by O, S, S(O), $SO_2$, N($R_8$), C(O), substituted or unsubstituted aryl, substituted or unsubstituted heteroaryl, substituted or unsubstituted heterocyclic; such divalent B linkers include but are not limited to alkyl, alkenyl, alkynyl, alkylaryl, alkenylaryl, alkynylaryl, alkylheterocyclylaryl, alkylheterocyclylarylalkyl, alkylheterocyclylheteroaryl, alkylheterocyclylheteroarylalkyl, alkoxyaryl, alkylaminoaryl, alkoxyalkyl, alkylaminoalkyl, alkylheterocycloalkyl, alkylheteroarylalkyl, alkylamino, N($R_8$)alkenyl, N($R_8$)alkynyl, N($R_8$)alkoxyalkyl, N($R_8$)alkylaminoalkyl, N($R_8$)alkylaminocarbonyl, N($R_8$)alkylaryl, N($R_8$)alkenylaryl, N($R_8$)alkynylaryl, N($R_8$)alkoxyaryl, N($R_8$)alkylaminoaryl, N($R_8$)cycloalkyl, N($R_8$)aryl, N($R_8$)heteroaryl, N($R_8$)heterocycloalkyl, N($R_8$)alkylheterocycloalkyl, alkoxy, O-alkenyl, O-alkynyl, O-alkoxyalkyl, O-alkylaminoalkyl, O-alkylaminocarbonyl, O-alkylaryl, O-alkenylaryl, O-alkynylaryl, O-alkoxyaryl, O-alkylaminoaryl, O-cycloalkyl, O-aryl, O-heteroaryl, O-heterocycloalkyl, O-alkylheterocycloalkyl, C(O)alkyl, C(O)-alkenyl, C(O)alkynyl, C(O)alkylaryl, C(O)alkenylaryl, C(O)alkynylaryl, C(O)alkoxyalkyl, C(O)alkylaminoalkyl, C(O)alkylaminocarbonyl, C(O)cycloalkyl, C(O)aryl, C(O)heteroaryl, C(O)heterocycloalkyl, CON($R_8$), CON($R_8$)alkyl, CON($R_8$)alkenyl, CON($R_8$)alkynyl, CON($R_8$)alkylaryl, CON($R_8$)alkenylaryl, CON($R_8$)alkynylaryl, CON($R_8$)alkoxyalkyl, CON($R_8$)alkylaminoalkyl, CON($R_8$)alkylaminocarbonyl, CON($R_8$)alkoxyaryl, CON($R_8$)alkylaminoaryl, CON($R_8$)cycloalkyl, CON($R_8$)aryl, CON($R_8$)heteroaryl, CON($R_8$)heterocycloalkyl, CON($R_8$)alkylheterocycloalkyl, N($R_8$)C(O)alkyl, N($R_8$)C(O)alkenyl, N($R_8$)C(O)— alkynyl, N($R_8$)C(O)alkylaryl, N($R_8$)C(O)alkenylaryl, N($R_8$)C(O)alkynylaryl, N($R_8$)C(O)alkoxyalkyl, N($R_8$)C(O)alkylaminoalkyl, N($R_8$)C(O)alkylaminocarbonyl, N($R_8$)C(O)alkoxyaryl, N($R_8$)C(O)alkylaminoaryl, N($R_8$)C(O)cycloalkyl, N($R_8$)C(O)aryl, N($R_8$)C(O)heteroaryl, N($R_8$)C(O)heterocycloalkyl, N($R_8$)C(O)alkylheterocycloalkyl, NHC(O)NH, NHC(O)NH-alkyl, NHC(O)NH-alkenyl, NHC(O)NH-alkynyl, NHC(O)NH-alkylaryl, NHC(O)NH-alkenylaryl, NHC(O)NH— alkynylaryl, NHC(O)NH-alkoxyaryl, NHC(O)NH-alkylaminoaryl, NHC(O)NH-cycloalkyl, NHC(O)NH-aryl, NHC(O)NH-heteroaryl, NHC(O)NH-heterocycloalkyl, NHC(O)NH— alkylheterocycloalkyl, S-alkyl, S-alkenyl, S-alkynyl, S-alkoxyalkyl, S-alkylaminoalkyl, S-alkylaryl, S-alkylaminocarbonyl, S-alkylaryl, S-alkynylaryl, S-alkoxyaryl, S-alkylaminoaryl, S-cycloalkyl, S-aryl, S-heteroaryl, S-heterocycloalkyl, S-alkylheterocycloalkyl, S(O)alkyl, S(O)alkenyl, S(O)alkynyl, S(O)alkoxyalkyl, S(O)alkylaminoalkyl, S(O)alkylaminocarbonyl, S(O)alkylaryl, S(O)alkenylaryl, S(O)alkynylaryl, S(O)alkoxyaryl, S(O)alkylaminoaryl, S(O)cycloalkyl, S(O)aryl, S(O)heteroaryl, S(O)heterocycloalkyl, S(O)alkylheterocycloalkyl, $S(O)_2$alkyl, $S(O)_2$alkenyl, $S(O)_2$alkynyl, $S(O)_2$alkoxyalkyl, $S(O)_2$alkylaminoalkyl, $S(O)_2$alkylaminocarbonyl, $S(O)_2$alkylaryl, $S(O)_2$alkenylaryl, $S(O)_2$alkynylaryl, $S(O)_2$alkoxyaryl, $S(O)_2$alkylaminoaryl, $S(O)_2$cycloalkyl, $S(O)_2$aryl, $S(O)_2$heteroaryl, $S(O)_2$heterocycloalkyl, $S(O)_2$alkylheterocycloalkyl, $S(O)_2$heterocyclylalkyl, $S(O)_2$heterocyclylalkenyl, $S(O)_2$heterocyclylalkynyl, $SO_2$NH, $SO_2$NH-alkyl, $SO_2$NH-alkenyl, $SO_2$NH-alkynyl, $SO_2$NH-alkylaryl, $SO_2$NH-alkenylaryl, $SO_2$NH-alkynylaryl, SO$_2$NH-cycloalkyl, SO$_2$NH-aryl, SO$_2$NH-heteroaryl, SO$_2$NH-heterocycloalkyl, SO$_2$NH-alkylheterocycloalkyl, alkylaryloxyalkoxy, alkylaryloxyalkylamino, alkylarylaminoalkoxy, alkylarylaminoalkylamino, alkylarylalkylaminoalkoxy, alkylarylalkylaminoalkoxy, alkenylaryloxyalkoxy, alkenylaryloxyalkylamino, alkenylarylaminoalkoxy, alkenylarylaminoalkylamino, alkenylarylalkylaminoalkoxy, alkenylarylalkylaminoalkylamino.

In a more preferred embodiment, B is a straight chain alkyl, alkenyl, alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl. One or more methylenes can be interrupted or terminated by —O—, —N(R$_8$)—, —C(O)—, —C(O)N(R$_8$)—, or —C(O)O—. Preferably, the C group is attached to B via an aliphatic moiety within B.

In one embodiment, the linker B is between 1-24 atoms, preferably 4-24 atoms, preferably 4-18 atoms, more preferably 4-12 atoms, and most preferably about 4-10 atoms.

In a preferred embodiment, B is selected from straight chain C$_1$-C$_{10}$ alkyl, C$_1$-C$_{10}$ alkenyl, C$_1$-C$_{10}$ alkynyl, C$_1$-C$_{10}$ alkoxy, alkoxyC$_1$-C$_{10}$alkoxy, C$_1$-C$_{10}$ alkylamino, alkoxyC$_1$-C$_{10}$alkylamino, C$_1$-C$_{10}$ alkylcarbonylamino, C$_1$-C$_{10}$ alkylaminocarbonyl, aryloxyC$_1$-C$_{10}$alkoxy, aryloxyC$_1$-C$_{10}$alkylamino, aryloxyC$_1$-C$_{10}$alkylamino carbonyl, C$_1$-C$_{10}$-alkylaminoalkylaminocarbonyl, C$_1$-C$_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxyC$_1$-C$_{10}$alkoxy, alkenylarylaminoC$_1$-C$_{10}$alkoxy, alkenylaryllalkylaminoC$_1$-C$_{10}$alkoxy, alkenylaryloxyC$_1$-C$_{10}$alkylamino, alkenylaryloxyC$_1$-C$_{10}$alkylaminocarbonyl, piperazinoalkylaryl, heteroarylC$_1$-C$_{10}$alkyl, heteroarylC$_2$-C$_{10}$alkenyl, heteroarylC$_2$-C$_{10}$alkynyl, heteroarylC$_1$-C$_{10}$alkylamino, heteroarylC$_1$-C$_{10}$alkoxy, heteroaryloxyC$_1$-C$_{10}$alkyl, heteroaryloxyC$_2$-C$_{10}$alkenyl, heteroaryloxyC$_2$-C$_{10}$alkynyl, heteroaryloxyC$_1$-C$_{10}$alkylamino, heteroaryloxyC$_1$-C$_{10}$alkoxy. In the most preferred embodiments, the C group is attached to B via an aliphatic moiety carbon chain, an aryl group or a heteroaryl group within B.

In a particularly preferred embodiment, B is an aryl, heteroaryl, C$_1$-C$_{10}$-alkylaryl, C$_1$-C$_{10}$-alkylheteroarylgroup, C$_1$-C$_{10}$-alkylheterocyclylaryl, C$_1$-C$_{10}$-alkylheterocyclylheteroaryl, C$_1$-C$_{10}$-alkylheterocyclylaryl-C$_1$-C$_{10}$-alkyl, or C$_1$-C$_{10}$-alkylheterocyclylheteroaryl-C$_1$-C$_{10}$-alkyl group.

It is understood that alkyl, alkenyl, alkynyl, aryl, heteroaryl, cycloalkyl, heterocyclyl and the like can be further substituted.

In certain embodiments of the compounds of Formulas I-XIX, B is selected from the group:

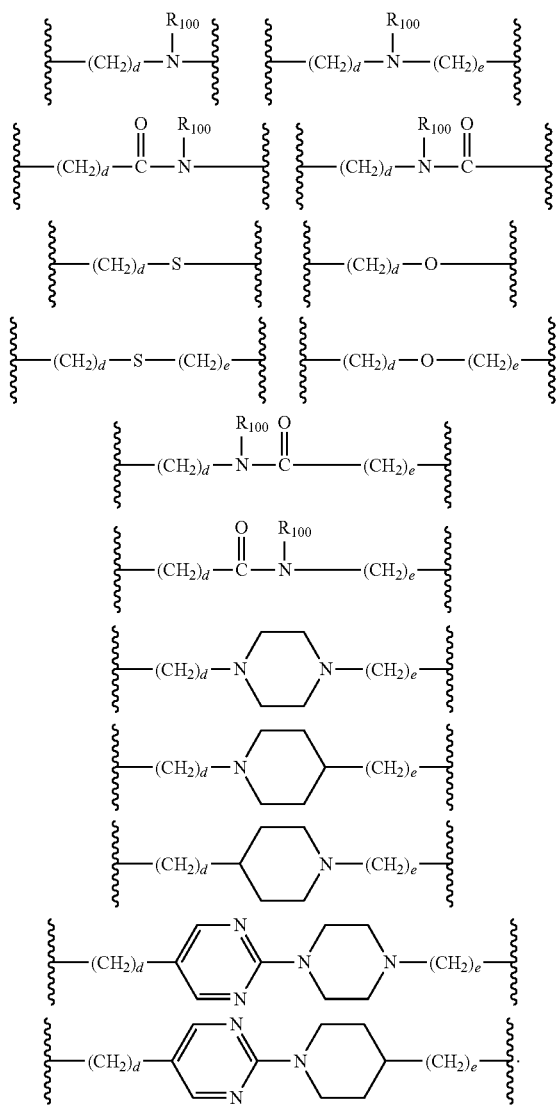

In another embodiment, B is

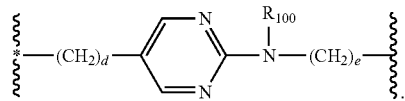

In the foregoing formulas, d and e are independently 0, 1, 2, 3, 4, 5, 6, 7 or 8; and R$_{100}$ is hydrogen or a group selected from C$_1$-C$_8$ alkyl, C$_2$-C$_8$ alkenyl, C$_2$-C$_8$ alkynyl, and C$_3$-C$_8$ cycloalkyl. Preferred alkyl groups are —CH$_3$, —CH$_2$CH$_3$, —CH$_2$CH$_2$CH$_3$, —CH(CH$_3$)CH$_3$, —C(CH$_3$)$_2$CH$_3$, —C(CH$_3$)$_3$. Preferably, R$_{100}$ is hydrogen or methyl.

Representative compounds according to the invention are those selected from the Table A below or the geometric isomers, enantiomers, diastereomers, racemates, pharmaceutically acceptable salts, and prodrugs thereof. It is to be understood that in any structure in Table A in which a nitrogen atom is represented with an open valence, that valence is occupied by a hydrogen atom.

TABLE A
| Compound No. | Structure |
|---|---|
| 1 | 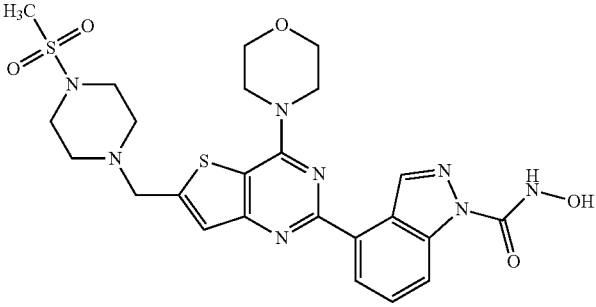 [SMILES: CS(=O)(=O)N1CCN(Cc2cc3nc(-c4cccc5c4cnn5C(=O)NO)nc(N4CCOCC4)c3s2)CC1] |
| 2 | 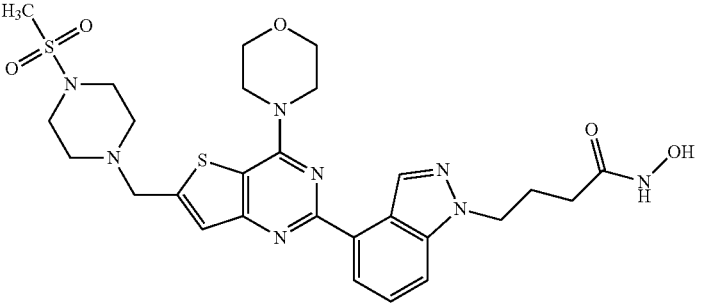 [SMILES: CS(=O)(=O)N1CCN(Cc2cc3nc(-c4cccc5c4cnn5CCCC(=O)NO)nc(N4CCOCC4)c3s2)CC1] |
| 3 | 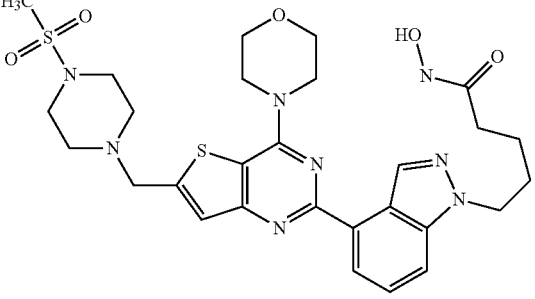 |
| 4 | 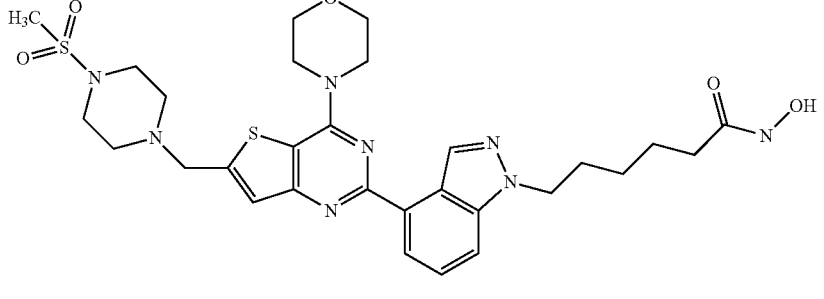 |
| 5 | 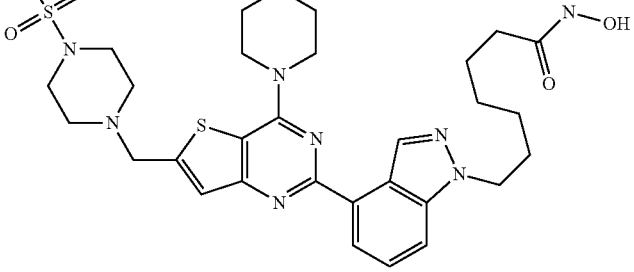 |

TABLE A-continued
| Compound No. | Structure |
|---|---|
| 6 | 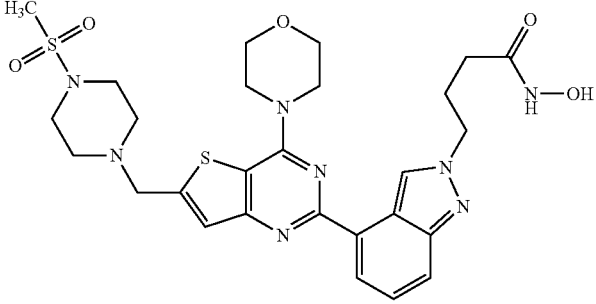 [SMILES: CS(=O)(=O)N1CCN(Cc2cc3nc(-c4cccc5nn(CCCC(=O)NO)cc45)nc(N4CCOCC4)c3s2)CC1] |
| 7 | 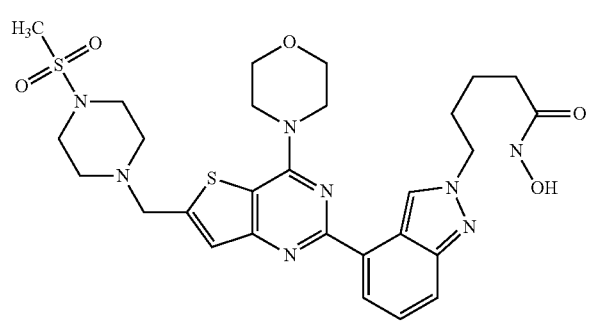 [SMILES: CS(=O)(=O)N1CCN(Cc2cc3nc(-c4cccc5nn(CCCCC(=O)NO)cc45)nc(N4CCOCC4)c3s2)CC1] |
| 8 | 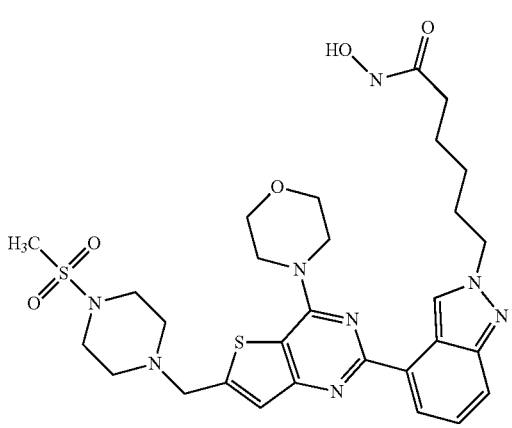 [SMILES: CS(=O)(=O)N1CCN(Cc2cc3nc(-c4cccc5nn(CCCCCC(=O)NO)cc45)nc(N4CCOCC4)c3s2)CC1] |
| 9 | 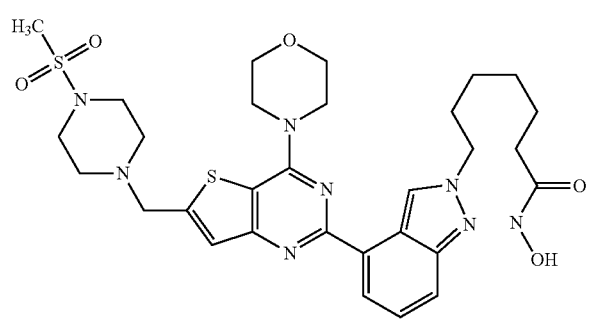 [SMILES: CS(=O)(=O)N1CCN(Cc2cc3nc(-c4cccc5nn(CCCCCCC(=O)NO)cc45)nc(N4CCOCC4)c3s2)CC1] |

TABLE A-continued
| Compound No. | Structure |
| --- | --- |
| 10 | 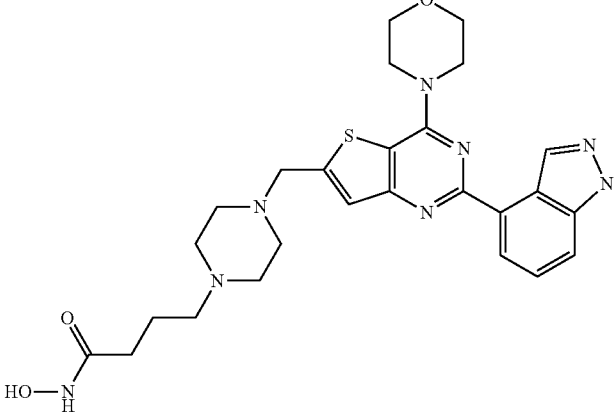 |
| 11 | 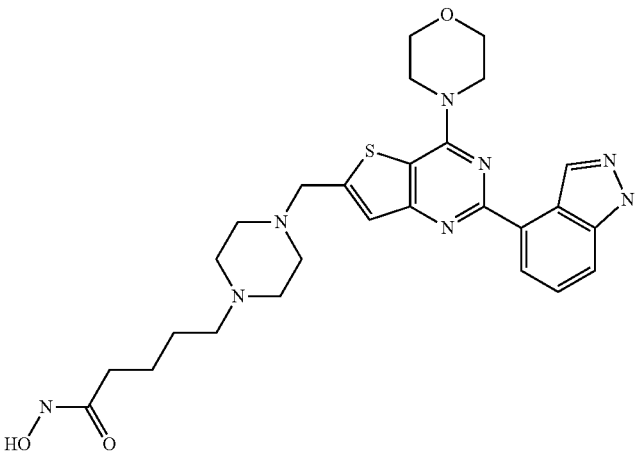 [SMILES: O=C(CCCCN1CCN(Cc2cc3nc(-c4cccc5[nH]ncc45)nc(N4CCOCC4)c3s2)CC1)NO] |
| 12 | 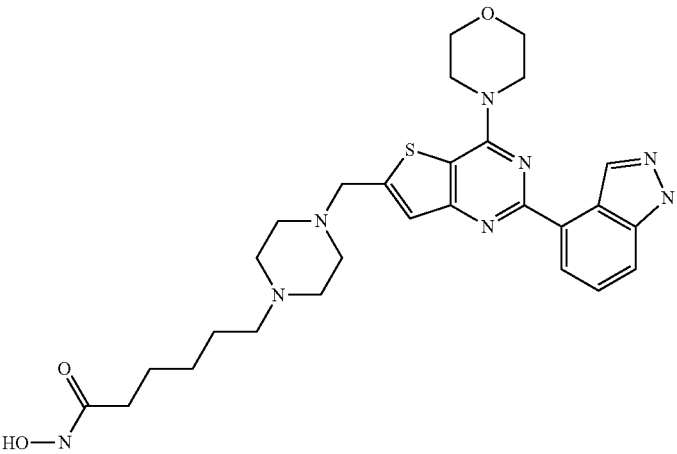 [SMILES: O=C(CCCCCN1CCN(Cc2cc3nc(-c4cccc5[nH]ncc45)nc(N4CCOCC4)c3s2)CC1)NO] |

TABLE A-continued
| Compound No. | Structure |
|---|---|
| 13 | 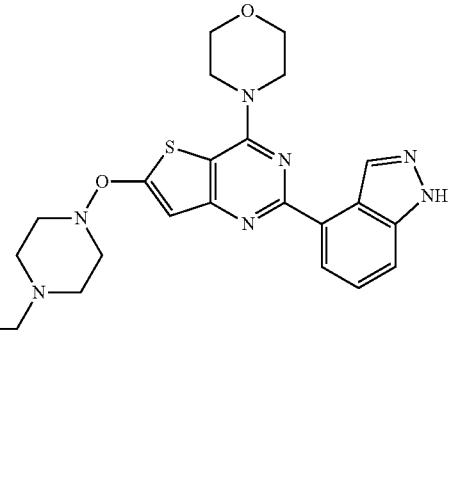 |
| 14 | 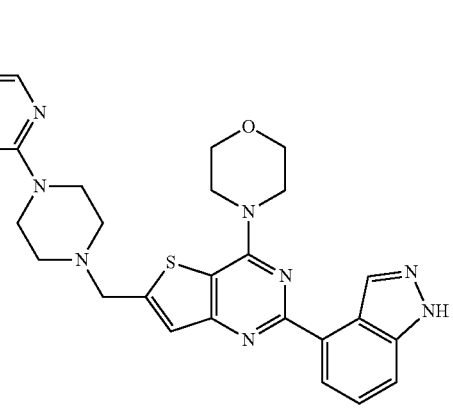 |
| 15 | 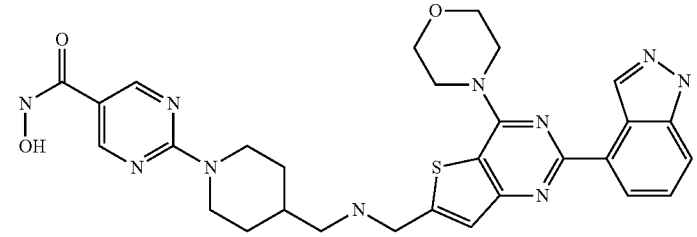 [SMILES: O=C(NO)c1cnc(N2CCC(CNCc3cc4nc(-c5cccc6[nH]ncc56)nc(N5CCOCC5)c4s3)CC2)nc1] |
| 16 | 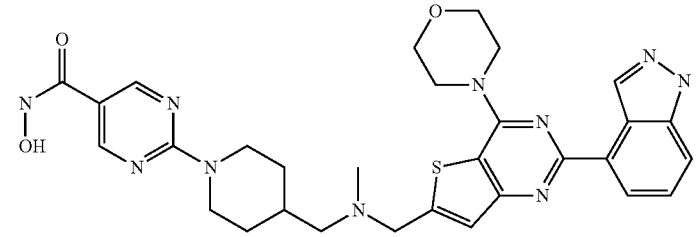 [SMILES: CN(Cc1cc2nc(-c3cccc4[nH]ncc34)nc(N3CCOCC3)c2s1)CC1CCN(c2ncc(C(=O)NO)cn2)CC1] |

TABLE A-continued

| Compound No. | Structure |
| --- | --- |
| 17 | *(structure: 4-morpholino-2-(1H-indazol-4-yl)thieno[3,2-d]pyrimidine with 6-NH-(CH2)3-C(O)NHOH substituent)* |
| 18 | *(structure: 4-morpholino-2-(1H-indazol-4-yl)thieno[3,2-d]pyrimidine with 6-NH-(CH2)4-C(O)NHOH substituent)* |
| 19 | *(structure: 4-morpholino-2-(1H-indazol-4-yl)thieno[3,2-d]pyrimidine with 6-NH-(CH2)5-C(O)NHOH substituent)* |
| 20 | *(structure: 4-morpholino-2-(1H-indazol-4-yl)thieno[3,2-d]pyrimidine with 6-NH-(CH2)6-C(O)NHOH substituent)* |

TABLE A-continued

| Compound No. | Structure |
|---|---|
| 21 | *(structure: morpholine-thienopyrimidine-indazole with O-(CH2)3-C(O)NHOH side chain)* |
| 22 | *(structure: morpholine-thienopyrimidine-indazole with O-(CH2)4-C(O)NHOH side chain)* |
| 23 | *(structure: morpholine-thienopyrimidine-indazole with O-(CH2)5-C(O)NHOH side chain)* |
| 24 | *(structure: morpholine-thienopyrimidine-indazole with O-(CH2)6-C(O)NHOH side chain)* |

TABLE A-continued
| Compound No. | Structure |
|---|---|
| 25 | 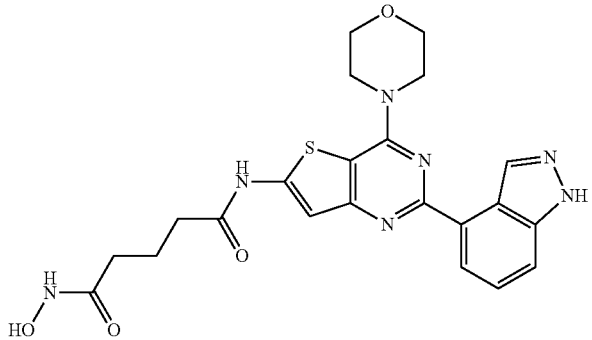 [SMILES: O=C(CCCC(=O)Nc1cc2nc(-c3cccc4[nH]ncc34)nc(N3CCOCC3)c2s1)NO] |
| 26 | 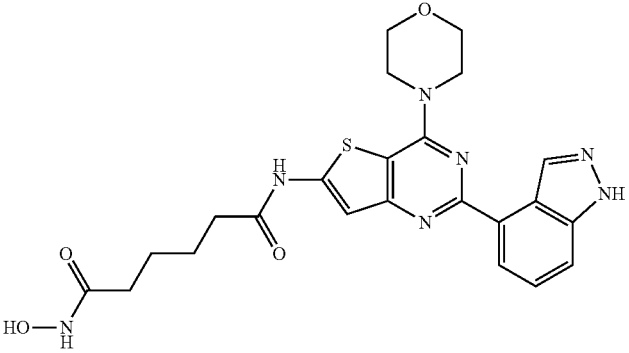 [SMILES: O=C(CCCCC(=O)Nc1cc2nc(-c3cccc4[nH]ncc34)nc(N3CCOCC3)c2s1)NO] |
| 27 | 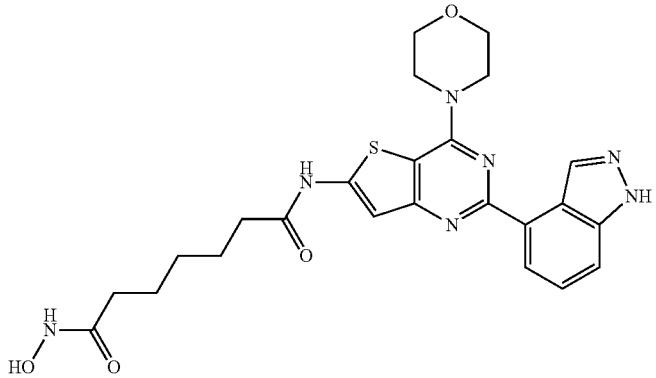 [SMILES: O=C(CCCCCC(=O)Nc1cc2nc(-c3cccc4[nH]ncc34)nc(N3CCOCC3)c2s1)NO] |
| 28 | 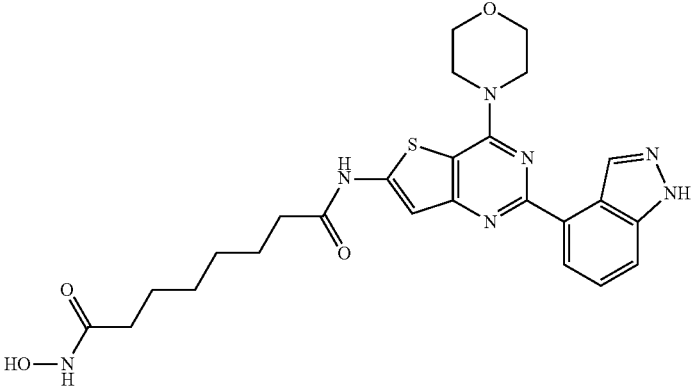 [SMILES: O=C(CCCCCCC(=O)Nc1cc2nc(-c3cccc4[nH]ncc34)nc(N3CCOCC3)c2s1)NO] |

TABLE A-continued

| Compound No. | Structure |
| --- | --- |
| 29 | 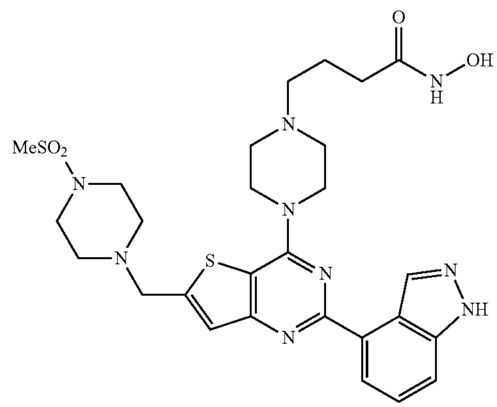 |
| 30 | 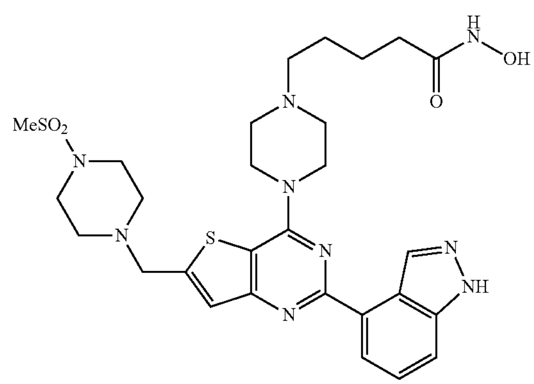 |
| 31 | 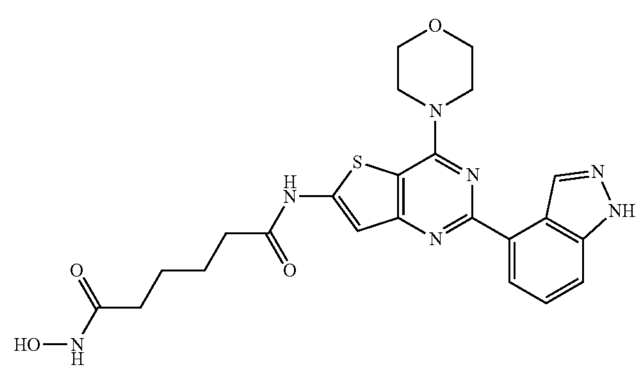 [SMILES: O=C(CCCCC(=O)Nc1cc2nc(-c3cccc4[nH]ncc34)nc(N3CCOCC3)c2s1)NO] |
| 32 | 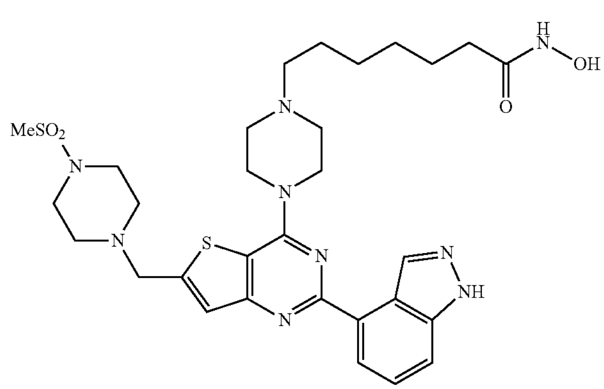 |

TABLE A-continued
| Compound No. | Structure |
|---|---|
| 33 | 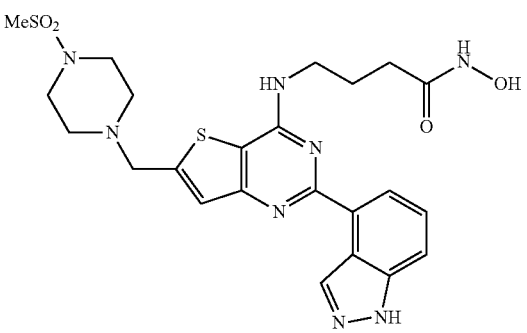 |
| 34 | 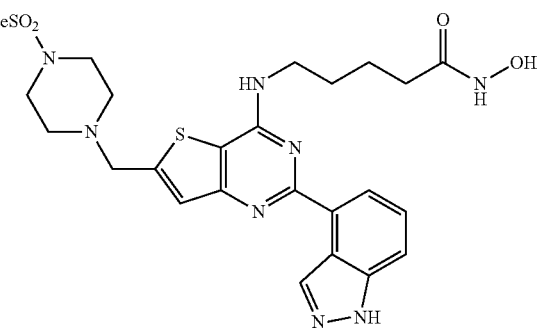 |
| 35 | 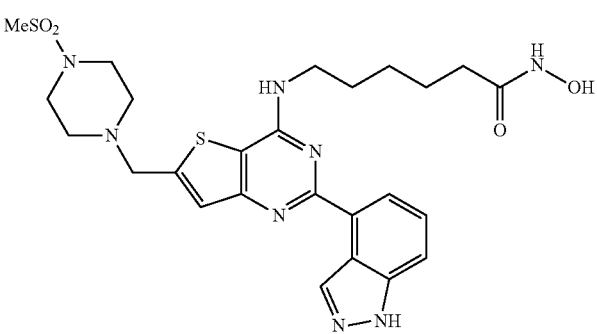 |
| 36 | 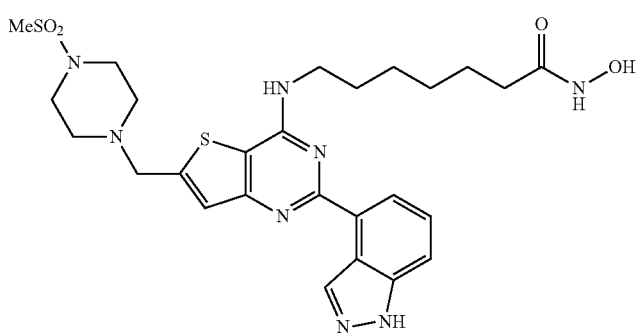 |

TABLE A-continued
| Compound No. | Structure |
|---|---|
| 37 | 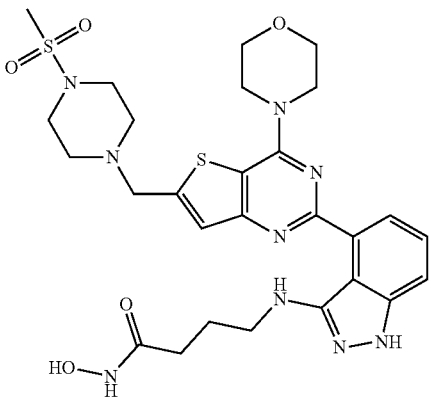 [SMILES: CS(=O)(=O)N1CCN(Cc2cc3nc(-c4cccc5[nH]nc(NCCCC(=O)NO)c45)nc(N4CCOCC4)c3s2)CC1] |
| 38 | 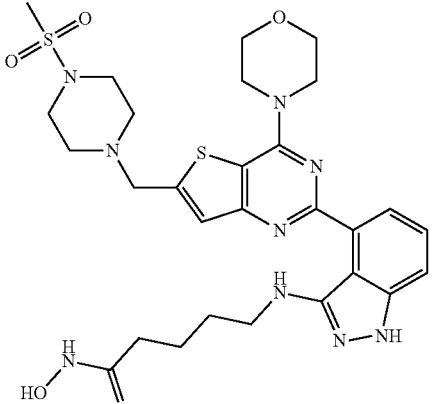 |
| 39 | 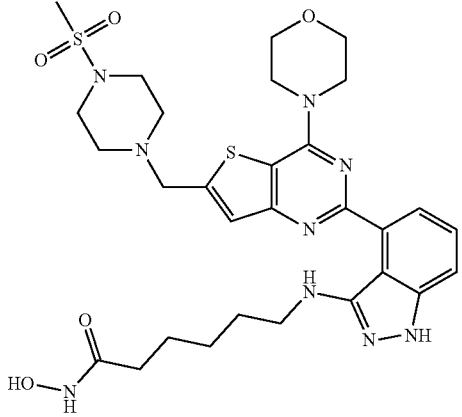 [SMILES: CS(=O)(=O)N1CCN(Cc2cc3nc(-c4cccc5[nH]nc(NCCCCCC(=O)NO)c45)nc(N4CCOCC4)c3s2)CC1] |

TABLE A-continued
| Compound No. | Structure |
|---|---|
| 40 | 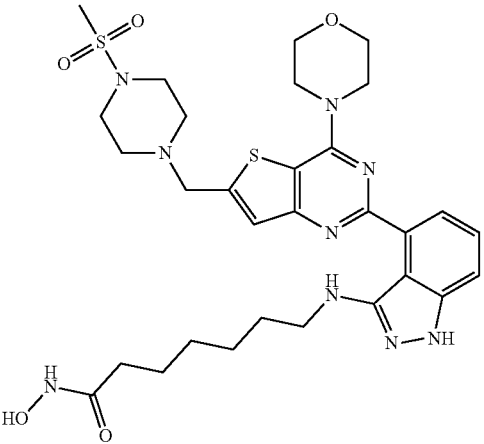 [SMILES: CS(=O)(=O)N1CCN(Cc2cc3nc(-c4cccc5[nH]nc(NCCCCCCC(=O)NO)c45)nc(N4CCOCC4)c3s2)CC1] |
| 41 | 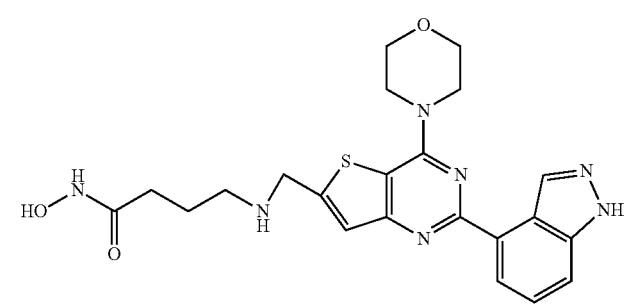 [SMILES: O=C(CCCNCc1cc2nc(-c3cccc4[nH]ncc34)nc(N3CCOCC3)c2s1)NO] |
| 42 | 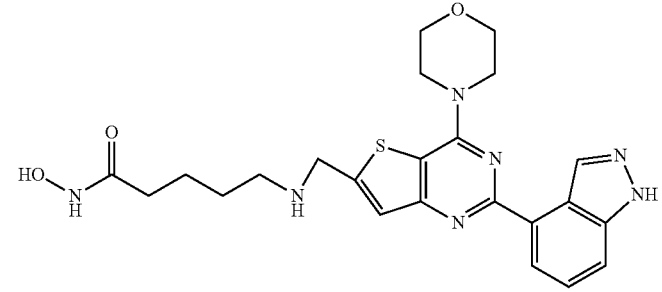 [SMILES: O=C(CCCCNCc1cc2nc(-c3cccc4[nH]ncc34)nc(N3CCOCC3)c2s1)NO] |
| 43 | 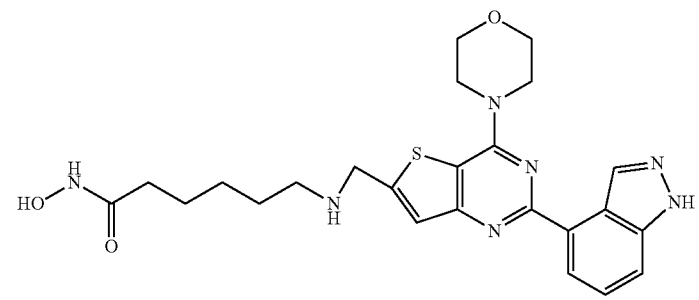 [SMILES: O=C(CCCCCNCc1cc2nc(-c3cccc4[nH]ncc34)nc(N3CCOCC3)c2s1)NO] |

TABLE A-continued

| Compound No. | Structure |
| --- | --- |
| 44 | 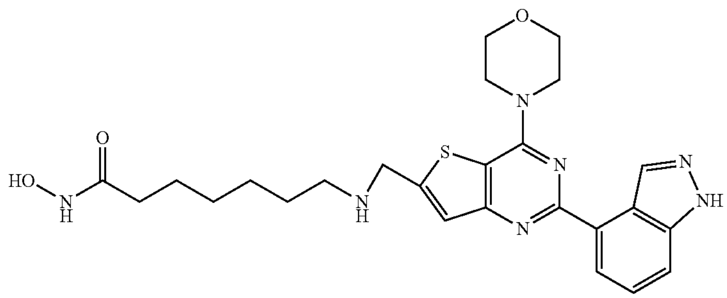 [SMILES: O=C(CCCCCCNCc1cc2nc(-c3cccc4[nH]ncc34)nc(N3CCOCC3)c2s1)NO] |
| 45 | 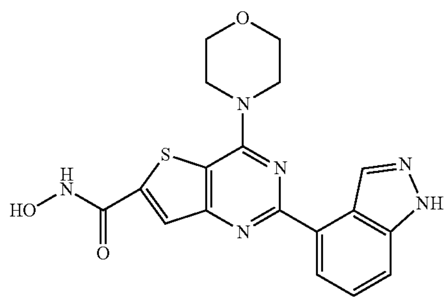 [SMILES: O=C(NO)c1cc2nc(-c3cccc4[nH]ncc34)nc(N3CCOCC3)c2s1] |
| 46 | 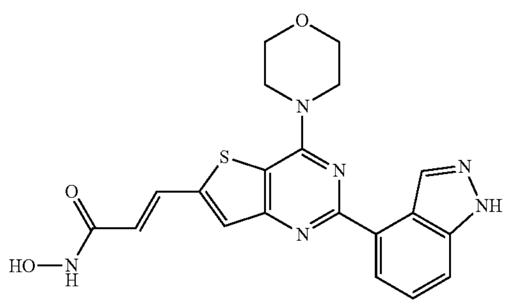 [SMILES: O=C(/C=C/c1cc2nc(-c3cccc4[nH]ncc34)nc(N3CCOCC3)c2s1)NO] |
| 47 | 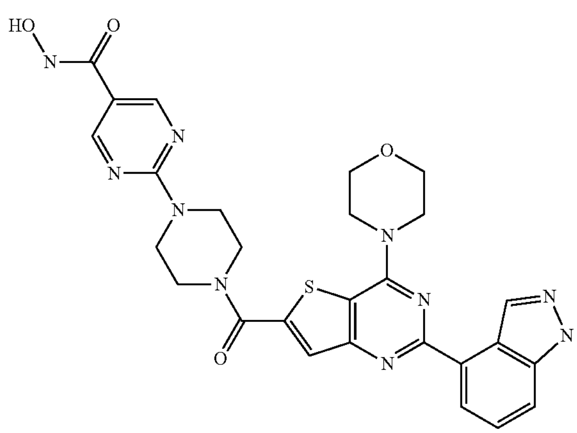 [SMILES: O=C(NO)c1cnc(N2CCN(C(=O)c3cc4nc(-c5cccc6[nH]ncc56)nc(N5CCOCC5)c4s3)CC2)nc1] |

TABLE A-continued
| Compound No. | Structure |
|---|---|
| 48 | 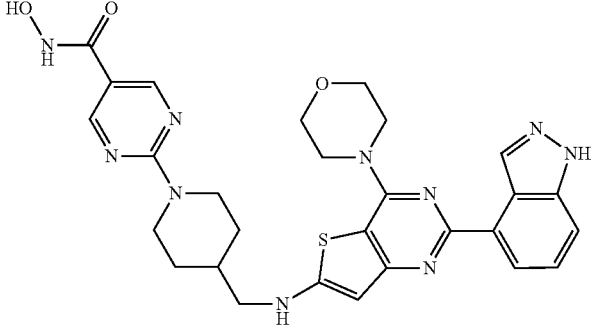 [SMILES: O=C(NO)c1cnc(N2CCC(CNc3cc4nc(-c5cccc6[nH]ncc56)nc(N5CCOCC5)c4s3)CC2)nc1] |
| 49 | 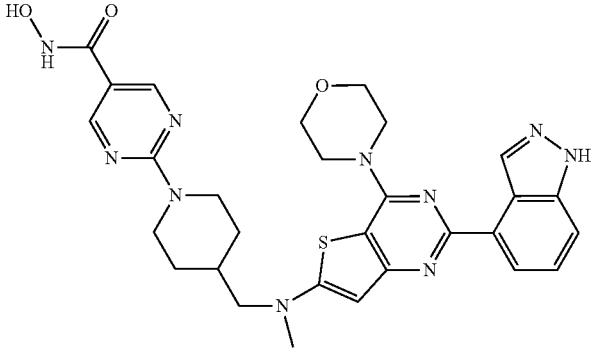 [SMILES: CN(CC1CCN(c2ncc(C(=O)NO)cn2)CC1)c1cc2nc(-c3cccc4[nH]ncc34)nc(N3CCOCC3)c2s1] |
| 50 | 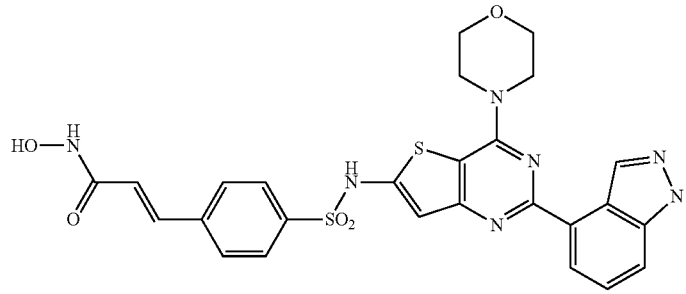 [SMILES: O=C(/C=C/c1ccc(S(=O)(=O)Nc2cc3nc(-c4cccc5[nH]ncc45)nc(N4CCOCC4)c3s2)cc1)NO] |
| 51 | 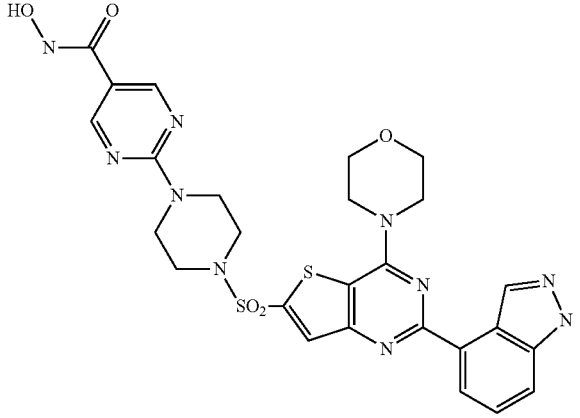 [SMILES: O=C(NO)c1cnc(N2CCN(S(=O)(=O)c3cc4nc(-c5cccc6[nH]ncc56)nc(N5CCOCC5)c4s3)CC2)nc1] |

TABLE A-continued
| Compound No. | Structure |
|---|---|
| 52 | 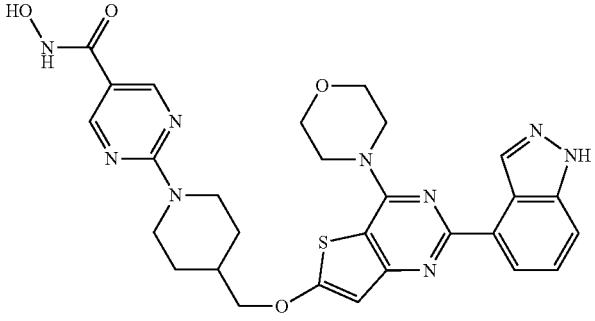 [SMILES: O=C(NO)c1cnc(N2CCC(COc3cc4nc(-c5cccc6[nH]ncc56)nc(N5CCOCC5)c4s3)CC2)nc1] |
| 53 | 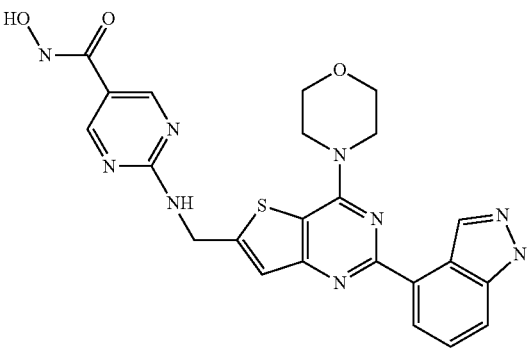 [SMILES: O=C(NO)c1cnc(NCc2cc3nc(-c4cccc5[nH]ncc45)nc(N4CCOCC4)c3s2)nc1] |
| 54 | 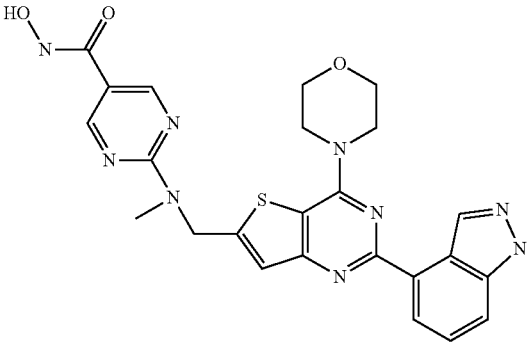 [SMILES: CN(Cc1cc2nc(-c3cccc4[nH]ncc34)nc(N3CCOCC3)c2s1)c1ncc(C(=O)NO)cn1] |
| 55 | 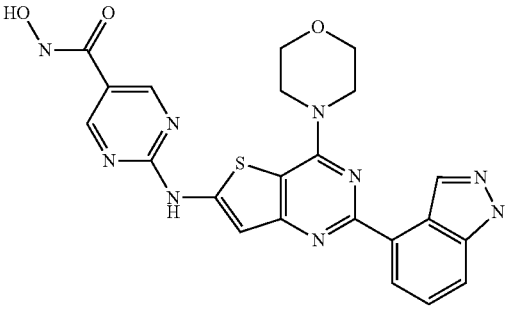 [SMILES: O=C(NO)c1cnc(Nc2cc3nc(-c4cccc5[nH]ncc45)nc(N4CCOCC4)c3s2)nc1] |

TABLE A-continued
| Compound No. | Structure |
|---|---|
| 56 | 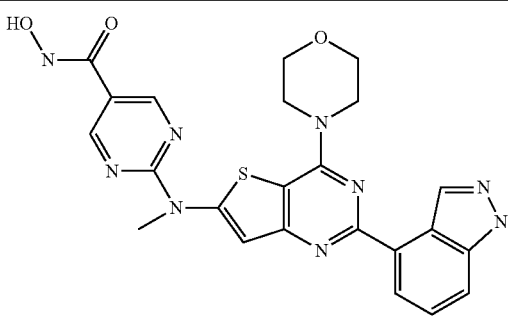 |
| 57 | 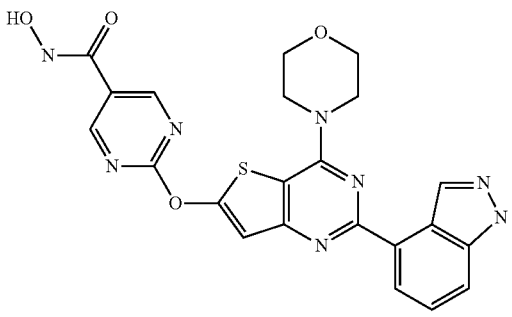 [SMILES: O=C(NO)c1cnc(Oc2cc3nc(-c4cccc5[nH]ncc45)nc(N4CCOCC4)c3s2)nc1] |
| 58 | 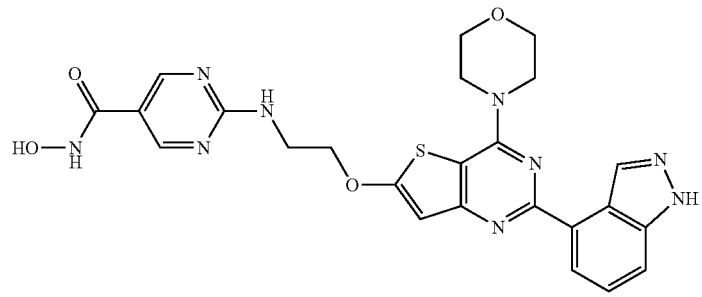 [SMILES: O=C(NO)c1cnc(NCCOc2cc3nc(-c4cccc5[nH]ncc45)nc(N4CCOCC4)c3s2)nc1] |
| 59 | 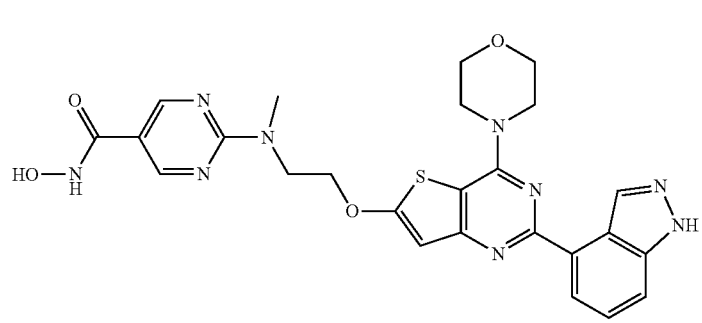 [SMILES: CN(CCOc1cc2nc(-c3cccc4[nH]ncc34)nc(N3CCOCC3)c2s1)c1ncc(C(=O)NO)cn1] |
| 60 | 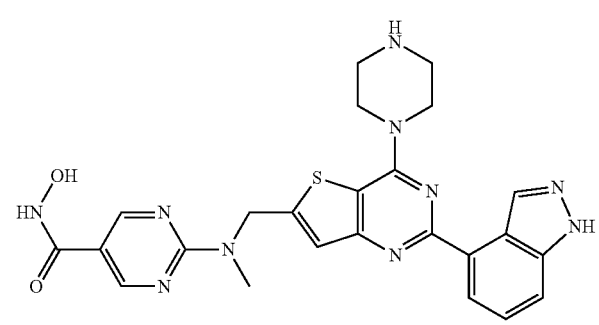 [SMILES: CN(Cc1cc2nc(-c3cccc4[nH]ncc34)nc(N3CCNCC3)c2s1)c1ncc(C(=O)NO)cn1] |

TABLE A-continued
| Compound No. | Structure |
|---|---|
| 61 | 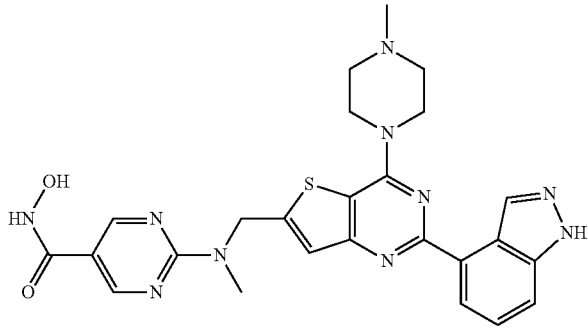 [SMILES: CN1CCN(c2nc(-c3cccc4[nH]ncc34)nc3cc(CN(C)c4ncc(C(=O)NO)cn4)sc23)CC1] |
| 62 | 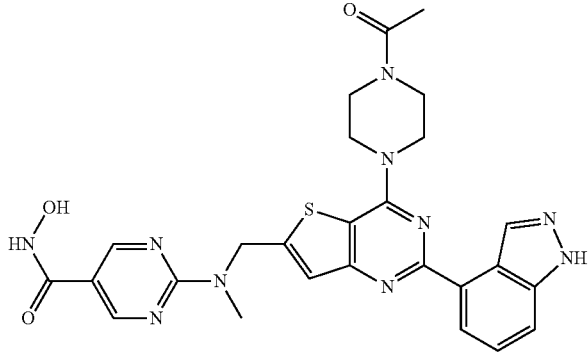 [SMILES: CC(=O)N1CCN(c2nc(-c3cccc4[nH]ncc34)nc3cc(CN(C)c4ncc(C(=O)NO)cn4)sc23)CC1] |
| 63 | 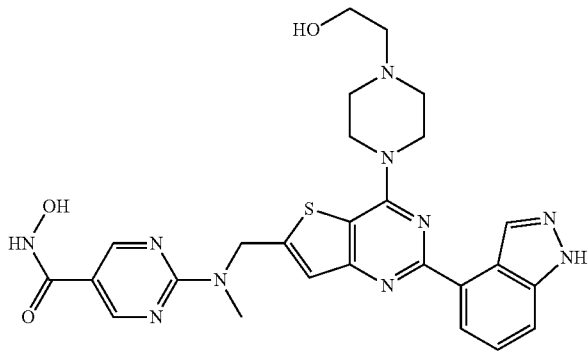 [SMILES: CN(Cc1cc2nc(-c3cccc4[nH]ncc34)nc(N3CCN(CCO)CC3)c2s1)c1ncc(C(=O)NO)cn1] |
| 64 | 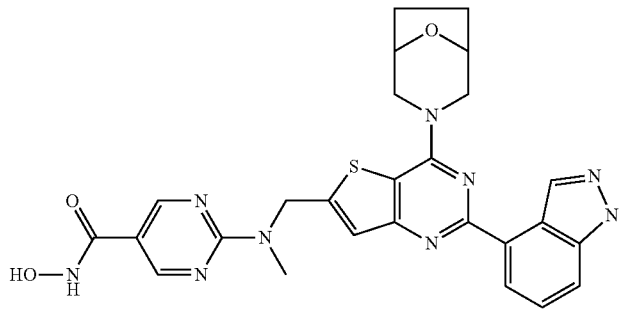 [SMILES: CN(Cc1cc2nc(-c3cccc4[nH]ncc34)nc(N3CC4CCC(C3)O4)c2s1)c1ncc(C(=O)NO)cn1] |

TABLE A-continued

| Compound No. | Structure |
|---|---|
| 65 | 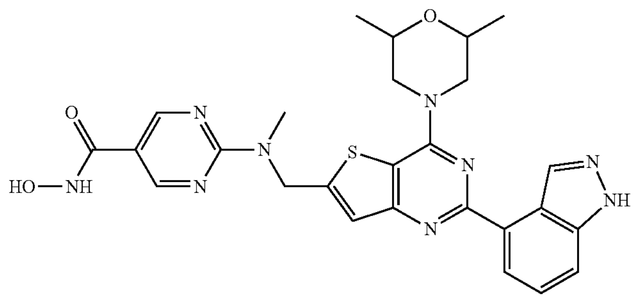 [SMILES: CC1CN(c2nc(-c3cccc4[nH]ncc34)nc3cc(CN(C)c4ncc(C(=O)NO)cn4)sc23)CC(C)O1] |
| 66 | 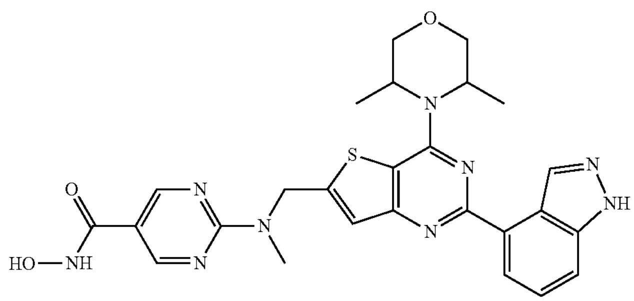 [SMILES: CC1COCC(C)N1c1nc(-c2cccc3[nH]ncc23)nc2cc(CN(C)c3ncc(C(=O)NO)cn3)sc12] |
| 67 | 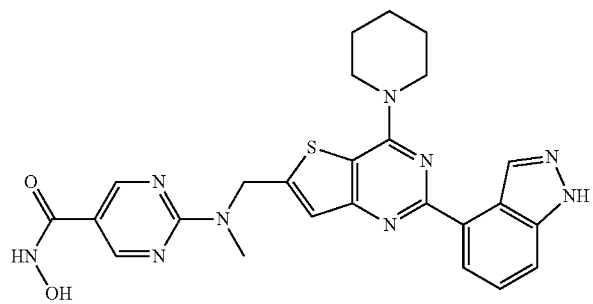 [SMILES: CN(Cc1cc2nc(-c3cccc4[nH]ncc34)nc(N3CCCCC3)c2s1)c1ncc(C(=O)NO)cn1] |
| 68 | 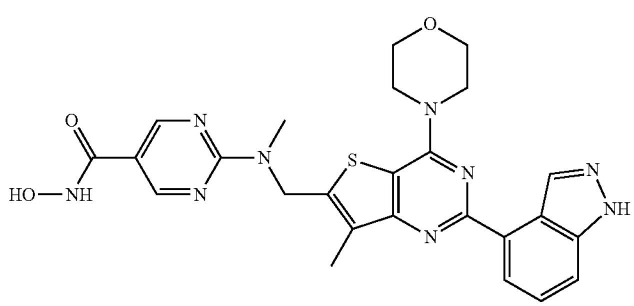 [SMILES: Cc1c(CN(C)c2ncc(C(=O)NO)cn2)sc2c(N3CCOCC3)nc(-c3cccc4[nH]ncc34)nc12] |
| 69 | 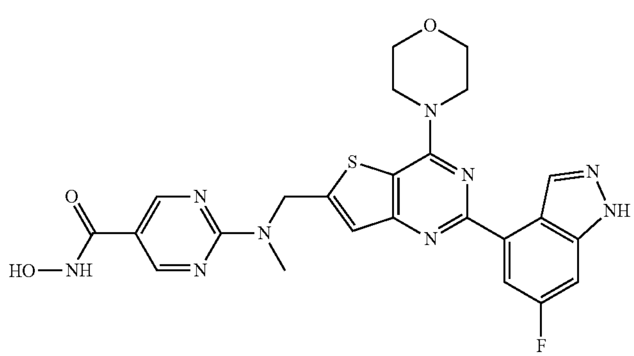 [SMILES: CN(Cc1cc2nc(-c3cc(F)cc4[nH]ncc34)nc(N3CCOCC3)c2s1)c1ncc(C(=O)NO)cn1] |

TABLE A-continued
| Compound No. | Structure |
|---|---|
| 70 | 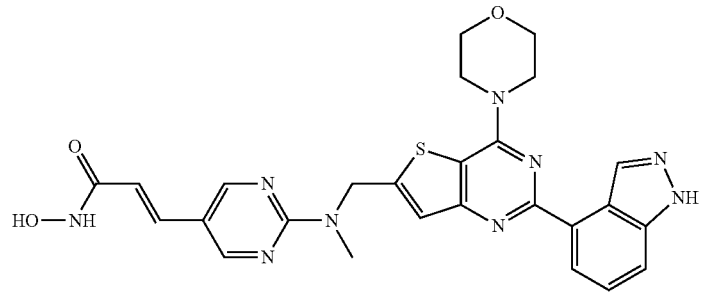 [SMILES: CN(Cc1cc2nc(-c3cccc4[nH]ncc34)nc(N3CCOCC3)c2s1)c1ncc(/C=C/C(=O)NO)cn1] |
| 71 | 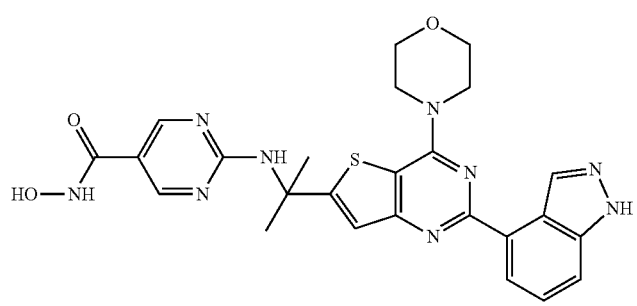 [SMILES: CC(C)(Nc1ncc(C(=O)NO)cn1)c1cc2nc(-c3cccc4[nH]ncc34)nc(N3CCOCC3)c2s1] |
| 72 | 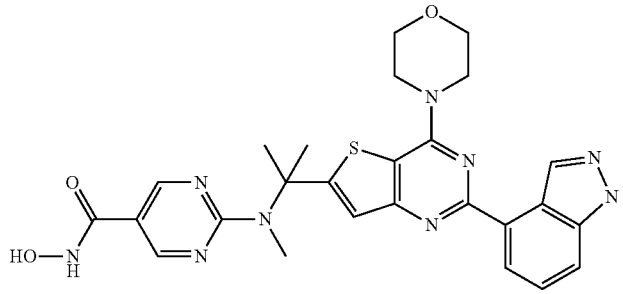 [SMILES: CN(c1ncc(C(=O)NO)cn1)C(C)(C)c1cc2nc(-c3cccc4[nH]ncc34)nc(N3CCOCC3)c2s1] |
| 73 | 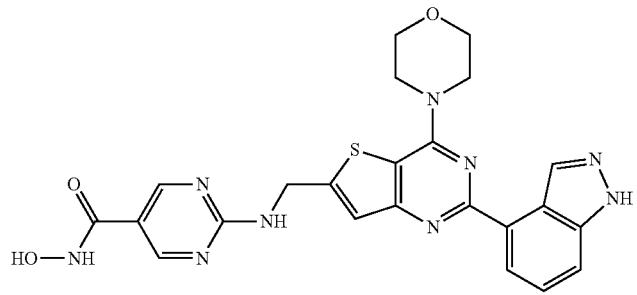 [SMILES: O=C(NO)c1cnc(NCc2cc3nc(-c4cccc5[nH]ncc45)nc(N4CCOCC4)c3s2)nc1] |
| 74 | 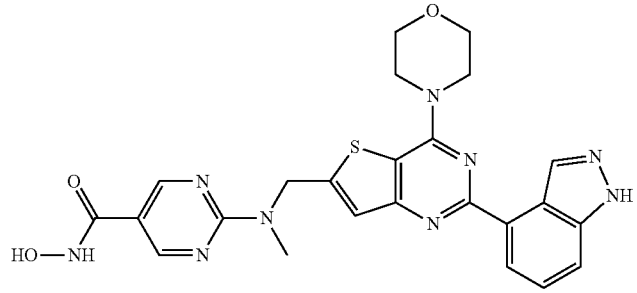 [SMILES: CN(Cc1cc2nc(-c3cccc4[nH]ncc34)nc(N3CCOCC3)c2s1)c1ncc(C(=O)NO)cn1] |

TABLE A-continued
| Compound No. | Structure |
|---|---|
| 75 | 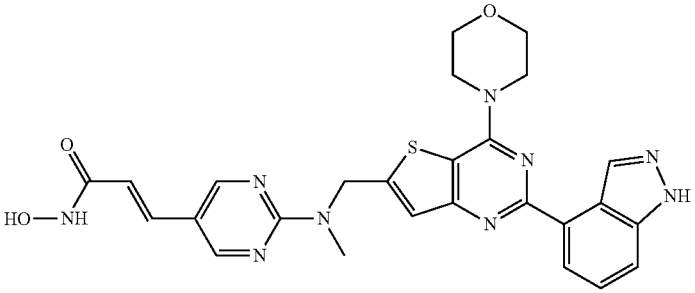 [SMILES: CN(Cc1cc2nc(-c3cccc4[nH]ncc34)nc(N3CCOCC3)c2s1)c1ncc(/C=C/C(=O)NO)cn1] |
| 76 | 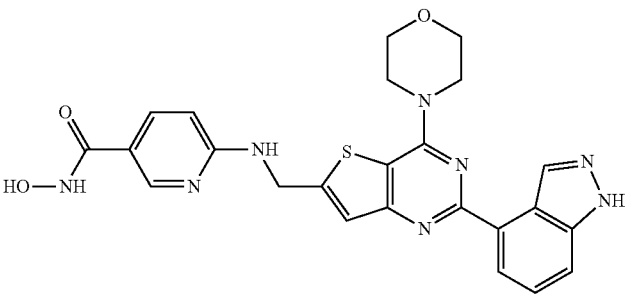 [SMILES: O=C(NO)c1ccc(NCc2cc3nc(-c4cccc5[nH]ncc45)nc(N4CCOCC4)c3s2)nc1] |
| 77 | 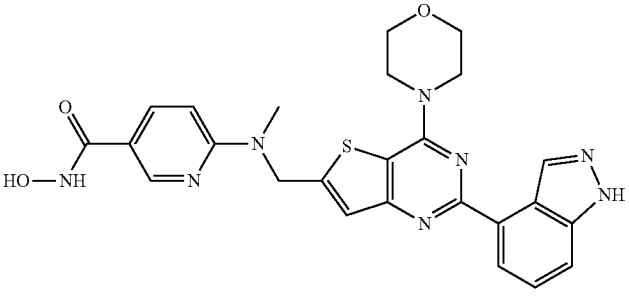 [SMILES: CN(Cc1cc2nc(-c3cccc4[nH]ncc34)nc(N3CCOCC3)c2s1)c1ccc(C(=O)NO)cn1] |
| 78 | 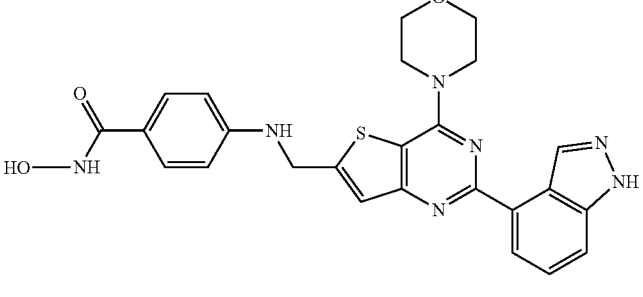 |
| 79 | 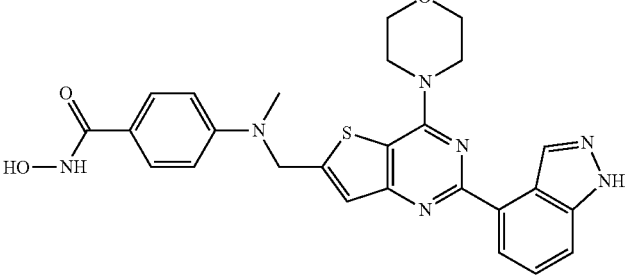 |

TABLE A-continued

| Compound No. | Structure |
|---|---|
| 80 | 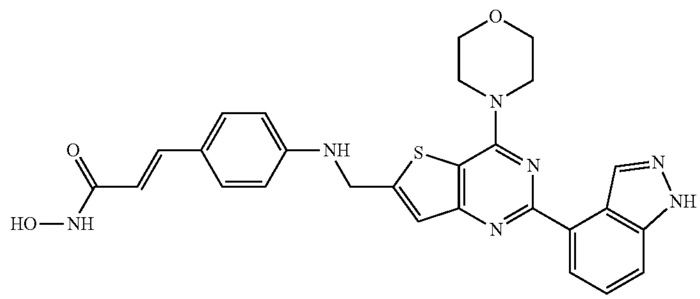 [SMILES: O=C(/C=C/c1ccc(NCc2cc3nc(-c4cccc5[nH]ncc45)nc(N4CCOCC4)c3s2)cc1)NO] |
| 81 | 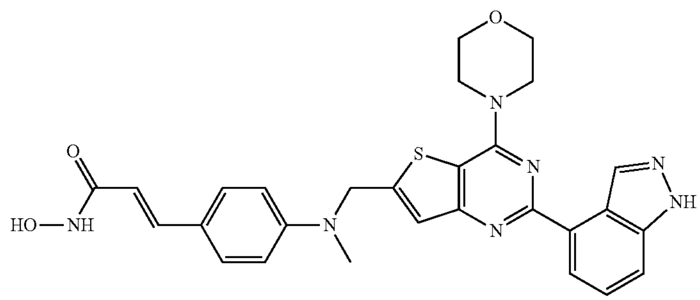 [SMILES: CN(Cc1cc2nc(-c3cccc4[nH]ncc34)nc(N3CCOCC3)c2s1)c1ccc(/C=C/C(=O)NO)cc1] |
| 82 | 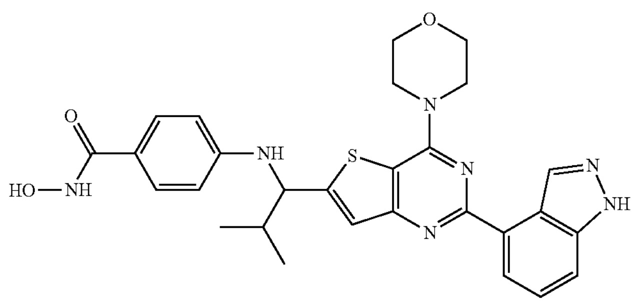 [SMILES: CC(C)C(Nc1ccc(C(=O)NO)cc1)c1cc2nc(-c3cccc4[nH]ncc34)nc(N3CCOCC3)c2s1] |
| 83 | 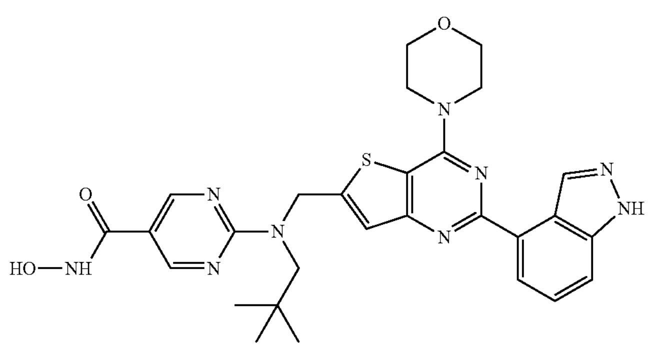 [SMILES: CC(C)(C)CN(Cc1cc2nc(-c3cccc4[nH]ncc34)nc(N3CCOCC3)c2s1)c1ncc(C(=O)NO)cn1] |
| 84 | 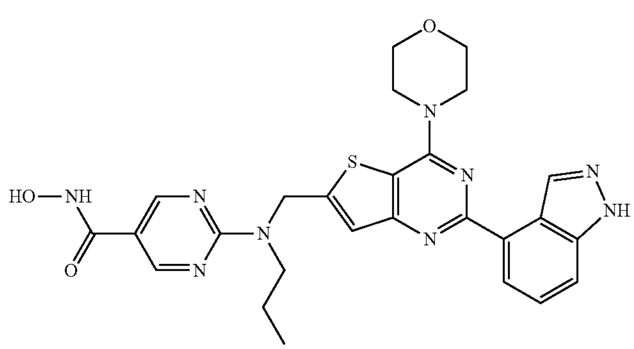 [SMILES: CCCN(Cc1cc2nc(-c3cccc4[nH]ncc34)nc(N3CCOCC3)c2s1)c1ncc(C(=O)NO)cn1] |

TABLE A-continued

| Compound No. | Structure |
| --- | --- |
| 85 | Chemical structure: N-hydroxy-2-[(butyl){[2-(1H-indazol-4-yl)-4-(morpholin-4-yl)thieno[3,2-d]pyrimidin-6-yl]methyl}amino]pyrimidine-5-carboxamide |
| 86 | Chemical structure: N-hydroxy-2-[(2-hydroxyethyl){[2-(1H-indazol-4-yl)-4-(morpholin-4-yl)thieno[3,2-d]pyrimidin-6-yl]methyl}amino]pyrimidine-5-carboxamide |
| 87 | Chemical structure: 2-({5-[(hydroxyamino)carbonyl]pyrimidin-2-yl}{[2-(1H-indazol-4-yl)-4-(morpholin-4-yl)thieno[3,2-d]pyrimidin-6-yl]methyl}amino)ethyl acetate |
| 88 | Chemical structure: N-{5-[(hydroxyamino)carbonyl]pyrimidin-2-yl}-N-{[2-(1H-indazol-4-yl)-4-(morpholin-4-yl)thieno[3,2-d]pyrimidin-6-yl]methyl}glycine |

TABLE A-continued

| Compound No. | Structure |
|---|---|
| 89 | 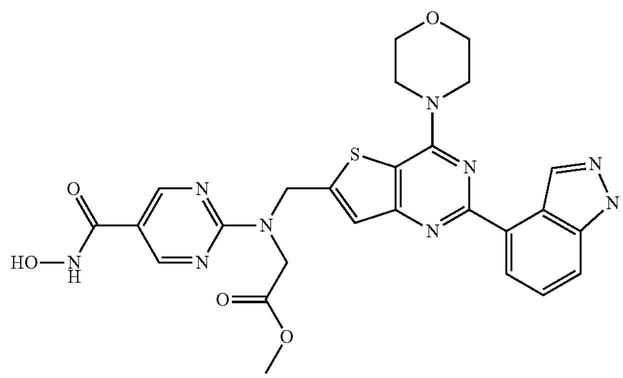 [SMILES: COC(=O)CN(Cc1cc2nc(-c3cccc4[nH]ncc34)nc(N3CCOCC3)c2s1)c1ncc(C(=O)NO)cn1] |
| 90 | 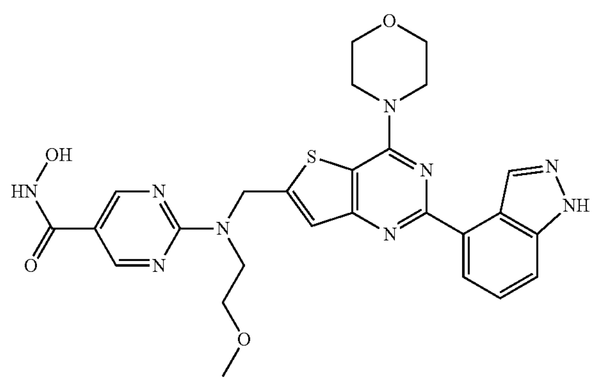 [SMILES: COCCN(Cc1cc2nc(-c3cccc4[nH]ncc34)nc(N3CCOCC3)c2s1)c1ncc(C(=O)NO)cn1] |
| 91 | 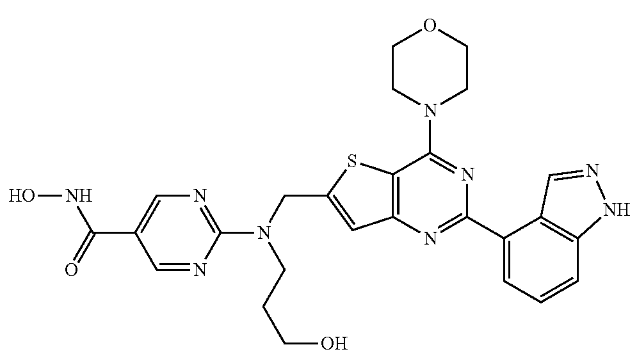 [SMILES: O=C(NO)c1cnc(N(CCCO)Cc2cc3nc(-c4cccc5[nH]ncc45)nc(N4CCOCC4)c3s2)nc1] |
| 92 | 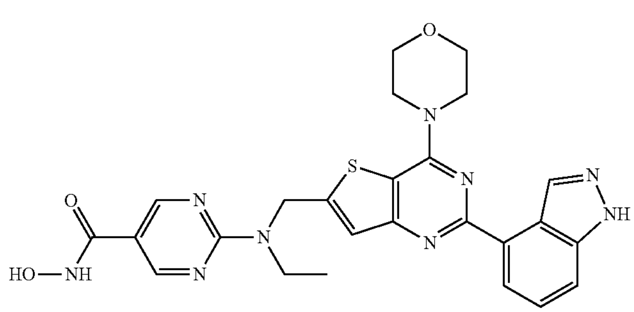 [SMILES: CCN(Cc1cc2nc(-c3cccc4[nH]ncc34)nc(N3CCOCC3)c2s1)c1ncc(C(=O)NO)cn1] |

TABLE A-continued
| Compound No. | Structure |
|---|---|
| 93 | 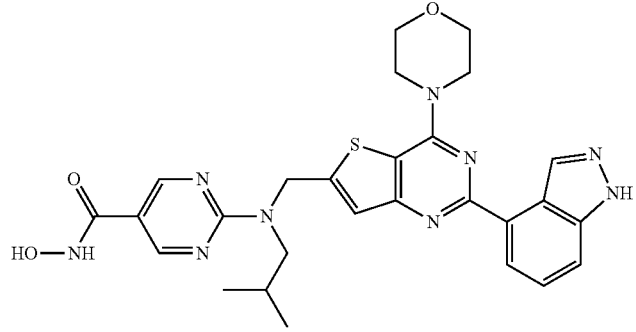 [SMILES: CC(C)CN(Cc1cc2nc(-c3cccc4[nH]ncc34)nc(N3CCOCC3)c2s1)c1ncc(C(=O)NO)cn1] |
| 94 | 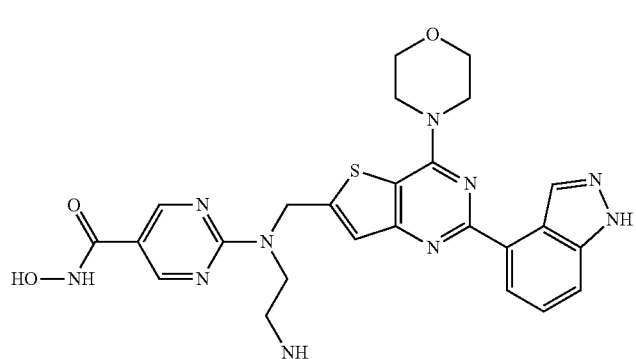 |
| 95 | 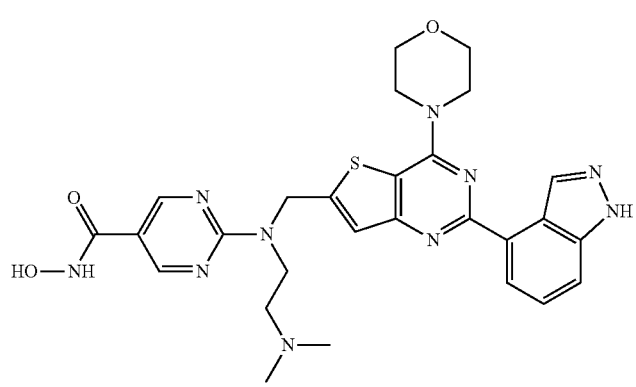 [SMILES: CN(C)CCN(Cc1cc2nc(-c3cccc4[nH]ncc34)nc(N3CCOCC3)c2s1)c1ncc(C(=O)NO)cn1] |
| 96 | 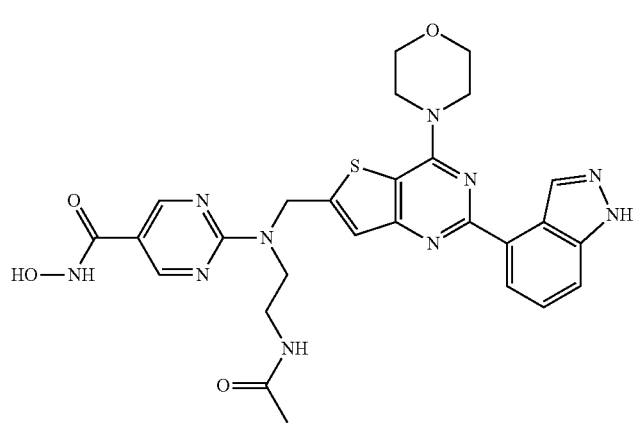 [SMILES: CC(=O)NCCN(Cc1cc2nc(-c3cccc4[nH]ncc34)nc(N3CCOCC3)c2s1)c1ncc(C(=O)NO)cn1] |

TABLE A-continued
| Compound No. | Structure |
|---|---|
| 97 | 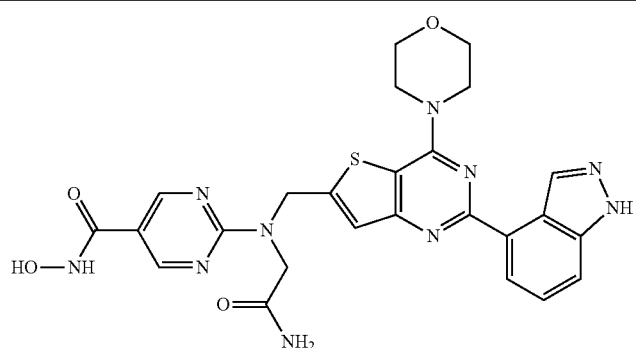 |
| 98 | 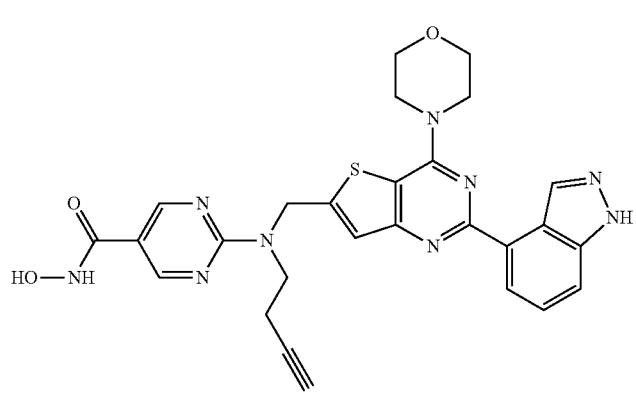 [SMILES: C#CCCN(Cc1cc2nc(-c3cccc4[nH]ncc34)nc(N3CCOCC3)c2s1)c1ncc(C(=O)NO)cn1] |
| 99 | 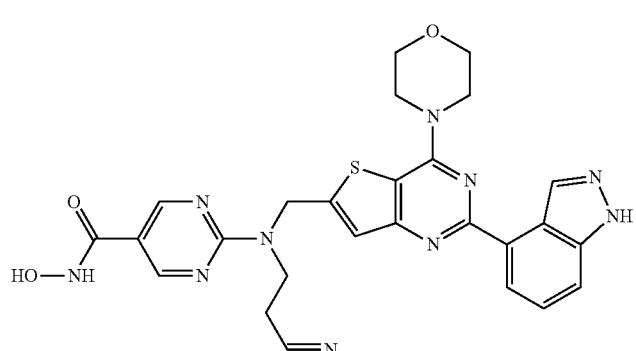 |
| 100 | 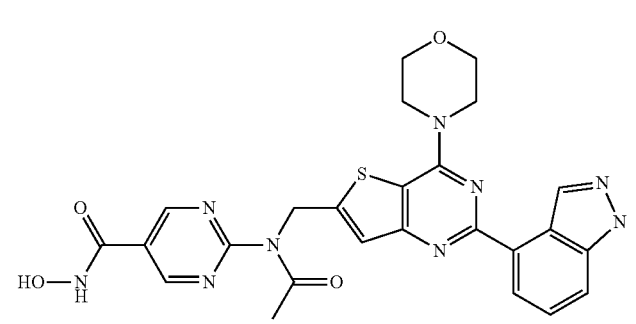 [SMILES: CC(=O)N(Cc1cc2nc(-c3cccc4[nH]ncc34)nc(N3CCOCC3)c2s1)c1ncc(C(=O)NO)cn1] |

TABLE A-continued

| Compound No. | Structure |
| --- | --- |
| 101 | 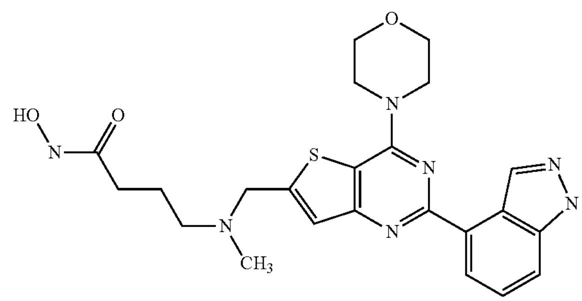 [SMILES: CN(CCCC(=O)NO)Cc1cc2nc(-c3cccc4[nH]ncc34)nc(N3CCOCC3)c2s1] |
| 102 | 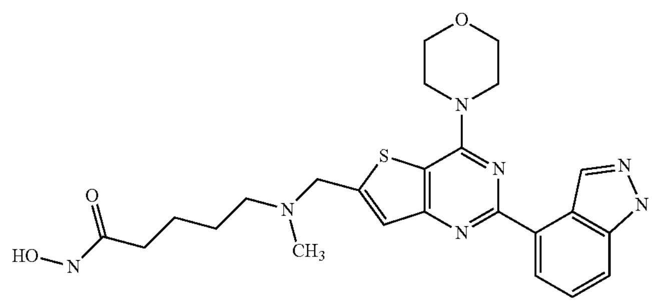 [SMILES: CN(CCCCC(=O)NO)Cc1cc2nc(-c3cccc4[nH]ncc34)nc(N3CCOCC3)c2s1] |
| 103 | 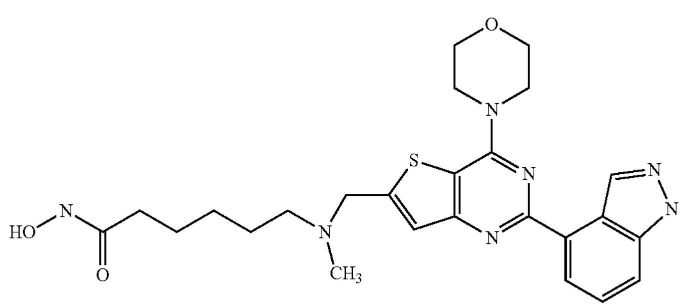 [SMILES: CN(CCCCCC(=O)NO)Cc1cc2nc(-c3cccc4[nH]ncc34)nc(N3CCOCC3)c2s1] |
| 104 | 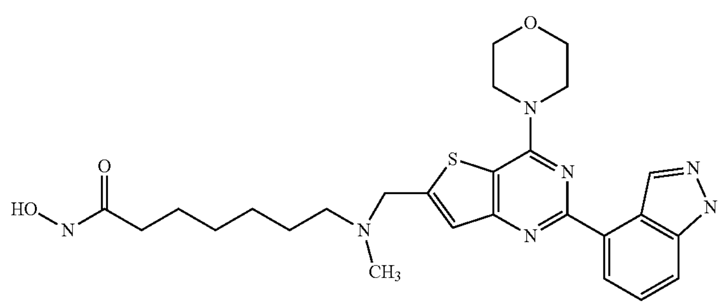 [SMILES: CN(CCCCCCC(=O)NO)Cc1cc2nc(-c3cccc4[nH]ncc34)nc(N3CCOCC3)c2s1] |
| 105 | 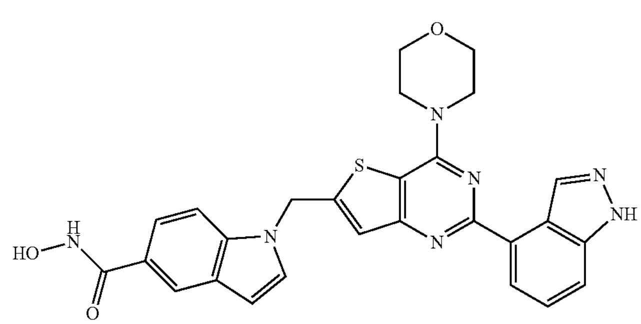 [SMILES: O=C(NO)c1ccc2c(ccn2Cc2cc3nc(-c4cccc5[nH]ncc45)nc(N4CCOCC4)c3s2)c1] |

TABLE A-continued
| Compound No. | Structure |
|---|---|
| 106 | 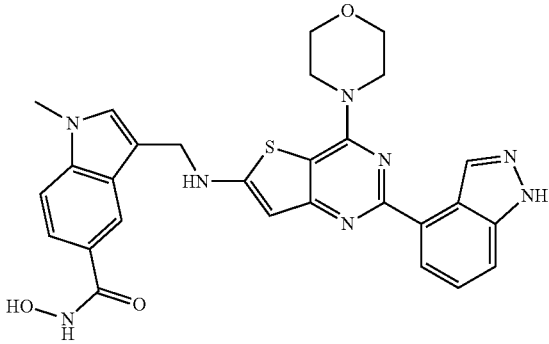 [SMILES: Cn1cc(CNc2cc3nc(-c4cccc5[nH]ncc45)nc(N4CCOCC4)c3s2)c2cc(C(=O)NO)ccc21] |
| 107 | 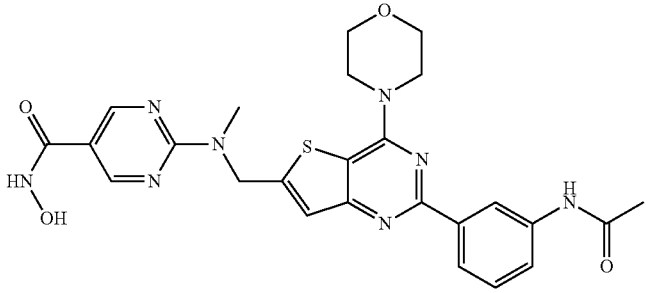 [SMILES: CC(=O)Nc1cccc(-c2nc(N3CCOCC3)c3sc(CN(C)c4ncc(C(=O)NO)cn4)cc3n2)c1] |
| 108 | 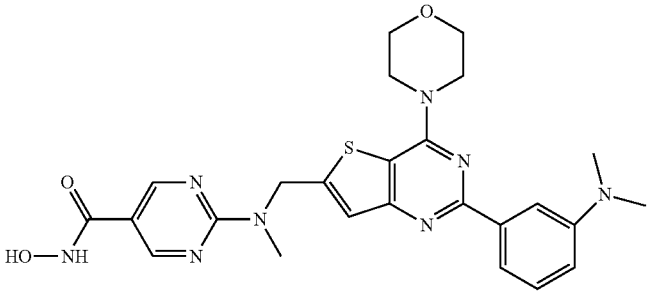 [SMILES: CN(C)c1cccc(-c2nc(N3CCOCC3)c3sc(CN(C)c4ncc(C(=O)NO)cn4)cc3n2)c1] |
| 109 | 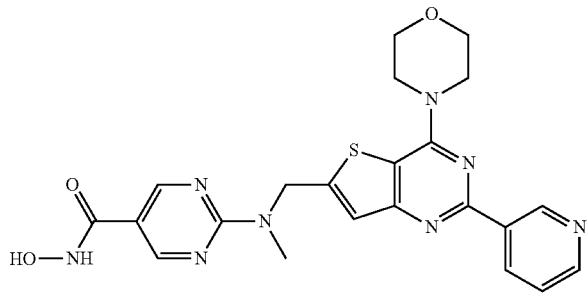 [SMILES: CN(Cc1cc2nc(-c3cccnc3)nc(N3CCOCC3)c2s1)c1ncc(C(=O)NO)cn1] |
| 110 | 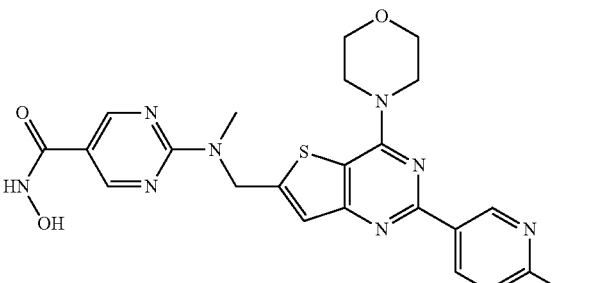 |

TABLE A-continued
| Compound No. | Structure |
|---|---|
| 111 | 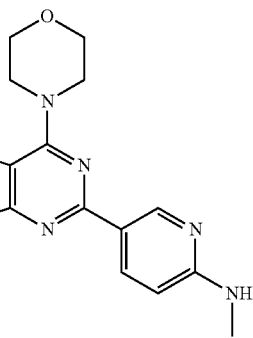 |
| 112 | 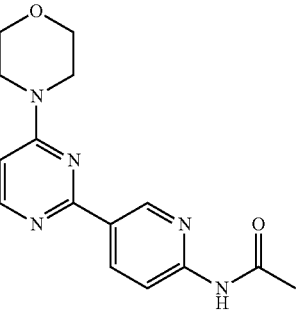 |
| 113 | 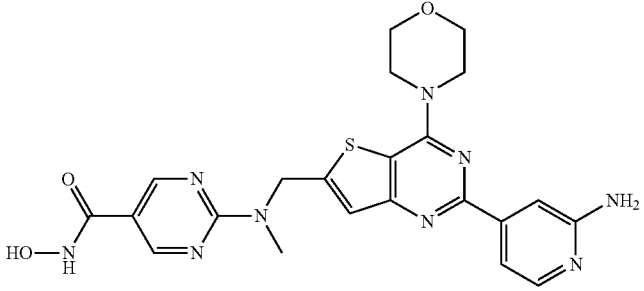 [SMILES: CN(Cc1cc2nc(-c3ccnc(N)c3)nc(N3CCOCC3)c2s1)c1ncc(C(=O)NO)cn1] |
| 114 | 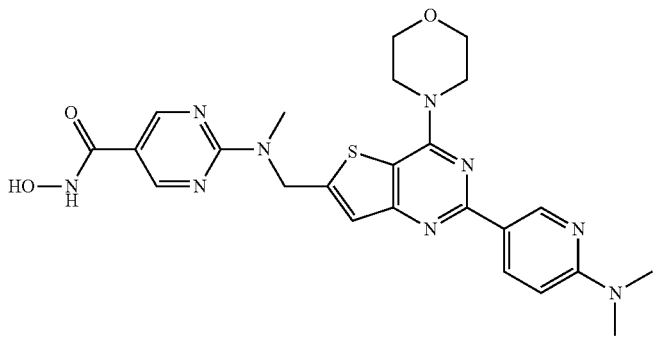 [SMILES: CN(C)c1ccc(-c2nc(N3CCOCC3)c3sc(CN(C)c4ncc(C(=O)NO)cn4)cc3n2)cn1] |
| 115 | 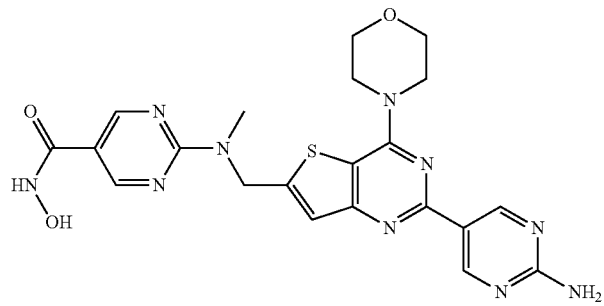 [SMILES: CN(Cc1cc2nc(-c3cnc(N)nc3)nc(N3CCOCC3)c2s1)c1ncc(C(=O)NO)cn1] |

TABLE A-continued
| Compound No. | Structure |
|---|---|
| 116 | 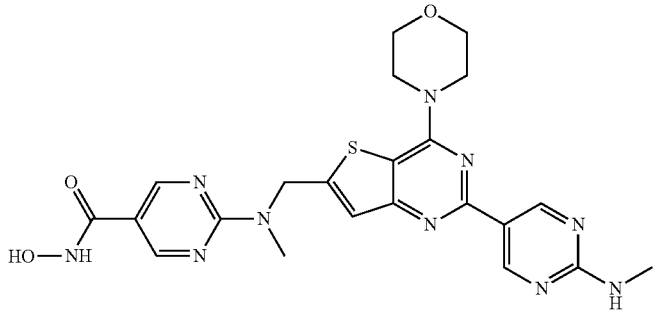 [SMILES: CNc1ncc(-c2nc(N3CCOCC3)c3sc(CN(C)c4ncc(C(=O)NO)cn4)cc3n2)cn1] |
| 117 | 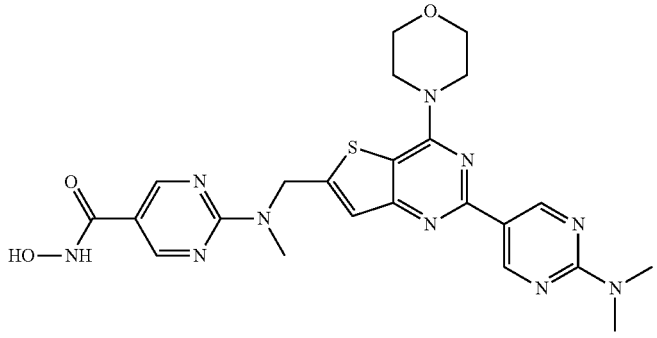 [SMILES: CN(C)c1ncc(-c2nc(N3CCOCC3)c3sc(CN(C)c4ncc(C(=O)NO)cn4)cc3n2)cn1] |
| 118 | 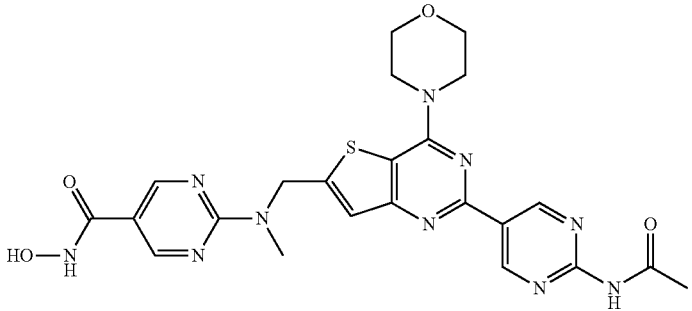 [SMILES: CC(=O)Nc1ncc(-c2nc(N3CCOCC3)c3sc(CN(C)c4ncc(C(=O)NO)cn4)cc3n2)cn1] |
| 119 | 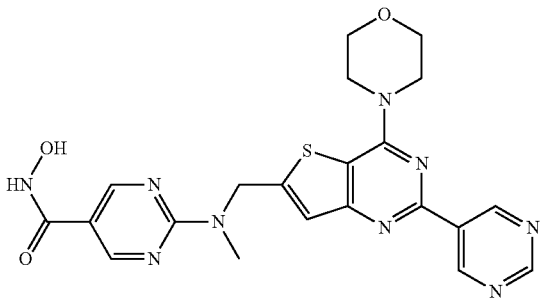 [SMILES: CN(Cc1cc2nc(-c3cncnc3)nc(N3CCOCC3)c2s1)c1ncc(C(=O)NO)cn1] |
| 120 | 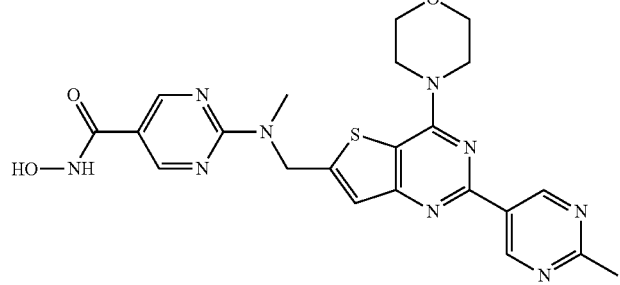 |

TABLE A-continued
| Compound No. | Structure |
|---|---|
| 121 | 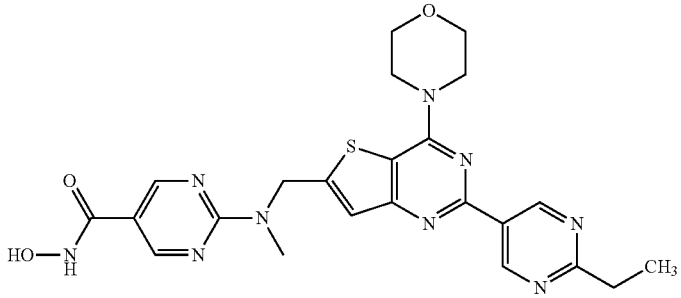 |
| 122 | 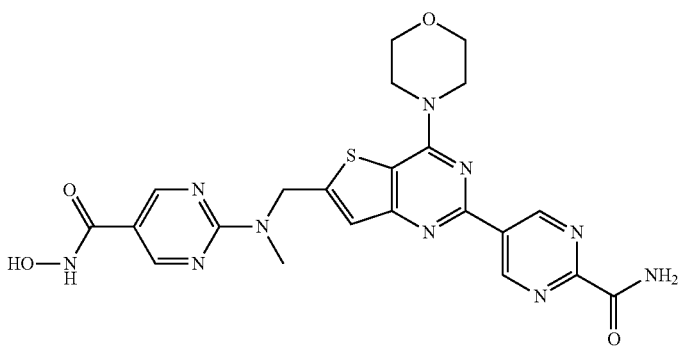 [SMILES: CN(Cc1cc2nc(-c3cnc(C(N)=O)nc3)nc(N3CCOCC3)c2s1)c1ncc(C(=O)NO)cn1] |
| 123 | 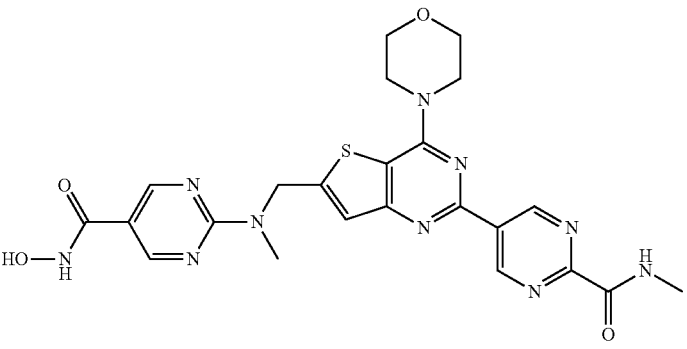 [SMILES: CNC(=O)c1ncc(-c2nc(N3CCOCC3)c3sc(CN(C)c4ncc(C(=O)NO)cn4)cc3n2)cn1] |
| 124 | 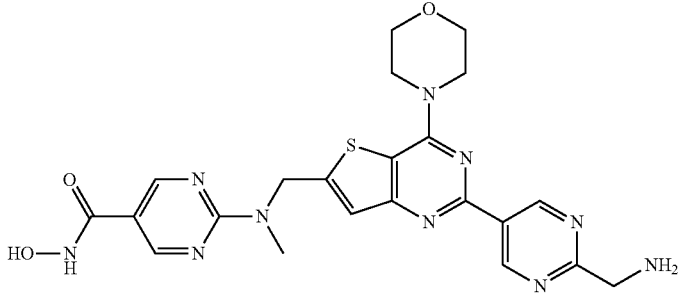 [SMILES: CN(Cc1cc2nc(-c3cnc(CN)nc3)nc(N3CCOCC3)c2s1)c1ncc(C(=O)NO)cn1] |

TABLE A-continued
| Compound No. | Structure |
|---|---|
| 125 | 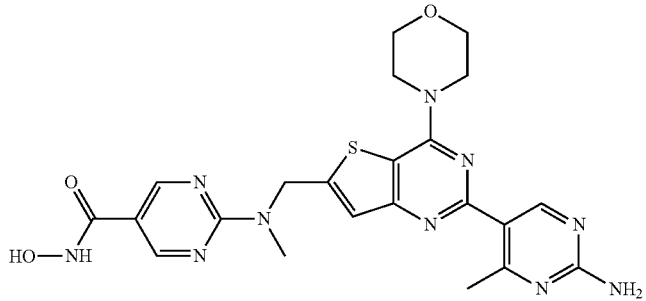 [SMILES: Cc1nc(N)ncc1-c1nc(N2CCOCC2)c2sc(CN(C)c3ncc(C(=O)NO)cn3)cc2n1] |
| 126 | 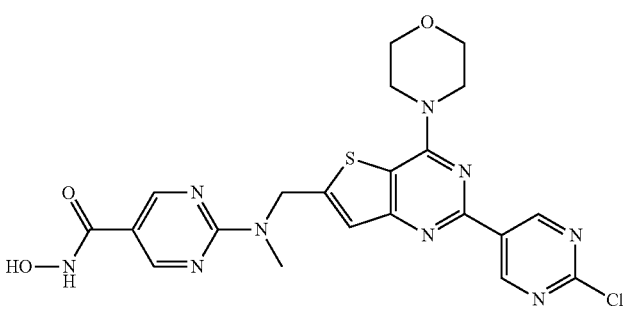 [SMILES: CN(Cc1cc2nc(-c3cnc(Cl)nc3)nc(N3CCOCC3)c2s1)c1ncc(C(=O)NO)cn1] |
| 127 | 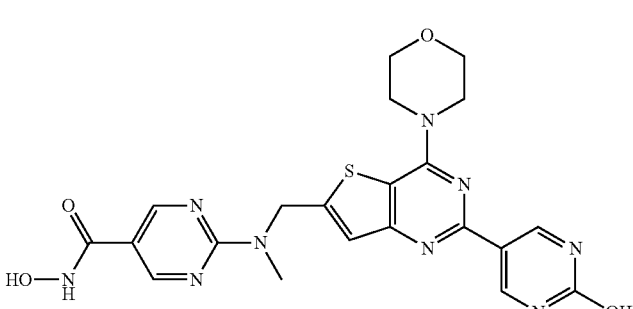 |
| 128 | 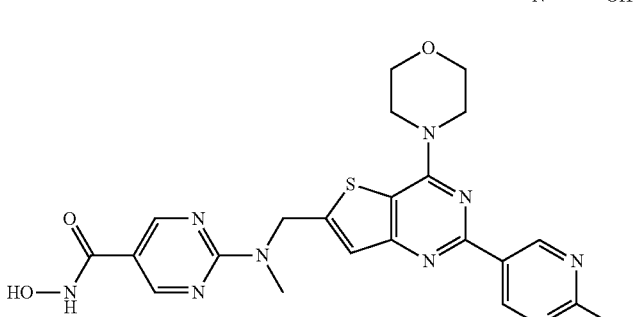 |
| 129 | 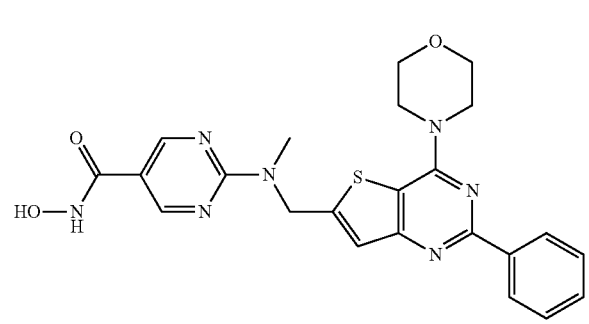 [SMILES: CN(Cc1cc2nc(-c3ccccc3)nc(N3CCOCC3)c2s1)c1ncc(C(=O)NO)cn1] |

TABLE A-continued

| Compound No. | Structure |
|---|---|
| 130 | (thieno[3,2-d]pyrimidine with 4-morpholino, 2-(3-methoxyphenyl), 6-[(N-methyl-N-(5-(hydroxycarbamoyl)pyrimidin-2-yl))aminomethyl]) |
| 131 | (thieno[3,2-d]pyrimidine with 4-morpholino, 2-(4-methoxyphenyl), 6-[(N-methyl-N-(5-(hydroxycarbamoyl)pyrimidin-2-yl))aminomethyl]) |
| 132 | (thieno[3,2-d]pyrimidine with 4-morpholino, 2-(3-hydroxyphenyl), 6-[(N-methyl-N-(5-(hydroxycarbamoyl)pyrimidin-2-yl))aminomethyl]) |
| 133 | (thieno[3,2-d]pyrimidine with 4-morpholino, 2-(4-hydroxyphenyl), 6-[(N-methyl-N-(5-(hydroxycarbamoyl)pyrimidin-2-yl))aminomethyl]) |
| 134 | (thieno[3,2-d]pyrimidine with 4-morpholino, 2-(3-aminophenyl), 6-[(N-methyl-N-(5-(hydroxycarbamoyl)pyrimidin-2-yl))aminomethyl]) |

TABLE A-continued
| Compound No. | Structure |
|---|---|
| 135 | 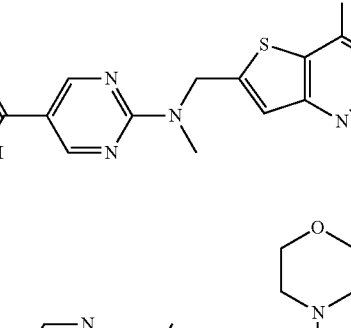 |
| 136 | 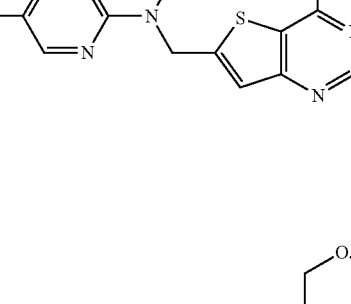 |
| 137 | 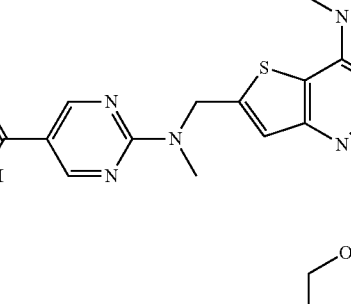 |
| 138 | 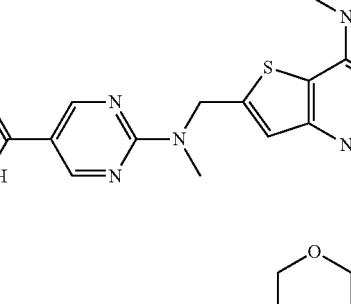 |
| 139 | 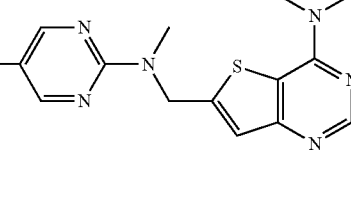 |

TABLE A-continued

| Compound No. | Structure |
|---|---|
| 140 | 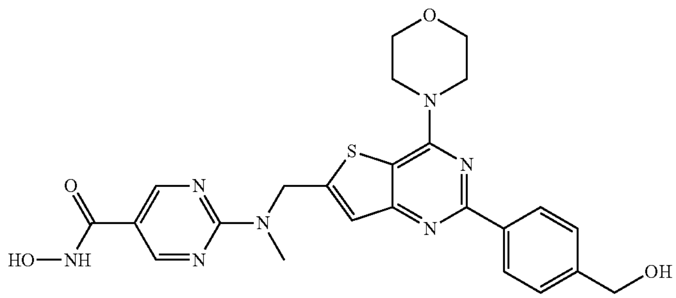 [SMILES: CN(Cc1cc2nc(-c3ccc(CO)cc3)nc(N3CCOCC3)c2s1)c1ncc(C(=O)NO)cn1] |
| 141 | 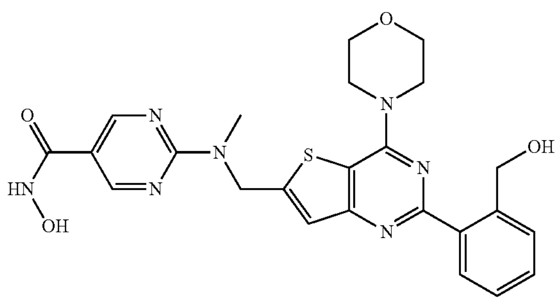 [SMILES: CN(Cc1cc2nc(-c3ccccc3CO)nc(N3CCOCC3)c2s1)c1ncc(C(=O)NO)cn1] |
| 142 | 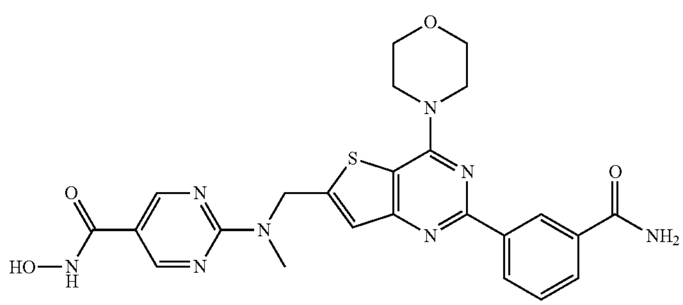 [SMILES: CN(Cc1cc2nc(-c3cccc(C(N)=O)c3)nc(N3CCOCC3)c2s1)c1ncc(C(=O)NO)cn1] |
| 143 | 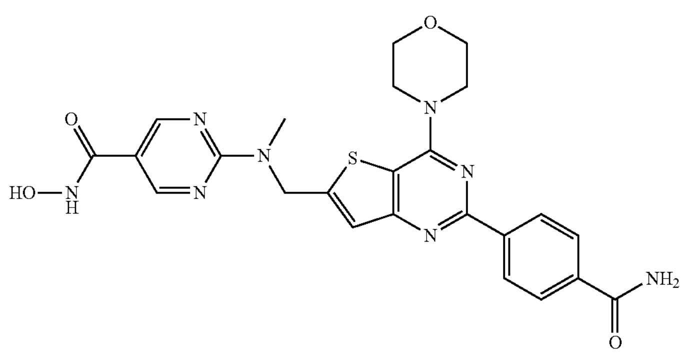 [SMILES: CN(Cc1cc2nc(-c3ccc(C(N)=O)cc3)nc(N3CCOCC3)c2s1)c1ncc(C(=O)NO)cn1] |
| 144 | 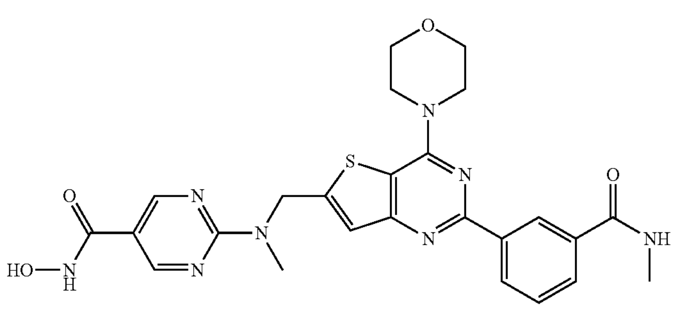 [SMILES: CNC(=O)c1cccc(-c2nc(N3CCOCC3)c3sc(CN(C)c4ncc(C(=O)NO)cn4)cc3n2)c1] |

TABLE A-continued

| Compound No. | Structure |
|---|---|
| 145 | 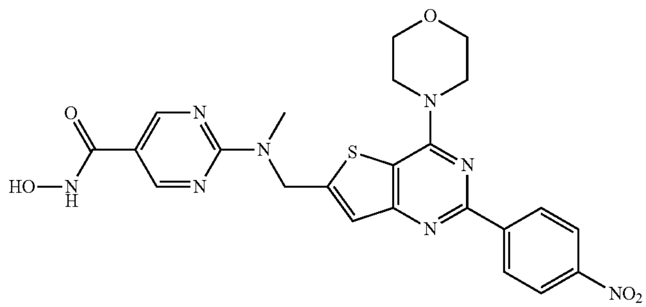 [SMILES: CN(Cc1cc2nc(-c3ccc([N+](=O)[O-])cc3)nc(N3CCOCC3)c2s1)c1ncc(C(=O)NO)cn1] |
| 146 | 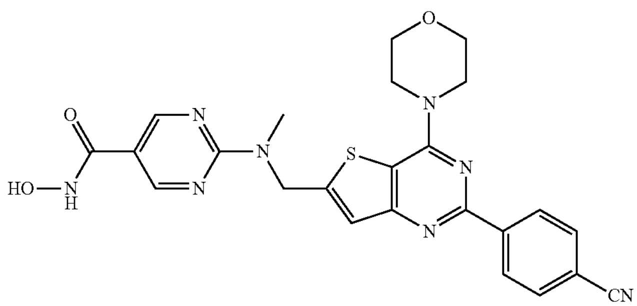 [SMILES: CN(Cc1cc2nc(-c3ccc(C#N)cc3)nc(N3CCOCC3)c2s1)c1ncc(C(=O)NO)cn1] |
| 147 | 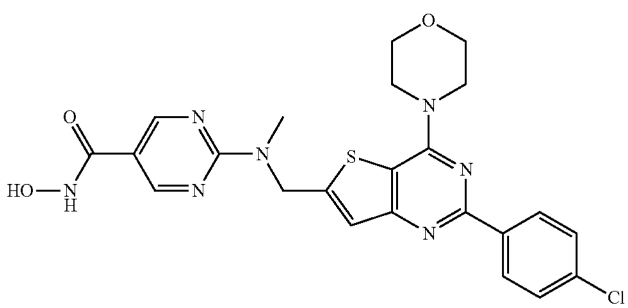 [SMILES: CN(Cc1cc2nc(-c3ccc(Cl)cc3)nc(N3CCOCC3)c2s1)c1ncc(C(=O)NO)cn1] |
| 148 | 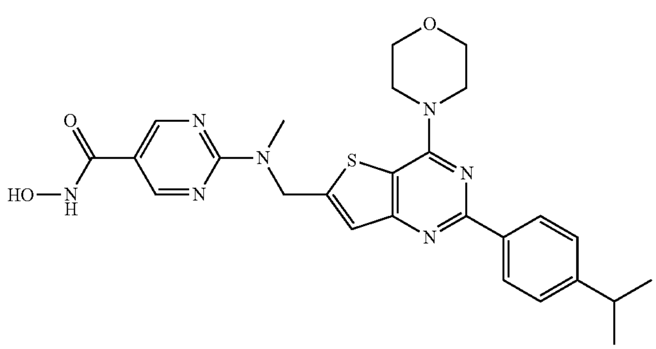 [SMILES: CC(C)c1ccc(-c2nc(N3CCOCC3)c3sc(CN(C)c4ncc(C(=O)NO)cn4)cc3n2)cc1] |
| 149 | 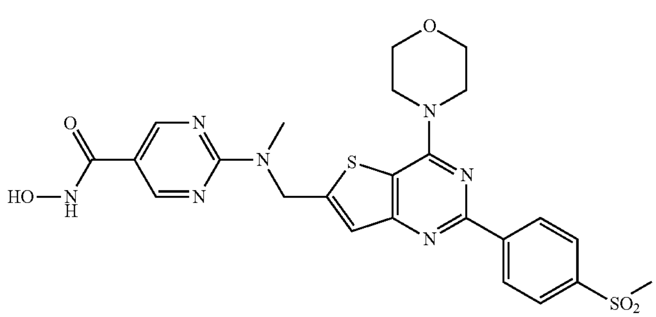 [SMILES: CN(Cc1cc2nc(-c3ccc(S(C)(=O)=O)cc3)nc(N3CCOCC3)c2s1)c1ncc(C(=O)NO)cn1] |

TABLE A-continued
| Compound No. | Structure |
|---|---|
| 150 | 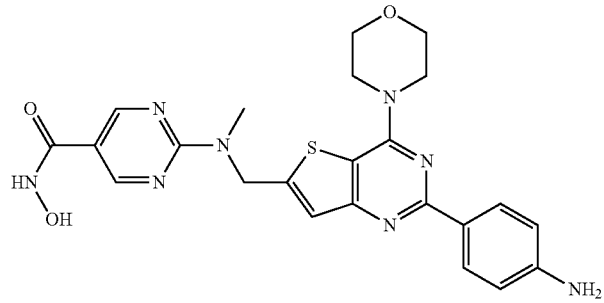 [SMILES: CN(Cc1cc2nc(-c3ccc(N)cc3)nc(N3CCOCC3)c2s1)c1ncc(C(=O)NO)cn1] |
| 151 | 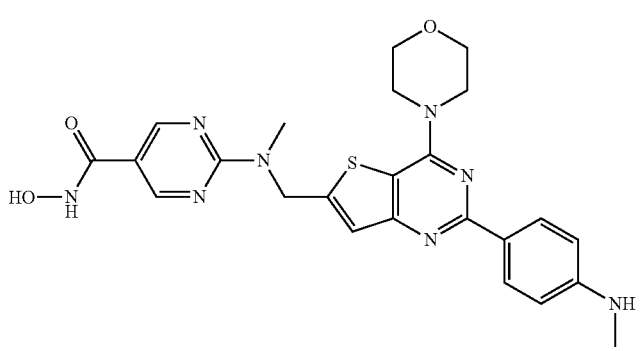 [SMILES: CNc1ccc(-c2nc(N3CCOCC3)c3sc(CN(C)c4ncc(C(=O)NO)cn4)cc3n2)cc1] |
| 152 | 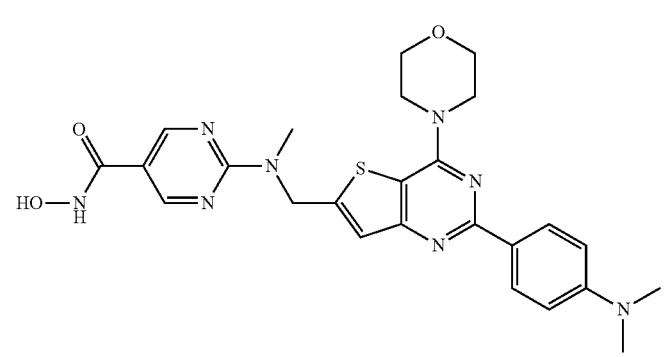 [SMILES: CN(C)c1ccc(-c2nc(N3CCOCC3)c3sc(CN(C)c4ncc(C(=O)NO)cn4)cc3n2)cc1] |
| 153 | 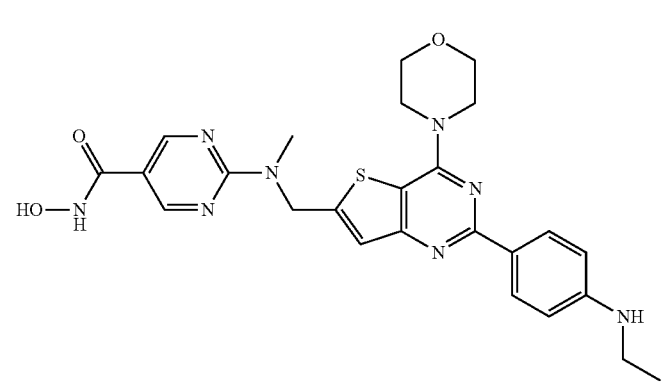 [SMILES: CCNc1ccc(-c2nc(N3CCOCC3)c3sc(CN(C)c4ncc(C(=O)NO)cn4)cc3n2)cc1] |

TABLE A-continued

| Compound No. | Structure |
|---|---|
| 154 | 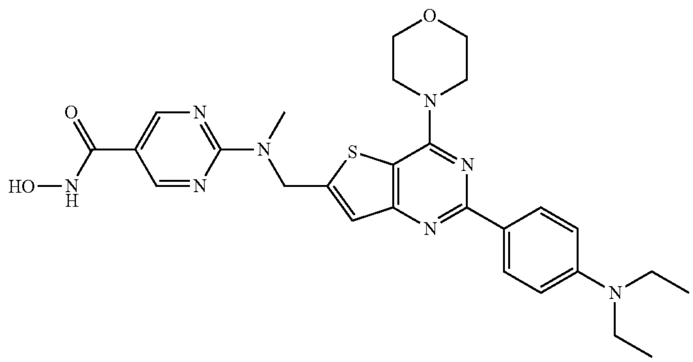 [SMILES: CCN(CC)c1ccc(-c2nc(N3CCOCC3)c3sc(CN(C)c4ncc(C(=O)NO)cn4)cc3n2)cc1] |
| 155 | 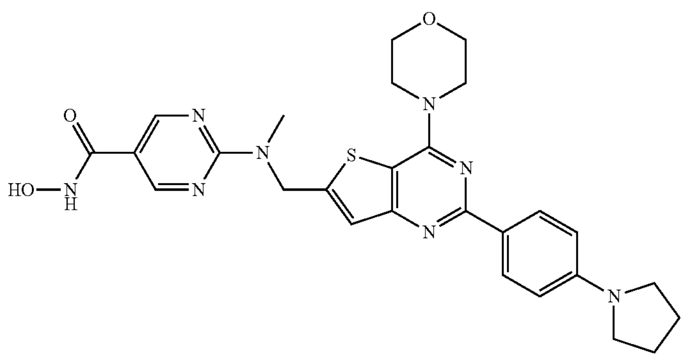 [SMILES: CN(Cc1cc2nc(-c3ccc(N4CCCC4)cc3)nc(N3CCOCC3)c2s1)c1ncc(C(=O)NO)cn1] |
| 156 | 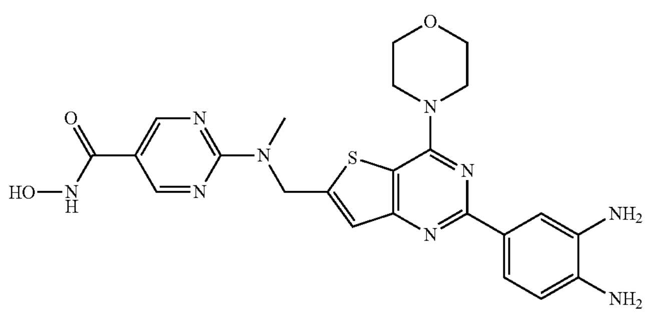 [SMILES: CN(Cc1cc2nc(-c3ccc(N)c(N)c3)nc(N3CCOCC3)c2s1)c1ncc(C(=O)NO)cn1] |
| 157 | 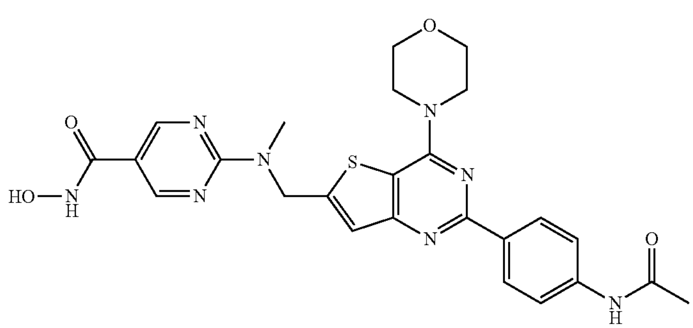 [SMILES: CC(=O)Nc1ccc(-c2nc(N3CCOCC3)c3sc(CN(C)c4ncc(C(=O)NO)cn4)cc3n2)cc1] |
| 158 | 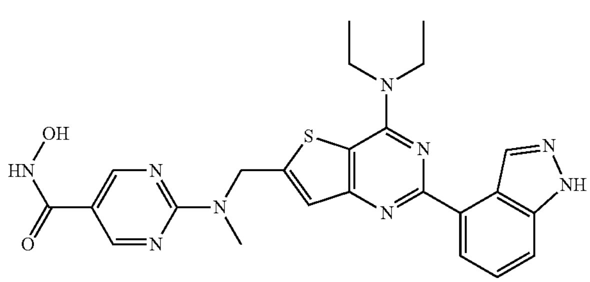 [SMILES: CCN(CC)c1nc(-c2cccc3[nH]ncc23)nc2cc(CN(C)c3ncc(C(=O)NO)cn3)sc12] |

TABLE A-continued
| Compound No. | Structure |
|---|---|
| 159 | 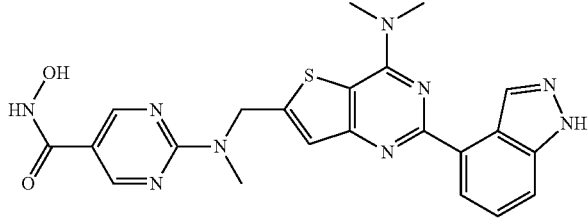 [SMILES: CN(C)c1nc(-c2cccc3[nH]ncc23)nc2cc(CN(C)c3ncc(C(=O)NO)cn3)sc12] |
| 160 | 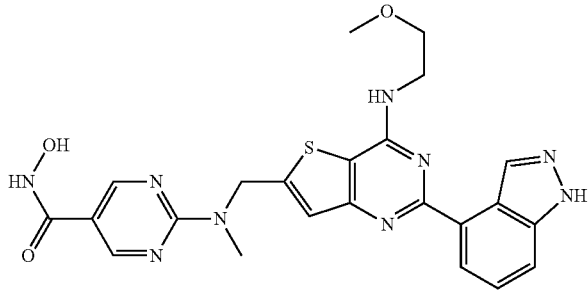 [SMILES: COCCNc1nc(-c2cccc3[nH]ncc23)nc2cc(CN(C)c3ncc(C(=O)NO)cn3)sc12] |
| 161 | 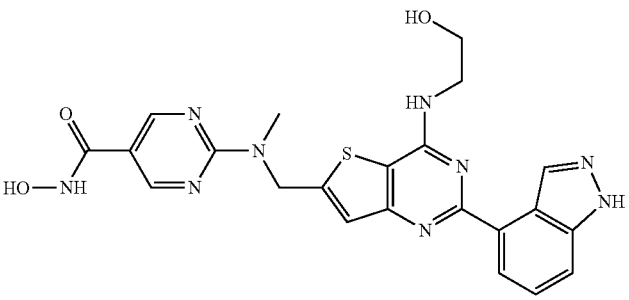 [SMILES: CN(Cc1cc2nc(-c3cccc4[nH]ncc34)nc(NCCO)c2s1)c1ncc(C(=O)NO)cn1] |
| 162 | 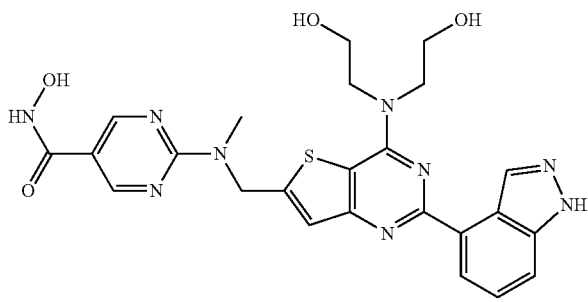 [SMILES: CN(Cc1cc2nc(-c3cccc4[nH]ncc34)nc(N(CCO)CCO)c2s1)c1ncc(C(=O)NO)cn1] |
| 163 | 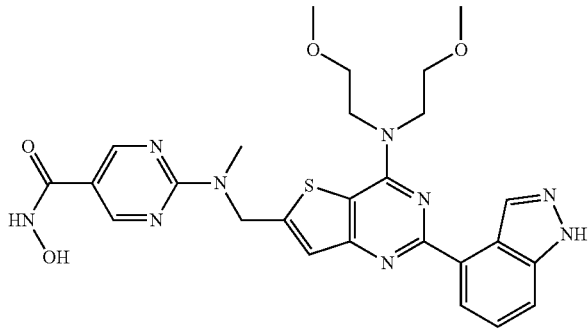 [SMILES: COCCN(CCOC)c1nc(-c2cccc3[nH]ncc23)nc2cc(CN(C)c3ncc(C(=O)NO)cn3)sc12] |

TABLE A-continued

| Compound No. | Structure |
|---|---|
| 164 | 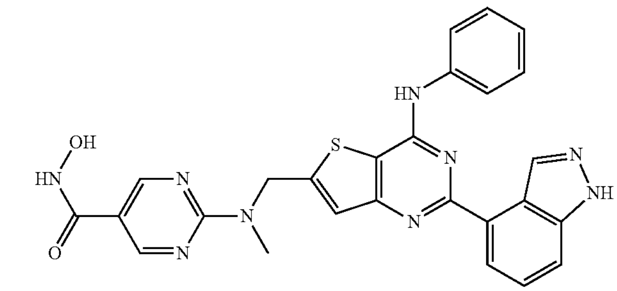 [SMILES: CN(Cc1cc2nc(-c3cccc4[nH]ncc34)nc(Nc3ccccc3)c2s1)c1ncc(C(=O)NO)cn1] |
| 165 | 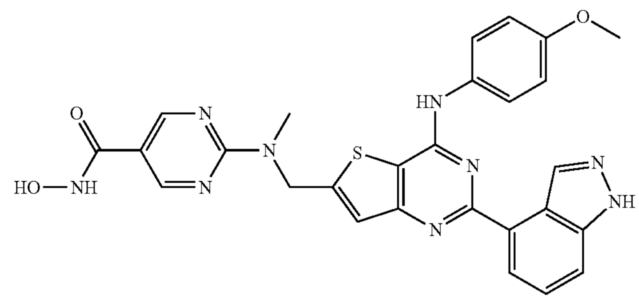 [SMILES: COc1ccc(Nc2nc(-c3cccc4[nH]ncc34)nc3cc(CN(C)c4ncc(C(=O)NO)cn4)sc23)cc1] |
| 166 | 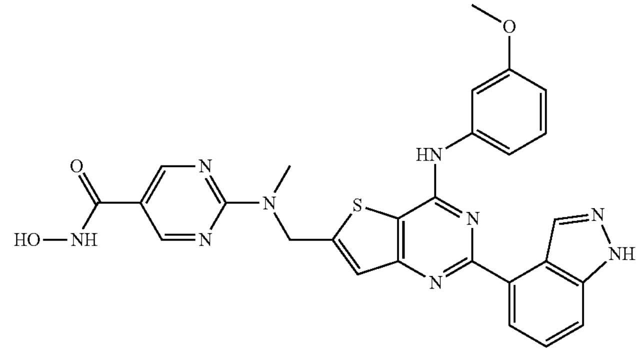 [SMILES: COc1cccc(Nc2nc(-c3cccc4[nH]ncc34)nc3cc(CN(C)c4ncc(C(=O)NO)cn4)sc23)c1] |
| 167 | 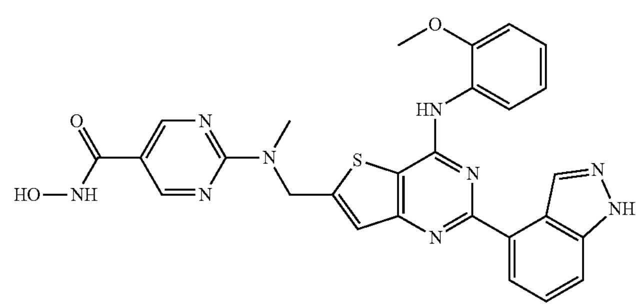 [SMILES: COc1ccccc1Nc1nc(-c2cccc3[nH]ncc23)nc2cc(CN(C)c3ncc(C(=O)NO)cn3)sc12] |
| 168 | 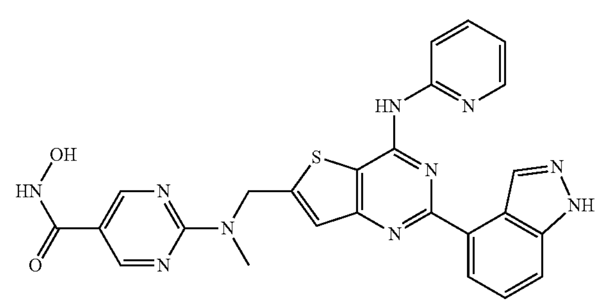 [SMILES: CN(Cc1cc2nc(-c3cccc4[nH]ncc34)nc(Nc3ccccn3)c2s1)c1ncc(C(=O)NO)cn1] |

TABLE A-continued
| Compound No. | Structure |
|---|---|
| 169 | 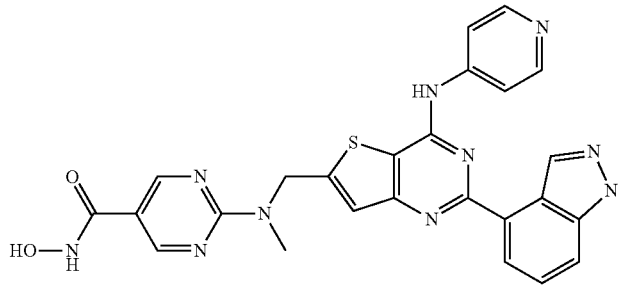 [SMILES: CN(Cc1cc2nc(-c3cccc4[nH]ncc34)nc(Nc3ccncc3)c2s1)c1ncc(C(=O)NO)cn1] |
| 170 | 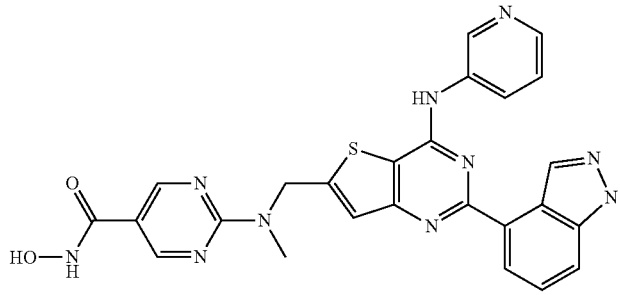 [SMILES: CN(Cc1cc2nc(-c3cccc4[nH]ncc34)nc(Nc3cccnc3)c2s1)c1ncc(C(=O)NO)cn1] |
| 171 | 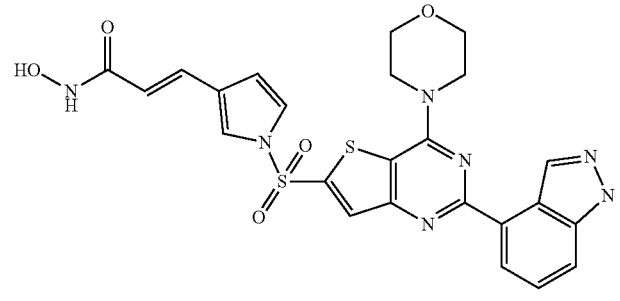 [SMILES: O=C(/C=C/c1ccn(S(=O)(=O)c2cc3nc(-c4cccc5[nH]ncc45)nc(N4CCOCC4)c3s2)c1)NO] |
| 172 | 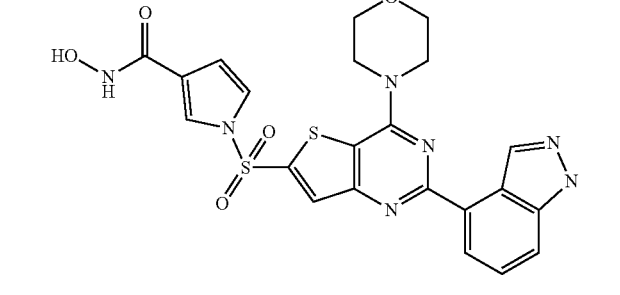 |
| 173 | 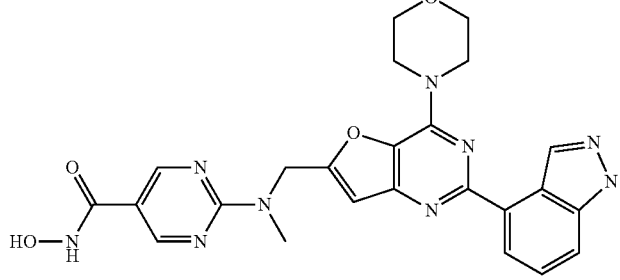 |

TABLE A-continued

| Compound No. | Structure |
|---|---|
| 174 | 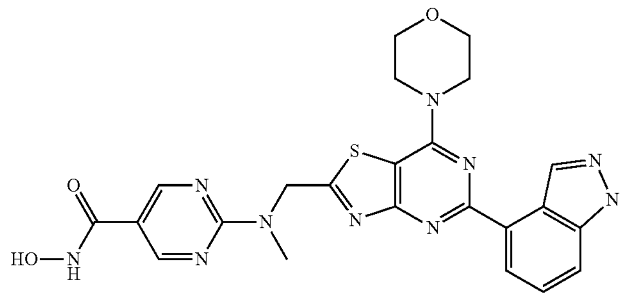 [SMILES: CN(Cc1nc2nc(-c3cccc4[nH]ncc34)nc(N3CCOCC3)c2s1)c1ncc(C(=O)NO)cn1] |
| 175 | 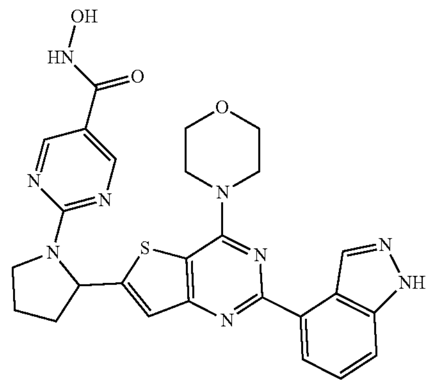 [SMILES: O=C(NO)c1cnc(N2CCCC2c2cc3nc(-c4cccc5[nH]ncc45)nc(N4CCOCC4)c3s2)nc1] |
| 176 | 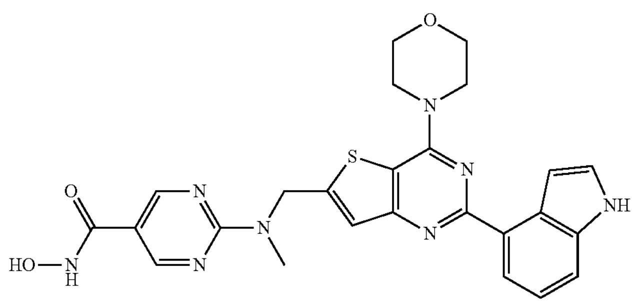 [SMILES: CN(Cc1cc2nc(-c3cccc4[nH]ccc34)nc(N3CCOCC3)c2s1)c1ncc(C(=O)NO)cn1] |
| 177 | 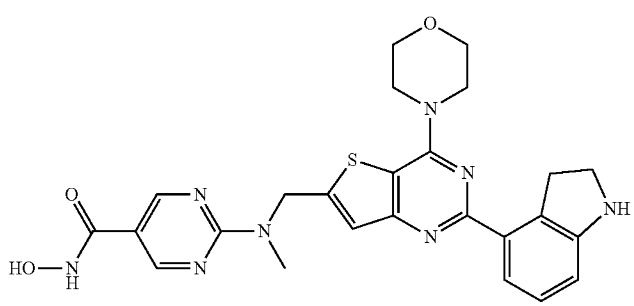 [SMILES: CN(Cc1cc2nc(-c3cccc4c3CCN4)nc(N3CCOCC3)c2s1)c1ncc(C(=O)NO)cn1] |
| 178 | 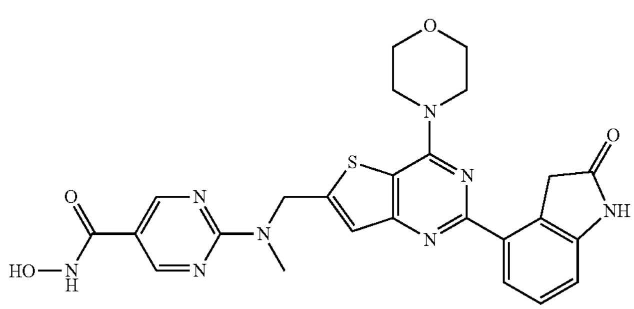 [SMILES: CN(Cc1cc2nc(-c3cccc4c3CC(=O)N4)nc(N3CCOCC3)c2s1)c1ncc(C(=O)NO)cn1] |

US 10,894,795 B2
99 100
TABLE A-continued
| Compound No. | Structure |
|---|---|
| 179 | 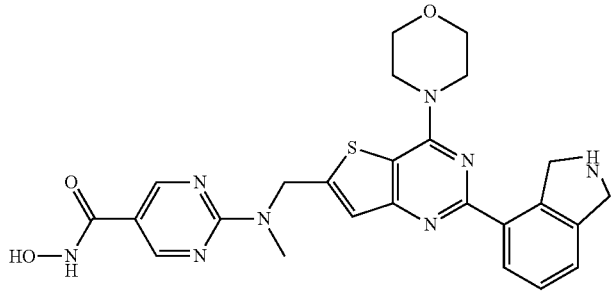 [SMILES: CN(Cc1cc2nc(-c3cccc4c3CNC4)nc(N3CCOCC3)c2s1)c1ncc(C(=O)NO)cn1] |
| 180 | 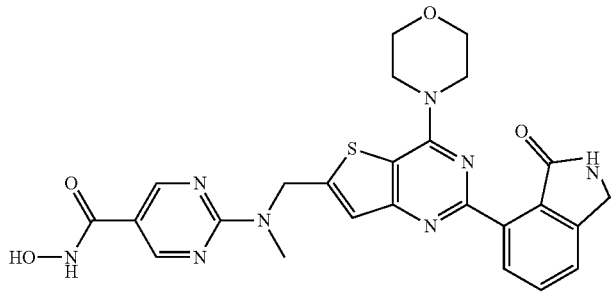 [SMILES: CN(Cc1cc2nc(-c3cccc4c3C(=O)NC4)nc(N3CCOCC3)c2s1)c1ncc(C(=O)NO)cn1] |
| 181 | 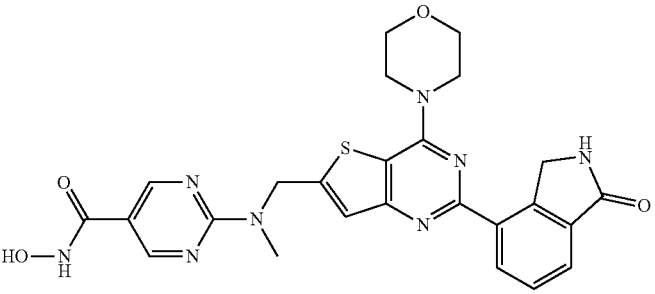 [SMILES: CN(Cc1cc2nc(-c3cccc4c3CNC4=O)nc(N3CCOCC3)c2s1)c1ncc(C(=O)NO)cn1] |
| 182 | 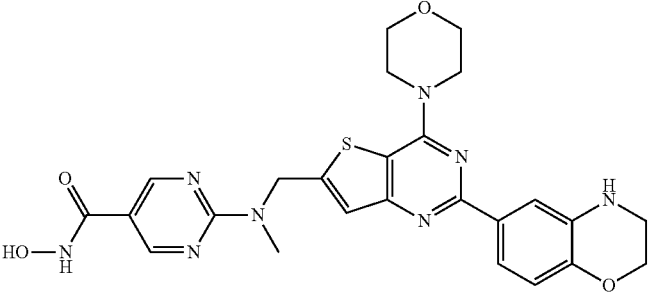 [SMILES: CN(Cc1cc2nc(-c3ccc4c(c3)NCCO4)nc(N3CCOCC3)c2s1)c1ncc(C(=O)NO)cn1] |
| 183 | 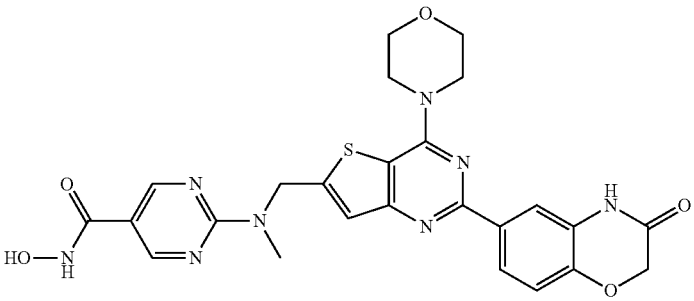 [SMILES: CN(Cc1cc2nc(-c3ccc4c(c3)NC(=O)CO4)nc(N3CCOCC3)c2s1)c1ncc(C(=O)NO)cn1] |

TABLE A-continued
| Compound No. | Structure |
|---|---|
| 184 | 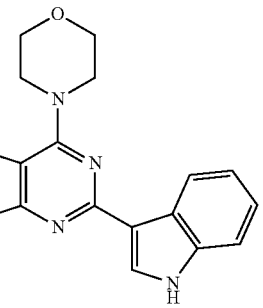 |
| 185 | 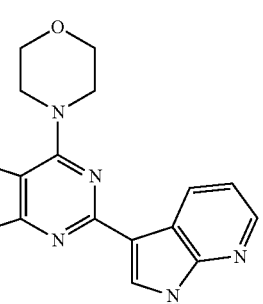 |
| 186 | 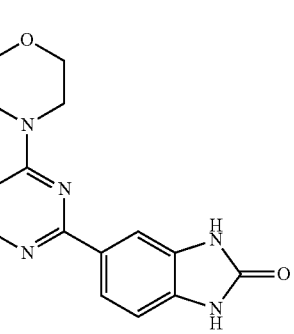 |
| 187 | 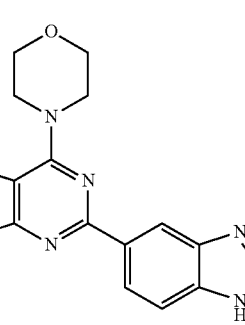 |
| 188 | 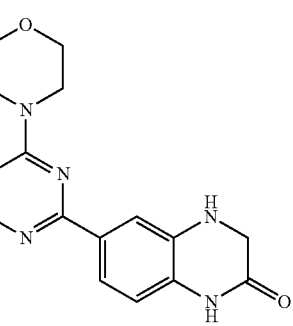 |

TABLE A-continued
| Compound No. | Structure |
|---|---|
| 189 | 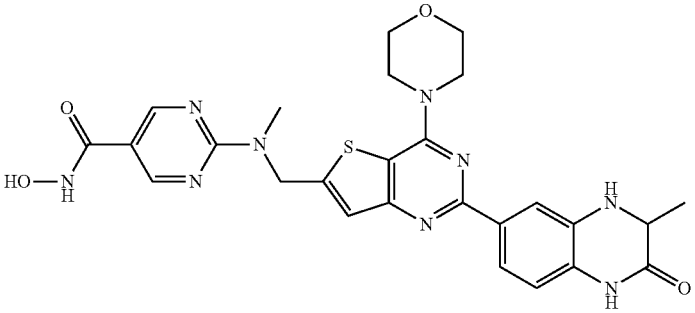 [SMILES: CC1Nc2cc(-c3nc(N4CCOCC4)c4sc(CN(C)c5ncc(C(=O)NO)cn5)cc4n3)ccc2NC1=O] |
| 190 | 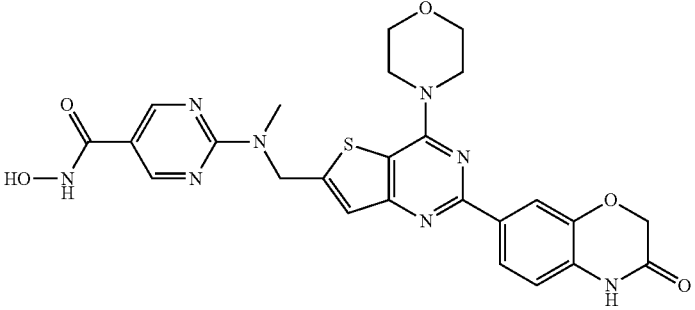 [SMILES: CN(Cc1cc2nc(-c3ccc4c(c3)OCC(=O)N4)nc(N3CCOCC3)c2s1)c1ncc(C(=O)NO)cn1] |
| 191 | 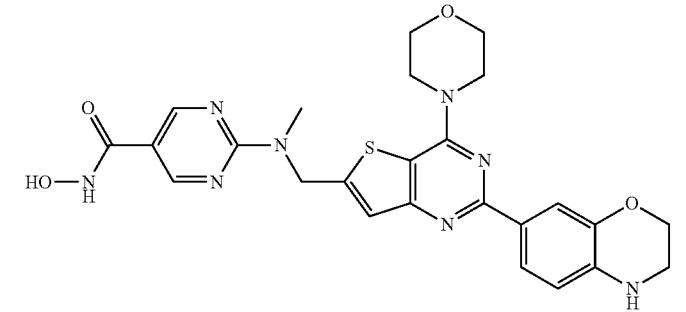 [SMILES: CN(Cc1cc2nc(-c3ccc4c(c3)OCCN4)nc(N3CCOCC3)c2s1)c1ncc(C(=O)NO)cn1] |
| 192 | 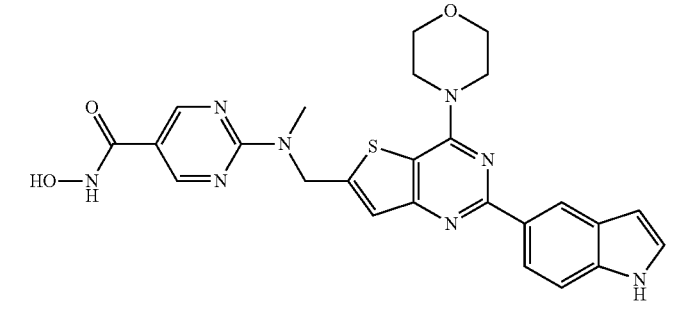 |
| 193 | 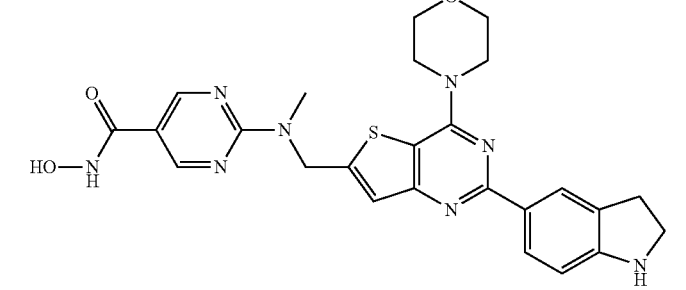 |

US 10,894,795 B2
105                                                                                              106
TABLE A-continued
| Compound No. | Structure |
|---|---|
| 194 | 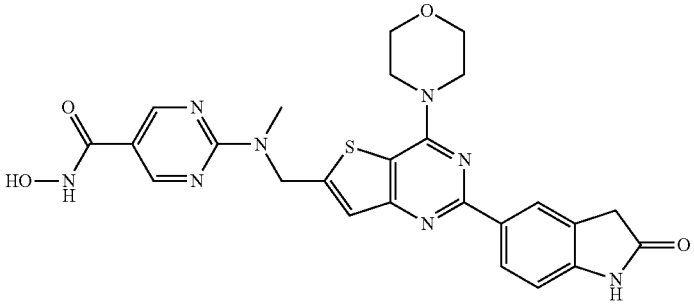 [SMILES: CN(Cc1cc2nc(-c3ccc4c(c3)CC(=O)N4)nc(N3CCOCC3)c2s1)c1ncc(C(=O)NO)cn1] |
| 195 | 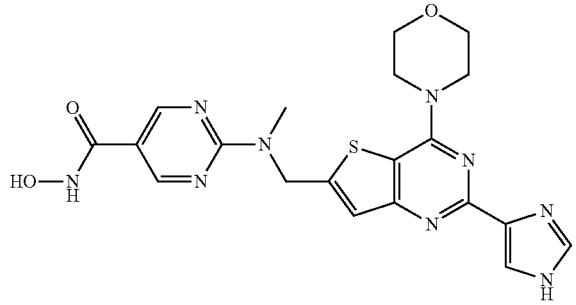 [SMILES: CN(Cc1cc2nc(-c3c[nH]cn3)nc(N3CCOCC3)c2s1)c1ncc(C(=O)NO)cn1] |
| 196 | 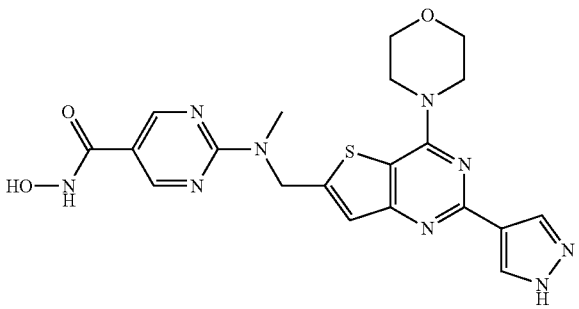 [SMILES: CN(Cc1cc2nc(-c3cn[nH]c3)nc(N3CCOCC3)c2s1)c1ncc(C(=O)NO)cn1] |
| 197 | 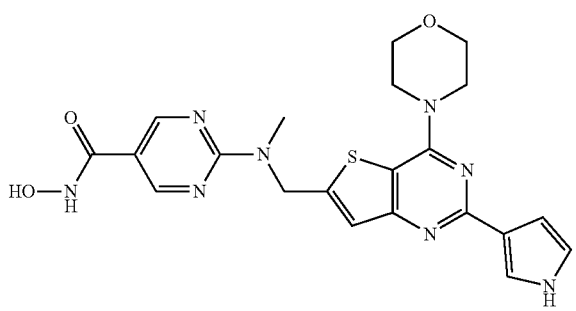 [SMILES: CN(Cc1cc2nc(-c3cc[nH]c3)nc(N3CCOCC3)c2s1)c1ncc(C(=O)NO)cn1] |
| 198 | 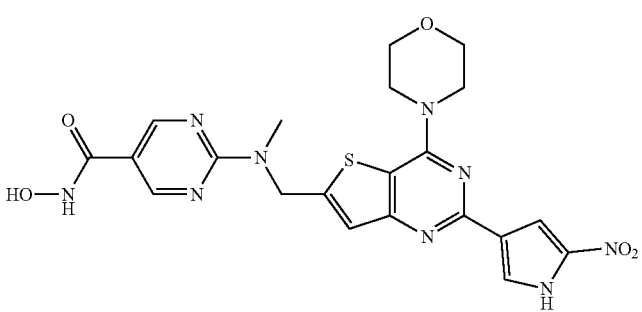 [SMILES: CN(Cc1cc2nc(-c3c[nH]c([N+](=O)[O-])c3)nc(N3CCOCC3)c2s1)c1ncc(C(=O)NO)cn1] |

TABLE A-continued

| Compound No. | Structure |
| --- | --- |
| 199 | 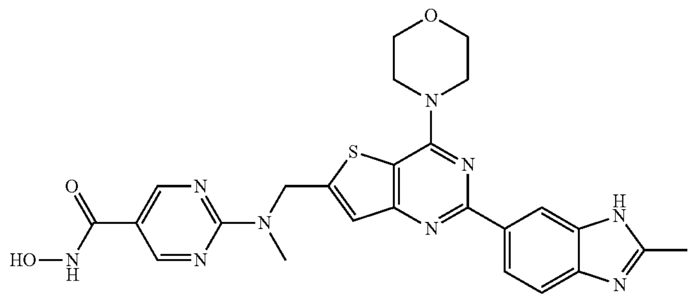 [SMILES: Cc1nc2ccc(-c3nc(N4CCOCC4)c4sc(CN(C)c5ncc(C(=O)NO)cn5)cc4n3)cc2[nH]1] |
| 200 | 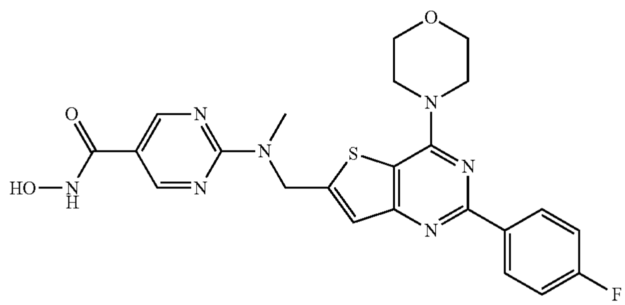 [SMILES: CN(Cc1cc2nc(-c3ccc(F)cc3)nc(N3CCOCC3)c2s1)c1ncc(C(=O)NO)cn1] |
| 201 | 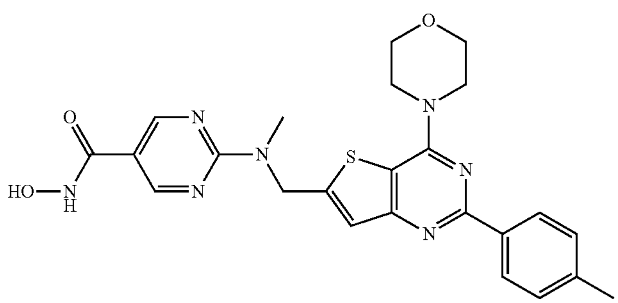 [SMILES: Cc1ccc(-c2nc(N3CCOCC3)c3sc(CN(C)c4ncc(C(=O)NO)cn4)cc3n2)cc1] |
| 202 | 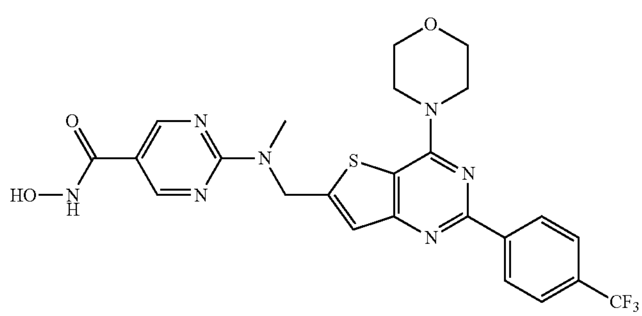 [SMILES: CN(Cc1cc2nc(-c3ccc(C(F)(F)F)cc3)nc(N3CCOCC3)c2s1)c1ncc(C(=O)NO)cn1] |
| 203 | 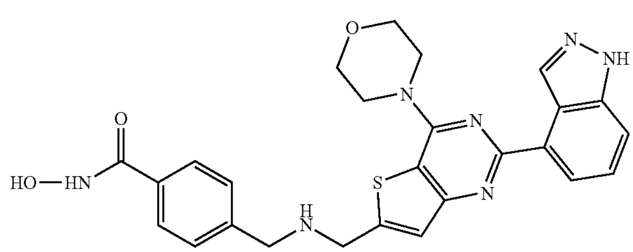 [SMILES: O=C(NO)c1ccc(CNCc2cc3nc(-c4cccc5[nH]ncc45)nc(N4CCOCC4)c3s2)cc1] |

TABLE A-continued
| Compound No. | Structure |
|---|---|
| 204 | 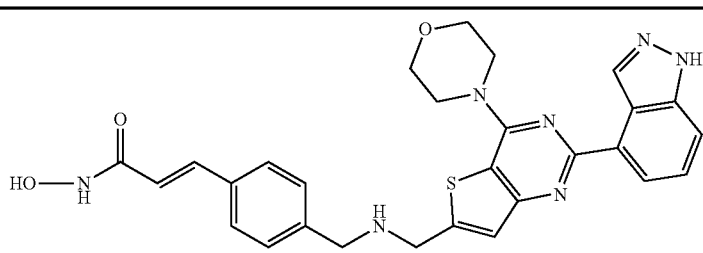 |
| 205 | 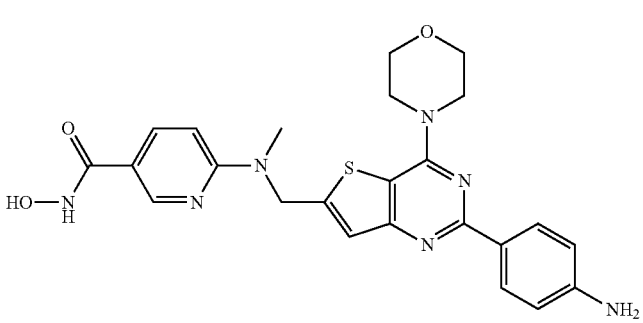 |
| 206 | 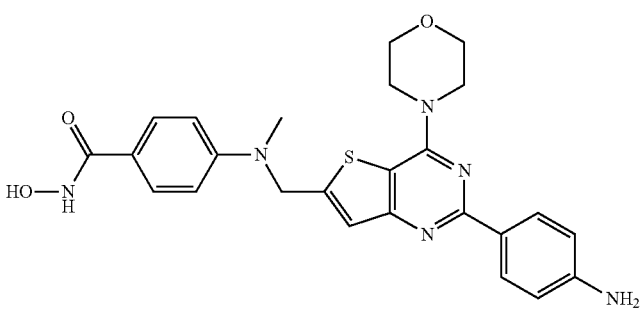 [SMILES: CN(Cc1cc2nc(-c3ccc(N)cc3)nc(N3CCOCC3)c2s1)c1ccc(C(=O)NO)cc1] |
| 207 | 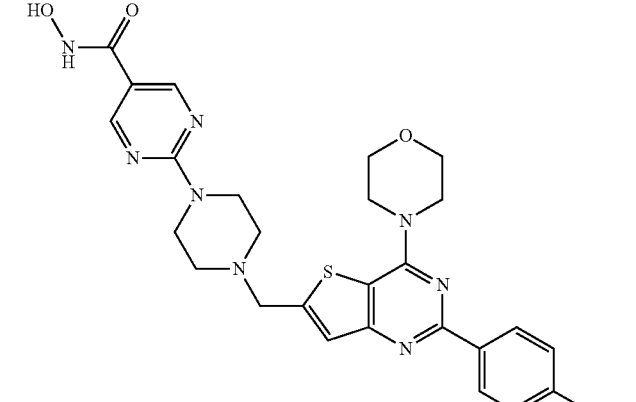 |
| 208 | 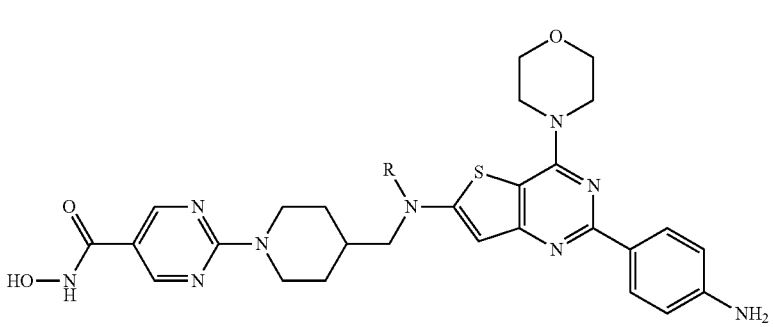 |

TABLE A-continued
| Compound No. | Structure |
|---|---|
| 209 | 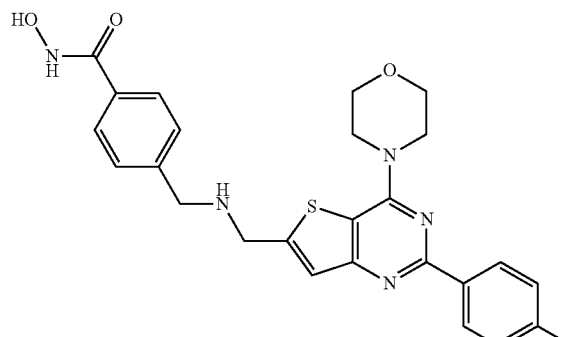 |
| 210 | 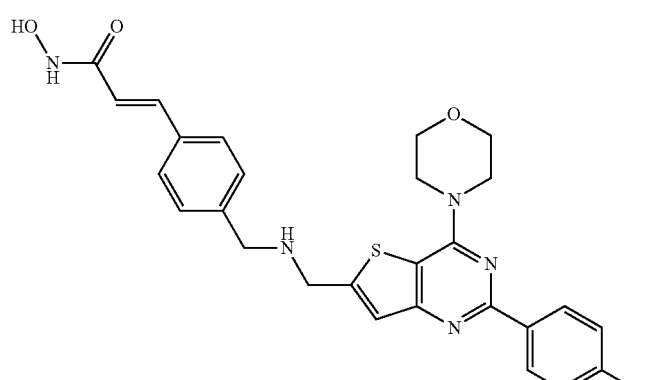 |
| 211 | 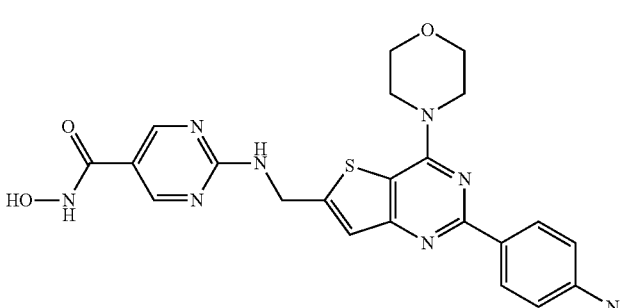 |
| 212 | 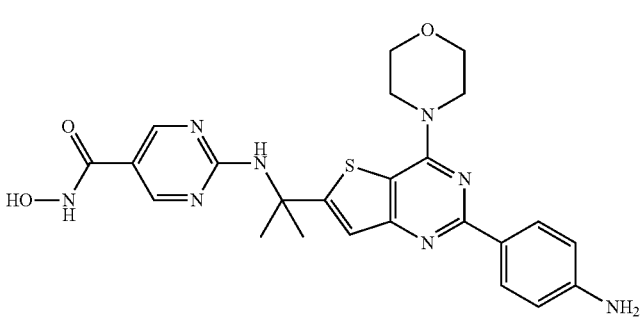 [SMILES: CC(C)(Nc1ncc(C(=O)NO)cn1)c1cc2nc(-c3ccc(N)cc3)nc(N3CCOCC3)c2s1] |

TABLE A-continued

| Compound No. | Structure |
|---|---|
| 213 | 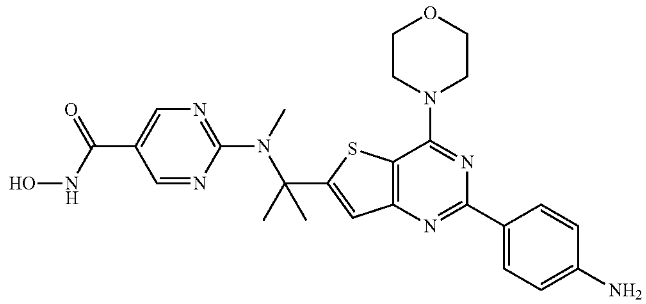 [SMILES: CN(c1ncc(C(=O)NO)cn1)C(C)(C)c1cc2nc(-c3ccc(N)cc3)nc(N3CCOCC3)c2s1] |
| 214 | 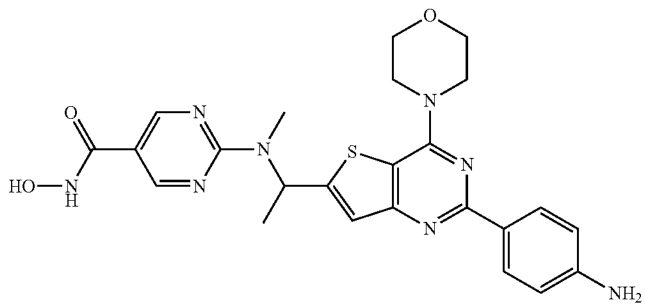 [SMILES: CC(c1cc2nc(-c3ccc(N)cc3)nc(N3CCOCC3)c2s1)N(C)c1ncc(C(=O)NO)cn1] |
| 215 | 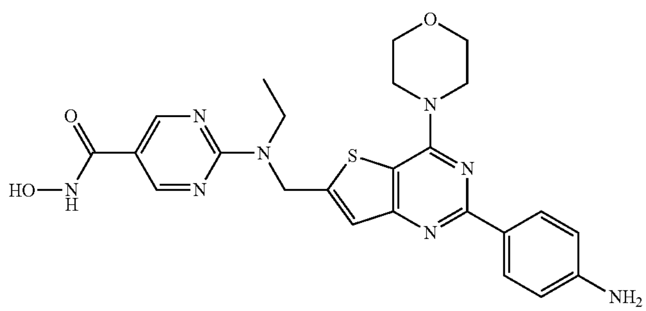 [SMILES: CCN(Cc1cc2nc(-c3ccc(N)cc3)nc(N3CCOCC3)c2s1)c1ncc(C(=O)NO)cn1] |
| 216 | 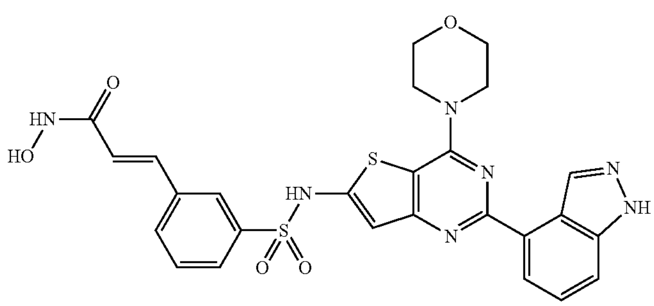 [SMILES: O=C(/C=C/c1cccc(S(=O)(=O)Nc2cc3nc(-c4cccc5[nH]ncc45)nc(N4CCOCC4)c3s2)c1)NO] |
| 217 | 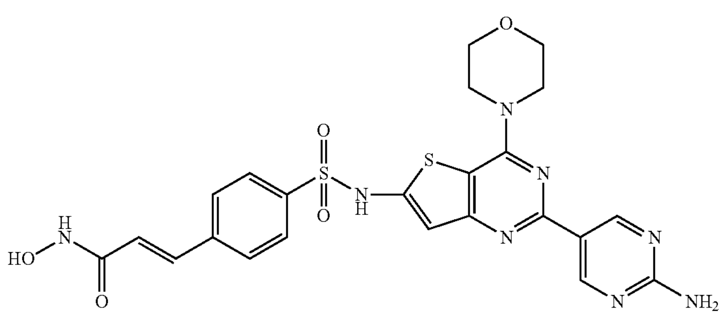 [SMILES: Nc1ncc(-c2nc(N3CCOCC3)c3sc(NS(=O)(=O)c4ccc(/C=C/C(=O)NO)cc4)cc3n2)cn1] |

TABLE A-continued
| Compound No. | Structure |
|---|---|
| 218 | 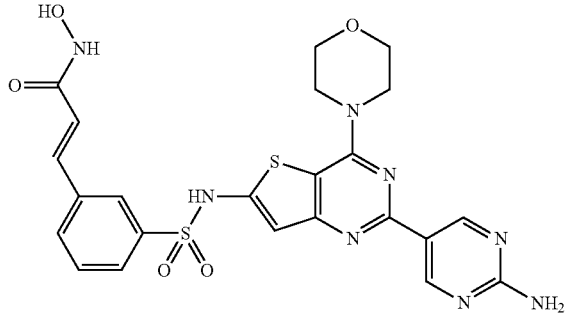 [SMILES: Nc1ncc(-c2nc(N3CCOCC3)c3sc(NS(=O)(=O)c4cccc(/C=C/C(=O)NO)c4)cc3n2)cn1] |
| 219 | 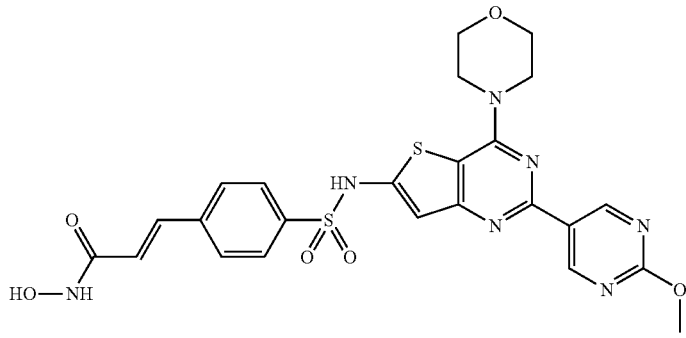 [SMILES: COc1ncc(-c2nc(N3CCOCC3)c3sc(NS(=O)(=O)c4ccc(/C=C/C(=O)NO)cc4)cc3n2)cn1] |
| 220 | 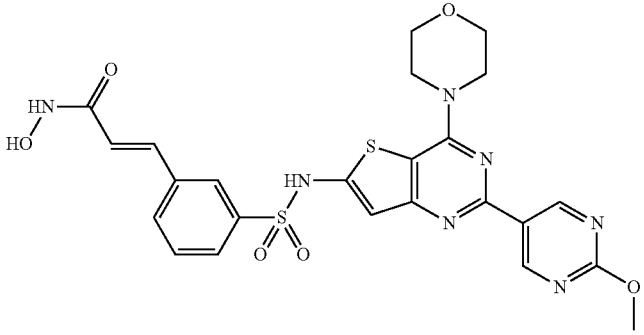 [SMILES: COc1ncc(-c2nc(N3CCOCC3)c3sc(NS(=O)(=O)c4cccc(/C=C/C(=O)NO)c4)cc3n2)cn1] |
| 221 | 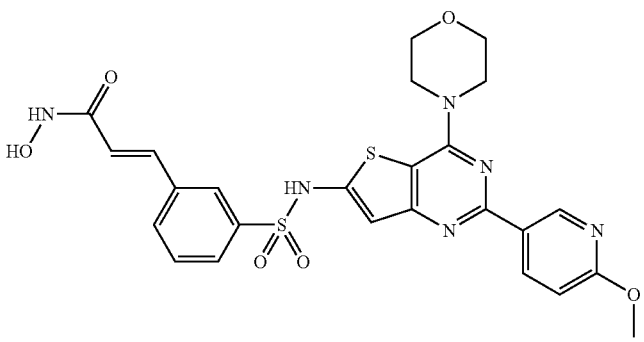 [SMILES: COc1ccc(-c2nc(N3CCOCC3)c3sc(NS(=O)(=O)c4cccc(/C=C/C(=O)NO)c4)cc3n2)cn1] |

TABLE A-continued
| Compound No. | Structure |
|---|---|
| 222 | 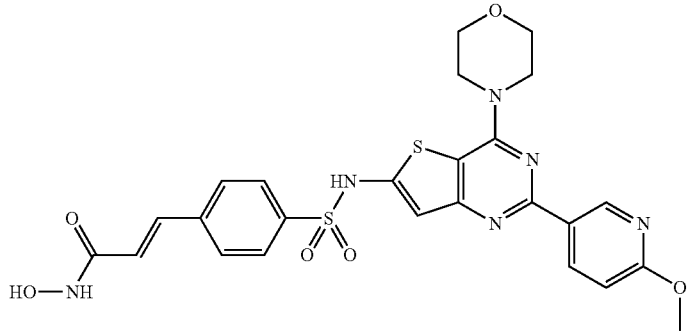 [SMILES: COc1ccc(-c2nc(N3CCOCC3)c3sc(NS(=O)(=O)c4ccc(/C=C/C(=O)NO)cc4)cc3n2)cn1] |
| 223 | 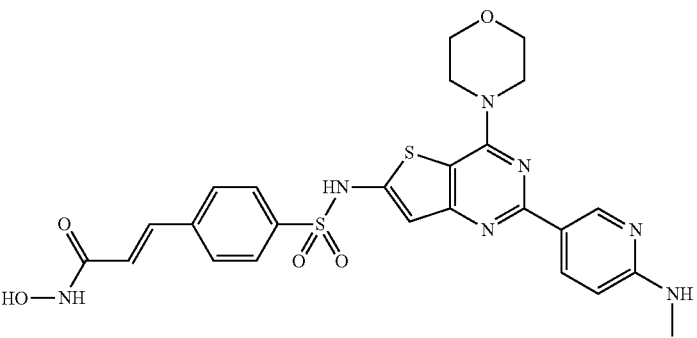 [SMILES: CNc1ccc(-c2nc(N3CCOCC3)c3sc(NS(=O)(=O)c4ccc(/C=C/C(=O)NO)cc4)cc3n2)cn1] |
| 224 | 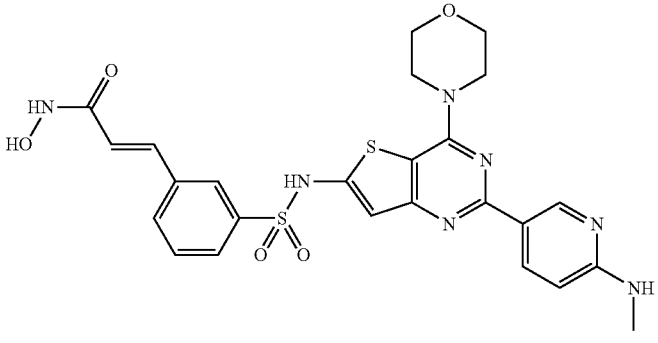 [SMILES: CNc1ccc(-c2nc(N3CCOCC3)c3sc(NS(=O)(=O)c4cccc(/C=C/C(=O)NO)c4)cc3n2)cn1] |
| 225 | 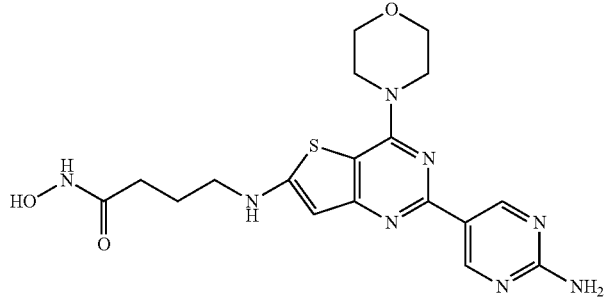 [SMILES: Nc1ncc(-c2nc(N3CCOCC3)c3sc(NCCCC(=O)NO)cc3n2)cn1] |

TABLE A-continued

| Compound No. | Structure |
|---|---|
| 226 | 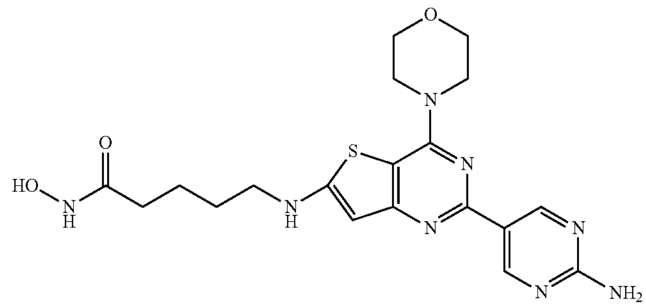 [SMILES: Nc1ncc(-c2nc(N3CCOCC3)c3sc(NCCCCC(=O)NO)cc3n2)cn1] |
| 227 | 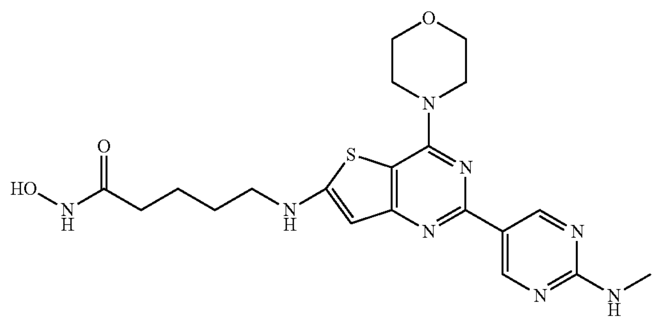 [SMILES: CNc1ncc(-c2nc(N3CCOCC3)c3sc(NCCCCC(=O)NO)cc3n2)cn1] |
| 228 | 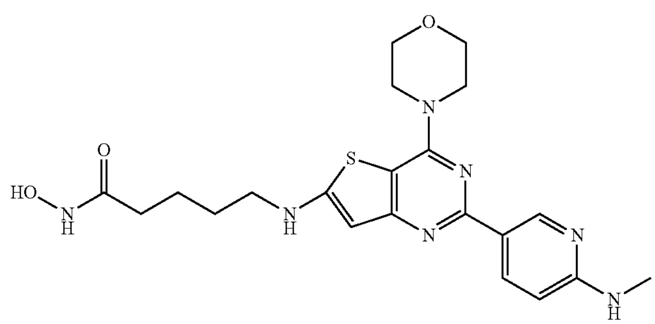 [SMILES: CNc1ccc(-c2nc(N3CCOCC3)c3sc(NCCCCC(=O)NO)cc3n2)cn1] |
| 229 | 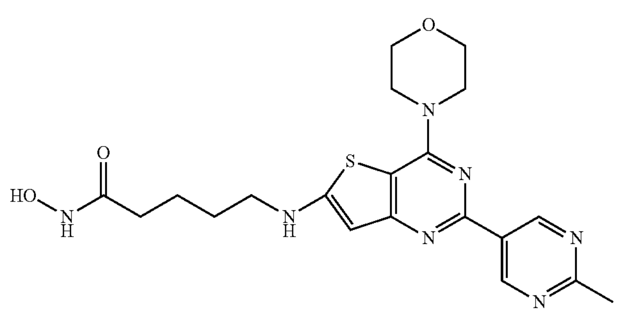 [SMILES: Cc1ncc(-c2nc(N3CCOCC3)c3sc(NCCCCC(=O)NO)cc3n2)cn1] |
| 230 | 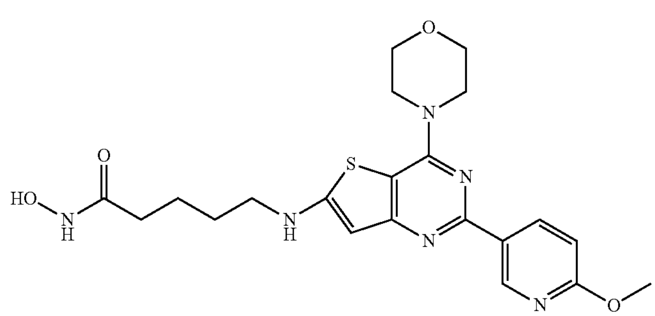 [SMILES: COc1ccc(-c2nc(N3CCOCC3)c3sc(NCCCCC(=O)NO)cc3n2)cn1] |

TABLE A-continued
| Compound No. | Structure |
|---|---|
| 231 | 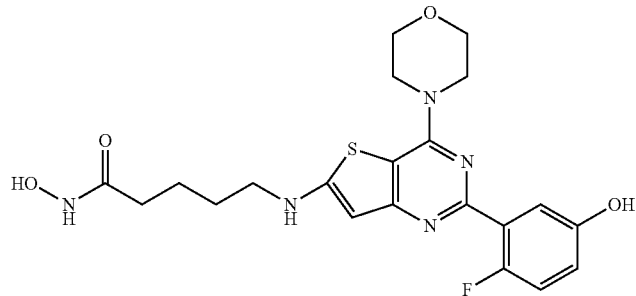 [SMILES: O=C(CCCCNc1cc2nc(-c3cc(O)ccc3F)nc(N3CCOCC3)c2s1)NO] |
| 232 | 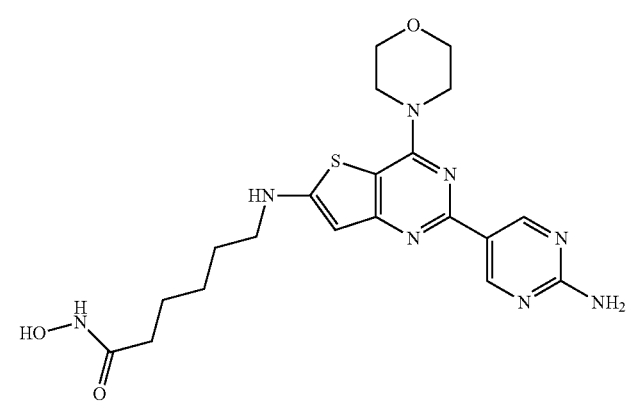 [SMILES: Nc1ncc(-c2nc(N3CCOCC3)c3sc(NCCCCCC(=O)NO)cc3n2)cn1] |
| 233 | 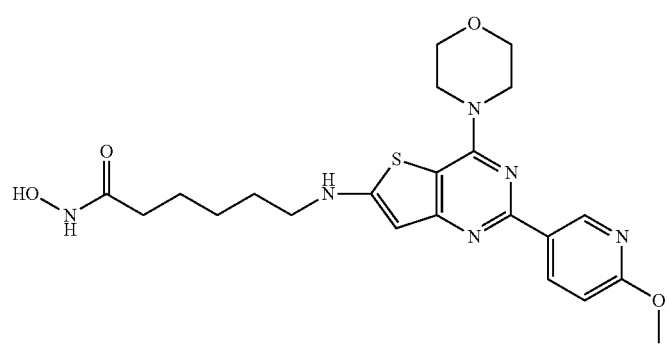 [SMILES: COc1ccc(-c2nc(N3CCOCC3)c3sc(NCCCCCC(=O)NO)cc3n2)cn1] |
| 234 | 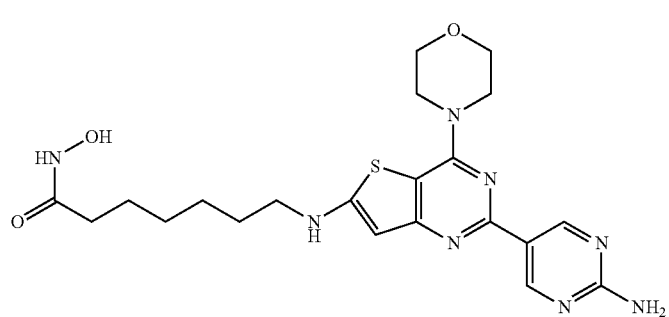 [SMILES: Nc1ncc(-c2nc(N3CCOCC3)c3sc(NCCCCCCC(=O)NO)cc3n2)cn1] |

TABLE A-continued
| Compound No. | Structure |
|---|---|
| 235 | 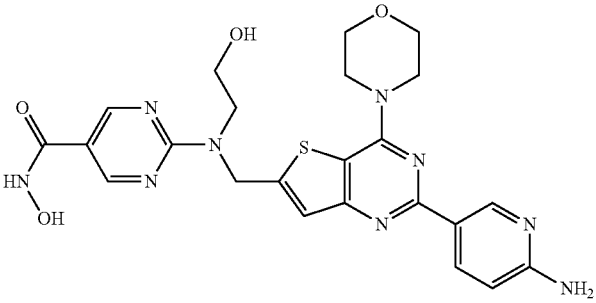 |
| 236 | 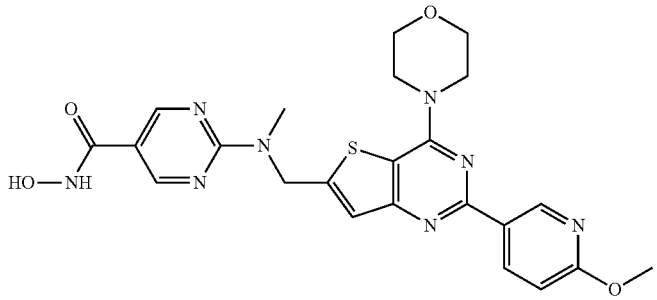 [SMILES: COc1ccc(-c2nc(N3CCOCC3)c3sc(CN(C)c4ncc(C(=O)NO)cn4)cc3n2)cn1] |
| 237 | 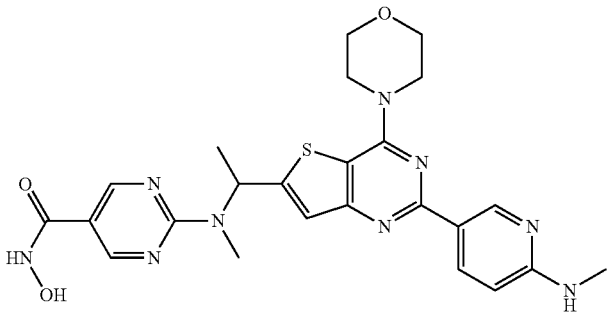 [SMILES: CNc1ccc(-c2nc(N3CCOCC3)c3sc(C(C)N(C)c4ncc(C(=O)NO)cn4)cc3n2)cn1] |
| 238 | 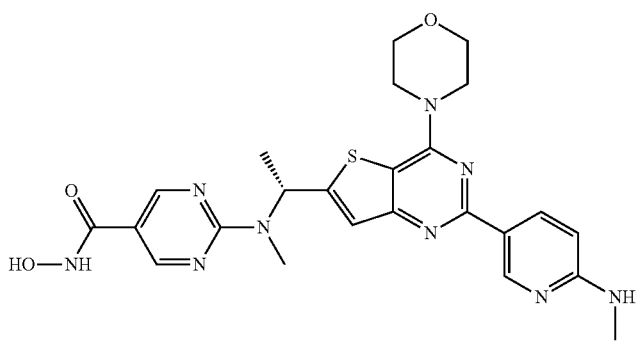 [SMILES: CNc1ccc(-c2nc(N3CCOCC3)c3sc([C@@H](C)N(C)c4ncc(C(=O)NO)cn4)cc3n2)cn1] |
| 239 | 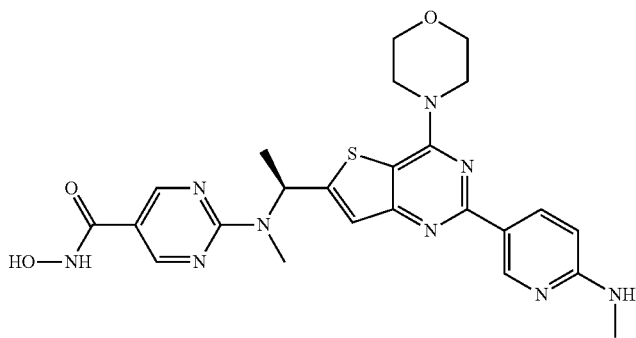 [SMILES: CNc1ccc(-c2nc(N3CCOCC3)c3sc([C@H](C)N(C)c4ncc(C(=O)NO)cn4)cc3n2)cn1] |

TABLE A-continued

| Compound No. | Structure |
| --- | --- |
| 240 | 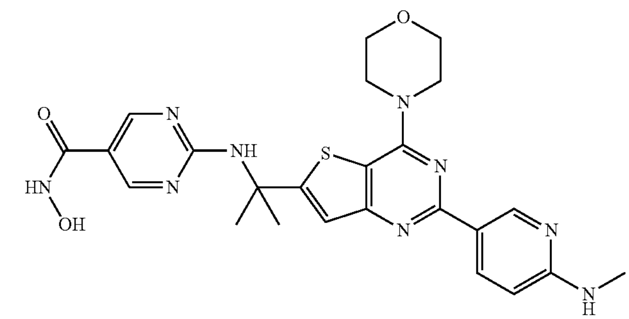 [SMILES: CNc1ccc(-c2nc(N3CCOCC3)c3sc(C(C)(C)Nc4ncc(C(=O)NO)cn4)cc3n2)cn1] |
| 241 | 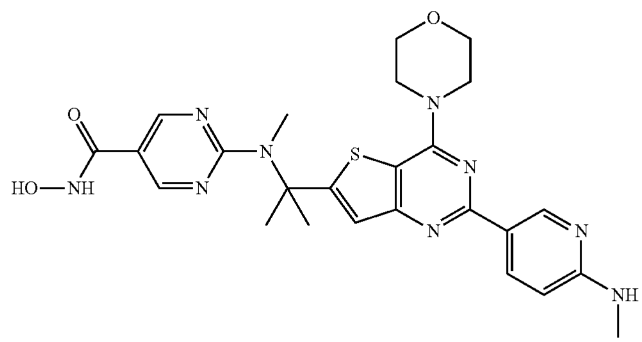 [SMILES: CNc1ccc(-c2nc(N3CCOCC3)c3sc(C(C)(C)N(C)c4ncc(C(=O)NO)cn4)cc3n2)cn1] |
| 242 | 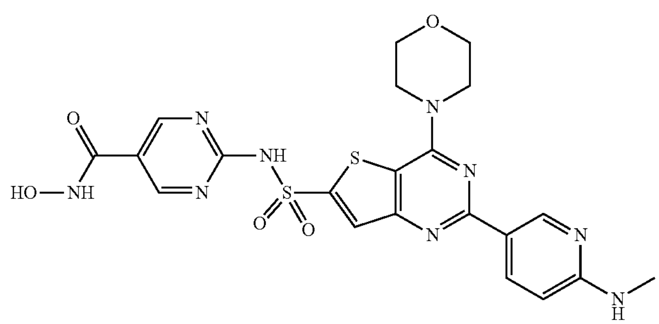 [SMILES: CNc1ccc(-c2nc(N3CCOCC3)c3sc(S(=O)(=O)Nc4ncc(C(=O)NO)cn4)cc3n2)cn1] |
| 243 | 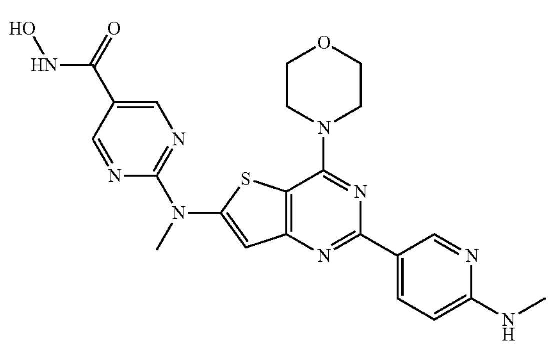 [SMILES: CNc1ccc(-c2nc(N3CCOCC3)c3sc(N(C)c4ncc(C(=O)NO)cn4)cc3n2)cn1] |

TABLE A-continued

| Compound No. | Structure |
|---|---|
| 244 | 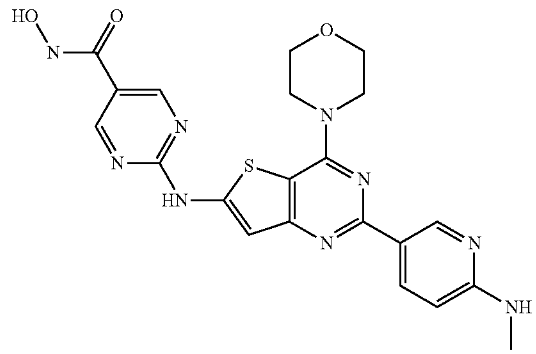 [SMILES: CNc1ccc(-c2nc(N3CCOCC3)c3sc(Nc4ncc(C(=O)NO)cn4)cc3n2)cn1] |
| 245 | 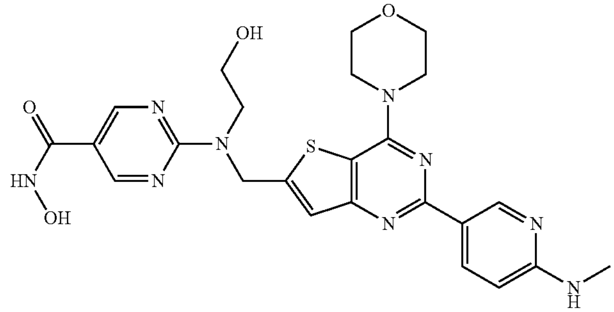 [SMILES: CNc1ccc(-c2nc(N3CCOCC3)c3sc(CN(CCO)c4ncc(C(=O)NO)cn4)cc3n2)cn1] |
| 246 | 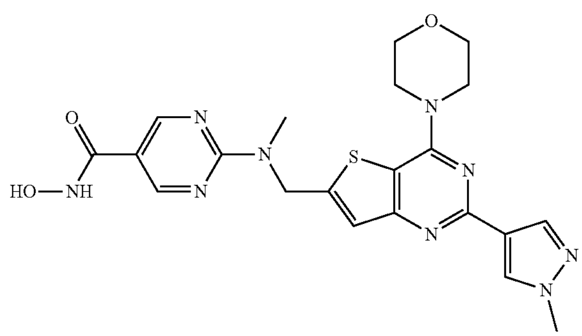 [SMILES: CN(Cc1cc2nc(-c3cnn(C)c3)nc(N3CCOCC3)c2s1)c1ncc(C(=O)NO)cn1] |
| 247 | 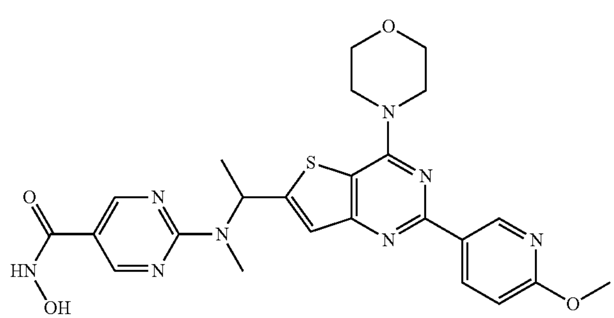 [SMILES: COc1ccc(-c2nc(N3CCOCC3)c3sc(C(C)N(C)c4ncc(C(=O)NO)cn4)cc3n2)cn1] |

US 10,894,795 B2
129                                                                                                      130
TABLE A-continued
| Compound No. | Structure |
|---|---|
| 248 | 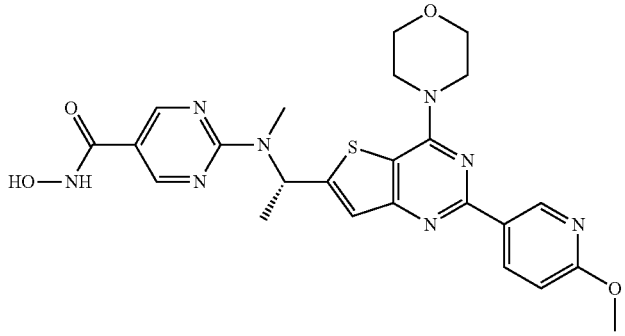 [SMILES: COc1ccc(-c2nc(N3CCOCC3)c3sc([C@H](C)N(C)c4ncc(C(=O)NO)cn4)cc3n2)cn1] |
| 249 | 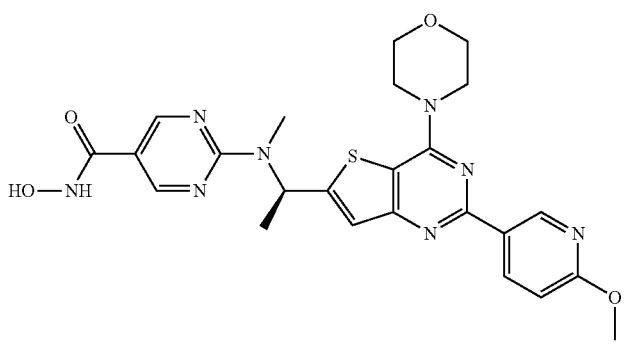 [SMILES: COc1ccc(-c2nc(N3CCOCC3)c3sc([C@@H](C)N(C)c4ncc(C(=O)NO)cn4)cc3n2)cn1] |
| 250 | 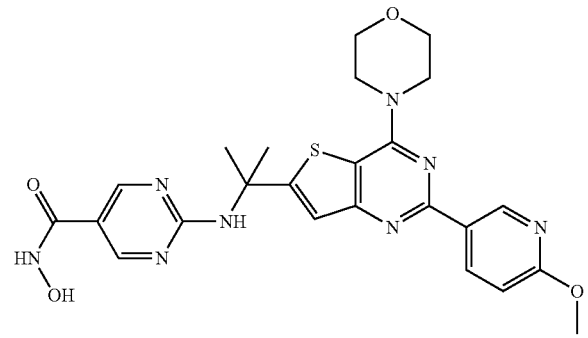 [SMILES: COc1ccc(-c2nc(N3CCOCC3)c3sc(C(C)(C)Nc4ncc(C(=O)NO)cn4)cc3n2)cn1] |
| 251 | 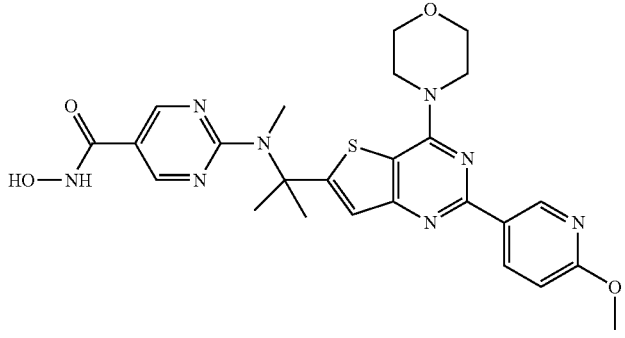 [SMILES: COc1ccc(-c2nc(N3CCOCC3)c3sc(C(C)(C)N(C)c4ncc(C(=O)NO)cn4)cc3n2)cn1] |

TABLE A-continued

| Compound No. | Structure |
|---|---|
| 252 | 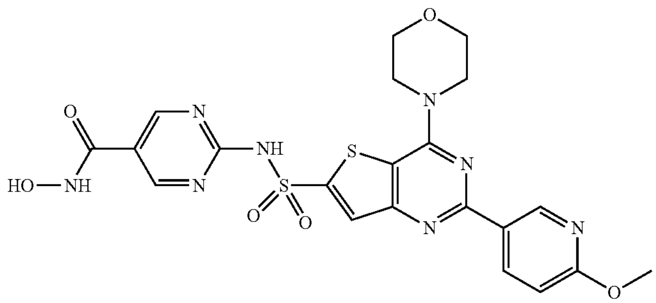 [SMILES: COc1ccc(-c2nc(N3CCOCC3)c3sc(S(=O)(=O)Nc4ncc(C(=O)NO)cn4)cc3n2)cn1] |
| 253 | 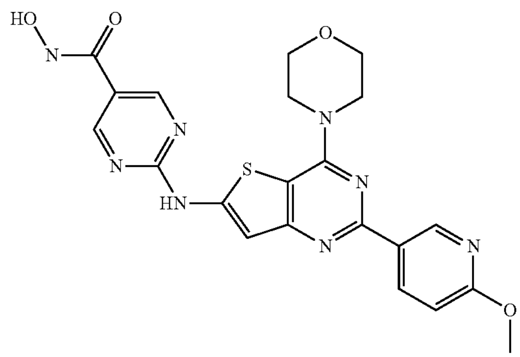 [SMILES: COc1ccc(-c2nc(N3CCOCC3)c3sc(Nc4ncc(C(=O)NO)cn4)cc3n2)cn1] |
| 254 | 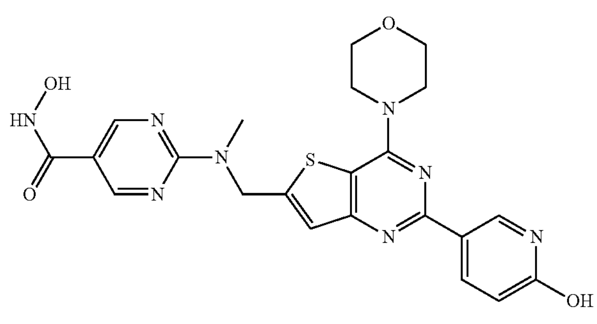 [SMILES: CN(Cc1cc2nc(-c3ccc(O)nc3)nc(N3CCOCC3)c2s1)c1ncc(C(=O)NO)cn1] |
| 255 | 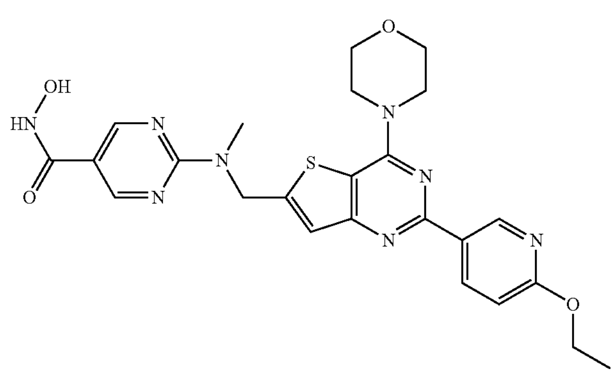 [SMILES: CCOc1ccc(-c2nc(N3CCOCC3)c3sc(CN(C)c4ncc(C(=O)NO)cn4)cc3n2)cn1] |

TABLE A-continued
| Compound No. | Structure |
|---|---|
| 256 | 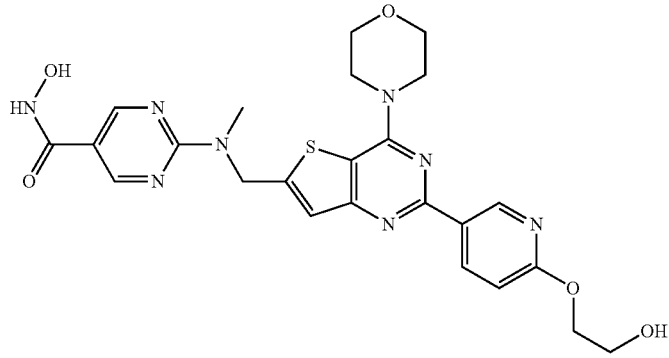 [SMILES: CN(Cc1cc2nc(-c3ccc(OCCO)nc3)nc(N3CCOCC3)c2s1)c1ncc(C(=O)NO)cn1] |
| 257 | 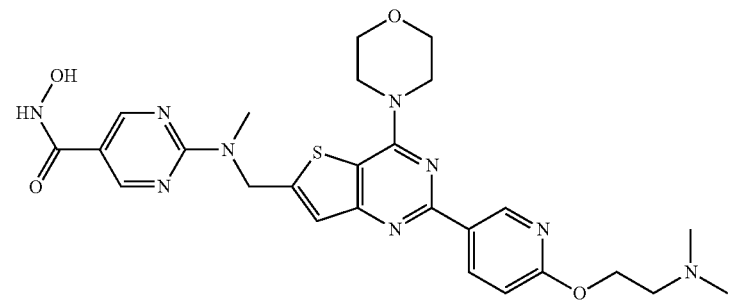 [SMILES: CN(C)CCOc1ccc(-c2nc(N3CCOCC3)c3sc(CN(C)c4ncc(C(=O)NO)cn4)cc3n2)cn1] |
| 258 | 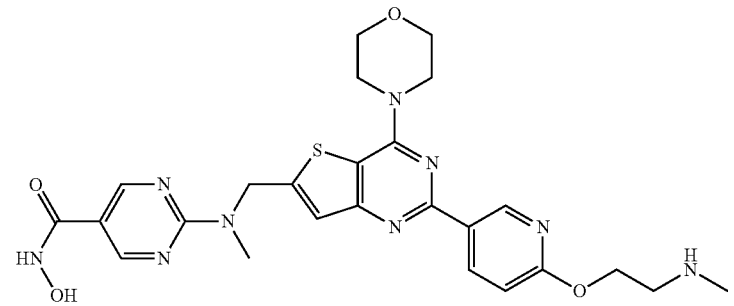 [SMILES: CNCCOc1ccc(-c2nc(N3CCOCC3)c3sc(CN(C)c4ncc(C(=O)NO)cn4)cc3n2)cn1] |
| 259 | 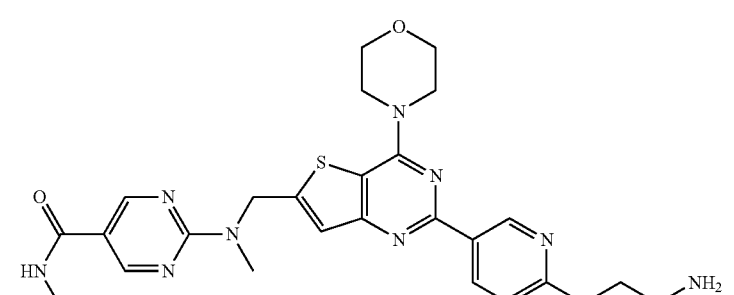 |

TABLE A-continued
| Compound No. | Structure |
|---|---|
| 260 | 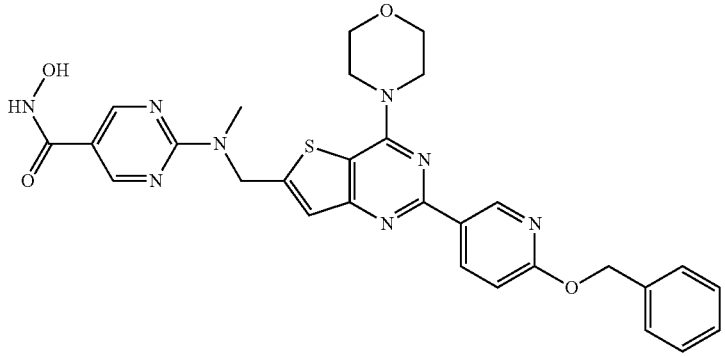 [SMILES: CN(Cc1cc2nc(-c3ccc(OCc4ccccc4)nc3)nc(N3CCOCC3)c2s1)c1ncc(C(=O)NO)cn1] |
| 261 | 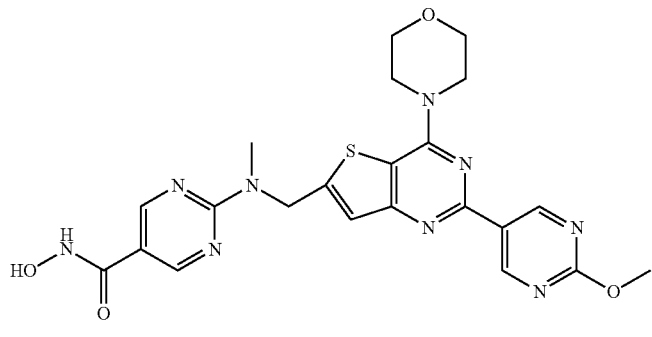 [SMILES: COc1ncc(-c2nc(N3CCOCC3)c3sc(CN(C)c4ncc(C(=O)NO)cn4)cc3n2)cn1] |
| 262 | 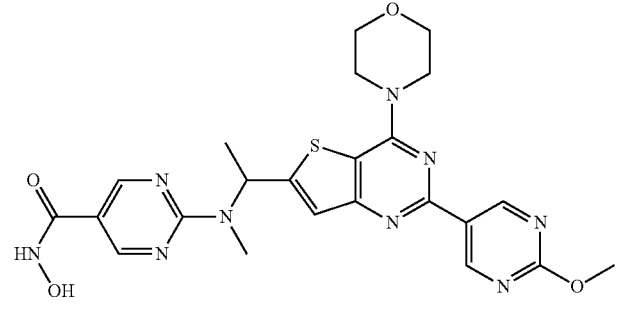 [SMILES: COc1ncc(-c2nc(N3CCOCC3)c3sc(C(C)N(C)c4ncc(C(=O)NO)cn4)cc3n2)cn1] |
| 263 | 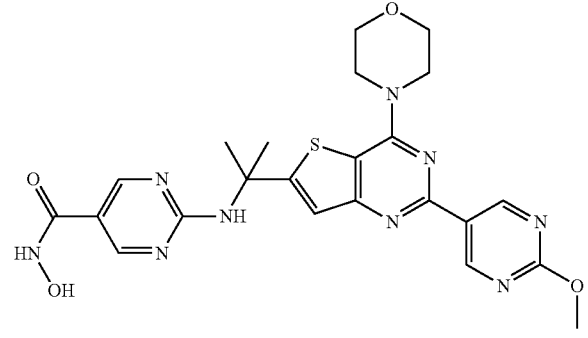 [SMILES: COc1ncc(-c2nc(N3CCOCC3)c3sc(C(C)(C)Nc4ncc(C(=O)NO)cn4)cc3n2)cn1] |

| Compound No. | Structure |
|---|---|
| 264 | 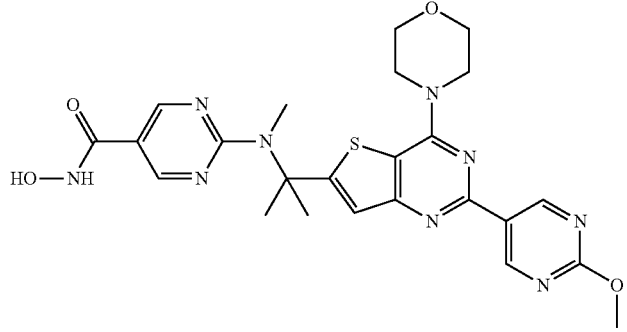 [SMILES: COc1ncc(-c2nc(N3CCOCC3)c3sc(C(C)(C)N(C)c4ncc(C(=O)NO)cn4)cc3n2)cn1] |
| 265 | 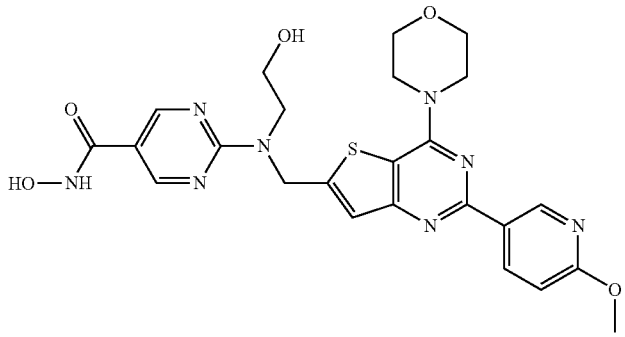 [SMILES: COc1ccc(-c2nc(N3CCOCC3)c3sc(CN(CCO)c4ncc(C(=O)NO)cn4)cc3n2)cn1] |
| 266 | 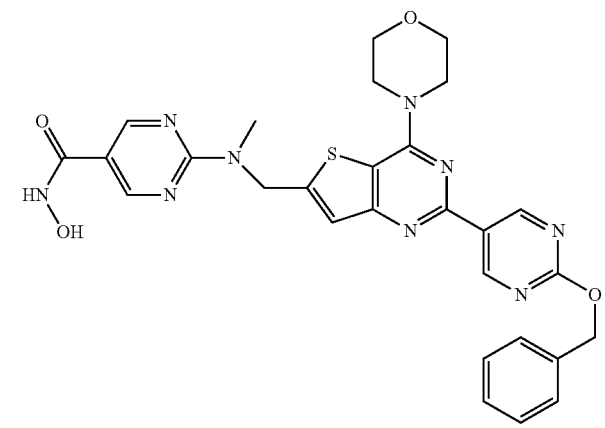 [SMILES: CN(Cc1cc2nc(-c3cnc(OCc4ccccc4)nc3)nc(N3CCOCC3)c2s1)c1ncc(C(=O)NO)cn1] |
| 267 | 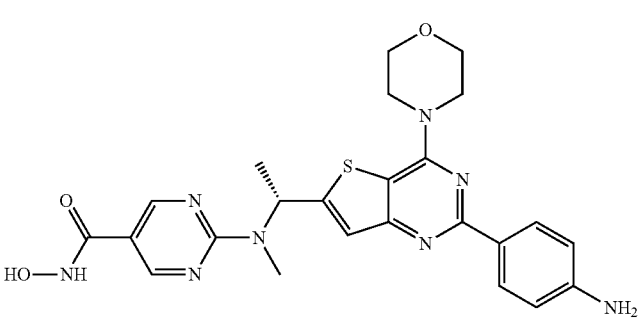 [SMILES: C[C@H](c1cc2nc(-c3ccc(N)cc3)nc(N3CCOCC3)c2s1)N(C)c1ncc(C(=O)NO)cn1] |

TABLE A-continued

| Compound No. | Structure |
|---|---|
| 268 | 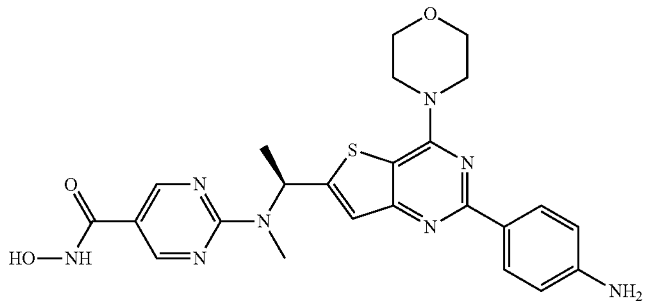 [SMILES: C[C@@H](c1cc2nc(-c3ccc(N)cc3)nc(N3CCOCC3)c2s1)N(C)c1ncc(C(=O)NO)cn1] |
| 269 | 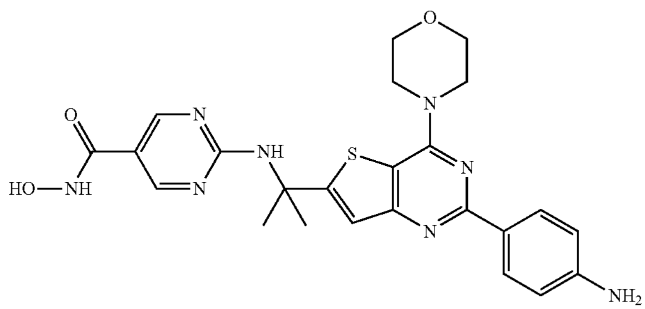 |
| 270 | 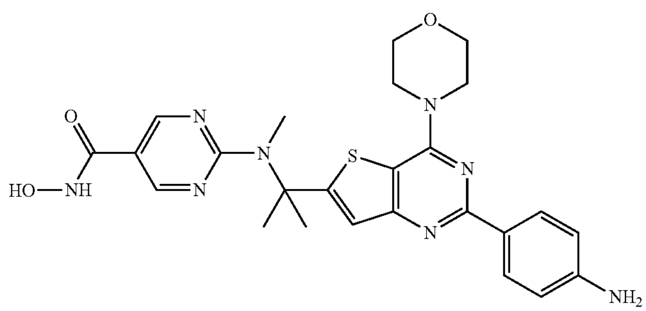 [SMILES: CN(c1ncc(C(=O)NO)cn1)C(C)(C)c1cc2nc(-c3ccc(N)cc3)nc(N3CCOCC3)c2s1] |
| 271 | 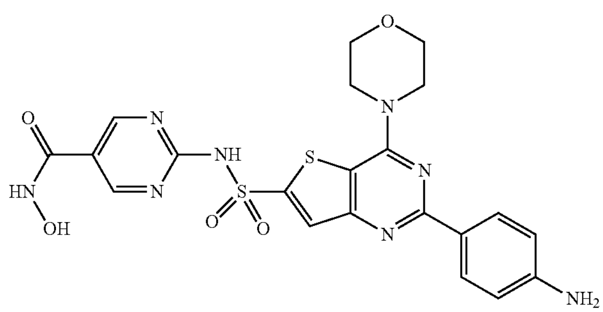 [SMILES: Nc1ccc(-c2nc(N3CCOCC3)c3sc(S(=O)(=O)Nc4ncc(C(=O)NO)cn4)cc3n2)cc1] |
| 272 | 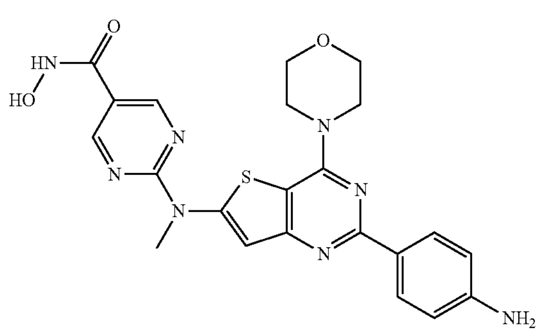 [SMILES: CN(c1ncc(C(=O)NO)cn1)c1cc2nc(-c3ccc(N)cc3)nc(N3CCOCC3)c2s1] |

TABLE A-continued
| Compound No. | Structure |
|---|---|
| 273 | 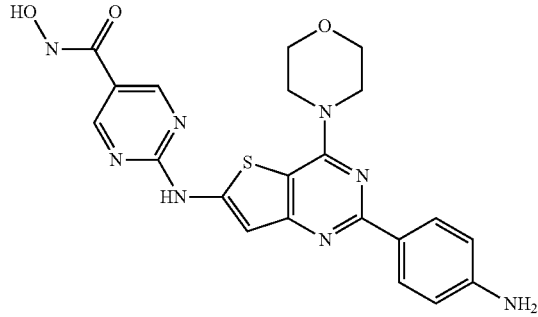 [SMILES: Nc1ccc(-c2nc(N3CCOCC3)c3sc(Nc4ncc(C(=O)NO)cn4)cc3n2)cc1] |
| 274 | 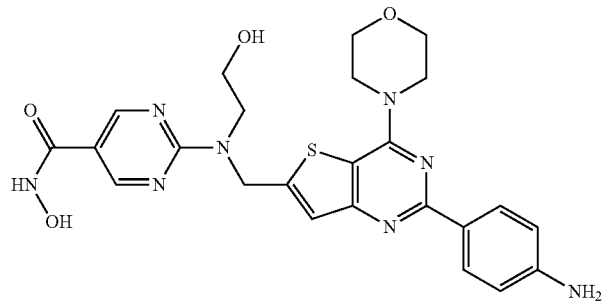 [SMILES: Nc1ccc(-c2nc(N3CCOCC3)c3sc(CN(CCO)c4ncc(C(=O)NO)cn4)cc3n2)cc1] |
| 275 | 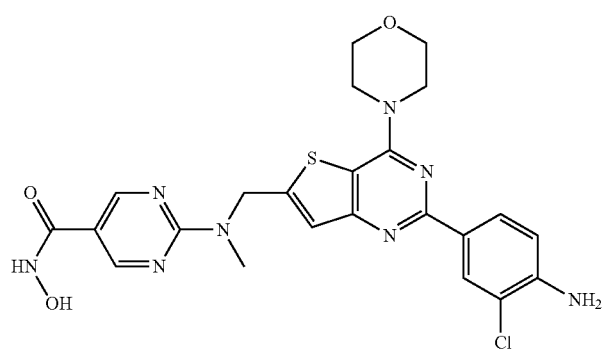 [SMILES: CN(Cc1cc2nc(-c3ccc(N)c(Cl)c3)nc(N3CCOCC3)c2s1)c1ncc(C(=O)NO)cn1] |
| 276 | 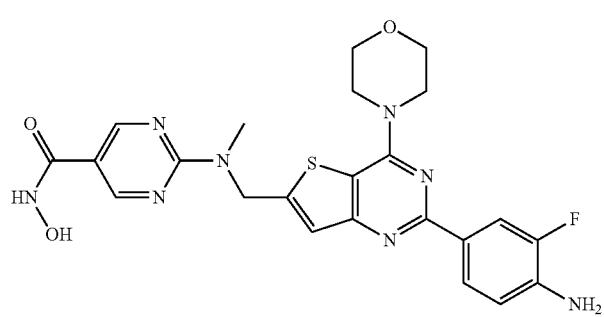 [SMILES: CN(Cc1cc2nc(-c3ccc(N)c(F)c3)nc(N3CCOCC3)c2s1)c1ncc(C(=O)NO)cn1] |
| 277 | 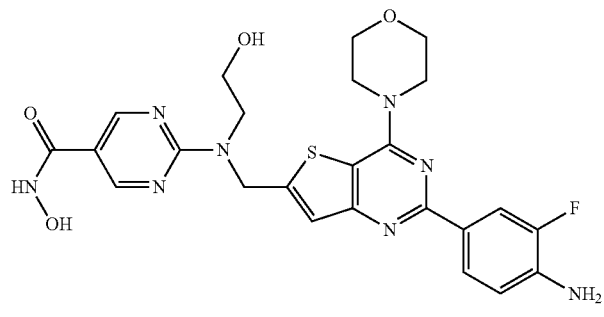 [SMILES: Nc1ccc(-c2nc(N3CCOCC3)c3sc(CN(CCO)c4ncc(C(=O)NO)cn4)cc3n2)cc1F] |

143
144
TABLE A-continued
| Compound No. | Structure |
|---|---|
| 278 | 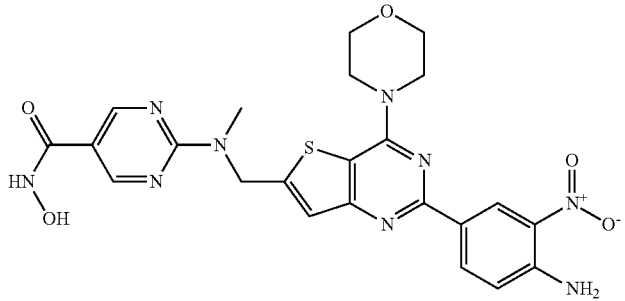 [SMILES: CN(Cc1cc2nc(-c3ccc(N)c([N+](=O)[O-])c3)nc(N3CCOCC3)c2s1)c1ncc(C(=O)NO)cn1] |
| 279 | 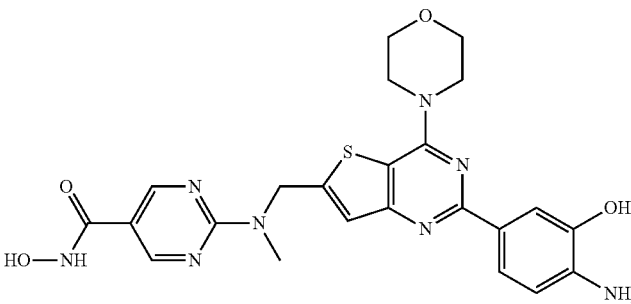 |
| 280 | 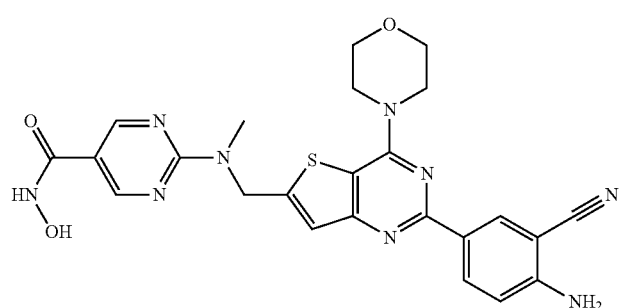 |
| 281 | 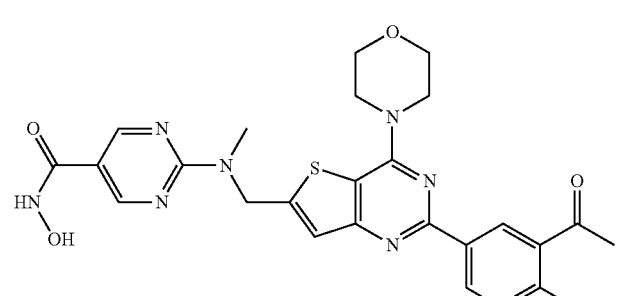 |
| 282 | 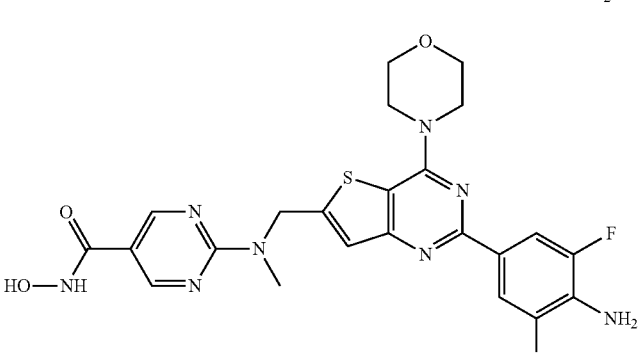 |

TABLE A-continued
| Compound No. | Structure |
|---|---|
| 283 | 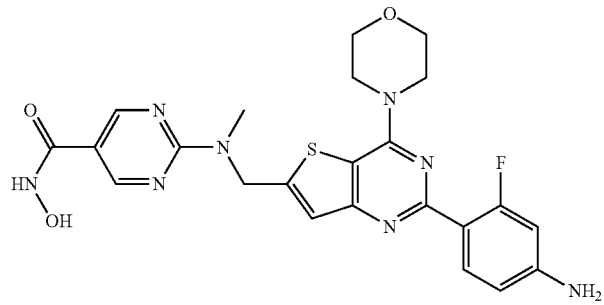 [SMILES: CN(Cc1cc2nc(-c3ccc(N)cc3F)nc(N3CCOCC3)c2s1)c1ncc(C(=O)NO)cn1] |
| 284 | 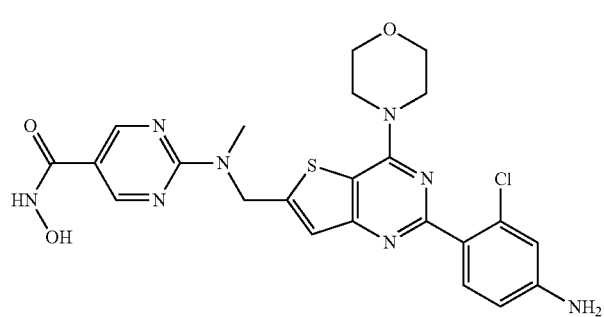 [SMILES: CN(Cc1cc2nc(-c3ccc(N)cc3Cl)nc(N3CCOCC3)c2s1)c1ncc(C(=O)NO)cn1] |
| 285 | 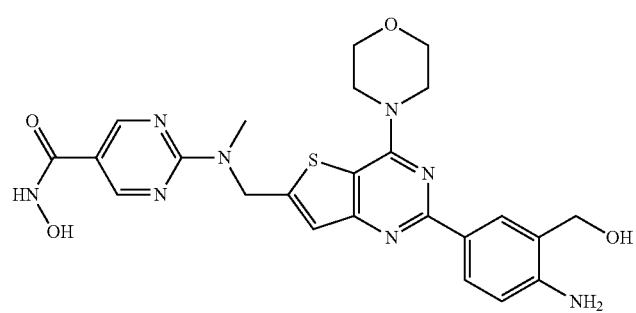 [SMILES: CN(Cc1cc2nc(-c3ccc(N)c(CO)c3)nc(N3CCOCC3)c2s1)c1ncc(C(=O)NO)cn1] |
| 286 | 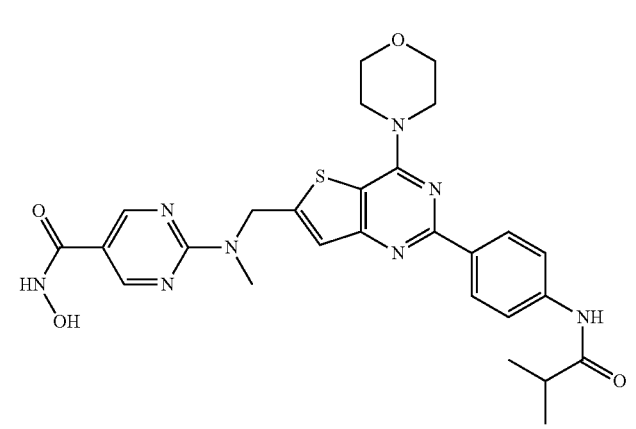 [SMILES: CC(C)C(=O)Nc1ccc(-c2nc(N3CCOCC3)c3sc(CN(C)c4ncc(C(=O)NO)cn4)cc3n2)cc1] |

TABLE A-continued

| Compound No. | Structure |
|---|---|
| 287 | 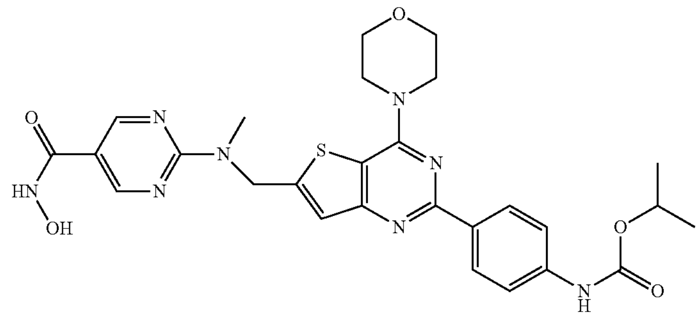 [SMILES: CC(C)OC(=O)Nc1ccc(-c2nc(N3CCOCC3)c3sc(CN(C)c4ncc(C(=O)NO)cn4)cc3n2)cc1] |
| 288 | 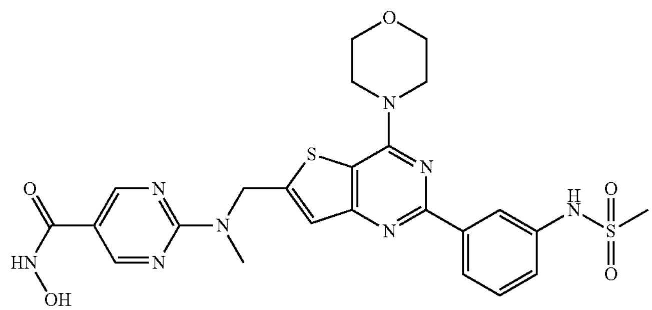 [SMILES: CN(Cc1cc2nc(-c3cccc(NS(C)(=O)=O)c3)nc(N3CCOCC3)c2s1)c1ncc(C(=O)NO)cn1] |
| 289 | 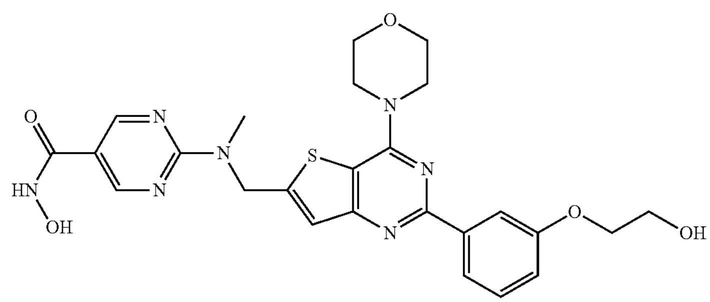 [SMILES: CN(Cc1cc2nc(-c3cccc(OCCO)c3)nc(N3CCOCC3)c2s1)c1ncc(C(=O)NO)cn1] |
| 290 | 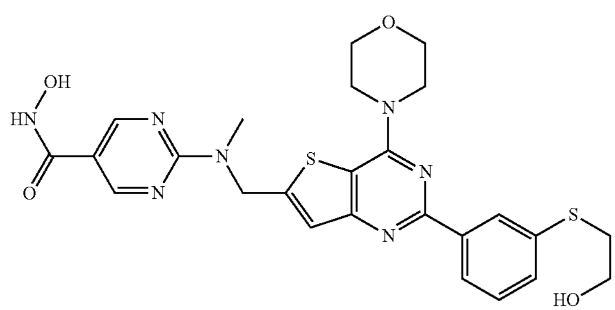 [SMILES: CN(Cc1cc2nc(-c3cccc(SCCO)c3)nc(N3CCOCC3)c2s1)c1ncc(C(=O)NO)cn1] |
| 291 | 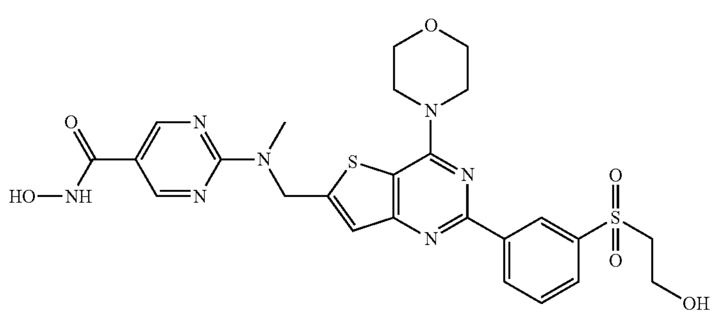 [SMILES: CN(Cc1cc2nc(-c3cccc(S(=O)(=O)CCO)c3)nc(N3CCOCC3)c2s1)c1ncc(C(=O)NO)cn1] |

TABLE A-continued

| Compound No. | Structure |
|---|---|
| 292 | 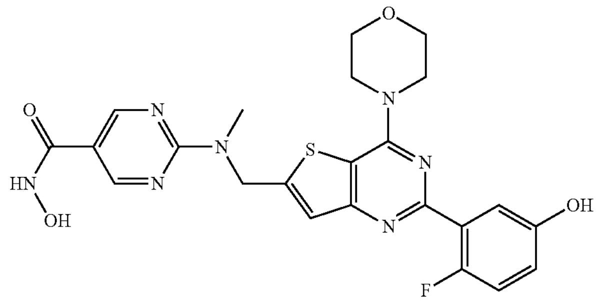 [SMILES: CN(Cc1cc2nc(-c3cc(O)ccc3F)nc(N3CCOCC3)c2s1)c1ncc(C(=O)NO)cn1] |
| 293 | 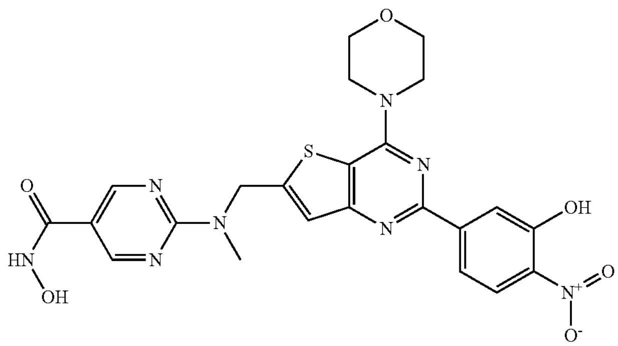 [SMILES: CN(Cc1cc2nc(-c3ccc([N+](=O)[O-])c(O)c3)nc(N3CCOCC3)c2s1)c1ncc(C(=O)NO)cn1] |
| 294 | 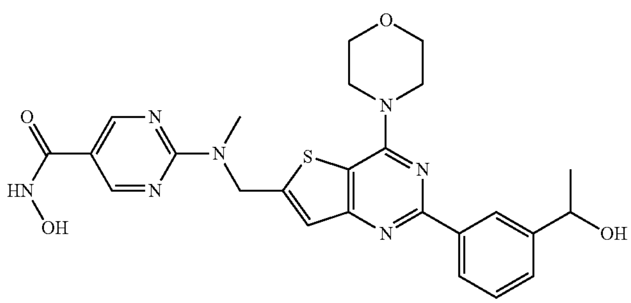 [SMILES: CC(O)c1cccc(-c2nc(N3CCOCC3)c3sc(CN(C)c4ncc(C(=O)NO)cn4)cc3n2)c1] |
| 295 | 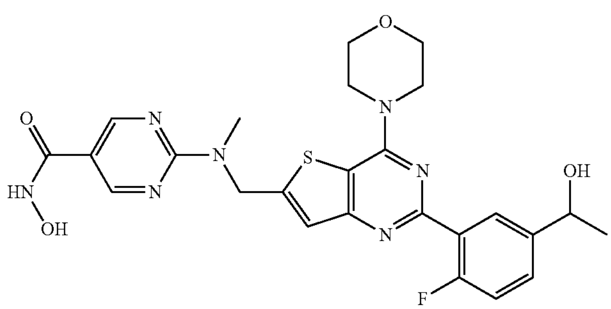 [SMILES: CC(O)c1ccc(F)c(-c2nc(N3CCOCC3)c3sc(CN(C)c4ncc(C(=O)NO)cn4)cc3n2)c1] |
| 296 | 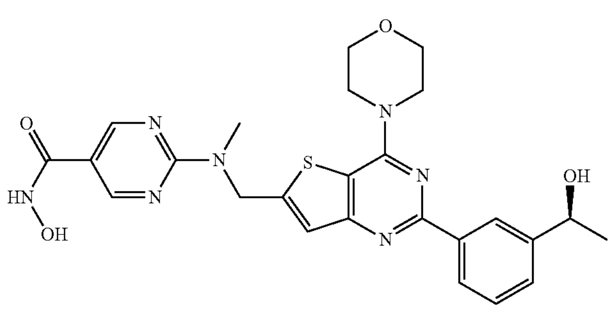 [SMILES: C[C@H](O)c1cccc(-c2nc(N3CCOCC3)c3sc(CN(C)c4ncc(C(=O)NO)cn4)cc3n2)c1] |

US 10,894,795 B2
151	152
TABLE A-continued
| Compound No. | Structure |
|---|---|
| 297 | 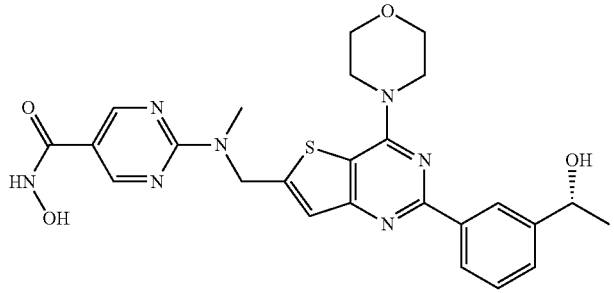 [SMILES: C[C@@H](O)c1cccc(-c2nc(N3CCOCC3)c3sc(CN(C)c4ncc(C(=O)NO)cn4)cc3n2)c1] |
| 298 | 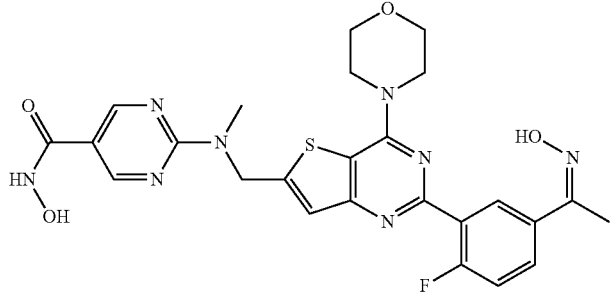 [SMILES: C/C(=N/O)c1ccc(F)c(-c2nc(N3CCOCC3)c3sc(CN(C)c4ncc(C(=O)NO)cn4)cc3n2)c1] |
| 299 | 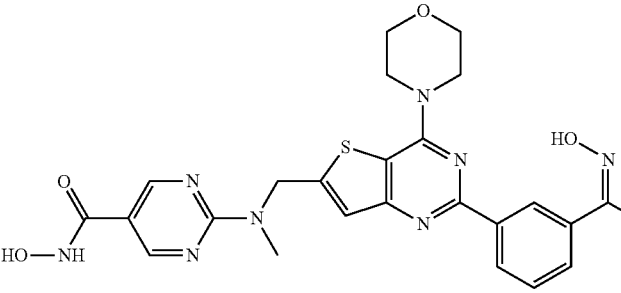 |
| 300 | 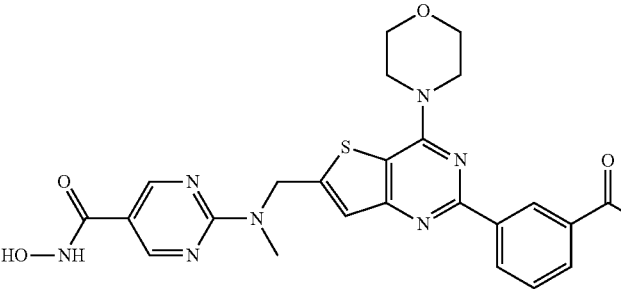 |
| 301 | 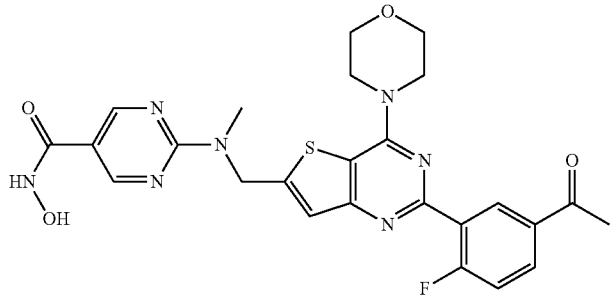 |

TABLE A-continued

| Compound No. | Structure |
|---|---|
| 302 | 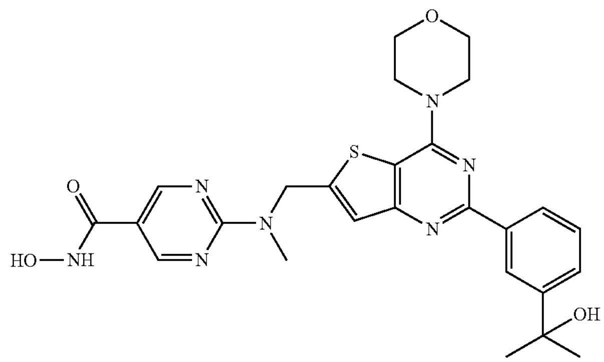 [SMILES: CN(Cc1cc2nc(-c3cccc(C(C)(C)O)c3)nc(N3CCOCC3)c2s1)c1ncc(C(=O)NO)cn1] |
| 303 | 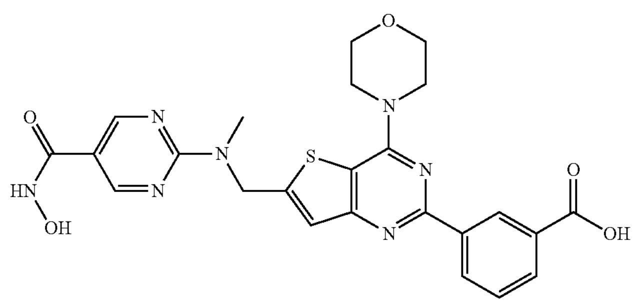 [SMILES: CN(Cc1cc2nc(-c3cccc(C(=O)O)c3)nc(N3CCOCC3)c2s1)c1ncc(C(=O)NO)cn1] |
| 304 | 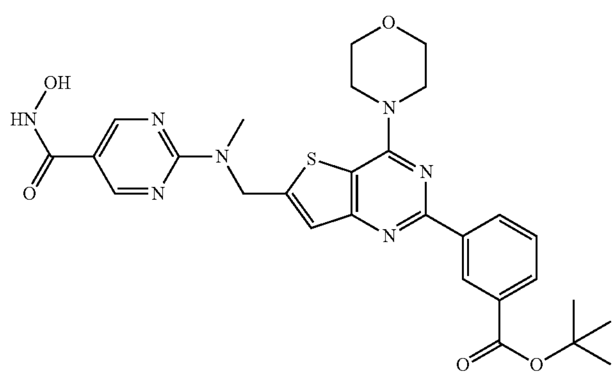 [SMILES: CN(Cc1cc2nc(-c3cccc(C(=O)OC(C)(C)C)c3)nc(N3CCOCC3)c2s1)c1ncc(C(=O)NO)cn1] |
| 305 | 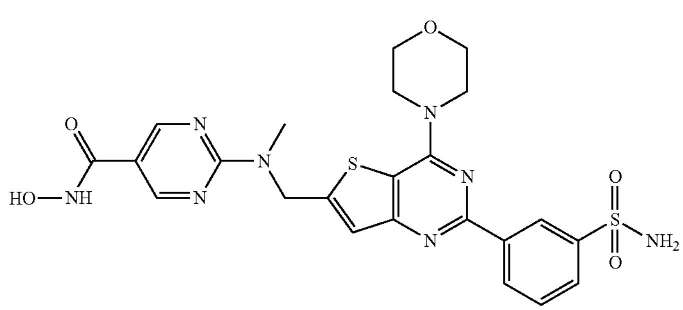 [SMILES: CN(Cc1cc2nc(-c3cccc(S(N)(=O)=O)c3)nc(N3CCOCC3)c2s1)c1ncc(C(=O)NO)cn1] |

TABLE A-continued

| Compound No. | Structure |
|---|---|
| 306 | 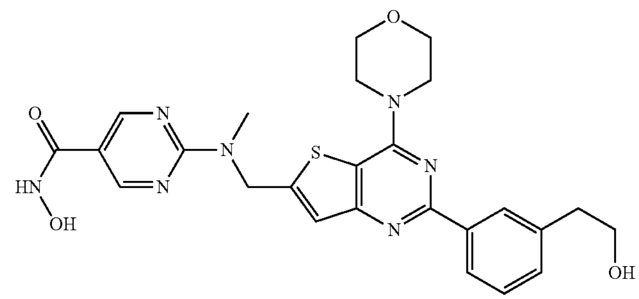 [SMILES: CN(Cc1cc2nc(-c3cccc(CCO)c3)nc(N3CCOCC3)c2s1)c1ncc(C(=O)NO)cn1] |
| 307 | 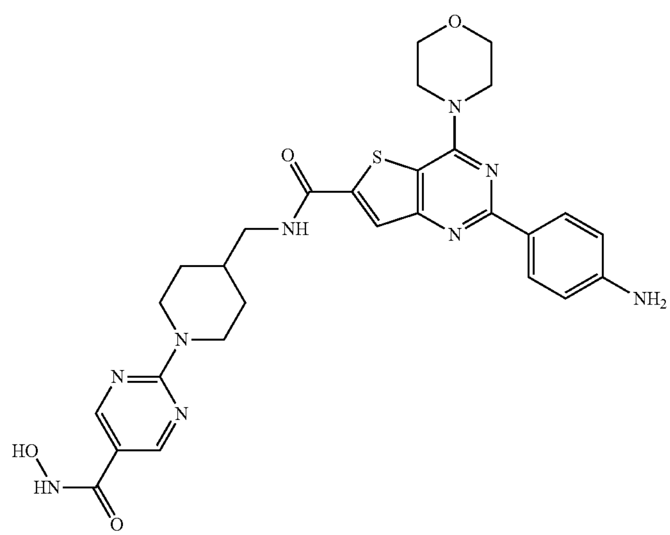 [SMILES: Nc1ccc(-c2nc(N3CCOCC3)c3sc(C(=O)NCC4CCN(c5ncc(C(=O)NO)cn5)CC4)cc3n2)cc1] |
| 308 | 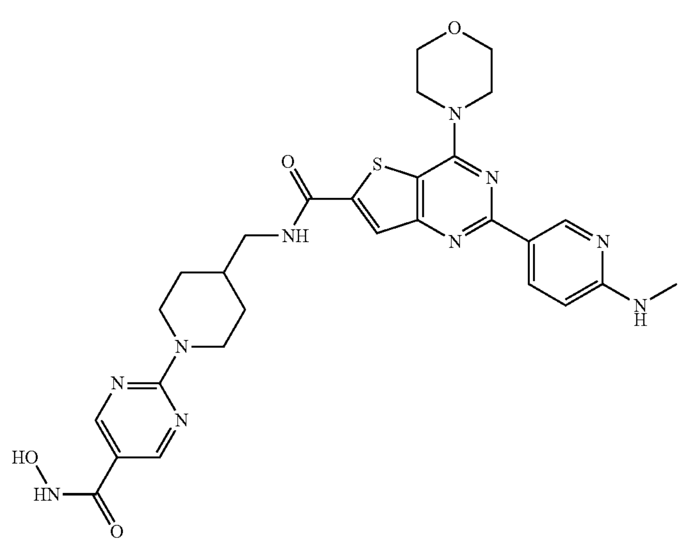 [SMILES: CNc1ccc(-c2nc(N3CCOCC3)c3sc(C(=O)NCC4CCN(c5ncc(C(=O)NO)cn5)CC4)cc3n2)cn1] |

TABLE A-continued
| Compound No. | Structure |
|---|---|
| 309 | 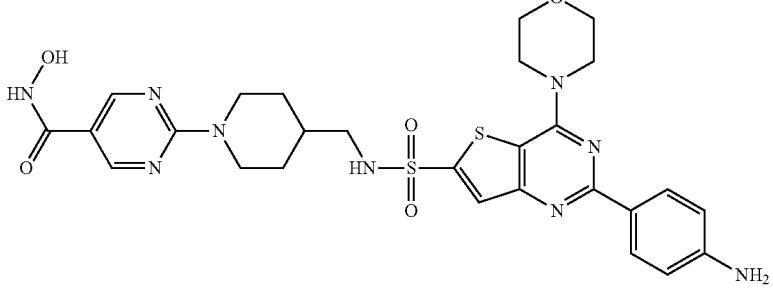 |
| 310 | 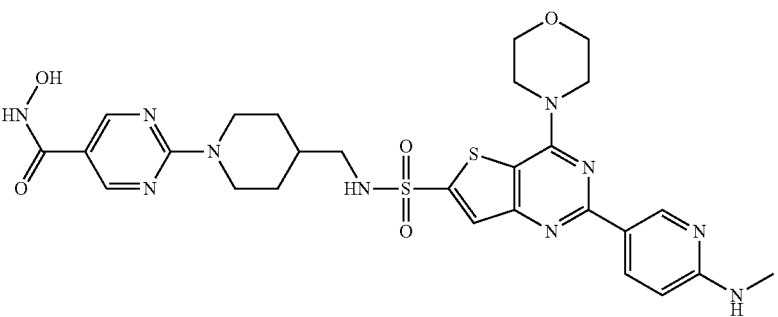 [SMILES: CNc1ccc(-c2nc(N3CCOCC3)c3sc(S(=O)(=O)NCC4CCN(c5ncc(C(=O)NO)cn5)CC4)cc3n2)cn1] |
| 311 | 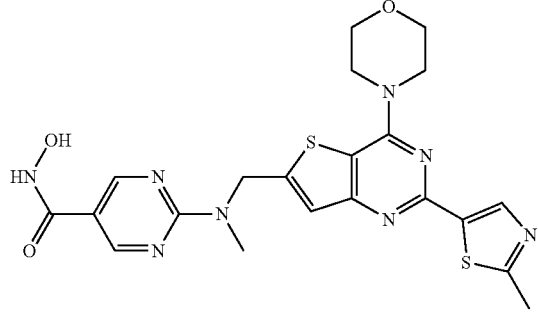 [SMILES: Cc1ncc(-c2nc(N3CCOCC3)c3sc(CN(C)c4ncc(C(=O)NO)cn4)cc3n2)s1] |
| 312 | 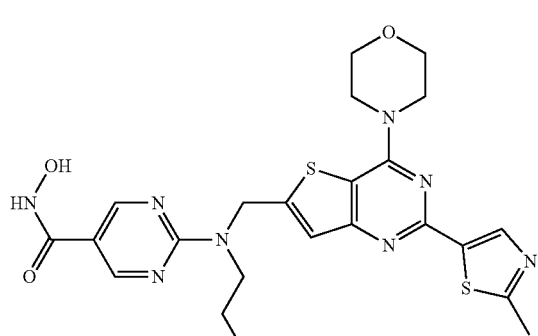 |

TABLE A-continued

| Compound No. | Structure |
|---|---|
| 313 | 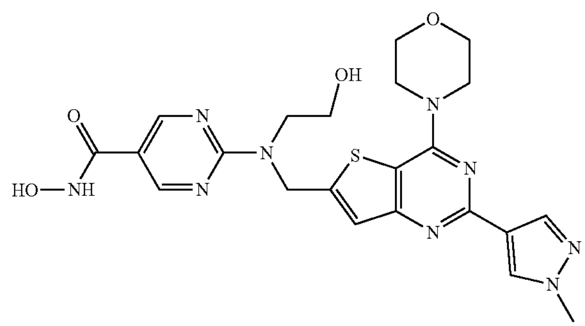 [SMILES: Cn1cc(-c2nc(N3CCOCC3)c3sc(CN(CCO)c4ncc(C(=O)NO)cn4)cc3n2)cn1] |
| 314 | 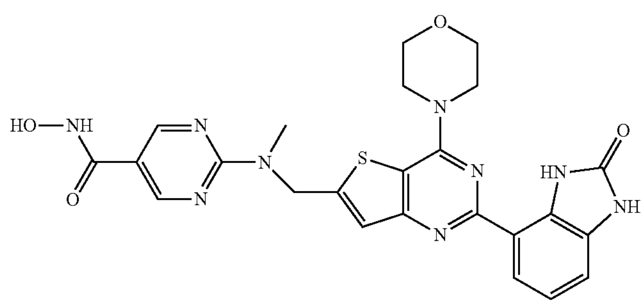 [SMILES: CN(Cc1cc2nc(-c3cccc4[nH]c(=O)[nH]c34)nc(N3CCOCC3)c2s1)c1ncc(C(=O)NO)cn1] |
| 315 | 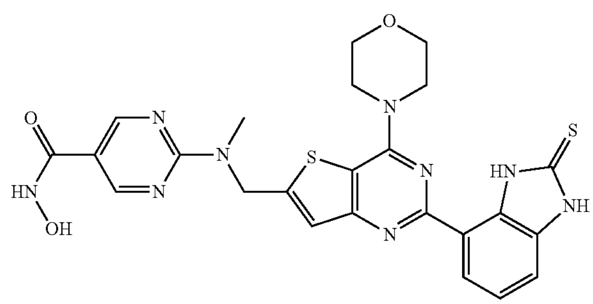 [SMILES: CN(Cc1cc2nc(-c3cccc4[nH]c(=S)[nH]c34)nc(N3CCOCC3)c2s1)c1ncc(C(=O)NO)cn1] |
| 316 | 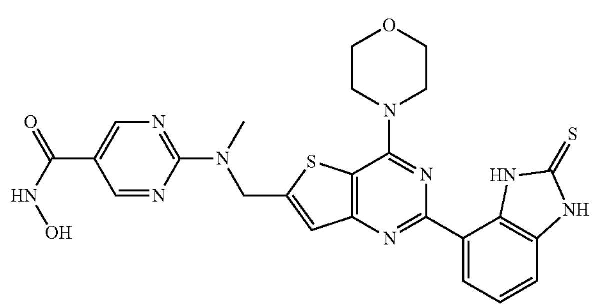 [SMILES: CN(Cc1cc2nc(-c3cccc4[nH]c(=S)[nH]c34)nc(N3CCOCC3)c2s1)c1ncc(C(=O)NO)cn1] |
| 317 | 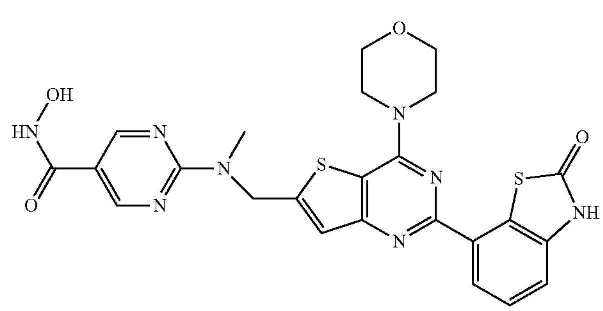 [SMILES: CN(Cc1cc2nc(-c3cccc4[nH]c(=O)sc34)nc(N3CCOCC3)c2s1)c1ncc(C(=O)NO)cn1] |

TABLE A-continued
| Compound No. | Structure |
|---|---|
| 318 | 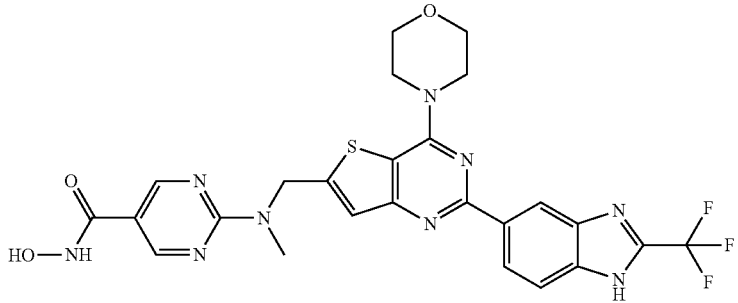 [SMILES: CN(Cc1cc2nc(-c3ccc4[nH]c(C(F)(F)F)nc4c3)nc(N3CCOCC3)c2s1)c1ncc(C(=O)NO)cn1] |
| 319 | 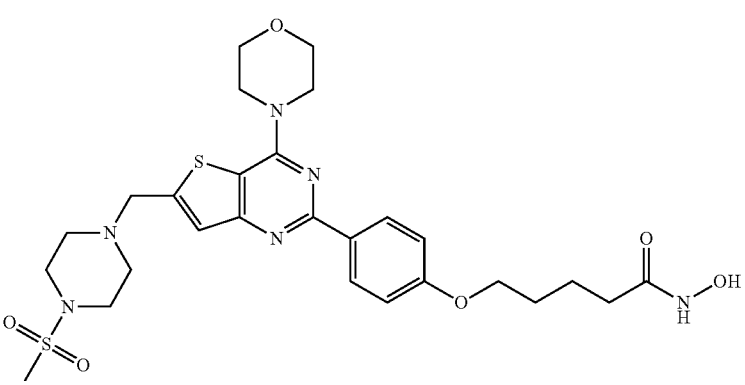 [SMILES: CS(=O)(=O)N1CCN(Cc2cc3nc(-c4ccc(OCCCCC(=O)NO)cc4)nc(N4CCOCC4)c3s2)CC1] |
| 320 | 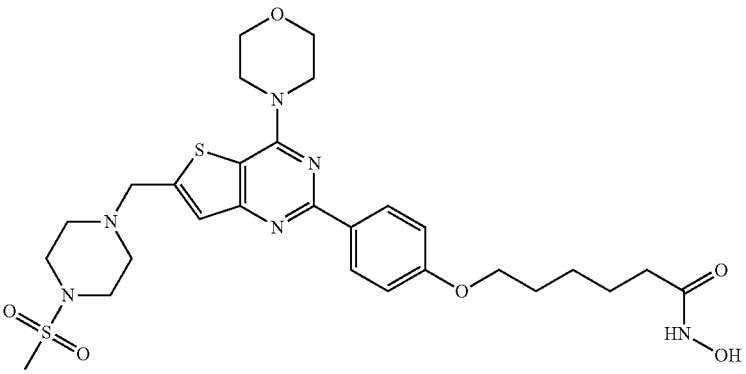 [SMILES: CS(=O)(=O)N1CCN(Cc2cc3nc(-c4ccc(OCCCCCC(=O)NO)cc4)nc(N4CCOCC4)c3s2)CC1] |
| 321 | 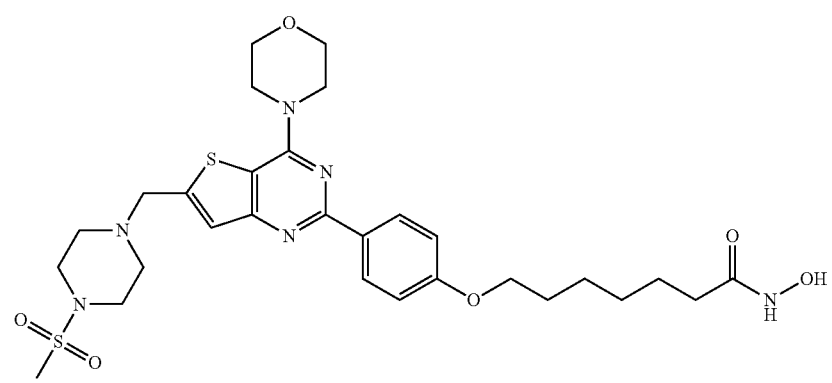 [SMILES: CS(=O)(=O)N1CCN(Cc2cc3nc(-c4ccc(OCCCCCCC(=O)NO)cc4)nc(N4CCOCC4)c3s2)CC1] |

TABLE A-continued
| Compound No. | Structure |
|---|---|
| 322 | 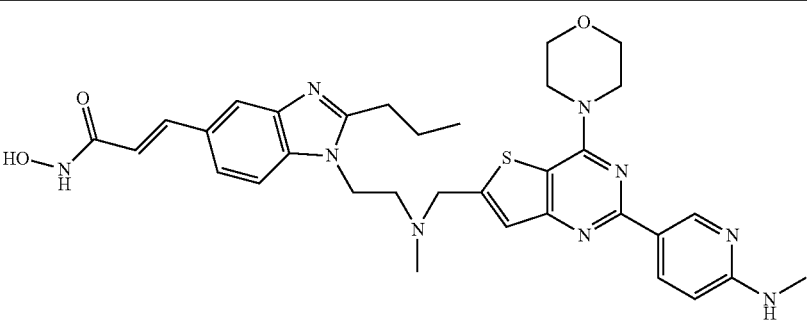 |
| 323 | 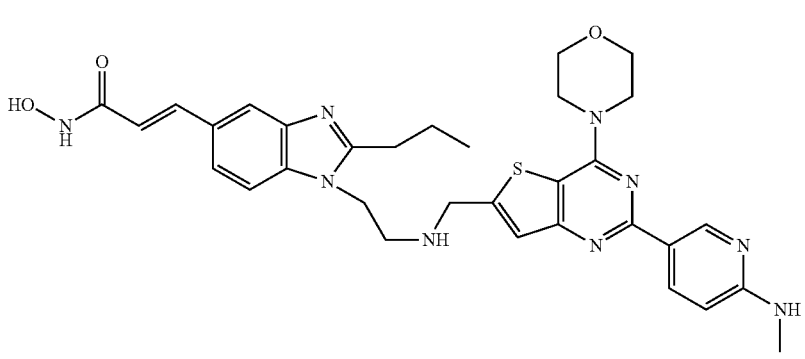 [SMILES: CCCc1nc2cc(/C=C/C(=O)NO)ccc2n1CCNCc1cc2nc(-c3ccc(NC)nc3)nc(N3CCOCC3)c2s1] |
| 324 | 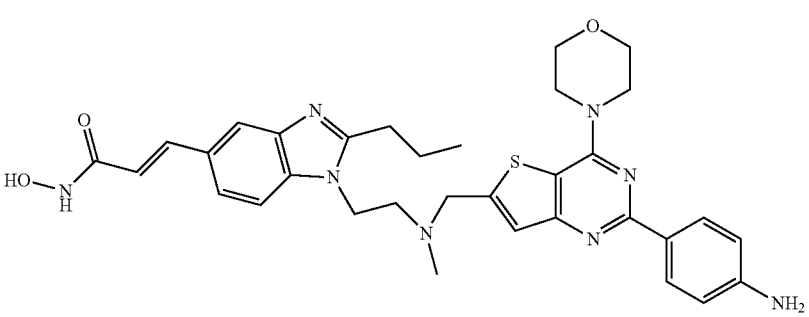 [SMILES: CCCc1nc2cc(/C=C/C(=O)NO)ccc2n1CCN(C)Cc1cc2nc(-c3ccc(N)cc3)nc(N3CCOCC3)c2s1] |
| 325 | 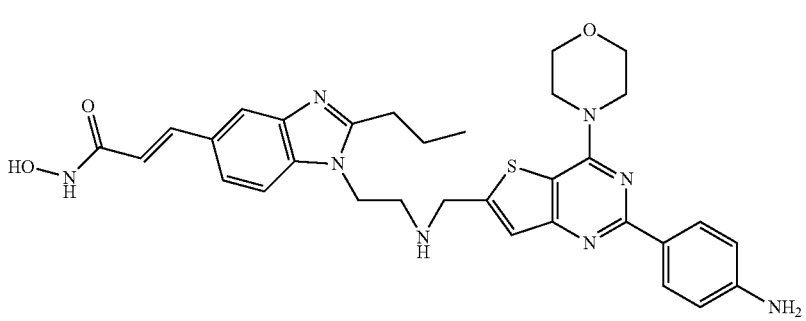 [SMILES: CCCc1nc2cc(/C=C/C(=O)NO)ccc2n1CCNCc1cc2nc(-c3ccc(N)cc3)nc(N3CCOCC3)c2s1] |

TABLE A-continued
| Compound No. | Structure |
| --- | --- |
| 326 | 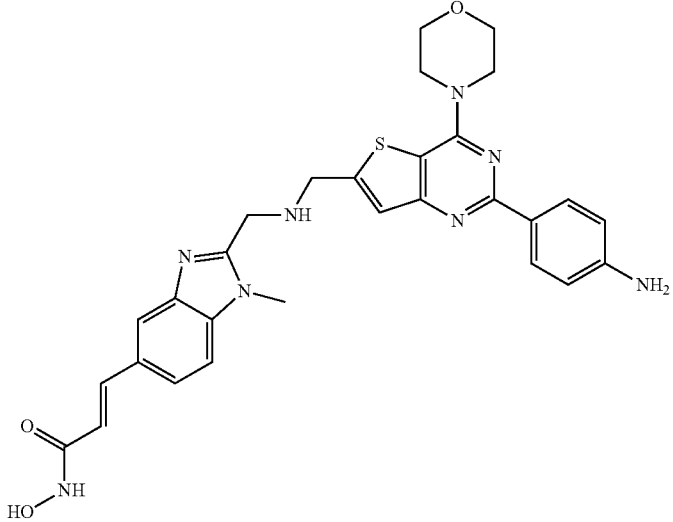 [SMILES: Cn1c(CNCc2cc3nc(-c4ccc(N)cc4)nc(N4CCOCC4)c3s2)nc2cc(/C=C/C(=O)NO)ccc21] |
| 327 | 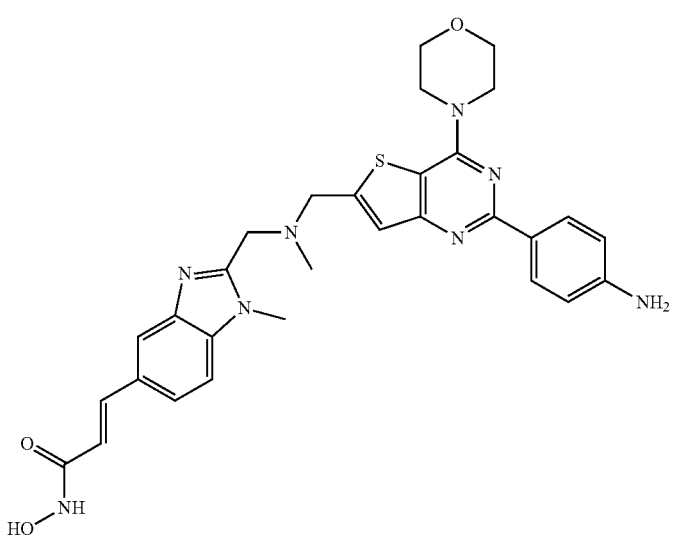 [SMILES: CN(Cc1cc2nc(-c3ccc(N)cc3)nc(N3CCOCC3)c2s1)Cc1nc2cc(/C=C/C(=O)NO)ccc2n1C] |
| 328 | 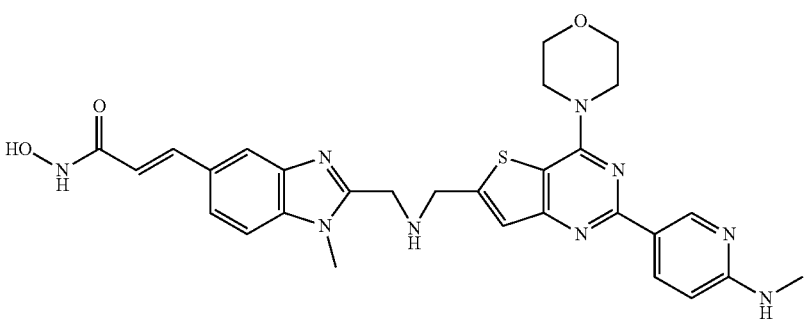 [SMILES: CNc1ccc(-c2nc(N3CCOCC3)c3sc(CNCc4nc5cc(/C=C/C(=O)NO)ccc5n4C)cc3n2)cn1] |

TABLE A-continued

| Compound No. | Structure |
|---|---|
| 329 | 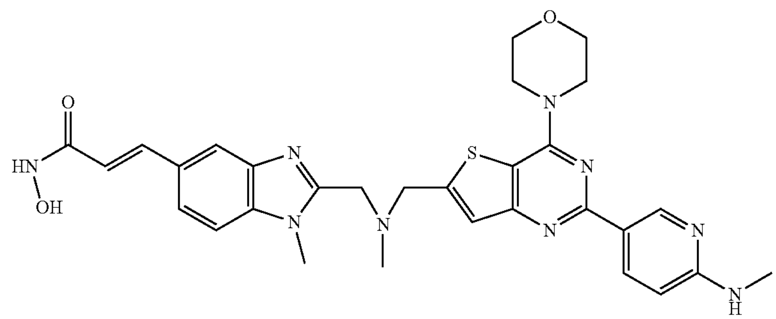 [SMILES: CNc1ccc(-c2nc(N3CCOCC3)c3sc(CN(C)Cc4nc5cc(/C=C/C(=O)NO)ccc5n4C)cc3n2)cn1] |
| 330 | 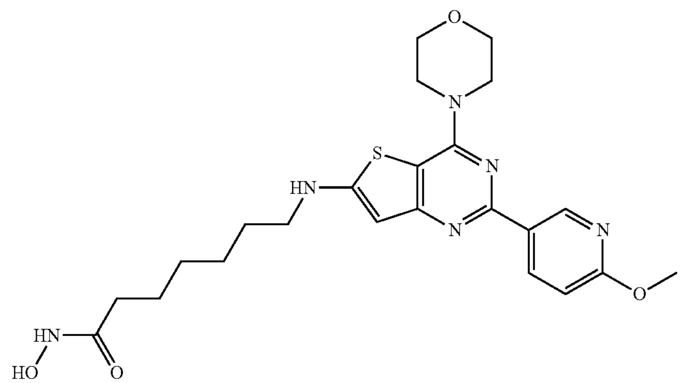 [SMILES: COc1ccc(-c2nc(N3CCOCC3)c3sc(NCCCCCCC(=O)NO)cc3n2)cn1] |
| 331 | 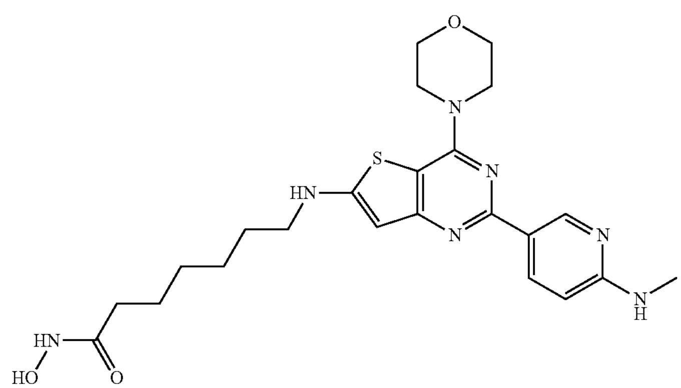 [SMILES: CNc1ccc(-c2nc(N3CCOCC3)c3sc(NCCCCCCC(=O)NO)cc3n2)cn1] |

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer. Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma, renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the compounds of the invention are used to treat a hematological cancer or hematological pre-cancerous conditions. Hematological cancers include leukemias, lymphomas and multiple myeloma. Examples include lymphocytic leukemias, such as acute lymphocytic leukemia, including precursor B acute lymphoblastic leukemia, precursor T acute lymphoblastic leukemia, Burkitt's leukemia, and acute biphenotypic leukemia; and chronic lymphocytic leukemia, including B-cell prolymphocytic leukemia; and myelogenous leukemias, such as acute myelogenous leukemia, including acute promyelocytic leukemia, acute myeloblastic leukemia, and acute megakaryoblastic leukemia; and chronic myelogenous leukemia, including chronic monocytic leukemia; acute monocytic leukemia. Other leukemias include hairy cell leukemia; T-cell prolymphocytic leukemia; large granular lymphocytic leukemia; and Adult T-cell leukemia. Lymphomas include Hodgkin's lymphoma and Non-Hodgkin's lymphoma, including B-cell lymphomas, T-cell lymphomas, such as cutaneous T-cell lymphoma, and NK cell lymphomas. Hematological precancerous conditions include myelodysplastic syndrome and myeloproliferative disorders, such as primary myelofibrosis, polycythemia vera, and essential thrombocythemia.

Compounds of the invention have been shown to induce lymphopenia and are therefore of use for removing circulating cancer cells of lymphocytic lineage. Such compounds are also of use for treating autoimmune disorders or for modulating an immune response.

In one embodiment, the invention provides a method for reducing the circulating lymphocyte count in a subject, comprising administering to the subject an effective amount of a compound of the invention. In a preferred embodiment, the reduced circulating lymphocyte count is reversible, that is, the circulating lymphocyte count returns to the normal range after dosing with the compound of the invention is stopped. In one embodiment, the reduced circulating lymphocyte count is below the normal range and the subject is lymphopenic. Preferably, the subject derives a therapeutic or prophylactic benefit from the reduced circulating lymphocyte count. Such subjects include those suffering from a hematologic disease, such as a hematologic cancer, those suffering from an autoimmune disorder, and those requiring modulation of an immune response such as patients suffering from diabetes or organ transplant recipients. In a human subject, the circulating lymphocyte count, for example, B-lymphocytes, T-lymphocytes or both, can drop from a normal range to a lymphopenic range. In certain diseases the circulating lymphocyte count is abnormally high. In such diseases, the circulating lymphocyte count can be reduced to the normal range or to a lymphopenic state.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g. MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g.

PDGFα-R, PDGβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), hedgehog pathway-related proteins (e.g. sonic hedgehog, patched, smoothened), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737, GDC-0449, IPI-926, BMS833923, LDE225, PF-04449913, and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), *Vinca* alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol., 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an NKi antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neuron stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

The compounds may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Anti-proliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including the prevention and treatment of ischemia-related or reperfusion-related vascular and myocardial tissue damage, heart failure, restenosis and arteriosclerosis; Fibrotic diseases including liver fibrosis, cystic fibrosis and angiofibroma; Infectious diseases including Fungal infections, such as candidiasis or *Candida Albicans*, Bacterial infections, Viral infections, such as Herpes Simplex, poliovirus, rhinovirus and coxsackievirus, Protozoal infections, such as Malaria, *Leishmania* infection, *Trypanosoma brucei* infection, Toxoplasmosis and coccidlosis and Haematopoietic disorders including thalassemia, anemia and sickle cell anemia.

Compounds of the invention may also be used in the treatment of a disorder involving, relating to or, associated with dysregulation of mammalian target of rapamycin (mTOR). mTOR dysregulation has been implicated in or shown to be involved in a variety of disorders. In certain cases, mTOR activity is involved in triggering disease onset, while in others, symptoms are known or have been shown to be alleviated by inhibitors of mTOR activity. Disorders of this type that would be expected to be amenable to treatment with the compounds of the invention include but are not limited to cancers, including breast cancer, prostate cancer, lung cancer, including non-small cell lung cancer and small cell lung cancer; pancreatic cancer, multiple myeloma, brain cancer, including glioblastoma multiforme, malignant glioma and gliosarcoma; skin cancer, including melanoma; renal cancer, including renal cell carcinoma; gastric cancer, colorectal cancer, colon cancer, lymphoma, leukemia, ovarian cancer, bladder cancer, uterine cancer, endometrial cancer and islet cell carcinoma; restenosis, atherosclerosis, bone disorders, arthritis, diabetic retinopathy, psoriasis, benign prostatic hypertrophy, atherosclerosis, inflammation, angiogenesis, immunological disorders, pancreatitis, and kidney disease.

The compounds can also be used in the treatment of a disorder involving, relating to or, associated with dysregulation of PI3 kinase. PI3 kinase activity has been implicated in or shown to be involved in a variety of disorders. In certain cases, PI3 kinase activity is involved in triggering disease onset, while in others, symptoms are known or have been shown to be alleviated by inhibitors of PI3 kinase activity. Disorders of this type that would be expected to be amenable to treatment with the compounds of the invention include but are not limited to cancers, including leukemia, skin cancer, bladder cancer, breast cancer, uterine cancer, ovarian cancer, prostate cancer, lung cancer, colon cancer, pancreatic cancer, renal cancer, gastric cancer and brain cancer; restenosis, atherosclerosis, bone disorders, arthritis, diabetic retinopathy, psoriasis, benign prostatic hypertrophy, atherosclerosis, inflammation, angiogenesis, immunological disorders, pancreatitis and kidney disease.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpes virus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *Staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis *nodosa* and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as: A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII. Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. The invention also encompasses solvates of the compounds of the invention and pharmaceutical compositions comprising such solvates, such as hydrates, methanolates or ethanolates. The term "solvate" refers to a solid, preferably crystalline, form of a compound which includes the presence of solvent molecules within the crystal lattice. A solvate of a compound comprising a given solvent is typically prepared by crystallization of the compound from that solvent. Solvates can include a variety of solvents, including water, methanol and ethanol. The term "hydrate" refers to a solvate in which the solvent is water, and includes, but is not limited to, hemihydrate, monohydrate, dihydrate, trihydrate and the like. The invention further encompasses pharmaceutical compositions comprising any solid or liquid physical form of the compound of the invention, including crystalline and crystalline solvate forms. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or solvates thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HC., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

Definitions

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group, when used as a linker, preferably contains between about 1 and about 24 atoms, more preferably between about 4 to about 24 atoms, more preferably between about 4-12 atoms, more typically between about 4 and about 8 atoms. An aliphatic group, when used as a substituent, preferably contains between about 1 and about 24 atoms, more preferably between about 1 to about 10 atoms, more preferably between about 1-8 atoms, more typically between about 1 and about 6 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

The term "substituted carbonyl" includes compounds and moieties which contain a carbon connected with a double bond to an oxygen atom, and tautomeric forms thereof. Examples of moieties that contain a substituted carbonyl include aldehydes, ketones, carboxylic acids, amides, esters, anhydrides, etc. The term "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide).

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g., 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_8$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker B is between 1-24 atoms, preferably 4-24 atoms, preferably 4-18 atoms, more preferably 4-12 atoms, and most preferably about 4-10 atoms. In some embodiments, the linker is a C(O)NH(alkyl) chain or an alkoxy chain. It is to be understood that an asymmetric linker, such as alkylaryl, can connect two structurally distinct moieties in either of its two possible orientations.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g., $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "device" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "PI3 kinase related disease or disorder" refers to a disease or disorder characterized by inappropriate phosphoinositide-3-kinase activity or over-activity of the phosphoinositide-3-kinase. Inappropriate activity refers to either; (i) PI3 kinase expression in cells which normally do not express PI3 kinase; (ii) increased PI3 kinase expression leading to unwanted cell proliferation, differentiation and/or growth; or, (iii) decreased PI3 kinase expression leading to unwanted reductions in cell proliferation, differentiation and/or growth. Over-activity of PI3 kinase refers to either amplification of the gene encoding a particular PI3 kinase or production of a level of PI3 kinase activity which can correlate with a cell proliferation, differentiation and/or growth disorder (that is, as the level of the PI3 kinase increases, the severity of one or more of the symptoms of the cellular disorder increases).

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion. The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P.G.M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)-for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds and processes of the present invention will be better understood in connection with the following synthetic schemes that illustrate the methods by which the compounds of the invention may be prepared, which are intended as an illustration only and not limiting of the scope of the invention.

Scheme 1

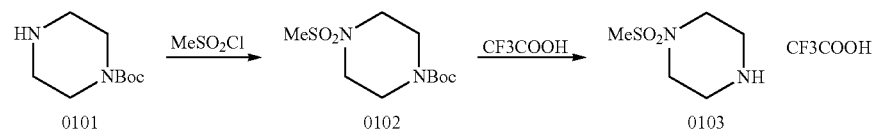

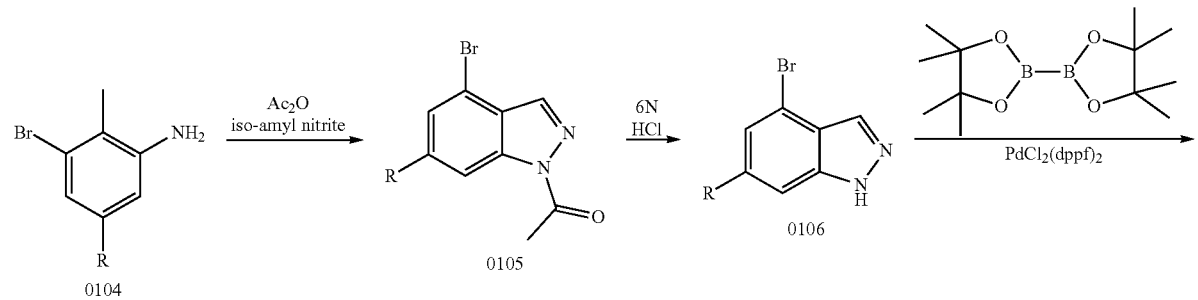

-continued
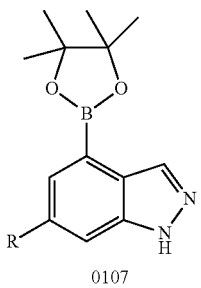
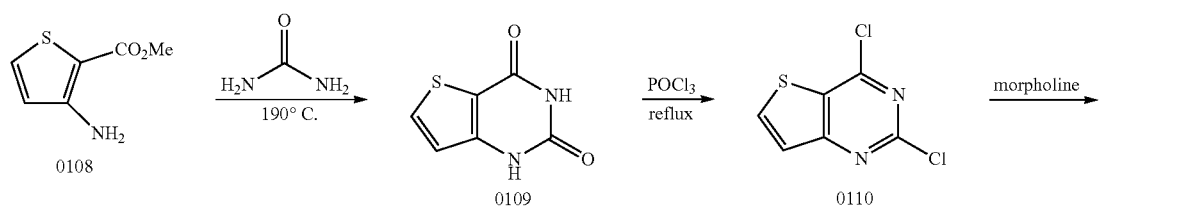
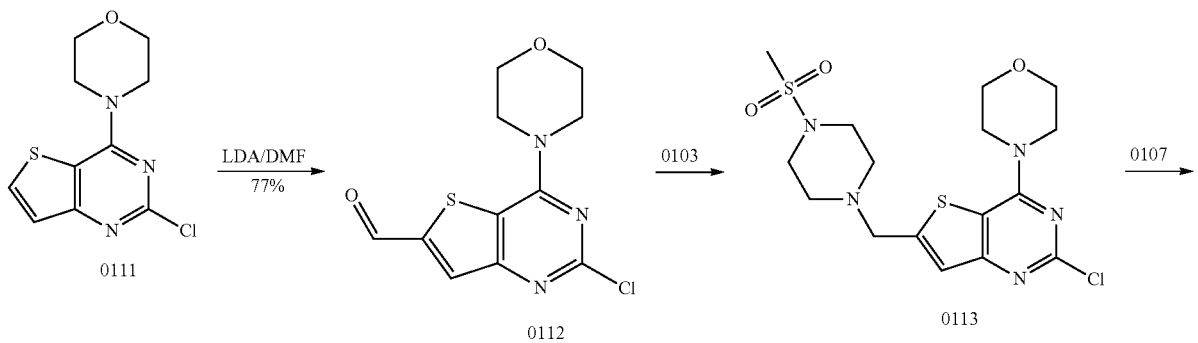
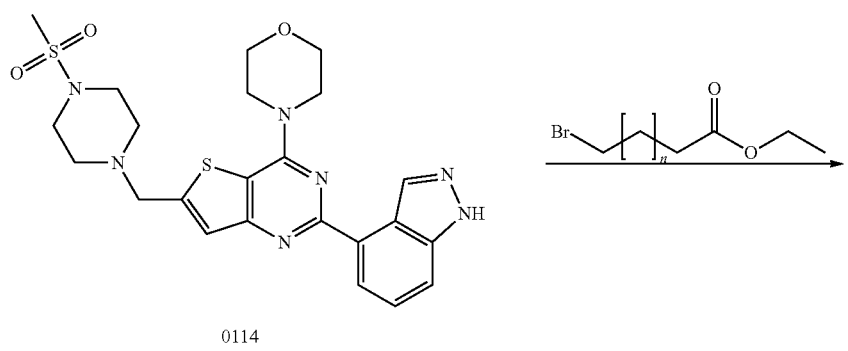
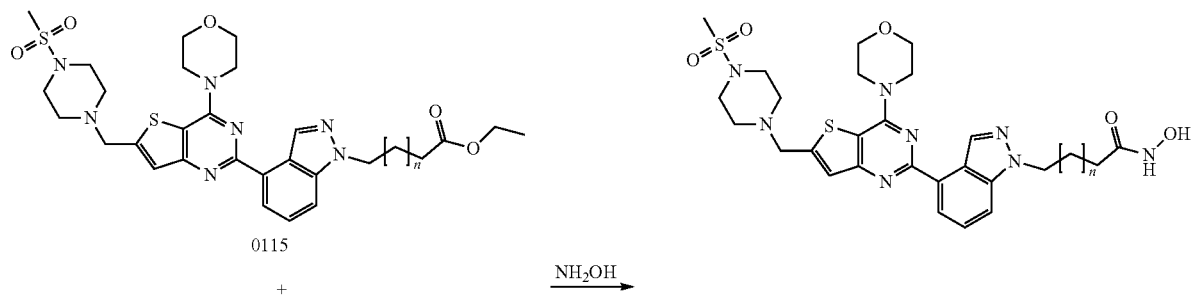

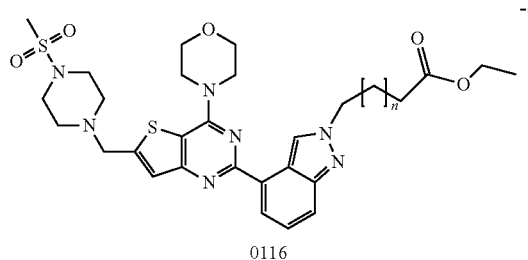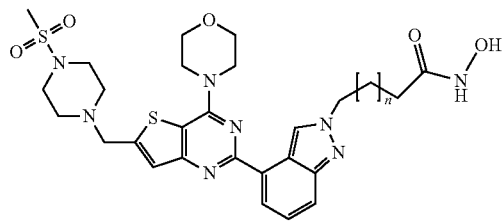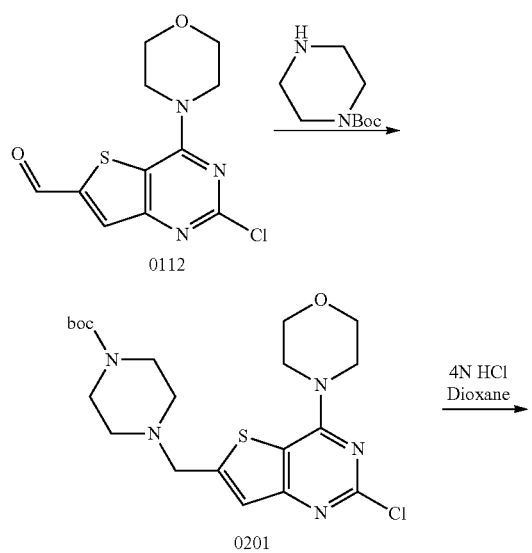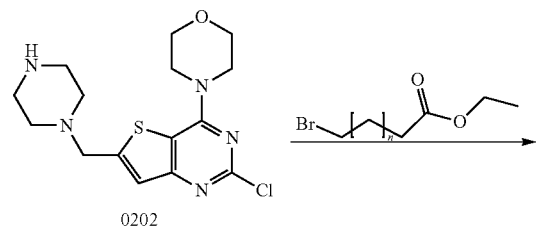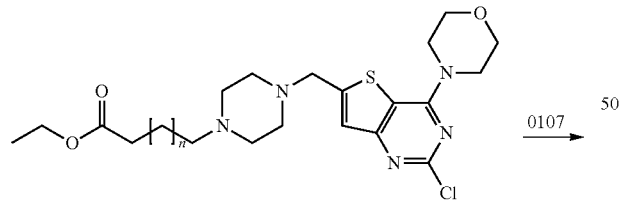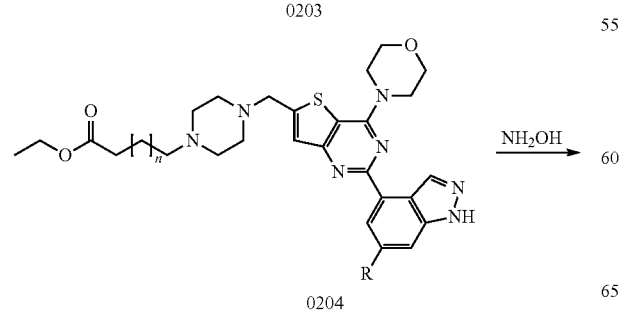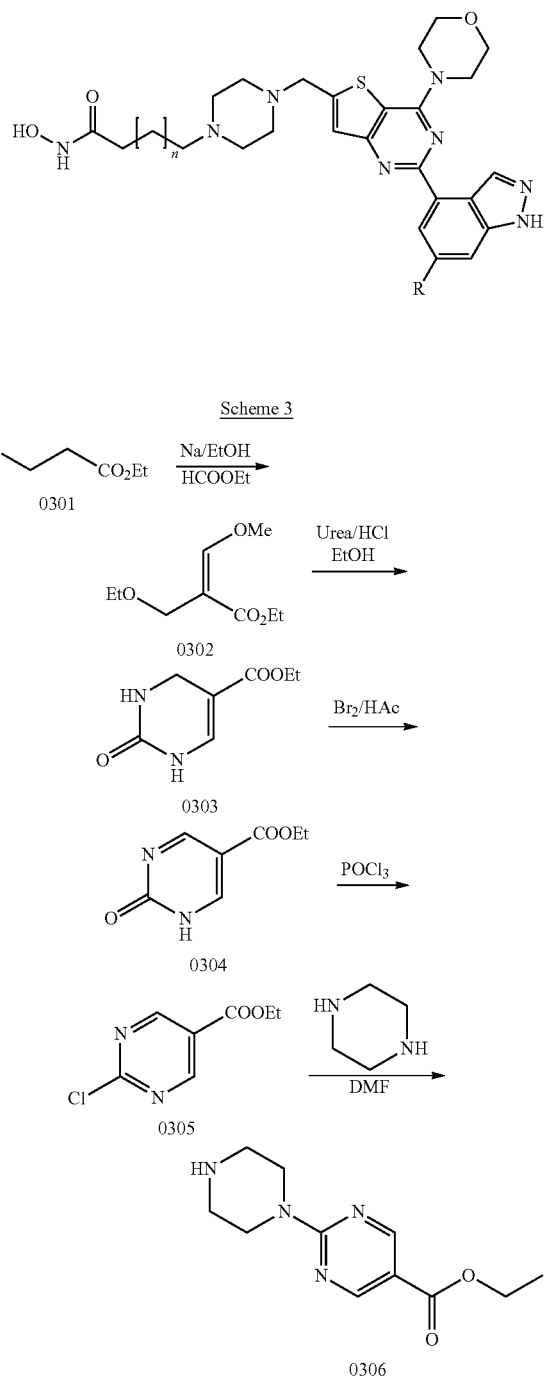

197
-continued
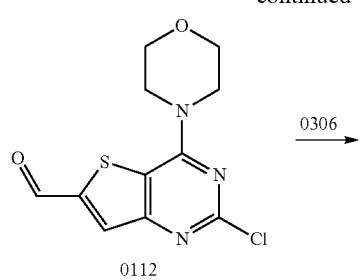
198
-continued
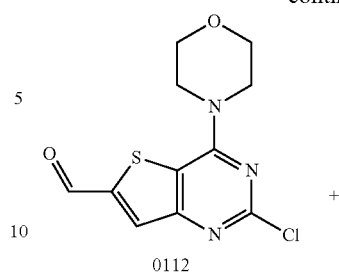
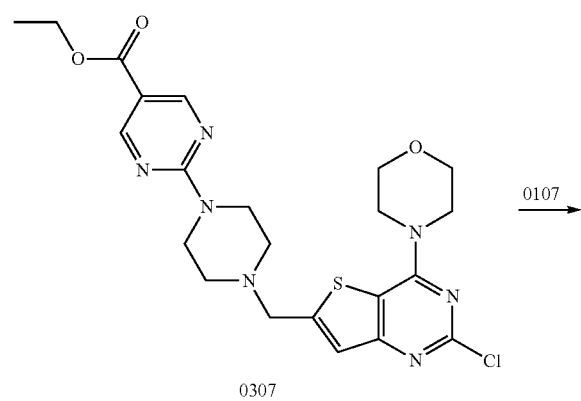
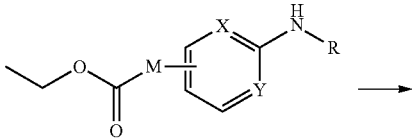
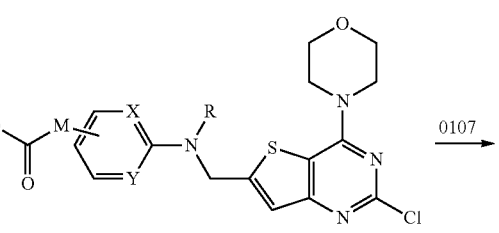
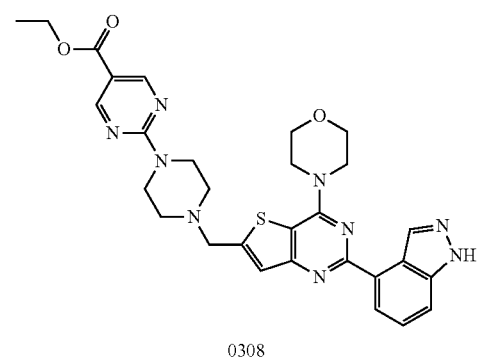
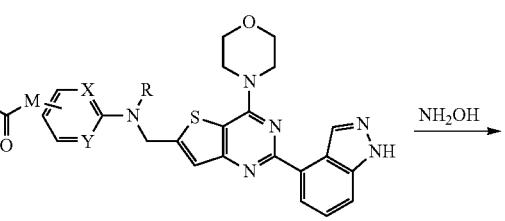
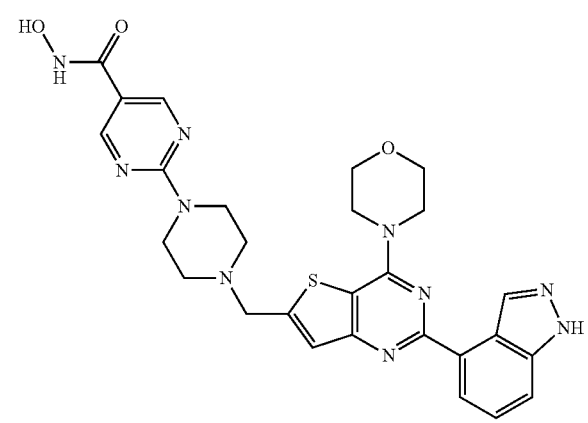
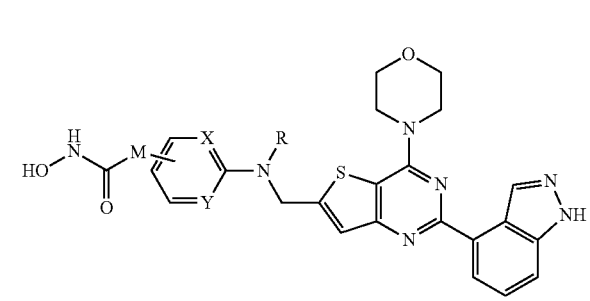

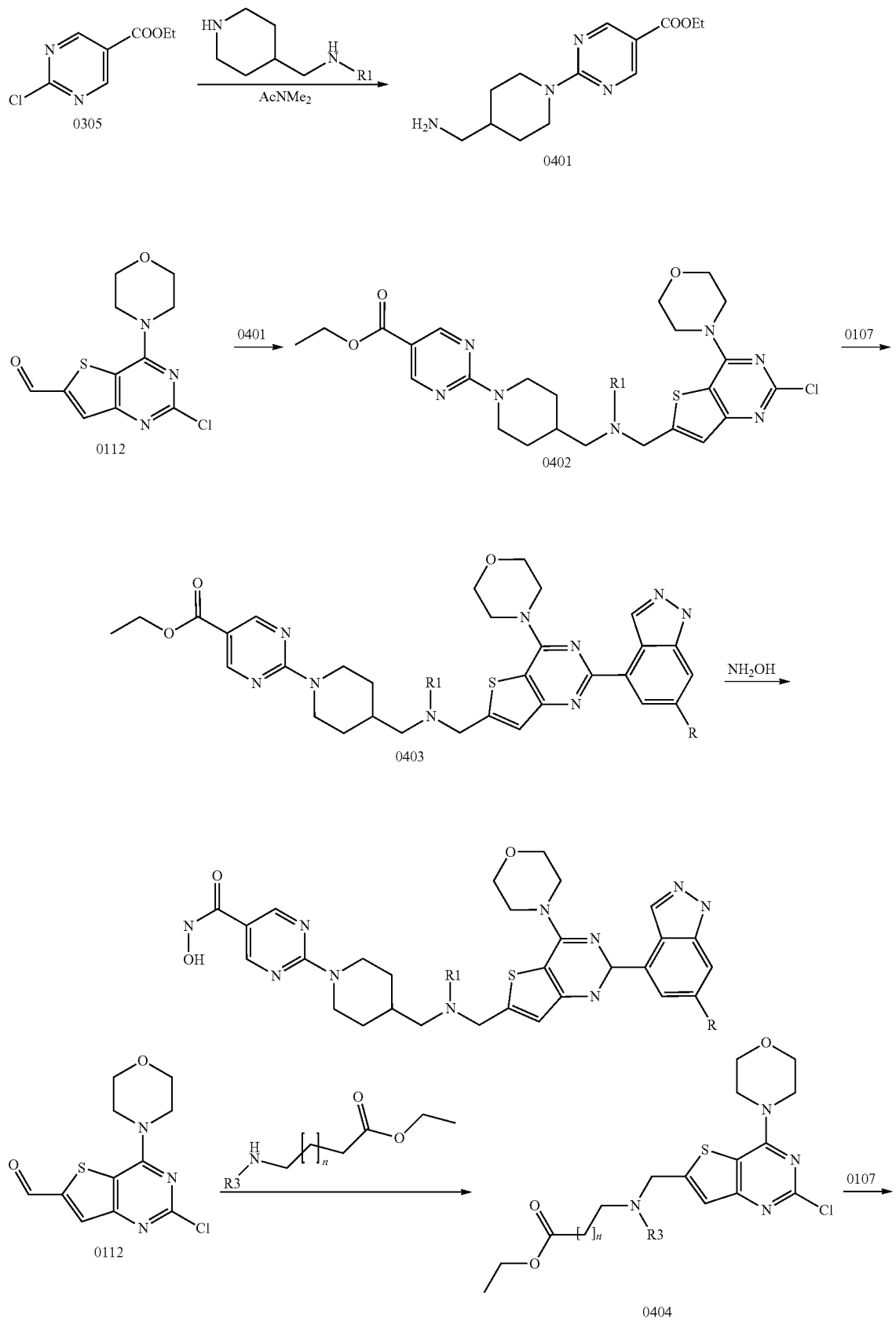

201                                                                                   202
-continued
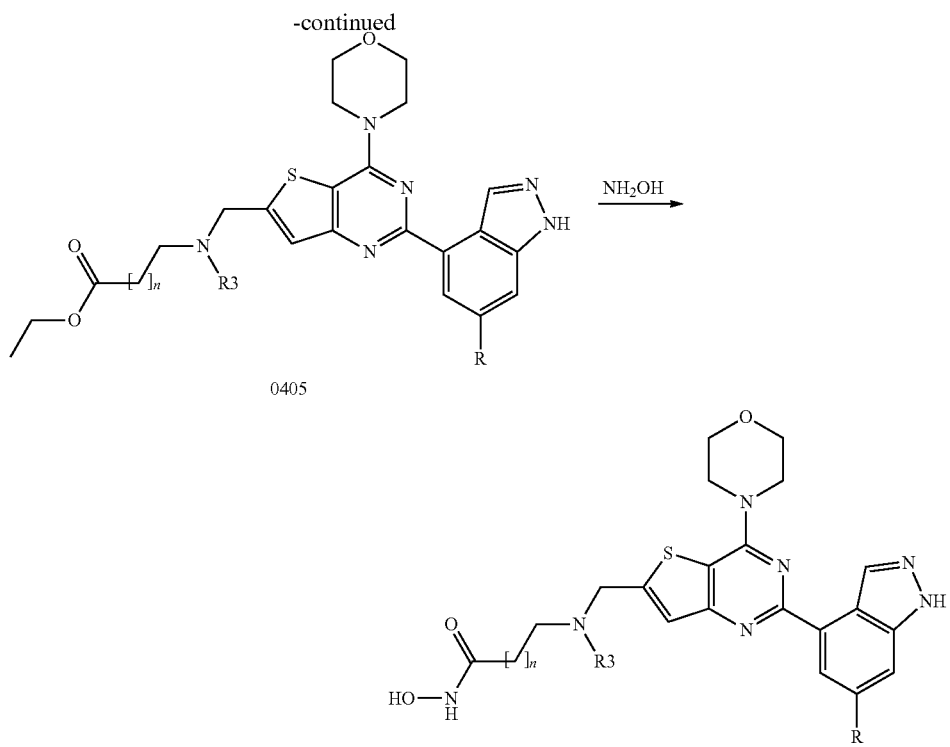
Scheme 5
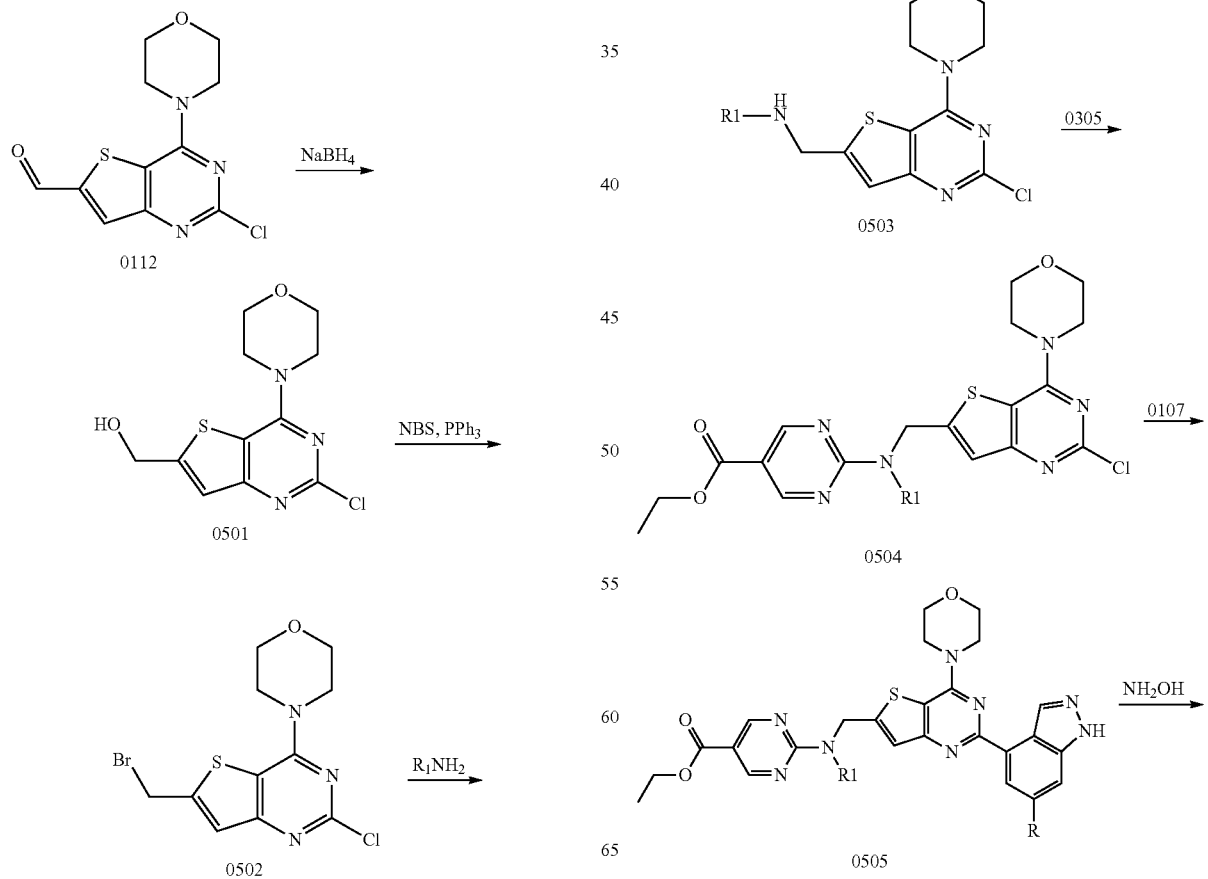

203
-continued
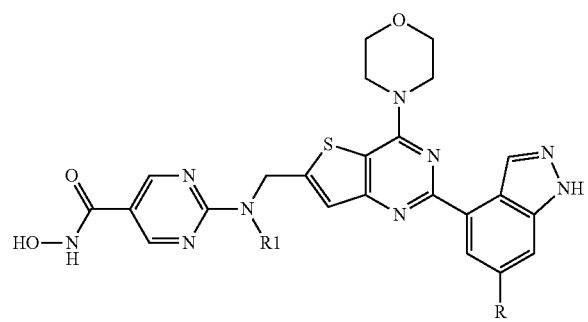
204
-continued
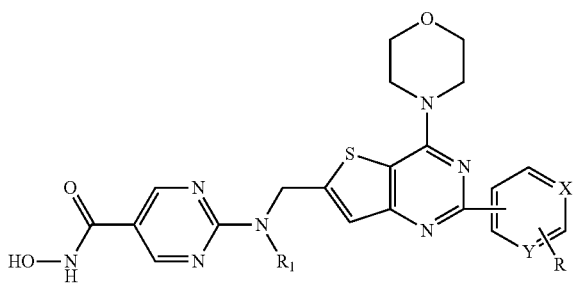
Scheme 6
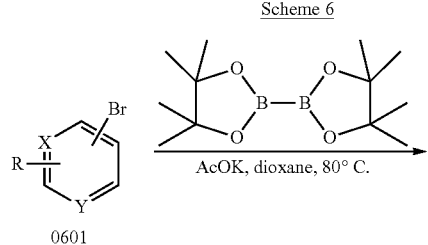
0601
0602
0504
0603
Scheme 7
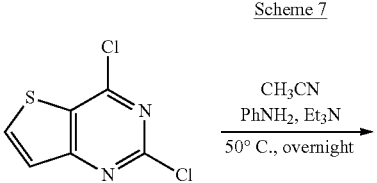
0110
CH₃CN
PhNH₂, Et₃N
50° C., overnight
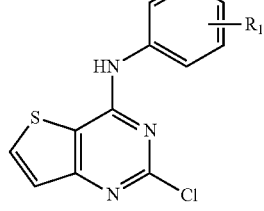
0701
THF
(Boc)₂O, DMAP
r.t., overnight
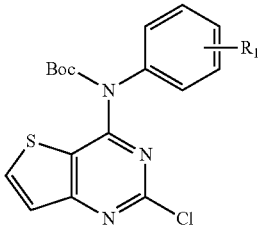
0702
LDA, THF, DMF
−30° C., 30 min
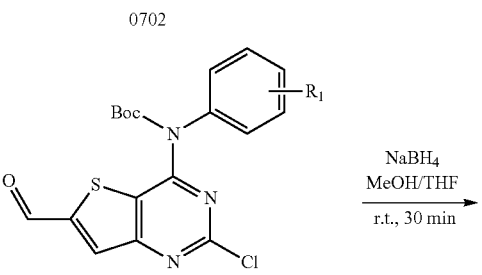
0703
NaBH₄
MeOH/THF
r.t., 30 min
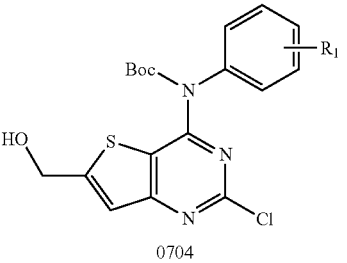
0704
MsCl, Et₃N, THF
r.t., 1 h
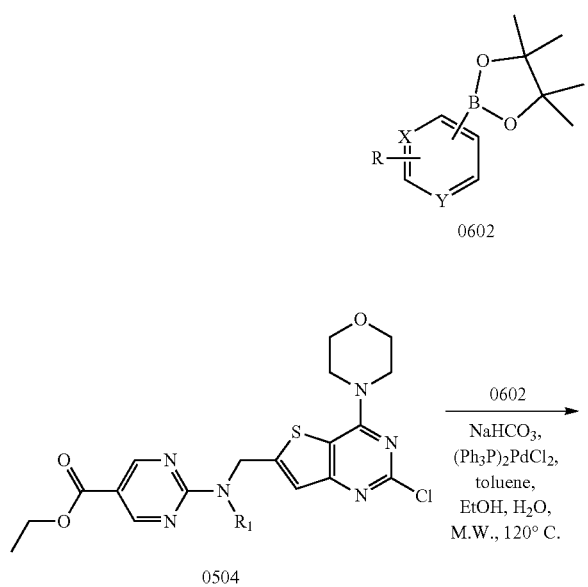
0602
NaHCO₃,
(Ph₃P)₂PdCl₂,
toluene,
EtOH, H₂O,
M.W., 120° C.
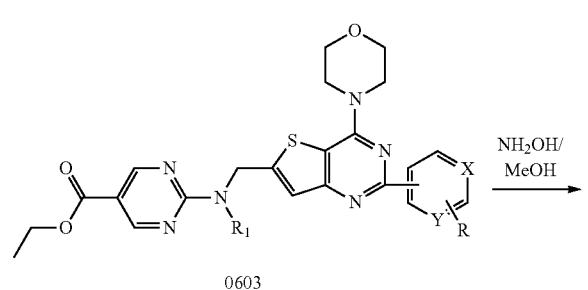
NH₂OH/
MeOH 205
-continued
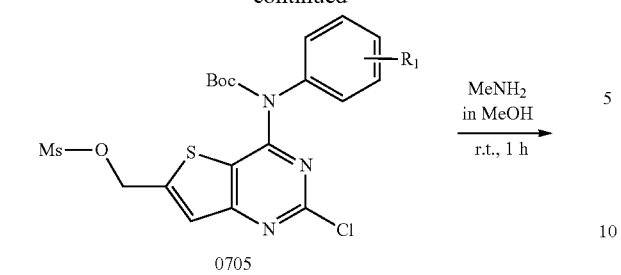
0705
MeNH₂ in MeOH
r.t., 1 h
→
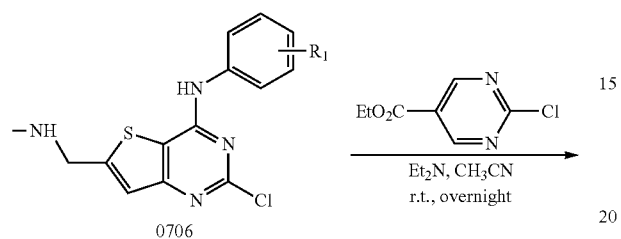
0706
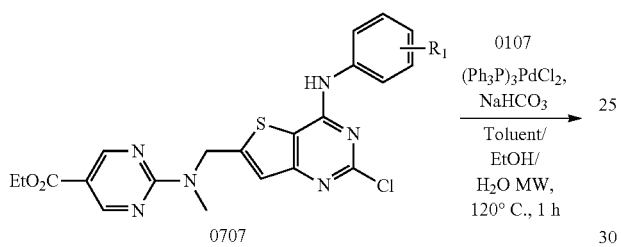
0707
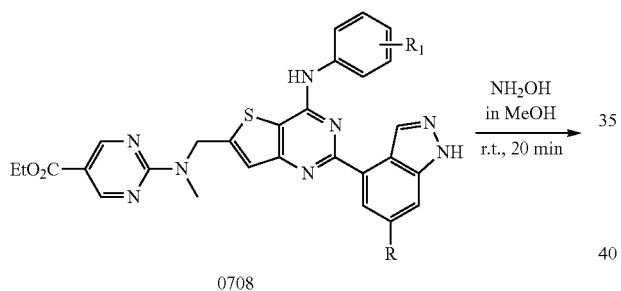
0708
NH₂OH in MeOH
r.t., 20 min
→
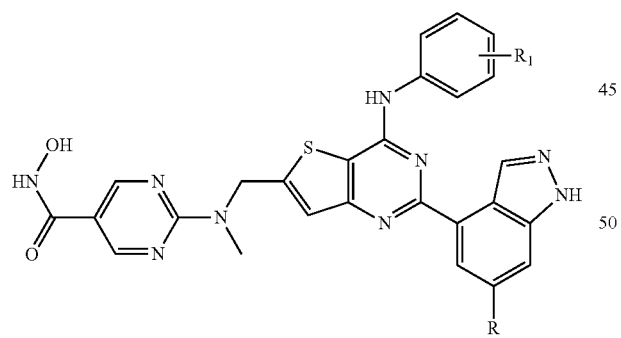
Scheme 8
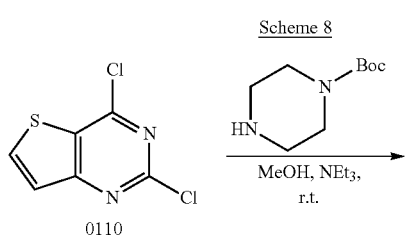
0110
MeOH, NEt₃,
r.t.
→
206
-continued
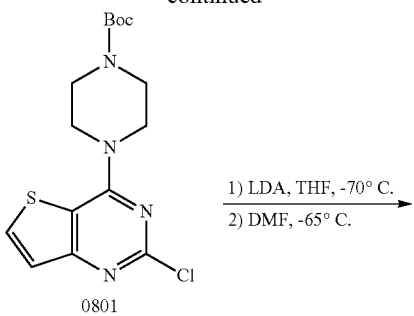
0801
1) LDA, THF, -70° C.
2) DMF, -65° C.
→
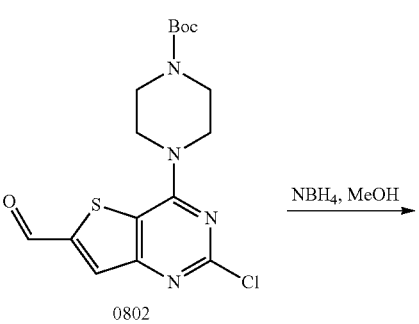
0802
NBH₄, MeOH
→
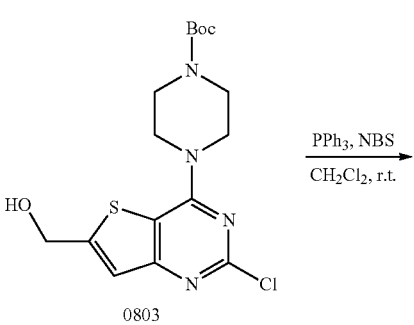
0803
PPh₃, NBS
CH₂Cl₂, r.t.
→
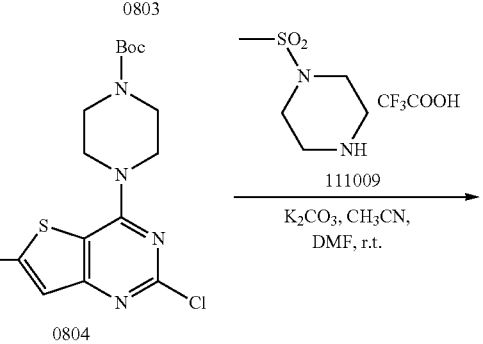
0804
K₂CO₃, CH₃CN,
DMF, r.t.
→
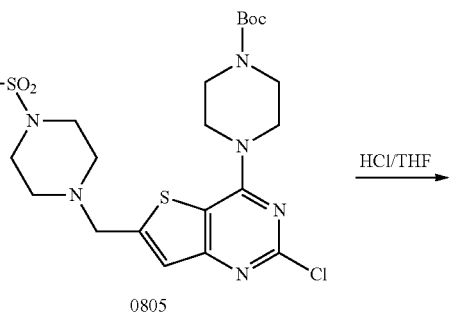
0805
HCl/THF
→

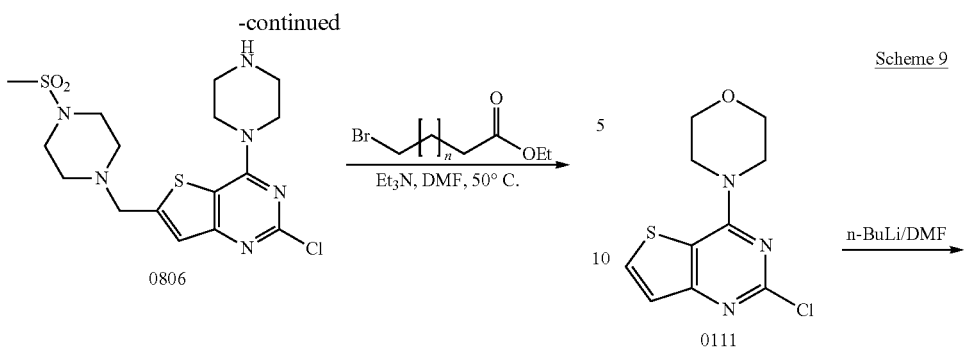
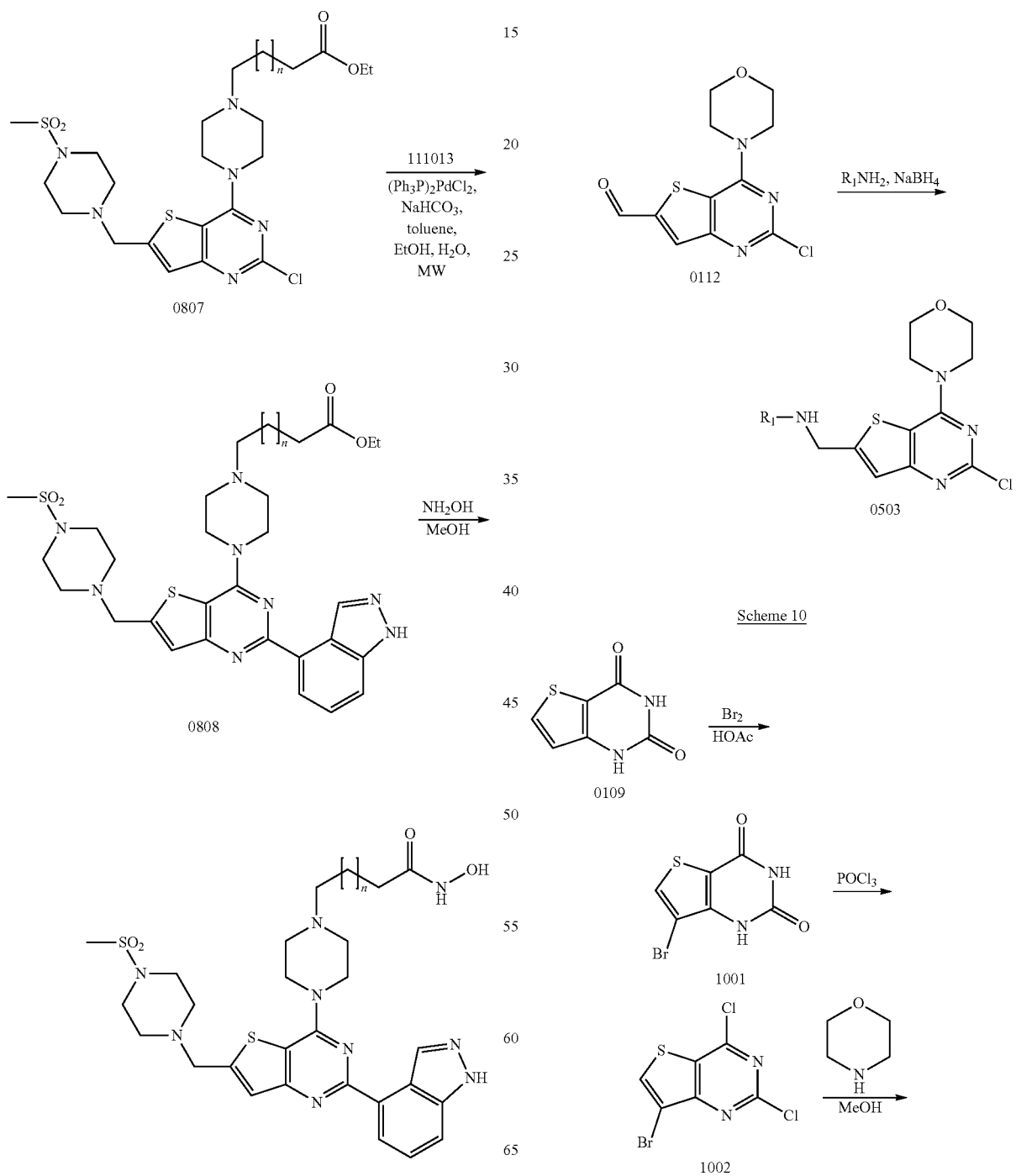

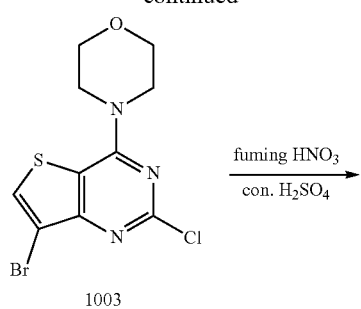
1003
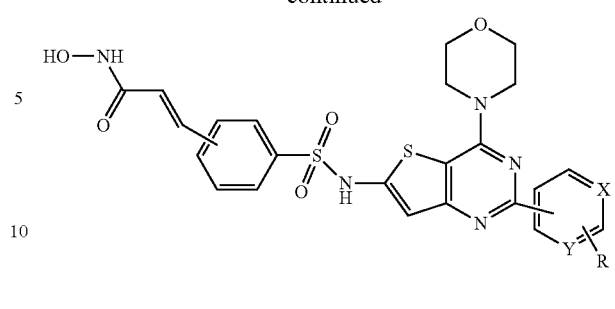
Scheme 11
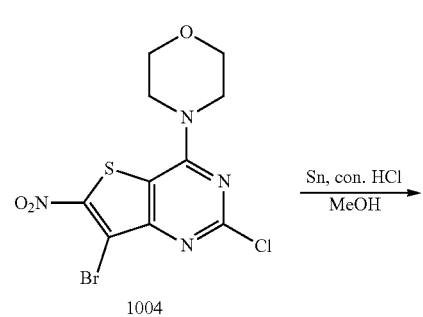
1004
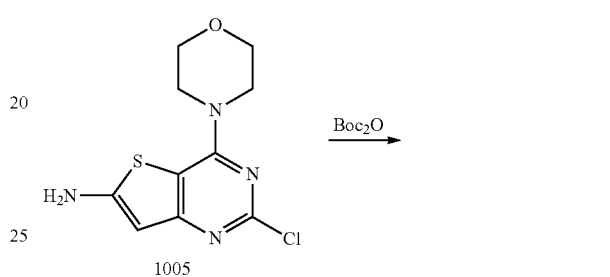
1005
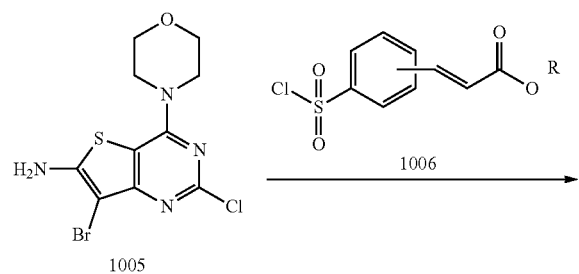
1005 1006
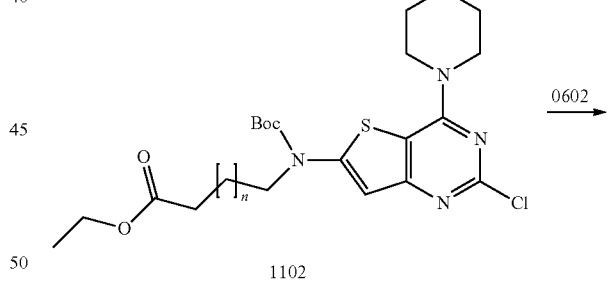
1101
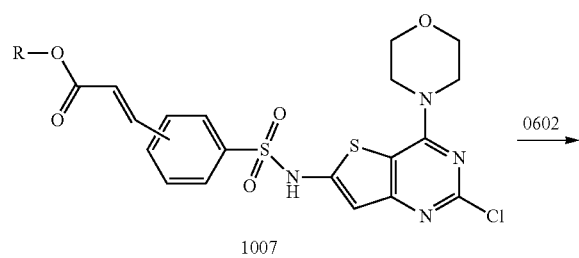
1007
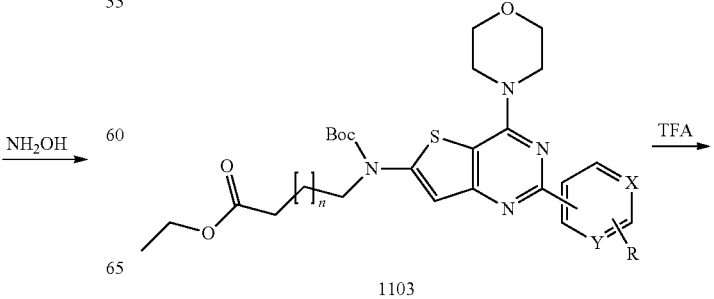
1102
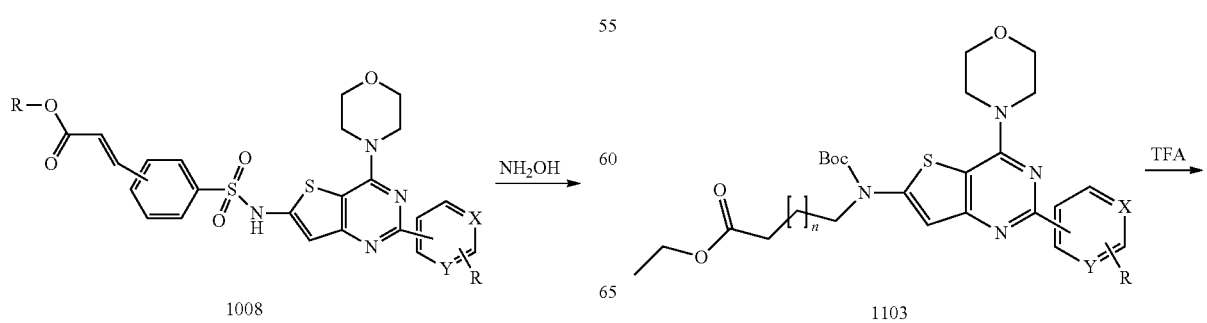
1008
1103

211
-continued
212
-continued
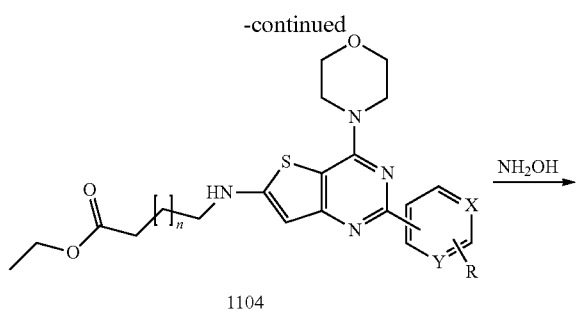
1104
NH₂OH
→
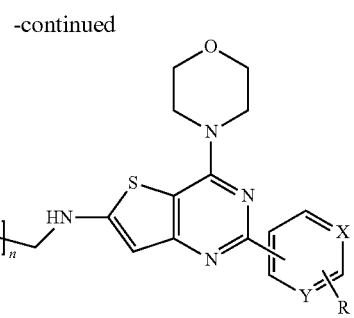
Scheme 12
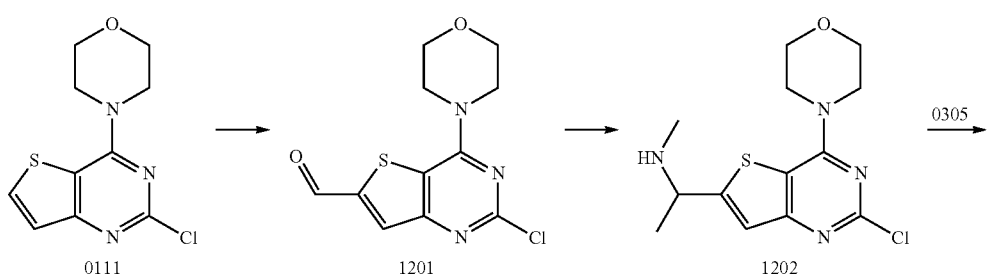
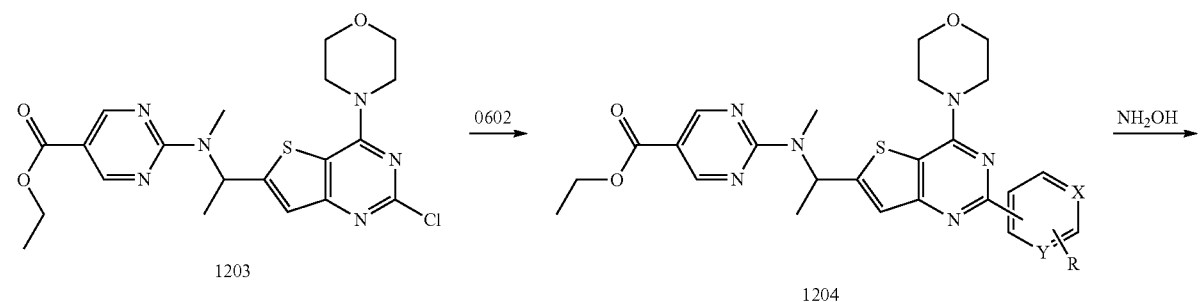
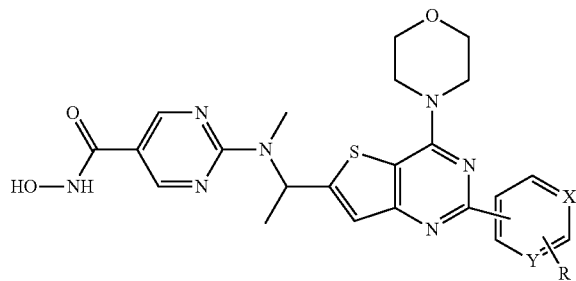
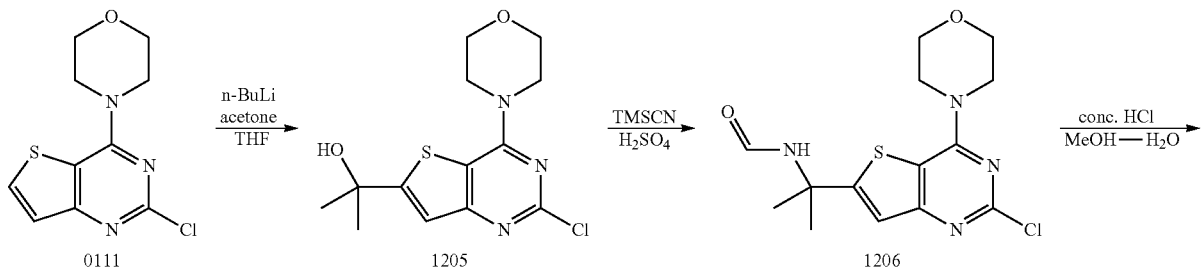

213
214
-continued
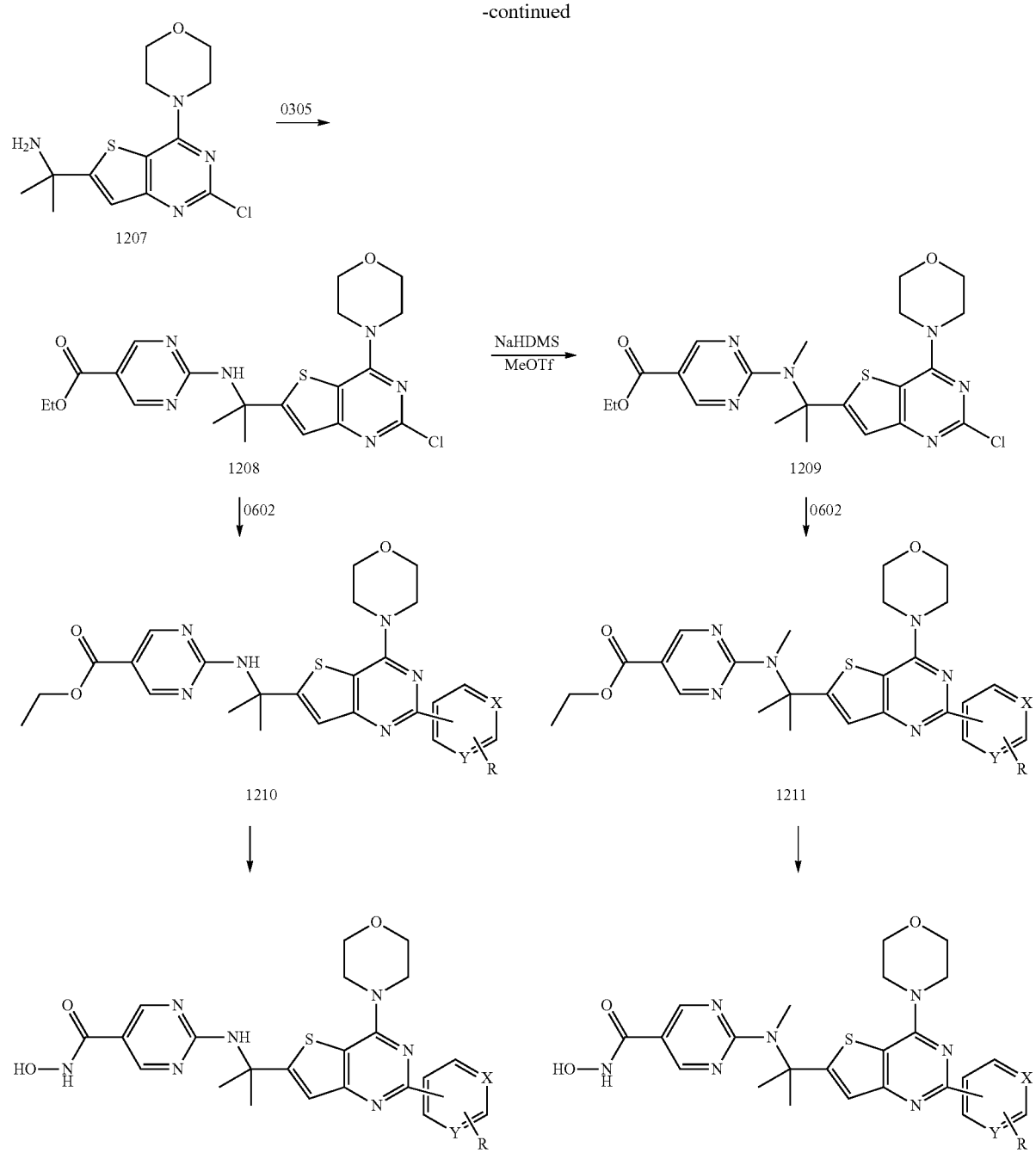
Scheme 13
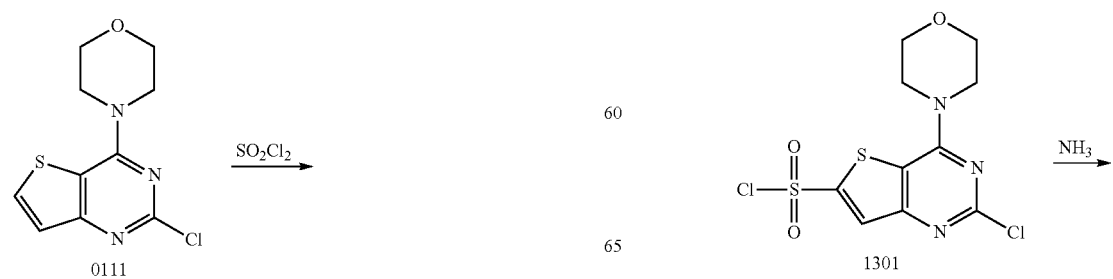

215
-continued
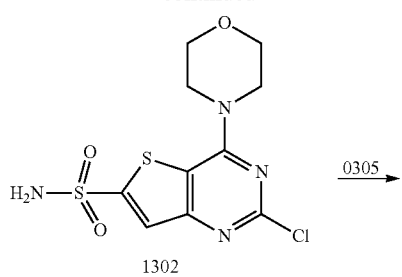
1302 →0305
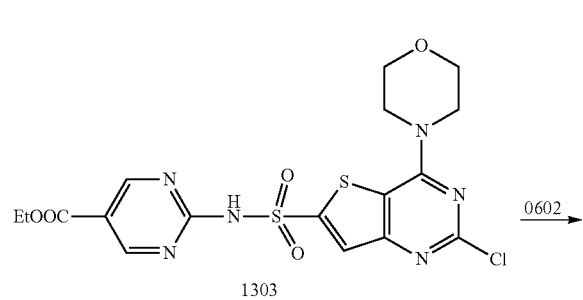
1303 →0602
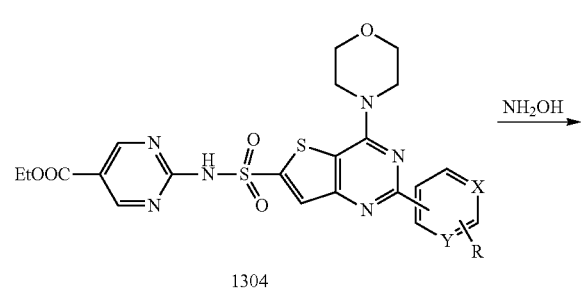
1304 →NH₂OH
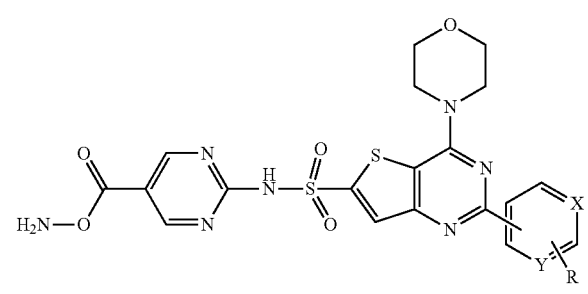
Scheme 14
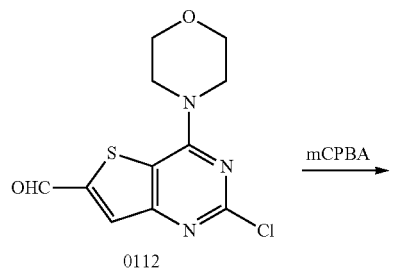
0112 →mCPBA
216
-continued
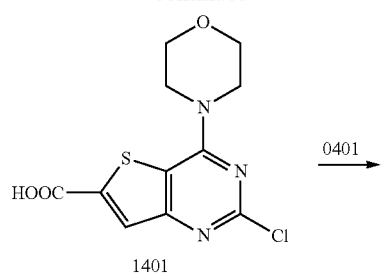
1401 →0401
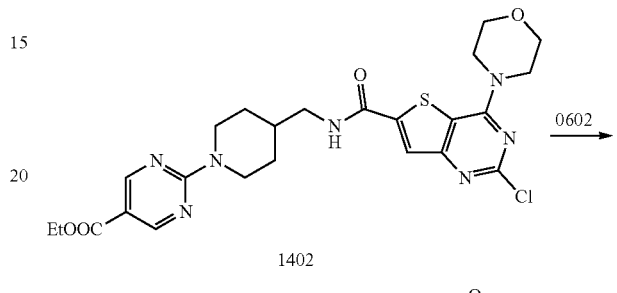
1402 →0602
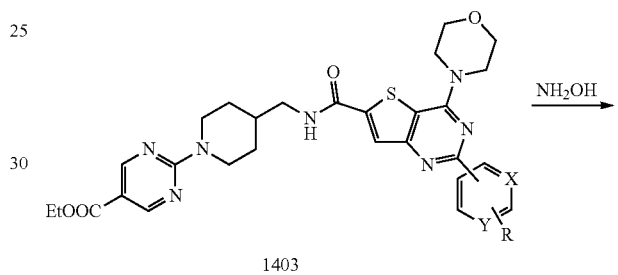
1403 →NH₂OH
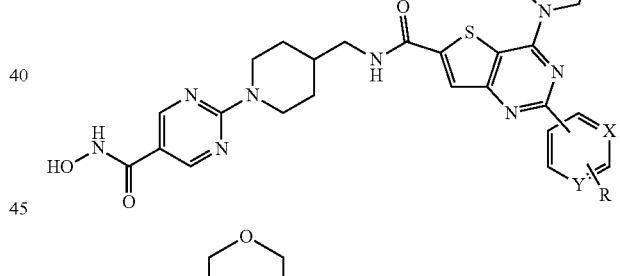
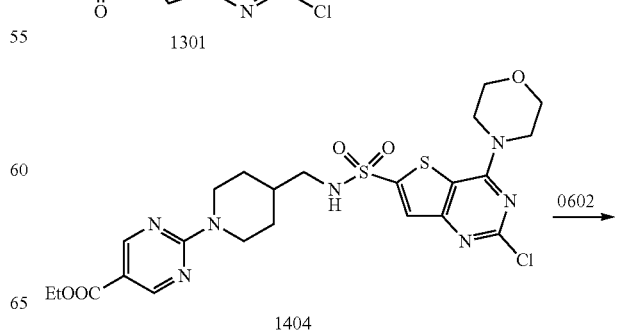
1301 →0401
1404 →0602

217
-continued
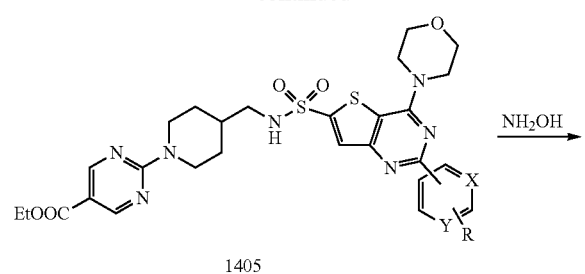
1405
218
-continued
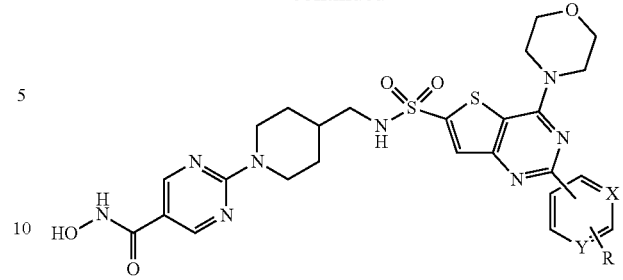
Scheme 15
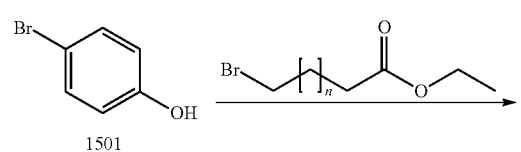
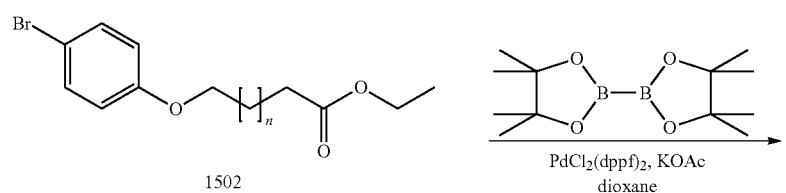
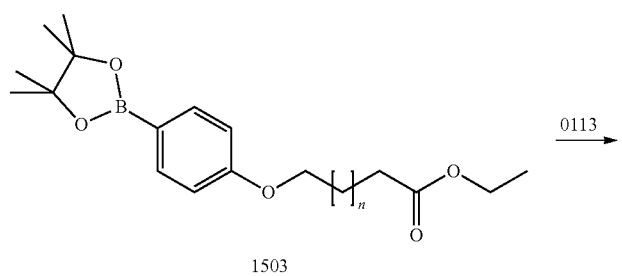

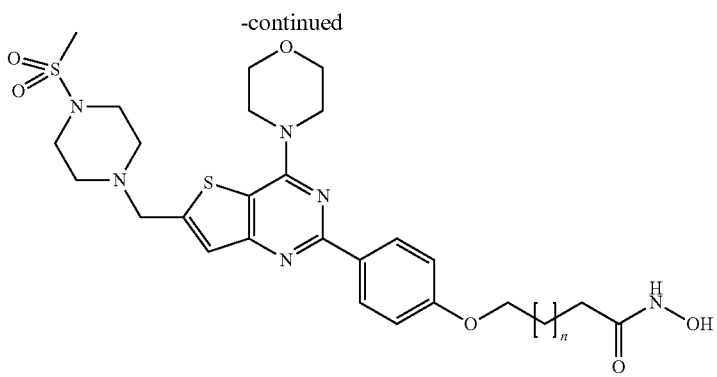

Scheme 16

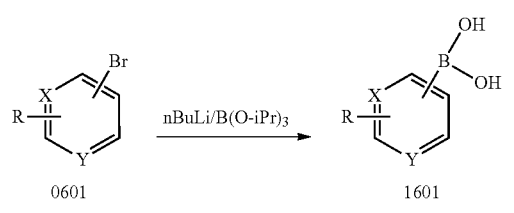

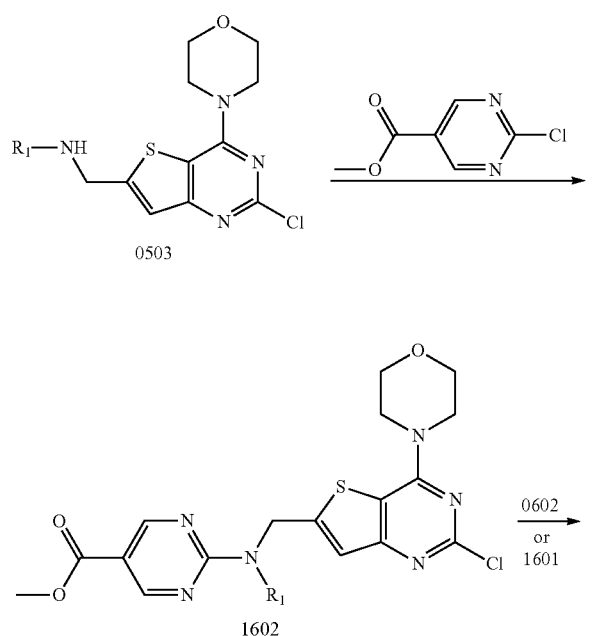

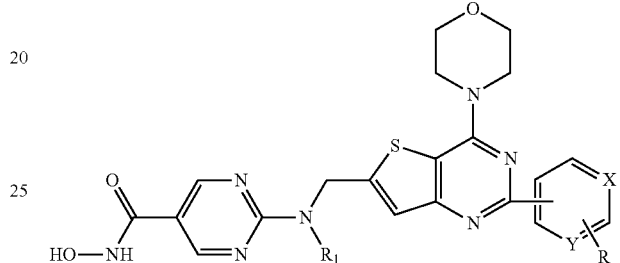

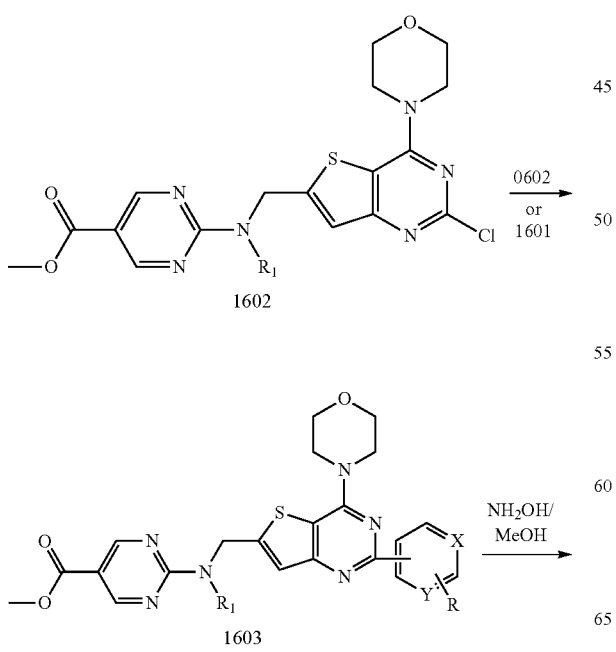

Examples

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: Preparation of N-hydroxy-5-(4-(6-((4-(methylsulfonyl) piperazin-1-yl)methyl)-4-morpholinothieno[3,2-d]pyrimidin-2-yl)-1H-indazol-1-yl) pentanamide (Compound 3)

Step 1a: 1-(Methylthioperoxy)piperazine trifluoroacetic acid salt (Compound 0103)

A mixture of compound 0101 (10.0 g, 54 mmol), methanesulfonyl chloride (6.5 g, 57 mmol) and triethylamine in $CH_2Cl_2$ (50 mL) was stirred at reflux overnight. The reaction was cooled to room temperature and filtered. The filtrate was concentrated to give compound 0102 which was used to the next step without further purification.

A mixture of compound 0102 and trifluoroacetic acid (15 mL) in $CH_2Cl_2$ (100 mL) was stirred at room temperature for 3 h. The reaction was filtered and the filtrate was concentrated to give the title compound 0103 (9.7 g, 66%) as a white solid. LCMS: 165 [M+1]$^+$; $^1$H NMR (400 MHz, $CDCl_3$): δ 2.99 (s, 3H), 3.21 (m, 4H), 3.33 (m, 4H), 8.95 (br s, 2H).

Step 1b: 4-Bromo-H-indazole (Compound 0106-3)

To a solution of 3-bromo-2-methyl aniline (0104) (0.50 g, 2.69 mmol) in chloroform (5 mL) was added potassium acetate (0.28 g, 2.82 mmol). The mixture was cooled with ice-water bath and then acetic anhydride (0.50 mL, 5.37 mmol) was added to it. Ice-water bath was then removed and the resulting mixture was stirred at room temperature for 10 minutes after which time a white gelatinous solid formed. 18-Crown-6 (0.14 g, 0.54 mmol) was then added followed by isoamyl nitrite (0.80 mL, 5.90 mmol). The mixture was then heated under reflux for 18 hours. The reaction mixture was allowed to cool, and was partitioned between chloroform (3×10 mL) and saturated aqueous sodium hydrogen carbonate (10 mL). The combined organic extracts were washed with brine (10 mL), dried over $Na_2SO_4$, filtered and evaporated to give a crude product which was purified by column chromatography (ethyl acetate in petroleum ether, 10% v/v) to give 1-(4-bromoindrazol-1-yl)-ethanone (0105) as an orange solid (0.31 g, 49%), and 4-bromo-1H-indazole (0106-3) as a pale orange solid (0.21 g, 40%). Compound 0105: LCMS: 239 [M+1]$^+$; $^1$H NMR (400 Hz, CDCl$_3$) δ 2.80 (s, 3H), 7.41 (t, J=6.8 Hz, 1H), 7.50 (d, J=6.0 Hz, 1H), 8.15 (s, 1H), 8.40 (d, J=6.8 Hz, 1H). Compound 0106: LCMS: 197 [M+1]$^+$; $^1$H NMR (400 Hz, CDCl$_3$) δ 7.25 (t, J=6.0 Hz, 1H), 7.34 (d, J=6.4 Hz, 1H), 7.46 (d, J=6.8 Hz, 1H), 8.12 (s, 1H).

To a solution of compound 0105 (0.30 g, 1.29 mmol) in methanol (5.0 mL) was added 6 N aqueous HCl (3.0 mL). The mixture was stirred at room temperature for 7 h. Methanol was evaporated and the mixture partitioned between EtOAc (2×50 mL) and water (5.0 mL). The combined organic layers were washed with brine (5.0 mL), dried over $Na_2SO_4$, filtered and evaporated to give 4-bromo-1H-indazole (0106-3) (0.24 g, 94%).

Step 1c: 4-(4,4,5,5-Tetramethyl-1,3,2-dioxaborolan-2-yl)-1H-indazole (Compound 0107-3)

To a stirred solution of compound 0106 (500 mg, 2.54 mmol) and bis(pinacolato)diboron (968 mg, 3.81 mmol) in DMSO (20 mL) was added potassium acetate (747 mg, 7.61 mmol) and $PdCl_2(dppf)_2$ (3 mol %, 62 mg, 0.076 mmol). The mixture was degassed with argon and heated at 80° C. for 40 hours. The reaction mixture was allowed to cool and partitioned between water (50 mL) and ether (3×50 mL). The combined organic layers were separated, washed with brine (50 mL), dried over $MgSO_4$, filtered and evaporated to give crude material which was purified by column chromatography (ethyl acetate in petroleum ether, 20% v/v) to give compound 0107-3 as an off-white solid (370 mg, 60%): LCMS: 245 [M+1]$^+$; $^1$H NMR (400 Hz, CDCl$_3$) δ 1.41 (s, 12H), 7.40 (dd, J=6.8 Hz, 8.4 Hz, 1H), 7.62 (d, J=8.8 Hz, 1H), 7.90 (d, J=6.8 Hz, 1H), 8.50 (s, 1H).

Step 1d: Thieno[3,2-d]pyrimidine-2,4 (1H,3H)-dione (Compound 0109)

A mixture of methyl 3-amino-2-thiophenecarboxylate (0108) (13.48 g, 85.85 mmol) and urea (29.75 g, 0.43 mol) was heated at 190° C. for 2 h. The hot reaction mixture was poured into sodium hydroxide solution and insoluble material was removed by filtration. The mixture was then acidified by 2 N HCl solution. The resulting solid was collected by filtration, dried to give title compound 0109 (9.62 g, 67%) as a white solid: LCMS: 169 [M+1]$^+$; $^1$H NMR (400 MHz, DMSO-d$_6$): δ 6.92 (d, J=4.0 Hz, 1H), 8.04 (d, J=4.0 Hz, 1H), 11.19 (d, J=14.0 Hz, 1H), 11.60 (s, 1H).

Step 1e: 2,4-Dichlorothieno[3,2-d]pyrimidine (Compound 0110)

A mixture of compound 0109 (9.49 g, 56.49 mmol) and phosphorous oxychloride (150 mL) was heated at reflux for 10 h. The solvent was then removed and the residue was poured onto ice/water with vigorous stirring to give title compound 0110 (8.62 g, 74%) as a white solid: LCMS: 205 [M+1]$^+$; $^1$H NMR (400 MHz, CDCl$_3$): δ 7.48 (d, J=5.6 Hz, 1H), 8.05 (d, J=5.6 Hz, 1H).

Step 1f: 4-(2-Chlorothieno[3,2-d]pyrimidin-4-yl) morpholine (Compound 0111)

A mixture of compound 0110 (8.68 g, 42.34 mmol) and morpholine (8.11 mL, 93.15 mmol) in methanol (150 mL) was stirred at room temperature for 1 h. The reaction mixture was then filtered, washed with water (50 mL×3) and methanol (50 mL×1) to give the title compound 0111 (11.04 g, 100%) as a white solid: LCMS: 256 [M+1]$^+$; $^1$H NMR (400 MHz, DMSO-d$_6$): δ 3.76 (t, J=4.8 Hz, 4H), 3.91 (t, J=4.8 Hz, 4H), 7.41 (d, J=5.6 Hz, 1H), 8.31 (d, J=5.6 Hz, 1H).

Step 1 g: 2-Chloro-4-morpholinothieno[3,2-d]pyrimidine-6-carbaldehyde (Compound 0112)

To a suspension of compound 0111 (1.75 g, 6.85 mmol) in dry tetrahydrofuran (40 mL) at −78° C. was added a 2.0 M solution of LDA in THF/hexane (20.55 mL, 41.1 mmol). After stirring for 1 h, dry N,N-dimethylformamide (3.2 mL, 41.1 mmol) was added. The reaction mixture was stirred for 1 h at −78° C. and then warmed slowly to room temperature. After a further stir for 10 h at room temperature, the reaction mixture was poured onto $NH_4Cl$ saturated solution, extracted with ethyl acetate (100 mL×3), dried over $Na_2SO_4$ and filtered. The filtrate was concentrated to leave a residue which was washed with ethyl acetate (10 mL×2) to give the title compound 0112 (0.66 g, 35%) as a yellow solid: LCMS: 284 [M+1]$^+$; $^1$H NMR (400 MHz, DMSO-d$_6$): δ3.76 (t, J=4.8 Hz, 4H), 4.10 (t, J=4.8 Hz, 4H), 8.29 (s, 1H), 10.21 (s, 1H).

Step 1 h: 4-(2-Cloro-6-((4-(methylthioperoxy)piperazin-1-yl)methyl)thieno[3,2-d]pyrimidin-4-yl)morpholine (Compound 0113)

A mixture of compound 0112 (1.10 g, 3.89 mmol), 0103 (2.20 g, 7.78 mmol), triethylamine (471 mg, 4.7 mmol) and titanium tetraisopropanolate (1.30 g, 4.67 mmol) in chloroform (30 ml) was stirred at reflux overnight. The solvent was then removed, and 1,2-dichloroethane (40 mL) and sodium cyanborohydride (368 mg, 5.84 mmol) were added. The reaction mixture was then stirred at room temperature for 12 h. The reaction was concentrated and the resulting solid was recrystallized with ethanol to give the title compound 0113 (800 mg, 48%) as a yellow solid: LCMS: 432 [M+1]$^+$; $^1$H NMR (400 MHz, DMSO-d$_6$): δ 2.57 (t, J=4.4 Hz, 4H), 2.89 (s, 3H), 3.13 (t, J=4.4 Hz, 4H), 3.74 (t, J=5.2 Hz, 4H), 3.88 (t, J=5.2 Hz, 4H), 3.91 (s, 2H), 7.31 (s, 1H).

Step 1i: 4-(2-Chloro-6-((4-(methylthioperoxy)piperazin-1-yl)methyl)thieno[3,2-d]pyrimidin-4-yl)morpholine (Compound 0114)

A mixture of compound 0113 (800 mg, 1.86 mmol), 0107-3 (500 mg, 2.04 mmol), sodium hydrogen carbonate (470 mg, 5.58 mmol) and bis(triphenylphosphine) palladium (0) chloride (80 mg, 0.093 mmol) in toluene (20 mL), ethanol (12 mL) and water (5.6 mL) was flushed with nitrogen and heated under microwave irradiation at 120° C. for 1 h. The reaction mixture was partitioned between dichloromethane and water. The organic layer was separated and washed with brine, dried over magnesium sulfate, filtered and evaporated. The resulting residue was purified by column chromatography (silica gel, dichloromethane, 2%, v/v, to give title compound 0114 (350 mg, 37%) as a white solid. mp 148-149° C. LCMS: 514 [M+1]$^+$; $^1$H NMR (400 MHz, CDCl$_3$): δ 2.70 (t, J=4.4 Hz, 4H), 2.81 (s, 3H), 3.13 (t, J=4.4 Hz, 4H), 3.92 (m, 6H), 4.09 (t, J=5.6 Hz, 4H), 7.41 (s, 1H), 7.50 (m, 1H), 7.59 (d, J=8.4 Hz, 1H), 8.28 (d, J=6.8 Hz, 1H), 9.00 (s, 1H), 10.32 (br s, 1H).

Step 1j: Ethyl 5-(4-(6-((4-(methylsulfonyl)piperazin-1-yl)methyl)-4-morpholinothieno[3,2-d]pyrimidin-2-yl)-2H-indazol-2-yl)pentanoate (Compound 0116-3) and ethyl 5-(4-(6-((4-(methylsulfonyl)piperazin-1-yl)methyl)-4-morpholinothieno[3,2-d]pyrimidin-2-yl)-1H-indazol-1-yl)pentanoate (Compound 0115-3)

A mixture of compound 0114 (370 mg, 0.72 mmol), ethyl 5-bromopentanoate (181 mg, 0.87 mmol) and potassium carbonate (199 mg, 1.44 mmol) in acetonitrile (50 mL) was refluxed for 58 hours. Solvent was removed and the residue was partitioned between dichloromethane and water. The organic layer was separated and washed with brine, dried over magnesium sulfate, filtered and evaporated to give a crude product which was purified by prep-HPLC to give the title compound 0115-3 (80 mg, 17%) and 0116-3 (60 mg, 13%). Compound 0115-3: a white solid; LCMS: 642 [M+1]$^+$; $^1$H NMR (400 MHz, CDCl$_3$): δ 1.15 (t, J=7.2 Hz, 3H), 1.61 (m, 2H), 1.94 (m, 2H), 2.26 (t, J=7.2 Hz, 2H), 2.62 (t, J=4.4 Hz, 4H), 2.74 (s, 3H), 3.23 (t, J=4.4 Hz, 4H), 3.84 (m, 6H), 4.01 (m, 6H), 4.38 (t, J=6.8 Hz, 2H), 7.33 (s, 1H), 7.42 (m, 2H), 8.17 (m, 1H), 8.81 (s, 1H). $^{13}$C NMR (100 MHz, CDCl$_3$): δ 172.2, 161.6, 159.5, 157.1, 147.8, 139.3, 133.7, 131.2, 125.0, 123.0, 121.4, 120.8, 112.1, 109.7, 65.8 (2C), 59.3, 56.3, 51.4, 47.5 (2C), 45.6 (2C), 44.8 (2C), 33.5, 32.8, 28.6, 21.2, 13.2.

Compound 0116-3: a white solid; LCMS: 642 [M+1]$^+$; $^1$H NMR (400 MHz, CDCl$_3$): δ 1.15 (t, J=7.2 Hz, 3H), 1.60 (m, 2H), 2.06 (m, 2H), 2.29 (t, J=7.2 Hz, 2H), 2.63 (s, 4H), 2.74 (s, 3H), 3.24 (s, 4H), 3.84 (m, 6H), 4.04 (m, 6H), 4.43 (t, J=6.8 Hz, 2H), 7.33 (m, 2H), 7.74 (d, J=8.4 Hz, 1H), 8.19 (d, J=6.8 Hz, 1H), 8.82 (s, 1H). $^{13}$C NMR (100 MHz, CDCl$_3$): δ 172.1, 161.5, 159.5, 156.9, 148.8, 147.4, 130.0, 124.6, 123.1, 122.2, 119.0, 118.8, 112.0, 65.8 (2C), 59.4, 56.3, 52.4, 51.4 (2C), 45.5 (2C), 44.8 (2C), 33.5, 32.7, 28.6, 21.1, 13.1.

Step 1k: N-Hydroxy-5-(4-(6-((4-(methylsulfonyl)piperazin-1-yl)methyl)-4-morpholinothien-[3,2-d]pyrimidin-2-yl)-1H-indazol-1-yl)pentanamide (Compound 3)

To a stirred solution of hydroxylamine hydrochloride (4.67 g, 67 mmol) in methanol (24 mL) at 0° C. was added a solution of potassium hydroxide (5.61 g, 100 mmol) in methanol (14 mL). After addition, the mixture was stirred for 30 minutes at 0° C. The resulting precipitate was filtered off and the filtrate was prepared as free hydroxylamine solution.

The above freshly prepared hydroxylamine solution (4.00 mL) was placed in 10 mL flask. Compound 0115-3 (80 mg, 0.12 mmol) was added to this solution and stirred at 0-10° C. for 15 minutes. The reaction process was monitored by TLC. After the reaction was completed, the reaction was filtered. The collected solid was washed with water and methanol, dried to give compound 3 (45 mg, 58%) as a white solid: mp 139-143° C. LCMS: 629 [M+1]$^+$; $^1$H NMR (400 MHz, DMSO-d$_6$) δ 1.47 (m, 2H), 1.83 (m, 2H), 1.98 (t, J=7.4 Hz, 2H), 2.62 (s, 4H), 2.91 (s, 3H), 3.17 (s, 4H), 3.84 (s, 4H), 3.86 (s, 2H), 4.01 (m, 4H), 4.47 (t, J=6.6 Hz, 2H), 7.52 (m, 2H), 7.82 (d, J=8.4 Hz, 1H), 8.24 (d, J=6.8 Hz, 1H), 8.67 (s, 1H), 8.86 (s, 1H), 10.36 (s, 1H).

Example 2: Preparation of N-hydroxy-3-(4-(6-((4-(methylsulfonyl)piperazin-1-yl)methyl)-4-morpholinothieno[3,2-d]pyrimidin-2-yl)-1H-indazol-1-yl)propanamide (Compound 4)

Step 2a: Ethyl 6-(4-(6-((4-(methylsulfonyl)piperazin-1-yl)methyl)-4-morpholinothieno[3,2-d]pyrimidin-2-yl)-2H-indazol-2-yl)hexanoate (Compound 0116-4) and ethyl 3-(4-(6-((4-(methylsulfonyl)piperazin-1-yl)methyl)-4-morpholinothieno[3,2-d]pyrimidin-2-yl)-1H-indazol-1-yl)propanoate (Compound 0115-4)

A mixture of compound 0114 (160 mg, 0.31 mmol), ethyl 6-bromohexanoate (83 mg, 0.37 mmol) and potassium carbonate (85 mg, 0.62 mmol) in acetonitrile (50 mL) was refluxed overnight. Solvent was removed and the residue was partitioned between dichloromethane and water. The organic layer was separated and washed with brine, dried over magnesium sulfate, filtered and evaporated in vacuo. The resulting residue was purified by prep-HPLC to give the title compound 0116-4 (40 mg, 20%) and 0115-4 (70 mg, 34%).

Compound 0116-4: an oil; LCMS: 657 [M+1]$^+$; $^1$H NMR (400 MHz, CDCl$_3$): δ 1.14 (t, J=7.2 Hz, 3H), 1.34 (m, 2H), 1.60 (m, 2H), 2.02 (m, 2H), 2.22 (t, J=7.2 Hz, 2H), 2.62 (s, 4H), 2.73 (s, 3H), 3.23 (m, 4H), 3.82 (s, 2H), 3.84 (m, 4H), 4.00 (m, 6H), 4.40 (t, J=7.2 Hz, 2H), 7.33 (m, 2H), 7.74 (d, J=8.4 Hz, 1H), 8.19 (d, J=6.8 Hz, 1H), 8.82 (s, 1H). $^{13}$C NMR (100 MHz, CDCl$_3$): δ 172.4, 161.7, 159.6, 156.7, 148.6, 147.5, 130.1, 124.6, 123.1, 122.1, 119.2, 118.8, 112.0, 65.8, 59.4, 56.4, 52.6, 51.2, 45.3, 44.8, 33.3, 32.9, 29.3, 25.1, 23.4, 13.4. Compound 0115-4: an oil; LCMS: 657 [M+1]$^+$; $^1$H NMR (400 MHz, CDCl$_3$): δ1.14 (t, J=7.2 Hz, 3H), 1.27 (m, 2H), 1.59 (m, 2H), 1.90 (m, 2H), 2.19 (t, J=7.2 Hz, 2H), 2.61 (m, 4H), 2.72 (s, 3H), 3.22 (m, 4H), 3.83 (m, 6H), 4.00 (m, 6H), 4.35 (t, J=7.2 Hz, 2H), 7.31 (s, 1H), 7.41 (m, 2H), 8.16 (m, 1H), 8.81 (s, 1H). $^{13}$C NMR (100 MHz, CDCl$_3$): δ 172.6, 161.7, 159.8, 157.1, 147.7, 139.2, 133.5, 131.2, 124.9, 123.2, 121.4, 120.7, 112.1, 109.7, 65.8 (2C), 59.2, 56.3, 51.4, 47.7, 45.6, 44.8, 33.5, 33.0, 28.6, 23.5, 19.8, 13.2.

Step 2b: N-hydroxy-3-(4-(6-((4-(methylsulfonyl)piperazin-1-yl)methyl)-4-morpholinothieno[3,2-d]pyrimidin-2-yl)-1H-indazol-1-yl)propanamide (Compound 4)

The title compound 4 was prepared as a yellow solid (45 mg, 22%) from 0115-4 (210 mg, 0.32 mmol) and freshly prepared hydroxylamine methanol solution (5.0 mL) using a procedure similar to that described for compound 3 (Example 1): mp 186-187° C. LCMS: 643 [M+1]$^+$; $^1$H NMR (400 MHz, DMSO-d$_6$) δ 1.22 (m, 2H), 1.52 (m, 2H), 1.84-1.93 (m, 4H), 2.61 (m, 4H), 2.91 (s, 3H), 3.17 (m, 4H), 3.82-3.85 (m, 4H), 3.95 (s, 2H), 3.99-4.01 (m, 4H), 4.44 (t, J=6.8 Hz, 2H), 7.51 (m, 2H), 7.80 (d, J=8.8 Hz, 1H), 8.23 (d, J=8.8 Hz, 1H), 8.63 (s, 1H), 8.85 (s, 1H), 10.30 (s, 1H).

Example 3: Preparation of N-hydroxy-7-(4-(6-((4-(methylsulfonyl)piperazin-1-yl)methyl)-4-morpholinothieno[3,2-d]pyrimidin-2-yl)-1H-indazol-1-yl) heptanamide (Compound 5)

Step 3a: Ethyl 7-(4-(6-((4-(methylsulfonyl)piperazin-1-yl)methyl)-4-morpholinothieno[3,2-d]pyrimidin-2-yl)-2H-indazol-2-yl)heptanoate (Compound 0116-5) and ethyl 7-(4-(6-((4-(methylsulfonyl)piperazin-1-yl)methyl)-4-morpholinothieno[3,2-d]pyrimidin-2-yl)-1H-indazol-1-yl)heptanoate (Compound 0115-5)

The title compound 0115-5 (110 mg, 27%) and 0116-5 (60 mg, 16%) were prepared from 0114 (280 mg, 0.55 mmol), ethyl 7-bromoheptanoate (133 mg, 0.65 mmol) and potassium carbonate (152 mg, 1.10 mmol) in acetonitrile (25 mL) using a procedure similar to that described for compound 0115-3 and compound 0116-3 (Example 1): Compound 0115-3: a white solid; LCMS: 670 [M+1]$^+$; $^1$H NMR (400 MHz, CDCl$_3$): δ 1.15 (t, J=7.2 Hz, 3H), 1.29 (m, 4H), 1.46 (m, 2H), 1.84 (m, 2H), 2.23 (t, J=7.2 Hz, 2H), 2.61 (s, 4H), 2.91 (s, 3H), 3.16 (s, 4H), 3.83 (m, 4H), 3.95 (s, 2H), 4.00 (m, 6H), 4.45 (t, J=6.6 Hz, 2H), 7.51 (m, 2H), 7.79 (d, J=8.8 Hz, 1H), 8.23 (d, J=6.8 Hz 1H), 8.86 (s, 1H). Compound 0116-3: a white solid; LCMS: 670 [M+1]$^+$; $^1$H NMR (400 MHz, CDCl$_3$): δ 1.14 (t, J=7.2 Hz, 3H), 1.31 (m, 4H), 1.53 (m, 2H), 1.97 (m, 2H), 2.25 (t, J=7.6 Hz, 2H), 2.61 (s, 4H), 2.91 (s, 3H), 3.17 (s, 4H), 3.83 (m, 4H), 3.95 (s, 2H), 4.00 (m, 6H), 4.50 (t, J=7.0 Hz, 2H), 7.37 (t, J=7.8 Hz, 1H), 7.52 (s, 1H), 7.46 (d, J=8.8 Hz, 1H), 8.17 (d, J=6.8 Hz 1H), 9.02 (s, 1H).

Step 3b: N-hydroxy-7-(4-(6-((4-(methylsulfonyl) piperazin-1-yl)methyl)-4-morpholinothieno[3,2-d] pyrimidin-2-yl)-1H-indazol-1-yl)heptanamide (Compound 5)

The title compound 5 was prepared as a white solid (70 mg, 71%) from 0115-5 (100 mg, 0.15 mmol) and freshly prepared hydroxylamine methanol solution (4.0 mL) using a procedure similar to that described for compound 3 (Example 1): mp 127-130° C. LCMS: 657 [M+1]$^+$; $^1$H NMR (400 MHz, DMSO-d$_6$) δ 1.26 (s, 4H), 1.44 (m, 2H), 1.84 (m, 2H), 1.91 (t, J=7.2 Hz, 2H), 2.61 (s, 4H), 2.91 (s, 3H), 3.16 (s, 4H), 3.83 (m, 4H), 3.95 (s, 2H), 4.00 (m, 4H), 4.45 (t, J=6.8 Hz, 2H), 7.5 (m, 2H), 7.80 (d, J=8.4 Hz, 1H), 8.23 (d, J=7.6 Hz, 1H), 8.65 (s, 1H), 8.86 (s, 1H), 10.32 (s, 1H).

Example 4: Preparation of N-hydroxy-5-(4-(6-((4-(methylsulfonyl)piperazin-1-yl)methyl)-4-morpholinothieno[3,2-d]pyrimidin-2-yl)-2H-indazol-2-yl) pentanamide (Compound 7)

The title compound 7 was prepared as a white solid (35 mg, 47%) from 0116-3 (60 mg, 0.12 mmol) and freshly prepared hydroxylamine methanol solution (4.0 mL) using a procedure similar to that described for compound 3 (Example 1): mp 146-169° C. LCMS: 629 [M+1]$^+$; $^1$H NMR (400 MHz, DMSO-d$_6$) δ 1.57 (m, 2H), 2.00 (m, 2H), 2.07 (t, J=7.2 Hz, 2H), 2.67 (m, 4H), 2.97 (s, 3H), 3.23 (s, 4H), 3.89 (s, 4H), 4.01 (s, 2H), 4.04 (m, 4H), 4.57 (t, J=7.0 Hz, 2H), 7.43 (t, J=7.8 Hz, 1H), 7.58 (s, 1H), 7.81 (d, J=8.4 Hz, 1H), 8.28 (d, J=6.8 Hz, 1H), 9.08 (s, 1H).

Example 5: Preparation of N-hydroxy-6-(4-(6-((4-(methylsulfonyl)piperazin-1-yl)methyl)-4-morpholinothieno[3,2-d]pyrimidin-2-yl)-2H-indazol-2-yl) hexanamide (Compound 8)

The title compound 8 was prepared as a yellow solid (15 mg, 11%) from 0116-4 (140 mg, 0.21 mmol) and freshly prepared hydroxylamine methanol solution (5.0 mL) using a procedure similar to that described for compound 3 (Example 1): mp 124-125° C. LCMS: 643 [M+1]$^+$; $^1$H NMR (400 MHz, DMSO-d$_6$) δ 1.23 (m, 2H), 1.55 (m, 2H), 1.92-1.97 (m, 4H), 2.61 (m, 4H), 2.91 (s, 3H), 3.17 (m, 4H), 3.82-3.85 (m, 4H), 3.95 (s, 2H), 3.99-4.01 (m, 4H), 4.50 (t, J=6.8 Hz, 2H), 7.37 (m, 1H), 7.53 (s, 2H), 7.74 (d, J=8.4 Hz, 1H), 8.21 (d, J=6.8 Hz, 1H), 8.64 (s, 1H), 9.02 (s, 1H), 10.31 (s, 1H).

Example 6: Preparation of N-hydroxy-7-(4-(6-((4-(methylsulfonyl)piperazin-1-yl)methyl)-4-morpholinothieno[3,2-d]pyrimidin-2-yl)-2H-indazol-2-yl) heptanamide (Compound 9)

The title compound 9 was prepared as a white solid (45 mg, 76%) from 0116-5 (60 mg, 0.09 mmol) and freshly prepared hydroxylamine methanol solution (4.0 mL) using a procedure similar to that described for compound 3 (Example 1): mp 123-126° C. LCMS: 657 [M+1]$^+$; $^1$H NMR (400 MHz, DMSO-d$_6$) δ 1.29 (s, 4H), 1.48 (m, 2H), 1.93 (m, 4H), 2.61 (s, 4H), 2.91 (s, 3H), 3.16 (s, 4H), 3.83 (m, 4H), 3.95 (s, 2H), 3.98 (m, 4H), 4.50 (t, J=7.0 Hz, 2H), 7.37 (t, J=7.8 Hz, 1H), 7.52 (s, 1H), 7.75 (d, J=8.8 Hz, 1H), 8.22 (d, J=6.8 Hz, 1H), 8.65 (s, 1H), 9.03 (s, 1H), 10.32 (s, 1H).

Example 7: Preparation of 5-(4-((2-(1H-indazol-4-yl)-4-morpholinothieno[3,2-d]pyrimidin-6-yl) methyl)piperazin-1-yl)-N-hydroxypentanamide (Compound 11)

Step 7a: Tert-butyl 4-((2-chloro-4-morpholinothieno [3,2-d]pyrimidin-6-yl)methyl) piperazine-1-carboxylate (Compound 0201)

To a mixture of 0112 (4.0 g, 14.10 mmol) and tert-butyl piperazine-1-carboxylate (3.94 g, 21.15 mmol) in chloroform (50 mL) was added tetraisopyl titanate (4.81 g, 16.92 mmol). The mixture was stirred at room temperature overnight. The solvent was removed under reduced pressure. The residue was dissolved in ClCH$_2$CH$_2$C$_1$ (60 mL) and NaBH$_3$CN (1.33 g, 21.15 mmol) was added to the mixture. The mixture was stirred at room temperature for 4 hours and was diluted with NaHCO$_3$ solution. The mixture was then extracted with ethyl acetate. The organic phase was separated, dried and concentrated to afford the product 0201 (5.2 g, 81%): LCMS: 454 [M+1]$^+$; $^1$H NMR (400 Hz, CDCl$_3$) δ 1.46 (s, 9H), 2.49 (s, 4H), 3.47 (t, J=4.4 Hz, 4H), 3.80 (s, 2H), 3.84 (t, J=5.2 Hz, 4H), 3.99 (t, J=4.8 Hz, 4H), 7.17 (s, 1H).

Step 7b: 4-(2-Chloro-6-(piperazin-1-ylmethyl)thieno [3,2-d]pyrimidin-4-yl) morpholine (Compound 0202)

To a mixture of 0201 (5.2 g, 11.45 mmol) in dioxane was added 4 N HCl/dioxane (30 mL) under N$_2$. The reaction mixture was stirred at room temperature for 5 h. The mixture was poured into water (30 mL), adjusted pH 7 with saturated NaHCO₃ solution, extracted with ethyl acetate, dried and concentrated to afford the product 0202 (3.0 g, 74%): LCMS: 354 [M+1]⁺; ¹H NMR (400 Hz, CDCl₃) δ 2.52 (s, 4H), 2.93 (t, J=4.8 Hz, 4H), 3.78 (s, 2H), 3.84 (t, J=4.8 Hz, 4H), 3.99 (t, J=4.4 Hz, 4H), 7.16 (s, 1H).

Step 7c: Ethyl 5-(4-((2-chloro-4-morpholinothieno[3,2-d]pyrimidin-6-yl)methyl) piperazin-1-yl)pentanoate (Compound 0203-11)

To a mixture of 0202 (0.3 g, 0.85 mmol) in DMF (3 mL) was added Cs₂CO₃ (0.61 g, 1.87 mmol) and ethyl 5-bromopentanoate (0.2 g, 0.93 mmol). The reaction mixture was stirred at room temperature overnight and then poured into water (10 mL). The mixture was extracted with ethyl acetate. The organic phase was separated and washed with water (10 mL×5) and brine, dried over Na₂SO₄, filtered and concentrated to afford the product 0203-11 (0.36 g, 80%) as a gray solid: LCMS: 482 [M+1]⁺; ¹H NMR (400 Hz, CDCl₃) δ 1.25 (t, J=7.2 Hz, 3H), 1.52-1.69 (m, 6H), 2.30-2.37 (s, 2H), 2.55 (m, 6H), 3.79 (s, 2H), 3.84 (t, J=5.2 Hz, 4H), 3.98 (t, J=4.4 Hz, 4H), 4.13 (q, J=6.8 Hz, 2H), 7.16 (s, 1H).

Step 7d: Ethyl 5-(4-((2-(1H-indazol-4-yl)-4-morpholinothieno[3,2-d]pyrimidin-6-yl)methyl)piperazin-1-yl)pentanoate (Compound 0204-11)

A mixture of 0203-11 (250 mg, 0.52 mmol), 0107-3 (140 mg, 0.57 mmol), NaHCO₃ (131 mg, 1.56 mmol) and Pd(dppf)₂Cl₂ (18 mg, 0.026 mmol) in toluene (4.8 mL), ethanol (2.5 mL) and water (1.3 mL) was flushed with N₂ and heated under microwave irradiation at 130° C. for 2 h. To the mixture was added water (10 mL) and extracted with ethyl acetate. The organic phase was separated and washed with brine, dried over Na₂SO₄, filtered and concentrated to give the crude product which was purified by silica gel column (methanol in dichloromethane 5% v/v) to afford the title product 0204-11 as a white solid (62 mg, 21%): LCMS: 565 [M+2]⁺; ¹H NMR (400 Hz, CDCl₃) δ 1.23 (m, 3H), 1.27 (m, 2H), 1.55 (m, 2H), 1.65 (m, 2H), 2.32 (t, J=7.6 Hz, 2H), 2.40 (m, 2H), 2.54 (m, 2H), 2.64 (m, 4H), 3.86 (s, 2H), 3.92 (t, J=4.8 Hz, 4H), 4.09 (t, J=5.2 Hz, 4H), 4.13 (q, J=7.2 Hz, 2H), 7.38 (s, 1H), 7.50 (t, J=7.2 Hz, 1H), 7.59 (d, J=8.0 Hz, 1H), 8.28 (dd, J=7.2 Hz, 0.8 Hz, 1H), 9.01 (d, J=1.2 Hz, 1H).

Step 7e: 5-(4-((2-(1H-indazol-4-yl)-4-morpholinothieno[3,2-d]pyrimidin-6-yl)methyl)piperazin-1-yl)-N-hydroxypentanamide (Compound 11)

The title compound 11 was prepared as a white solid (21 mg, 17%) from 0204-11 (129 mg, 0.23 mmol) and freshly prepared hydroxylamine methanol solution (1.0 mL, 1.77 mol/L) using a procedure similar to that described for compound 3 (Example 1): m.p. 125-127° C., LCMS: 552 [M+2]⁺; ¹H NMR (400 Hz, DMSO-d₆) δ 1.23 (s, 2H), 1.39 (m, 2H), 1.48 (m, 2H), 1.94 (t, J=7.6 Hz, 2H), 2.09 (s, 2H), 2.26 (t, J=6.8 Hz, 2H), 2.50 (m, 4H), 2.64 (m, 4H), 3.86 (m, 6H), 4.00 (m, 4H), 7.47 (d, J=6.8 Hz, 1H), 7.67 (d, J=8.4 Hz, 1H), 8.22 (d, J=6.8 Hz, 1H), 8.88 (s, 1H), 10.27 (s, 1H), 13.20 (s, 1H).

Example 8: Preparation of 6-(4-((2-(1H-indazol-4-yl)-4-morpholinothieno[3,2-d]pyrimidin-6-yl)methyl)piperazin-1-yl)-N-hydroxyhexanamide (Compound 12)

Step 8a: Ethyl 6-(4-((2-chloro-4-morpholinothieno[3,2-d]pyrimidin-6-yl) methyl)piperazin-1-yl)hexanoate (Compound 0203-12)

The title compound 0203-12 was prepared as a gray solid (0.57 g, 82%) from 0202 (0.5 g, 1.41 mmol), Cs₂CO₃ (0.92 g, 2.82 mmol) and ethyl 6-bromohexanoate (0.35 g, 1.55 mmol) using a procedure similar to that described for compound 0203-11 (Example 7): LCMS: 496 [M+1]⁺; ¹H NMR (400 Hz, CDCl₃) δ 1.25 (m, 4H), 1.34 (m, 2H), 1.64 (m, 2H), 2.30 (t, J=7.6 Hz, 2H), 2.38 (m, 2H), 2.60 (m, 8H), 3.80 (s, 2H), 3.84 (t, J=4.4 Hz, 4H), 3.40 (t, J=4.8 Hz, 4H), 4.11 (q, J=7.2 Hz, 2H), 7.16 (s, 1H).

Step 8b: Ethyl 6-(4-((2-(1H-indazol-4-yl)-4-morpholinothieno[3,2-d]pyrimidin-6-yl)methyl)piperazin-1-yl)hexanoate (Compound 0204-12)

The title compound 0204-12 was prepared as a white solid (56 mg, 16%) from 0203-12 (295 mg, 0.61 mmol), 0107-3 (164 mg, 0.67 mmol), NaHCO₃ (150 mg, 1.79 mmol) and Pd(dppf)₂Cl₂ (23 mg, 0.031 mmol) in toluene (5.6 mL), ethanol (3 mL) and water (1.5 mL) using a procedure similar to that described for compound 0204-11 (Example 7): LCMS: 579 [M+2]⁺; ¹H NMR (400 Hz, CDCl₃) δ 1.25 (t, J=7.6 Hz, 3H), 1.41 (m, 2H), 1.67 (m, 2H), 1.81 (m, 2H), 2.32 (t, J=7.2 Hz, 2H), 3.02 (m, 8H), 3.61 (m, 2H), 3.96 (m, 5H), 4.13 (q, J=14.4 Hz, 2H), 4.19 (m, 2H), 7.39 (t, J=7.2 Hz, 1H), 7.55 (s, 1H), 7.60 (d, J=8.8 Hz, 1H), 7.97 (d, J=6.8 Hz, 1H), 8.50 (s, 1H).

Step 8c: 6-(4-((2-(1H-indazol-4-yl)-4-morpholinothieno[3,2-d]pyrimidin-6-yl)methyl)piperazin-1-yl)-N-hydroxyhexanamide (Compound 12)

The title compound 12 was prepared as a white solid (15 mg, 13%) from 0204-12 (120 mg, 0.21 mmol) and freshly prepared hydroxylamine methanol solution (1.0 mL, 1.77 mol/L) using a procedure similar to that described for compound 3 (Example 1): m.p. 123-124° C., LCMS: 565 [M+1]⁺; ¹H NMR (400 Hz, DMSO-d₆) δ 1.23 (m, 2H), 1.26 (m, 2H), 1.36 (m, 2H), 1.93 (t, J=7.2 Hz, 2H), 2.25 (t, J=6.8 Hz, 2H), 2.39 (m, 4H), 3.30 (m, 4H), 3.85 (m, 6H), 4.00 (t, J=5.2 Hz, 4H), 7.47 (d, J=15.2 Hz, 2H), 7.66 (d, J=8.4 Hz, 1H), 8.22 (d, J=6.8 Hz, 1H), 8.65 (s, 1H), 8.88 (s, 1H).

Example 9: Preparation of 7-(4-((2-(1H-indazol-4-yl)-4-morpholinothieno[3,2-d]pyrimidin-6-yl)methyl)piperazin-1-yl)-N-hydroxyheptanamide (Compound 13)

Step 9a: Ethyl 7-(4-((2-chloro-4-morpholinothieno[3,2-d]pyrimidin-6-yl)methyl) piperazin-1-yl)heptanoate (Compound 0203-13)

The title compound 0203-13 was prepared as a gray solid (0.55 g, 76%) from 0202 (0.5 g, 1.41 mmol), Cs₂CO₃ (0.92 g, 2.82 mmol) and ethyl 6-bromohexanoate (0.35 g, 1.55 mmol) using a procedure similar to that described for compound 0203-11 (Example 7): 512 [M+2]⁺; ¹H NMR (400 Hz, DMSO-d₆) δ 1.17 (t, J=6.8 Hz, 3H), 1.28 (m, 4H), 1.52 (m, 2H), 1.61 (m, 2H), 2.28 (t, J=7.2 Hz, 2H), 2.49 (m, 4H), 3.05 (m, 6H), 3.75 (t, J=4.4 Hz, 4H), 3.88 (t, J=4.8 Hz, 2H), 3.97 (m, 2H), 4.04 (q, J=14 Hz, 2H), 7.34 (s, 1H).

Step 9b: Ethyl 7-(4-((2-(1H-indazol-4-yl)-4-morpholinothieno[3,2-d]pyrimidin-6-yl)methyl)piperazin-1-yl)heptanoate (Compound 0204-13)

The title compound 0204-13 was prepared as a white solid (56 mg, 16%) from 0203-13 (300 mg, 0.60 mmol), 0107-3 (162 mg, 0.67 mmol), NaHCO$_3$ (151 mg, 1.80 mmol) and Pd(dppf)$_2$Cl$_2$ (21 mg, 0.03 mmol) in toluene (5.5 mL), EtOH (3 mL) and water (1.5 mL) using a procedure similar to that described for compound 0204-11 (Example 7): LCMS: 592 [M+1]$^+$; $^1$H NMR (400 Hz, CDCl$_3$) δ 1.25 (m, 3H), 1.33 (m, 4H), 1.51 (m, 2H), 1.63 (m, 2H), 2.29 (t, J=7.6 Hz, 2H), 2.37 (m, 2H), 2.52 (m, 4H), 2.64 (m, 4H), 3.86 (s, 2H), 3.92 (t, J=4.4 Hz, 4H), 4.09 (t, J=6.0 Hz, 4H), 4.12 (q, J=14.4 Hz, 2H), 7.38 (s, 1H), 7.50 (t, J=8.4 Hz, 1H), 7.59 (d, J=8.4 Hz, 1H), 8.28 (dd, J=7.6 Hz, 0.8 Hz, 1H), 9.02 (d, J=0.8 Hz, 1H).

Step 9c: 7-(4-((2-(1H-indazol-4-yl)-4-morpholinothieno[3,2-d]pyrimidin-6-yl)methyl)piperazin-1-yl)-N-hydroxyheptanamide (Compound 13)

The title compound 13 was prepared as a white solid (25 mg, 37%) from 0204-13 (68 mg, 0.11 mmol) and freshly prepared hydroxylamine methanol solution (0.5 mL, 1.77 mol/L) using a procedure similar to that described for compound 3 (Example 1): m.p. 119-122° C., LCMS: 580 [M+2]$^+$; $^1$H NMR (400 Hz, DMSO-d$_6$) δ 1.27 (m, 4H), 1.50 (m, 2H), 1.62 (m, 2H), 1.94 (t, J=6.8 Hz, 2H), 2.47 (m, 4H), 3.06 (m, 6H), 3.85 (t, J=4.0 Hz, 4H), 4.02 (m, 6H), 4.00 (t, J=5.2 Hz, 4H), 7.49 (t, J=8.4 Hz, 1H), 7.56 (s, 1H), 7.69 (d, J=8.0 Hz, 1H), 8.21 (d, J=7.2 Hz, 1H), 8.87 (s, 1H), 9.39 (s, 1H), 10.35 (s, 1H).

Example 10: Preparation of 2-(4-((2-(1H-indazol-4-yl)-4-morpholinothieno[3,2-d]pyrimidin-6-yl)methyl)piperazin-1-yl)-N-hydroxypyrimidine-5-carboxamide (Compound 14)

Step 10a: (Z)-Ethyl-2-(ethoxymethyl)-3-methoxyacrylate (Compound 0302)

Sodium (13.8 g) was added to a mixture of benzene (200 mL) and ethanol (27 g) at room temperature. To the above mixture was added a mixture of ethyl formate (45.0 g, 0.61 mol) and ethyl 3-ethoxypropionate (44.0 g, 0.30 mol) slowly at 0° C. The resulting reaction mixture was stirred for 2 hours and then dimethyl sulfate (76.0 g, 0.61 mol) was added and stirred at 50° C. for 3 h. The mixture was filtered, and the filtrate was washed with water. The organic layer was separated and was added triethylammonium chloride (40.0 g, 0.29 mol) and sodium hydroxide (7.00 g, 0.175 mol). The resulting mixture was stirred for 4 h. and then filtered. The filtrate was washed with water, dried over Na$_2$SO$_4$, filtered and evaporated to give a residue which was distilled under vacuum to provide compound 0302 (18.8 g, 33%) which was used directly to the next step without further purification: $^1$H NMR (400 MHz, CDCl$_3$): δ 1.26 (m, 6H), 3.48 (m, 3H), 3.63 (m, 3H), 4.20 (m, 2H).

Step 10b: Ethyl 2-oxo-1,2,3,4-tetrahydropyrimidine-5-carboxylate (Compound 0303)

A mixture of compound 0302 (21.4 g, 0.11 mol), urea (5.70 g, 0.095 mol), and concentrated hydrochloric acid (36%-38%, 5 mL) in ethanol (300 mL) was heated at reflux overnight. After evaporation, the residue was recrystallized from ethanol to give compound 0303 (7.80 g, 65%) as a colorless prisms: LCMS: 171 [M+1]$^+$, $^1$H NMR (400 MHz, CDCl$_3$): δ 1.27 (t, J=7.2 Hz, 3H), 4.19 (m, 4H), 5.28 (s, 1H), 7.21 (d, J=5.6 Hz, 1H), 7.40 (s, 1H).

Step 10c: Ethyl 2-oxo-1,2-dihydropyrimidine-5-carboxylate (Compound 0304)

A solution of compound 0303 (2.50 g, 14.7 mmol) and bromine (2.40 g, 15 mmol) in acetic acid (55 mL) was heated at reflux for 1.5 h. Removal of the solvent afforded crude compound 0304 (3.60 g, 99%) which was used directly to the next step without further purification: LCMS: 169 [M+1]$^+$, $^1$H NMR (400 MHz, CDCl$_3$): δ 1.27 (t, J=7.2 Hz, 3H), 4.28 (q, J=7.2 Hz, 2H), 8.85 (s, 2H), 12.19 (ds, 2H).

Step 10d: Ethyl 2-chloropyrimidine-5-carboxylate (Compound 0305)

A mixture of compound 0304 (3.60 g, 21 mmol), phosphorus oxychloride (25 mL), and N,N-dimethylaniline (2.5 mL) was heated at reflux for 1.5 h. After removal of the solvent, ice water (10 mL) was added to the residue. The mixture was added to 2 N NaOH (90 ml), and extracted with EtOAc. The organic layer was evaporated and purified by column chromatography (ethyl acetate in petroleum ether, 5% v/v) to give compound 0305 (1.20 g, 30%): LCMS: 187 [M+1]$^+$, $^1$H NMR (300 MHz, CDCl$_3$): δ 1.42 (t, J=7.5 Hz, 3H), 4.48 (q, J=7.5 Hz, 2H), 9.15 (s, 2H); $^1$H NMR (400 MHz, DMSO-d$_6$): δ 1.33 (t, J=6.8 Hz, 3H); 4.37 (q, J=6.8 Hz, 2H), 9.18 (s, 2H).

Step 10e: Ethyl 2-(piperazin-1-yl)pyrimidine-5-carboxylate (Compound 0306)

A mixture of compound 0305 (1.10 g, 5.9 mmol) and piperazine (1.02 g, 11.8 mmol) in DMF (50 mL) was stirred at room temperature for 1.5 h. The mixture was diluted with water and extracted with ethyl acetate. The organic layer was washed with water and dried, concentrate to give compound 0306 (1.20 g, 86%): LCMS: 237 [M+1]$^+$, $^1$H NMR (400 MHz, DMSO-d$_6$): δ 1.29 (t, J=7.2 Hz, 3H), 2.73 (t, J=5.2 Hz, 4H), 3.77 (t, J=5.2 Hz, 4H), 4.25 (q, J=7.2 Hz, 2H), 8.76 (s, 2H).

Step 10f: Ethyl 2-(4-((2-chloro-4-morpholinothieno[3,2-d]pyrimidin-6-yl) methyl)piperazin-1-yl)pyrimidine-5-carboxylate (Compound 0307)

To a mixture of compound 0112 (500 mg, 1.77 mmol) and compound 0306 (376 mg, 1.59 mmol) in chloroform (40 mL) was added tetraisopyl titanate (754 mg, 2.66 mmol). The mixture was stirred at reflux overnight. Solvent was evaporated and then 1,2-dichloroethane (50 mL) and sodium cyanborohydride (168 mg, 2.66 mmol) were added. The resulting mixture was stirred at room temperature for 12 h. The mixture was poured into saturated NaHCO$_3$ and extract with ethyl acetate (2×50 mL). The organic layer was separated and evaporated to afford a mixture which was purified by silica gel column chromatography (ethyl acetate in petroleum ether 10% v/v) to geve compound 0307 (270 mg, 34%) as a yellow solid: LCMS: 504 [M+1]$^+$; $^1$H NMR (400 MHz, CDCl$_3$) δ 1.35 (t, J=6.8 Hz, 3H), 2.62 (s, 4H), 3.85 (m, 6H), 4.00 (m, 8H), 4.33 (q, J=6.8 Hz, 2H), 7.26 (s, 1H), 8.84 (s, 2H).

Step 10 g: Ethyl 2-(4-((2-(1H-indazol-4-yl)-4-morpholinothieno[3,2-d]pyrimidin-6-yl)methyl)piperazin-1-yl)pyrimidine-5-carboxylate (Compound 0308)

The title compound 0308 was prepared as a yellow solid (60 mg, 23%) from 0307 (220 mg, 0.44 mmol), 0107-3 (161 mg, 0.66 mmol), NaHCO$_3$ (111 mg, 1.32 mmol) and Pd(dppf)$_2$Cl$_2$ (19 mg, 0.022 mmol) in toluene (4.7 mL), ethanol (2.8 mL) and water (1.2 mL) using a procedure similar to that described for compound 0204-11 (Example 7): LCMS: 586 [M+1]$^+$; $^1$H NMR (400 MHz, CDCl$_3$): δ 1.35 (t, J=6.8 Hz, 3H), 2.66 (s, 4H), 3.93 (m, 6H), 4.01 (m, 4H), 4.11 (m, 4H), 4.33 (q, J=6.8 Hz, 2H), 7.41 (s, 1H), 7.51 (m, 1H), 7.69 (d, J=8.4 Hz, 1H), 8.28 (d, J=6.8 Hz, 1H), 8.84 (s, 2H), 9.01 (s, 1H).

Step 10 h: 2-(4-((2-(1H-indazol-4-yl)-4-morpholinothieno[3,2-d]pyrimidin-6-yl)methyl)piperazin-1-yl)-N-hydroxypyrimidine-5-carboxamide (Compound 14)

The title compound 14 was prepared as a yellow solid (30 mg, 52%) from 0308 (60 mg, 0.10 mmol) and freshly prepared hydroxylamine methanol solution (3.0 mL, 1.77 mol/L) using a procedure similar to that described for compound 3 (Example 1): mp 209-221° C. LCMS: 573 [M+1]$^+$; $^1$H NMR (400 MHz, DMSO-d$_6$) δ 2.59 (s, 4H), 3.85 (m, 8H), 3.95 (s, 2H), 4.01 (m, 4H), 7.47 (m, 1H), 7.52 (m, 1H), 7.67 (d, J=8.4 Hz, 1H), 8.23 (d, J=6.8 Hz, 1H), 8.68 (s, 2H), 8.89 (s, 1H), 9.00 (s, 1H), 11.07 (s, 1H), 13.19 (s, 1H).

Example 11: Preparation of 2-(4-(((2-(1H-indazol-4-yl)-4-morpholinothieno[3,2-d]pyrimidin-6-yl) methylamino)methyl)piperidin-1-yl)-N-hydroxypyrimidine-5-carboxamide (Compound 15)

Step 11a: Ethyl 2-(4-(aminomethyl)piperidin-1-yl) pyrimidine-5-carboxylate (Compound 0401)

A mixture of 0405 (1.10 g, 5.9 mmol), piperidin-4-ylmethanamine (1.35 g, 11.8 mmol) in 2-(dimethylamino) acetamide (50 mL) was stirred at room temperature for 1.5 h. After removal of the solvent, the residue was purified by column chromatography on silica gel (CH$_3$OH in CH$_2$Cl$_2$ 6% v/v) to give desired product 0401 (1.27 g, 81%): LCMS: 265 [M+1]$^+$, $^1$H NMR (400 MHz, CDCl$_3$): δ 1.16 (m, 2H), 1.22 (m, 5H), 1.36 (m, 1H), 1.64 (m, 1H), 1.85 (d, J=12 Hz, 2H), 2.62 (d, J=6.42 Hz, 2H), 2.94 (ds, J=12.8 Hz, J=2.4 Hz, 2H), 4.91 (d, J=11.2 Hz, 2H), 7.26 (s, 1H), 8.82 (s, 2H).

Step 11b: Ethyl 2-(4-(((2-chloro-4-morpholinothieno[3,2-d]pyrimidin-6-yl)methylamino)methyl) piperidin-1-yl)pyrimidine-5-carboxylate (Compound 0402-15)

To a mixture of compound 0112 (589 mg, 2.08 mmol) and compound 0401 (500 mg, 1.89 mmol) in chloroform (50 mL) was added tetraisopyl titanate (644 mg, 2.26 mmol). The mixture was stirred at reflux overnight. The solvent was removed and 1,2-dichloroethane (30 mL) and sodium cyanborohydride (179 mg, 2.84 mmol) were then added. The mixture was stirred at room temperature for 12 h. The mixture was poured into saturated NaHCO$_3$ and extract with ethyl acetate (2×50 mL). The organic layer was separated evaporated. The residue was purified by column on silica gel (ethyl acetate in petroleum ether 10% v/v) to give compound 0402 (630 mg, 57%). LCMS: 533 [M+1]$^+$. $^1$H NMR (400 MHz, DMSO-d$_6$) δ 1.05-1.14 (m, 2H), 1.29 (t, J=7.2 Hz, 3H), 1.78-1.85 (m, 3H), 2.46 (d, J=6.0 Hz, 2H), 2.68 (brs, 1H), 2.98 (t, J=11 Hz, 2H), 3.75 (t, J=4.8 Hz, 4H), 3.88 (t, J=4.8 Hz, 4H), 4.02 (s, 2H), 4.26 (t, J=7.2 Hz, 2H), 4.74 (d, J=13 Hz, 2H), 7.23 (s, 1H), 8.74 (s, 2H).

Step 11c: Ethyl 2-(4-(((2-(1H-indazol-4-yl)-4-morpholinothieno[3,2-d]pyrimidin-6-yl)methylamino) methyl)piperidin-1-yl)pyrimidine-5-carboxylate (Compound 0403-15)

The title compound 0403 was prepared as a white solid (120 mg, 17%) from 0402 (630 mg, 1.18 mmol), 0107-3 (580 mg, 2.37 mmol), NaHCO$_3$ (297 mg, 3.54 mmol) and Pd(dppf)$_2$Cl$_2$ (25 mg, 0.036 mmol) in toluene (11 mL), ethanol (6.6 mL) and water (3.1 mL) using a procedure similar to that described for compound 0204-11 (Example 7): LCMS: 614 [M+1]$^+$; $^1$H NMR (400 MHz, DMSO-d$_6$): δ 1.09-1.14 (m, 2H), 1.28 (t, J=7.2 Hz, 3H), 1.82-1.87 (m, 3H), 3.00 (t, J=12 Hz, 2H), 3.83 (t, J=4.6 Hz, 4H), 4.01 (t, J=4.6 Hz, 4H), 4.07 (s, 2H), 4.26 (t, J=7.2 Hz, 2H), 4.75 (d, J=13 Hz, 2H), 7.47 (t, J=7.6 Hz, 2H), 7.66 (d, J=8.0 Hz, 1H), 8.22 (d, J=7.2 Hz, 1H), 8.75 (s, 2H), 8.89 (s, 1H), 13.18 (s, 1H).

Step 1d: 2-(4-(((2-(1H-indazol-4-yl)-4-morpholinothieno[3,2-d]pyrimidin-6-yl)methylamino)methyl) piperidin-1-yl)-N-hydroxypyrimidine-5-carboxamide (Compound 15)

The title compound 15 was prepared as a white solid (30 mg, 63%) from 0403 (50 mg, 0.08 mmol) and freshly prepared hydroxylamine methanol solution (3.0 mL, 1.77 mol/L) using a procedure similar to that described for compound 3 (Example 1): mp 170-172° C. LCMS: 601 [M+1]$^+$; $^1$H NMR (400 MHz, DMSO-d$_6$) δ 1.05-1.13 (m, 2H), 1.23 (m, 1H), 1.82-1.85 (m, 3H), 2.95 (t, J=12 Hz, 2H), 3.84 (s, 4H), 4.01 (s, 4H), 4.07 (s, 2H), 4.71 (d, J=13 Hz, 2H), 7.47 (t, J=7.6 Hz, 2H), 7.66 (d, J=8.0 Hz, 1H), 8.22 (d, J=7.2 Hz, 1H), 8.65 (s, 2H), 8.88 (s, 1H), 8.98 (s, 1H), 11.03 (s, 1H), 13.18 (s, 1H).

Example 12: Preparation of 2-(((2-(1H-indazol-4-yl)-4-morpholinothieno[3,2-d]pyrimidin-6-yl) methyl)(methyl)amino)-N-hydroxypyrimidine-5-carboxamide (Compound 54)

Step 12a: (2-Chloro-4-morpholinothieno[3,2-d]pyrimidin-6-yl)methanol (Compound 0501)

To a mixture of compound 0112 (500 mg, 1.77 mmol) in methanol (10 mL) was added sodium borohydride (200 mg, 5.3 mmol). The mixture was stirred at room temperature for 1 hour. The reaction was quenched with water and extracted with ethyl acetate, dried over Na$_2$SO$_4$ and concentrated to obtain crude compound 0501 (500 mg, 99%) as a yellow solid: LCMS: 286 [M+1]$^+$; $^1$H NMR (400 MHz, DMSO-d$_6$). δ 3.74 (t, J=4.4 Hz, 4H), 3.88 (t, J=4.4 Hz, 4H), 4.80 (d, J=5.6 Hz, 2H), 5.93 (t, J=5.6 Hz, 1H), 7.21 (s, 1H).

Step 12b: 4-(6-(Bromomethyl)-2-chlorothieno[3,2-d]pyrimidin-4-yl)morpholine (Compound 0502)

To a solution of compound 0501 (1.6 g, 5.6 mmol) in dichloromethane (100 mL) was added N-bromosuccinimide (1.2 g, 6.7 mmol) and triphenylphosphine (1.75 g, 6.7 mmol). The mixture was stirred at 25° C. for 3 hours. Solvent was removed the residue was purified by column chromatography (ethyl acetate in petroleum ether 20% v/v) to give title compound 0502 (1.16 mg, 60%) as a yellow solid: LCMS: 348 [M+1]$^+$; $^1$H NMR (400 MHz, DMSO-d$_6$). δ 3.74 (t, J=4.8 Hz, 4H), 3.88 (t, J=4.4 Hz, 4H), 4.79 (s, 2H), 7.21 (s, 1H).

Step 12c: (2-Chloro-4-morpholinothieno[3,2-d]pyrimidin-6-yl)-N-methylmethanamine (Compound 0503-54)

A mixture of compound 0502 (190 mg) and methanamine alcohol solution (50 mL) was stirred at reflux temperature for 1 hour. The solvent was removed at reduce pressure and the residue was purified by column chromatography (methanol in dichloromethane, 12% v/v) to give title compound 0503-54 (190 mg, 54%) as a yellow solid: LCMS: 299 [M+1]$^+$; $^1$H NMR (400 MHz, DMSO-d$_6$): δ 2.06 (s, 3H), 2.93 (s, 1H), 3.45 (t, J=4.4 Hz, 4H), 3.57 (t, J=4.4 Hz, 4H), 3.73 (s, 2H), 7.02 (s, 1H).

Step 12d: Ethyl 2-(((2-chloro-4-morpholinothieno[3,2-d]pyrimidin-6-yl)methyl) (methyl)amino)pyrimidine-5-carboxylate (Compound 0504-54)

A mixture of compound 0503-54 (215 mg, 0.72 mmol), compound 0305 (336 mg, 1.8 mmol) and N, N-diisopropylethylamine (20 mL) in acetonitrile (30 mL) was stirred at room temperature overnight. The solvent was removed at reduce pressure and the resulting precipitation was washed with ethyl acetate and dried to provide the title compound 0504-54 (210 mg, 65%) as a yellow solid: LCMS: 531 [M+1]$^+$; $^1$H NMR (400 MHz, DMSO-d$_6$): δ 1.4 (t, J=6.8 Hz, 3H), 3.35 (s, 3H), 3.81 (t, J=4 Hz, 4H), 3.93 (t, J=4 Hz, 4H), 4.38 (q, J=7.2 Hz, 2H), 5.31 (s, 2H), 7.05 (s, 1H), 8.97 (s, 2H).

Step 12e: Ethyl 2-(((2-(1H-indazol-4-yl)-4-morpholinothieno[3,2-d]pyrimidin-6-yl) methyl)(methyl)amino)pyrimidine-5-carboxylate (Compound 0505)

A mixture of compound 0504 (210 mg, 0.47 mmol), 0107-3 (171 mg, 0.7 mmol), sodium hydrogen carbonate (118 mg, 1.4 mmol) and bis(triphenylphosphine) palladium (a) chloride (16 mg, 0.02 mmol) in toluene (5 mL), ethanol (3 mL) and water (1.3 mL) was flushed with nitrogen and heated under microwave irradiation at 120° C. for 1 h. The reaction mixture was added water and extracted with ethyl acetate. The ethyl acetate layer was collected and washed with brine, dried over magnesium sulfate, filtered and evaporated to give a residue which was washed with dichloromethane to obtain the title compound 0505-54 (130 mg, 52%) as a white solid: LCMS: 449 [M+1]$^+$; $^1$H NMR (400 MHz, DMSO-d$_6$): δ 1.37 (t, J=6.8 Hz, 3H), 3.36 (s, 3H), 3.86 (t, J=4.8 Hz, 4H), 4.02 (t, J=4.8 Hz, 4H), 4.35 (q, J=6.8 Hz, 2H), 5.33 (s, 2H), 7.53 (m, 1H), 7.66 (s, 1H), 7.73 (d, J=8 Hz, 1H), 8.28 (d, J=7.2 Hz, 1H), 8.95 (dd, J$_1$=8 Hz, J$_2$=7.6 Hz, 1H), 13.28 (s, 1H).

Step 12f: 2-(((2-(1H-indazol-4-yl)-4-morpholinothieno[3,2-d]pyrimidin-6-yl)methyl)(methyl)amino)-N-hydroxypyrimidine-5-carboxamide (Compound 54)

The title compound 54 was prepared as a white solid (17 mg, 15%) from 0505-54 (120 mg, 0.22 mmol) and freshly prepared hydroxylamine methanol solution (4.0 mL, 1.77 mol/L) using a procedure similar to that described for compound 3 (Example 1): m.p. 197-200° C. LCMS: 518 [M+1]$^+$; $^1$H NMR (400 MHz, DMSO-d$_6$): δ 3.26 (s, 3H), 3.86 (t, J=4.0 Hz, 4H), 3.96 (t, J=4.0 Hz, 4H), 5.23 (s, 2H), 7.47 (t, J=7.6 Hz, 1H), 7.58 (s, 1H), 7.67 (d, J=8 Hz, 1H), 8.22 (d, J=7.2 Hz, 1H), 8.76 (s, 2H), 8.87 (s, 1H), 9.09 (s, 1H), 11.16 (s, 1H), 13.22 (s, 1H).

Example 13: Preparation of 2-((2-(1H-indazol-4-yl)-4-morpholinothieno[3,2-d]pyrimidin-6-yl)methylamino)-N-hydroxypyrimidine-5-carboxamide (Compound 53)

Step 13a: (2-Chloro-4-morpholinothieno[3,2-d]pyrimidin-6-yl)methanamine (Compound 0503-53)

To a solution of compound 0502 (1.5 g, 4.3 mmol) in methanol (20 mL) was added NH$_3$.H$_2$O (20 mL). The mixture was stirred overnight at 65° C. The solvent was removed at reduce pressure and the resulting residue was purified by column chromatography (ethyl acetate in petroleum ether, 50% v/v) to give title compound 0503-53 (270 mg, 22%) as a yellow solid: LCMS: 285 [M+1]$^+$; $^1$H NMR (400 MHz, DMSO-d$_6$): δ 3.75 (t, J=4.8 Hz, 4H), 3.89 (t, J=4.4 Hz, 4H), 4.06 (s, 2H), 7.22 (s, 1H).

Step 13b: Ethyl 2-((2-chloro-4-morpholinothieno[3,2-d]pyrimidin-6-yl)methylamino) pyrimidine-5-carboxylate (Compound 0504-53)

A mixture of compound 0503-53 (270 mg, 0.95 mmol), compound 0305 (353 mg, 1.9 mmol) and N, N-Diisopropylethylamine (2 mL) in acetonitrile (10 mL) was stirred at room temperature overnight. The solvent was removed at reduce pressure and the precipitation was washed with dichloromethane, dried to provide the title compound 0504-53 (160 mg, 39%) as a white solid: LCMS: 435 [M+1]$^+$; $^1$H NMR (400 MHz, DMSO-d$_6$): δ 1.29 (t, J=7.2 Hz, 3H), 3.72 (t, J=5.2 Hz, 4H), 3.84 (t, J=4.8 Hz, 4H), 4.27 (dd, J$_1$=14.0 Hz, J$_2$=6.8 Hz, 2H), 4.88 (d, J=6 Hz, 2H), 7.30 (s, 1H), 8.79 (s, 2H), 8.85 (t, J=6 Hz, 1H).

Step 13c: Ethyl 2-((2-(1H-indazol-4-yl)-4-morpholinothieno[3,2-d]pyrimidin-6-yl) methylamino)pyrimidine-5-carboxylate (Compound 0505-53)

A mixture of compound 0504-53 (160 mg, 0.37 mmol), 0107-3 (135 mg, 0.55 mmol), sodium hydrogen carbonate (93 mg, 1.11 mmol) and bis(triphenylphosphine) palladium (a) chloride (13 mg, 0.02 mmol) in toluene (5 mL), ethanol (3 mL) and water (1.3 mL) was flushed with nitrogen and heated under microwave irradiation at 120° C. for 1 h. The reaction mixture was added water and extracted with ethyl acetate. The organic layer was collected and washed with brine, dried over magnesium sulfate, filtered and evaporated to give a residue which was washed with dichloromethane to give title compound 0505-53 (80 mg, 42%) as a white solid: LCMS: 517 [M+1]$^+$; $^1$H NMR (400 MHz, DMSO-d$_6$): δ 1.29 (t, J=6.8 Hz, 3H), 3.81 (t, J=4.8 Hz, 4H), 3.97 (t, J=4.0

Hz, 4H), 4.27 (dd, J$_1$=14.0 Hz, J$_2$=6.8 Hz, 2H), 4.93 (d, J=6.0 Hz, 2H), 7.45-7.50 (m, 2H), 7.66 (d, J=8.0 Hz, 1H), 8.22 (d, J=7.6 Hz, 1H), 8.81 (d, J=6.4 Hz, 2H), 8.88 (s, 2H), 13.2 (s, 1H).

Step 13d: 2-((2-(1H-indazol-4-yl)-4-morpholinothieno[3,2-d]pyrimidin-6-yl) methylamino)-N-hydroxypyrimidine-5-carboxamide (Compound 53)

The title compound 53 was prepared as a light yellow solid (19 mg, 24%) from 0505-53 (80 mg, 0.15 mmol) and freshly prepared hydroxylamine methanol solution (5.0 mL, 1.77 mol/L) using a procedure similar to that described for compound 3 (Example 1): m.p. 234-237° C. LCMS: 504 [M+1]$^+$; $^1$H NMR (400 MHz, DMSO-d$_6$): δ 2.09 (s, 2H), 3.81 (t, J=4.8 Hz, 4H), 3.97 (t, J=4.4 Hz, 4H), 4.90 (d, J=6.0 Hz, 2H), 7.47 (t, J=9.2 Hz, 2H), 7.66 (d, J=8.4 Hz, 1H), 8.22 (d, J=6.8 Hz, 1H), 8.56 (t, J=6.0 Hz, 1H), 8.68 (s, 2H), 8.88 (s, 1H), 9.04 (s, 1H), 11.09 (s, 1H), 13.21 (s, 1H).

Example 14: Preparation of 2-(4-((((2-(1H-indazol-4-yl)-4-morpholinothieno[3,2-d]pyrimidin-6-yl)methyl)(methyl)amino)methyl)piperidin-1-yl)-N-hydroxypyrimidine-5-carboxamide (Compound 16)

Step 14a: Ethyl 2-(4-((((2-chloro-4-morpholinothieno[3,2-d]pyrimidin-6-yl)methyl)(methyl)amino)methyl)piperidin-1-yl)pyrimidine-5-carboxylate (Compound 0402-16)

of 0402-15 (510 mg, 0.96 mmol) and paraformaldehyde (58 mg, 1.92 mmol) was solved in methanol (20 mL), then NaBH$_3$CN (121 mg, 1.92 mmol) was added, the mixture was stirred at room temperature overnight. Methanol was removed and the residue was added ethyl acetate and water. The organic layer was washed by water and brine water, dried with anhydrous Na$_2$SO$_4$. Filtered, concentrated and the residue was purified by column (ethyl acetate in petroleum ether 40% v/v) to get compound 0402-16 (265 mg, 51%) as a yellow solid. LCMS: 546 [M+1]$^+$. $^1$H NMR (400 MHz, DMSO-d$_6$): δ 1.04 (m, 2H), 1.28 (t, J=7.2, 3H), 1.84-1.88 (m, 3H), 2.24 (s, 3H), 2.28 (d, J=6.8 Hz, 2H), 3.01 (t, J=11.6 Hz, 2H), 3.75 (m, 4H), 3.83 (m, 2H), 3.88 (m, 4H), 4.25 (q, J=7.2 Hz, 2H), 4.74 (d, J=13.2 Hz, 2H), 7.27 (s, 1H), 8.75 (s, 2H).

Step 14b: Ethyl 2-(4-((((2-(1H-indazol-4-yl)-4-morpholinothieno[3,2-d]pyrimidin-6-yl)methyl)(methyl)amino)methyl)piperidin-1-yl)pyrimidine-5-carboxylate (Compound 0403-16)

A mixture of compound 0402-16 (246 mg, 0.45 mmol), 0107-3 (221 mg, 0.90 mmol), sodium hydrogen carbonate (12.6 mg, 1.5 mmol) and bis(triphenylphosphine) palladium (II) chloride (19 mg, 0.023 mmol) in toluene (5 mL), ethanol (2.9 mL) and water (1.3 mL) was flushed with nitrogen and heated under microwave irradiation at 120° C. for 2 h. The reaction mixture was partitioned between dichloromethane and water, organic layer was washed with brine, dried over magnesium sulfate, filtered and evaporated in vacuo. The resulting residue was purified using column chromatography eluting methanol in dichloromethane (2%, v/v), to give title compound 0403-16 (200 mg, 71%) as a yellow solid. LCMS: 628 [M+1]$^+$; $^1$H NMR (400 MHz, CDCl$_3$): δ 1.18 (m, 2H), 1.35 (t, J=7.2 Hz, 3H), 1.94-1.97 (m, 3H), 2.34-2.36 (m, 5H), 2.97 (t, J=12.8 Hz, 2H), 3.84 (m, 4H), 3.94 (m, 4H), 4.10 (m, 4H), 4.32 (q, J=7.2 Hz, 2H), 4.90 (d, J=13.2 Hz, 2H), 7.36 (s, 1H), 7.49 (t, J=8.0 Hz, 1H), 7.57 (d, J=8.0 Hz, 1H), 8.27 (d, J=7.2 Hz, 1H), 8.82 (s, 2H), 9.01 (s, 1H), 10.42 (s, 1H).

Step 14c: 2-(4-((((2-(1H-indazol-4-yl)-4-morpholinothieno[3,2-d]pyrimidin-6-yl)methyl)(methyl)amino)methyl)piperidin-1-yl)-N-hydroxypyrimidine-5-carboxamide (Compound 16)

To a stirred solution of hydroxylamine hydrochloride (4.67 g, 67 mmol) in methanol (24 mL) at 0° C. was added a solution of potassium hydroxide (5.61 g, 100 mmol) in methanol (14 mL). After addition, the mixture was stirred for 30 minutes at 0° C., and was allowed to stand at low temperature. The resulting precipitate was isolated, and the solution was prepared to give free Hydroxylamine.

The above freshly prepared hydroxylamine solution (10.00 mL) was placed in 100 mL flask. Compound 111-47-2 (200 mg, 0.32 mmol) was added to this solution and degassed at 0° C. for 15 minutes. The reaction process was monitored by TLC. The mixture was neutralized with dry ice, filtered and washed with water, methanol and DCM to give the title compound 111-47 (130 mg, 66%) as a yellow solid: mp 174-175° C. LCMS: 616 [M+1]$^+$; $^1$H NMR (400 MHz, DMSO-d$_6$): δ 1.03 (m, 2H), 1.85-1.94 (m, 3H), 2.27-2.31 (m, 5H), 2.97 (t, J=12.0 Hz, 2H), 3.84 (m, 6H), 4.00 (m, 4H), 4.71 (d, J=12.8 Hz, 2H), 7.45-7.49 (m, 2H), 7.66 (d, J=8.4 Hz, 1H), 8.22 (d, J=7.2 Hz, 1H), 8.65 (s, 2H), 8.89 (s, 1H), 9.00 (s, 1H), 11.06 (s, 1H), 13.22 (s, 1H).

Example 15: Preparation of 4-((2-(1H-indazol-4-yl)-4-morpholinothieno[3,2-d]pyrimidin-6-yl)methylamino)-N-hydroxybutanamide (Compound 41)

Step 15a: Ethyl 4-(tert-butoxycarbonyl((2-chloro-4-morpholinothieno[3,2-d]pyrimidin-6-yl)methyl)amino)butanoate (Compound 0404-41)

15a-1: Ethyl 4-((2-chloro-4-morpholinothieno[3,2-d]pyrimidin-6-yl)methylamino)butanoate Ethyl 4-aminobutanoate hydrochloride (1.97 g, 11.77 mmol) was solved in chloroform (30 mL) and the pH of mixture was adjusted to 8-9 with triethylamine, then compound 0112 (1.66 g, 5.88 mmol) and tetraisopyl titanate (2.01 g, 7.06 mmol) were added and the mixture was stirred at reflux overnight. Removed the solvent, then 1,2-dichloroethane (50 mL) and sodium cyanborohydride (1.48 g, 23.53 mmol) were added and then stirred at room temperature for 12 h. The mixture was poured into saturated NaHCO$_3$ solution and extract with ethyl acetate (3×50 mL) and purified by column (ethyl acetate in petroleum ether 50% v/v) to get 4-((2-chloro-4-morpholinothieno[3,2-d]pyrimidin-6-yl)methylamino)butanoate (1.38 g, 59%) as a yellow solid. LCMS: 399 [M+1]$^+$; $^1$H NMR (400 MHz, CDCl$_3$) δ 1.15 (t, J=7.2 Hz, 3H), 1.68 (m, 2H), 2.35 (t, J=7.2 Hz, 2H), 2.55 (t, J=7.2 Hz, 2H), 3.74 (t, J=4.8 Hz, 4H), 3.89 (t, J=4.8 Hz, 4H), 4.00 (s, 2H), 4.03 (q, J=7.2 Hz, 2H), 7.25 (s, 1H).

15a-2: Ethyl 4-(tert-butoxycarbonyl((2-chloro-4-morpholinothieno[3,2-d]pyrimidin-6-yl)methyl)amino)butanoate (0404-41)

To a solution of 4-((2-chloro-4-morpholinothieno[3,2-d]pyrimidin-6-yl)methylamino)butanoate (400 mg, 1.0 mmol) in THF (10 mL) was added (Boc)$_2$O (218 mg, 1.0 mmol).

Then the mixture was stirred at room temperature overnight. The reaction mixture was extracted with ethyl acetate and washed with water, brine and dried over sodium sulfate. The crude product was purified using column chromatography (ethyl acetate in petroleum ether 75% v/v), to give title compound 0404-41 (330 mg, 66%) as a colorless liquid. LCMS: 499 [M+1]$^+$; $^1$H NMR (400 MHz, DMSO-d$_6$) δ 1.16 (t, J=7.2 Hz, 3H), 1.42 (s, 9H), 1.74 (m, 2H), 2.26 (t, J=7.2 Hz, 2H), 3.23 (t, J=7.2 Hz, 2H), 3.74 (t, J=4.4 Hz, 4H), 3.87 (t, J=4.4 Hz, 4H), 4.03 (q, J=7.2 Hz, 2H), 4.64 (s, 2H), 7.30 (s, 1H).

Step 15b. Ethyl 4-(((2-(1H-indazol-4-yl)-4-morpholinothieno[3,2-d]pyrimidin-6-yl)methyl)(tert-butoxycarbonyl)amino)butanoate (Compound 0405-41)

A mixture of compound 0404-41 (386 mg, 0.78 mmol), 0107-3 (378 mg, 1.55 mmol), sodium hydrogen carbonate (196 mg, 2.33 mmol) and bis(triphenylphosphine)palladium (a) chloride (27 mg, 0.05 mmol) in toluene (8 mL), ethanol (5 mL) and water (2 mL) was flushed with nitrogen and heated under microwave irradiation at 120° C. for 1 h. The reaction mixture was partitioned between dichloromethane and water, organic layer was washed with brine, dried over sodium sulfate, filtered and evaporated in vacuum. The resulting residue was purified using column chromatography eluting methanol in dichloromethane (2-5%, v/v), to give title compound 0405-41 (396 mg, 79%) as a white solid. LCMS: 581 [M+1]$^+$; $^1$H NMR (400 MHz, DMSO-d$_6$): δ1.16 (t, J=7.2 Hz, 3H), 1.44 (s, 9H), 1.78 (m, 2H), 2.28 (t, J=7.2 Hz, 2H), 3.28 (t, J=6.8 Hz, 2H), 3.83 (m, 4H), 4.03 (m, 6H), 4.70 (s, 2H), 7.47 (t, J=8.0 Hz, 1H), 7.51 (s, 1H), 7.67 (d, J=8.0 Hz, 1H), 8.22 (d, J=8.0 Hz, 1H), 8.88 (s, 1H), 13.22 (s, 1H).

Step 15c: 4-((2-(1H-indazol-4-yl)-4-morpholinothieno[3,2-d]pyrimidin-6-yl)methylamino)-N-hydroxybutanamide (Compound 41)

To a stirred solution of hydroxylamine hydrochloride (4.67 g, 67 mmol) in methanol (24 mL) at 0° C. was added a solution of potassium hydroxide (5.64 g, 100 mmol) in methanol (14 mL). After addition, the mixture was stirred for 30 minutes at 0° C., and was allowed to stand at low temperature. The resulting precipitate was isolated, and the solution was prepared to give free Hydroxylamine.

The freshly prepared hydroxylamine solution (6.00 mL) was placed in 50 mL flask. Compound 0405-41 (300 mg, 0.51 mmol) was added to this solution and degassed at room temperature for 30 minutes. The reaction process was monitored by TLC. The mixture was neutralized with dry ice, filtered, and the precipitation was washed with methanol and water to give tert-butyl (2-(1H-indazol-4-yl)-4-morpholinothieno[3,2-d]pyrimidin-6-yl)methyl(4-(hydroxyamino)-4-oxobutyl)carbamate (267 mg, 91%) as a white solid. LCMS: 568 [M+1]$^+$; $^1$H NMR (400 MHz, DMSO-d$_6$): δ1.45 (s, 9H), 1.74 (m, 2H), 1.96 (t, J=7.2 Hz, 2H), 3.23 (m, 2H), 3.83 (m, 4H), 4.00 (m, 4H), 7.47 (t, J=8.0 Hz, 1H), 7.50 (s, 1H), 7.67 (d, J=8.0 Hz, 1H), 8.22 (d, J=8.0 Hz, 1H), 8.70 (s, 1H), 8.88 (s, 1H), 10.39 (s, 1H), 13.22 (s, 1H).

The above prepared compound was then added to a freshly prepared isopropanol hydrogen chloride solution (7.00 mL). The reaction mixture was stirred at room temperature for 2 h. The mixture was evaporated and dissolved in water. Then the mixture was neutralized with ammonia at 0° C., filtered and the precipitation was washed with methanol and water to give the crude product which was purified with pre-HPLC. Compound 41 was got (50 mg, 24%) as an orange solid: m.p. 149-152° C. LCMS: 468 [M+1]$^+$; $^1$H NMR (400 MHz, DMSO-d$_6$): δ1.55 (m, 2H), 1.87 (t, J=7.2 Hz, 2H), 2.45 (t, J=7.2 Hz, 2H), 3.68 (m, 4H), 3.86 (m, 6H), 3.96 (s, 2H), 7.32 (m, 2H), 7.51 (d, J=8.0 Hz, 1H), 7.98 (s, 1H), 8.07 (d, J=8.0 Hz, 1H), 8.56 (s, 1H), 8.73 (s, 1H), 13.06 (s, 1H).

Example 16: Preparation of 5-((2-(1H-indazol-4-yl)-4-morpholinothieno[3,2-d]pyrimidin-6-yl)methylamino)-N-hydroxypentanamide (Compound 42)

Step 16a: Methyl 5-(tert-butoxycarbonyl((2-chloro-4-morpholinothieno[3,2-d]pyrimidin-6-yl)methyl)amino)pentanoate (Compound 0404-42)

The title compound 0404-42 (0.75 g, 33.3%) was prepared as a white solid without further purification from 0112 (1.2 g, 4.24 mmol), 5-aminopentanoate hydrochloride (1.416 g, 8.48 mmol) using a procedure similar to that described for compound 0404-41 (Example 15): LCMS: 399 [M+1]$^+$; $^1$H NMR (400 MHz, DMSO-d$_6$) δ 1.39-1.47 (m, 2H), 1.52-1.60 (m, 2H), 2.30 (t, J=7.2 Hz, 2H), 2.53 (t, J=6.8 Hz, 2H), 3.58 (s, 3H), 3.74 (t, J=4.8 Hz, 4H), 3.88 (t, J=4.8 Hz, 4H), 3.99 (s, 2H), 7.23 (s, 1H). Compound 0404-42: LCMS: 499 [M+1]$^+$; $^1$H NMR (400 MHz, DMSO-d$_6$) δ1.23 (s, 9H), 1.47-1.49 (m, 4H), 2.30 (t, J=6.8 Hz, 2H), 3.20 (s, 2H), 3.56 (s, 3H), 3.74 (t, J=4.8 Hz, 4H), 3.88 (t, J=4.8 Hz, 4H), 4.64 (s, 2H), 7.31 (s, 1H).

Step 16b: Methyl 5-(((2-(1H-indazol-4-yl)-4-morpholinothieno[3,2-d]pyrimidin-6-yl)methyl)(tert-butoxycarbonyl)amino)pentanoate (Compound 0405-42)

The title compound 0405-42 (260 mg, 55.8%) was prepared as a yellow solid from 0404-42 (400 mg, 0.803 mmol), 0107-3 (216 mg, 0.884 mmol), sodium hydrogen carbonate (202.4 mg, 2.41 mmol) and bis(triphenylphosphine)palladium(a) chloride (30 mg, 0.0402 mmol) in toluene (8 mL), ethanol (5 mL) and water (2 mL) using a procedure similar to that described for compound 0404-42 (Example 15): LCMS: 581 [M+1]$^+$; $^1$H NMR (400 MHz, DMSO-d$_6$): δ 1.44 (s, 9H), 1.50-1.52 (m, 4H), 3.25 (s, 2H), 3.56 (s, 3H), 3.83 (m, J=5.2 Hz, 4H), 4.00-4.10 (m, 6H), 4.69 (s, 2H), 7.47-7.51 (m, 2H), 7.67 (d, J=8.4 Hz, 1H), 8.23 (d, J=6.8 Hz, 1H), 8.88 (s, 1H), 13.20 (s, 1H).

Step 16c: 5-((2-(1H-indazol-4-yl)-4-morpholinothieno[3,2-d]pyrimidin-6-yl)methylamino)-N-hydroxypentanamide (Compound 42)

The title compound 42 was prepared as a white solid (23 mg, 13.9%) from 0405-42 (260 mg, 0.45 mmol) and freshly prepared hydroxylamine methanol solution (8.0 mL) followed by deprotection using a procedure similar to that described for compound 41 (Example 15): m.p 145-147° C. LCMS: 482 [M+1]$^+$; $^1$H NMR (400 MHz, DMSO-d$_6$): δ1.54-1.63 (m, 4H), 1.99 (t, J=7.2 Hz, 2H), 3.02 (s, 2H), 3.87 (m, 4H), 4.05 (m, 4H), 4.58 (t, J=4.4 Hz, 2H), 7.49 (t, J=8.4 Hz, 1H), 7.70 (d, J=8 Hz, 1H), 7.78 (s, 1H), 8.24 (d, J=10.4 Hz, 1H), 8.87 (s, 1H), 9.11 (s, 2H), 10.42 (s, 1H), 13.28 (s, 1H).

Example 17: Preparation of 6-((2-(1H-indazol-4-yl)-4-morpholinothieno[3,2-d]pyrimidin-6-yl)methylamino)-N-hydroxyhexanamide (Compound 43)

Step 17a: Ethyl 6-((2-chloro-4-morpholinothieno[3,2-d]pyrimidin-6-yl)methylamino)hexanoate (Compound 0404-43)

The title compound 0404-43 (343 mg, 38%) was prepared as a yellow solid from 0112 (0.6 g, 2.12 mmol) and ethyl 6-aminohexanoate hydrochloride (0.83 g, 4.24 mmol) using a procedure similar to that described for compound 0404-41 (Example 15): LCMS: 427 [M+1]$^+$; $^1$H NMR (400 MHz, CDCl$_3$) δ1.17 (t, J=6.4 Hz, 3H), 1.24-1.33 (m, 2H), 1.40-1.45 (m, 2H), 1.48-1.55 (m, 2H), 2.09 (s, 1H), 2.27 (t, J=7.2 Hz, 2H), 2.53 (t, J=6.8 Hz 2H), 3.74 (t, J=5.2 Hz, 4H), 3.88 (t, J=4.8 Hz, 4H), 3.99 (s, 2H), 4.03 (q, J=6.4 Hz, 2H), 7.23 (s, 1H).

Step 17b: Ethyl 6-((2-(1H-indazol-4-yl)-4-morpholinothieno[3,2-d]pyrimidin-6-yl)methylamino)hexanoate (Compound 0405-43)

A mixture of compound 0404-43 (343 mg, 0.80 mmol), 0107-3 (294 mg, 1.2 mmol), sodium hydrogen carbonate (294 mg, 2.4 mmol) and bis(triphenylphosphine)palladium (a) chloride (29 mg, 0.05 mmol) in toluene (8 mL), ethanol (5 mL) and water (2 mL) was flushed with nitrogen and heated under microwave irradiation at 120° C. for 1 h. The reaction mixture was partitioned between dichloromethane and water, organic layer was washed with brine, dried over magnesium sulfate, filtered and evaporated in vacuum. The resulting residue was purified using column chromatography eluting methanol in dichloromethane (2-5%, v/v), to give title compound 0405-43 (120 mg, 29%) as a yellow solid. LCMS: 509 [M+1]$^+$; $^1$H NMR (400 MHz, CDCl$_3$): δ 1.17 (t, J=7.2 Hz, 3H), 1.28-1.35 (m, 2H), 1.42-1.57 (m, 4H), 2.28 (t, J=7.2 Hz, 2H), 2.57 (t, J=6.8 Hz, 2H), 3.83 (t, J=4.0 Hz, 4H), 3.97-4.06 (m, 6H), 7.45 (s, 1H), 7.47 (d, J=7.6 Hz, 1H), 7.66 (d, J=8.0 Hz, 1H), 8.22 (d, J=7.2 Hz, 1H), 8.88 (s, 1H), 13.21 (s, 1H).

Step 17c: 6-((2-(1H-indazol-4-yl)-4-morpholinothieno[3,2-d]pyrimidin-6-yl)methylamino)-N-hydroxyhexanamide (43)

The title compound 43 was prepared (17 mg, 15%) as a yellow solid from 0405-43 (120 mg, 0.24 mmol) and freshly prepared hydroxylamine methanol solution (4.0 mL) using a procedure similar to that described for compound 3 (Example 1): m.p. 128-130° C. LCMS: 496 [M+1]$^+$; $^1$H NMR (400 MHz, DMSO-d$_6$): δ 1.23-1.32 (m, 2H), 1.42-1.53 (m, 4H), 1.95 (t, J=6.8 Hz, 2H), 2.57 (t, J=7.2 Hz, 2H), 3.84 (t, J=4.0 Hz, 4H), 4.01 (t, J=4.0 Hz, 4H), 4.06 (s, 2H), 7.45 (s, 1H), 7.48 (d, J=7.6 Hz, 1H), 7.66 (d, J=8 Hz, 1H), 8.22 (d, J=7.2 Hz, 1H), 8.66 (s, 1H), 8.88 (s, 1H), 10.34 (s, 1H), 13.21 (s, 1H).

Example 18: Preparation of 7-((2-(1H-indazol-4-yl)-4-morpholinothieno[3,2-d]pyrimidin-6-yl)methylamino)-N-hydroxyheptanamide (Compound 44)

Step 18a: Ethyl 7-((2-chloro-4-morpholinothieno[3,2-d]pyrimidin-6-yl)methylamino)heptanoate (Compound 0404-44)

The title compound 0404-44 (700 mg, 45%) was prepared as a yellow solid from 0112 (1 g, 3.5 mmol) and 7-aminoheptanoate hydrochloride (1.5 g, 7.0 mmol) using a procedure similar to that described for compound 0404-41 (Example 15): LCMS: 442 [M+1]$^+$; $^1$H NMR (400 MHz, CDCl$_3$) δ1.16 (t, J=7.2 Hz, 3H), 1.21-1.27 (m, 4H), 1.45 (m, 2H), 1.50 (m, 2H), 2.21-2.28 (m, 2H), 2.52 (t, J=7.2 Hz, 2H), 2.66 (s, 1H), 3.74 (t, J=5.2 Hz, 4H), 3.88 (t, J=4.8 Hz, 4H), 4.00-4.06 (m, 4H), 7.23 (s, 1H).

Step 18b: Ethyl 7-((2-(1H-indazol-4-yl)-4-morpholinothieno[3,2-d]pyrimidin-6-yl)methylamino)heptanoate (Compound 0405-44)

The title compound 0405-44 (260 mg, 63%) was prepared as a yellow solid from 0404-44 (350 mg, 0.79 mmol) and 0107-3 (290 mg, 1.19 mmol) using a procedure similar to that described for compound 0405-43 (Example 17): LCMS: 523 [M+1]$^+$; $^1$H NMR (400 MHz, CDCl$_3$): δ 1.16 (t, J=6 Hz, 3H), 1.26-1.31 (m, 4H), 1.44 (m, 2H), 1.52 (m, 2H), 2.21-2.28 (m, 2H), 2.56 (t, J=7.2 Hz, 2H), 3.83 (t, J=4.8 Hz, 4H), 4.01 (t, J=4.8 Hz, 4H), 4.04 (s, 2H), 7.46 (m, 2H), 7.66 (d, J=8.4 Hz, 1H), 8.22 (d, J=7.2 Hz, 1H), 8.88 (s, 1H), 13.20 (s, 1H).

Step 18c: 7-((2-(1H-indazol-4-yl)-4-morpholinothieno[3,2-d]pyrimidin-6-yl)methylamino)-N-hydroxyheptanamide (Compound 44)

The title compound 44 was prepared (37 mg, 24%) as a yellow solid from 0405-44 (160 mg, 0.31 mmol) and freshly prepared hydroxylamine methanol solution (3.0 mL) using a procedure similar to that described for compound 3 (Example 1): m.p. 188-190° C. LCMS: 510 [M+1]$^+$; $^1$H NMR (400 MHz, DMSO-d$_6$): δ 1.19-1.33 (m, 4H), 1.41-1.52 (m, 4H), 1.93 (t, J=7.2 Hz, 2H), 2.56 (t, J=6.8 Hz, 2H), 3.83 (t, J=4.4 Hz, 4H), 4.01 (t, J=4.4 Hz, 4H), 4.05 (s, 2H), 7.44 (s, 1H), 7.48 (d, J=7.6 Hz, 1H), 7.66 (d, J=8 Hz, 1H), 8.22 (d, J=6.8 Hz, 2H), 8.68 (s, 1H), 8.88 (s, 1H), 10.34 (s, 1H), 13.21 (s, 1H).

Example 19: Preparation of 4-(((2-(1H-indazol-4-yl)-4-morpholinothieno[3,2-d]pyrimidin-6-yl)methyl)(methyl)amino)-N-hydroxybutanamide (Compound 101)

Step 19a: Ethyl 4-(((2-(1H-indazol-4-yl)-4-morpholinothieno[3,2-d]pyrimidin-6-yl)methyl)(methyl)amino)butanoate (Compound 0404-101)

To a solution of ethyl 4-((2-chloro-4-morpholinothieno[3,2-d]pyrimidin-6-yl)methylamino)butanoate (100 mg, 0.25 mmol) in methanol (5 mL) was added poly-formaldehyde (15 mg, 0.50 mmol). After stirred for 30 min at room temperature, NaBH$_3$CN (32 mg, 0.50 mmol) was added slowly, and the mixture was stirred for another 30 min. The reaction was terminated by adding water (5 mL) at 0° C. and stirred. The resulting precipitate was filtered and washed with water to give 0404-101 (85 mg, 83%) as a yellow solid. LCMS: 413 [M+1]$^+$; $^1$H NMR (400 MHz, DMSO-d$_6$) δ 1.14 (t, J=7.2 Hz, 3H), 1.72 (m, 2H), 2.22 (s, 3H), 2.32 (t, J=7.2 Hz, 2H), 2.41 (t, J=7.2 Hz, 2H), 3.75 (t, J=4.4 Hz, 4H), 3.82 (s, 2H), 3.88 (t, J=4.4 Hz, 4H), 4.02 (q, J=7.2 Hz, 2H), 7.27 (s, 1H).

Step 19b: Ethyl 4-(((2-(1H-indazol-4-yl)-4-morpholinothieno[3,2-d]pyrimidin-6-yl)methyl)(methyl)amino)butanoate (Compound 111-48-3)

The title compound 0405-101 (200 mg, 56%) was prepared as a yellow solid from 0404-101 (300 mg, 0.73 mmol)

and 0107-3 (356 mg, 1.46 mmol) using a procedure similar to that described for compound 0405-43 (Example 17): LCMS: 495 [M+1]$^+$; $^1$H NMR (400 MHz, CDCl$_3$): δ1.15 (t, J=7.2 Hz, 3H), 1.75 (m, 2H), 2.25 (s, 3H), 2.35 (t, J=7.2 Hz, 2H), 2.44 (t, J=7.2 Hz, 2H), 3.83 (m, 6H), 4.02 (m, 6H), 7.47 (m, 2H), 7.67 (d, J=8.0 Hz, 1H), 8.22 (d, J=8.0 Hz, 1H), 8.89 (s, 1H), 13.21 (s, 1H).

Step 19c: 4-(((2-(1H-indazol-4-yl)-4-morpholinothieno[3,2-d]pyrimidin-6-yl)methyl)(methyl)amino)-N-hydroxybutanamide (Compound 101)

The title compound 101 was prepared (160 mg, 88%) as a yellow solid from 0405-101 (187 mg, 0.38 mmol) and freshly prepared hydroxylamine methanol solution (6.0 mL) using a procedure similar to that described for compound 3 (Example 1): m.p. 115-118° C. LCMS: 482 [M+1]$^+$; $^1$H NMR (400 MHz, DMSO-d$_6$): δ 1.72 (m, 2H), 2.02 (t, J=6.0 Hz, 2H), 2.25 (s, 3H), 2.42 (t, J=6.0 Hz, 2H), 3.85 (m, 6H), 4.01 (m, 4H), 7.47 (m, 2H), 7.67 (d, J=7.6 Hz, 1H), 8.22 (d, J=6.8 Hz, 1H), 8.89 (s, 1H), 13.26 (s, 1H).

Example 20: Preparation of 5-(((2-(1H-indazol-4-yl)-4-morpholinothieno[3,2-d]pyrimidin-6-yl)methyl)(methyl)amino)-N-hydroxypentanamide (Compound 102)

Step 20a: Methyl 5-(((2-chloro-4-morpholinothieno[3,2-d]pyrimidin-6-yl)methyl)(methyl)amino)pentanoate (Compound 0404-102)

The title compound 0404-102 (0.62 g, 86%) was prepared as a white solid from Methyl 5-((2-chloro-4-morpholinothieno[3,2-d]pyrimidin-6-yl)methylamino) pentanoate (700 mg, 1.76 mmol), paraformaldehyde (106 mg, 3.52 mmol) in methanol (30 mL) and NaBH$_3$CN (221 mg, 3.52 mmol) using a procedure similar to that described for compound 0404-101 (Example 19): LCMS: 413 [M+1]$^+$; $^1$H NMR (400 MHz, DMSO-d$_6$) δ 1.45-1.59 (m, 4H), 2.21 (s, 3H), 2.32 (t, J=6.8 Hz, 2H), 2.40 (t, J=7.2 Hz, 2H), 3.58 (s, 3H), 3.75 (t, J=5.2 Hz, 4H), 3.81 (s, 2H), 3.88 (t, J=4.8 Hz, 4H), 7.26 (s, 1H).

Step 20b: Methyl 5-(((2-(1H-indazol-4-yl)-4-morpholinothieno[3,2-d]pyrimidin-6-yl)methyl)(methyl)amino)pentanoate (Compound 0405-102)

The title compound 0405-102 (305 mg, 61.7%) was prepared as a yellow solid from 0404-102 (350 mg, 0.85 mmol) and 0107-3 (311 mg, 1.27 mmol) using a procedure similar to that described for compound 0405-43 (Example 17): LCMS: 495 [M+1]$^+$; $^1$H NMR (400 MHz, DMSO-d$_6$): δ 1.48-1.57 (m, 4H), 2.24 (s, 3H), 2.34 (t, J=6.8 Hz, 2H), 2.44 (t, J=6.8 Hz, 2H), 3.58 (s, 3H), 3.84 (d, J=8.4 Hz, 6H), 3.97-4.04 (m, 4H), 7.49 (m, 2H), 7.67 (d, J=8.4 Hz, 1H), 8.22 (d, J=7.2 Hz, 1H), 8.88 (s, 1H), 13.20 (s, 1H).

Step 20c: 5-(((2-(1H-indazol-4-yl)-4-morpholinothieno[3,2-d]pyrimidin-6-yl)methyl)(methyl)amino)-N-hydroxypentanamide (Compound 102)

The title compound 102 was prepared (60 mg, 25%) as a yellow solid from 0405-102 (240 mg, 0.48 mmol) and freshly prepared hydroxylamine methanol solution (8.0 mL) using a procedure similar to that described for compound 3 (Example 1): m.p. 120-122° C. LCMS: 496 [M+1]$^+$; $^1$H NMR (400 MHz, DMSO-d$_6$) δ 1.48-1.54 (m, 4H), 1.98 (t, J=6.8 Hz, 2H), 2.24 (s, 3H), 2.44 (t, J=7.2 Hz, 2H), 3.85 (d, J=6.8 Hz, 4H), 4.01 (s, 4H), 7.46 (s, 2H), 7.66 (d, J=7.2 Hz, 1H), 8.22 (d, J=7.6 Hz, 1H), 8.88 (s, 1H), 10.31 (s, 1H), 13.18 (s, 1H).

Example 21: Preparation of 6-(((2-(1H-indazol-4-yl)-4-morpholinothieno[3,2-d]pyrimidin-6-yl)methyl)(methyl)amino)-N-hydroxyhexanamide (Compound 103)

Step 21a: Ethyl 6-(((2-chloro-4-morpholinothieno[3,2-d]pyrimidin-6-yl)methyl)(methyl)amino)hexanoate (Compound 0404-103)

The title compound 0404-103 (0.62 g, 86%) was prepared as a white solid from 0404-43 (0.67 g, 1.57 mmol), paraformaldehyde (94 mg, 3.14 mmol) and NaBH$_3$CN (197 mg, 3.14 mmol) using a procedure similar to that described for compound 0404-101 (Example 19): LCMS: 441 [M+1]$^+$; $^1$H NMR (400 MHz, DMSO-d$_6$): δ 1.16 (t, J=7.2 Hz, 3H), 1.24-1.32 (m, 2H), 1.43-1.55 (m, 4H), 2.21 (s, 3H), 2.27 (t, J=7.2 Hz, 2H), 2.39 (t, J=7.6 Hz, 2H), 3.75 (t, J=4.8 Hz, 4H), 3.81 (s, 2H), 3.88 (t, J=4.4 Hz, 4H), 4.03 (q, J=7.2 Hz, 2H), 7.26 (s, 1H).

Step 21b: Ethyl 6-(((2-(1H-indazol-4-yl)-4-morpholinothieno[3,2-d]pyrimidin-6-yl)methyl)(methyl)amino)hexanoate (Compound 0405-103)

The title compound 0405-103 (190 mg, 54%) was prepared as a yellow solid from 0404-103 (300 mg, 0.68 mmol) and 0107-3 (199 mg, 0.82 mmol) using a procedure similar to that described for compound 0405-43 (Example 17): LCMS: 523 [M+1]$^+$; $^1$H NMR (400 MHz, DMSO-d$_6$): δ 1.16 (t, J=7.2 Hz, 3H), 1.28-1.35 (m, 2H), 1.47-1.57 (m, 4H), 2.27 (m, 5H), 2.41 (t, J=6.4 Hz, 2H), 3.84 (m, 6H), 4.04 (m, 6H), 7.47 (m, 2H), 7.67 (d, J=8 Hz, 1H), 8.23 (d, J=6.8 Hz, 1H), 8.89 (s, 1H), 13.21 (s, 1H).

Step 21c: 6-(((2-(1H-indazol-4-yl)-4-morpholinothieno[3,2-d]pyrimidin-6-yl)methyl)(methyl)amino)-N-hydroxyhexanamide (Compound 103)

The title compound 103 was prepared (75 mg, 41%) as a white solid from 0405-103 (190 mg, 0.22 mmol) and freshly prepared hydroxylamine methanol solution (4.0 mL) using a procedure similar to that described for compound 3 (Example 1): m.p. 115-118° C. LCMS: 510 [M+1]$^+$; $^1$H NMR (400 MHz, DMSO-d$_6$): δ 1.23-1.27 (m, 2H), 1.45-1.55 (m, 4H), 1.95 (t, J=7.2 Hz, 2H), 2.24 (s, 3H), 2.42 (t, J=7.2 Hz, 2H), 3.84 (m, 6H), 4.00 (m, 4H), 7.47 (m, 2H), 7.66 (d, J=8.4 Hz, 1H), 8.22 (d, J=7.6 Hz, 1H), 8.68 (s, 1H), 8.89 (s, 1H), 10.35 (s, 1H), 13.21 (s, 1H).

Example 22: Preparation of 7-(((2-(1H-indazol-4-yl)-4-morpholinothieno[3,2-d]pyrimidin-6-yl)methyl)(methyl)amino)-N-hydroxyheptanamide (Compound 104)

Step 22a: Ethyl 7-(((2-chloro-4-morpholinothieno[3,2-d]pyrimidin-6-yl)methyl)(methyl)amino)heptanoate (Compound 0404-104)

The title compound 0404-104 (670 mg, 95%) was prepared as a yellow solid from 0404-44 (0.67 g, 1.52 mmol), paraformaldehyde (91 mg, 3.04 mmol) and NaBH$_3$CN (191 mg, 3.04 mmol) using a procedure similar to that described for compound 0404-101 (Example 19): LCMS: 455 [M+1]$^+$; $^1$H NMR (400 MHz, DMSO-d$_6$): δ1.16 (t, J=7.2 Hz, 3H), 1.23-1.32 (m, 4H), 1.42-1.54 (m, 4H), 2.21 (s, 3H), 2.25 (t, J=7.6 Hz, 2H), 2.39 (t, J=7.2 Hz, 2H), 3.74 (t, J=4 Hz, 4H), 3.80 (s, 2H), 3.88 (t, J=4.8 Hz, 4H), 4.03 (q, J=7.2 Hz, 2H), 7.25 (s, 1H).

Step 22b: Ethyl 7-(((2-(1H-indazol-4-yl)-4-morpholinothieno[3,2-d]pyrimidin-6-yl)methyl)(methyl)amino)heptanoate (Compound 0405-104)

The title compound 0405-104 (260 mg, 67%) was prepared as a yellow solid from 0404-104 (330 mg, 0.73 mmol) and 0107-3 (176 mg, 0.73 mmol) using a procedure similar to that described for compound 0405-43 (Example 17): LCMS: 537 [M+1]$^+$; $^1$H NMR (400 MHz, DMSO-d$_6$): δ 1.14 (t, J=7.2 Hz, 3H), 1.28-1.41 (m, 4H), 1.49-1.55 (m, 4H), 2.25 (m, 5H), 2.41 (t, J=6.8 Hz, 2H), 3.83 (m, 6H), 4.01 (m, 6H), 7.46 (m, 2H), 7.65 (d, J=7.6 Hz, 1H), 8.21 (d, J=6.8 Hz, 1H), 8.87 (s, 1H), 13.17 (s, 1H).

Step 22c: 7-(((2-(1H-indazol-4-yl)-4-morpholinothieno[3,2-d]pyrimidin-6-yl)methyl)(methyl)amino)-N-hydroxyheptanamide (Compound 104)

The title compound 104 was prepared (65 mg, 55%) as a white solid from 0405-104 (120 mg, 0.22 mmol) and freshly prepared hydroxylamine methanol solution (4.0 mL) using a procedure similar to that described for compound 3 (Example 1): m.p. 131-133° C. LCMS: 524 [M+1]$^+$; $^1$H NMR (400 MHz, DMSO-d$_6$): δ 1.21-1.27 (m, 4H), 1.34-1.43 (m, 4H), 1.94 (t, J=7.6 Hz, 2H), 2.24 (s, 3H), 2.43 (t, J=7.6 Hz, 2H), 3.84 (m, 6H), 4.00 (m, 4H), 7.47 (m, 2H), 7.67 (d, J=8 Hz, 1H), 8.22 (d, J=7.2 Hz, 1H), 8.68 (s, 1H), 8.89 (s, 1H), 10.34 (s, 1H), 13.21 (s, 1H).

Example 23: Preparation of 2-(((2-(6-fluoro-1H-indazol-4-yl)-4-morpholinothieno[3,2-d]pyrimidin-6-yl)methyl)(methyl)amino)-N-hydroxypyrimidine-5-carboxamide (Compound 69)

Step 23a: 3-Bromo-5-fluoro-2-methylbenzenamine (Compound 0104-69)

To a solution of 4-fluoro-2-nitrotoluene (10.0 g, 64.4 mmol) in trifluoroacetic acid (40 mL) was added con. sulfuric acid (12.5 mL) followed by NBS (17.2 g, 96.6 mmol) and the reaction mixture was stirred at room temperature for 16 h. Then the reaction mixture was poured into ice and water and stirred for 15 min. Extracted with ethyl acetate and the organic layer was washed with brine, dried, concentrated to get compound 1-bromo-5-fluoro-2-methyl-3-nitrobenzene (15.0 g, 100%) as a yellow oil. $^1$H NMR (400 MHz, DMSO-d$_6$) δ 2.41 (s, 3H), 7.96 (dd, J=8.0, 2.4 Hz, 1H), 8.02 (dd, J=8.0, 2.4 Hz, 1H). A mixture of above prepared compound (15.0 g, 64.4 mmol), Fe (18.0 g, 0.32 mol), con. HCl (2 mL) in MeOH (150 mL) and water (30 mL) was stirred at reflux for 4 h. Then the mixture was adjusted to pH 12 with aqueous NaOH solution and filtered. The solvent was removed and diluted with water. Extracted with ethyl acetate, dried, concentrated. The residue was purified by column chromatograph (ethyl acetate in petroleum ether, 7%) to get compound 0104-69 (5.8 g, 44%) as yellow oil. LCMS: 204 [M+1]$^+$, $^1$H NMR (400 MHz, DMSO-d$_6$) δ 2.12 (s, 3H), 5.57 (s, 2H), 6.45 (dd, J=11.2, 2.4 Hz, 1H), 6.60 (dd, J=8.0, 2.4 Hz, 1H).

Step 23b: 4-Bromo-6-fluoro-1H-indazole (Compound 0106-69)

The title compound 0106-69 (3.7 g, 61%) was prepared as a yellow solid from 0104-69 (5.8 g, 28.4 mmol), potassium acetate (2.93 g, 29.8 mmol), Ac$_2$O (5.8 g, 56.8 mmol) and iso-amyl nitrite (7.32 g, 62.5 mmol) followed by hydrolysis by aqueous hydrochloric acid (6N, 35 mL) using a procedure similar to that described for compound 0106-3 (Example 1): LCMS: 215 [M+1]$^+$, $^1$H NMR (400 MHz, DMSO-d$_6$) δ 7.37-7.44 (m, 2H), 8.07 (s, 1H), 13.54 (s, 1H).

Step 23c: 6-Fluoro-4-(4,4,5,5-tetramethyl-1,3,2-dioxaborolan-2-yl)-1H-indazole (Compound 107-69)

The title compound 0107-69 (700 mg, 57%) was prepared as a yellow solid from 0106-69 (1.0 g, 4.65 mmol), bis(pinacolato)diboron (1.77 g, 6.98 mmol), PdCl$_2$(dppf)$_2$ (380 mg, 0.47 mmol) and dried potassium acetate (1.37 g, 14.0 mmol) in dioxane (40 mL) using a procedure similar to that described for compound 0107-3 (Example 1): LCMS: 263 [M+1]$^+$.

Step 23d: Ethyl 2-(((2-(6-fluoro-1H-indazol-4-yl)-4-morpholinothieno[3,2-d]pyrimidin-6-yl)methyl)(methyl)amino)pyrimidine-5-carboxylate (Compound 0505-69)

A mixture of compound 0504-54 (200 mg, 0.45 mmol), 0107-69 (135 mg, 0.5 mmol), sodium hydrogen carbonate (115 mg, 1.3 mmol) and bis(triphenylphosphine)palladium (II) chloride (15 mg, 0.02 mmol) in toluene (8 mL), ethanol (5 mL) and water (2 mL) was flushed with nitrogen and heated under microwave irradiation at 120° C. for 5 h. The reaction mixture was partitioned between ethyl acetate and water, organic layer was washed with brine, dried over sodium sulfate, filtered, concentrated and washed with ethyl acetate to obtain the title compound 0505-69 (100 mg, 41%) as a yellow solid. LCMS: 549 [M+1]$^+$; $^1$H NMR (400 MHz, DMSO-d$_6$): δ 1.30 (t, J=7.2 Hz, 3H), 3.29 (s, 3H), 3.79 (t, J=4.4 Hz, 4H), 3.96 (t, J=4.4 Hz, 4H), 4.29 (q, J=7.2 Hz, 2H), 5.27 (s, 2H), 7.46 (d, J=7.2 Hz, 1H), 7.62 (s, 1H), 7.98 (dd, J=10.4 Hz, 2.4 Hz, 1H), 8.94 (m, 3H), 13.27 (s, 1H).

Step 23e: 2-(((2-(6-Fluoro-1H-indazol-4-yl)-4-morpholinothieno[3,2-d]pyrimidin-6-yl)methyl)(methyl)amino)-N-hydroxypyrimidine-5-carboxamide (Compound 69)

The title compound 69 was prepared (24 mg, 25%) as a yellow solid from 0505-69 (100 mg, 0.18 mmol) and freshly prepared hydroxylamine methanol solution (10.0 mL) using a procedure similar to that described for compound 3 (Example 1): m.p. 215-217° C. LCMS: 536 [M+1]$^+$; $^1$H NMR (400 MHz, DMSO-d$_6$) δ 3.26 (s, 3H), 3.79 (m, 4H), 3.96 (m, 4H), 5.24 (s, 2H), 7.46 (d, J=7.6 Hz, 1H), 7.59 (s, 1H), 7.98 (dd, J=10.8, 2.0 Hz, 1H), 8.76 (s, 2H), 8.89 (s, 1H), 9.08 (s, 1H), 11.14 (s, 1H), 13.28 (s, 1H).

Example 24: Preparation of 2-(((2-(1H-indazol-4-yl)-4-morpholinothieno[3,2-d]pyrimidin-6-yl)methyl)(neopentyl)amino)-N-hydroxypyrimidine-5-carboxamide (Compound 83)

Step 24a: N-((2-Chloro-4-morpholinothieno[3,2-d]pyrimidin-6-yl)methyl)-2,2-dimethylpropan-1-amine (Compound 0503-83)

The solution of compound 0503-53 (600 mg, 2.1 mmol), pivalaldehyde (912 mg, 10.6 mmol) and Ti(OEt)$_4$ (958 mg, 4.2 mmol) in CHCl$_3$/MeOH (8 mL/4 mL) was stirred at 35° C. for 20 hr. Then NaBH$_3$CN (530 mg, 8.4 mmol) was added and stirred for 3 hr at 45° C. This mixture was diluted with H$_2$O, extracted with CH$_2$Cl$_2$, dried by Na$_2$SO$_4$, and concentrated to obtain 0503-83 (631 mg, 85%) as a yellow solid. LCMS: 355 [M+1]$^+$. $^1$H-NMR (400 MHz, DMSO-d$_6$) δ 0.95 (s, 9H), 2.29 (s, 2H), 3.74 (m, 4H), 3.88 (m, 4H), 4.02 (s, 2H), 7.23 (s, 1H).

Step 24b: Ethyl 2-(((2-chloro-4-morpholinothieno [3,2-d]pyrimidin-6-yl)methyl)(neopentyl) amino) pyrimidine-5-carboxylate (Compound 0504-83)

A mixture of compound 0503-83 (400 mg, 1.13 mmol), 0305 (846 mg, 4.52 mmol) and DIPEA (1.5 g, 11.3 mmol) in MeCN (8 mL) was stirred at 70° C. for 24 hr, concentrated, purified by column chromatograph (ethyl acetate in petroleum ether, 10% v/v) to provide compound 0504-83 (530 mg, 93%) as a yellow solid. LCMS: 505 [M+1]$^+$, $^1$H NMR (400 MHz, DMSO-d$_6$) δ 0.97 (s, 9H), 1.29 (m, 3H), 3.67 (s, 2H), 3.72 (m, 4H), 3.87 (m, 4H), 4.27 (m, 2H), 5.19 (s, 2H), 7.35 (s, 1H), 8.84 (s, 2H).

Step 24c: Ethyl 2-(((2-(1H-indazol-4-yl)-4-morpholinothieno[3,2-d]pyrimidin-6-yl)methyl) (neopentyl)amino)pyrimidine-5-carboxylate (Compound 0505-83)

A mixture of compound 0504-83 (300 mg, 0.6 mmol), 0107-3 (176 mg, 0.72 mmol), NaHCO$_3$ (152 mg, 1.8 mmol) and bis(triphenylphosphine)palladium(II) chloride (22 mg, 0.03 mmol) in toluene (4 mL), ethanol (2 mL) and water (1 mL) was flushed with nitrogen and heated under microwave irradiation at 120° C. for 1 h. The reaction mixture was partitioned between dichloromethane and water, organic layer was washed with brine, dried over Na$_2$SO$_4$, filtered and evaporated in vacuum. The resulting residue was purified using column chromatography (methanol in dichloromethane, 2-5% v/v) to give title compound 0505-83 (300 mg, 85%) as a white solid. LCMS: 587 [M+1]$^+$; $^1$H NMR (400 MHz, DMSO-d$_6$) δ 0.99 (s, 9H), 1.29 (t, J=7.2 Hz, 3H), 3.70 (s, 2H), 3.79 (m, 4H), 3.95 (m, 4H), 4.27 (q, J=7.6 Hz, 2H), 5.24 (s, 2H), 7.46 (t, J=7.6 Hz, 1H), 7.55 (s, 1H), 7.67 (d, J=8.4 Hz, 1H), 8.21 (d, J=7.2 Hz, 1H), 8.85 (s, 2H), 8.89 (s, 1H), 13.21 (s, 1H).

Step 24d: 2-(((2-(1H-indazol-4-yl)-4-morpholinothieno[3,2-d]pyrimidin-6-yl)methyl)(neopentyl) amino)-N-hydroxypyrimidine-5-carboxamide (Compound 83)

The title compound 83 was prepared (191 mg, 65%) as a yellow solid from 0505-83 (300 mg, 0.51 mmol) and freshly prepared hydroxylamine methanol solution (20.0 mL) using a procedure similar to that described for compound 3 (Example 1): m.p. 240-242° C. LCMS: 574 [M+1]$^+$; $^1$H NMR (400 MHz, DMSO-d$_6$) δ 0.99 (s, 9H), 3.67 (s, 2H), 3.80 (m, 4H), 3.95 (m, 4H), 5.22 (s, 2H), 7.46 (t, J=8.0 Hz, 1H), 7.54 (s, 1H), 7.67 (d, J=8.0 Hz, 1H), 8.21 (d, J=7.2 Hz, 1H), 8.73 (s, 2H), 8.89 (s, 1H), 9.07 (s, 1H), 11.12 (s, 1H), 13.20 (s, 1H).

Example 25: Preparation of 2-(((2-(1H-indazol-4-yl)-4-morpholinothieno[3,2-d]pyrimidin-6-yl) methyl)(propyl)amino)-N-hydroxypyrimidine-5-carboxamide (Compound 84)

Step 25a: N-((2-chloro-4-morpholinothieno[3,2-d] pyrimidin-6-yl)methyl)propan-1-amine (Compound 0503-84)

Compound 0502 (500 mg, 1.43 mmol) was dissolved in methanol (30 mL) and then propan-1-amine (5 mL) was added. The mixture was stirred at 65° C. and the reaction process was monitored by TLC. Then the solvent was removed at reduce pressure and the precipitation was partitioned between dichloromethane and water, organic layer was washed with brine and dried over sodium sulfate anhydrous, filtered, evaporated in vacuum and then purified by column chromatography (methanol in dichloromethane, 1.7% v/v) to give title compound 0503-84 (412 mg, 88%) as a light yellow solid. LCMS: 327 [M+1]$^+$; $^1$H NMR (400 MHz, DMSO-d$_6$) δ 0.86 (t, J=7.4 Hz, 3H), 1.39-1.48 (m, 2H), 2.49 (t, J=2.0 Hz, 2H), 2.82 (s, 1H), 3.73 (t, J=4.8 Hz, 4H), 3.87 (t, J=4.8 Hz, 4H), 4.00 (s, 2H), 7.23 (s, 1H).

Step 25b: Ethyl 2-(((2-chloro-4-morpholinothieno [3,2-d]pyrimidin-6-yl)methyl)(propyl)amino)pyrimidine-5-carboxylate (Compound 0504-84)

The title compound 0504-84 was prepared (477 mg, 79%) as a yellow solid from 0503-84 (412 mg, 1.26 mmol) and 0305 (353 mg, 1.89 mmol) in acetonitrile (30 mL), and N,N-Diisopropylethylamine (3 mL) using a procedure similar to that described for compound 0504-83 (Example 24): LCMS: 477 [M+1]$^+$; $^1$H NMR (400 MHz, DMSO-d$_6$) δ 0.86 (t, J=7.6 Hz, 3H), 1.30 (t, J=7.2 Hz, 3H), 1.57-1.66 (m, 2H), 3.65 (t, J=7.6 Hz, 2H), 3.71 (t, J=4.8 Hz, 4H), 3.83 (t, J=4.6 Hz, 4H), 4.28 (q, J=7.2 Hz, 2H), 5.17 (s, 2H), 7.42 (s, 1H), 8.86 (s, 2H).

Step 25c: Ethyl 2-(((2-(1H-indazol-4-yl)-4-morpholinothieno[3,2-d]pyrimidin-6-yl)methyl)(propyl) amino)pyrimidine-5-carboxylate (Compound 0505-84)

The title compound 0505-84 was prepared (240 mg, 82%) as a white solid from 0504-84 (250 mg, 0.52 mmol), 0107-3 (154 mg, 0.63 mmol), sodium hydrogen carbonate (132 mg, 1.57 mmol) and bis(triphenylphosphine)palladium(II) chloride (18.5 mg, 0.026 mmol) in toluene (8 mL), ethanol (5 mL) and water (2 mL) using a procedure similar to that described for compound 0505-83 (Example 24): LCMS: 559 [M+1]$^+$; $^1$H NMR (400 MHz, DMSO-d$_6$) δ 0.88 (t, J=7.2 Hz, 3H), 1.30 (t, J=7.0 Hz, 3H), 1.61-1.71 (m, 2H), 3.70 (t, J=7.4 Hz, 2H), 3.80 (t, J=4.6 Hz, 4H), 3.96 (t, J=4.6 Hz, 4H), 4.29 (q, J=7.2 Hz, 2H), 5.23 (s, 2H), 7.47 (t, J=7.8 Hz, 1H), 7.61 (s, 1H), 7.67 (d, J=8.4 Hz, 1H), 8.22 (d, J=6.8 Hz, 1H), 8.88 (s, 3H), 13.20 (s, 1H).

Step 25d: 2-(((2-(1H-indazol-4-yl)-4-morpholinothieno[3,2-d]pyrimidin-6-yl)methyl)(propyl)amino)-N-hydroxypyrimidine-5-carboxamide (Compound 84)

The title compound 84 was prepared (189 mg, 81%) as a white solid from 0505-84 (240 mg, 0.43 mmol) and freshly prepared hydroxylamine methanol solution (16.0 mL) using a procedure similar to that described for compound 3 (Example 1): m.p. 224-226° C. LCMS: 546 [M+1]$^+$; $^1$H NMR (400 MHz, DMSO-d$_6$) δ 0.88 (t, J=7.4 Hz, 3H), 1.60-1.69 (m, 2H), 3.67 (t, J=7.6 Hz, 2H), 3.80 (t, J=4.4 Hz, 4H), 3.96 (t, J=4.8 Hz, 4H), 5.20 (s, 2H), 7.47 (t, J=7.8 Hz, 1H), 7.59 (s, 1H), 7.67 (d, J=8.0 Hz, 1H), 8.22 (d, J=6.8 Hz, 1H), 8.75 (s, 2H), 8.88 (s, 1H), 9.07 (s, 1H), 11.12 (s, 1H), 13.20 (s, 1H).

Example 26: Preparation of 2-(((2-(1H-indazol-4-yl)-4-morpholinothieno[3,2-d]pyrimidin-6-yl)methyl)(butyl)amino-N-hydroxypyrimidine-5-carboxamide (Compound 85)

Step 26a: N-((2-chloro-4-morpholinothieno[3,2-d]pyrimidin-6-yl)methyl)butan-1-amine (Compound 0503-85)

The title compound 0503-85 was prepared (430 mg, 88%) as a light yellow solid from 0502 (500 mg, 1.43 mmol) and butan-1-amine (5 mL) in methanol (30 mL) using a procedure similar to that described for compound 0503-84 (Example 25): LCMS: 341 [M+1]$^+$; $^1$H NMR (400 MHz, DMSO-d$_6$): δ 0.93 (t, J=7.4 Hz, 3H), 1.33-1.42 (m, 2H), 1.45-1.52 (m, 2H), 2.61 (t, J=7.0 Hz, 2H), 2.90 (s, 1H), 3.81-3.82 (m, 4H), 3.94-3.95 (d, 4H), 4.07 (s, 2H), 7.30 (s, 1H).

Step 26b: Ethyl 2-(butyl((2-chloro-4-morpholinothieno[3,2-d]pyrimidin-6-yl)methyl)amino)pyrimidine-5-carboxylate (Compound 0504-84)

The title compound 0504-85 was prepared (519 mg, 84%) as a light yellow solid from 0503-85 (430 mg, 1.26 mmol) and (353 mg, 1.89 mmol) in acetonitrile (30 mL) and N,N-Diisopropylethylamine (3 mL) using a procedure similar to that described for compound 0504-83 (Example 24): LCMS: 491 [M+1]$^+$; $^1$H NMR (400 MHz, DMSO-d$_6$): δ 0.88 (t, J=7.4 Hz, 3H), 1.26-1.34 (m, 5H), 1.55-1.62 (m, 2H), 3.67-3.72 (m, 6H), 3.83 (t, J=4.8 Hz, 4H), 4.28 (q, J=7.1 Hz, 2H), 5.17 (s, 2H), 7.41 (s, 1H), 8.86 (s, 2H).

Step 26c: Ethyl 2-(((2-(1H-indazol-4-yl)-4-morpholinothieno[3,2-d]pyrimidin-6-yl)methyl)(butyl)amino)pyrimidine-5-carboxylate (Compound 0505-85)

The title compound 0505-85 was prepared (255 mg, 87%) as a light yellow solid from 0504-85 (250 mg, 0.51 mmol), 0107-3 (149 mg, 0.61 mmol), sodium hydrogen carbonate (128 mg, 1.53 mmol) and bis(triphenylphosphine)palladium(a) chloride (17.8 mg, 0.025 mmol) in toluene (8 mL), ethanol (5 mL) and water (2 mL) using a procedure similar to that described for compound 0505-83 (Example 24): LCMS: 573 [M+1]$^+$; $^1$H NMR (400 MHz, DMSO-d$_6$): δ 1.04 (t, J=7.4 Hz, 3H), 1.43-1.48 (m, 5H), 1.73-1.81 (m, 2H), 3.88 (t, J=7.6 Hz, 2H), 3.94 (t, J=4.6 Hz, 4H), 4.10 (t, J=4.6 Hz, 4H), 4.43 (q, J=7.1 Hz, 2H), 5.37 (s, 2H), 7.61 (t, J=7.8 Hz, 1H), 7.75 (s, 1H), 7.81 (d, J=8.0 Hz, 1H), 8.36 (d, J=6.8 Hz, 1H), 9.02 (s, 3H), 13.34 (s, 1H).

Step 26d: 2-(((2-(1H-indazol-4-yl)-4-morpholinothieno[3,2-d]pyrimidin-6-yl)methyl)(butyl)amino)-N-hydroxypyrimidine-5-carboxamide (Compound 85)

The title compound 85 was prepared (131 mg, 53%) as an off-white solid from 0505-85 (255 mg, 0.45 mmol) and freshly prepared hydroxylamine methanol solution (16.0 mL) using a procedure similar to that described for compound 3 (Example 1): m.p. 234-236° C. LCMS: 560 [M+1]$^+$; $^1$H NMR (400 MHz, DMSO-d$_6$): δ 0.96 (t, J=7.4 Hz, 3H), 1.32-1.42 (m, 2H), 1.64-1.72 (m, 2H), 3.77 (t, J=7.2 Hz, 2H), 3.86 (t, J=4.2 Hz, 4H), 4.02 (t, J=4.4 Hz, 4H), 5.26 (s, 2H), 7.53 (t, J=7.8 Hz, 1H), 7.66 (s, 1H), 7.73 (d, J=8.4 Hz, 1H), 8.28 (d, J=7.2 Hz, 1H), 8.81 (s, 2H), 8.94 (s, 1H), 9.14 (s, 1H), 11.18 (s, 1H), 13.27 (s, 1H).

Example 27: Preparation of 2-(((2-(1H-indazol-4-yl)-4-morpholinothieno[3,2-d]pyrimidin-6-yl)methyl)(2-hydroxyethyl)amino)-N-hydroxypyrimidine-5-carboxamide (Compound 86)

Step 27a: 2-((2-Chloro-4-morpholinothieno[3,2-d]pyrimidin-6-yl)methylamino)ethanol (Compound 0503-86)

The title compound 0503-86 was prepared (230 mg, 41%) as a light yellow solid from 0502 (600 mg, 1.72 mmol) and 2-aminoethanol (6 mL) in methanol (60 mL) using a procedure similar to that described for compound 0503-84 (Example 25): LCMS: 329 [M+1]$^+$; $^1$H NMR (400 MHz, DMSO-d$_6$): δ 2.62 (t, J=5.8 Hz, 2H), 2.74 (s, 1H), 3.47 (dd, J$_1$=11.2 Hz, J$_2$=6.0 Hz, 2H), 3.73 (t, J=4.8 Hz, 4H), 3.88 (t, J=5.0 Hz, 4H), 4.04 (s, 2H), 4.53 (t, J=5.2 Hz, 1H), 7.24 (s, 1H).

Step 27b: Ethyl 2-(((2-chloro-4-morpholinothieno[3,2-d]pyrimidin-6-yl)methyl)(2-hydroxyethyl)amino)pyrimidine-5-carboxylate (Compound 0504-86)

The title compound 0504-86 was prepared (170 mg, 51%) as a white solid from 0503-86 (230 mg, 0.7 mmol) and 0305 (157 mg, 0.84 mmol). in acetonitrile (20 mL) and N,N-Diisopropylethylamine (4 mL) using a procedure similar to that described for compound 0504-83 (Example 24): LCMS: 479 [M+1]$^+$; $^1$H NMR (400 MHz, DMSO-d$_6$): δ 1.29 (t, J=7.2 Hz, 3H), 3.62 (dd, J$_1$=11.2 Hz, J$_2$=6.0 Hz, 2H), 3.70 (t, J=4.6 Hz, 4H), 3.76 (t, J=6.0 Hz, 2H), 3.82 (t, J=4.6 Hz, 4H), 4.27 (dd, J$_1$=13.6 Hz, J$_2$=6.8 Hz, 2H), 4.86 (t, J=5.2 Hz, 1H), 5.23 (s, 2H), 7.39 (s, 1H), 8.85 (s, 2H).

Step 27c: Ethyl 2-(((2-(1H-indazol-4-yl)-4-morpholinothieno[3,2-d]pyrimidin-6-yl)methyl)(2-hydroxyethyl)amino)pyrimidine-5-carboxylate (0505-86)

The title compound 0505-86 was prepared (120 mg, 60%) as a white solid from 0504-86 (170 mg, 0.35 mmol), 0107-3 (104 mg, 0.43 mmol), sodium hydrogen carbonate (89 mg, 1.06 mmol) and bis(triphenylphosphine)palladium(a) chloride (13 mg, 0.02 mmol) in toluene (4 mL), ethanol (2.5 mL) and water (1 mL) using a procedure similar to that described for compound 0505-83 (Example 24): LCMS: 561 [M+1]$^+$; $^1$H NMR (400 MHz, DMSO-d$_6$): 1.29 (t, J=6.8 Hz, 3H), 3.66 (dd, J$_1$=10.8 Hz, J$_2$=5.6 Hz, 2H), 3.78-3.83 (m, 6H), 3.95 (t, J=4.6 Hz, 4H), 4.28 (dd, J$_1$=14.4 Hz, J$_2$=7.2 Hz, 2H), 4.88 (t, J=5.4 Hz, 1H), 5.29 (s, 2H), 7.46 (t, J=7.8 Hz, 1H), 7.59 (s, 1H), 7.66 (d, J=8.4 Hz, 1H), 8.21 (d, J=7.2 Hz, 1H), 8.87 (s, 3H), 13.2 (s, 1H).

Step 27d: 2-(((2-(1H-indazol-4-yl)-4-morpholinothieno[3,2-d]pyrimidin-6-yl)methyl)(2-hydroxyethyl)amino)-N-hydroxypyrimidine-5-carboxamide (86)

The title compound 86 was prepared (42 mg, 36%) as an off-white solid from 0505-86 (120 mg, 0.21 mmol) and freshly prepared hydroxylamine methanol solution (8.0 mL) using a procedure similar to that described for compound 3 (Example 1): m.p. 190-194° C. LCMS: 548 [M+1]$^+$; $^1$H NMR (400 MHz, DMSO-d$_6$): δ 3.64 (dd, J$_1$=10.8 Hz, J$_2$=5.6 Hz, 2H), 3.79 (dd, J$_1$=8.4 Hz, J$_2$=4.4 Hz, 6H), 3.95 (t, J=4.4 Hz, 4H), 4.85 (t, J=5.2 Hz, 1H), 5.25 (s, 2H), 7.46 (t, J=7.8 Hz, 1H), 7.57 (s, 1H), 7.66 (d, J=8.4 Hz, 1H), 8.21 (d, J=6.8 Hz, 1H), 8.74 (s, 2H), 8.87 (s, 1H), 9.07 (s, 1H), 11.13 (s, 1H), 13.20 (s, 1H).

Example 28: 2-(((2-(1H-indazol-4-yl)-4-morpholinothieno[3,2-d]pyrimidin-6-yl)methyl)(2-methoxyethyl)amino)-N-hydroxypyrimidine-5-carboxamide (Compound 90)

Step 28a: N-((2-chloro-4-morpholinothieno[3,2-d]pyrimidin-6-yl)methyl)-2-methoxyethanamine (Compound 0503-90)

The title compound 0503-90 was prepared (410 mg, 80%) as oil from 0502 (520 mg, 1.5 mmol) and 2-methoxyethanamine (1.1 g. 10.0 mmol) in methanol (20 mL) using a procedure similar to that described for compound 0503-84 (Example 25): LCMS: 343 [M+1]$^+$; $^1$H NMR (400 MHz, CDCl$_3$) δ 2.858 (t, J=7.2 Hz, 3H), 3.37 (s, 3H), 3.53 (t, J=5.2 Hz, 2H), 3.53 (t, J=5.2 Hz, 2H), 3.83 (t, J=5.2 Hz, 4H), 3.99 (t, J=4.8 Hz, 4H), 4.12 (s, 2H), 7.16 (s, 1H).

Step 28b: Ethyl 2-(((2-chloro-4-morpholinothieno[3,2-d]pyrimidin-6-yl)methyl)(2-methoxyethyl)amino)pyrimidine-5-carboxylate (Compound 0504-90)

The title compound 0504-90 was prepared (400 mg, 81%) as a yellow solid from 0503-90 (342 mg, 1.0 mmol) and 0305 (205 mg, 1.1 mmol) in acetonitrile (20 mL) and N,N-Diisopropylethylamine (400 mg, 3.3 mmol) using a procedure similar to that described for compound 0504-83 (Example 24): LCMS: 493 [M+1]$^+$; $^1$H NMR (400 MHz, DMSO-d$_6$) δ 1.29 (t, J=6.8 Hz, 3H), 3.22 (s, 3H), 3.56 (t, J=5.2 Hz, 2H), 3.70 (brs, 4H), 3.82 (brs, 4H), 3.88 (t, J=5.2 Hz, 2H), 4.27 (q, J=6.8 Hz, 2H), 5.19 (s, 2H), 7.39 (s, 1H), 8.86 (s, 1H).

Step 28c: Ethyl 2-(((2-(1H-indazol-4-yl)-4-morpholinothieno[3,2-d]pyrimidin-6-yl)methyl)(2-methoxyethyl)amino)pyrimidine-5-carboxylate (Compound 0505-90)

The title compound 0505-90 was prepared (260 mg, 90%) as a white solid from 0504-90 (246 mg, 0.5 mmol), 0107-3 (146 mg, 0.6 mmol), sodium hydrogen carbonate (126 mg, 1.5 mmol) and bis(triphenylphosphine)palladium(a) chloride (18 mg, 0.025 mmol) in toluene (8.0 mL), ethanol (5 mL) and water (3 mL) using a procedure similar to that described for compound 0505-83 (Example 24): LCMS: 575 [M+1]$^+$ $^1$H NMR (400 MHz, DMSO$_6$) δ 1.38 (t, J=7.2 Hz, 3H), 3.44 (s, 3H), 3.69 (t, J=5.6 Hz, 2H), 3.87 (m, 4H), 4.02 (m, 6H), 4.27 (q, J=7.2 Hz, 2H), 5.34 (s, 2H), 7.55 (t, J=7.6 Hz, 1H), 7.67 (s, 1H), 7.75 (d, J=8.0 Hz, 1H), 8.30 (d, J=6.8 Hz, 1H), 8.97 (s, 2H), 13.29 (s, 1H).

Step 28d: 2-(((2-(1H-indazol-4-yl)-4-morpholinothieno[3,2-d]pyrimidin-6-yl)methyl)(2-methoxyethyl)amino)-N-hydroxypyrimidine-5-carboxamide (Compound 90)

The title compound 90 was prepared (180 mg, 71%) as a white solid from 0505-90 (260 mg, 0.45 mmol) and freshly prepared hydroxylamine methanol solution (15.0 mL) using a procedure similar to that described for compound 3 (Example 1): m.p. 219-222° C. LCMS: 482 [M+1]$^+$. $^1$H-NMR (400 MHz. DMSO-d$_6$) δ 3.26 (s, 3H), 3.59 (t, J=5.6 Hz, 2H), 3.79 (m, 4H), 3.90 (t, J=5.6 Hz, 2H), 3.95 (m, 4H), 5.22 (s, 2H), 7.46 (t, J=7.2 Hz, 1H), 7.56 (s, 1H), 7.65 (d, J=8.4 Hz, 1H), 8.21 (d, J=7.2 Hz, 1H), 8.74 (s, 2H), 8.87 (s, 1H), 9.07 (brs, 1H), 11.12 (s, 1H), 13.19 (s, 1H).

Example 29: Preparation of 2-(((2-(1H-indazol-4-yl)-4-morpholinothieno[3,2-d]pyrimidin-6-yl)methyl)(isobutyl)amino)-N-hydroxypyrimidine-5-carboxamide (Compound 93)

Step 29a: N-((2-chloro-4-morpholinothieno[3,2-d]pyrimidin-6-yl)methyl)-2-methylpropan-1-amine (Compound 0503-93)

The title compound 0503-93 was prepared (0.6 g, 88%) as a yellow solid from 0502 (694 g, 2.0 mmol), 2-methylpropan-1-amine (1.5 g, 20 mmol) and DIPEA (2.6 g, 20 mmol) in MeOH (5 mL) using a procedure similar to that described for compound 0503-84 (Example 25): LCMS: 341 [M+1]$^+$. $^1$H-NMR (400 MHz, DMSO-d$_6$) δ 0.87 (d, J=6.8 Hz, 6H), 1.69 (m, 1H), 2.35 (d, J=6.8 Hz, 2H), 2.60 (s, 1H), 3.74 (m, 4H), 3.88 (m, 4H), 4.00 (s, 2H), 7.23 (s, 1H).

Step 29b: Ethyl 2-(((2-chloro-4-morpholinothieno[3,2-d]pyrimidin-6-yl)methyl)(isobutyl) amino)pyrimidine-5-carboxylate (Compound 0504-93)

The title compound 0504-93 was prepared (500 mg, 57%) as a yellow solid from 0503-93 (613 mg, 1.8 mmol) and 0305 (675 mg, 3.6 mmol) in acetonitrile (8 mL) and N,N-Diisopropylethylamine (1.2 g, 9 mmol) using a procedure similar to that described for compound 0504-83 (Example 24): LCMS: 491 [M+1]$^+$, $^1$H NMR (400 MHz, DMSO-d$_6$) δ 0.87 (d, J=6.8 Hz, 6H), 1.29 (t, J=7.2 Hz, 3H), 2.17 (m, 1H), 3.58 (d, J=7.6 Hz, 2H), 3.71 (m, 4H), 3.83 (m, 4H), 4.28 (q, J=7.2 Hz, 2H), 5.17 (s, 2H), 7.41 (s, 1H), 8.85 (s, 2H).

Step 29c: Ethyl 2-(((2-(1H-indazol-4-yl)-4-morpholinothieno[3,2-d]pyrimidin-6-yl)methyl)(isobutyl)amino)pyrimidine-5-carboxylate (Compound 0505-93)

The title compound 0505-93 was prepared (257 mg, 91%) as a white solid from 0504-93 (245 mg, 0.5 mmol), 0107-3 (147 mg, 0.6 mmol), sodium hydrogen carbonate (126 mg, 1.5 mmol) and bis(triphenylphosphine)palladium(a) chloride (18 mg, 0.025 mmol) in toluene (4.0 mL), ethanol (2 mL) and water (1 mL) using a procedure similar to that described for compound 0505-83 (Example 24): LCMS: 573 [M+1]$^+$; $^1$H NMR (400 MHz, DMSO-d$_6$): 0.89 (d, J=6.8 Hz, 6H), 1.29 (m, 3H), 2.20 (m, 1H), 3.60 (d, J=7.6 Hz, 2H), 3.79 (m, 4H), 3.95 (m, 4H), 4.27 (m, 2H), 5.21 (s, 2H), 7.47 (t, J=8.0 Hz, 1H), 7.60 (s, 1H), 7.68 (d, J=8.4 Hz, 1H), 8.22 (d, J=8.0 Hz, 1H), 8.86 (s, 2H), 8.90 (s, 1H), 13.22 (s, 1H).

Step 29d: 2-(((2-(1H-indazol-4-yl)-4-morpholinothieno[3,2-d]pyrimidin-6-yl)methyl)(isobutyl)amino)-N-hydroxypyrimidine-5-carboxamide (Compound 93)

The title compound 93 was prepared (90 mg, 26%) as a white solid from 0505-93 (357 mg, 0.6 mmol) and freshly prepared hydroxylamine methanol solution (20.0 mL) using a procedure similar to that described for compound 3 (Example 1): m.p. 196-198° C. LCMS: 560 [M+1]+; $^1$H NMR (400 MHz, DMSO-$d_6$) δ 0.89 (d, J=6.4 Hz, 6H), 2.20 (m, 1H), 3.59 (d, J=7.6 Hz, 2H), 3.80 (m, 4H), 3.96 (m, 4H), 5.20 (s, 2H), 7.47 (t, J=8.0 Hz, 1H), 7.59 (s, 1H), 7.68 (d, J=8.0 Hz, 1H), 8.22 (d, J=7.2 Hz, 1H), 8.75 (s, 2H), 8.90 (s, 1H), 9.12 (s, 1H), 11.14 (s, 1H), 13.23 (s, 1H).

Example 30: Preparation of 6-((2-(1H-indazol-4-yl)-4-morpholinothieno[3,2-d]pyrimidin-6-yl)methylamino)-N-hydroxynicotinamide (Compound 76)

Step 30a: Isopropyl 6-((2-chloro-4-morpholinothieno[3,2-d]pyrimidin-6-yl)methylamino)nicotinate (Compound 0309-76)

To a suspension of 0112 (3.4 g, 12 mmol) and ethyl 6-aminonicotinate (912 mg, 6 mmol) in toluene (50 mL) was added tetraisopropyl titanate (2 g, 7.2 mmol) and the mixture was stirred at 120° C. overnight. NaBH(OAc)$_3$ (1.9 g, 9 mmol) was added to the reaction mixture, then the mixture was cooled to room temperature and stirred for additional 4 hours, extracted with dichloromethane (10 mL×2). The combined organic layer was washed with saturated NaHCO$_3$ (aq., 20 mL), brine (20 mL×2), dried and concentrated. The residue was purified by column chromatography on silica gel (ethyl acetate in petroleum ether, 20% v/v) to obtain 0309-76 (1.5 g, 28%) as a white solid. LCMS: 448 [M+1]+; $^1$H-NMR (400 MHz. DMSO-$d_6$) δ 1.29 (d, J=6 Hz, 6H) 3.73 (m, 4H), 3.85 (m, 4H), 4.89 (d, J=5.6 Hz, 2H), 5.09 (m, 1H), 6.64 (d, J=8.8 Hz, 1H), 6.81 (s, 1H), 7.31 (s, 1H), 7.86 (d, J=2 Hz, 1H), 8.58 (s, 1H).

Step 30b: Methyl 6-((2-(1H-indazol-4-yl)-4-morpholinothieno[3,2-d]pyrimidin-6-yl)methylamino)nicotinate (Compound 0310-76)

The isopropyl 6-((2-(1H-indazol-4-yl)-4-morpholinothieno[3,2-d]pyrimidin-6-yl)methylamino)-nicotinate was prepared (200 mg, 82%) as a yellow solid from 0309-76 (200 mg, 0.462 mmol), 0107-3 (124 mg, 0.51 mmol), sodium hydrogen carbonate (120 mg, 1.4 mmol) and bis(triphenylphosphine)palladium(II) chloride (16 mg, 0.0231 mmol) in toluene (8 mL), ethanol (5 mL) and water (2 mL) using a procedure similar to that described for compound 0505-83 (Example 24): LCMS: 530 [M+1]+ $^1$H-NMR (400 MHz. DMSO-$d_6$) δ 1.28 (d, J=6 Hz, 6H) 3.81 (m, 4H), 3.98 (m, 4H), 4.94 (d, J=5.6 Hz, 2H), 5.08 (m, 1H), 6.67 (d, J=8.8 Hz, 1H), 7.47 (t, J=8.4 Hz, 1H), 7.51 (s, 1H), 7.677 (d, J=8.4 Hz, 1H), 7.90 (d, J=2.4 Hz, 1H), 8.21 (d, J=7.6 Hz, 2H), 8.60 (s, 1H), 8.87 (s, 1H), 13.20 (s, 1H).

To a mixture of above compound (200 mg, 0.378 mmol) in MeOH (8 mL) was added dropwise conc. H$_2$SO$_4$ (2 ml). The mixture was refluxed overnight. Evaporated to give the crude methyl ester, 0310-76 (140 mg, 75%) which was used in next step directly without further purification. LCMS: 502 [M+1]+ $^1$H-NMR (400 MHz. DMSO-$d_6$) δ 3.77 (s, 3H), 3.81 (m, 4H), 3.98 (m, 4H), 4.94 (d, J=5.6 Hz, 2H), 6.67 (d, J=8.8 Hz, 1H), 7.47 (t, J=8.4 Hz, 1H), 7.51 (s, 1H), 7.677 (d, J=8.4 Hz, 1H), 7.91 (d, J=2.4 Hz, 1H), 8.21 (d, J=7.6 Hz, 2H), 8.62 (s, 1H), 8.87 (s, 1H), 13.21 (s, 1H).

Step 30c: 6-((2-(1H-indazol-4-yl)-4-morpholinothieno[3,2-d]pyrimidin-6-yl)methylamino)-N-hydroxynicotinamide (Compound 76)

The title compound 76 was prepared (23 mg, 16%) as a brown solid from 0310-76-2 (140 mg, 0.28 mmol) and freshly prepared hydroxylamine methanol solution (10.0 mL) using a procedure similar to that described for compound 3 (Example 1). m.p 218-220° C. LCMS: 503 [M+1]+. $^1$H-NMR (400 MHz. DMSO-$d_6$): δ 3.81 (m, 4H), 3.98 (m, 4H), 4.90 (d, J=4.8 Hz, 2H), 6.62 (d, J=6.8 Hz, 1H), 7.46 (t, J=8 Hz, 1H), 7.50 (s, 1H), 7.62 (d, J=8 Hz, 1H), 7.78 (d, J=4 Hz, 1H), 7.89 (t, J=4.8 Hz, 1H), 8.21 (d, J=6.4 Hz, 1H), 8.43 (s, 1H), 8.85 (s, 1H), 10.95 (s, 1H), 13.19 (s, 1H).

Example 31: Preparation of 4-((2-(1H-indazol-4-yl)-4-morpholinothieno[3,2-d]pyrimidin-6-yl)methylamino)-N-hydroxybenzamide (Compound 78)

Step 31a: Ethyl 4-((2-chloro-4-morpholinothieno[3,2-d]pyrimidin-6-yl)methylamino)benzoate (Compound 0309-78)

The title compound, 0309-78 was prepared (580 mg, 95%) as an orange solid from ethyl 4-aminobenzoate (256 mg, 1.55 mmol), 0112 (400 mg, 1.41 mmol) and tetraisopyl titanate (480 mg, 1.69 mmol) using a procedure similar to that described for compound 0309-76 (Example 30). LCMS: 433 [M+1]+; $^1$H NMR (400 MHz, DMSO-$d_6$) δ 1.26 (t, J=7.2 Hz, 3H), 3.71 (t, J=4.8 Hz, 4H), 3.83 (t, J=4.6 Hz, 4H), 4.20 (q, J=5.3 Hz, 2H), 4.71 (d, J=6.0 Hz, 2H), 6.68 (d, J=9.2 Hz, 2H), 7.35 (t, J=6.4 Hz, 1H), 7.36 (s, 1H), 7.69 (d, J=8.4 Hz, 2H).

Step 31b: Ethyl 4-((2-(1H-indazol-4-yl)-4-morpholinothieno[3,2-d]pyrimidin-6-yl)methylamino)benzoate (Compound 0310-78)

The title compound, 0310-78 was prepared (85 mg, 33%) as a white solid from 0309-78 (216 mg, 0.5 mmol), 0107-3 (256 mg, 0.53 mmol), sodium hydrogen carbonate (126 mg, 1.5 mmol) and bis(triphenylphosphine)palladium(II) chloride (18 mg, 0025 mmol) in toluene (4.0 mL), ethanol (2.5 mL) and water (1.5 mL) using a procedure similar to that described for compound 0310-76 (Example 30). LCMS: 515 [M+1]+ $^1$H NMR (400 MHz, DMSO-$d_6$) δ 1.25 (t, J=7.2 Hz, 3H), 3.80 (t, J=4.6 Hz, 4H), 3.97 (t, J=4.6 Hz, 4H), 4.20 (q, J=5.3 Hz, 2H), 4.75 (d, J=6.0 Hz, 2H), 6.73 (d, J=8.8 Hz, 2H), 7.39 (t, J=6.0 Hz, 1H), 7.47 (t, J=8.0 Hz, 1H), 7.56 (s, 1H), 7.67 (d, J=8.4 Hz, 1H), 7.71 (d, J=8.8 Hz, 2H), 8.22 (d, J=7.2 Hz, 1H), 8.88 (s, 1H).

Step 31c: 4-((2-(1H-indazol-4-yl)-4-morpholinothieno[3,2-d]pyrimidin-6-yl)methylamino)-N-hydroxybenzamide (Compound 78)

The title compound 78 was prepared (41 mg, 28%) as a yellow solid from 0310-78 (150 mg, 0.29 mmol) and freshly prepared hydroxylamine methanol solution (10.0 mL) using a procedure similar to that described for compound 3 (Example 1). m.p. 180-183° C. LCMS: 502 [M+1]+; $^1$H NMR (400 MHz, DMSO-$d_6$) δ 3.80 (br s, 4H), 3.96 (t, 4H), 4.72 (d, J=5.6 Hz, 2H), 6.68 (d, J=8.8 Hz, 2H), 7.09 (t, J=6.0 Hz, 1H), 7.47 (t, J=8.0 Hz, 1H), 7.54 (d, J=8.4 Hz, 2H), 7.57 (s, 1H), 7.67 (d, J=8.0 Hz, 1H), 8.22 (d, J=7.2 Hz, 1H), 8.72 (s, 1H), 8.87 (s, 1H), 10.81 (s, 1H), 13.22 (s, 1H).

Example 32: Preparation of (E)-3-(4-((2-(1H-indazol-4-yl)-4-morpholinothieno[3,2-d]pyrimidin-6-yl)methylamino)phenyl)-N-hydroxyacrylamide (Compound 80)

Step 32a: (E)-ethyl 3-(4-((2-chloro-4-morpholinothieno[3,2-d]pyrimidin-6-yl)methylamino)phenyl)acrylate (Compound 0309-80)

The title compound, 0309-80 was prepared (968 mg, 71%) as a light yellow solid from (E)-ethyl 3-(4-aminophenyl)acrylate (623 mg, 3.26 mmol), 0112 (840 mg, 2.96 mmol), and tetraisopyl titanate (1 g, 3.55 mmol) using a procedure similar to that described for compound 0309-76 (Example 30). LCMS: 459 [M+1]$^+$; $^1$H NMR (400 MHz, DMSO-d$_6$) δ 1.22 (t, J=7.2 Hz, 3H), 3.71 (t, J=4.6 Hz, 4H), 3.83 (t, J=4.6 Hz, 4H), 4.13 (q, J=7.2 Hz, 2H), 4.69 (d, J=6.0 Hz, 2H), 6.27 (d, J=16.0 Hz, 1H), 6.65 (d, J=8.8 Hz, 2H), 7.17 (t, J=6.0 Hz, 1H), 7.36 (s, 1H), 7.44 (d, J=8.8 Hz, 2H), 7.48 (d, J=16.0 Hz, 1H).

Step 32b: (E)-ethyl 3-(4-((2-(1H-indazol-4-yl)-4-morpholinothieno[3,2-d]pyrimidin-6-yl)methylamino)phenyl)acrylate (Compound 0310-80)

The title compound, 0310-80 was prepared (490 mg, 69%) as a light yellow solid from 0309-80 (600 mg, 1.31 mmol), 0107-3 (383 mg, 1.57 mmol), sodium hydrogen carbonate (329 mg, 3.92 mmol) and bis(triphenylphosphine)palladium(II) chloride (46 mg, 0.065 mmol) in toluene (16.0 mL), ethanol (10 mL) and water (4 mL) using a procedure similar to that described for compound 0310-76 (Example 30). LCMS: 541 [M+1]$^+$ $^1$H NMR (400 MHz, DMSO-d$_6$) δ 1.22 (t, J=7.2 Hz, 3H), 3.82 (t, J=4.0 Hz, 4H), 3.97 (t, J=4.4 Hz, 4H), 4.12 (q, J=7.2 Hz, 2H), 4.74 (d, J=5.2 Hz, 2H), 6.27 (d, J=15.6 Hz, 1H), 6.70 (d, J=8.8 Hz, 2H), 7.21 (t, J=5.8 Hz, 1H), 7.45-7.50 (m, 4H), 7.57 (s, 1H), 7.67 (d, J=8.0 Hz, 1H), 8.22 (d, J=6.8 Hz, 1H), 8.87 (s, 1H), 13.21 (s, 1H).

Step 32c: (E)-3-(4-((2-(1H-indazol-4-yl)-4-morpholinothieno[3,2-d]pyrimidin-6-yl)methylamino)phenyl)-N-hydroxyacrylamide (Compound 80)

The title compound 80 was prepared (71 mg, 15%) as a light yellow solid from 0310-80 (490 mg, 0.91 mmol) and freshly prepared hydroxylamine methanol solution (20.0 mL) using a procedure similar to that described for compound 3 (Example 1). m.p.>300° C. LCMS: 528 [M+1]$^+$; $^1$H NMR (400 MHz, DMSO-d$_6$): δ 3.87 (t, J=4.6 Hz, 4H), 4.03 (t, J=4.6 Hz, 4H), 4.78 (d, J=5.6 Hz, 2H), 6.21 (d, J=15.6 Hz, 1H), 6.76 (d, J=8.8 Hz, 2H), 7.11 (t, J=5.8 Hz, 1H), 7.34-7.39 (m, 3H), 7.53 (t, J=7.8 Hz, 1H), 7.63 (s, 1H), 7.73 (d, J=8.0 Hz, 1H), 8.29 (d, J=7.6 Hz, 1H), 8.93 (d, J=4.8 Hz, 2H), 10.60 (s, 1H), 13.27 (s, 1H).

Example 33: Preparation of (E)-3-(4-(((2-(1H-indazol-4-yl)-4-morpholinothieno[3,2-d]pyrimidin-6-yl)methyl)(methyl)amino)phenyl)-N-hydroxyacrylamide (Compound 81)

Step 33a: (E)-ethyl 3-(4-(((2-chloro-4-morpholinothieno[3,2-d]pyrimidin-6-yl)methyl) (methyl)amino)phenyl)acrylate (Compound 0309-81)

The solution of compound 0309-80 (1.0 g, 2.2 mmol), CH$_3$I (6.2 g, 44 mmol), and Cs$_2$CO$_3$ (1.44 g, 4.4 mmol) in dry CH$_3$CN/DMF solution (5 mL/5 mL) was stirred at room temperature for 3 days. CH$_3$I and CH$_3$CN was removed in vacuo and the residue was diluted with H$_2$O, extracted with ethyl acetate, dried over Na$_2$SO$_4$, and the crude product was purified by column chromatography on silica gel (ethyl acetate in petroleum ether, 20% v/v) to obtain 0309-81 (0.3 g, 30%) as a yellow solid. LCMS: 473 [M+1]$^+$. $^1$H-NMR (400 MHz, DMSO-d$_6$) δ 1.23 (t, J=7.2 Hz, 3H), 3.12 (s, 3H), 3.70 (m, 4H), 3.82 (m, 4H), 4.14 (q, J=7.2 Hz, 2H), 4.97 (s, 2H), 6.33 (d, J=16.4 Hz, 1H), 6.82 (d, J=8.8 Hz, 2H), 7.31 (s, 1H), 7.53 (m, 3H).

Step 33b: (E)-ethyl 3-(4-(((2-(1H-indazol-4-yl)-4-morpholinothieno[3,2-d]pyrimidin-6-yl) methyl) (methyl)amino)phenyl)acrylate (Compound 0310-81)

The title compound, 0310-81 was prepared (200 mg, 71%) as a white solid from 0309-81 (240 mg, 0.5 mmol), 0107-3 (135 mg, 0.55 mmol), NaHCO$_3$ (126 mg, 1.5 mmol), and bis(triphenylphosphine)palladium(II) chloride (18 mg, 0.025 mmol) in toluene (4 mL), ethanol (2 mL) and water (1 mL) using a procedure similar to that described for compound 0310-76 (Example 30). LCMS: 555 [M+1]$^+$; $^1$H NMR (400 MHz, DMSO-d$_6$) δ 1.23 (m, 3H), 3.17 (s, 3H), 3.80 (m, 4H), 3.95 (m, 4H), 4.15 (m, 2H), 5.01 (s, 2H), 6.33 (d, J=15.6 Hz, 1H), 6.86 (d, J=8.8 Hz, 2H), 7.46 (m, 1H), 7.54 (m, 4H), 7.66 (d, J=8.0 Hz, 1H), 8.21 (d, J=7.2 Hz, 1H), 8.87 (s, 1H), 13.21 (s, 1H).

Step 33c: (E)-3-(4-(((2-(1H-indazol-4-yl)-4-morpholinothieno[3,2-d]pyrimidin-6-yl)methyl)(methyl)amino)phenyl)-N-hydroxyacrylamide (Compound 81)

The title compound 81 was prepared (24 mg, 10%) as a light yellow solid from 0310-81 (250 mg, 0.45 mmol) and freshly prepared hydroxylamine methanol solution (20.0 mL) using a procedure similar to that described for compound 3 (Example 1). m.p. 188-190° C. LCMS: 542 [M+1]$^+$; $^1$H NMR (400 MHz, DMSO-d$_6$) δ 3.14 (s, 3H), 3.80 (m, 4H), 3.95 (m, 4H), 4.98 (s, 2H), 6.21 (d, J=15.2 Hz, 1H), 6.86 (d, J=8.8 Hz, 2H), 7.32 (d, J=15.2 Hz, 1H), 7.40 (d, J=8.4 Hz, 2H), 7.46 (t, J=7.6 Hz, 1H), 7.50 (s, 1H), 7.66 (d, J=8.0 Hz, 1H), 8.21 (d, J=7.2 Hz, 1H), 8.34 (s, 1H), 8.87 (s, 1H), 10.58 (s, 1H), 13.23 (s, 1H).

Example 34: Preparation of (2-(((2-(3-acetamidophenyl)-4-morpholinothieno[3,2-d]pyrimidin-6-yl)methyl)(methyl)amino)-N-hydroxypyrimidine-5-carboxamide (Compound 107)

Step 34a: N-(3-bromophenyl)acetamide (Compound 0601-107)

To the solution of 3-bromoaniline (6.3 g, 63.7 mmol) in CH$_2$Cl$_2$ (50 mL) was added acetyl chloride (3.75 g, 47.7 mmol) and TEA (7.4 g, 73.4 mmol) at 0° C., stirred for 2 hours. The mixture was washed with water, brine, dried over Na$_2$SO$_4$, filtered, and concentrated under reduced pressure to give the title compound 0601-107 (7.8 g, 99.3%) as a brown solid. LCMS: 215 [M+1]$^+$. $^1$H NMR (400 MHz, DMSO-d$_6$) δ 2.05 (s, 3H), 7.22 (m, 2H), 7.46 (d, J=7.6 Hz, 1H), 7.95 (s, 1H), 10.11 (s, 1H).

Step 34b: N-(3-(4,4,5,5-tetramethyl-1,3,2-dioxaborolan-2-yl)phenyl)acetamide (Compound 0602-107)

To a solution of compound 0601-107 (2.5 g, 11.6 mmol) and bis(pinacolato)diboron (4.4 g, 17.5 mmol) in dioxane (100 mL) was added potassium acetate (3.4 g, 35 mmol) and PdCl$_2$(dppf)$_2$ (0.95 g, 1.1 mmol). The mixture was degassed with nitrogen and heated at 85° C. for overnight. The reaction mixture was concentrated under reduced pressure to afford the crude product, which purified by column chromatography (ethyl acetate in petroleum ether, 15% v/v) to give the compound 0602-107 (1.55 g, 51%) as a pink solid. LCMS: 262 [M+1]$^+$. $^1$H NMR (400 MHz, DMSO-d$_6$) δ 1.29

(s, 12H), 2.03 (s, 3H), 7.30 (s, 1H), 7.31 (d, J=2.0 Hz 1H), 7.73 (d, J=2.0 Hz, 1H), 7.89 (d, J=1.6 Hz, 1H), 9.93 (s, 1H).

Step 34c: Ethyl 2-(((2-(3-acetamidophenyl)-4-morpholinothieno[3,2-d]pyrimidin-6-yl)methyl)(methyl) amino)pyrimidine-5-carboxylate (Compound 0603-107)

The title compound, 0603-107 was prepared (160 mg, 99%) as a gray solid from 0504-54 (130 mg, 0.30 mmol), 0602-107 (84 mg, 0.7 mmol), sodium hydrogen carbonate (74 mg, 0.88 mmol) and bis(triphenylphosphine)palladium (II) chloride (12 mg, 0.014 mmol) in toluene (2.5 mL), ethanol (1.6 mL) and water (0.7 mL) using a procedure similar to that described for compound 0310-76 (Example 30). LCMS: 548 [M+1]$^+$; $^1$H NMR (400 MHz, DMSO-d$_6$): δ 1.31 (t, J=6.8 Hz, 3H), 2.07 (s, 3H), 3.27 (s, 1H), 3.77 (t, J=5.2 Hz, 4H), 3.94 (t, J=5.2 Hz, 4H), 4.29 (q, J=7.2 Hz, 2H), 5.24 (s, 2H), 7.39 (t, J=8.4 Hz, 1H), 7.49 (s, 1H), 7.82 (d, J=8.0 Hz, 1H), 8.05 (d, J=8.8 Hz, 1H), 8.52 (s, 1H), 8.89 (s, 2H), 10.08 (s, 1H).

Step 34d: 2-(((2-(3-acetamidophenyl)-4-morpholinothieno[3,2-d]pyrimidin-6-yl)methyl)(methyl) amino)-N-hydroxypyrimidine-5-carboxamide (Compound 107)

The title compound 107 was prepared (64 mg, 50%) as a white solid from 0603-107 (130 mg, 0.23 mmol) and freshly prepared hydroxylamine methanol solution (4.0 mL) using a procedure similar to that described for compound 3 (Example 1). m.p. 183-185° C. LCMS: 535 [M+1]$^+$; $^1$H NMR (400 MHz, DMSO-d$_6$): δ 2.07 (s, 3H), 3.24 (s, 3H), 3.77 (t, J=4.0 Hz, 4H), 3.94 (t, J=4.0 Hz, 4H), 5.21 (s, 2H), 7.39 (t, J=8 Hz, 1H), 7.46 (s, 1H), 7.82 (d, J=7.6 Hz, 1H), 8.05 (d, J=8 Hz, 1H), 8.51 (s, 1H), 8.75 (s, 2H), 9.07 (s, 1H), 10.08 (s, 1H), 11.13 (s, 1H).

Example 35: Preparation of 2-(((2-(3-(dimethylamino)phenyl)-4-morpholinothieno[3,2-d]pyrimidin-6-yl)methyl)(methyl)amino)-N-hydroxypyrimidine-5-carboxamide (Compound 108)

Step 35a: Ethyl 6-(2-chloro-4-morpholinothieno[3,2-d]pyrimidin-6-ylamino) hexanoate (Compound 0602-108)

The title compound, 0602-108 was prepared (600 mg, 80%) as oil from 3-bromo-N,N-dimethylaniline (600 mg, 3.0 mmol), bis(pinacolato)diboron (1.14 g, 4.5 mmol), potassium acetate (882 g, 9.0 mmol), and PdCl$_2$(dppf)$_2$ (245 mg, 0.3 mmol) using a procedure similar to that described for compound 0602-107 (Example 34). LCMS: 248 [M+1]$^+$. $^1$H NMR (400 MHz, DMSO-d$_6$) δ 1.34 (s, 12H), 2.97 (s, 6H), 7.19 (m, 2H), 7.26 (m 2H).

Step 35b: Ethyl 2-(((2-(3-(dimethylamino)phenyl)-4-morpholinothieno[3,2-d]pyrimidin-6-yl)methyl) (methyl)amino)pyrimidine-5-carboxylate (Compound 0603-108)

The title compound 0603-108 was prepared (245 mg, 91%) as a white solid from 0504-54 (224 mg, 0.5 mmol), 0602-108 (490 mg, 2.0 mmol), NaHCO$_3$ (126 mg, 1.5 mmol) and bis(triphenylphosphine)palladium(II) chloride (18 mg, 0.025 mmol) in toluene (4 mL), ethanol (2 mL) and water (1 mL) using a procedure similar to that described for compound 0603-107 (Example 30). LCMS: 534 [M+1]$^+$; $^1$H NMR (400 MHz, DMSO-d$_6$): δ 1.30 (t, J=6.8 Hz, 3H), 2.97 (s, 3H), 3.27 (s, 2H), 3.76 (m, 4H), 3.92 (m, 4H), 4.28 (q, J=6.8 Hz, 2H), 5.23 (s, 2H), 6.85 (m, 1H), 7.28 (t, J=8.0 Hz, 1H), 7.49 (s, 1H), 7.71 (d, J=7.2 Hz, 1H), 7.79 (br s, 1H), 8.79 (s, 1H).

Step 35c: 2-(((2-(3-(dimethylamino)phenyl)-4-morpholinothieno[3,2-d]pyrimidin-6-yl)methyl)(methyl) amino)-N-hydroxypyrimidine-5-carboxamide (Compound 108)

The title compound 108 was prepared (35 mg, 15%) as a yellow solid from 0603-108 (130 mg, 0.23 mmol) and freshly prepared hydroxylamine methanol solution (20 mL) using a procedure similar to that described for compound 3 (Example 1). m.p. 172-175° C. LCMS: 521 [M+1]$^+$; $^1$H NMR (400 MHz, DMSO-d$_6$) δ 2.96 (s, 3H), 3.23 (s, 2H), 3.75 (m, 4H), 3.91 (m, 4H), 5.19 (s, 2H), 6.84 (m, 1H), 7.27 (t, J=8.0 Hz, 1H), 7.46 (s, 1H), 7.70 (d, J=7.2 Hz, 1H), 7.75 (br s, 1H), 8.74 (s, 1H), 9.11 (br s, 1H), 11.16 (br s, 1H).

Example 36: Preparation of N-hydroxy-2-(methyl ((4-morpholino-2-(pyridin-3-yl)thieno[3,2-d]pyrimidin-6-yl)methyl)amino)pyrimidine-5-carboxamide (Compound 109)

Step 36a: Ethyl 2-(methyl((4-morpholino-2-(pyridin-3-yl)thieno[3,2-d]pyrimidin-6-yl)methyl)amino) pyrimidine-5-carboxylate (compound 0603-109)

The title compound, 0603-109 was prepared (140 mg, 94%) as a yellow solid from 0504-54 (135 mg, 0.30 mmol), 3-pyridylboronic acid (41 mg, 0.60 mmol), NaHCO$_3$ (76 mg, 0.90 mmol) and Pd(dppf)$_2$Cl$_2$ (11 mg, 0.015 mmol) in toluene (2.5 mL), ethanol (1.6 mL) and water (0.7 mL) using a procedure similar to that described for compound 0603-107 (Example 30). LCMS: 492 [M+1]$^+$. $^1$HNMR (400 MHz, DMSO-d$_6$) δ 1.30 (t, J=7.2 Hz, 3H), 3.28 (s, 3H), 3.76 (m, 4H), 3.95 (m, 4H), 5.25 (s, 2H), 7.53 (m, 2H), 8.66 (m, 2H), 8.88 (s, 2H), 9.51 (s, 1H).

Step 36b: N-hydroxy-2-(methyl((4-morpholino-2-(pyridin-3-yl)thieno[3,2-d]pyrimidin-6-yl)methyl) amino)pyrimidine-5-carboxamide (Compound 109)

The title compound 109 was prepared (30 mg, 44%) as a yellow solid from 0603-109 (70 mg, 0.14 mmol) and freshly prepared hydroxylamine methanol solution (10 mL) using a procedure similar to that described for compound 3 (Example 1). mp: 160-164° C. LCMS: 479 [M+1]$^+$. $^1$H NMR (400 MHz, DMSO-d$_6$) δ 3.24 (s, 3H), 3.77 (s, 4H), 3.94 (s, 4H), 5.21 (s, 2H), 7.52 (m, 2H), 8.67 (m, 2H), 8.76 (s, 2H), 9.09 (s, 1H), 9.52 (s, 1H), 11.15 (s, H).

Example 37: Preparation of 2-(((2-(6-aminopyridin-3-yl)-4-morpholinothieno[3,2-d]pyrimidin-6-yl) methyl)(methyl)amino)-N-hydroxypyrimidine-5-carboxamide (Compound 110)

Step 37a: 5-(4,4,5,5-Tetramethyl-1,3,2-dioxaborolan-2-yl)pyridin-2-amine (Compound 0602-110)

The title compound, 0602-110 was prepared (500 mg, 23%) as an oil from 2-amino-5-bromopyridine (1.73 g, 10 mmol), bis(pinacolato)diboron (3.81 g, 15 mmol), potassium acetate (3 g, 30 mmol), and PdCl$_2$(dppf)$_2$ (408 mg, 5 mmol) using a procedure similar to that described for compound 0602-107 (Example 34). LCMS: 221 [M+1]$^+$. $^1$H NMR (400 MHz, DMSO-d$_6$) δ 1.25 (s, 12H), 6.30 (s, 2H), 6.39 (d, J=8.0 Hz, 1H), 7.54 (d, J=10.0 Hz, 1H), 8.16 (s, 1H).

Step 37b: Ethyl 2-(((2-(6-aminopyridin-3-yl)-4-morpholinothieno[3,2-d]pyrimidin-6-yl)methyl)(methyl)amino)pyrimidine-5-carboxylate (Compound 0603-110)

The title compound, 0603-110 was prepared (200 mg, 59%) as a white solid from 0602-110 (300 mg, 0.67 mmol), 0504-54 (176 mg, 0.8 mmol), NaHCO$_3$ (172 mg, 2 mmol) and bis(triphenylphosphine)palladium(II) chloride (23 mg, 0.0335 mmol) in toluene (8 mL), ethanol (5 mL) and water (2 mL) using a procedure similar to that described for compound 0603-107 (Example 30). LCMS: 507 [M+1]$^+$; $^1$H NMR (400 MHz, DMSO-d$_6$): δ 1.29 (t, J=6.8 Hz, 3H), 3.29 (s, 3H), 3.81 (m, 4H), 3.95 (m, 4H), 4.28 (m, 2H), 5.24 (s, 2H), 6.42 (s, 2H), 6.56 (d, J=8.8 Hz, 1H), 7.44 (s, 1H), 8.327 (d, J=8.8 Hz, 1H), 8.81 (s, 2H), 8.99 (s, 1H), 9.13 (s, 1H), 11.69 (s, 1H).

Step 37c: 2-(((2-(6-Aminopyridin-3-yl)-4-morpholinothieno[3,2-d]pyrimidin-6-yl)methyl)(methyl)amino)-N-hydroxypyrimidine-5-carboxamide (Compound 110)

The title compound 110 was prepared (25 mg, 13%) as a yellow solid from 0603-110 (200 mg, 0.4 mmol) and freshly prepared hydroxylamine methanol solution (20 mL) using a procedure similar to that described for compound 3 (Example 1). m.p. 175-181° C. LCMS: 494 [M+1]$^+$; $^1$H NMR (400 MHz, DMSO-d$_6$) δ 3.29 (s, 3H), 3.81 (m, 4H), 3.95 (m, 4H), 5.24 (s, 2H), 6.42 (s, 2H), 6.56 (d, J=8.8 Hz, 1H), 7.44 (s, 1H), 8.327 (d, J=8.8 Hz, 1H), 8.81 (s, 2H), 8.99 (s, 1H), 9.13 (s, 1H), 11.195 (s, 1H).

Example 38: Preparation of 2-(((2-(2-aminopyrimidin-5-yl)-4-morpholinothieno[3,2-d]pyrimidin-6-yl)methyl)(methyl)amino)-N-hydroxypyrimidine-5-carboxamide (Compound 115)

Step 38a: 5-(4,4,5,5-Tetramethyl-1,3,2-dioxaborolan-2-yl)pyrimidin-2-amine (Compound 0602-115)

The title compound, 0602-115 was prepared (120 mg, 11%) as an oil from 2-amino-5-bromopyrimidine (865 mg, 5.0 mmol) and bis(pinacolato)diboron (2.54 g, 10 mmol), potassium acetate (1.47 g, 15 mmol), and PdCl$_2$(dppf)$_2$ (204 mg, 0.25 mmol) using a procedure similar to that described for compound 0602-107 (Example 34). LCMS: 222 [M+1]$^+$. $^1$H NMR (400 MHz, DMSO-d$_6$) δ 1.26 (s, 12H), 7.04 (s, 2H), 8.37 (s, 2H).

Step 38b: Ethyl 2-(((2-(2-aminopyrimidin-5-yl)-4-morpholinothieno[3,2-d]pyrimidin-6-yl)methyl)(methyl)amino)pyrimidine-5-carboxylate (Compound 0603-115)

The title compound, 0603-115 was prepared (110 mg, 51%) as a white solid from 0602-115 (120 mg, 0.54 mmol), 0504-54 (200 mg, 0.45 mmol), NaHCO$_3$ (114 mg, 1.35 mmol), and bis(triphenylphosphine)palladium(II) chloride (16 mg, 0.0225 mmol) in toluene (8 mL), ethanol (5 mL) and water (2 mL) using a procedure similar to that described for compound 0603-107 (Example 30). LCMS: 508 [M+1]$^+$; $^1$H NMR (400 MHz, DMSO-d$_6$) δ 1.39 (t, J=6.8 Hz, 3H), 3.32 (s, 3H), 3.89 (m, 4H), 4.02 (m, 4H), 4.36 (q, J=6.8 Hz, 2H), 5.20 (s, 2H), 5.43 (s, 2H), 7.44 (s, 1H), 8.94 (s, 2H), 9.31 (s, 2H).

Step 38c: 2-(((2-(2-Aminopyrimidin-5-yl)-4-morpholinothieno[3,2-d]pyrimidin-6-yl)methyl)(methyl)amino)-N-hydroxypyrimidine-5-carboxamide (Compound 115)

The title compound 115 was prepared (25 mg, 23%) as a yellow solid from 0603-115 (110 mg, 0.2 mmol) and freshly prepared hydroxylamine methanol solution (20 mL) using a procedure similar to that described for compound 3 (Example 1). m.p. 175-181° C. LCMS: 495 [M+1]$^+$; $^1$H NMR (400 MHz, DMSO-d$_6$) δ 3.21 (s, 3H), 3.75 (m, 4H), 3.91 (m, 4H), 5.19 (s, 2H), 7.13 (s, 2H), 7.41 (s, 1H), 8.74 (s, 2H), 9.02 (br s, 1H), 9.10 (s, 2H), 11.13 (br s, 1H).

Example 39: Preparation of N-hydroxy-2-(methyl((2-(2-(methylamino)pyrimidin-5-yl)-4-morpholinothieno[3,2-d]pyrimidin-6-yl)methyl)amino)pyrimidine-5-carboxamide (Compound 116)

Step 39a: 5-Bromo-N-methylpyrimidin-2-amine (compound 0601-116) and 5-bromo-N,N-dimethylpyrimidin-2-amine (compound 0601-117)

A mixture of 5-bromopyrimidin-2-amine (3.48 g, 20 mmol) and DMF (20 mL) was cooled to 0° C. To the mixture NaH (60%, 1.44 g, 36 mmol) was added. After 15 minutes, iodomethane (5 mL, 80 mmol) was added and stirred at 0° C. for 0.5 h and the mixture was warmed to room temperature for additional 4 hours. Water (30 mL) was added and extracted with ethyl acetate (3×30 mL). The combined organic layers was washed with brine, dried over Na$_2$SO$_4$, concentrated and purified by column chromatograph on silica gel (ethyl acetate in petroleum ether, 10% v/v) to give two compounds: compound 0601-116 (0.76 g, 20%) as a white solid, LCMS: 190 [M+2]$^+$; $^1$HNMR (400 MHz, DMSO-d$_6$) δ 2.75 (d, J=4.8 Hz, 3H), 7.35 (d, J=4.0 Hz, 1H), 8.34 (s, 2H); compound 0601-117 (1.96 g, 49%) as a yellow solid, LCMS: 202 [M+1]$^+$; $^1$HNMR (400 MHz, DMSO-d$_6$) δ 3.12 (s, 6H), 8.43 (s, 2H).

Step 39b: N-methyl-5-(4,4,5,5-tetramethyl-1,3,2-dioxaborolan-2-yl)pyrimidin-2-amine (Compound 0602-116)

The title compound, 0602-116 was prepared (350 mg, 50%) as yellow solid from 5-bromo-N-methylpyrimidin-2-amine (0.56 g, 3 mmol), bis(pinacolato)diboron (1.14 g, 4.5 mmol), potassium acetate (0.88 g, 9 mmol), and Pd(dppf)$_2$Cl$_2$ (490 mg, 0.6 mmol) using a procedure similar to that described for compound 0602-107 (Example 34). LCMS: 236 [M+1]$^+$; $^1$HNMR (400 MHz, DMSO-d$_6$) δ 1.27 (s, 12H), 2.82 (d, J=4.8 Hz, 3H), 7.47 (m, 1H), 8.38 (m, 1H), 8.45 (m, 1H).

Step 39c: Ethyl 2-(methyl((2-(2-(methylamino)pyrimidin-5-yl)-4-morpholinothieno[3,2-d]pyrimidin-6-yl)methyl)amino)pyrimidine-5-carboxylate (Compound 0603-116)

The title compound, 0603-116 was prepared (100 mg, 64%) as a yellow solid from 0504-54 (135 mg, 0.30 mmol), 0602-116 (106 mg, 0.45 mmol), NaHCO$_3$ (76 mg, 0.90 mmol) and Pd(dppf)$_2$Cl$_2$ (11 mg, 0.015 mmol) in toluene (2.5 mL), ethanol (1.6 mL) and water (0.7 mL) using a procedure similar to that described for compound 0603-107 (Example 30). LCMS: 522 [M+1]$^+$; $^1$HNMR (400 MHz, CDCl$_3$) δ 1.39 (t, J=7.2 Hz, 3H), 3.09 (d, J=5.2 Hz, 3H), 3.31 (s, 3H), 3.85 (t, J=4.8 Hz, 4H), 3.98 (t, J=4.8 Hz, 4H), 4.36 (q, J=7.2 Hz, 2H), 5.19 (s, 2H), 5.47 (d, J=4.8 Hz, 1H), 7.34 (s, 1H), 8.93 (s, 2H), 9.26 (s, 2H).

Step 39d: N-hydroxy-2-(methyl((2-(2-(methylamino)pyrimidin-5-yl)-4-morpholinothieno[3,2-d]pyrimidin-6-yl)methyl)amino)pyrimidine-5-carboxamide (Compound 116)

The title compound 116 was prepared (50 mg, 54%) as a yellow solid from 0603-116 (96 mg, 0.13 mmol) and freshly prepared hydroxylamine methanol solution (5 mL) using a procedure similar to that described for compound 3 (Example 1). m.p.: 183-187° C. LCMS: 509 [M+1]$^+$; $^1$HNMR (400 MHz, DMSO-d$_6$) δ 2.88 (d, J=4.4 Hz, 3H), 3.23 (s, 3H), 3.74 (s, 4H), 3.90 (s, 4H), 5.19 (s, 2H), 7.40 (s, 1H), 7.55 (d, J=4.4 Hz, 1H), 8.75 (s, 2H), 9.07 (s, 1H), 9.13 (m, 2H), 11.13 (s, 1H).

Example 40: Preparation of 2-(((2-(2-(dimethylamino)pyrimidin-5-yl)-4-morpholinothieno[3,2-d]pyrimidin-6-yl)methyl)(methyl)amino)-N-hydroxypyrimidine-5-carboxamide (Compound 117)

Step 40a: N,N-dimethyl-5-(4,4,5,5-tetramethyl-1,3,2-dioxaborolan-2-yl)pyrimidin-2-amine (Compound 0602-117)

The title compound, 0602-117 was prepared (194 mg, 26%) as yellow solid from 5-bromo-N,N-dimethylpyrimidin-2-amine (0.61 g, 3 mmol), bis(pinacolato)diboron (1.14 g, 4.5 mmol), potassium acetate (0.88 g, 9 mmol), and Pd(dppf)$_2$Cl$_2$ (490 mg, 0.6 mmol) using a procedure similar to that described for compound 0602-107 (Example 34). LCMS: 168 [M−81]$^+$; $^1$HNMR (400 MHz, DMSO-d$_6$) δ 1.27 (s, 12H), 3.14 (s, 6H), 8.47 (s, 2H).

Step 40b: Ethyl 2-(((2-(2-(dimethylamino)pyrimidin-5-yl)-4-morpholinothieno[3,2-d]pyrimidin-6-yl)methyl)(methyl)amino)pyrimidine-5-carboxylate (0603-117)

The title compound, 0603-117 was prepared (100 mg, 64%) as a yellow solid from 0504-54 (135 mg, 0.30 mmol), 0602-117 (112 mg, 0.45 mmol), NaHCO$_3$ (76 mg, 0.90 mmol) and Pd(dppf)$_2$Cl$_2$ (11 mg, 0.015 mmol) in toluene (2.5 mL), ethanol (1.6 mL) and water (0.7 mL) using a procedure similar to that described for compound 0603-107 (Example 30). LCMS: 536 [M+1]$^+$; $^1$HNMR (400 MHz, CDCl$_3$) δ 1.38 (t, J=7.2 Hz, 3H), 2.37 (s, 6H), 3.30 (s, 3H), 3.83 (t, J=4.8 Hz, 4H), 3.97 (t, J=4.8 Hz, 4H), 4.36 (q, J=7.2 Hz, 2H), 5.18 (s, 2H), 7.35 (s, 1H), 8.93 (s, 2H), 9.30 (s, 2H).

Step 40c: 2-(((2-(2-(Dimethylamino)pyrimidin-5-yl)-4-morpholinothieno[3,2-d]pyrimidin-6-yl)methyl)(methyl)amino)-N-hydroxypyrimidine-5-carboxamide (Compound 117)

The title compound 117 was prepared (60 mg, 66%) as a yellow solid from 0603-117 (93 mg, 0.17 mmol) and freshly prepared hydroxylamine methanol solution (5 mL) using a procedure similar to that described for compound 3 (Example 1). m.p.: 200-206° C. LCMS: 523 [M+1]$^+$; $^1$HNMR (400 MHz, DMSO-d$_6$) δ 3.18 (d, J=8.8 Hz, 6H), 3.23 (s, 3H), 3.74 (d, J=4.8 Hz, 4H), 3.90 (d, J=4.4 Hz, 4H), 5.17 (s, 2H), 7.39 (s, 1H), 8.75 (s, 2H), 9.19 (s, 2H).

Example 41: Preparation of N-hydroxy-2-(methyl((4-morpholino-2-(pyrimidin-5-yl)thieno[3,2-d]pyrimidin-6-yl)methyl)amino)pyrimidine-5-carboxamide (Compound 119)

Step 41a: Ethyl 2-(methyl((4-morpholino-2-(pyrimidin-5-yl)thieno[3,2-d]pyrimidin-6-yl)methyl)amino)pyrimidine-5-carboxylate (Compound 0603-119)

The title compound, 0603-119 was prepared (160 mg, 46%) as a white solid from 0504-54 (314 mg, 0.7 mmol), pyrimidin-2-ylboronic acid (175 mg, 1.4 mmol), NaHCO$_3$ (176 mg, 2.1 mmol) and bis(triphenylphosphine)palladium (II) chloride (24 mg, 0.03 mmol) in toluene (8 mL), ethanol (5 mL) and water (3 mL) using a procedure similar to that described for compound 0603-107 (Example 30). LCMS: 493 [M+1]$^+$; $^1$H NMR (400 MHz, DMSO-d$_6$): δ 1.35 (t, J=7.2 Hz, 3H), 3.31 (d, J=8.4 Hz, 3H), 3.76 (m, 4H), 3.92 (m, 4H), 4.33 (q, J=6.8 Hz, 2H), 5.28 (d, J=12.0 Hz, 2H), 7.47 (s, 0.5H), 7.59 (s, 0.5H), 8.53 (s, 0.5H), 8.92 (d, J=6.0 Hz, 2H), 9.34 (s, 0.5H), 9.67 (s, 1H).

Step 41b: N-hydroxy-2-(methyl((4-morpholino-2-(pyrimidin-5-yl)thieno[3,2-d]pyrimidin-6-yl)methyl)amino)pyrimidine-5-carboxamide (Compound 119)

The title compound 119 was prepared (60 mg, 40%) as a white solid from 0603-119 (150 mg, 0.3 mmol) and freshly prepared hydroxylamine methanol solution (5 mL) using a procedure similar to that described for compound 3 (Example 1). m.p. 159-160° C. LCMS: 480 [M+1]$^+$; $^1$H NMR (400 MHz, DMSO-d$_6$) δ 3.40 (s, 3H), 3.92 (m, 4H), 4.13 (m, 4H), 5.19 (s, 2H), 6.84 (m, 1H), 7.27 (t, J=8.0 Hz, 1H), 7.46 (s, 1H), 7.70 (d, J=7.2 Hz, 1H), 7.75 (br s, 1H), 8.74 (s, 1H), 9.11 (br s, 1H), 11.16 (br s, 1H).

Example 42: Preparation of N-hydroxy-2-(methyl((2-(2-methylpyrimidin-5-yl)-4-morpholinothieno[3,2-d]pyrimidin-6-yl)methyl)amino)pyrimidine-5-carboxamide (Compound 120)

Step 42a: 5-Bromo-2-methylpyrimidine (Compound 0601-120)

Sodium (356 mg, 15.5 mmol) was carefully added to ethanol (5.9 mL) to prepare sodium ethoxide solution in ethanol. The above freshly prepared sodium ethoxide in ethanol solution (3.5 mL) was added to a stirred suspension of acetamidine hydrochloride (0.91 g, 9.69 mmol). The mixture was warmed to 50° C., then the heating bath was removed and a solution of mucobromic acid (1 g, 3.87 mmol) in ethanol was added dropwise at a rate which maintained a constant temperature, followed by a further sodium ethoxide in ethanol solution (2 mL). After cooling, the mixture was filtered and evaporated to a residue which was shaken vigorously with hydrochloric acid (2 M×2.4 mL). The brown precipitate was filtered and washed with cold water, then freeze-dried to give 5-bromo-2-methylpyrimidine-4-carboxylic acid (350 mg, 42%) as a brown solid. LCMS: 218 [M+1]$^+$, $^1$H NMR (400 MHz, DMSO-d$_6$): 2.62 (s, 3H), 9.03 (s, 1H).

A mixture of compound 5-bromo-2-methylpyrimidine-4-carboxylic acid (350 mg, 1.6 mmol) in xylene (5 mL) was refluxed for 2 h. After cooling, the mixture was applied directly to a silica column, which was eluted with petroleum ether, then ethyl acetate in petroleum ether (5% v/v) to give compound 0601-120 (170 mg, 61%) as a white solid. LCMS: 173 [M+1]$^+$, $^1$H NMR (400 MHz, DMSO-d$_6$): δ 2.59 (s, 3H), 8.87 (s, 2H).

Step 42b: 2-Methyl-5-(4,4,5,5-tetramethyl-1,3,2-dioxaborolan-2-yl)pyrimidine (Compound 0602-120)

The title compound, 0602-120 was prepared (100 mg, 52%) as a yellow oil from 0601-120 (150 mg, 0.87 mmol), bis(pinacolato)diboron (331 mg, 1.3 mmol), PdCl$_2$(dppf)$_2$ (21 mg, 0.026 mmol) and dried potassium acetate (256 mg, 2.62 mmol) using a procedure similar to that described for compound 0602-107 (Example 34). LCMS: 221 [M+1]$^+$; $^1$H NMR (400 MHz, DMSO-d$_6$): δ 1.32 (s, 12H), 2.64 (s, 3H), 8.81 (s, 2H).

Step 42c: Ethyl 2-(methyl((2-(2-methylpyrimidin-5-yl)-4-morpholinothieno[3,2-d]pyrimidin-6-yl)methyl)amino)pyrimidine-5-carboxylate (Compound 0603-120)

The title compound, 0603-120 was prepared (210 mg, 74%) as an off-white solid from 0504-54 (250 mg, 0.56 mmol), 0602-120 (880 mg, 4 mmol), sodium hydrogen carbonate (168 mg, 2 mmol), and bis(triphenylphosphine)palladium(II) chloride (23 mg, 0.03 mmol) in toluene (8 mL), ethanol (5 mL) and water (2 mL) using a procedure similar to that described for compound 0603-107 (Example 30). LCMS: 507 [M+1]$^+$; $^1$H NMR (400 MHz, CDCl$_3$): δ 1.31 (t, J=7.2 Hz, 3H), 2.74 (s, 3H), 3.25 (s, 3H), 3.79 (t, J=4.4 Hz, 4H), 3.94 (t, J=4.4 Hz, 4H), 4.29 (q, J=7.2 Hz, 2H), 5.14 (s, 2H), 7.32 (s, 1H), 8.86 (s, 2H), 9.48 (s, 2H).

Step 42d: N-hydroxy-2-(methyl((2-(2-methylpyrimidin-5-yl)-4-morpholinothieno[3,2-d]pyrimidin-6-yl)methyl)amino)pyrimidine-5-carboxamide (Compound 120)

The title compound 120 was prepared (150 mg, 73%) as a white solid from 0603-120 (210 mg, 0.41 mmol) and freshly prepared hydroxylamine methanol solution (5 mL) using a procedure similar to that described for compound 3 (Example 1). m.p. 184-186° C. LCMS: 494 [M+1]$^+$; $^1$H NMR (400 MHz, DMSO-d$_6$): δ 2.69 (s, 3H), 3.24 (s, 3H), 3.76 (t, J=4.4 Hz, 4H), 3.94 (t, J=4.4 Hz, 4H), 5.21 (s, 2H), 7.49 (s, 1H), 8.76 (s, 2H), 9.06 (s, 1H), 9.9.48 (s, 2H), 11.14 (s, 1H).

Example 43: Preparation of 2-(((2-(2-ethylpyrimidin-5-yl)-4-morpholinothieno[3,2-d]pyrimidin-6-yl)methyl)(methyl)amino)-N-hydroxypyrimidine-5-carboxamide (Compound 121)

Step 43a: 5-Bromo-2-ethylpyrimidine (0601-121)

After dissolving propionitrile (38 g, 0.69 mol) in anhydrous ethanol (100 mL), HCl gas was bubbled in at 0° C. for 4 h. The mixture was stirred overnight at room temperature and the excess HCl gas and ethanol were removed in vacuum. Ether (100 mL) was added in and the solid substance were filtered and washed with ether (100 mL). The solid was dried and then dissolved in ethanol (100 mL) and NH$_3$ gas was bubbled in at 0° C. for an hour, the solution was filtered and the filtrate was concentrated to half of the original volume, the solid was filtered off. The solid substance thus obtained was filtered off again and the filtrate was concentrated to give propionimidamide hydrochloride (34 g, 45%) as a white solid. GCMS: 71 [M−1]$^+$, $^1$H NMR (400 MHz, DMSO-d$_6$): δ 1.17 (t, J=7.6 Hz, 3H), 2.40 (q, J=7.6 Hz, 2H), 8.79 (s, 2H), 9.09 (s, 2H).

Sodium (356 mg, 15.5 mmol) was carefully added to ethanol (5.9 mL) to prepare sodium ethoxide solution in ethanol. The above freshly prepared ethanol solution (3.5 mL) was added to a stirred suspension of propionimidamide hydrochloride (1.05 g, 9.69 mmol). The mixture was warmed to 55° C., then the heating bath was removed and a solution of mucobromic acid (1 g, 3.87 mmol) in ethanol was added dropwise at a rate which maintained a constant temperature, followed by a further sodium ethoxide solution (2 mL). After cooling, the mixture was filtered and evaporated to a residue which was shaken vigorously with hydrochloric acid (2 M×2.4 mL). The brown precipitate was filtered off and washed with cold water, then freeze-dried to give 5-Bromo-2-ethylpyrimidine-4-carboxylic acid (330 mg, 37%) as a yellow solid. LCMS: 231 [M+1]$^+$, $^1$H NMR (400 MHz, DMSO-d$_6$): δ 1.25 (t, J=7.6 Hz, 3H), 2.88 (q, J=7.6 Hz, 2H), 9.05 (s, 1H).

A mixture of 5-Bromo-2-ethylpyrimidine-4-carboxylic acid (5.6 g, 24.3 mmol) in xylene (50 mL) was refluxed for 2 h. After cooling, the mixture was applied directly to a silica column, which was eluted with petroleum ether, then ethyl acetate in petroleum ether (5%) to give compound 0601-121 (1.7 g, 38%) as a yellow liquid. $^1$H NMR (400 MHz, DMSO-d$_6$): 1.26 (t, J=7.6 Hz, 3H), 2.87 (q, J=7.6 Hz, 2H), 8.90 (s, 2H).

Step 43b: 2-Ethyl-5-(4,4,5,5-tetramethyl-1,3,2-dioxaborolan-2-yl)pyrimidine (Compound 0602-121)

The title compound, 0602-121 was prepared (crude 3.7 g) as a yellow oil from 0601-121 (1.7 g, 9.1 mmol), bis(pinacolato)diboron (3.5 g, 13.6 mmol), PdCl$_2$(dppf)$_2$ (222 mg, 0.27 mmol) and potassium acetate (2.7 g, 27 mmol) using a procedure similar to that described for compound 0602-107 (Example 34). LCMS: 235 [M+1]$^+$; $^1$H NMR (400 MHz, DMSO-d$_6$): 1.27 (t, J=7.6 Hz, 3H), 1.32 (s, 12H), 2.91 (q, J=7.6 Hz, 2H), 8.84 (s, 2H).

Step 43c: Ethyl 2-(((2-(2-ethylpyrimidin-5-yl)-4-morpholinothieno[3,2-d]pyrimidin-6-yl)methyl)(methyl)amino)pyrimidine-5-carboxylate (Compound 0603-121)

The title compound, 0603-121 was prepared (120 mg, 41%) as a yellow solid from 0504-54 (250 mg, 0.56 mmol), 0602-121 (3.7 g, crude), sodium hydrogen carbonate (168 mg, 2 mmol) and bis(triphenylphosphine)palladium(II) chloride (23 mg, 0.03 mmol) in toluene (8 mL), ethanol (5 mL) and water (2 mL) using a procedure similar to that described for compound 0603-107 (Example 30). LCMS: 521 [M+1]$^+$; $^1$H NMR (400 MHz, CDCl$_3$): δ 1.29-1.36 (m, 6H), 3.00 (q, J=8 Hz, 2H), 3.25 (s, 3H), 3.79 (t, J=4.4 Hz, 4H), 3.94 (t, J=4.4 Hz, 4H), 4.29 (q, J=7.2 Hz, 2H), 5.14 (s, 2H), 7.32 (s, 1H), 8.86 (s, 2H), 9.51 (s, 2H).

Step 43d: N-Hydroxy-2-(methyl((2-(2-methylpyrimidin-5-yl)-4-morpholinothieno[3,2-d]pyrimidin-6-yl)methyl)amino)pyrimidine-5-carboxamide (Compound 121)

The title compound 121 was prepared (66 mg, 56%) as a white solid from 0603-121 (120 mg, 0.23 mmol) and freshly prepared hydroxylamine methanol solution (8 mL) using a procedure similar to that described for compound 3 (Example 1). m.p. 153-156° C. LCMS: 508 [M+1]$^+$; $^1$H NMR (400 MHz, DMSO-d$_6$): δ 1.32 (t, J=7.2 Hz, 3H), 2.97 (q, J=7.2 Hz, 2H), 3.24 (s, 3H), 3.76 (t, J=4.4 Hz, 4H), 3.95 (t, J=4.4 Hz, 4H), 5.21 (s, 2H), 7.49 (s, 1H), 8.75 (s, 2H), 9.06 (s, 1H), 9.52 (s, 2H), 11.13 (s, 1H).

Example 44: Preparation of 2-(((2-(2-amino-4-methylpyrimidin-5-yl)-4-morpholinothieno[3,2-d]pyrimidin-6-yl)methyl)(methyl)amino)-N-hydroxy-pyrimidine-5-carboxamide (Compound 125)

Step 44a: 5-Bromo-4-methylpyrimidin-2-amine (Compound 0601-125)

A mixture of 2-amino-4-methylpyrimidine (4.0 g, 36.7 mmol), NBS (7.18 g, 40.3 mmol) in chloroform (100 mL) was stirred for 2 h at room temperature, then the solvent was removed in vacuum. Water (100 mL) was added and stirred for 30 min at room temperature, filtered. The solid was washed with water and dried to get compound 0601-125 (6.3 g, 91%) as a white solid. LCMS: 188 [M+1]$^+$, $^1$H NMR (400 MHz, DMSO-d$_6$) δ 2.32 (s, 3H), 6.79 (s, 2H), 8.21 (s, 1H).

Step 44b: 4-Methyl-5-(4,4,5,5-tetramethyl-1,3,2-dioxaborolan-2-yl)pyrimidin-2-amine (Compound 0602-125)

The title compound, 0602-125 was prepared (430 mg, 69%) as a grey solid from 0601-125 (500 mg, 2.66 mmol), bis(pinacolato)diboron (1.01 g, 4.0 mmol), PdCl$_2$(dppf)$_2$ (217.2 mg, 0.27 mmol), potassium acetate (783 mg, 7.98 mmol) using a procedure similar to that described for compound 0602-107 (Example 34). LCMS: 236 [M+1]$^+$, $^1$H NMR (400 MHz, DMSO-d$_6$) δ 1.27 (s, 12H), 2.37 (s, 3H), 6.89 (s, 2H), 8.30 (s, 1H).

Step 44c: Ethyl 2-(((2-(2-amino-4-methylpyrimidin-5-yl)-4-morpholinothieno[3,2-d]pyrimidin-6-yl)methyl)(methyl)amino)pyrimidine-5-carboxylate (Compound 0603-125)

The title compound, 0603-125 was prepared (160 mg, 55%) as a white solid from 0504-54 (376 mg, 0.84 mmol), 0602-125 (130 mg, 0.56 mmol), C$_8$F (256 mg, 1.68 mmol) and bis(triphenylphosphine)palladium(II) chloride (59 mg, 0.084 mmol) in 1,4-dioxane (5 mL) and water (1 mL) using a procedure similar to that described for compound 0603-107 (Example 30). LCMS: 522 [M+1]$^+$; $^1$H NMR (400 MHz, CDCl$_3$): δ 1.38 (d, J=7.2 Hz, 3H), 2.73 (s, 3H), 3.31 (s, 3H), 3.84 (m, 4H), 3.96 (m, 4H), 4.37 (q, J=7.2 Hz, 2H), 5.20 (s, 2H), 5.23 (s, 2H), 7.35 (s, 1H), 8.89 (s, 1H), 8.93 (s, 2H).

Step 44d: 2-(((2-(2-Amino-4-methylpyrimidin-5-yl)-4-morpholinothieno[3,2-d]pyrimidin-6-yl)methyl)(methyl)amino)-N-hydroxypyrimidine-5-carboxamide (Compound 125)

The title compound 125 was prepared (92 mg, 62%) as a white solid from 0603-125 (150 mg, 0.29 mmol) and freshly prepared hydroxylamine methanol solution (20 mL) using a procedure similar to that described for compound 3 (Example 1). m.p. 195-198° C. LCMS: 509 [M+1]$^+$; $^1$H NMR (400 MHz, DMSO-d$_6$) δ 2.62 (s, 3H), 3.23 (s, 3H), 3.74 (m, 4H), 3.86 (m, 4H), 5.20 (s, 2H), 6.86 (s, 2H), 7.42 (s, 1H), 8.77 (s, 2H), 8.81 (s, 1H), 9.10 (s, 1H), 11.21 (s, 1H).

Example 45: Preparation of N-hydroxy-2-(((2-(3-methoxyphenyl)-4-morpholinothieno[3,2-d]pyrimidin-6-yl)methyl)(methyl)amino)pyrimidine-5-carboxamide (Compound 130)

Step 45a: 2-(3-Methoxyphenyl)-4,4,5,5-tetramethyl-1,3,2-dioxaborolane (Compound 0602-130)

The title compound, 0602-130 was prepared (800 mg, 68%) as an oil from 1-bromo-methoxybenzene (930 mg, 5.0 mmol), bis(pinacolato)diboron (2.54 g, 10 mmol), potassium acetate (1.47 g, 15 mmol), and PdCl$_2$(dppf)$_2$ (204 mg, 0.25 mmol) using a procedure similar to that described for compound 0602-107 (Example 34). LCMS: 235 [M+1]$^+$. $^1$H NMR (400 MHz, DMSO-d$_6$) δ 1.34 (s, 12H), 3.83 (s, 3H), 7.0 (d, J=6.4 Hz, 2H), 7.29 (m, 2H), 7.41 (d, J=5.6 Hz, 1H).

Step 45b: Ethyl 2-(((2-(3-methoxyphenyl)-4-morpholinothieno[3,2-d]pyrimidin-6-yl)methyl)(methyl)amino)pyrimidine-5-carboxylate (Compound 0603-130)

The title compound, 0603-130 was prepared (120 mg, 51%) as a white solid from 0602-130 (126 mg, 0.54 mmol), 0504-54 (200 mg, 0.45 mmol), NaHCO$_3$ (114 mg, 1.35 mmol), and bis(triphenylphosphine)palladium(II) chloride (16 mg, 0.0225 mmol) in toluene (8 mL), ethanol (5 mL), and water (2 mL) using a procedure similar to that described for compound 0603-107 (Example 30). LCMS: 521 [M+1]$^+$; $^1$H NMR (400 MHz, DMSO-d$_6$): 1.30 (t, J=6.8 Hz, 3H), 3.27 (s, 3H), 3.76 (m, 4H), 3.83 (s, 3H), 3.92 (m, 4H), 3.94 (s, 2H), 4.29 (q, J=6.8 Hz, 2H), 5.23 (s, 2H), 7.06 (d, J=7.2 Hz 1H), 7.39 (t, J=10.4 Hz, 1H), 7.49 (s, 1H), 7.92 (s, 1H), 7.99 (d, J=8 Hz, 1H), 8.82 (s, 1H).

Step 45c: N-hydroxy-2-(((2-(3-methoxyphenyl)-4-morpholinothieno[3,2-d]pyrimidin-6-yl)methyl)(methyl)amino)pyrimidine-5-carboxamide (Compound 130)

The title compound 130 was prepared (15 mg, 15%) as a yellow solid from 0603-130 (110 mg, 0.2 mmol) and freshly prepared hydroxylamine methanol solution (20 mL) using a procedure similar to that described for compound 3 (Example 1). m.p. 179-181° C. LCMS: 508 [M+1]$^+$; $^1$H NMR (400 MHz, DMSO-d$_6$) δ 3.23 (s, 3H), 3.77 (m, 4H), 3.83 (s, 3H), 3.93 (m, 4H), 5.21 (s, 2H), 7.07 (d, J=9.2 Hz, 1H), 7.39 (t, J=10.4 Hz, 1H), 7.42 (s, 1H), 7.91 (s, 1H), 8.0 (d, J=16.4 Hz, 1H), 8.75 (s, 2H), 9.02 (br s, 1H), 11.14 (br s, 1H).

Example 46: Preparation of N-hydroxy-2-(((2-(3-hydroxyphenyl)-4-morpholinothieno[3,2-d]pyrimidin-6-yl)methyl)(methyl)amino)pyrimidine-5-carboxamide (Compound 132)

Step 46a: 3-(4,4,5,5-Tetramethyl-1,3,2-dioxaborolan-2-yl)phenol (Compound 0602-132)

The title compound, 0602-132 was prepared (600 mg, 68%) as an oil from 3-bromophenol (700 mg, 4.0 mmol), bis(pinacolato)diboron (1.5 g, 6 mmol), potassium acetate (1.2 g, 12 mmol), and PdCl$_2$(dppf)$_2$ (163 mg, 0.2 mmol) using a procedure similar to that described for compound 0602-107 (Example 34). LCMS: 221 [M+1]$^+$. 1H NMR (400 MHz, CDCl₃) δ 1.34 (s, 12H), 5.37 (s, 1H), 6.96 (d, J=4.0 Hz, 1H), 7.26 (m, 2H), 7.36 (d, J=7.2 Hz, 1H).

Step 46b: Ethyl 2-(((2-(3-hydroxyphenyl)-4-morpholinothieno[3,2-d]pyrimidin-6-yl)methyl)(methyl)amino)pyrimidine-5-carboxylate (Compound 0603-132)

The title compound, 0603-132 was prepared (160 mg, 47%) as a white solid from 0602-132 (300 mg, 0.67 mmol), 0504-54 (176 mg, 0.8 mmol), NaHCO₃ (172 mg, 2 mmol), and bis(triphenylphosphine)palladium(II) chloride (23 mg, 0.0335 mmol) in toluene (8 mL), ethanol (5 mL) and water (2 mL) using a procedure similar to that described for compound 0603-107 (Example 30). LCMS: 507 [M+1]⁺; ¹H NMR (400 MHz, DMSO-d₆): δ 1.30 (t, J=6.8 Hz, 3H), 3.27 (s, 3H), 3.76 (m, 4H), 3.92 (m, 4H), 4.29 (q, J=6.8 Hz, 2H), 5.24 (s, 2H), 6.84 (d, J=16.8 Hz, 2H), 7.24 (t, J=8 Hz, 1H), 7.48 (s, 1H), 7.83 (m, 2H), 8.88 (s, 2H), 9.49 (s, 1H).

Step 46c: N-hydroxy-2-(((2-(3-hydroxyphenyl)-4-morpholinothieno[3,2-d]pyrimidin-6-yl)methyl)(methyl)amino)pyrimidine-5-carboxamide (Compound 132)

The title compound 132 was prepared (53 mg, 34%) as a yellow solid from 0603-132 (160 mg, 0.32 mmol) and freshly prepared hydroxylamine methanol solution (20 mL) using a procedure similar to that described for compound 3 (Example 1). m.p. 175-181° C. LCMS: 494 [M+1]⁺; ¹H NMR (400 MHz, DMSO-d₆) δ 3.23 (s, 3H), 3.76 (m, 4H), 3.92 (m, 4H), 5.19 (s, 2H), 6.85 (d, J=10.4 Hz, 1H), 7.24 (t, J=6.8 Hz, 1H), 7.44 (s, 1H), 7.82 (m, 2H), 8.74 (s, 2H), 9.51 (br s, 1H).

Example 47: Preparation of 2-(((2-(3-aminophenyl)-4-morpholinothieno[3,2-d]pyrimidin-6-yl)methyl)(methyl)amino)-N-hydroxypyrimidine-5-carboxamide (Compound 134)

Step 47a: Ethyl-2-(((2-(3-aminophenyl)-4-morpholinothieno[3,2-d]pyrimidin-6-yl)methyl)(methyl)amino)pyrimidine-5-carboxylate (compound 0603-134)

To the solution of 0603-107 (170 mg, 0.31 mmol) in THF (10 mL) was added aqueous HCl solution (6M, 10 mL) at 50° C. and the mixture was stirred for 2 hours at this temperature. The reaction mixture was neutralized with saturated aqueous NaHCO₃ and extracted with ethyl acetate. The separated organic layer was washed with water, brine, dried over Na₂SO₄, filtered, and concentrated under reduced pressure to give the title compound 0603-134 (130 mg, 83%) as a white solid. LCMS: 506 [M+1]⁺. ¹H NMR (400 MHz, DMSO-d₆) δ 1.30 (t, J=7.6 Hz, 3H), 3.27 (s, 3H), 3.40 (s, 2H), 3.76 (t, J=5.2 Hz, 4H), 3.93 (t, J=4.8 Hz, 4H), 7.89 (q, J=7.6 Hz, 2H), 5.24 (s, 1H), 6.79 (d, J=7.6 Hz, 1H), 7.19 (t, J=8.0 Hz, 1H), 7.47 (s, 1H), 7.69 (d, J=8.0 Hz, 1H), 7.77 (s, 1H), 8.88 (s, 1H).

Step 47b: 2-(((2-(3-Aminophenyl)-4-morpholinothieno[3,2-d]pyrimidin-6-yl)methyl)(methyl)amino)-N-hydroxypyrimidine-5-carboxamide (Compound 134)

The title compound 134 was prepared (35 mg, 28%) as a white solid from 0603-134 (130 mg, 0.25 mmol) and freshly prepared hydroxylamine methanol solution (4 mL) using a procedure similar to that described for compound 3 (Example 1). m.p. 179-182° C. LCMS: 493 [M+1]⁺; ¹H NMR (400 MHz, DMSO-d₆): δ 3.24 (s, 3H), 3.77 (t, J=4.0 Hz, 4H), 3.96 (t, J=4.0 Hz, 4H), 5.22 (s, 2H), 6.98 (d, J=7.6 Hz, 1H), 7.32 (t, J=7.6 Hz, 1H), 7.47 (s, 1H), 7.86 (d, J=7.6 Hz, 1H), 7.91 (s, 1H), 8.76 (s, 2H), 9.07 (s, 1H), 11.15 (s, 1H).

Example 48: Preparation of 2-(((2-(4-(aminomethyl)phenyl)-4-morpholinothieno[3,2-d]pyrimidin-6-yl)methyl)(methyl)amino)-N-hydroxypyrimidine-5-carboxamide (Compound 135)

Step 48a: N-(4-bromobenzyl)acetamide (Compound 0601-135)

To the solution of 4-bromobenzylamine hydrochloride (1.2 g, 5.4 mmol) and Et₃N (5.5 g, 54 mmol) in dichloromethane (10 mL) was added CH₃COCl (555 mg, 7.02 mmol) at 0° C. and stirred for 2 hr at 30° C. Then the mixture was concentrated and the residue was dissolved in CH₂Cl₂ (30 mL), washed with water, dried over Na₂SO₄ and concentrated to obtain 0601-135 (1.3 g, 100%) as a yellow solid. LCMS: 228 [M+1]⁺, ¹H NMR (400 MHz, DMSO-d₆) δ 2.00 (s, 3H), 4.33 (d, J=6.4 Hz, 2H), 6.26 (s, 1H), 7.13 (d, J=8.4 Hz, 2H), 7.43 (d, J=8.4 Hz, 2H).

Step 48b: N-(4-(4,4,5,5-tetramethyl-1,3,2-dioxaborolan-2-yl)benzyl)acetamide (Compound 0602-135)

The title compound, 0602-135 was prepared (825 mg, 60%) as a yellow solid from 0601-135 (1.2 g, 5 mmol), bis(pinacolato)diboron (1.9 g, 7.5 mmol), potassium acetate (1.47 g, 15 mmol), and Pd(dppf)₂Cl₂ (410 mg, 0.5 mmol) using a procedure similar to that described for compound 0602-107 (Example 34). LCMS: 276 [M+1]⁺, ¹H NMR (400 MHz, DMSO-d₆) δ 1.27 (s, 12H), 1.87 (s, 3H), 4.26 (d, J=6.0 Hz, 2H), 7.25 (d, J=8.0 Hz, 2H), 7.62 (d, J=8.0 Hz, 2H), 8.36 (t, J=5.6 Hz, 1H).

Step 48c: Methyl 2-(((2-(4-(aminomethyl)phenyl)-4-morpholinothieno[3,2-d]pyrimidin-6-yl)methyl)(methyl)amino)pyrimidine-5-carboxylate (Compound 0603-135)

A mixture of compound 0602-135 (200 mg, 0.73 mmol), 0504-54 (261 mg, 0.58 mmol), NaHCO₃ (184 mg, 2.2 mmol) and bis(triphenylphosphine)palladium(II) chloride (52 mg, 0.073 mmol) in toluene (4 mL), ethanol (2 mL) and water (0.5 mL) was flushed with nitrogen and heated under microwave irradiation at 130° C. for 2 h. The reaction mixture was partitioned between dichloromethane and water, organic layer was washed with brine, dried over Na₂SO₄, filtered and evaporated in vacuum. The resulting residue was purified by column chromatography (methanol in dichloromethane, 2-5% v/v) to give ethyl 2-(((2-(4-(acetamidomethyl)phenyl)-4-morpholinothieno[3,2-d]pyrimidin-6-yl)methyl)(methyl)amino)pyrimidine-5-carboxylate (300 mg, 92%) as a white solid. LCMS: 562 [M+1]⁺; ¹H NMR (400 MHz, DMSO-d₆): δ 1.36 (m, 3H), 1.96 (s, 3H), 3.33 (s, 3H), 3.83 (m, 4H), 3.94 (m, 4H), 4.36 (m, 4H), 5.29 (s, 2H), 7.41 (d, J=7.6 Hz, 2H), 7.54 (s, 1H), 8.39 (d, J=8.0 Hz, 2H), 8.47 (m, 1H), 8.94 (s, 2H).

The above ethyl ester (250 mg, 0.45 mmol) was dissolved in THF (8 mL), then aqueous HCl solution (6M, 12 mL) was added and stirred for 12 hr at 85° C. Then the mixture was adjusted pH 4 with NaOH at 0° C., filtered and washed with CH$_2$Cl$_2$ to get 2-(((2-(4-(aminomethyl)phenyl)-4-morpholinothieno[3,2-d]pyrimidin-6-yl)methyl)(methyl)amino)pyrimidine-5-carboxylic acid (200 mg, 91%) as a white solid. The solid was directly used in next step without further purification. LC-MS: 492 [M+1]$^+$.

The above acid (230 mg, 0.47 mmol) was dissolved in MeOH (10 mL). SOCl$_2$ (5 mL) was added to above solution at 0° C. and stirred for 1.5 hr at reflux. Then the mixture was concentrated, added water, adjusted to pH8 with saturated aqueous NaHCO$_3$ solution, extracted with CH$_2$Cl$_2$ and evaporated in vacuum to get compound 0603-135 (210 mg, 88%) as a yellow solid. LC-MS: 506 [M+1]$^+$. $^1$H NMR (400 MHz, DMSO-d$_6$) δ 3.28 (s, 3H), 3.83 (m, 9H), 3.97 (m, 4H), 5.20 (m, 2H), 7.38 (m, 3H), 8.34 (m, 2H), 8.86 (m, 2H).

Step 48d: 2-(((2-(4-(aminomethyl)phenyl)-4-morpholinothieno[3,2-d]pyrimidin-6-yl)methyl)(methyl)amino)-N-hydroxypyrimidine-5-carboxamide (Compound 135)

The title compound 135 was prepared (60 mg, 30%) as a light yellow solid from 0603-135 (200 mg, 0.40 mmol) and freshly prepared hydroxylamine methanol solution (20 mL) using a procedure similar to that described for compound 3 (Example 1). m.p. 184-186° C. LCMS: 507 [M+1]$^+$; $^1$H NMR (400 MHz, DMSO-d$_6$) δ 3.23 (s, 3H), 3.76 (m, 4H), 3.93 (m, 6H), 5.20 (s, 2H), 7.45 (s, 1H), 7.49 (d, J=8.4 Hz, 2H), 8.36 (d, J=8.0 Hz, 2H), 8.75 (s, 2H).

Example 49: Preparation of 2-(((2-(3-(aminomethyl)phenyl)-4-morpholinothieno[3,2-d]pyrimidin-6-yl)methyl)(methyl)amino)-N-hydroxypyrimidine-5-carboxamide (Compound 137)

Step 49a: N-(3-bromobenzyl)acetamide (Compound 0601-137)

To the solution of 3-bromobenzylamine hydrochloride (1.2 g, 5.4 mmol) and Et$_3$N (5.5 g, 54 mmol) in CH$_2$Cl$_2$ (10 mL) was added CH$_3$COCl (555 mg, 7.02 mmol) at 0° C. and stirred for 2 hr at 30° C. Then the mixture was concentrated and the residue was dissolved in CH$_2$Cl$_2$, washed with water, dried over Na$_2$SO$_4$, and concentrated to obtain 0601-137 (1.2 g, 98%) as a yellow solid. LCMS: 228 [M+1]$^+$. $^1$H NMR (400 MHz, DMSO-d$_6$) δ 1.88 (s, 3H), 4.25 (d, J=6.0 Hz, 2H), 7.28 (m, 2H), 7.43 (m, 2H), 8.39 (s, 1H).

Step 49b: N-(3-(4,4,5,5-tetramethyl-1,3,2-dioxaborolan-2-yl)benzyl)acetamide (Compound 0602-137)

The title compound, 0602-137 was prepared (1.0 g, 72%) as a yellow solid from 0601-137 (1.2 g, 5 mmol), bis(pinacolato)diboron (1.9 g, 7.5 mmol), potassium acetate (1.47 g, 15 mmol), and Pd(dppf)$_2$Cl$_2$ (410 mg, 0.5 mmol) using a procedure similar to that described for compound 0602-107 (Example 34). LCMS: 276 [M+1]$^+$, $^1$H NMR (400 MHz, DMSO-d$_6$) δ 1.28 (s, 12H), 1.85 (s, 3H), 4.23 (d, J=6.0 Hz, 2H), 7.33 (m, 2H), 7.54 (d, J=7.2 Hz, 1H), 7.57 (s, 1H), 8.35 (t, J=5.6 Hz, 1H).

Step 49c: Methyl 2-(((2-(3-(aminomethyl)phenyl)-4-morpholinothieno[3,2-d]pyrimidin-6-yl) methyl)(methyl)amino)pyrimidine-5-carboxylate (Compound 0603-137)

A mixture of 0602-137 (400 mg, 1.46 mmol), 0504-54 (522 mg, 1.16 mmol), NaHCO$_3$ (368 mg, 4.4 mmol), and bis(triphenylphosphine)palladium(II) chloride (104 mg, 0.146 mmol) in toluene (4 mL), ethanol (2 mL) and water (0.5 mL) was flushed with nitrogen and heated under microwave irradiation at 130° C. for 2 h. The reaction mixture was partitioned between dichloromethane and water, organic layer was washed with brine, dried over Na$_2$SO$_4$, filtered and evaporated in vacuum. The resulting residue was purified by column chromatography (methanol in dichloromethane, 2-5% v/v) to give ethyl 2-(((2-(3-(acetamidomethyl)phenyl)-4-morpholinothieno[3,2-d]pyrimidin-6-yl)methyl)(methyl)amino)pyrimidine-5-carbo-xylate (580 mg, 89%) as a white solid. LCMS: 562 [M+1]$^+$; $^1$H NMR (400 MHz, DMSO-d$_6$): δ 1.28 (m, 3H), 1.88 (s, 3H), 3.27 (s, 3H), 3.76 (m, 4H), 3.92 (m, 4H), 4.27 (m, 4H), 5.23 (s, 2H), 7.38 (m, 2H), 7.49 (m, 1H), 8.30 (m, 2H), 8.43 (m, 1H), 8.87 (s, 2H).

The above ethyl ester (300 mg, 0.53 mmol) was dissolved in THF (8 mL), then aqueous HCl solution (6M, 12 mL) was added and stirred for 12 hr at 85° C. Then the above mixture was adjusted pH 4 with NaOH at 0° C., filtered and washed by CH$_2$Cl$_2$ to get 2-(((2-(3-(Aminomethyl)phenyl)-4-morpholinothieno[3,2-d]pyrimidin-6-yl) methyl)(methyl)amino)pyrimidine-5-carboxylic acid (245 mg, 93%) as a white solid. LC-MS: 492 [M+1]$^+$.

The acid (300 mg, 0.61 mmol) was dissolved in MeOH (10 mL). SOCl$_2$ (5 mL) was added to above solution at 0° C. and stirred for 1.5 hr at reflux. Then the mixture was concentrated, added water, adjusted PH 8 with NaHCO$_3$, extracted with CH$_2$Cl$_2$ and evaporated in vacuum to get compound 0603-137 (260 mg, 84%) as a yellow solid. LC-MS: 506 [M+1]$^+$. $^1$H NMR (400 MHz, DMSO-d$_6$) δ 3.27 (s, 3H), 3.76 (m, 4H), 3.82 (s, 3H), 3.95 (m, 6H), 5.24 (s, 2H), 7.45 (m, 3H), 8.31 (m, 1H), 8.41 (s, 1H), 8.88 (m, 2H).

Step 49d: 2-(((2-(3-(aminomethyl)phenyl)-4-morpholinothieno[3,2-d]pyrimidin-6-yl)methyl)(methyl)amino)-N-hydroxypyrimidine-5-carboxamide (Compound 137)

The title compound 137 was prepared (46 mg, 18%) as a light yellow solid from 0603-137 (250 mg, 0.5 mmol) and freshly prepared hydroxylamine methanol solution (20 mL) using a procedure similar to that described for compound 3 (Example 1). m.p. 173-176° C. LCMS: 507 [M+1]$^+$; $^1$H NMR (400 MHz, DMSO-d$_6$) δ 3.23 (s, 3H), 3.76 (m, 4H), 3.94 (m, 4H), 3.99 (s, 2H), 5.20 (s, 2H), 7.45 (s, 1H), 7.50 (m, 2H), 8.32 (m, 1H), 8.38 (s, 2H), 8.43 (s, 1H), 8.75 (s, 2H).

Example 50: preparation of N-hydroxy-2-(((2-(3-(hydroxymethyl)phenyl)-4-morpholinothieno[3,2-d]pyrimidin-6-yl)methyl)(methyl)amino)pyrimidine-5-carboxamide (Compound 138)

Step 50a: (3-(4,4,5,5-Tetramethyl-1,3,2-dioxaborolan-2-yl)phenyl)methanol (Compound 0602-138)

The title compound, 0602-138 was prepared (300 mg, 43%) as a yellow oil from m-bromobenzyl alcohol (0.56 g, 3 mmol), bis(pinacolato)diboron (1.14 g, 4.5 mmol), potassium acetate (1.32 g, 9 mmol), and Pd(dppf)$_2$Cl$_2$ (490 mg, 0.6 mmol) using a procedure similar to that described for compound 0602-107 (Example 34). LCMS: 252 [M+18]$^+$; $^1$HNMR (400 MHz, CDCl$_3$) δ 1.35 (s, 12H), 1.66 (s, 1H), 4.70 (s, 2H), 7.38 (t, J=7.2 Hz, 1H), 7.49 (d, J=7.6 Hz, 1H), 7.74 (d, J=7.2 Hz, 1H), 7.80 (s, 1H).

Step 50b: Ethyl 2-(((2-(3-(hydroxymethyl)phenyl)-4-morpholinothieno[3,2-d]pyrimidin-6-yl)methyl)(methyl)amino)pyrimidine-5-carboxylate (0603-138)

The title compound, 0603-138 was prepared (140 mg, 90%) as a white solid from 0504-54 (135 mg, 0.30 mmol), 0602-138 (105 mg, 0.45 mmol), NaHCO$_3$ (76 mg, 0.90 mmol), and Pd(dppf)$_2$Cl$_2$ (11 mg, 0.015 mmol) in toluene (2.5 mL), ethanol (1.6 mL), and water (0.7 mL) using a procedure similar to that described for compound 0603-107 (Example 30). LCMS: 521 [M+1]$^+$; $^1$HNMR (400 MHz, DMSO-d$_6$) δ 1.30 (t, J=7.2 Hz, 3H), 3.27 (s, 3H), 3.77 (m, 4H), 3.93 (q, J=7.2 Hz, 2H), 4.59 (d, J=6.0 Hz, 2H), 5.24 (s, 2H), 5.29 (t, J=5.6 Hz, 1H), 7.43 (m, 2H), 7.50 (s, 1H), 8.26 (m, 1H), 8.37 (s, 1H), 8.88 (s, 2H).

Step 50c: N-hydroxy-2-(((2-(3-(hydroxymethyl)phenyl)-4-morpholinothieno[3,2-d]pyrimidin-6-yl)methyl)(methyl)amino)pyrimidine-5-carboxamide (Compound 138)

The title compound 138 was prepared (30 mg, 44%) as a light yellow solid from 0603-138 (70 mg, 0.13 mmol) and freshly prepared hydroxylamine methanol solution (10 mL) using a procedure similar to that described for compound 3 (Example 1). mp 160-164° C. LCMS: 508 [M+1]$^+$; $^1$HNMR (400 MHz, DMSO-d$_6$) δ 3.24 (s, 3H), 3.77 (s, 4H), 3.94 (s, 2H), 4.59 (d, J=5.6 Hz, 2H), 5.21 (s, 2H), 5.28 (t, J=5.6 Hz, 1H), 7.44 (m, 3H), 8.27 (m, 1H), 8.37 (s, 1H), 8.75 (s, 2H), 9.07 (s, 1H).

Example 51: Preparation of N-hydroxy-2-(((2-(3-(methoxymethyl)phenyl)-4-morpholinothieno[3,2-d]pyrimidin-6-yl)methyl)(methyl)amino)pyrimidine-5-carboxamide (Compound 139)

Step 51a: 1-Bromo-3-(methoxymethyl)benzene (Compound 0601-139)

To a solution of m-bromobenzyl alcohol (1.0 g, 5.3 mmol) in THF (10 mL) was added NaH (0.26 g, 10.6 mmol) at 0° C., stirred for 10 minutes, followed by addition of iodomethane (1.1 g, 7.9 mmol). The resulting reaction mixture was stirred for 1 hour. To the mixture ethyl acetate (30 mL) was added, washed with water, brine, dried over Na$_2$SO$_4$, filtered, and concentrated under reduced pressure to give the title compound 0601-139 (1.0 g, 93%) as an oil. $^1$H NMR (400 MHz, DMSO-d$_6$) δ 3.30 (s, 3H), 4.41 (s, 2H), 7.29 (t, J=8.0 Hz, 1H), 7.40 (t, J=7.6 Hz, 1H), 7.47 (d, J=8.0 Hz, 1H), 7.64 (d, J=8.0 Hz, 1H).

Step 51b: 2-(3-(methoxymethyl)phenyl)-4,4,5,5-tetramethyl-1,3,2-dioxaborolane (Compound 0602-139)

The title compound, 0602-139 was prepared (1.2 g, 97%) as an oil from 0601-139 (1.1 g, 5.4 mmol), bis(pinacolato)diboron (2.1 g, 8.1 mmol), potassium acetate (1.6 g, 16.3 mmol), and PdCl$_2$(dppf)$_2$ (45 mg, 0.05 mmol) using a procedure similar to that described for compound 0602-107 (Example 34). $^1$H NMR (400 MHz, DMSO-d$_6$) δ 1.28 (s, 12H), 3.28 (s, 3H), 4.40 (s, 2H), 7.35 (t, J=7.2 Hz, 1H), 7.42 (d, J=7.2 Hz, 1H), 7.58 (d, J=7.2 Hz, 1H), 7.63 (s, 1H).

Step 51c: Ethyl-2-(((2-(3-(methoxymethyl)phenyl)-4-morpholinothieno[3,2-d]pyrimidin-6-yl)methyl)(methyl)amino)pyrimidine-5-carboxylate (Compound 0603-139)

The title compound, 0603-139 was prepared (180 mg, 71%) as a white solid from 0504-54 (210 mg, 0.46 mmol), 0602-139 (174 mg, 0.7 mmol), sodium hydrogen carbonate (118 mg, 1.4 mmol), and bis(triphenylphosphine)palladium (II) chloride (16 mg, 0.02 mmol) in toluene (8 mL), ethanol (2 mL), and water (1 mL) using a procedure similar to that described for compound 0603-107 (Example 30). LCMS: 535 [M+1]$^+$; $^1$H NMR (400 MHz, DMSO-d$_6$): δ 1.30 (t, J=7.2 Hz, 3H), 3.27 (s, 3H), 3.33 (s, 3H), 3.76 (m, 4H), 3.93 (m, 4H), 4.28 (q, J=7.2 Hz, 2H), 4.50 (s, 2H), 5.23 (s, 2H), 7.45 (q, J=7.2 Hz, 1H), 7.49 (s, 1H), 8.31 (d, J=7.6 Hz, 1H), 8.34 (s, 1H), 8.87 (m, 2H).

Step 51d: N-hydroxy-2-(((2-(3-(methoxymethyl)phenyl)-4-morpholinothieno[3,2-d]pyrimidin-6-yl)methyl)(methyl)amino)pyrimidine-5-carboxamide (Compound 139)

The title compound 139 was prepared (56 mg, 47%) as an orange solid from 0603-139 (120 mg, 0.22 mmol) and freshly prepared hydroxylamine methanol solution (8 mL) using a procedure similar to that described for compound 3 (Example 1). m.p. 178-181° C. LCMS: 522 [M+1]$^+$; $^1$H NMR (400 MHz, DMSO-d$_6$): δ 3.24 (s, 3H), 3.33 (s, 3H), 3.77 (m, 4H), 3.93 (m, 4H), 4.51 (s, 2H), 5.21 (s, 2H), 7.43 (q, J=7.6 Hz, 2H), 7.47 (s, 1H), 8.31 (d, J=7.2 Hz, 1H), 8.34 (s, 1H), 8.75 (s, 2H), 9.05 (s, 1H), 11.12 (s, 1H).

Example 52: Preparation of N-hydroxy-2-(((2-(4-(hydroxymethyl)phenyl)-4-morpholinothieno[3,2-d]pyrimidin-6-yl)methyl)(methyl)amino)pyrimidine-5-carboxamide (Compound 140)

Step 52a: (4-(4,4,5,5-Tetramethyl-1,3,2-dioxaborolan-2-yl)phenyl)methanol (compound 0602-140)

The title compound, 0602-140 was prepared (670 mg, 94%) as an oil from (4-bromophenyl)methanol (0.56 g, 3 mmol), bis(pinacolato)diboron (1.14 g, 4.5 mmol), potassium acetate (1.32 g, 9 mmol), and PdCl$_2$(dppf)$_2$ (490 mg, 0.6 mmol) using a procedure similar to that described for compound 0602-107 (Example 34). LCMS: 217 [M-OH]$^+$; $^1$HNMR (400 MHz, DMSO-d$_6$) δ 1.28 (s, 12H), 4.51 (d, J=5.6 Hz, 2H), 5.23 (t, J=6.0 Hz, 1H), 7.32 (d, J=8.0 Hz, 2H), 7.62 (d, J=7.6 Hz, 2H).

Step 52b: Ethyl 2-(((2-(4-(hydroxymethyl)phenyl)-4-morpholinothieno[3,2-d]pyrimidin-6-yl)methyl)(methyl)amino)pyrimidine-5-carboxylate (compound 0603-140)

The title compound, 0603-140 was prepared (120 mg, 77%) as a white solid from 0504-54 (135 mg, 0.30 mmol), 0602-140 (105 mg, 0.45 mmol), NaHCO$_3$ (76 mg, 0.90 mmol), and (PPh$_3$)PdCl$_2$ (11 mg, 0.015 mmol) in toluene (2.5 mL), ethanol (1.6 mL), and water (0.7 mL) using a procedure similar to that described for compound 0603-107 (Example 30). LCMS: 521 [M+1]$^+$; $^1$HNMR (400 MHz, DMSO-d$_6$) δ 1.28 (t, J=7.2 Hz, 3H), 3.25 (s, 3H), 3.74 (t, J=4.4 Hz, 4H), 3.90 (t, J=7.2 Hz, 4H), 4.26 (q, J=7.2 Hz, 2H), 4.56 (d, J=6.4 Hz, 2H), 5.21 (s, 2H), 5.26 (t, J=5.6 Hz, 1H), 7.41 (d, J=8.0 Hz, 2H), 7.46 (s, 1H), 8.34 (d, J=8.8 Hz, 2H), 8.85 (s, 2H).

Step 52c: N-Hydroxy-2-(((2-(4-(hydroxymethyl)phenyl)-4-morpholinothieno[3,2-d]pyrimidin-6-yl)methyl)(methyl)amino)pyrimidine-5-carboxamide (compound 140)

The title compound 140 was prepared (61 mg, 63%) as a yellow solid from 0603-140 (100 mg, 0.19 mmol) and freshly prepared hydroxylamine methanol solution (10 mL) using a procedure similar to that described for compound 3 (Example 1). m.p. 218-223° C. LCMS: 508 [M+1]$^+$; $^1$HNMR (400 MHz, DMSO-d$_6$) δ 3.23 (s, 3H), 3.76 (d, J=4.4 Hz, 4H), 3.91 (d, J=4.0 Hz, 4H), 4.56 (d, J=4.8 Hz, 2H), 5.19 (s, 2H), 5.27 (t, J=5.6 Hz, 1H), 7.42 (t, J=8.8 Hz, 3H), 8.34 (d, J=8.0 Hz, 2H), 8.74 (s, 2H), 9.08 (s, 1H), 11.13 (s, 1H).

Example 53: Preparation of N-hydroxy-2-(((2-(2-(hydroxymethyl)phenyl)-4-morpholinothieno[3,2-d]pyrimidin-6-yl)methyl)(methyl)amino)pyrimidine-5-carboxamide (Compound 141)

Step 53a: 2-Bromobenzyl acetate (Compound 0601-141)

To a solution of o-bromobenzyl alcohol (2.0 g, 10.7 mmol) in CH$_2$Cl$_2$ (20 mL) was added acetyl chloride (1.1 g, 13.9 mmol) and TEA (2.16 g, 21.4 mmol) at 0° C., then stirred for 2 hours. The reaction mixture was washed with water, brine, dried over Na$_2$SO$_4$, filtered, and concentrated under reduced pressure to give the title compound 0601-141 (2.4 g, 97%) as a yellow solid. $^1$H NMR (400 MHz, DMSO-d$_6$) δ 2.09 (s, 3H), 5.10 (s, 2H), 7.29 (t, J=8.0 Hz, 1H), 7.40 (t, J=7.6 Hz, 1H), 7.47 (d, J=8.0 Hz, 1H), 7.64 (d, J=8.0 Hz, 1H).

Step 53b: 2-(4,4,5,5-tetramethyl-1,3,2-dioxaborolan-2-yl)benzyl acetate (Compound 0602-141)

The title compound, 0602-141 was prepared (2.3 g, 80%) as an oil from 0601-141 (2.4 g, 10.5 mmol), bis(pinacolato)diboron (4.1 g, 16.3 mmol), potassium acetate (3.2 g, 32.7 mmol), and PdCl$_2$(dppf)$_2$ (89 mg, 0.11 mmol) using a procedure similar to that described for compound 0602-107 (Example 34). LCMS: 277 [M+1]$^+$. $^1$H NMR (400 MHz, DMSO-d$_6$) δ 1.28 (s, 12H), 2.03 (s, 3H), 5.23 (s, 2H), 7.34 (t, J=7.2 Hz, 1H), 7.37 (d, J=7.2 Hz, 1H), 7.89 (t, J=7.6 Hz, 1H), 7.70 (d, J=7.2 Hz, 1H).

Step 53c: Ethyl 2-(((2-(2-(hydroxymethyl)phenyl)-4-morpholinothieno[3,2-d]pyrimidin-6-yl)methyl)(methyl)amino)pyrimidine-5-carboxylate (Compound 0603-141)

The title compound, 0603-141 was prepared (80 mg, 17%) as a white solid from 0504-54 (420 mg, 0.92 mmol), 0602-141 (386 mg, 1.4 mmol), sodium hydrogen carbonate (236 mg, 2.8 mmol), and bis(triphenylphosphine)palladium (II) chloride (32 mg, 0.04 mmol) in toluene (8 mL), ethanol (4 mL), and water (2 mL) using a procedure similar to that described for compound 0603-107 (Example 30). LCMS: 521 [M+1]$^+$; $^1$H NMR (400 MHz, DMSO-d$_6$): δ 1.29 (t, J=7.2 Hz, 3H), 3.26 (s, 3H), 3.74 (m, 4H), 3.88 (m, 4H), 4.28 (q, J=6.8 Hz, 2H), 4.75 (d, J=6.0 Hz, 2H), 5.24 (s, 2H), 5.44 (t, J=6.0 Hz, 1H), 7.35 (t, J=7.2 Hz, 1H), 7.44 (t, J=7.6 Hz, 1H), 7.45 (s, 1H), 7.62 (m, 1H), 7.92 (d, J=6.8 Hz, 1H), 8.87 (s, 1H).

Step 53d: N-hydroxy-2-(((2-(2-(hydroxymethyl)phenyl)-4-morpholinothieno[3,2-d]pyrimidin-6-yl)methyl)(methyl)amino)pyrimidine-5-carboxamide (Compound 141)

The title compound 141 was prepared (58 mg, 37%) as a yellow solid from 0603-141 (160 mg, 0.3 mmol) and freshly prepared hydroxylamine methanol solution (4 mL) using a procedure similar to that described for compound 3 (Example 1). m.p. 173-176° C. LCMS: 508 [M+1]$^+$; $^1$H NMR (400 MHz, DMSO-d$_6$): δ 3.23 (s, 3H), 3.73 (m, 4H), 3.88 (m, 4H), 4.75 (d, J=6.0 Hz, 2H), 5.20 (s, 2H), 5.45 (t, J=6.0 Hz, 1H), 7.35 (t, J=6.8 Hz, 1H), 7.42 (d, J=7.6 Hz, 1H), 7.46 (s, 1H), 7.61 (d, J=7.6 Hz, 1H), 7.92 (d, J=7.6 Hz, 1H), 8.74 (s, 2H), 9.05 (s, 1H), 11.12 (s, 1H).

Example 54: Preparation of 2-(((2-(3-carbamoylphenyl)-4-morpholinothieno[3,2-d]pyrimidin-6-yl)methyl)(methyl)amino)-N-hydroxypyrimidine-5-carboxamide (Compound 142)

Step 54a: 3-Bromobenzamide (Compound 0601-142)

To a solution of m-bromobenzonitrile (2 g, 10 mol) in DMSO (6 mL) was added 30% H$_2$O$_2$ (5 g, 13 mmol) and K$_2$CO$_3$ at 0° C., and stirred at room temperature for 30 min. The mixture was poured into water and filtered, the solid was washed with water, dried to got the compound 0601-142 (1.8 g, 82%) as a white solid. LCMS: 200 [M+1]$^+$; $^1$H NMR (400 MHz, DMSO-d$_6$) δ 7.41 (t, J=8.0 Hz, 1H), 7.50 (s, 1H), 7.70 (dd, J$_{1,2}$=8.0, 0.8 Hz, 1H), 7.85 (d, J=8.0 Hz, 1H), 8.03 (t, J=1.6 Hz, 1H), 8.06 (s, 1H).

Step 54b: 3-(4,4,5,5-Tetramethyl-1,3,2-dioxaborolan-2-yl)benzamide (Compound 0602-142)

The title compound, 0602-142 was prepared (450 mg, 73%) as a solid from 0601-142 (500 mg, 2.5 mmol), bis(pinacolato)diboron (952 mg, 3.75 mmol), potassium acetate (735 mg, 7.5 mmol), and PdCl$_2$(dppf)$_2$ (61 mg, 0.075 mmol) using a procedure similar to that described for compound 0602-107 (Example 34). LCMS: 248 [M+1]$^+$; $^1$H NMR (400 MHz, DMSO-d$_6$) δ 1.31 (s, 12H), 7.34 (s, 1H), 7.46 (t, J=7.2 Hz, 1H), 7.79 (d, J=7.2 Hz, 1H), 7.98 (m, 1H), 8.04 (s, 1H), 8.19 (s, 1H).

Step 54c: Ethyl 2-(((2-(3-carbamoylphenyl)-4-morpholinothieno[3,2-d]pyrimidin-6-yl)methyl)(methyl)amino)pyrimidine-5-carboxylate (Compound 0603-142)

The title compound, 0603-142 was prepared (180 mg, 50%) as a yellow solid from 0504-54 (305 mg, 0.68 mmol), 0602-142 (200 mg, 0.81 mmol), Pd(PPh$_3$)$_2$Cl$_2$ (21 mg, 0.03 mmol), and NaHCO$_3$ (171 mg, 2.04 mmol) in toluene (5 mL), ethanol (3 ml), and water (1.3 ml) using a procedure similar to that described for compound 0603-107 (Example 30). LCMS: 534 [M+1]$^+$. $^1$H NMR (400 MHz, CDCl$_3$) δ 1.38 (t, J 7.6 Hz, 3H), 3.32 (s, 3H), 3.87 (t, J 4.6 Hz, 4H), 4.03 (t, J 4.8 Hz, 4H), 4.37 (q, J 7.6 Hz, 2H), 5.20 (s, 2H), 5.77 (br, 1H), 6.37 (br, 1H), 7.39 (s, 1H), 7.55 (t, J=7.8 Hz, 1H), 7.96 (d, J 7.6 Hz, 4H), 8.59 (d, J 7.6 Hz, 1H), 8.84 (s, 1H), 8.93 (s, 2H).

Step 54d: 2-(((2-(3-carbamoylphenyl)-4-morpholinothieno[3,2-d]pyrimidin-6-yl)methyl)(methyl)amino)-N-hydroxypyrimidine-5-carboxamide (Compound 142)

The title compound 142 was prepared (65 mg, 44%) as a yellow solid from 0603-142 (150 mg, 0.28 mmol) and freshly prepared hydroxylamine methanol solution (8 mL) using a procedure similar to that described for compound 3 (Example 1). LCMS: 521 [M+1]+; $^1$H NMR (400 MHz, DMSO-d$_6$) δ 3.25 (s, 3H), 2.77-3.79 (m, 4H), 3.95-3.97 (m, 4H), 5.22 (s, 2H), 7.44 (s, 1H), 7.50 (s, 1H), 7.56 (t, J 7.6 Hz, 1H), 7.97 (d, J 8.0 Hz, 1H), 8.13 (s, 1H), 8.52 (d, J=7.6 Hz, 1H), 8.76 (s, 2H), 8.96 (s, 1H), 9.03 (br, 1H), 10.93 (br, 1H).

Example 55: Preparation of N-hydroxy-2-(methyl((2-(3-(methylcarbamoyl)phenyl)-4-morpholinothieno[3,2-d]pyrimidin-6-yl)methyl)amino)pyrimidine-5-carboxamide (Compound 144)

Step 55a: 3-Bromo-N-methylbenzamide (Compound 0601-144)

A suspension of MeNH$_2$.HCl (1.85 g, 27 mmol) and Et$_3$N (4.6 g, 45 mmol) in anhydrous CH$_2$Cl$_2$ (50 mL) was cooled to 0° C. and treated with m-bromobenzoyl chloride (2 g, 9 mmol). The mixture was warmed to room temperature and stirred for 4 h. To the reaction mixture was added ethyl acetate, washed with water, brine, and dried over Na$_2$SO$_4$, concentrated to give compound 0601-144 (1.9 g, 97%) as a white solid. LCMS: 214 [M+1]+; $^1$H NMR (400 MHz, DMSO-d$_6$) δ 2.78 (d, J=4.4 Hz, 3H), 7.43 (t, J=7.6 Hz, 1H), 7.72 (d, J=8.8 Hz, 1H), 7.83 (d, J=7.6 Hz, 1H), 8.00 (s, 1H), 8.57 (s, 1H).

Step 55b: N-methyl-3-(4,4,5,5-tetramethyl-1,3,2-dioxaborolan-2-yl)benzamide (Compound 0602-144)

The title compound, 0602-144 was prepared (480 mg, 82%) as a white solid from 0601-144 (500 mg, 2.3 mmol), bis(pinacolato)diboron (890 mg, 3.5 mmol), potassium acetate (687 mg, 7 mmol), and PdCl$_2$(dppf)$_2$ (57.2 mg, 0.07 mmol) using a procedure similar to that described for compound 0602-107 (Example 34). LCMS: 262 [M+1]+; $^1$H NMR (400 MHz, DMSO-d$_6$) δ 1.21 (s, 12H), 2.77 (d, J=4.8 Hz, 3H), 7.47 (t, J=7.6 Hz, 1H), 7.79 (d, J=7.6 Hz, 1H), 7.94 (d, J=8.0 Hz, 1H), 8.14 (s, 1H), 8.51 (m, 1H).

Step 55c: Ethyl 2-(methyl((2-(3-(methylcarbamoyl)phenyl)-4-morpholinothieno[3,2-d]pyrimidin-6-yl)methyl)amino)pyrimidine-5-carboxylate (Compound 0603-144)

The title compound, 0603-144 was prepared (250 mg, 68%) as a yellow solid from 0504-54 (300 mg, 0.67 mmol), compound 0602-144 (349 mg, 1.34 mmol), NaHCO$_3$ (168 mg, 2.0 mmol), (Ph$_3$P)$_2$PdCl$_2$ (23 mg, 0.03 mmol) in toluene (5 mL), ethanol (3 mL) and water (1.3 mL) using a procedure similar to that described for compound 0603-107 (Example 30). LCMS: 548 [M+1]+. $^1$H NMR (400 MHz, DMSO-d$_6$) δ 1.30 (t, J=6.8 Hz, 3H), 2.82 (d, J=4.8 Hz, 3H), 3.28 (s, 3H), 3.77 (m, 4H), 3.95 (m, 4H), 4.28 (q, J=6.8 Hz, 2H), 5.24 (s, 2H), 7.52 (s, 1H), 7.56 (t, J=8.0 Hz, 1H), 7.91 (d, J=8.0 Hz, 1H), 8.51 (d, J=8.0 Hz, 1H), 8.56 (m, 1H), 8.82 (s, 1H), 8.88 (s, 1H).

Step 55d: N-hydroxy-2-(methyl((2-(3-(methylcarbamoyl)phenyl)-4-morpholinothieno[3,2-d]pyrimidin-6-yl)methyl)amino)pyrimidine-5-carboxamide (Compound 144)

The title compound 144 was prepared (116 mg, 48%) as a yellow solid from 0603-144 (250 mg, 0.45 mmol) and freshly prepared hydroxylamine methanol solution (8 mL) using a procedure similar to that described for compound 3 (Example 1). m.p.: 215-217° C. LCMS: 535 [M+1]+. $^1$H NMR (400 MHz, DMSO-d$_6$) δ 2.81 (d, J=4.4 Hz, 3H), 3.25 (s, 3H), 3.78 (m, 4H), 3.95 (m, 4H), 5.22 (s, 2H), 7.50 (s, 1H), 7.56 (t, J=7.6 Hz, 1H), 7.91 (d, J=7.6 Hz, 1H), 8.51 (d, J=7.6 Hz, 1H), 8.56 (m, 1H), 8.76 (s, 2H), 8.82 (s, 1H).

Example 56: Preparation of 2-(((2-(4-aminophenyl)-4-morpholinothieno[3,2-d]pyrimidin-6-yl)methyl)(methyl)amino)-N-hydroxypyrimidine-5-carboxamide (Compound 150)

Step 56a: N-(4-bromophenyl)acetamide (Compound 0601-150)

To the solution of 4-bromoaniline (6.3 g, 63.7 mmol) in CH$_2$Cl$_2$ (50 mL) was added acetyl chloride (3.75 g, 47.7 mmol) and TEA (7.4 g, 73.4 mmol) at 0° C., stirred for 2 hours. The reaction mixture was washed with water, brine, dried over Na$_2$SO$_4$, filtered, and concentrated under reduced pressure to give the title compound 0601-150 (3.6 g, 46%) as a brown solid. LCMS: 214 [M+1]+; $^1$H NMR (400 MHz, DMSO-d$_6$). δ 2.05 (s, 3H), 7.46 (d, J=8.8 Hz, 2H), 7.57 (d, J=8.8 Hz, 2H), 10.12 (s, 1H).

Step 56b: N-(4-(4,4,5,5-tetramethyl-1,3,2-dioxaborolan-2-yl)phenyl)acetamide (Compound 0602-150)

The title compound, 0602-150 was prepared (2.3 g, 94%) as a white solid from 0601-150 (2.0 g, 9.3 mmol), bis(pinacolato)diboron (4.4 g, 17.5 mmol), potassium acetate (3.5 g, 14 mmol), and PdCl$_2$(dppf)$_2$ (76 mg, 0.088 mmol) using a procedure similar to that described for compound 0602-107 (Example 34). LCMS: 262 [M+1]+. $^1$H NMR (400 MHz, DMSO-d$_6$) δ 1.27 (d, J=6.8 Hz, 12H), 2.04 (s, 3H), 7.58 (s, 4H), 10.03 (s, 1H).

Step 56c: Ethyl 2-(((2-(4-aminophenyl)-4-morpholinothieno[3,2-d]pyrimidin-6-yl)methyl)(methyl)amino)pyrimidine-5-carboxylate (Compound 0603-150)

A mixture of compound 0504-54 (210 mg, 0.46 mmol), 0602-150 (159 mg, 0.60 mmol), sodium hydrogen carbonate (118 mg, 1.4 mmol), and bis(triphenylphosphine)palladium (II) chloride (17 mg, 0.02 mmol) in toluene (4 mL), ethanol (2 mL) and water (1 mL) was flushed with nitrogen and heated under microwave irradiation at 120° C. for 2 h. The reaction mixture was partitioned between ethyl acetate and water, organic layer was washed with brine, dried over magnesium sulfate, filtered and evaporated in vacuum. The residue was washed with dichloromethane to obtain ethyl 2-(((2-(4-acetamidophenyl)-4-morpholinothieno-[3,2-d]pyrimidin-6-yl)methyl)(methyl)amino)pyrimidine-5-carboxylate (136 mg, 53%) as a white solid. LCMS: 548 [M+1]$^+$, $^1$H NMR (400 MHz, DMSO-$d_6$): δ 1.29 (t, J=7.2 Hz, 3H), 2.06 (s, 6H), 3.26 (s, 3H), 3.75 (m, 4H), 3.91 (m, 4H), 4.28 (q, J=7.2 Hz, 2H), 5.22 (s, 2H), 7.45 (s, 1H), 7.67 (d, J=8.8 Hz, 1H), 8.31 (d, J=8.8 Hz, 1H), 8.87 (s, 1H), 10.10 (s, 1H).

To the solution of above ethyl ester (280 mg, 0.51 mmol) in THF (10 mL) was added aqueous HCl solution (6M, 15 mL) at 40° C., stirred for 2 hours, the reaction mixture was neutralized with NaHCO$_3$ and extracted with CH$_2$Cl$_2$, the organic layer was washed with water, brine, dried over Na$_2$SO$_4$, filtered, and concentrated, purified by column chromatography (methanol in dichloromethane, 2% v/v), to give title compound 0603-150 (180 mg, 48%) as a white solid. LCMS: 506 [M+1]$^+$. $^1$H NMR (400 MHz, DMSO-$d_6$) δ 1.29 (t, J=7.6 Hz, 3H), 3.24 (s, 3H), 3.73 (m, 4H), 3.86 (m, 4H), 4.27 (q, J=6.8 Hz, 2H), 5.20 (s, 2H), 6.59 (d, J=8.8 Hz, 2H), 7.36 (s, 1H), 8.07 (d, J=8.0 Hz, 2H), 8.86 (s, 1H).

Step 56d: 2-(((2-(4-aminophenyl)-4-morpholinothieno[3,2-d]pyrimidin-6-yl)methyl)(methyl)amino)-N-hydroxypyrimidine-5-carboxamide (Compound 150)

The title compound 150 was prepared (43 mg, 26%) as a yellow solid from 0603-150 (170 mg, 0.3 mmol) and freshly prepared hydroxylamine methanol solution (4 mL) using a procedure similar to that described for compound 3 (Example 1). m.p. 183-186° C. LCMS: 493 [M+1]$^+$; $^1$H NMR (400 MHz, DMSO-$d_6$): δ 3.22 (s, 3H), 3.74 (m, 4H), 3.87 (m, 4H), 4.27 (q, J=6.8 Hz, 2H), 5.20 (s, 2H), 5.50 (s, 2H), 6.59 (d, J=8.8 Hz, 2H), 7.36 (s, 1H), 8.07 (d, J=8.0 Hz, 2H), 8.86 (s, 2H).

Example 57: Preparation of 2-(((2-(4-acetamidophenyl)-4-morpholinothieno[3,2-d]pyrimidin-6-yl)methyl)(methyl)amino)-N-hydroxypyrimidine-5-carboxamide (Compound 157)

Step 57a: 2-(((2-(4-Acetamidophenyl)-4-morpholinothieno[3,2-d]pyrimidin-6-yl)methyl)(methyl)amino)-N-hydroxypyrimidine-5-carboxamide (Compound 157)

The title compound 157 was prepared (104 mg, 61%) as a gray solid from ethyl 2-(((2-(4-acetamidophenyl)-4-morpholinothieno[3,2-d]pyrimidin-6-yl)methyl)(methyl)amino) pyrimidine-5-carboxylate (170 mg, 0.3 mmol) and freshly prepared hydroxylamine methanol solution (10 mL) using a procedure similar to that described for compound 3 (Example 1). m.p. 228-230° C. LCMS: 535 [M+1]$^+$; $^1$H NMR (400 MHz, DMSO-$d_6$): δ 2.07 (s, 3H), 3.24 (s, 3H), 3.77 (m, 4H), 3.91 (m, 4H), 5.19 (s, 2H), 7.44 (s, 1H), 7.68 (d, J=8.8 Hz, 2H), 8.31 (d, J=8.8 Hz, 2H), 8.75 (s, 2H), 9.06 (s, 1H), 10.12 (s, 1H), 11.13 (s, 1H).

Example 58: Preparation of 2-(((2-(1H-indazol-4-yl)-4-(phenylamino)thieno[3,2-d]pyrimidin-6-yl)methyl)(methyl)amino)-N-hydroxypyrimidine-5-carboxamide (Compound 164)

Step 58a: 2-Chloro-N-phenylthieno[3,2-d]pyrimidin-4-amine (Compound 0701-164)

To a suspension of compound 0110 (4.00 g, 19.608 mmol) in CH$_3$CN (100 mL) was added Et$_3$N (4.00 g, 39.216 mmol) and aniline (2.00 g, 21.581 mmol) at room temperature. The mixture was stirred at 50° C. overnight, evaporated. The residue was purified by column chromatography on silica gel (ethyl acetate in petroleum ether, 20%-30% v/v) to obtained compound 0701-164 (2.00 g, 39%) as a pale yellow solid. LCMS: 262 [M+1]$^+$; $^1$H NMR (400 MHz, DMSO-$d_6$): δ 7.20 (t, J=7.6 Hz, 1H), 7.42 (m, 3H), 7.69 (d, J=7.6 Hz, 1H), 8.27 (d, J=5.2 Hz, 1H), 10.16 (s, 1H).

Step 58b: Tert-butyl 2-chlorothieno[3,2-d]pyrimidin-4-yl(phenyl)carbamate (Compound 0702-164)

To a solution of compound 0701-164 (5.60 g, 21.456 mmol) and (Boc)$_2$O (5.60 g, 25.747 mmol) in THF (100 mL) was added DMAP (130 mg, 1.073 mmol) at room temperature and stirred for 3 h. Solvent was removed and the residue was purified by column chromatography (ethyl acetate in petroleum ether, 15%-30% v/v) to obtained compound 0702-164 (6.20 g, 80%) as a white solid. LCMS: 362 [M+1]$^+$; $^1$H NMR (400 MHz, DMSO-$d_6$): δ 1.44 (s, 9H), 7.31 (d, J=7.6 Hz, 2H), 7.39 (m, 1H), 7.43 (m, 2H), 7.56 (d, J=5.6 Hz, 1H), 8.48 (d, J=5.2 Hz, 1H).

Step 58c: Tert-butyl 2-chloro-6-formylthieno[3,2-d]pyrimidin-4-yl(phenyl)carbamate (Compound 0703-164)

Compound 0702-164 (2.90 g, 8.033 mmol) was suspended in THF (80 mL) and cooled to −50° C. To the mixture LDA solution (2M, 12 mL, 24.099 mmol) was added dropwise while temperature was kept below −30° C. and stirred for 1 h followed by the addition of DMF (2 mL) at −50° C. The mixture was stirred for additional 30 min. A saturated aqueous NH$_4$Cl (20 mL) was added dropwise at −50~−60° C. Ethyl acetate (300 mL) was added to the mixture, washed with saturated aqueous NH$_4$Cl (2×100 mL), water (2×100 mL), brine (200 mL), dried over anhydrous Na$_2$SO$_4$, concentrated and the residue was purified by column chromatography on silica gel (ethyl in petroleum ether, 20%-50% v/v) to obtain compound 0703-164 (900 mg, 29%) as a yellowish solid. LCMS: 390 [M+1]$^+$; $^1$H NMR (400 MHz, DMSO-$d_6$): δ 1.46 (s, 9H), 7.30 (d, J=6.8 Hz, 1H), 7.36 (m, 2H), 7.43 (m, 2H), 8.43 (s, 1H), 10.21 (s, 1H).

Step 58d: Tert-butyl 2-chloro-6-(hydroxymethyl) thieno[3,2-d]pyrimidin-4-yl(phenyl)carbamate (Compound 0704-164)

To a solution of 0703-164 (900 mg, 2.314 mmol) in MeOH/THF (10/5 mL) was added NaBH$_4$ (176 mg, 4.627 mmol) slowly at room temperature and stirred for 30 min. After solvent removed, the residue was washed with water and filtered to obtain 0704-164 (800 g, 88%) as a white solid. LCMS: 392 [M+1]$^+$; $^1$H NMR (400 MHz, DMSO-$d_6$): δ 1.44 (s, 9H), 4.80 (d, J=5.6 Hz, 2H), 6.02 (t, J=5.6 Hz, 1H), 7.28 (d, J=4.8 Hz, 2H), 7.37 (m, 2H), 7.45 (m, 2H).

Step 58e: (4-(Tert-butoxycarbonyl(phenyl)amino)-2-chlorothieno[3,2-d]pyrimidin-6-yl)methyl methanesulfonate (Compound 0705-164)

To a solution of 0704-164 (500 mg, 1.279 mmol) and Et$_3$N (2 mL) in THF (20 mL) was added MsCl (175 mg, 1.534 mmol) at ice bath temperature. The mixture with white solid was stirred at room temperature for 30 min. After solvent removed, the residue was washed with water and filtered to obtain 0705-164 (600 mg, 83%) as a white solid. LCMS: 470 [M+1]$^+$.

Step 58f: 2-Chloro-6-((methylamino)methyl)-N-phenylthieno[3,2-d]pyrimidin-4-amine (Compound 0706-164)

Compound 0705-164 (600 mg, 1.279 mmol) was dissolved in a solution of 32% MeNH$_2$ in MeOH (5 mL). This solution was stirred at room temperature for 1 h. The solvent was removed under reduced pressure and the residue was washed with water, filtered to obtained 0706-164 (300 mg, 77%) as a white solid. LCMS: 305 [M+1]$^+$.

Step 58 g: Ethyl 2-(((2-chloro-4-(phenylamino)thieno[3,2-d]pyrimidin-6-yl)methyl)(methyl)amino)pyrimidine-5-carboxylate (Compound 0707-164)

To a solution of compound 0706-164 (260 mg, 0.855 mmol) and compound 0305 (159 mg, 0.855 mmol) in CH$_3$CN (5 mL) was added Et$_3$N (0.5 mL) at room temperature and stirred overnight. After concentrated, the residue was washed with water, filtered to obtained compound 0707-164 (200 mg, 52%) as a white solid. LCMS: 455 [M+1]$^+$; $^1$H NMR (400 MHz, DMSO-d$_6$): δ 1.31 (t, J=4.2 Hz, 3H), 3.25 (s, 3H), 4.29 (m, 2H), 5.23 (s, 2H), 7.15 (t, J=6.0 Hz. 1H), 7.37 (t, J=6.4 Hz, 2H), 7.42 (s, 1H), 7.64 (d, J=6.4 Hz, 2H), 8.88 (s, 2H), 9.98 (s, 1H).

Step 58 h: Ethyl 2-(((2-(1H-indazol-4-yl)-4-(phenylamino)thieno[3,2-d]pyrimidin-6-yl)methyl)(methyl)amino)pyrimidine-5-carboxylate (Compound 0708-164)

The title compound, 0708-164 was prepared (210 mg, 89%) as a white solid from 0706-164 (200 mg, 0.440 mmol), compound 0107-3 (118 mg, 0.484 mmol), NaHCO$_3$ (110 mg, 1.320 mmol), and bis(triphenylphosphine)-palladium (II) chloride (15 mg, 0.022 mmol) in toluene (5.6 mL), ethanol (3.5 mL), and water (1.4 mL) using a procedure similar to that described for compound 0603-107 (Example 30). LCMS: 537 [M+1]$^+$; $^1$H NMR (400 MHz, DMSO-d$_6$): δ 1.33 (t, J=7.2 Hz, 3H), 3.31 (s, 3H), 4.31 (m, 2H), 5.31 (s, 2H), 7.16 (t, J=7.2 Hz, 1H), 7.41 (t, J=4.4 Hz, 2H), 7.47 (t, J=8.0 Hz, 1H), 7.62 (s, 1H), 7.65 (d, J=8.4 Hz, 1H), 7.79 (d, J=7.6 Hz, 2H), 8.21 (d, J=7.2 Hz, 1H), 8.63 (s, 1H), 8.92 (s, 2H), 9.66 (s, 1H), 13.16 (s, 1H).

Step 58i: 2-(((2-(1H-indazol-4-yl)-4-(phenylamino)thieno[3,2-d]pyrimidin-6-yl)methyl)(methyl)amino)-N-hydroxypyrimidine-5-carboxamide (Compound 164)

The title compound 164 was prepared (100 mg, 49%) as a pale white solid from 0708-164 (210 mg, 0.392 mmol) and freshly prepared hydroxylamine methanol solution (8 mL) using a procedure similar to that described for compound 3 (Example 1). m.p.: 232-235° C.; LCMS: 524 [M+1]$^+$; $^1$H NMR (400 MHz, DMSO-d$_6$): δ 3.27 (s, 3H), 5.27 (s, 2H), 7.16 (t, J=7.2 Hz, 1H), 7.41 (t, J=4.4 Hz, 2H), 7.47 (t, J=8.0 Hz, 1H), 7.59 (s, 1H), 7.65 (d, J=8.4 Hz, 1H), 7.78 (d, J=7.6 Hz, 2H), 8.21 (d, J=7.2 Hz, 1H), 8.78 (s, 2H), 8.81 (s, 1H), 9.07 (s, 1H), 9.64 (s, 1H), 11.15 (s, 1H), 13.14 (s, 1H).

Example 59: Preparation of 2-(((2-(1H-indazol-4-yl)-4-(pyridin-2-ylamino)thieno[3,2-d]pyrimidin-6-yl)methyl)(methyl)amino)-N-hydroxypyrimidine-5-carboxamide (Compound 168)

Step 59a: 2-Chloro-N-(pyridin-2-yl)thieno[3,2-d]pyrimidin-4-amine (Compound 0701-168)

To a suspension of compound 0110 (5.00 g, 24.510 mmol) in THF (200 mL) was added t-BuOK (4.19 g, 36.765 mmol) and pyridin-2-amine (2.30 g, 24.510 mmol) at room temperature. The mixture was stirred at 50° C. overnight, then the mixture was purified by column chromatography on silica gel eluting with ethyl acetate in petroether (20% to 40%, v/v) to obtained compound 0701-168 (3.00 g, 47%) as a pale yellow solid. LCMS: 263 [M+1]$^+$; $^1$H NMR (400 MHz, DMSO-d$_6$): δ 7.18 (m, 1H), 7.43 (d, J=5.2 Hz, 1H), 7.87 (m, 2H), 8.33 (d, J=5.6 Hz, 1H), 8.40 (d, J=4.8 Hz, 1H), 10.94 (s, 1H).

Step 59b: Tert-butyl 2-chlorothieno[3,2-d]pyrimidin-4-yl(pyridin-2-yl)carbamate (Compound 0702-168)

The title compound 0702-168 was prepared (2.80 g, 100%) as a white solid from 0701-168 (2.40 g, 9.160 mmol), (Boc)$_2$O (3.00 g, 13.740 mmol), and DMAP (56 mg, 0.458 mmol) using a procedure similar to that described for compound 0702-164 (Example 58). LCMS: 363 [M+1]$^+$; $^1$H NMR (400 MHz, DMSO-d$_6$): δ 1.44 (s, 9H), 7.36 (m, 1H), 7.64 (m, 2H), 7.97 (t, J=7.6 Hz, 1H), 8.34 (m, 1H), 8.54 (d, J=5.6 Hz, 1H).

Step 59c: Tert-butyl 2-chloro-6-formylthieno[3,2-d]pyrimidin-4-yl(pyridin-2-yl)carbamate (Compound 0703-168)

The title compound 0703-168 was prepared (1.90 g, 48%) as a light yellow solid from 0702-168 (3.69 g, 10.199 mmol), LDA solution (2M, 15.3 mL, 30.597 mmol), and DMF (4 mL) using a procedure similar to that described for compound 0703-164 (Example 58). LCMS: 391 [M+1]$^+$; $^1$H NMR (400 MHz, DMSO-d$_6$): δ 1.46 (s, 9H), 7.41 (m, 1H), 77.66 (d, J=8.0 Hz, 1H), 8.00 (m, 1H), 8.40 (m, 1H), 8.49 (s, 1H), 10.12 (s, 1H).

Step 59d: Tert-butyl 2-chloro-6-(hydroxymethyl)thieno[3,2-d]pyrimidin-4-yl(pyridin-2-yl)carbamate (Compound 0704-168)

The title compound 0704-168 was prepared (1.9 g, 100%) as a white solid from 0703-168 (1.9 g, 4.870 mmol) and NaBH$_4$ (277 mg, 7.31 mmol) using a procedure similar to that described for compound 0704-164 (Example 58). LCMS: 393 [M+1]$^+$; $^1$H NMR (400 MHz, DMSO-d$_6$): δ 1.44 (s, 9H), 4.84 (d, J=5.4 Hz, 2H), 6.05 (t, J=6.0 Hz, 1H), 7.34 (m, 1H), 7.43 (s, 1H), 7.65 (d, J=8.0 Hz, 1H), 7.96 (t, J=7.6 Hz, 1H), 8.33 (m, 1H).

Step 59e: (4-(Tert-butoxycarbonyl(pyridin-2-yl)amino)-2-chlorothieno[3,2-d]pyrimidin-6-yl)methyl methanesulfonate (Compound 0705-168)

The title compound 0705-168 was prepared (2.10 g, 92%) as a white solid from 0704-168 (1.90 g, 4.847 mmol), Et$_3$N (2 mL), and MsCl (1.10 g, 9.694 mmol) using a procedure similar to that described for compound 0705-164 (Example 58). LCMS: 471 [M+1]$^+$. $^1$H NMR (400 MHz, DMSO-d$_6$): 1.44 (s, 9H), 3.31 (s, 3H), 5.68 (s, 2H), 7.37 (m, 1H), 7.65 (d, J=8.0 Hz, 1H), 7.74 (s, 1H), 7.99 (t, J=7.6 Hz, 1H), 8.36 (m, 1H).

Step 59f: 2-Chloro-6-((methylamino)methyl)-N-(pyridin-2-yl)thieno[3,2-d]pyrimidin-4-amine (Compound 0706-168)

The title compound 0706-168 was prepared (1.80 g, 100%) as a white solid from 0705-168 (2.00 g, 4.255 mmol)

and 32% MeNH$_2$ in MeOH (5 mL) using a procedure similar to that described for compound 0706-164 (Example 58). LCMS: 306 [M+1]$^+$. $^1$H NMR (400 MHz, DMSO-d$_6$): δ 2.32 (s, 3H), 3.97 (s, 2H), 7.15 (m, 1H), 7.26 (s, 1H), 7.83 (m, 2H), 8.38 (m, 1H), 9.71 (s, 1H).

Step 59 g: Ethyl 2-(((2-chloro-4-(pyridin-2-ylamino)thieno[3,2-d]pyrimidin-6-yl)methyl)(methyl)amino)pyrimidine-5-carboxylate (Compound 0707-168)

The title compound 0707-168 was prepared (410 mg, 69%) as a white solid from 0706-168 (400 mg, 1.311 mmol) and compound 0305 (244 mg, 1.311 mmol) using a procedure similar to that described for compound 0707-164 (Example 58). LCMS: 456 [M+1]$^+$; $^1$H NMR (400 MHz, DMSO-d$_6$): δ 1.31 (t, J=7.2 Hz, 3H), 3.25 (s, 3H), 4.29 (m, 2H), 5.21 (s, 2H), 7.13 (m, 1H), 7.40 (s, 1H), 7.84 (m, 2H), 8.30 (m, 1H), 8.88 (s, 2H), 10.84 (s, 1H).

Step 59 h: Ethyl 2-(((2-(1H-indazol-4-yl)-4-(pyridin-2-ylamino)thieno[3,2-d]pyrimidin-6-yl)methyl)(methyl)amino)pyrimidine-5-carboxylate (Compound 0708-168)

The title compound, 0708-168 was prepared (200 mg, 85%) as a white solid from 0707-168 (200 mg, 0.440 mmol), compound 0107-3 (118 mg, 0.484 mmol), NaHCO$_3$ (110 mg, 1.320 mmol), and bis(triphenylphosphine)-palladium (II) chloride (15 mg, 0.022 mmol) in toluene (8 mL), ethanol (5 mL), and water (2 mL) using a procedure similar to that described for compound 0603-107 (Example 30). LCMS: 538 [M+1]$^+$; $^1$H NMR (400 MHz, DMSO-d$_6$): δ 1.33 (t, J=7.2 Hz, 3H), 3.29 (s, 3H), 4.30 (m, 2H), 5.26 (s, 2H), 7.12 (m, 1H), 7.7.57 (s, 1H), 7.84 (m, 1H), 8.23 (d, J=7.2 Hz, 1H), 8.33 (m, 1H), 8.89 (s, 2H), 10.39 (s, 1H), 13.19 (s, 1H).

Step 59i: 2-(((2-(1H-indazol-4-yl)-4-(pyridin-2-ylamino)thieno[3,2-d]pyrimidin-6-yl)methyl)(methyl)amino)-N-hydroxypyrimidine-5-carboxamide (Compound 168)

The title compound 168 was prepared (80 mg, 82%) as a pale white solid from 0708-168 (100 mg, 0.186 mmol) and freshly prepared hydroxylamine methanol solution (8 mL) using a procedure similar to that described for compound 3 (Example 1). m.p.: 200-203° C.; LCMS: 525 [M+1]$^+$; $^1$H NMR (400 MHz, DMSO-d$_6$): δ 3.34 (s, 3H), 5.30 (s, 2H), 7.19 (t, J=6.0 Hz, 1H), 7.55 (t, J=8.0 Hz, 1H), 7.62 (s, 1H), 7.47 (d, J=8.0 Hz, 1H), 7.91 (t, J=8.8 Hz, 1H), 8.00 (d, J=8.4 Hz, 1H), 8.30 (d, J=7.6 Hz, 1H), 8.41 (s, 1H), 8.84 (s, 2H), 9.04 (s, 1H), 9.14 (s, 1H), 10.46 (s, 1H), 11.01 (s, 1H), 13.25 (s, 1H).

Example 60: Preparation of 5-(4-(2-(1H-indazol-4-yl)-6-((4-(methylsulfonyl)piperazin-1-yl)methyl)thieno[3,2-d]pyrimidin-4-yl)piperazin-1-yl)-N-hydroxypentanamide (Compound 30)

Step 60a: Tert-butyl 4-(2-chlorothieno[3,2-d]pyrimidin-4-yl)piperazine-1-carboxylate (Compound 0801-30)

A mixture of compound 0110 (20 g, 98 mmol), tert-butyl 1-piperazinecarboxylate (21.9 g, 118 mmol), and triethylamine (14.8 g, 147 mmol) in methanol (400 mL) was stirred at room temperature for 4 h. The reaction mixture was filtered to give a solid as first batch of crude product. The mother liquid was concentrated and diluted with water (500 mL) and the solid was collected as second batch of crude product. The combined products were dried to give compound 0801-30 (22 g, 63%) as a yellow solid. LCMS: 355 [M+1]$^+$. $^1$H NMR (400 MHz, DMSO-d$_6$): δ 1.43 (s, 9H), 3.53 (m, 4H), 3.95 (m, 4H), 7.41 (d, J=5.6 Hz, 1H), 8.32 (d, J=5.6 Hz, 1H).

Step 60b: Tert-butyl 4-(2-chloro-6-formylthieno[3,2-d]pyrimidin-4-yl)piperazine-1-carboxylate (Compound 0802-30)

Compound 0801-30 (10 g, 28.2 mmol) was suspended in THF (200 mL) and cooled to −70° C. followed by the addition of LDA solution (2M, 71 mL) dropwise and kept the reaction temperature below −65° C. The mixture was then stirred for 1 h. DMF (15 mL) was added dropwise to the mixture while the reaction temperature was kept below −65° C. The resulting mixture was stirred for 30 min. and quenched with saturated aqueous NH$_4$Cl (50 mL) at −50~-60° C. The mixture was diluted with ethyl acetate (500 mL), washed with saturated aqueous NH$_4$HCO$_3$ (2×300 mL), water (2×500 mL), brine (200 mL), dried over Na$_2$SO$_4$, concentrated and the residue was purified by column chromatography on silica gel (methanol in dichloromethane, 2% v/v) to give compound 0802-30 (4.9 g, 45%) as a light yellow solid. LCMS: 383 [M+1]$^+$. $^1$H NMR (400 MHz, DMSO-d$_6$): δ 1.43 (s, 9H), 3.55 (m, 4H), 3.99 (m, 4H), 8.29 (s, 1H), 10.21 (s, 1H).

Step 60c: Tert-butyl 4-(2-chloro-6-(hydroxymethyl)thieno[3,2-d]pyrimidin-4-yl)piperazine-1-carboxylate (Compound 0803-30)

To a suspension of compound 0802-30 (3.73 g, 9.764 mmol) in MeOH (20 mL) was added NaBH$_4$ (1.11 g, 29.293 mmol) slowly at 0° C. within 10 minutes. The formed clear solution was stirred for 10 min., evaporated. The residue was washed with water and filtered to obtain compound 0803-30 (3.10 g, 83%) as a white solid. LCMS: 385 [M+1]$^+$; $^1$H NMR (400 MHz, DMSO-d$_6$): δ 1.43 (s, 9H), 3.52 (br s, 4H), 3.92 (br s, 4H), 4.81 (d, J=4.8 Hz, 2H), 5.96 (t, J=5.2 Hz, 1H), 7.22 (s, 1H).

Step 60d: Tert-butyl 4-(6-(bromomethyl)-2-chlorothieno[3,2-d]pyrimidin-4-yl)piperazine-1-carboxylate (Compound 0804-30)

To a suspension of compound 0803-30 (3.10 g, 8.073 mmol) and PPh$_3$ (2.54 g, 9.687 mmol) in dichloromethane (30 mL) was added NBS (1.72 g, 9.687 mmol) at room temperature. The mixture was stirred at room temperature for 2 h and concentrated. The residue was purified by column chromatography on silica gel (dichloromethane in petroleum ether, 10% to 50% v/v) to obtain compound 0804-30 (2.60 g, 72%) as a white solid. LCMS: 447 [M+1]$^+$; $^1$H NMR (400 MHz, DMSO-d$_6$): δ 1.42 (s, 9H), 3.52 (br s, 4H), 3.90 (br s, 4H), 5.10 (s, 2H), 7.49 (s, 1H).

Step 60e: Tert-butyl 4-(2-chloro-6-((4-(methylsulfonyl)piperazin-1-yl)methyl)thieno[3,2-d]pyrimidin-4-yl)piperazine-1-carboxylate (Compound 0805-30)

A mixture of compound 0804-30 (3.5 g, crude product), compound 0103 (1.14 g, 4.1 mmol), and K$_2$CO$_3$ (1.58 g, 11.4 mmol) in acetonitrile (35 mL) and DMF (17 mL) was stirred at room temperature overnight. The reaction mixture was diluted with water (200 mL) and extracted with dichloromethane (200 mL). The organic layer was washed with water (5×200 mL), brine, dried over Na$_2$SO$_4$, concentrated to give crude product, compound 0805-30 (3.9 g with some Ph$_3$PO) as a yellow solid which was used in next step reaction without further purification. LCMS: 531 [M+1]$^+$. $^1$H NMR (400 MHz, DMSO-d$_6$) δ 1.42 (s, 9H), 2.59 (m, 4H), 2.90 (s, 3H), 3.15 (m, 4H), 3.52 (m, 4H), 3.91 (m, 6H), 7.31 (s, 1H).

Step 60f: 2-Chloro-6-((4-(methylsulfonyl)piperazin-1-yl)methyl)-4-(piperazin-1-yl)thieno[3,2-d]pyrimidine (Compound 0806-30)

To a solution of compound 0805-30 (5 g) in THF (50 mL) was added concentrated hydrochloric acid (10 mL) and stirred at room temperature overnight. The reaction mixture was diluted with water (200 mL) and extracted with dichloromethane (100 mL). The orange layer was discarded after washed with 0.1 M aqueous HCl (100 mL). The aqueous layer was adjusted to pH 7 with solid NaHCO$_3$, extracted with dichloromethane (200 mL). During extraction, small amount of methanol was added until the color of the solution turned to colorless from orange. The extract was dried over Na$_2$SO$_4$ and concentrated to give compound 0806-30 (1.9 g, 76% in two steps) as a yellow solid. LCMS: 431 [M+1]$^+$. $^1$H NMR (400 MHz, DMSO-d$_6$) δ 2.57 (t, J=4.4 Hz, 4H), 2.83 (t, J=5.2 Hz, 4H), 2.90 (s, 3H), 3.14 (t, J=4.4 Hz, 4H), 3.82 (t, J=4.4 Hz, 4H), 3.90 (s, 2H), 7.28 (s, 1H).

Step 60 g: Ethyl 5-(4-(2-chloro-6-((4-(methylsulfonyl)piperazin-1-yl)methyl)thieno[3,2-d]pyrimidin-4-yl)piperazin-1-yl)pentanoate (Compound 0807-30)

A mixture of compound 0806-30 (450 mg, 1.04 mmol), ethyl 5-bromopentanoate (327 mg, 1.6 mmol), and triethylamine (211 mg, 2.1 mmol) in DMF (8 mL) was stirred for 2 h at 80° C. The mixture was poured into water (100 mL) with stirring. The solid was collected by filtration and purified by column chromatography on silica gel (methanol in dichloromethane, 2% v/v) to give compound 0807-30 (500 mg, 86%) as a light yellow solid. LCMS: 560 [M+1]$^+$. $^1$H NMR (400 MHz, DMSO-d$_6$) δ 1.18 (t, J=7.2 Hz, 3H), 1.46 (m, 2H), 1.56 (m, 2H), 2.32 (m, 4H), 2.46 (m, 4H), 2.57 (m, 4H), 2.90 (s, 3H), 3.14 (m, 4H), 3.88 (m, 6H), 4.05 (q, J=7.6 Hz, 2H), 7.29 (s, 1H).

Step 60 h: Ethyl 5-(4-(2-(1H-indazol-4-yl)-6-((4-(methylsulfonyl)piperazin-1-yl)methyl)thieno[3,2-d]pyrimidin-4-yl)piperazin-1-yl)pentanoate (Compound 0808-30)

The title compound, 0808-30 was prepared (250 mg, 73%) as a yellow solid from 0807-30 (300 mg, 0.54 mmol), compound 0107-3 (157 mg, 0.64 mmol), NaHCO$_3$ (135 mg, 1.61 mmol), (Ph$_3$P)$_2$PdCl$_2$ (19 mg, 0.03 mmol) in toluene (5 mL), ethanol (3 mL), and water (1.3 mL) using a procedure similar to that described for compound 0603-107 (Example 30). LCMS: 641 [M+1]$^+$. $^1$H NMR (400 MHz, DMSO-d$_6$) δ 1.19 (t, J=7.2 Hz, 3H), 1.51 (m, 2H), 1.56 (m, 2H), 2.33 (m, 4H), 2.58 (m, 8H), 2.91 (s, 3H), 3.17 (m, 4H), 3.94 (m, 2H), 4.06 (m, 6H), 7.47 (m, 2H), 7.66 (d, J=8.4 Hz, 1H). 8.21 (d, J=7.2 Hz, 1H), 8.88 (s, 1H), 13.20 (s, 1H).

Step 60i: 5-(4-(2-(1H-indazol-4-yl)-6-((4-(methylsulfonyl)piperazin-1-yl)methyl)thieno[3,2-d]pyrimidin-4-yl)piperazin-1-yl)-N-hydroxypentanamide (Compound 30)

The title compound 30 was prepared (95 mg, 39%) as a white solid from 0808-30 (250 mg, 0.39 mmol) and freshly prepared hydroxylamine methanol solution (6 mL) using a procedure similar to that described for compound 3 (Example 1). mp 142-145° C. LCMS: 628 [M+1]$^+$. $^1$H NMR (400 MHz, DMSO-d$_6$) δ 1.53 (m, 4H), 1.99 (t, J=6.8 Hz, 2H) 2.35 (t, J=6.8 Hz, 2H), 2.59 (m, 8H), 2.91 (s, 3H), 3.17 (m, 4H), 3.94 (s, 2H), 4.02 (m, 4H), 7.47 (m, 2H), 7.66 (d, J=8.0 Hz, 1H), 8.16 (s, 1H), 8.22 (d, J=6.8 Hz, 1H), 8.88 (s, 1H), 10.36 (s, 1H), 13.20 (s, 1H).

Example 61: Preparation of 6-(4-(2-(1H-indazol-4-yl)-6-((4-(methylsulfonyl)piperazin-1-yl)methyl)thieno[3,2-d]pyrimidin-4-yl)piperazin-1-yl)-N-hydroxyhexanamide (Compound 31)

Step 61a: Ethyl 6-(4-(2-chloro-6-((4-(methylsulfonyl)piperazin-1-yl)methyl)thieno[3,2-d]pyrimidin-4-yl)piperazin-1-yl)hexanoate (Compound 0807-31)

The title compound, 0807-31 was prepared (290 mg, 44%) as a yellow solid from 0806 (400 mg, 0.928 mmol), ethyl 6-bromohexanoate (310 mg, 1.39 mmol), and triethylamine (187 mg, 1.86 mmol) using a procedure similar to that described for compound 0807-30 (Example 60). LCMS: 573 [M+1]$^+$. $^1$H NMR (400 MHz, DMSO-d$_6$) δ 1.18 (t, J=7.2 Hz, 3H), 1.29 (m, 2H), 1.45 (m, 2H), 1.54 (m, 2H), 2.29 (m, 4H), 2.50 (m, 4H), 2.57 (m, 4H), 2.90 (s, 3H), 3.14 (m, 4H), 3.88 (m, 6H), 4.05 (q, J=7.2 Hz, 2H), 7.29 (s, 1H).

Step 61b: Ethyl 6-(4-(2-(1H-indazol-4-yl)-6-((4-(methylsulfonyl)piperazin-1-yl)methyl)thieno[3,2-d]pyrimidin-4-yl)piperazin-1-yl)hexanoate (Compound 0808-31)

The title compound, 0808-31 was prepared (300 mg, 91%) as a yellow solid from 0807-31 (290 mg, 0.506 mmol), compound 0107-3 (185 mg, 0.607 mmol), NaHCO$_3$ (128 mg, 1.52 mmol), (Ph$_3$P)$_2$PdCl$_2$ (18 mg, 0.025 mmol) in toluene (5 mL), ethanol (3 mL) and water (1.3 mL) using a procedure similar to that described for compound 0603-107 (Example 30). LCMS: 655 [M+1]$^+$. $^1$H NMR (400 MHz, DMSO-d$_6$) δ 1.17 (t, J=6.8 Hz, 3H), 1.20 (m, 2H), 1.52 (m, 4H), 2.32 (m, 4H), 2.58 (m, 8H), 2.91 (s, 3H), 3.17 (m, 4H), 3.95 (m, 2H), 4.01 (m, 4H), 4.05 (q, J=6.8 Hz, 2H), 7.48 (m, 2H), 7.66 (d, J=8.0 Hz, 1H). 8.21 (d, J=6.8 Hz, 1H), 8.88 (s, 1H), 13.20 (s, 1H).

Step 61c: 6-(4-(2-(1H-indazol-4-yl)-6-((4-(methylsulfonyl)piperazin-1-yl)methyl)thieno[3,2-d]pyrimidin-4-yl)piperazin-1-yl)-N-hydroxyhexanamide (Compound 31)

The title compound 31 was prepared (41 mg, 14%) as a white solid from 0808-31 (300 mg, 0.46 mmol) and freshly prepared hydroxylamine methanol solution (5 mL) using a procedure similar to that described for compound 3 (Example 1). m.p. 140-145° C. LCMS: 642 [M+1]$^+$. $^1$H NMR (400 MHz, DMSO-d$_6$) δ1.28 (m, 2H), 1.51 (m, 4H), 1.96 (t, J=7.2 Hz, 2H) 2.33 (t, J=7.2 Hz, 2H), 2.60 (m, 8H), 2.91 (s, 3H), 3.17 (m, 4H), 3.94 (s, 2H), 4.01 (m, 4H), 7.47 (m, 2H), 7.66 (d, J=8.0 Hz, 1H). 8.21 (d, J=7.2 Hz, 1H), 8.68 (s, 1H), 8.88 (s, 1H), 10.35 (s, 1H), 13.20 (s, 1H).

Example 62: Preparation of 7-(4-(2-(1H-indazol-4-yl)-6-((4-(methylsulfonyl)piperazin-1-yl)methyl)thieno[3,2-d]pyrimidin-4-yl)piperazin-1-yl)-N-hydroxyheptanamide (compound 32)

Step 62a: Ethyl 7-(4-(2-chloro-6-((4-(methylsulfonyl)piperazin-1-yl)methyl)thieno[3,2-d]pyrimidin-4-yl)piperazin-1-yl)heptanoate (Compound 0807-32)

The title compound, 0807-32 was prepared (550 mg, 81%) as a yellow solid from 0806 (500 mg, 1.16 mmol), ethyl 7-bromoheptanoate (412 mg, 1.74 mmol), triethylamine (235 mg, 2.3 mmol) using a procedure similar to that described for compound 0807-30 (Example 60). LCMS: 587 [M+1]$^+$. $^1$H NMR (400 MHz, DMSO-d$_6$) δ 1.18 (t, J=7.2 Hz, 3H), 1.28 (m, 4H), 1.45 (m, 2H), 1.52 (m, 2H), 2.29 (m, 4H), 2.46 (m, 4H), 2.57 (m, 4H), 2.90 (s, 3H), 3.14 (m, 4H), 3.89 (m, 6H), 4.05 (q, J=7.2 Hz, 2H), 7.29 (s, 1H).

Step 62b: Ethyl 7-(4-(2-(1H-indazol-4-yl)-6-((4-(methylsulfonyl)piperazin-1-yl)methyl)thieno[3,2-d]pyrimidin-4-yl)piperazin-1-yl)heptanoate (Compound 0808-32)

The title compound, 0808-32 was prepared (220 mg, 63%) as a yellow solid from 0807-32 (300 mg, 0.51 mmol), compound 0107-3 (150 mg, 0.61 mmol), NaHCO$_3$ (129 mg, 1.53 mmol), (Ph$_3$P)$_2$PdCl$_2$ (18 mg, 0.026 mmol) in toluene (5 mL), ethanol (3 mL), and water (1.3 mL) using a procedure similar to that described for compound 0603-107 (Example 30). LCMS: 669 [M+1]$^+$. $^1$H NMR (400 MHz, DMSO-d$_6$) δ 1.18 (t, J=7.2 Hz, 3H), 1.30 (m, 4H), 1.52 (m, 2H), 1.55 (m, 2H), 2.30 (m, 4H), 2.57 (m, 8H), 2.91 (s, 3H), 3.17 (m, 4H), 3.94 (m, 2H), 4.06 (m, 6H), 7.47 (m, 2H), 7.66 (d, J=8.4 Hz, 1H). 8.21 (d, J=7.2 Hz, 1H), 8.88 (s, 1H), 13.19 (s, 1H).

Step 62c: 7-(4-(2-(1H-indazol-4-yl)-6-((4-(methylsulfonyl)piperazin-1-yl)methyl)thieno[3,2-d]pyrimidin-4-yl)piperazin-1-yl)-N-hydroxyheptanamide (Compound 32)

The title compound 32 was prepared (80 mg, 37%) as a white solid from 0808-32 (220 mg, 0.33 mmol) and freshly prepared hydroxylamine methanol solution (6 mL) using a procedure similar to that described for compound 3 (Example 1). mp 131-134° C. LCMS: 656 [M+1]$^+$. $^1$H NMR (400 MHz, DMSO-d$_6$) δ 1.29 (m, 4H), 1.49 (m, 4H), 1.95 (t, J=6.8 Hz, 2H), 2.35 (t, J=6.4 Hz, 2H), 2.60 (m, 8H), 2.91 (s, 3H), 3.17 (m, 4H), 3.95 (m, 6H), 7.47 (m, 2H), 7.66 (d, J=8.0 Hz, 1H), 8.16 (s, 1H), 8.22 (d, J=7.2 Hz, 1H), 8.88 (s, 1H), 10.35 (s, 1H), 13.20 (s, 1H).

Example 63: Preparation of 2-(((2-(6-acetamidopyridin-3-yl)-4-morpholinothieno[3,2-d]pyrimidin-6-yl)methyl)(methyl)amino)-N-hydroxypyrimidine-5-carboxamide (Compound 112)

Step 63a: N-(5-bromopyridin-2-yl)acetamide (Compound 0601-112)

To a solution of 2-amino-5-bromopyridine (0.50 g, 2.9 mmol) in THF (10 mL) was added pyridine (343 mg, 4.3 mmol) and acetic anhydride (295 mg, 2.9 mmol) at room temperature and stirred overnight. To the mixture water (30 mL) was added, extracted with ethyl acetate (3×30 mL). The combined organic layers were washed with saturated aqueous NaHCO$_3$ and brine, dried over Na$_2$SO$_4$, concentrated to give the title compound (0.58 g, 92%) as a white solid LCMS: 215 [M+2]$^+$; $^1$HNMR (400 MHz, DMSO-d$_6$) δ 2.09 (s, 3H), 7.97 (dd, J=8.8, 2.4 Hz, 1H), 8.06 (d, J=8.8 Hz, 1H), 8.41 (d, J=1.2 Hz, 1H), 10.64 (s, 1H).

Step 63b: N-(5-(4,4,5,5-tetramethyl-1,3,2-dioxaborolan-2-yl)pyridin-2-yl)acetamide (compound 0602-112)

The title compound 0602-112 was prepared (400 mg, 57%) as a yellow solid from 0601-112 (0.57 g, 2.7 mmol), bis(pinacolato)diboron (1.00 g, 4.0 mmol), potassium acetate (0.78 g, 8.0 mmol), and PdCl$_2$(dppf)$_2$ (217 mg, 0.3 mmol) using a procedure similar to that described for compound 0602-107 (Example 34). LCMS: 263 [M+1]$^+$; $^1$HNMR (400 MHz, DMSO-d$_6$) δ 1.30 (s, 12H), 2.10 (s, 3H), 7.96 (dd, J=8.4, 1.6 Hz, 1H), 8.09 (d, J=8.4 Hz, 1H), 8.51 (d, J=0.4 Hz, 1H), 10.65 (s, 1H).

Step 63c: Ethyl 2-(((2-(6-acetamidopyridin-3-yl)-4-morpholinothieno[3,2-d]pyrimidin-6-yl)methyl)(methyl)amino)pyrimidine-5-carboxylate (compound 0603-112)

The title compound 0603-112 was prepared (120 mg, 73%) as an off-white solid from 0504-54 (135 mg, 0.30 mmol), 0602-112 (157 mg, 0.60 mmol), NaHCO$_3$ (76 mg, 0.90 mmol), (Ph$_3$P)$_2$PdCl$_2$ (11 mg, 0.015 mmol) in toluene (2.5 mL), ethanol (1.6 mL) and water (0.7 mL) using a procedure similar to that described for compound 0603-107 (Example 34). LCMS: 549 [M+1]$^+$; $^1$HNMR (400 MHz, CDCl$_3$) δ 1.38 (t, J=7.2 Hz, 3H), 2.25 (s, 3H), 3.31 (s, 3H), 3.87 (t, J=4.4 Hz, 4H), 4.01 (t, J=4.4 Hz, 4H), 4.36 (q, J=7.2 Hz, 2H), 5.20 (s, 2H), 7.38 (s, 1H), 8.28 (m, 2H), 8.70 (dd, J=8.8, 2.0 Hz, 1H), 9.28 (d, J=2.0 Hz, 1H).

Step 63d: 2-(((2-(6-Acetamidopyridin-3-yl)-4-morpholinothieno[3,2-d]pyrimidin-6-yl)methyl)(methyl)amino)-N-hydroxypyrimidine-5-carboxamide (compound 112)

The title compound 112 was prepared (20 mg, 19%) as a yellow solid from 0603-112 (108 mg, 0.20 mmol) and freshly prepared hydroxylamine methanol solution (10 mL) using a procedure similar to that described for compound 3 (Example 1). m.p.: 197-201° C. LCMS: 536 [M+1]$^+$; $^1$HNMR (400 MHz, DMSO-d$_6$) δ 2.13 (s, 3H), 3.24 (s, 3H), 3.76 (t, J=4.4 Hz, 4H), 3.93 (t, J=4.4 Hz, 4H), 5.21 (s, 2H), 7.46 (s, 1H), 8.18 (d, J=8.8 Hz, 1H), 8.64 (d, J=1.2 Hz, 1H), 8.75 (s, 2H), 9.24 (d, J=2.0 Hz, 1H), 10.72 (s, 1H).

Example 64: preparation of 2-(((2-(6-(dimethylamino)pyridin-3-yl)-4-morpholinothieno[3,2-d]pyrimidin-6-yl)methyl)(methyl)amino)-N-hydroxypyrimidine-5-carboxamide (Compound 114)

Step 64a: 5-Bromo-N,N-dimethylpyridin-2-amine (Compound 0601-114)

To a solution of 5-bromopyridin-2-amine (1.0 g, 5.8 mmol) in THF (25 mL) was added NaH (0.92 g, 23.1 mmol) at 0° C. and stirred for 10 min. followed by the addition of CH₃I (1 mL, 16 mmol) and stirred for 1 h. Water (30 mL) was added and extracted with ethyl acetate (3×30 mL). The combined organic layers were washed with brine, dried over $Na_2SO_4$, concentrated and purified by column chromatography on silica gel (ethyl acetate in petroleum ether, 10% v/v) to give the title compound (1.1 g, 94%) as a white solid LCMS: 203 [M+2]$^+$; $^1$HNMR (400 MHz, DMSO-d₆) δ 2.99 (s, 6H), 6.61 (d, J=9.6 Hz, 1H), 7.62 (dd, J=9.2, 2.8 Hz, 1H), 8.12 (d, J=2.4 Hz, 1H).

Step 64b: N,N-dimethyl-5-(4,4,5,5-tetramethyl-1,3,2-dioxaborolan-2-yl)pyridin-2-amine (Compound 0602-114)

The title compound 0602-114 was prepared (0.81 g, 67%) as a yellow solid from 0601-114 (1.0 g, 5.0 mmol), bis(pinacolato)diboron (1.90 g, 7.5 mmol), potassium acetate (1.46 g, 14.9 mmol), and $PdCl_2(dppf)_2$ (1.90 g, 7.5 mmol) using a procedure similar to that described for compound 0602-107 (Example 34). LCMS: 167 [M−81]$^+$; $^1$HNMR (400 MHz, DMSO-d₆) δ 1.27 (s, 12H), 3.05 (s, 6H), 6.58 (d, J=8.8 Hz, 1H), 7.67 (dd, J=8.4, 1.6 Hz, 1H), 8.32 (d, J=1.2 Hz, 1H).

Step 64c: Ethyl 2-(((2-(6-(dimethylamino)pyridin-3-yl)-4-morpholinothieno[3,2-d]pyrimidin-6-yl)methyl)(methyl)amino)pyrimidine-5-carboxylate (Compound 0603-114)

The title compound 0603-114 was prepared (98 mg, 61%) as an off-white solid from 0504-54 (135 mg, 0.30 mmol), 0602-114 (149 mg, 0.60 mmol), NaHCO₃ (76 mg, 0.90 mmol), $(Ph_3P)_2PdCl_2$ (11 mg, 0.015 mmol) in toluene (2.5 mL), ethanol (1.6 mL) and water (0.7 mL) using a procedure similar to that described for compound 0603-107 (Example 34). LCMS: 535 [M+1]$^+$; $^1$HNMR (400 MHz, CDCl₃) δ 1.38 (t, J=7.2 Hz, 3H), 3.18 (s, 6H), 3.30 (s, 3H), 3.84 (t, J=4.8 Hz, 4H), 3.99 (t, J=4.8 Hz, 4H), 4.36 (q, J=7.2 Hz, 2H), 5.18 (s, 2H), 6.58 (d, J=9.2 Hz, 1H), 7.37 (s, 1H), 8.49 (d, J=7.6 Hz, 1H), 8.93 (s, 2H), 9.25 (d, J=2.0 Hz, 1H).

Step 64d: 2-(((2-(6-(Dimethylamino)pyridin-3-yl)-4-morpholinothieno[3,2-d]pyrimidin-6-yl)methyl)(methyl)amino)-N-hydroxypyrimidine-5-carboxamide (compound 114)

The title compound 114 was prepared (75 mg, 82%) as a yellow solid from 0603-114 (93 mg, 0.17 mmol) and freshly prepared hydroxylamine methanol solution (5 mL) using a procedure similar to that described for compound 3 (Example 1). m.p.: 190-195° C. LCMS: 522 [M+1]$^+$; $^1$HNMR (400 MHz, DMSO-d₆) δ 3.10 (s, 6H), 3.23 (s, 3H), 3.74 (s, 4H), 3.89 (s, 4H), 5.19 (s, 2H), 6.89 (d, J=7.6 Hz, 1H), 7.40 (s, 1H), 8.37 (d, J=7.2 Hz, 1H), 8.75 (s, 2H), 9.09 (s, 2H), 11.14 (d, J=1.2 Hz, 1H).

Example 65: preparation of 2-(((2-(2-(aminomethyl)pyrimidin-5-yl)-4-morpholinothieno[3,2-d]pyrimidin-6-yl)methyl)(methyl)amino)-N-hydroxypyrimidine-5-carboxamide (Compound 124)

Step 65a: Tert-butyl (5-bromopyrimidin-2-yl)methylcarbamate (Compound 0601-124)

A mixture of 5-bromo-2-methylpyrimidine (100 mg, 0.58 mmol), NBS (103 mg, 0.58 mmol), dibenzoyl peroxide (10 mg, 0.04 mmol) in tetrachloromethane (10 mL) was refluxed for 36 h. The solvent was removed in vacuo and the residue was purified by column chromatography on silica gel (ethyl acetate in petroleum ether, 1% v/v) to give 5-Bromo-2-(bromomethyl)pyrimidine (70 mg, 48%) as a white solid. $^1$HNMR (400 MHz, CDCl₃) δ 4.49 (s, 2H), 8.72 (s, 2H).

A solution of 5-Bromo-2-(bromomethyl)pyrimidine (350 mg, 1.4 mmol) in methanol (5 mL) was added to aqueous ammonia solution (25-28%, 10 mL) and stirred for 2 hours at room temperature. The solvent was removed followed by addition of ethanol (20 mL). The solvent was evaporated and to the residue was added dichloromethane (10 mL), triethylamine (379 mg, 3.72 mmol), Boc₂O (603 mg, 2.79 mmol), DMAP (22 mg, 0.19 nmmol). The resulting mixture was stirred for 2 hours at room temperature. The solvent was removed and purified by column chromatography on silica gel to give 0601-124 (380 mg, 82%) as a white solid. LCMS: 232 [M−56]$^+$; $^1$HNMR (400 MHz, DMSO-d₆) δ 1.38 (s, 9H), 4.28 (d, J=5.6 Hz, 2H), 7.30 (t, J=6.4 Hz, 1H), 8.95 (s, 2H).

Step 65b: Tert-butyl (5-(4,4,5,5-tetramethyl-1,3,2-dioxaborolan-2-yl) pyrimidin-2-yl)methylcarbamate (Compound 0602-124)

The title compound 0602-124 was prepared (410 mg, 93%) as a yellow oil from 0601-124 (380 mg, 1.3 mmol), bis(pinacolato)diboron (0.50 g, 2.0 mmol), potassium acetate (388 mg, 4.0 mmol), and $PdCl_2(dppf)_2$ (108 mg, 0.1 mmol) using a procedure similar to that described for compound 0602-107 (Example 34). LCMS: 198 [M−137]$^+$; $^1$HNMR (400 MHz, DMSO-d₆) δ 1.32 (s, 12H), 1.39 (s, 9H), 4.33 (d, J=6.0 Hz, 2H), 7.30 (t, J=6.0 Hz, 1H), 8.87 (s, 1H).

Step 65c: Ethyl 2-(((2-(2-(aminomethyl)pyrimidin-5-yl)-4-morpholinothieno[3,2-d]pyrimidin-6-yl)methyl)(methyl)amino)pyrimidine-5-carboxylate (Compound 0603-124)

The compound ethyl 2-(((2-(2-((tert-butoxycarbonylamino)methyl) pyrimidin-5-yl)-4-morpholinothieno[3,2-d]pyrimidin-6-yl)methyl)(methyl)amino)pyrimidine-5-carboxylate was prepared (248 mg, 66%) as a white solid from 0504-54 (270 mg, 0.6 mmol), 0602-124 (395 mg, 1.2 mmol), NaHCO₃ (152 mg, 1.8 mmol), $(Ph_3P)_2PdCl_2$ (21 mg, 0.03 mmol) in toluene (5 mL), ethanol (3.2 mL) and water (1.4 mL) using a procedure similar to that described for compound 0603-107 (Example 34). LCMS: 622 [M+1]$^+$; $^1$HNMR (400 MHz, CDCl₃) δ 1.39 (t, J=7.2 Hz, 3H), 1.49 (s, 9H), 3.33 (s, 3H), 3.87 (t, J=4.4 Hz, 4H), 4.01 (t, J=4.4 Hz, 4H), 4.37 (q, J=7.2 Hz, 2H), 4.68 (d, J=4.4 Hz, 2H), 5.21 (s, 2H), 5.79 (s, 1H), 7.40 (s, 1H), 8.94 (s, 2H), 9.62 (s, 2H).

To a solution of above compound (247 mg, 0.4 mmol) in $CH_2Cl_2$ (3 mL) was added TFA (1.5 mL) and stirred at room temperature for 4 h. Water (50 mL) was added and extracted with $CH_2Cl_2$ (200 mL). The organic layer was washed with saturated aqueous NaHCO₃, brine, dried and concentrated. The residue was recrystallized from ethyl acetate and petroleum ether (50% v/v) to give 0603-124 (300 mg, 100%) as an off-white solid. LCMS: 522 [M+1]$^+$; $^1$HNMR (400 MHz, CDCl₃) δ 1.28 (t, J=6.8 Hz, 3H), 3.26 (s, 3H), 3.75 (d, J=4.4

Hz, 4H), 3.94 (d, J=4.4 Hz, 6H), 4.26 (q, J=7.2 Hz, 2H), 5.23 (s, 2H), 7.51 (s, 1H), 8.86 (s, 2H), 9.54 (s, 2H).

Step 65d: 2-(((2-(2-(Aminomethyl)pyrimidin-5-yl)-4-morpholinothieno[3,2-d]pyrimidin-6-yl)methyl)(methyl)amino)-N-hydroxypyrimidine-5-carboxamide (Compound 124)

The title compound 124 was prepared (110 mg, 54%) as a yellow solid from 0603-124 (300 mg, 0.6 mmol) and freshly prepared hydroxylamine methanol solution (16 mL) using a procedure similar to that described for compound 3 (Example 1). m.p.: >300° C. LCMS: 509 [M+1]$^+$; $^1$HNMR (400 MHz, DMSO-$d_6$) δ 3.17 (s, 6H), 3.17 (s, 3H), 3.74 (s, 4H), 3.92 (s, 4H), 3.95 (s, 2H), 5.19 (s, 2H), 7.48 (s, 1H), 8.73 (s, 2H), 9.53 (s, 2H).

Example 66: Preparation of N-hydroxy-2-(methyl((4-morpholino-2-phenylthieno[3,2-d]pyrimidin-6-yl)methyl)amino)pyrimidine-5-carboxamide (Compound 129)

Step 66a: Ethyl 2-(methyl((4-morpholino-2-phenylthieno[3,2-d]pyrimidin-6-yl) methyl)amino)pyrimidine-5-carboxylate (Compound 0603-129)

The title compound 0603-129 was prepared (250 mg, 64%) as a yellow solid from 0504-54 (358 mg, 0.80 mmol), phenylboronic acid (195 mg, 1.60 mmol), $Cs_2CO_3$ (520 mg, 1.60 mmol) and Pd(dppf)$_2$Cl$_2$ (65 mg, 0.08 mmol) in 1,4-dioxane (6 mL) and water (0.2 mL) using a procedure similar to that described for compound 0603-107 (Example 34). LCMS: 491 [M+1]$^+$; $^1$H NMR (400 MHz, DMSO-$d_6$) δ 1.30 (t, J=7.2 Hz, 3H), 3.28 (s, 3H), 3.76 (t, J=4.8 Hz, 4H), 3.94 (t, J=4.8 Hz, 4H), 4.29 (q, J=7.2 Hz, 2H), 5.24 (s, 2H), 7.47-7.50 (m, 4H), 8.38-8.41 (m, 2H), 8.89 (s, 2H).

Step 66b: N-hydroxy-2-(methyl((4-morpholino-2-phenylthieno[3,2-d]pyrimidin-6-yl) methyl)amino)pyrimidine-5-carboxamide (Compound 129)

The title compound 129 was prepared (140 mg, 72%) as a yellow solid from 0603-129 (200 mg, 0.41 mmol) and freshly prepared hydroxylamine methanol solution (15 mL) using a procedure similar to that described for compound 3 (Example 1). m.p. 199-200° C. LCMS: 478 [M+1]$^+$; $^1$H NMR (400 MHz, DMSO-$d_6$) δ 3.23 (s, 3H), 3.76 (s, 4H), 3.93 (s, 4H), 5.20 (s, 2H), 7.47 (m, 4H), 8.39 (m, 2H), 8.75 (s, 2H).

Example 67: Preparation of N-hydroxy-2-(((2-(4-methoxyphenyl)-4-morpholinothieno[3,2-d]pyrimidin-6-yl)methyl)(methyl)amino)pyrimidine-5-carboxamide (compound 131)

Step 67a: Ethyl 2-(((2-(4-methoxyphenyl)-4-morpholinothieno[3,2-d]pyrimidin-6-yl)methyl)(methyl)amino)pyrimidine-5-carboxylate (Compound 0603-131)

The title compound 0603-131 was prepared (230 mg, 66%) as a yellow solid from 0504-54 (300 mg, 0.67 mmol), 4-methoxylphenylboronic acid (204 mg, 1.34 mmol), Pd(PPh$_3$)$_2$Cl$_2$ (24 mg, 0.03 mmol), NaHCO$_3$ (202 mg, 2.01 mmol) in toluene (5 mL), ethanol (3 mL), and water (1.3 mL) using a procedure similar to that described for compound 0603-107 (Example 34). LCMS: 521 [M+1]$^+$. $^1$H NMR (400 M Hz, DMSO-$d_6$) δ 1.30 (t, J=7.2 Hz, 3H), 3.27 (s, 1H), 3.75 (t, J=4.4 Hz, 4H), 3.82 (s, 3H), 3.91 (t, J=4.6 Hz, 4H), 4.29 (dd, J=7.2, 7.2 Hz, 2H), 5.22 (s, 2H), 7.02 (d, J=9.2 Hz, 2H), 7.45 (s, 1H), 8.33 (d, J=8.8 Hz, 2H), 8.88 (s, 2H).

Step 67b: N-hydroxy-2-(((2-(4-methoxyphenyl)-4-morpholinothieno[3,2-d]pyrimidin-6-yl)methyl)(methyl)amino)pyrimidine-5-carboxamide (Compound 131)

The title compound 131 was prepared (60 mg, 23%) as a yellow solid from 0603-131 (230 mg, 0.44 mmol) and freshly prepared hydroxylamine methanol solution (8 mL) using a procedure similar to that described for compound 3 (Example 1). m.p. 247° C. (Decomposed); LCMS: 509 [M+1]$^+$; $^1$H NMR (400 MHz, DMSO-$d_6$) δ 3.24 (s, 3H), 3.75-3.77 (m, 4H), 3.82 (s, 3H), 3.90-3.92 (m, 4H), 5.20 (s, 2H), 7.02 (d, J=8.4 Hz, 2H), 7.43 (s, 1H), 8.34 (d, J 8.4 Hz, 2H), 8.75 (s, 2H), 9.08 (br, 1H), 11.12 (br, 1H).

Example 68: Preparation of N-hydroxy-2-(((2-(4-hydroxyphenyl)-4-morpholinothieno[3,2-d]pyrimidin-6-yl)methyl)(methyl)amino)pyrimidine-5-carboxamide (Compound 133)

Step 68a: Ethyl 2-(((2-(4-hydroxyphenyl)-4-morpholinothieno[3,2-d]pyrimidin-6-yl) methyl)(methyl)amino)pyrimidine-5-carboxylate (Compound 0603-133)

The title compound 0603-133 was prepared (170 mg, 50%) as a yellow solid from 0504-54 (300 mg, 0.67 mmol), 4-hydroxylphenylboronic acid (111 mg, 0.802 mmol), NaHCO$_3$ (168 mg, 2.00 mmol), (Ph$_3$P)$_2$PdCl$_2$ (23 mg, 0.0334 mmol) in ethanol (2.3 mL), toluene (4 mL), and water (1 mL) using a procedure similar to that described for compound 0603-107 (Example 34). LCMS: 507 [M+1]$^+$. $^1$H NMR (400 MHz, DMSO-$d_6$) δ 1.30 (t, J=6.8 Hz, 3H), 3.27 (s, 3H), 3.75 (m, 4H), 3.90 (m, 4H), 4.29 (q, J=7.2 Hz, 2H), 5.22 (s, 2H), 6.84 (d, J=8.8 Hz, 2H), 7.43 (s, 1H), 8.23 (d, J=8.4 Hz, 2H), 8.88 (s, 2H), 9.81 (s, 1H).

Step 68b: N-hydroxy-2-(((2-(4-hydroxyphenyl)-4-morpholinothieno[3,2-d]pyrimidin-6-yl)methyl)(methyl)amino)pyrimidine-5-carboxamide (Compound 133)

The title compound 133 was prepared (69 mg, 42%) as a white solid from 0603-133 (170 mg, 0.336 mmol) and freshly prepared hydroxylamine methanol solution (10 mL) using a procedure similar to that described for compound 3 (Example 1). mp. 185-195° C. LCMS: 494 [M+1]$^+$. $^1$H NMR (400 MHz, DMSO-$d_6$) δ 3.23 (s, 3H), 3.75 (m, 4H), 3.90 (m, 4H), 5.19 (s, 2H), 6.84 (d, J=8.4 Hz, 2H), 7.40 (s, 1H), 8.23 (d, J=8.4 Hz, 2H), 8.75 (s, 2H), 9.90 (s, 2H).

Example 69: Preparation of 2-(((2-(4-(acetamidomethyl)phenyl)-4-morpholinothieno[3,2-d]pyrimidin-6-yl)methyl)(methyl)amino)-N-hydroxypyrimidine-5-carboxamide (Compound 136)

Step 69a: 2-(((2-(4-(Acetamidomethyl)phenyl)-4-morpholinothieno[3,2-d]pyrimidin-6-yl)methyl)(methyl)amino)-N-hydroxypyrimidine-5-carboxamide (Compound 136)

The title compound 136 was prepared (75 mg, 31%) as a white solid from ethyl 2-(((2-(4-(acetamidomethyl)phenyl)-

4-morpholinothieno[3,2-d]pyrimidin-6-yl) methyl)(methyl)amino)pyrimidine-5-carbo-xylate (250 mg, 0.45 mmol, example 48) and freshly prepared hydroxylamine methanol solution (20 mL) using a procedure similar to that described for compound 3 (Example 1). m.p. 178-180° C. LCMS: 549 [M+1]+; $^1$H NMR (400 MHz, DMSO-$d_6$) δ 1.89 (s, 3H), 3.23 (s, 3H), 3.76 (m, 4H), 3.91 (m, 4H), 4.31 (d, J=5.6 Hz, 2H), 5.20 (s, 2H), 7.34 (d, J=8.0 Hz, 2H), 7.45 (s, 1H), 8.33 (d, J=8.4 Hz, 2H), 8.41 (t, J=5.6 Hz, 1H), 8.75 (s, 2H).

Example 70: Preparation of 2-(((2-(4-carbamoylphenyl)-4-morpholinothieno[3,2-d]pyrimidin-6-yl)methyl)(methyl)amino)-N-hydroxypyrimidine-5-carboxamide (Compound 143)

Step 70a: 4-Bromobenzamide (Compound 0601-143)

To a solution of 4-bromobenzonitrile (2 g, 10 mol) in DMSO (6 mL) was added 30% $H_2O_2$ (5 g, 13 mmol) and $K_2CO_3$ at 0° C. and the mixture was stirred at room temperature for 30 min. The reaction mixture was poured into water and filtered. The collected solid was washed with water and dried to get the compound 0601-143 (2.1 g, 96%) as a white solid. LCMS: 200 [M+1]+; $^1$H NMR (400 MHz, DMSO-$d_6$) δ 7.48 (s, 1H), 7.67 (d, J=8.4 Hz, 2H), 7.81 (d, J=8.4 Hz, 2H), 8.06 (s, 1H).

Step 70b: 4-(4,4,5,5-Tetramethyl-1,3,2-dioxaborolan-2-yl)benzamide (Compound 0602-143)

The title compound 0602-143 was prepared (570 mg, 92%) from 0601-143 (500 mg, 2.5 mmol), bis(pinacolato)diboron (952 mg, 3.75 mmol), potassium acetate (735 mg, 7.5 mmol), and $PdCl_2(dppf)_2$ (61 mg, 0.075 mmol) using a procedure similar to that described for compound 0602-107 (Example 34). LCMS: 248 [M+1]+; $^1$H NMR (400 MHz, DMSO-$d_6$) δ 1.31 (s, 12H), 7.43 (s, 1H), 7.73 (d, J=8.4 Hz, 2H), 7.87 (d, J=7.6 Hz, 2H), 8.03 (s, 1H).

Step 70c: Ethyl 2-(((2-(4-carbamoylphenyl)-4-morpholinothieno[3,2-d]pyrimidin-6-yl)methyl)(methyl)amino)pyrimidine-5-carboxylate (Compound 0603-143)

The title compound 0603-143 was prepared (300 mg, 84%) as a yellow solid from 0504-54 (300 mg, 0.67 mmol), 0602-143 (330 mg, 1.34 mmol), $NaHCO_3$ (168 mg, 2.0 mmol), $(Ph_3P)_2PdCl_2$ (23 mg, 0.03 mmol) in toluene (5 mL), ethanol (3 mL) and water (1.3 mL) using a procedure similar to that described for compound 0603-107 (Example 34). LCMS: 534 [M+1]+. $^1$H NMR (400 MHz, DMSO-$d_6$) δ 1.30 (t, J=6.8 Hz, 3H), 3.28 (s, 3H), 3.77 (m, 4H), 3.93 (m, 4H), 4.28 (q, J=7.2 Hz, 2H), 5.24 (s, 2H), 7.45 (s, 1H), 7.51 (s, 1H), 7.97 (d, J=8.4 Hz, 2H), 8.07 (s, 1H), 8.43 (d, J=8.4 Hz, 2H), 8.88 (s, 2H).

Step 70d: 2-(((2-(4-Carbamoylphenyl)-4-morpholinothieno[3,2-d]pyrimidin-6-yl) methyl)(methyl)amino)-N-hydroxypyrimidine-5-carboxamide (Compound 143)

The title compound 143 was prepared (183 mg, 63%) as a yellow solid from 0603-143 (300 mg, 0.47 mmol) and freshly prepared hydroxylamine methanol solution (8 mL) using a procedure similar to that described for compound 3 (Example 1). mp 200-202° C. LCMS: 521 [M+1]+. $^1$H NMR (400 MHz, DMSO-$d_6$) δ 3.25 (s, 3H), 3.77 (m, 4H), 3.94 (m, 4H), 5.21 (s, 2H), 7.46 (s, 1H), 7.49 (s, 1H), 7.97 (d, J=8.4 Hz, 2H), 8.08 (s, 1H), 8.44 (d, J=8.4 Hz, 2H), 8.76 (s, 1H).

Example 71: Preparation of 2-(((2-(4-cyanophenyl)-4-morpholinothieno[3,2-d]pyrimidin-6-yl)methyl)(methyl)amino)-N-hydroxypyrimidine-5-carboxamide (Compound 146)

Step 71a: Ethyl 2-(((2-(4-cyanophenyl)-4-morpholinothieno[3,2-d]pyrimidin-6-yl) methyl)(methyl)amino)pyrimidine-5-carboxylate (Compound 0603-146)

The title compound 0603-146 was prepared (400 mg, 70%) as an off-white solid from 0504-54 (500 mg, 1.1 mmol), 4-cyanophenylboronic acid (245 mg, 1.67 mmol), $NaHCO_3$ (280 mg, 3.34 mmol), $(Ph_3P)_2PdCl_2$ (39 mg, 0.05 mmol) in toluene (5 mL), ethanol (3 mL) and water (1.3 mL) using a procedure similar to that described for compound 0603-107 (Example 34). LCMS: 516 [M+1]+. $^1$H NMR (400 MHz, $CDCl_3$) δ 1.39 (t, J=7.6 Hz, 3H), 3.32 (s, 3H), 3.87 (m, 4H), 4.02 (m, 4H), 4.36 (q, J=7.2 Hz, 2H), 5.21 (s, 2H), 7.39 (s, 1H), 7.74 (d, J=8.0 Hz, 2H), 8.53 (d, J=8.8 Hz, 2H), 8.93 (s, 2H).

Step 71b: 2-(((2-(4-Cyanophenyl)-4-morpholinothieno[3,2-d]pyrimidin-6-yl) methyl)(methyl)amino)-N-hydroxypyrimidine-5-carboxamide (Compound 146)

The title compound 146 was prepared (40 mg, 10%) as an off-white solid from 0603-146 (400 mg, 0.77 mmol) and freshly prepared hydroxylamine methanol solution (12 mL) using a procedure similar to that described for compound 3 (Example 1). mp 214-216° C. LCMS: 503 [M+1]+. $^1$H NMR (400 MHz, DMSO-$d_6$) δ 3.24 (s, 3H), 3.77 (m, 4H), 3.95 (m, 4H), 5.22 (s, 2H), 7.51 (s, 1H), 7.95 (d, J=8.4 Hz, 2H), 8.54 (d, J=8.2 Hz, 2H), 8.75 (s, 2H), 9.13 (s, 1H), 11.11 (s, 1H).

Example 72: Preparation of 2-(((2-(4-chlorophenyl)-4-morpholinothieno[3,2-d]pyrimidin-6-yl)methyl)(methyl)amino)-N-hydroxypyrimidine-5-carboxamide (compound 147)

Step 72a: Ethyl 2-(((2-(4-chlorophenyl)-4-morpholinothieno[3,2-d]pyrimidin-6-yl)methyl)(methyl)amino)pyrimidine-5-carboxylate (Compound 0603-147)

The title compound 0603-147 was prepared (250 mg, 73%) as a yellow solid from 0504-54 (300 mg, 0.67 mmol), 4-chlorophenylboronic acid (209 mg, 1.34 mmol), $Pd(PPh_3)_2Cl_2$ (24 mg, 0.03 mmol), $NaHCO_3$ (202 mg, 2.01 mmol) in toluene (5 mL), ethanol (3 mL), and water (1.3 mL) using a procedure similar to that described for compound 0603-107 (Example 34). LCMS: 525 [M+1]+. $^1$H NMR (400 M Hz, DMSO-$d_6$) δ 1.30 (t, J=7.0 Hz, 3H), 3.27 (s, 3H), 3.76 (t, J=4.8 Hz, 4H), 3.92 (t, J=4.8 Hz, 4H), 4.29 (dd, J=6.8, 7.2 Hz, 2H), 5.24 (s, 2H), 7.50 (s, 1H), 7.54 (d, J=8.8 Hz, 2H), 8.40 (d, J=8.4 Hz, 2H), 8.88 (s, 2H).

Step 72b: 2-(((2-(4-chlorophenyl)-4-morpholinothieno[3,2-d]pyrimidin-6-yl) methyl)(methyl)amino)-N-hydroxypyrimidine-5-carboxamide (Compound 147)

The title compound 147 was prepared (69 mg, 29%) as a white solid from 0603-147 (250 mg, 0.48 mmol) and freshly prepared hydroxylamine methanol solution (8 mL) using a procedure similar to that described for compound 3 (Example 1). mp. 153-153° C.; LCMS: 512 [M+1]+; $^1$H NMR (400 MHz, DMSO-$d_6$) δ 3.24 (s, 3H), 3.75-3.77 (m, 4H), 3.91-3.93 (m, 4H), 5.21 (s, 2H), 7.47 (s, 1H), 7.54 (d, J=7.6 Hz, 2H), 8.39 (d, J 8.0 Hz, 2H), 8.76 (s, 2H), 9.07 (br, 1H), 11.14 (br, 1H).

Example 73: Preparation of N-hydroxy-2-(((2-(4-isopropylphenyl)-4-morpholinothieno[3,2-d]pyrimidin-6-yl)methyl)(methyl)amino)pyrimidine-5-carboxamide (compound 148)

Step 73a: Ethyl 2-(((2-(4-isopropylphenyl)-4-morpholinothieno[3,2-d]pyrimidin-6-yl)methyl)(methyl)amino)pyrimidine-5-carboxylate (Compound 0603-148)

The title compound 0603-148 was prepared (250 mg, 73%) as a yellow solid from 0504-54 (300 mg, 0.67 mmol), 4-isopropylphenylboronic acid (220 mg, 1.34 mmol), Pd(PPh$_3$)$_2$Cl$_2$ (24 mg, 0.03 mmol), NaHCO$_3$ (202 mg, 2.01 mmol) in toluene (5 mL), ethanol (3 mL), and water (1.3 mL) using a procedure similar to that described for compound 0603-107 (Example 34). LCMS: 533 [M+1]+. $^1$H NMR (400 M Hz, DMSO-$d_6$) δ 1.24 (d, J=7.2 Hz, 6H), 1.30 (t, J=7.2 Hz, 3H), 2.90-2.98 (m, 1H), 3.27 (s, 3H), 3.76 (t, J=4.6 Hz, 4H), 3.92 (t, J=4.4 Hz, 4H), 4.29 (dd, J=7.2, 7.2 Hz, 2H), 5.23 (s, 2H), 7.34 (d, J=8.0 Hz, 2H), 7.48 (s, 1H), 8.30 (d, J=8.4 Hz, 2H), 8.88 (s, 2H).

Step 73b: N-hydroxy-2-(((2-(4-isopropylphenyl)-4-morpholinothieno[3,2-d]pyrimidin-6-yl)methyl)(methyl)amino)pyrimidine-5-carboxamide (Compound 148)

The title compound 148 was prepared (58 mg, 27%) as a white solid from 0603-148 (250 mg, 0.47 mmol) and freshly prepared hydroxylamine methanol solution (8 mL) using a procedure similar to that described for compound 3 (Example 1). mp. 155° C. (decomposed); LCMS: 520 [M+1]+; $^1$H NMR (400 MHz, DMSO-$d_6$) δ 1.24 (d, J=6.4 Hz, 6H), 2.92-2.98 (m, 1H), 3.24 (s, 3H), 3.75-3.77 (m, 4H), 3.91-3.93 (m, 4H), 5.20 (s, 2H), 7.34 (d, J=8.0 Hz, 2H), 7.46 (s, 1H), 8.30 (d, J 8.0 Hz, 2H), 8.76 (s, 2H), 9.08 (br, 1H), 11.10 (br, 1H).

Example 74: Preparation of N-hydroxy-2-(methyl((2-(4-(methylsulfonyl)phenyl)-4-morpholinothieno[3,2-d]pyrimidin-6-yl)methyl)amino)pyrimidine-5-carboxamide (Compound 149)

Step 74a: Ethyl 2-(methyl((2-(4-(methylsulfonyl)phenyl)-4-morpholinothieno[3,2-d]pyrimidin-6-yl)methyl)amino)pyrimidine-5-carboxylate (Compound 0603-149)

The title compound 0603-149 was prepared (250 mg, 77%) as a yellow solid from 0504-54 (300 mg, 0.67 mmol), 4-(methanesulfonyl)phenylboronic acid (268 mg, 1.34 mmol), Pd(PPh$_3$)$_2$Cl$_2$ (24 mg, 0.03 mmol), NaHCO$_3$ (202 mg, 2.01 mmol) in toluene (5 mL), ethanol (3 mL), and water (1.3 mL) using a procedure similar to that described for compound 0603-107 (Example 34). LCMS: 569 [M+1]+. $^1$H NMR (400 M Hz, DMSO-$d_6$) δ 1.30 (t, J=7.2 Hz, 3H), 3.27 (s, 3H), 3.28 (s, 3H), 3.76-3.78 (m, 4H), 3.95-3.97 (m, 4H), 4.29 (q, J=7.2 Hz, 2H), 5.25 (s, 2H), 7.54 (s, 1H), 8.03 (d, J=8.4 Hz, 2H), 8.61 (d, J=8.8 Hz, 2H), 8.88 (s, 2H).

Step 74b: N-hydroxy-2-(methyl((2-(4-(methylsulfonyl)phenyl)-4-morpholinothieno[3,2-d]pyrimidin-6-yl)methyl)amino)pyrimidine-5-carboxamide (Compound 149)

The title compound 149 was prepared (160 mg, 65%) as a white solid from 0603-149 (250 mg, 0.44 mmol) and freshly prepared hydroxylamine methanol solution (8 mL) using a procedure similar to that described for compound 3 (Example 1). mp. 206-208° C.; LCMS: 556 [M+1]+; $^1$H NMR (400 MHz, DMSO-$d_6$) δ 3.24 (s, 3H), 3.26 (s, 3H), 3.77 (t, J=4.4 Hz, 4H), 3.96 (t, J=4.4 Hz, 4H), 5.22 (s, 2H), 7.52 (s, 1H), 8.03 (d, J=8.4 Hz, 2H), 8.61 (d, J 8.8 Hz, 2H), 8.75 (s, 2H), 9.06 (br, 1H), 11.13 (br, 1H).

Example 75: Preparation of 2-(((2-(4-fluorophenyl)-4-morpholinothieno[3,2-d]pyrimidin-6-yl)methyl)(methyl)amino)-N-hydroxypyrimidine-5-carboxamide (Compound 200)

Step 75a: Ethyl 2-(((2-(4-fluorophenyl)-4-morpholinothieno[3,2-d]pyrimidin-6-yl)methyl)(methyl)amino)pyrimidine-5-carboxylate (Compound 0603-200)

The title compound 0603-200 was prepared (300 mg, 76%) as a white solid from 0504-54 (350 mg, 0.78 mmol), 4-fluorophenylboronic acid (164 mg, 1.17 mmol), Pd(PPh$_3$)$_2$Cl$_2$ (27 mg, 0.039 mmol), NaHCO$_3$ (196 mg, 2.34 mmol) in toluene (8 mL), ethanol (5 mL), and water (2 mL) using a procedure similar to that described for compound 0603-107 (Example 34). LCMS: 509 [M+1]+; $^1$H NMR (400 MHz, CDCl$_3$): δ 1.31 (t, J=7.2 Hz, 3H), 3.24 (s, 3H) 3.80 (t, J=4.8 Hz, 4H), 3.94 (t, J=4.6 Hz, 4H), 4.30 (q, J=7.1 Hz, 2H), 5.13 (s, 2H), 7.04-7.08 (m, 2H), 7.30 (s, 1H), 8.34-8.37 (m, 2H), 8.86 (s, 2H).

Step 75b: 2-(((2-(4-fluorophenyl)-4-morpholinothieno[3,2-d]pyrimidin-6-yl) methyl)(methyl)amino)-N-hydroxypyrimidine-5-carboxamide (Compound 200)

The title compound 200 was prepared (240 mg, 82%) as an off-white solid from 0603-200 (300 mg, 0.59 mmol) and freshly prepared hydroxylamine methanol solution (16 mL) using a procedure similar to that described for compound 3 (Example 1). m.p. 168-170° C. LCMS: 496 [M+1]+; $^1$H NMR (400 MHz, DMSO-$d_6$): δ 3.23 (s, 3H), 3.76 (t, J=4.6 Hz, 4H), 3.92 (t, J=4.4 Hz, 4H), 5.20 (s, 2H), 7.28-7.32 (m, 2H), 7.46 (s, 1H), 8.41-8.45 (m, 2H), 8.74 (s, 2H), 9.05 (s, 1H), 11.12 (s, 1H).

Example 76: Preparation of N-hydroxy-2-(methyl((4-morpholino-2-p-tolylthieno[3,2-d]pyrimidin-6-yl)methyl)amino)pyrimidine-5-carboxamide (Compound 201)

Step 76a: Ethyl 2-(methyl((4-morpholino-2-p-tolylthieno[3,2-d]pyrimidin-6-yl)methyl)amino)pyrimidine-5-carboxylate (Compound 0603-201)

The title compound 0603-201 was prepared (306 mg, 78%) as a white solid from 0504-54 (350 mg, 0.78 mmol), 4-methylphenylboronic acid (212 mg, 1.56 mmol), Pd(PPh$_3$)

$_2Cl_2$ (27 mg, 0.039 mmol), $NaHCO_3$ (196 mg, 2.34 mmol) in toluene (8 mL), ethanol (5 mL), and water (2 mL) using a procedure similar to that described for compound 0603-107 (Example 34). LCMS: 505 [M+1]$^+$; $^1$H NMR (400 MHz, $CDCl_3$): δ 1.31 (t, J=7.0 Hz, 3H), 2.34 (s, 3H), 3.23 (s, 3H), 3.79 (t, J=4.8 Hz, 4H), 3.93 (t, J=4.8 Hz, 4H), 4.29 (q, J=7.2 Hz, 2H), 5.12 (s, 2H), 7.19 (d, J=8.0 Hz, 2H), 7.31 (s, 1H), 8.24 (d, J=8.0 Hz, 2H), 8.86 (s, 2H).

Step 76b: N-Hydroxy-2-(methyl((4-morpholino-2-p-tolylthieno[3,2-d]pyrimidin-6-yl)methyl)amino)pyrimidine-5-carboxamide (Compound 201)

The title compound 201 was prepared (27 mg, 9%) as an off-white solid from 0603-201 (306 mg, 0.61 mmol) and freshly prepared hydroxylamine methanol solution (16 mL) using a procedure similar to that described for compound 3 (Example 1). m.p.: 170-172° C. LCMS: 492 [M+1]$^+$; $^1$H NMR (400 MHz, DMSO-$d_6$): δ 2.35 (s, 3H), 3.22 (s, 3H), 3.75 (m, 4H), 3.90 (m, 4H), 5.19 (s, 2H), 7.27 (d, J=7.6 Hz, 2H), 7.43 (s, 1H), 8.27 (d, J=8.4 Hz, 2H), 8.73 (s, 2H).

Example 77: Preparation of N-hydroxy-2-(methyl((4-morpholino-2-(4-(trifluoromethyl)phenyl)thieno[3,2-d]pyrimidin-6-yl)methyl)amino)pyrimidine-5-carboxamide (Compound 202)

Step 77a: Ethyl 2-(methyl((4-morpholino-2-(4-(trifluoromethyl)phenyl)thieno[3,2-d]pyrimidin-6-yl)methyl)amino)pyrimidine-5-carboxylate (Compound 0603-202)

The title compound 0603-202 was prepared (527 mg, crude) as a white solid from 0504-54 (350 mg, 0.78 mmol), 4-trifluoromethylphenylboronic acid (296 mg, 1.56 mmol), Pd(PPh$_3$)$_2$Cl$_2$ (27 mg, 0.039 mmol), NaHCO$_3$ (196 mg, 2.34 mmol) in toluene (8 mL), ethanol (5 mL), and water (2 mL) using a procedure similar to that described for compound 0603-107 (Example 34). LCMS: 559 [M+1]$^+$; $^1$H NMR (400 MHz, CDCl$_3$): δ 1.32 (t, J=7.0 Hz, 3H), 3.24 (s, 3H), 3.81 (t, J=4.8 Hz, 4H), 3.96 (t, J=4.6 Hz, 4H), 4.30 (q, J=7.1 Hz, 2H), 5.12 (s, 2H), 7.34 (s, 1H), 7.63 (d, J=8.4 Hz, 2H), 8.45 (d, J=8.0 Hz, 2H), 8.86 (s, 2H).

Step 77b: N-Hydroxy-2-(methyl((4-morpholino-2-(4-(trifluoromethyl)phenyl) thieno[3,2-d]pyrimidin-6-yl)methyl)amino)pyrimidine-5-carboxamide (Compound 202)

The title compound 202 was prepared (162 mg, 38%) as an off-white solid from 0603-202 (527 mg, crude) and freshly prepared hydroxylamine methanol solution (16 mL) using a procedure similar to that described for compound 3 (Example 1). m.p. 222-223° C. LCMS: 546 [M+1]$^+$; $^1$H NMR (400 MHz, DMSO-$d_6$): δ 3.23 (s, 3H), 3.76 (t, J=4.4 Hz, 4H), 3.94 (t, J=4.2 Hz, 4H), 5.21 (s, 2H), 7.50 (s, 1H), 7.84 (d, J=8.8 Hz, 2H), 8.57 (d, J=8.4 Hz, 2H), 8.74 (s, 2H), 9.06 (s, 1H), 11.13 (s, 1H).

Example 78: Preparation of N-hydroxy-2-(methyl((2-(4-(methylamino) phenyl)-4-morpholinothieno[3,2-d]pyrimidin-6-yl)methyl)amino)pyrimidine-5-carboxamide (Compound 151)

Step 78a: 4-Bromo-N-methylbenzenamine (Compound 0601-151) and 4-bromo-N,N-dimethylbenzenamine (Compound 0601-152)

To a solution of 4-bromobenzenamine (3 g, 17.4 mmol) and K$_2$CO$_3$ (3.62 g, 26.2 mmol) in THF (30 mL) was added methyl iodide (2.2 ml, 34.8 mmol) at room temperature and stirred overnight. Water (6 mL) was added to the reaction mixture and the mixture was extracted with ethyl acetate (50 mL×3). The organic layer was dried, concentrated and purified by column chromatography on silica gel (ethyl acetate in petroleum ether, 10% v/v) to give 0601-151 (840 mg, 26%) as a white solid LCMS: 187 [M+1]$^+$. $^1$H NMR (400 MHz, DMSO-$d_6$) δ 2.63 (s, 3H), 5.85 (br, 1H), 6.48 (d, J=9.2 Hz, 2H), 7.20 (d, J=8.4 Hz, 2H) and 0601-152 (680 mg, 20%) as a white solid. LCMS: 201 [M+1]$^+$. $^1$H NMR (400 MHz, DMSO-$d_6$) δ 2.87 (s, 6H), 6.65 (d, J=9.2 Hz, 2H), 7.29 (d, J=8.8 Hz, 2H).

Step 78b: N-methyl-4-(4,4,5,5-tetramethyl-1,3,2-dioxaborolan-2-yl)benzenamine (Compound 0602-151)

The title compound 0602-151 was prepared (301 mg, 60%) as a white solid from 0601-151 (400 mg, 2.15 mmol), bis(pinacolato)diboron (819 mg, 3.23 mmol), potassium acetate (632 mg, 6.4 mmol) and Pd(dppf)$_2$Cl$_2$ (351 mg, 0.43 mmol) using a procedure similar to that described for compound 0602-107 (Example 34). LCMS: 234 [M+1]$^+$. $^1$H NMR (400 MHz, DMSO-$d_6$) δ 1.24 (s, 12H), 2.67 (d, J=5.2 Hz, 3H), 6.04 (br, 1H), 6.48 (d, J=8.4 Hz, 2H), 7.39 (d, J=8.4 Hz, 2H).

Step 78c: Ethyl 2-(methyl((2-(4-(methylamino)phenyl)-4-morpholinothieno[3,2-d]pyrimidin-6-yl)methyl)amino)pyrimidine-5-carboxylate (Compound 0603-151)

The title compound 0603-151 was prepared (100 mg, 64%) as a white solid from 0504-54 (135 mg, 0.3 mmol), 0602-151 (100 mg, 0.42 mmol), Pd(PPh$_3$)$_2$Cl$_2$ (10.5 mg, 0.015 mmol), NaHCO$_3$ (76 mg, 0.9 mmol) in toluene (2.5 mL), ethanol (1.6 mL), and water (0.7 mL) using a procedure similar to that described for compound 0603-107 (Example 34). LCMS: 520 [M+1]$^+$. $^1$H NMR (400 MHz, DMSO-$d_6$) δ 1.30 (t, J=7.2 Hz, 3H), 2.73 (d, J=4.8 Hz, 3H), 3.26 (s, 3H), 3.75 (m, 4H), 3.88 (m, 4H), 4.29 (q, J=7.2 Hz, 2H), 5.21 (s, 2H), 6.10 (m, 1H), 6.58 (d, J=8.8 Hz, 2H), 7.39 (s, 1H), 8.15 (d, J=8.4 Hz, 2H), 8.88 (d, J=4.8 Hz, 2H).

Step 78d: N-hydroxy-2-(methyl((2-(4-(methylamino)phenyl)-4-morpholinothieno[3,2-d]pyrimidin-6-yl)methyl)amino)pyrimidine-5-carboxamide (Compound 151)

The title compound 151 was prepared (40 mg, 42%) as a yellow solid from 0603-151 (100 mg, 0.19 mmol) and freshly prepared hydroxylamine methanol solution (6 mL) using a procedure similar to that described for compound 3 (Example 1). m.p.: 218-220° C. LCMS: 507 [M+1]$^+$. $^1$H NMR (400 MHz, DMSO-$d_6$) δ 2.73 (d, J=4.4 Hz, 3H), 3.75 (d, J=4.0 Hz, 4H), 3.87 (d, J=4.0 Hz, 4H), 5.18 (s, 2H), 6.11 (d, J=4.8 Hz, 1H), 6.58 (d, J=8.0 Hz, 2H), 7.37 (s, 1H), 8.15 (d, J=8.4 Hz, 2H), 8.75 (s, 2H), 9.06 (s, 1H), 11.13 (br, 1H).

Example 79: Preparation of 2-(((2-(4-(dimethylamino)phenyl)-4-morpholinothieno[3,2-d]pyrimidin-6-yl)methyl)(methyl)amino)-N-hydroxypyrimidine-5-carboxamide (Compound 152)

Step 79a: N,N-dimethyl-4-(4,4,5,5-tetramethyl-1,3,2-dioxaborolan-2-yl)benzenamine (Compound 0602-152)

The title compound 0602-152 was prepared (360 mg, 61%) as a white solid from 0601-152 (480 mg, 2.4 mmol), bis(pinacolato)diboron (914 mg, 3.6 mmol), potassium acetate (706 mg, 7.2 mmol) and Pd(dppf)$_2$Cl$_2$ (390 mg, 0.48 mmol) using a procedure similar to that described for compound 0602-107 (Example 34). LCMS: 248 [M+1]$^+$. $^1$H NMR (400 MHz, DMSO-d$_6$) δ 1.25 (s, 12H), 2.93 (s, 6H), 6.66 (d, J=8.8 Hz, 2H), 7.48 (d, J=8.8 Hz, 2H).

Step 79b: Ethyl 2-(((2-(4-(dimethylamino)phenyl)-4-morpholinothieno[3,2-d]pyrimidin-6-yl)methyl)(methyl)amino)pyrimidine-5-carboxylate (Compound 0603-152)

The title compound 0603-152 was prepared (100 mg, 53%) as a white solid from 0504-54 (161 mg, 0.36 mmol), 0602-152 (150 mg, 0.61 mmol), Pd(PPh$_3$)$_2$Cl$_2$ (13 mg, 0.018 mmol), NaHCO$_3$ (91 mg, 1.08 mmol) in toluene (2.5 mL), ethanol (1.6 mL), and water (0.7 mL) using a procedure similar to that described for compound 0603-107 (Example 34). LCMS: 534 [M+1]$^+$. $^1$H NMR (400 MHz, DMSO-d$_6$) δ 1.22 (m, 3H), 2.97 (s, 6H), 3.22 (s, 3H), 3.74 (m, 4H), 3.87 (m, 4H), 4.14 (m, 2H), 5.17 (s, 2H), 6.75 (d, J=8.8 Hz, 2H), 7.37 (s, 1H), 8.20 (d, J=9.2 Hz, 2H), 8.73 (s, 2H).

Step 79c: 2-(((2-(4-(dimethylamino)phenyl)-4-morpholinothieno[3,2-d]pyrimidin-6-yl)methyl)(methyl)amino)-N-hydroxypyrimidine-5-carboxamide (Compound 152)

The title compound 152 was prepared (30 mg, 30%) as a yellow solid from 0603-152 (100 mg, 0.19 mmol) and freshly prepared hydroxylamine methanol solution (6 mL) using a procedure similar to that described for compound 3 (Example 1). m.p.: 208-210° C. LCMS: 521 [M+1]$^+$. $^1$H NMR (400 MHz, DMSO-d$_6$) δ 2.98 (s, 6H), 3.23 (s, 3H), 3.76 (d, J=4.0 Hz, 4H), 3.89 (s, 4H), 5.18 (s, 2H), 6.76 (d, J=8.8 Hz, 2H), 7.39 (s, 1H), 8.22 (d, J=8.4 Hz, 2H), 8.75 (s, 2H), 9.07 (br, 1H).

Example 80: Preparation of 2-(((2-(4-(ethylamino)phenyl)-4-morpholinothieno[3,2-d]pyrimidin-6-yl)methyl)(methyl)amino)-N-hydroxypyrimidine-5-carboxamide (Compound 153)

Step 80a: 4-Bromo-N-ethylbenzenamine (Compound 0601-153)

To a solution of 4-bromobenzenamine (2.00 g, 11.67 mmol) and iodoethane (5.50 g, 35.28 mmol) in CH$_3$CN (50 mL) was added K$_2$CO$_3$ (6.48 g, 47.04 mmol). The mixture was stirred at 60° C. overnight. The reaction mixture was concentrated in vacuo and the residue was purified by column chromatography on silica gel (ethyl acetate in petroleum ether, 0%-10% v/v) to give compound 0601-153 (800 mg, 38%) as a light yellow oil. LCMS: 200 [M+1]$^+$; $^1$H NMR (400 MHz, DMSO-d$_6$): δ 1.13 (t, J=6.8 Hz, 3H), 2.97 (m, 2H), 5.73 (br s, 1H), 6.48 (d, J=8.8 Hz, 2H), 7.17 (d, J=8.8 Hz, 2H).

Step 80b: N-ethyl-4-(4,4,5,5-tetramethyl-1,3,2-dioxaborolan-2-yl)benzenamine (Compound 0602-153)

The title compound 0602-153 was prepared (640 mg, 72%) as a white solid from 0601-153 (884 mg, 4.420 mmol), bis(pinacolato)diboron (1.68 g, 6.630 mmol), potassium acetate (1.30 g, 13.3 mmol) and Pd(dppf)$_2$Cl$_2$ (362 mg, 0.44 mmol) using a procedure similar to that described for compound 0602-107 (Example 34). LCMS: 248 [M+1]$^+$; $^1$H NMR (400 MHz, DMSO-d$_6$): δ 1.13 (m, 15H), 3.03 (m, 2H), 5.94 (br s, 1H), 6.49 (d, J=8.4 Hz, 2H), 7.37 (d, J=8.8 Hz, 2H).

Step 80c: Ethyl 2-(((2-(4-(ethylamino)phenyl)-4-morpholinothieno[3,2-d]pyrimidin-6-yl)methyl)(methyl)amino)pyrimidine-5-carboxylate (Compound 0603-153)

The title compound 0603-153 was prepared (200 mg, 71%) as a white solid from 0504-54 (240 mg, 0.53 mmol), 0602-153 (172 mg, 0.69 mmol), Pd(PPh$_3$)$_2$Cl$_2$ (37 mg, 0.053 mmol), NaHCO$_3$ (134 mg, 1.6 mmol) in toluene (8 mL), ethanol (5 mL), and water (2 mL) using a procedure similar to that described for compound 0603-107 (Example 34). LCMS: 534 [M+1]$^+$; $^1$H NMR (400 MHz, DMSO-d$_6$): δ 1.17 (t, J=7.2 Hz, 3H), 2.29 (t, J=7.6 Hz, 3H), 3.09 (m, 2H), 3.25 (s, 3H), 3.73 (br s, 4H), 3.87 (br s, 4H), 4.27 (m, 2H), 5.20 (s, 2H), 6.02 (t, J=4.8 Hz, 1H), 6.58 (d, J=8.8 Hz, 2H), 7.37 (s, 1H), 8.12 (d, J=8.8 Hz, 2H), 8.87 (s, 2H). P49.

Step 80d: 2-(((2-(4-(Ethylamino)phenyl)-4-morpholinothieno[3,2-d]pyrimidin-6-yl) methyl)(methyl)amino)-N-hydroxypyrimidine-5-carboxamide (Compound 153)

The title compound 153 was prepared (110 mg, 56%) as an off-white solid from 0603-153 (200 mg, 0.38 mmol) and freshly prepared hydroxylamine methanol solution (8 mL) using a procedure similar to that described for compound 3 (Example 1). m.p.: 185-187° C.; LCMS: 521 [M+1]$^+$; $^1$H NMR (400 MHz, DMSO-d$_6$): δ 1.18 (t, J=6.8 Hz, 3H), 3.09 (m, 2H), 3.23 (s, 3H), 3.75 (br s, 4H), 3.87 (br s, 4H), 5.18 (s, 2H), 6.02 (t, J=4.8 Hz, 1H), 6.59 (d, J=8.8 Hz, 2H), 7.36 (s, 1H), 8.13 (d, J=8.4 Hz, 2H), 8.74 (s, 2H), 9.06 (s, 1H), 11.13 (s, 1H).

Example 81: Preparation of 2-(((2-(4-(Diethylamino)phenyl)-4-morpholinothieno[3,2-d]pyrimidin-6-yl)methyl)(methyl)amino)-N-hydroxypyrimidine-5-carboxamide (Compound 154)

Step 81a: 4-Bromo-N,N-diethylbenzenamine (Compound 0601-154)

The title compound 0601-154 (1.10 g, 40%) was synthesized according to the synthetic procedure of making compound 0601-153 using 4-bromobenzenamine (2.00 g, 11.67 mmol) and iodoethane (5.50 g, 35.28 mmol) as starting material. LCMS: 228 [M+1]$^+$; $^1$H NMR (400 MHz, DMSO-d$_6$): δ 1.05 (t, J=7.2 Hz, 6H), 3.30 (m, 4H), 6.58 (d, J=8.8 Hz, 2H), 7.22 (d, J=8.8 Hz, 2H).

Step 81b: N,N-diethyl-4-(4,4,5,5-tetramethyl-1,3,2-dioxaborolan-2-yl)benzenamine (Compound 0602-154)

The title compound 0602-154 was prepared (860 mg, 63%) as a white solid from 0601-154 (1.21 g, 5.33 mmol), bis(pinacolato)diboron (2.03 g, 8.00 mmol), potassium acetate and Pd(dppf)$_2$Cl$_2$ using a procedure similar to that described for compound 0602-107 (Example 34). LCMS: 276 [M+1]$^+$; $^1$H NMR (400 MHz, DMSO-d$_6$): δ 1.06 (t, J=6.8 Hz, 6H), 1.24 (s, 12H), 3.34 (m, 4H), 6.60 (d, J=8.4 Hz, 2H), 7.44 (d, J=8.8 Hz, 2H).

Step 81c: Ethyl 2-(((2-(4-(diethylamino)phenyl)-4-morpholinothieno[3,2-d]pyrimidin-6-yl)methyl)(methyl)amino)pyrimidine-5-carboxylate (Compound 0603-154)

The title compound 0603-154 was prepared (260 mg, 85%) as a white solid from 0504-54 (240 mg, 0.53 mmol), 0602-154 (220 mg, 0.8 mmol), Pd(PPh$_3$)$_2$Cl$_2$, NaHCO$_3$ in toluene (8 mL), ethanol (5 mL), and water (2 mL) using a procedure similar to that described for compound 0603-107 (Example 34). LCMS: 562 [M+1]$^+$; $^1$H NMR (400 MHz, DMSO-d$_6$): δ 1.12 (t, J=7.2 Hz, 6H), 1.29 (t, J=6.8 Hz, 3H), 3.25 (s, 3H), 3.40 (m, 4H), 3.74 (br s, 4H), 3.87 (br s, 4H), 4.27 (m, 2H), 5.20 (s, 2H), 6.69 (d, J=8.8 Hz, 2H), 7.39 (s, 1H), 8.18 (d, J=8.8 Hz, 2H), 8.87 (s, 2H).

Step 81d: 2-(((2-(4-(Diethylamino)phenyl)-4-morpholinothieno[3,2-d]pyrimidin-6-yl)methyl)(methyl)amino)-N-hydroxypyrimidine-5-carboxamide (Compound 154)

The title compound 154 was prepared (180 mg, 71%) as an off-white solid from 0603-154 (260 g, 0.463 mmol) and freshly prepared hydroxylamine methanol solution (8 mL) using a procedure similar to that described for compound 3 (Example 1). m.p.: 192-196° C.; LCMS: 549 [M+1]$^+$; $^1$H NMR (400 MHz, DMSO-d$_6$): δ 1.12 (t, J=7.2 Hz, 6H), 3.23 (s, 3H), 3.41 (m, 4H), 3.75 (br s, 4H), 3.87 (br s, 4H), 5.18 (s, 2H), 6.70 (d, J=8.8 Hz, 2H), 7.37 (s, 1H), 8.19 (d, J=8.8 Hz, 2H), 8.74 (s, 2H), 9.06 (s, 1H), 11.11 (s, 1H).

Example 82: Preparation of N-hydroxy-2-(methyl ((4-morpholino-2-(4-(pyrrolidin-1-yl)phenyl)thieno [3,2-d]pyrimidin-6-yl)methyl)amino)pyrimidine-5-carboxamide (Compound 155)

Step 82a: 1-(4-Bromophenyl)pyrrolidine (Compound 0601-155)

A mixture of 4-bromoaniline (1 g, 5.81 mmol), Cs$_2$CO$_3$ (5.68 g, 17.44 mmol), 1,4-dibromobutane (1.88 g, 8.72 mmol) in DMF (20 mL) was stirred at 60° C. overnight. After cooled to room temperature, the mixture was diluted with water (200 mL) and extracted with ethyl acetate (2×100 mL). The organic layer was washed with water (3×100 mL) and brine (100 mL), dried over Na$_2$SO$_4$, concentrated and purified by column chromatography on silica gel (petroleum ether) to give compound 0601-155 (720 mg, 46%) as a colorless oil. LCMS: 226 [M+1]$^+$. $^1$H NMR (400 MHz, DMSO-d$_6$) δ 1.94 (t, J=6.4 Hz, 4H), 3.18 (t, J=6.4 Hz, 4H), 6.47 (d, J=9.2 Hz, 1H), 7.27 (d, J=9.2 Hz, 1H).

Step 82b: 1-(4-(4,4,5,5-Tetramethyl-1,3,2-dioxaborolan-2-yl)phenyl)pyrrolidineate (Compound 0602-155)

The title compound 0602-155 was prepared (500 mg, 57%) as a yellow solid from 0601-155 (720 mg, 3.18 mmol), bis(pinacolato)diboron (1.21 g, 4.78 mmol), AcOK (938 mg, 9.56 mmol), PdCl$_2$(dppf)$_2$ (78 mg, 0.0956 mmol) using a procedure similar to that described for compound 0602-107 (Example 34). LCMS: 274 [M+1]$^+$. $^1$H NMR (400 MHz, DMSO-d$_6$) δ 1.25 (s, 12H), 1.95 (t, J=6.8 Hz, 4H), 3.23 (t, J=6.4 Hz, 4H), 6.49 (d, J=8.8 Hz, 1H), 7.46 (d, J=8.4 Hz, 1H).

Step 82c: Ethyl 2-(methyl((4-morpholino-2-(4-(pyrrolidin-1-yl)phenyl)thieno[3,2-d]pyrimidin-6-yl)methyl)amino)pyrimidine-5-carboxylate (Compound 0603-155)

The title compound 0603-155 was prepared (320 mg, 86%) as a yellow solid from 0504-54 (300 mg, 0.668 mmol), 0602-155 (219 mg, 0.80 mmol), NaHCO$_3$ (168 mg, 2.00 mmol), (Ph$_3$P)$_2$PdCl$_2$ (23 mg, 0.033 mmol) in ethanol (2.3 mL), toluene (4 mL) and water (1 mL) using a procedure similar to that described for compound 0603-107 (Example 34). LCMS: 560 [M+1]$^+$. $^1$H NMR (400 MHz, DMSO-d$_6$) δ 1.30 (t, J=7.6 Hz, 3H), 1.98 (m, 4H), 3.26 (s, 3H), 3.30 (m, 4H), 3.75 (m, 4H), 3.90 (m, 4H), 4.29 (q, J=6.8 Hz, 2H), 5.22 (s, 2H), 6.59 (d, J=8.8 Hz, 2H), 7.40 (s, 1H), 8.21 (d, J=8.8 Hz, 2H), 8.88 (s, 2H).

Step 82d: N-Hydroxy-2-(methyl((4-morpholino-2-(4-(pyrrolidin-1-yl)phenyl) thieno[3,2-d]pyrimidin-6-yl)methyl)amino)pyrimidine-5-carboxamide (Compound 155)

The title compound 155 was prepared (55 mg, 28%) as a yellow solid from 0603-155 (200 mg, 0.49 mmol) and freshly prepared hydroxylamine methanol solution (10 mL) using a procedure similar to that described for compound 3 (Example 1). mp. 187-192° C. LCMS: 547 [M+1]$^+$. $^1$H NMR (400 MHz, DMSO-d$_6$) δ 1.97 (m, 4H), 3.23 (s, 3H), 3.30 (m, 4H), 3.76 (m, 4H), 3.88 (m, 4H), 5.18 (s, 2H), 6.59 (d, J=8.8 Hz, 2H), 7.37 (s, 1H), 8.21 (d, J=8.4 Hz, 2H), 8.75 (s, 2H), 9.06 (s, 1H), 11.12 (s, 1H).

Example 83: Preparation of 2-(((2-(3,4-diaminophenyl)-4-morpholinothieno[3,2-d]pyrimidin-6-yl)methyl)(methyl)amino)-N-hydroxypyrimidine-5-carboxamide (Compound 156)

Step 83a: 4-(4,4,5,5-Tetramethyl-1,3,2-dioxaborolan-2-yl)benzene-1,2-diamine (Compound 0602-156)

The title compound 0602-156 was prepared (1.0 g, 43%) as a yellow solid from 4-bromobenzene-1,2-diamine (1.87 g, 10 mmol), bis(pinacolato)diboron (3.9 g, 15 mmol), Pd(dppf)$_2$Cl$_2$ (817 mg, 1 mmol) and AcOK (2.9 g, 30 mmol) using a procedure similar to that described for compound 0602-107 (Example 34). LCMS: 235 [M+1]$^+$, $^1$H NMR (400 MHz, DMSO-d$_6$) δ 1.23 (s, 12H), 4.38 (s, 2H), 4.82 (s, 2H), 6.46 (d, J=7.6 Hz, 1H), 6.77 (dd, J=7.6, 0.8 Hz, 1H), 6.88 (d, J=0.8 Hz, 1H).

Step 83b: Ethyl 2-(((2-(3,4-diaminophenyl)-4-morpholinothieno[3,2-d]pyrimidin-6-yl) methyl)(methyl)amino)pyrimidine-5-carboxylate (Compound 0603-156)

The title compound 0603-156 was prepared (300 mg, 86%) as a white solid from 0504-54 (300 mg, 0.67 mmol), 0602-156 (190 mg, 0.80 mmol), NaHCO$_3$ (169 mg, 2.0 mmol), CsF (203 mg, 1.34 mmol), (Ph$_3$P)$_2$PdCl$_2$ (47 mg, 0.067 mmol) in toluene (4 mL), ethanol (2 mL) and water (0.5 mL) using a procedure similar to that described for compound 0603-107 (Example 34). LCMS: 521 [M+1]$^+$; $^1$H NMR (400 MHz, DMSO-d$_6$): δ 1.30 (t, J=7.2 Hz, 3H), 3.26 (s, 3H), 3.75 (m, 4H), 3.87 (m, 4H), 4.29 (q, J=7.2 Hz, 2H), 4.55 (s, 2H), 4.89 (s, 2H), 5.21 (s, 2H), 6.54 (d, J=8.4 Hz, 1H), 7.36 (s, 1H), 7.52 (dd, J=8.4, 2.0 Hz, 1H), 7.63 (d, J=2.0 Hz, 1H), 8.88 (s, 2H).

Step 83c: 2-(((2-(3,4-diaminophenyl)-4-morpholinothieno[3,2-d]pyrimidin-6-yl) methyl)(methyl) amino)-N-hydroxypyrimidine-5-carboxamide (Compound 156)

The title compound 156 was prepared (128 mg, 44%) as a yellow solid from 0603-156 (300 mg, 0.58 mmol) and freshly prepared hydroxylamine methanol solution (20 mL) using a procedure similar to that described for compound 3 (Example 1). m.p. 222-225° C. LCMS: 508 [M+1]$^+$; $^1$H NMR (400 MHz, DMSO-d$_6$) δ 3.21 (s, 3H), 3.75 (m, 4H), 3.87 (m, 4H), 4.54 (s, 2H), 4.88 (s, 2H), 5.14 (s, 2H), 6.53 (d, J=8.4 Hz, 1H), 7.33 (s, 1H), 7.52 (d, J=7.6 Hz, 1H), 7.62 (s, 1H), 8.73 (s, 2H).

Example 84: Preparation of 2-(((2-(1H-indol-4-yl)-4-morpholinothieno[3,2-d]pyrimidin-6-yl)methyl)(methyl)amino)-N-hydroxypyrimidine-5-carboxamide (Compound 176)

Step 84a: Tert-butyl 4-bromo-1H-indole-1-carboxylate (Compound 0601-176)

The solution of 4-bromoindole (394 mg, 2.00 mmol), (Boc)$_2$O (523 mg, 2.40 mmol), DMAP (293 mg, 2.4 mmol) and Et$_3$N (0.4 mL) in MeCN (6 mL) was stirred at room temperature for 2 hours. The solvent was removed and the residue was dissolved in ethyl acetate (40 mL), washed with water (3×20 mL) and brine (1×20 mL), the organic layer was concentrated and purified by column chromatography on silica gel (petroleum ether) to afford compound 0601-176 (508 mg, 85%) as a colorless oil. $^1$H-NMR (400 MHz. DMSO-d$_6$) δ 1.64 (s, 9H), 6.67 (d, J=3.2 Hz, 1H), 7.28 (t, J=8.0 Hz, 1H), 7.48 (m, 1H), 7.80 (d, J=3.2 Hz, 1H), 8.08 (m, 1H).

Step 84b: Tert-butyl 4-(4,4,5,5-tetramethyl-1,3,2-dioxaborolan-2-yl)-1H-indole-1-carboxylate (Compound 0602-176)

The title compound 0602-176 was prepared (448 mg, 77%) as a white solid from 0601-176 (503 mg, 1.69 mmol), bis(pinacolato)diboron (644 mg, 2.54 mmol), Pd(dppf)$_2$Cl$_2$ (138 mg, 0.17 mmol) and AcOK (497 mg, 5.07 mmol) using a procedure similar to that described for compound 0602-107 (Example 34). $^1$H-NMR (400 MHz. DMSO-d$_6$) δ 1.34 (s, 12H), 1.64 (s, 9H), 6.98 (d, J=2.8 Hz, 1H), 7.33 (t, J=8.0 Hz, 1H), 7.58 (m, 1H), 7.72 (d, J=2.8 Hz, 1H), 8.20 (m, 1H).

Step 84c: Ethyl 2-(((2-(1H-indol-4-yl)-4-morpholinothieno[3,2-d]pyrimidin-6-yl) methyl)(methyl) amino)pyrimidine-5-carboxylate (Compound 0603-176)

The compound tert-butyl 4-(6-(((5-(ethoxycarbonyl)pyrimidin-2-yl)(methyl) amino)methyl)-4-morpholinothieno[3,2-d]pyrimidin-2-yl)-1H-indole-1-carboxylate was prepared (368 mg, 59%) as a white solid from 0504-54 (448 mg, 1.00 mmol), 0602-176 (343 mg, 1.00 mmol), Cs$_2$CO$_3$ (652 mg, 2.00 mmol) and Pd(dppf)$_2$Cl$_2$ (82 mg, 0.10 mmol) in 1,4-dioxane (6 mL) and water (0.2 mL) using a procedure similar to that described for compound 0603-107 (Example 34). LCMS: 630 [M+1]$^+$. $^1$H-NMR (400 MHz. DMSO-d$_6$) δ 1.30 (t, J=7.2 Hz, 3H), 1.65 (s, 9H), 3.28 (s, 3H), 3.78 (m, 4H), 3.93 (m, 4H), 4.29 (q, J=7.2 Hz, 2H), 5.25 (s, 2H), 7.44 (m, 1H), 7.55 (s, 1H), 7.72 (m, 1H), 7.77 (m, 1H), 8.25 (m, 2H), 8.88 (s, 2H).

A mixture of above solid (368 mg, 0.59 mmol) trifluoroacetic acid (4 mL) was stirred at room temperature for 1 hour. Adjusted to pH7 with 10% aqueous NaOH, and extracted with CH$_2$Cl$_2$ (60 mL). The organic layer was washed with brine (1×30 mL), dried and concentrated to get compound 0603-176 (312 mg, 100%) as a yellow solid. LCMS: 530 [M+1]$^+$. $^1$H-NMR (400 MHz. DMSO-d$_6$) δ 1.31 (t, J=6.8 Hz, 3H), 3.29 (s, 3H), 3.79 (m, 4H), 3.94 (m, 4H), 4.30 (q, J=7.2 Hz, 2H), 5.26 (s, 2H), 7.19 (t, J=8.0 Hz, 1H), 7.43 (m, 2H), 7.53 (s, 1H), 8.11 (m, 1H), 8.89 (s, 2H), 11.23 (s, 1H).

Step 84d: 2-(((2-(1H-indol-4-yl)-4-morpholinothieno[3,2-d]pyrimidin-6-yl) methyl)(methyl)amino)-N-hydroxypyrimidine-5-carboxamide (Compound 176)

The title compound 176 was prepared (78 mg, 25%) as a white solid from 0603-176 (318 mg, 0.60 mmol) and freshly prepared hydroxylamine methanol solution (10 mL) using a procedure similar to that described for compound 3 (Example 1). m.p. 200-212° C. LCMS: 517 [M+1]$^+$. $^1$H-NMR (400 MHz. DMSO-d$_6$) δ 3.26 (s, 3H), 3.79 (m, 4H), 3.94 (m, 4H), 5.22 (s, 2H), 7.19 (t, J=8.0 Hz, 1H), 7.43 (m, 2H), 7.52 (m, 2H), 8.12 (d, J=8.0 Hz, 1H), 8.77 (s, 2H), 9.07 (s, 1H), 11.14 (s, 1H), 11.24 (s, 1H).

Example 85: Preparation of N-hydroxy-2-(((2-(indolin-4-yl)-4-morpholinothieno[3,2-d]pyrimidin-6-yl)methyl)(methyl)amino)pyrimidine-5-carboxamide (Compound 177)

Step 85a: Tert-butyl 4-bromoindoline-1-carboxylate (Compound 0601-177)

A mixture of 4-bromooxindole (2.77 g, 0.01 mol) and a solution of BH$_3$ in THF (2 M, 40 mL) was stirred at room temperature overnight. The mixture was cooled to 0° C. and diluted with 30 mL of methanol, followed by addition of 12 N HCl (7.5 mL). The resulting mixture was stirred at room temperature for 1 hour, adjusted to pH 8-9 with 10% aqueous NaOH. Water was added to the mixture and extracted with ethyl acetate (3×100 mL). The organic layer was dried and concentrated to get the crude product which was washed through a silica gel column (ethyl acetate in petroleum ether (10%). The crude product was dissolved in 10% HCl (3×10 mL). The aqueous layer was adjusted to pH7 with NaHCO$_3$, extracted with ethyl acetate (3×20 mL). The organic layer was dried and concentrated to get 4-bromoindoline (1.16 g, 45%) as an oil. LCMS: 200 [M+1]$^+$. $^1$H-NMR (400 MHz. DMSO-d$_6$) δ 2.90 (t, J=8.8 Hz, 2H), 3.46 (t, J=8.8 Hz, 2H), 5.86 (s, 1H), 6.43 (m, 1H), 6.64 (m, 1H), 6.83 (t, J=8.0 Hz, 1H).

A mixture of above obtained 4-bromoindoline (759 mg, 3.81 mmol), and (Boc)$_2$O (976 mg, 4.48 mmol) in MeCN (8 mL) was stirred at room temperature overnight. After evaporated, the residue was dissolved in ethyl acetate (40 mL), washed with water (3×20 mL) and brine (1×20 mL). The organic layer was concentrated and purified by column chromatography on silica gel (petroleum ether) to give 0601-177 (840 mg, 74%) as a white solid. $^1$H-NMR (400

MHz. DMSO-d$_6$) δ 1.50 (s, 9H), 3.02 (t, J=8.8 Hz, 2H), 3.94 (t, J=8.8 Hz, 2H), 7.12 (m, 2H), 7.56 (m, 1H).

Step 85b: Tert-butyl 4-(4,4,5,5-tetramethyl-1,3,2-dioxaborolan-2-yl)indoline-1-carboxylate (Compound 0602-177)

The title compound 0602-177 was prepared (814 mg, 84%) as a white solid from 0601-177 (840 mg, 2.81 mmol), bis(pinacolato)diboron (1.07 g, 4.21 mmol), Pd(dppf)$_2$Cl$_2$ (229 mg, 0.28 mmol) and AcOK (826 mg, 8.43 mmol) using a procedure similar to that described for compound 0602-107 (Example 34). LCMS: 290 [M−55]$^+$; $^1$H-NMR (400 MHz. DMSO-d$_6$) δ 1.35 (s, 12H), 1.57 (s, 9H), 3.24 (t, J=8.4 Hz, 2H), 3.94 (t, J=8.4 Hz, 2H), 7.20 (m, 1H), 7.28 (m, 1H), 7.88 (m, 1H).

Step 85c: Ethyl 2-(((2-(indolin-4-yl)-4-morpholinothieno[3,2-d]pyrimidin-6-yl)methyl)(methyl)amino)pyrimidine-5-carboxylate (Compound 0603-177)

Compound tert-butyl 4-(6-(((5-(ethoxycarbonyl)pyrimidin-2-yl)(methyl)amino) methyl)-4-morpholinothieno[3,2-d]pyrimidin-2-yl)indoline-1-carboxylate was prepared (463 mg, 73%) as a white solid from 0504-54 (448 mg, 1.00 mmol), 0602-177 (345 mg, 1.00 mmol), Cs$_2$CO$_3$ (652 mg, 2.00 mmol) and Pd(dppf)$_2$Cl$_2$ (82 mg, 0.10 mmol) in 1,4-dioxane (6 mL) and water (0.2 mL) using a procedure similar to that described for compound 0603-107 (Example 34). LCMS: 632 [M+1]$^+$. $^1$H-NMR (400 MHz. DMSO-d$_6$) δ 1.30 (t, J=7.2 Hz, 3H), 1.52 (s, 9H), 3.27 (s, 3H), 3.55 (m, 2H), 3.87 (m, 4H), 3.94 (m, 6H), 4.29 (q, J=7.2 Hz, 2H), 5.23 (s, 2H), 7.26 (m, 1H), 7.46 (s, 1H), 7.81 (m, 1H), 7.89 (m, 1H), 8.87 (s, 2H).

A mixture of above product (463 mg, 0.73 mmol) and trifluoroacetic acid (4 mL) was stirred at room temperature for 1 hour. The mixture was adjusted to pH 7 with 10% aqueous NaOH, extracted with CH$_2$Cl$_2$ (60 mL). The organic layer was washed with brine (1×30 mL), dried and concentrated to give 0603-177 (283 mg, 73%) as an off-white solid. LCMS: 532 [M+1]$^+$. $^1$H-NMR (400 MHz. DMSO-d$_6$) δ 1.30 (t, J=6.8 Hz, 3H), 3.27 (s, 3H), 3.41 (m, 4H), 3.75 (m, 4H), 3.86 (m, 4H), 4.29 (q, J=6.8 Hz, 2H), 5.23 (s, 2H), 5.58 (s, 1H), 6.58 (m, 1H), 7.01 (t, J=8.0 Hz, 1H), 7.47 (m, 2H), 8.88 (s, 2H).

Step 85d: N-Hydroxy-2-(((2-(indolin-4-yl)-4-morpholinothieno[3,2-d]pyrimidin-6-yl) methyl)(methyl)amino)pyrimidine-5-carboxamide (Compound 177)

The title compound 177 was prepared (130 mg, 49%) as a white solid from 0603-177 (273 mg, 0.51 mmol) and freshly prepared hydroxylamine methanol solution (8 mL) using a procedure similar to that described for compound 3 (Example 1). m.p.: 146-156° C. LCMS: 519 [M+1]$^+$. $^1$H-NMR (400 MHz. DMSO-d$_6$) δ 3.24 (s, 3H), 3.42 (m, 4H), 3.75 (m, 4H), 3.87 (m, 4H), 5.20 (s, 2H), 5.57 (s, 1H), 6.58 (m, 1H), 7.01 (t, J=8.0 Hz, 1H), 7.43 (s, 1H), 7.48 (m, 1H), 8.76 (s, 2H), 9.07 (s, 1H), 11.13 (s, 1H).

Example 86: Preparation of 2-(((2-(3,4-dihydro-2H-benzo[b][1,4]oxazin-6-yl)-4-morpholinothieno[3,2-d]pyrimidin-6-yl)methyl)(methyl)amino)-N-hydroxypyrimidine-5-carboxamide (Compound 182)

Step 86a: Tert-butyl 6-bromo-2,3-dihydrobenzo[b][1,4]oxazine-4-carboxylate (Compound 0601-182)

A mixture of compound 4-bromo-2-nitrophenol (1 g, 4.59 mmol) and SnCl$_2$ (5.2 g, 22.9 mmol) in ethanol (10 mL) was stirred at 70° C. for 2 h. After cooled down, the mixture was diluted with water (100 mL), adjusted to pH 7 with saturated aqueous NaHCO$_3$ and extracted with ethyl acetate (100 mL). The organic layer was washed with brine (50 mL), dried over Na$_2$SO$_4$, concentrated to give 2-amino-4-bromophenol (770 mg, 89%) as a grey solid. LCMS: 188 [M+1]$^+$. $^1$H NMR (400 MHz, DMSO-d$_6$) δ 4.79 (s, 2H), 6.48 (dd, J$_1$=2.4 Hz, J$_2$=8.4 Hz, 1H), 6.55 (d, J=8.4 Hz, 1H), 6.71 (d, J=2.4 Hz, 1H), 9.26 (s, 1H).

A mixture of the product 2-amino-4-bromophenol (500 mg, 2.66 mmol), 1,2-dibromoethane (2.5 g, 13.3 mmol) and K$_2$CO$_3$ (1.84 g, 13.3 mmol) in DMF (10 mL) was stirred at room temperature for 4 h. The mixture was diluted with water (100 mL) and extracted with ethyl acetate (100 mL). The organic layer was washed with water (3×50 mL) and brine (50 mL), concentrated and purified by column chromatography on silica gel (ethyl acetate in petroleum, 10% v/v) to give 5-bromo-2-(2-bromoethoxy)benzenamine (250 mg, 37%) as a yellow solid. LCMS: 294 [M+1]$^+$. $^1$H NMR (400 MHz, DMSO-d$_6$) δ 3.79 (t, J=6.0 Hz, 2H), 4.25 (t, J=5.6 Hz, 2H), 5.06 (s, 2H), 6.63 (dd, J$_1$=2.4 Hz, J$_2$=8.0 Hz, 1H), 6.77 (d, J=8.4 Hz, 1H), 6.82 (d, J=2.4 Hz, 1H).

A mixture of the product 5-bromo-2-(2-bromoethoxy) benzenamine (250 mg, 0.848 mmol) and K$_2$CO$_3$ (234 mg, 1.695 mmol) in DMF (5 mL) was stirred at 60° C. for 4 h. The mixture was diluted with water (100 mL) and extracted with ethyl acetate (100 mL). The organic layer was washed with water (3×50 mL) and brine (50 mL), concentrated to give 6-bromo-3,4-dihydro-2H-benzo[b][1,4]oxazine (170 mg, 94%) as a yellow oil. LCMS: 214 [M+1]$^+$. $^1$H NMR (400 MHz, DMSO-d$_6$) δ 3.26 (m, 2H), 4.08 (t, J=4.8 Hz, 2H), 6.06 (s, 1H), 6.56 (m, 2H), 6.69 (d, J=1.6 Hz, 1H).

A mixture of the product 6-bromo-3,4-dihydro-2H-benzo [b][1,4]oxazine (1.37 g, 6.4 mmol), Boc$_2$O (1.676 g, 7.68 mmol), Et$_3$N (970 mg, 9.6 mmol), DMAP (78 mg, 0.64 mmol) in THF (27 mL) was stirred at room temperature overnight. The reaction mixture was diluted with water (200 mL) and extracted with ethyl acetate (100 mL). The organic layer was washed with water (50 mL) and brine, dried over Na$_2$SO$_4$ and concentrated to give compound 0601-182 (1.3 g, 65%) as a yellow oil. LCMS: 258 [M−55]$^+$. $^1$H NMR (400 MHz, DMSO-d$_6$) δ 1.49 (s, 9H), 3.78 (t, J=4.8 Hz, 2H), 4.21 (t, J=4.4 Hz, 2H), 6.83 (d, J=4.4 Hz, 1H), 7.12 (dd, J$_1$=2.0 Hz, J$_2$=8.4 Hz, 2H), 8.01 (s, 1H).

Step 86b: Tert-butyl 6-(4,4,5,5-tetramethyl-1,3,2-dioxaborolan-2-yl)-2,3-dihydrobenzo[b][1,4] oxazine-4-carboxylate (Compound 0602-182)

The title compound 0602-182 was prepared (1.4 g, 98%) as an oil from 0601-182 (1.16 g, 3.69 mmol), bis(pinacolato) diboron (1.41 g, 5.54 mmol), Pd(dppf)$_2$Cl$_2$ (90 mg, 0.111 mmol) and AcOK (1.09 g, 11.07 mmol) using a procedure similar to that described for compound 0602-107 (Example 34). LCMS: 306 [M−55]$^+$. $^1$H NMR (400 MHz, DMSO-d$_6$) δ1.27 (s, 12H), 1.49 (s, 9H), 3.79 (t, J=4.4 Hz, 2H), 4.23 (t, J=4.0 Hz, 2H), 6.88 (d, J=8.0 Hz, 1H), 7.25 (d, J=9.6 Hz, 2H), 8.13 (s, 1H).

Step 86c: Ethyl 2-(((2-(3,4-dihydro-2H-benzo[b][1,4]oxazin-6-yl)-4-morpholinothieno[3,2-d]pyrimidin-6-yl)methyl)(methyl)amino)pyrimidine-5-carboxylate (Compound 0603-182)

Compound tert-butyl 6-(6-(((5-(ethoxycarbonyl)pyrimidin-2-yl)(methyl)amino) methyl)-4-morpholinothieo[3,2-d] pyrimidin-2-yl)-2,3-dihydrobenzo[b][1,4]oxazine-4-carboxylate was prepared (250 mg, 58%) as a yellow solid from 0504-54 (300 mg, 0.668 mmol), 0602-182 (290 mg, 0.802 mmol), NaHCO$_3$ (168 mg, 2.00 mmol), (Ph$_3$P)$_2$PdCl$_2$ (23 mg, 0.0334 mmol) in ethanol (2.3 mL), toluene (4 mL) and water (1 mL) using a procedure similar to that described for compound 0603-107 (Example 34). LCMS: 648 [M+1]$^+$. $^1$H NMR (400 MHz, DMSO-d$_6$) δ 1.30 (t, J=6.8 Hz, 3H), 1.52 (s, 9H), 3.26 (s, 3H), 3.75 (m, 4H), 3.83 (m, 2H), 3.92 (m, 4H), 4.28 (m, 4H), 5.23 (s, 2H), 6.93 (d, J=8.4 Hz, 1H), 7.45 (s, 1H), 8.02 (d, J=8.8 Hz, 1H), 8.80 (s, 1H), 8.88 (s, 2H).

To a solution of the above prepared compound (250 mg, 0.386 mmol) in dichloromethane (25 ml) was added CF$_3$COOH (2.5 mL) and stirred at room temperature overnight. The mixture was diluted with ethyl acetate (100 mL) and washed with saturated aqueous NaHCO$_3$ (50 mL), water (100 mL) and brine (50 mL), dried over Na$_2$SO$_4$, concentrated to give 0603-182 (200 mg, 95%) as a yellow solid. LCMS: 548 [M+1]$^+$. $^1$H NMR (400 MHz, DMSO-d$_6$) δ 1.30 (t, J=7.2 Hz, 3H), 3.26 (s, 3H), 3.30 (m, 2H), 3.75 (m, 4H), 3.89 (m, 4H), 4.17 (m, 2H), 4.28 (q, J=7.2 Hz, 2H), 5.22 (s, 2H), 5.92 (s, 1H), 6.70 (d, J=8.4 Hz, 1H), 7.42 (s, 1H), 7.56 (d, J=10.0 Hz, 1H), 7.68 (s, 1H), 8.88 (s, 2H).

Step 86d: 2-(((2-(3,4-dihydro-2H-benzo[b][1,4]oxazin-6-yl)-4-morpholinothieno[3,2-d]pyrimidin-6-yl)methyl)(methyl)amino)-N-hydroxypyrimidine-5-carboxamide (Compound 182)

The title compound 182 was prepared (72 mg, 37%) as a white solid from 0603-182 (200 mg, 0.365 mmol) and freshly prepared hydroxylamine methanol solution (10 mL) using a procedure similar to that described for compound 3 (Example 1). mp. 170-183° C. LCMS: 535 [M+1]$^+$. $^1$H NMR (400 MHz, DMSO-d$_6$) δ 3.23 (s, 3H), 3.30 (m, 2H), 3.75 (m, 4H), 3.89 (m, 4H), 4.17 (m, 2H), 5.19 (s, 2H), 5.91 (s, 1H), 6.70 (d, J=8.0 Hz, 1H), 7.40 (s, 1H), 7.57 (d, J=8.0 Hz, 1H), 7.68 (s, 1H), 8.75 (s, 2H), 9.07 (s, 1H), 11.01 (s, 1H).

Example 87: Preparation of 2-(((2-(1H-benzo[d]imidazol-5-yl)-4-morpholinothieno[3,2-d]pyrimidin-6-yl)methyl)(methyl)amino)-N-hydroxypyrimidine-5-carboxamide (Compound 187)

Step 87a: Tert-butyl 5-bromo-1H-benzo[d]imidazole-1-carboxylate (Compound 0601-187)

To a solution of 4-bromobenzene-1,2-diamine (3 g, 16 mmol) in DMF (22 mL) were added trimethyl orthoformate (44 mL) and conc. HCl (1.5 mL) and the mixture was stirred at room temperature for 1 h. The mixture was diluted with water (200 mL) and adjusted to pH7 with saturated aqueous NaHCO$_3$, extract with ethyl acetate (200 mL). The organic layer was dried over Na$_2$SO$_4$, concentrated to give 5-bromo-1H-benzo[d]imidazole (3.25 g, 100%) as an off-white solid. LCMS: 197 [M+1]$^+$. $^1$H NMR (400 MHz, DMSO-d$_6$) δ 7.33 (t, J=8.8 Hz, 1H), 7.55 (dd, J$_1$=7.6 Hz, J=40 Hz, 1H), 7.79 (d, J=47.2 Hz, 1H), 8.26 (s, 1H), 12.61 (d, J=25.6 Hz, 1H).

To a solution of above prepared 5-bromo-1H-benzo[d]imidazole (3.25 g, 22.1 mmol) in THF (65 mL) was added Boc$_2$O (5.79 g, 26.5 mmol), Et$_3$N (3.35, 33.15 mmol) and DMAP (270 mg, 2.21 mmol). The mixture was stirred at room temperature for 4 h, diluted with water (200 mL), extracted with ethyl acetate (200 mL). The organic layer was washed with water (2×100 mL) and brine (100 mL), dried over Na$_2$SO$_4$, concentrated to give 0601-187 (4.8 g, 98%) as a oil. LCMS: 241 [M−55]$^+$. $^1$H NMR (400 MHz, DMSO-d$_6$) δ 1.65 (s, 9H), 7.57 (dd, J$_1$=8.4 Hz, J$_2$=20 Hz, 1H), 7.73 (d, J=8.4 Hz, 1H), 7.88 (d, J=9.2 Hz, 1H), 8.03 (d, J=35.6 Hz, 1H), 8.70 (d, J=8.0 Hz, 1H).

Step 87b: Tert-butyl 5-(4,4,5,5-tetramethyl-1,3,2-dioxaborolan-2-yl)-1H-benzo[d]imidazole-1-carboxylate (Compound 0602-187)

The title compound 0602-187 was prepared (0.94 g, 81%) as a colorless oil from 0601-187 (1 g, 3.37 mmol), bis(pinacolato)diboron (1.28 g, 5.05 mmol), Pd(dppf)$_2$Cl$_2$ (82 mg, 0.101 mmol) and AcOK (991 mg, 10.1 mmol) using a procedure similar to that described for compound 0602-107 (Example 34). LCMS: 289 [M−55]$^+$. $^1$H NMR (400 MHz, DMSO-d$_6$) δ 1.32 (s, 12H), 1.65 (s, 9H), 7.65 (d, J=7.2 Hz, 0.5H), 7.74 (t, J=8.4 Hz, 1H), 7.97 (d, J=8.4 Hz, 1H), 8.37 (s, 0.5H), 8.69 (d, J=18.8 Hz, 1H).

Step 87c: Ethyl 2-(((2-(1H-benzo[d]imidazol-5-yl)-4-morpholinothieno[3,2-d]pyrimidin-6-yl)methyl)(methyl)amino)pyrimidine-5-carboxylate (Compound 0603-187)

The compound 0603-187 was prepared (260 mg, 62%) as a yellow solid from 0504-54 (300 mg, 0.668 mmol), 0602-187 (276 mg, 0.8 mmol), NaHCO$_3$ (168 mg, 2.00 mmol), (Ph$_3$P)$_2$PdCl$_2$ (23 mg, 0.0334 mmol) in ethanol (2.3 mL), toluene (4 mL) and water (1 mL) using a procedure similar to that described for compound 0603-107 (Example 34). LCMS: 531 [M+1]$^+$. $^1$H NMR (400 MHz, DMSO-d$_6$) δ 1.30 (t, J=7.2 Hz, 3H), 3.28 (s, 3H), 3.78 (m, 4H), 3.95 (m, 4H), 4.29 (q, J=6.8 Hz, 2H), 5.24 (s, 2H), 7.50 (s, 1H), 7.65 (d, J=8.0 Hz, 1H), 8.32 (m, 2H), 8.64 (s, 1H), 8.88 (s, 2H), 12.59 (s, 1H).

Step 87d: 2-(((2-(1H-benzo[d]imidazol-5-yl)-4-morpholinothieno[3,2-d]pyrimidin-6-yl)methyl)(methyl)amino)-N-hydroxypyrimidine-5-carboxamide (Compound 187)

The title compound 187 was prepared (34 mg, 13%) as a yellow solid from 0603-187 (260 mg, 0.49 mmol) and freshly prepared hydroxylamine methanol solution (10 mL) using a procedure similar to that described for compound 3 (Example 1). mp. 231-239° C. LCMS: 518 [M+1]$^+$. $^1$H NMR (400 MHz, DMSO-d$_6$) δ 3.25 (s, 3H), 3.79 (m, 4H), 3.95 (m, 4H), 5.21 (s, 2H), 7.48 (s, 1H), 7.65 (dd, J$_1$=8.4 Hz, J$_2$=47.2 Hz, 1H), 8.31 (m, 2H), 8.64 (d, J=44.8 Hz, 1H), 8.76 (s, 2H), 9.09 (s, 1H), 11.03 (s, 1H), 12.59 (s, 1H).

Example 88: Preparation of N-hydroxy-2-(methyl((2-(2-methyl-3H-benzo[d]imidazol-5-yl)-4-morpholinothieno[3,2-d]pyrimidin-6-yl)methyl)amino)pyrimidine-5-carboxamide (Compound 199)

Step 88a: N,N'-(4-bromo-1,2-phenylene)diacetamide (Compound 0601-199)

To the solution of 4-bromobenzene-1,2-diamine (1.87 g, 10 mmol) and Et$_3$N (10.1 g, 100 mmol) in CH$_2$Cl$_2$ (20 mL) was added CH$_3$COCl (1.73 g, 22 mmol) at 0° C. and stirred for 2 hr at 30° C. The mixture was concentrated and the residue was dissolved in CH$_2$Cl$_2$, washed with water, dried over Na$_2$SO$_4$, concentrated to give 0601-199 (1.4 g, 52%) as a yellow solid. LCMS: 271 [M+1]$^+$. $^1$H NMR (400 MHz, DMSO-d$_6$) δ 2.08 (d, J=3.2 Hz, 6H), 7.28 (m, 1H), 7.50 (d, J=8.8 Hz, 1H), 7.83 (s, 1H), 9.38 (d, J=3.2 Hz, 2H).

Step 88b: N,N'-(4-(4,4,5,5-tetramethyl-1,3,2-dioxaborolan-2-yl)-1,2-phenylene) diacetamide (Compound 0602-199)

The title compound 0602-189 was prepared (1.0 g, 63%) as a yellow solid from 0601-199 (1.4 g, 5.2 mmol), bis (pinacolato)diboron (2.0 g, 7.8 mmol), Pd(dppf)$_2$Cl$_2$ (425 mg, 0.52 mmol) and AcOK (1.53 g, 15.6 mmol) using a procedure similar to that described for compound 0602-107 (Example 34). LCMS: 319 [M+1]$^+$, $^1$H NMR (400 MHz, DMSO-d$_6$) δ 1.28 (s, 12H), 2.07 (d, J=6.0 Hz, 6H), 7.41 (d, J=8.0 Hz, 1H), 7.70 (d, J=8.4 Hz, 1H), 7.79 (s, 1H), 9.36 (d, J=9.6 Hz, 2H).

Step 88c: Ethyl 2-(methyl((2-(2-methyl-3H-benzo[d]imidazol-5-yl)-4-morpholinothieno[3,2-d]pyrimidin-6-yl)methyl)amino)pyrimidine-5-carboxylate (Compound 0603-199)

Compound ethyl 2-(((2-(3,4-diacetamidophenyl)-4-morpholinothieno[3,2-d]pyrimidin-6-yl) methyl)(methyl) amino)pyrimidine-5-carboxylate was prepared (260 mg, 75%) as a white solid from 0504-54 (261 mg, 0.58 mmol), 0602-199 (240 mg, 0.75 mmol), NaHCO$_3$ (147 mg, 1.8 mmol) and bis(triphenylphosphine)palladium(II) chloride (41 mg, 0.058 mmol) in toluene (4 mL), ethanol (2 mL) and water (0.5 mL) using a procedure similar to that described for compound 0603-107 (Example 34). LCMS: 605 [M+1]$^+$; $^1$H NMR (400 MHz, DMSO-d$_6$): δ 1.30 (m, 3H), 2.11 (s, 6H), 3.27 (s, 3H), 3.76 (m, 4H), 3.92 (m, 4H), 4.30 (m, 2H), 5.24 (s, 2H), 7.48 (m, 1H), 7.76 (m, 1H), 8.15 (m, 1H), 8.50 (m, 1H), 8.88 (m, 2H), 8.45 (m, 2H).

To the solution of above prepared compound (360 mg, 0.6 mmol) in THE (8 mL) was added 6M HCl (12 mL) and stirred for 10 hr at 40° C. The mixture was adjusted to pH8 with saturated aqueous Na$_2$CO$_3$ at 0° C., extracted with ethyl acetate. The organic layer was dried, concentrated and purified by column chromatography on silica gel (methanol in dichloromethane, 2-5 v/v) to give title compound 0603-199 (160 mg, 50%) as a white solid. LC-MS: 545 [M+1]$^+$. $^1$H NMR (400 MHz, CDCl$_3$) δ 1.38 (t, J=6.8 Hz, 3H), 2.60 (s, 3H), 3.30 (s, 3H), 3.85 (m, 4H), 4.01 (m, 4H), 4.36 (q, J=7.2 Hz, 2H), 5.18 (s, 2H), 7.38 (s, 1H), 7.60 (d, J=8.0 Hz, 1H), 8.36 (d, J=8.4 Hz, 1H), 8.67 (s, 1H), 8.92 (s, 2H).

Step 88d: N-hydroxy-2-(methyl((2-(2-methyl-3H-benzo[d]imidazol-5-yl)-4-morpholinothieno[3,2-d]pyrimidin-6-yl)methyl)amino)pyrimidine-5-carboxamide (Compound 199)

The title compound 199 was prepared (38 mg, 24%) as a white solid from 0603-199 (160 mg, 0.30 mmol) and freshly prepared hydroxylamine methanol solution (20 mL) using a procedure similar to that described for compound 3 (Example 1). m.p. 230-233° C. LCMS: 532 [M+1]$^+$; $^1$H NMR (400 MHz, DMSO-d$_6$) δ 2.51 (s, 3H), 3.24 (s, 3H), 3.78 (m, 4H), 3.93 (m, 4H), 5.21 (s, 2H), 7.47 (s, 1H), 7.50 (d, J=42.8, 8.4 Hz, 1H), 8.25 (t, J=8.8 Hz, 1H), 8.48 (d, J=42.8 Hz, 1H), 8.76 (s, 2H), 9.09 (s, 1H), 11.00 (s, 1H), 12.33 (s, 1H).

Example 89: Preparation of N-hydroxy-2-(methyl ((4-morpholino-2-(2-oxo-2,3-dihydro-1H-benzo[d]imidazol-5-yl)thieno[3,2-d]pyrimidin-6-yl)methyl) amino)pyrimidine-5-carboxamide (Compound 186)

Step 89a: 5-Bromo-1H-benzo[d]imidazol-2 (3H)-one (Compound 0601-186)

A mixture of 4-bromobenzene-1,2-diamine (3.74 g, 20 mmol), CDI (3.9 g, 24 mmol) in 1,4-dioxane (20 mL) was stirred for 1 hr at 40° C. The mixture was filtered and washed with petroleum ether and dichloromethane to get compound 0601-186 (3.0 g, 70%) as a white solid. LCMS: 213 [M+1]$^+$, $^1$H NMR (400 MHz, DMSO-d$_6$) δ 6.86 (d, J=8.0 Hz, 1H), 7.06 (m, 1H), 7.08 (m, 1H), 10.77 (s, 2H).

Step 89b: 5-(4,4,5,5-tetramethyl-1,3,2-dioxaborolan-2-yl)-1H-benzo[d]imidazol-2 (3H)-one (Compound 0602-186)

The title compound 0602-186 was prepared (340 mg, 21%) as a yellow solid from 0601-186 (1.3 g, 6 mmol), bis(pinacolato)diboron (2.3 g, 9 mmol), Pd(dppf)$_2$Cl$_2$ (490 mg, 0.6 mmol) and AcOK (1.8 g, 18 mmol) using a procedure similar to that described for compound 0602-107 (Example 34). LCMS: 261 [M+1]$^+$, $^1$H NMR (400 MHz, DMSO-d$_6$) δ 1.27 (s, 12H), 6.91 (d, J=7.6 Hz, 1H), 7.17 (s, 1H), 7.28 (d, J=7.6 Hz, 1H), 10.65 (s, 1H), 10.77 (s, 1H).

Step 89c: Ethyl 2-(methyl((4-morpholino-2-(2-oxo-2,3-dihydro-1H-benzo[d]imidazol-5-yl) thieno[3,2-d]pyrimidin-6-yl)methyl)amino)pyrimidine-5-carboxylate (Compound 0603-186)

The title compound 0603-186 was prepared (214 mg, 68%) as a white solid from 0504-54 (261 mg, 0.58 mmol), 0602-186 (197 mg, 0.75 mmol), NaHCO$_3$ (147 mg, 1.8 mmol) and bis(triphenylphosphine)palladium(II) chloride (41 mg, 0.058 mmol) in toluene (4 mL), ethanol (2 mL) and water (0.5 mL) using a procedure similar to that described for compound 0603-107 (Example 34). LCMS: 547 [M+1]$^+$; $^1$H NMR (400 MHz, DMSO-d$_6$): δ 1.30 (t, J=6.8 Hz, 3H), 3.27 (s, 3H), 3.77 (m, 4H), 3.91 (m, 4H), 4.28 (q, J=6.8 Hz, 2H), 5.23 (s, 2H), 6.99 (d, J=8.0 Hz, 1H), 7.46 (s, 1H), 7.97 (s, 1H), 8.08 (d, J=9.2 Hz, 1H), 8.88 (s, 2H), 10.71 (s, 1H), 10.80 (s, 1H).

Step 89d: N-hydroxy-2-(methyl((4-morpholino-2-(2-oxo-2,3-dihydro-1H-benzo[d]imidazol-5-yl) thieno[3,2-d]pyrimidin-6-yl)methyl)amino)pyrimidine-5-carboxamide (Compound 186)

The title compound 186 was prepared (75 mg, 36%) as a white solid from 0603-186 (214 mg, 0.40 mmol) and freshly prepared hydroxylamine methanol solution (20 mL) using a procedure similar to that described for compound 3 (Example 1). m.p. 272-275° C. LCMS: 534 [M+1]$^+$; $^1$H NMR (400 MHz, DMSO-d$_6$) δ 3.23 (s, 3H), 3.77 (m, 4H), 3.91 (m, 4H), 5.20 (s, 2H), 7.00 (d, J=8.0 Hz, 1H), 7.44 (s, 1H), 7.98 (s, 1H), 8.09 (d, J=8.4 Hz, 1H), 8.75 (s, 2H), 10.71 (s, 1H), 10.82 (s, 1H).

Example 90: Preparation of N-hydroxy-2-(methyl ((4-morpholino-2-(2-oxoindolin-5-yl)thieno[3,2-d] pyrimidin-6-yl)methyl)amino)pyrimidine-5-carboxamide (Compound 194)

Step 90a: 5-Bromoindolin-2-one (Compound 0601-194)

To a mixture of 5-bromoindole-2,3-dione (2.25 g, 10 mmol), ethyleneglycol (45 mL) and hydrazine hydrate (1.06 g, 21.10 mmol) was added KOH (1.68 g, 30 mmol). The reaction mixture was stirred at 80° C. for 4 hours. The mixture was cooled to room temperature and poured into ice cold water and the mixture was adjusted to pH 1-2 with 12N hydrochloric acid and stirred at room temperature for 12 hours. The mixture was filtered and solid was washed with water (5 mL) and dried to get the crude product which was purified by column chromatography on silica gel (methanol in dichloromethane, 0.5% v/v) to give 0601-194 (785 mg, 37%) as a yellow solid. LCMS: 214 [M+1]$^+$. $^1$H-NMR (400 MHz. DMSO-d) δ 3.51 (s, 2H), 6.76 (d, J=8.0 Hz, 1H), 7.34 (dd, J=8.0, 2.0 Hz, 1H), 7.38 (m, 1H), 10.49 (s, 1H).

Step 90b: 5-(4,4,5,5-Tetramethyl-1,3,2-dioxaborolan-2-yl)indolin-2-one (Compound 0602-194)

The title compound 0602-194 was prepared (323 mg, 83%) as a yellow solid from 0601-194 (317 mg, 1.5 mmol), bis(pinacolato)diboron (572 mg, 2.25 mmol), Pd(dppf)$_2$Cl$_2$ (126 mg, 0.15 mmol) and AcOK (441 mg, 4.5 mmol) using a procedure similar to that described for compound 0602-107 (Example 34). LCMS: 260 [M+1]$^+$. $^1$H-NMR (400 MHz. DMSO-d$_6$) δ 1.27 (s, 12H), 3.46 (s, 2H), 6.81 (d, J=8.0 Hz, 1H), 7.50 (m, 2H), 10.54 (s, 1H).

Step 90c: Ethyl 2-(methyl((4-morpholino-2-(2-oxoindolin-5-yl)thieno[3,2-d]pyrimidin-6-yl)methyl)amino)pyrimidine-5-carboxylate (Compound 0603-194)

The title compound 0603-194 was prepared (350 mg, 80%) as a yellow solid from 0504-54 (358 mg, 0.80 mmol), 0602-194 (207 mg, 0.80 mmol), Cs$_2$CO$_3$ (522 mg, 1.60 mmol) and Pd(dppf)$_2$Cl$_2$ (65 mg, 0.08 mmol) in 1,4-dioxane (6 mL) and water (0.2 mL) using a procedure similar to that described for compound 0603-107 (Example 34). LCMS: 546 [M+1]$^+$. $^1$H-NMR (400 MHz. DMSO-d$_6$) δ 1.30 (t, J=7.2 Hz, 3H), 3.27 (s, 3H), 3.57 (m, 2H), 3.76 (m, 4H), 3.91 (m, 4H), 4.29 (q, J=7.2 Hz, 2H), 5.23 (s, 2H), 6.90 (d, J=8.4 Hz, 1H), 7.44 (s, 1H), 8.28 (m, 2H), 8.88 (s, 2H), 10.59 (s, 1H).

Step 90d: N-hydroxy-2-(methyl((4-morpholino-2-(2-oxoindolin-5-yl)thieno[3,2-d]pyrimidin-6-yl)methyl)amino)pyrimidine-5-carboxamide (Compound 194)

The title compound 194 was prepared (85 mg, 25%) as a white solid from 0603-194 (350 mg, 0.64 mmol) and freshly prepared hydroxylamine methanol solution (7.5 mL) using a procedure similar to that described for compound 3 (Example 1). m.p.: 270° C. (decomposed). LCMS: 533 [M+1]$^+$. $^1$H-NMR (400 MHz, DMSO-d$^6$) δ 3.24 (s, 3H), 3.57 (s, 2H), 3.77 (m, 4H), 3.91 (m, 4H), 5.20 (s, 2H), 6.90 (m, 1H), 7.42 (m, 1H), 8.26 (m, 2H), 8.76 (s, 2H), 10.52 (s, 1H).

Example 91: Preparation of N-hydroxy-2-(methyl((4-morpholino-2-(1H-pyrazol-4-yl)thieno[3,2-d]pyrimidin-6-yl)methyl)amino)pyrimidine-5-carboxamide (Compound 196)

Step 91a: 4-(4,4,5,5-Tetramethyl-1,3,2-dioxaborolan-2-yl)-1H-pyrazole (Compound 0602-196)

The title compound 0602-196 was prepared (400 mg, 30%) as a yellow solid from 4-bromopyrazole (1 g, 6.8 mmol), bis(pinacolato)diboron (2.6 g, 10.2 mmol), Pd(dppf)$_2$Cl$_2$ (166 mg, 0.2 mmol) and AcOK (g, 20.4 mmol) using a procedure similar to that described for compound 0602-107 (Example 34). LCMS: 195 [M+1]$^+$; $^1$H NMR (400 MHz, DMSO-d$_6$) δ 1.25 (s, 12H), 7.93 (s, 2H), 13.09 (s, 1H).

Step 91b: Ethyl 2-(methyl((4-morpholino-2-(1H-pyrazol-4-yl)thieno[3,2-d]pyrimidin-6-yl)methyl)amino)pyrimidine-5-carboxylate (Compound 0603-196)

The title compound 0603-196 was prepared (150 mg, 47%) as a yellow solid from 0504-54 (300 mg, 0.67 mmol), 0602-196 (259 mg, 1.33 mmol), NaHCO$_3$ (168 mg, 2.0 mmol), (Ph$_3$P)$_2$PdCl$_2$ (23 mg, 0.03 mmol) in toluene (5 mL), ethanol (3 mL) and water (1.3 mL) using a procedure similar to that described for compound 0603-107 (Example 34). LCMS: 481 [M+1]$^+$. $^1$H NMR (400 MHz, DMSO-d$_6$) δ 1.30 (t, J=6.8 Hz, 3H), 3.26 (s, 3H), 3.73 (m, 4H), 3.88 (m, 4H), 4.28 (q, J=7.6 Hz, 2H), 5.21 (s, 2H), 7.38 (s, 1H), 8.04 (s, 1H), 8.30 (s, 1H), 8.88 (s, 2H), 13.07 (s, 1H).

Step 91c: N-hydroxy-2-(methyl((4-morpholino-2-(1H-pyrazol-4-yl)thieno[3,2-d]pyrimidin-6-yl)methyl)amino)pyrimidine-5-carboxamide (Compound 196)

The title compound 196 was prepared (59 mg, 41%) as a yellow solid from 0603-196 (150 mg, 0.31 mmol) and freshly prepared hydroxylamine methanol solution (8 mL) using a procedure similar to that described for compound 3 (Example 1). m.p.: 214-217° C. LCMS: 468 [M+1]$^+$. $^1$H NMR (400 MHz, DMSO-d$_6$) δ 3.23 (s, 3H), 3.73 (m, 4H), 3.87 (m, 4H), 5.18 (s, 2H), 7.35 (s, 1H), 8.05 (s, 1H), 8.30 (s, 1H), 8.74 (s, 2H), 9.07 (s, 1H), 11.11 (s, 1H), 13.07 (s, 1H).

Example 92: Preparation of N-hydroxy-2-(methyl((4-morpholino-2-(1H-pyrrol-3-yl)thieno[3,2-d]pyrimidin-6-yl)methyl)amino)pyrimidine-5-carboxamide (Compound 197)

Step 92a: 3-Bromo-1-(triisopropylsilyl)-1H-pyrrole (Compound 0601-197)

A solution n-BuLi in THF (2.5 M, 19.6 mL, 49 mmol) was added to a stirred solution of pyrrole (3 g, 44.7 mmol) in anhydrous THF (20 mL) at −78° C. in an N$_2$ atmosphere. Then the mixture was warmed to room temperature and stirred at this temperature for 10 min. The mixture was cooled again to −78° C., and chlorotriisopropylsilane (10.5 g, 44.7 mmol) was added dropwisely with stirring. Then the mixture was warmed to room temperature and stirred for additional 30 min., diluted with water (200 mL), extracted with ether (200 mL). The organic layer was washed with water (2×100 mL) and brine (100 mL), dried over Na$_2$SO$_4$, concentrated to give crude 1-(triisopropylsilyl)-1H-pyrrole (11 g, 100%) as a oil. LCMS: 224 [M+1]$^+$. $^1$H NMR (400 MHz, DMSO-d$_6$) δ 0.98 (m, 18H), 1.40 (m 3H), 6.20 (m, 2H), 6.80 (m, 2H).

To a solution of the above prepared 1-(triisopropylsilyl)-1H-pyrrole (5.85 g, 26.2 mmol) in THF (50 mL) was added NBS (4.66 g, 26.2 mmol) at −78° C. and the resulting mixture was stirred at −78° C. for 2 h. The mixture was warmed to room temperature and stirred for additional 1 h. The mixture was concentrated and purified by column chromatography on silica gel (petroleum) to give compound 0601-197 (6.8 g, 63%) as a colorless oil. LCMS: 302

[M+1]+. 1H NMR (400 MHz, DMSO-d$_6$) δ 0.98 (m, 18H), 1.47 (m 3H), 6.26 (d, J=6.0 Hz, 1H), 6.82 (m, 1H), 6.89 (m, 1H).

Step 92b:
1-(Triisopropylsilyl)-1H-pyrrol-3-ylboronic acid (Compound 0602-197)

A solution n-BuLi in THE (2.5 M, 1.58 mL, 3.96 mmol) was added to a stirred solution of 0601-197 (1 g, 3.31 mmol) in anhydrous THE (20 mL) at −78° C. in an N$_2$ atmosphere. The resulting mixture was stirred at this temperature for 30 min. To the mixture was added trimethyl borate (687 mg, 6.6 mmol) dropwise. Then the mixture was warmed to room temperature and stirred for additional 1 h. The mixture was diluted with water (200 mL), extracted with ethyl acetate (200 mL). The organic layer was washed with water (2×100 mL) and brine (100 mL), dried over Na$_2$SO$_4$, concentrated to give crude compound 0602-197 (280 mg, 32%) as a oil which was used in next step directly without further purification. LCMS: 268 [M+1]+.

Step 92c: Ethyl 2-(methyl((4-morpholino-2-(1H-pyrrol-3-yl)thieno[3,2-d]pyrimidin-6-yl)methyl) amino)pyrimidine-5-carboxylate (Compound 0603-197)

The title compound 0603-197 was prepared (260 mg, 81%) as a yellow solid from 0504-54 (300 mg, 0.67 mmol), 0602-197 (0.8 g), NaHCO$_3$ (168 mg, 2.0 mmol), (Ph$_3$P)$_2$PdCl$_2$ (23 mg, 0.03 mmol) in toluene (5 mL), ethanol (3 mL) and water (1 mL) using a procedure similar to that described for compound 0603-107 (Example 34). LCMS: 480 [M+1]+. 1H NMR (400 MHz, DMSO-d$_6$) δ 1.28 (t, J=7.2 Hz, 3H), 3.24 (s, 3H), 3.71 (m, 4H), 3.84 (m, 4H), 4.27 (q, J=7.2 Hz, 2H), 5.18 (s, 2H), 6.65 (s, 1H), 6.77 (s, 1H), 7.33 (s, 1H), 7.47 (s, 1H), 8.86 (s, 2H), 11.07 (s, 1H).

Step 92d: N-Hydroxy-2-(methyl((4-morpholino-2-(1H-pyrrol-3-yl)thieno[3,2-d]pyrimidin-6-yl)methyl) amino)pyrimidine-5-carboxamide (Compound 197)

The title compound 197 was prepared (63 mg, 25%) as a yellow solid from 0603-197 (260 mg, 0.54 mmol) and freshly prepared hydroxylamine methanol solution (10 mL) using a procedure similar to that described for compound 3 (Example 1). m.p.: 175-189° C. LCMS: 467 [M+1]+. 1H NMR (400 MHz, DMSO-d$_6$) δ 3.21 (s, 3H), 3.72 (m, 4H), 3.83 (m, 4H), 5.15 (s, 2H), 6.65 (s, 1H), 6.75 (s, 1H), 7.30 (s, 1H), 7.46 (s, 1H), 8.73 (m, 2H), 9.05 (s, 1H), 11.05 (s, 1H), 11.11 (s, 1H).

Example 93: Preparation of 2-((2-(4-aminophenyl)-4-morpholinothieno[3,2-d]pyrimidin-6-yl)methylamino)-N-hydroxypyrimidine-5-carboxamide (Compound 211)

Step 93a: Ethyl 2-((2-(4-aminophenyl)-4-morpholinothieno[3,2-d]pyrimidin-6-yl)methylamino)pyrimidine-5-carboxylate (Compound 0603-211)

The title compound 0603-211 was prepared (65 mg, 22%) as a yellow solid from 0504-53 (256 mg, 0.59 mmol), 4-(4,4,5,5-tetramethyl-1,3,2-dioxaborolan-2yl)phenylamine (155 mg, 0.71 mmol), Cs$_2$CO$_3$ (577 mg, 1.77 mmol) and Pd(dppf)$_2$Cl$_2$ (48 mg, 0.06 mmol) in 1,4-dioxane (6 mL) and water (0.2 mL) using a procedure similar to that described for compound 0603-107 (Example 34). LCMS: 492 [M+1]+. 1H-NMR (400 MHz. DMSO-d$_6$) δ 1.29 (t, J=7.2 Hz, 3H), 3.75 (m, 4H), 3.89 (m, 4H), 4.27 (q, J=7.2 Hz, 2H), 4.87 (d, J=6.0 Hz, 2H), 5.53 (s, 2H), 6.60 (m, 2H), 7.28 (s, 1H), 8.09 (m, 2H), 8.83 (m, 3H).

Step 93b: 2-((2-(4-aminophenyl)-4-morpholinothieno[3,2-d]pyrimidin-6-yl) methylamino)-N-hydroxypyrimidine-5-carboxamide (Compound 211)

The title compound 211 was prepared (28 mg, 45%) as a yellow solid from 0603-211 (65 mg, 0.13 mmol) and freshly prepared hydroxylamine methanol solution (6 mL) using a procedure similar to that described for compound 3 (Example 1). m.p.: 217-223° C. LCMS: 479 [M+1]+. 1H-NMR (400 MHz. DMSO-d$_6$) δ 3.76 (m, 4H), 3.89 (m, 4H), 4.84 (d, J=5.6 Hz, 2H), 5.53 (s, 2H), 6.60 (m, 2H), 7.27 (s, 1H), 8.90 (m, 2H), 8.51 (t, J=5.6 Hz, 1H), 8.66 (s, 2H), 9.05 (s, 1H), 11.09 (s, 1H).

Example 94: (E)-3-(4-(N-(2-(2-aminopyrimidin-5-yl)-4-morpholinothieno[3,2-d]pyrimidin-6-yl)sulfamoyl)phenyl)-N-hydroxyacrylamide (Compound 217)

Step 94a: 7-Bromothieno[3,2-d]pyrimidine-2,4 (1H,3H)-dione (Compound 1001)

Bromine (9.1 mL, 178 mmol) was added to a solution of compound 0109 (10 g, 0.059 mol) in AcOH (166 mL) at room temperature. After the addition, the reaction was heated to 70° C. and stirred overnight. The reaction mixture was cooled to room temperature and poured into ice-water (1 L). The resulting mixture was filtered and washed with water. The solid was suspended in saturated Na$_2$S2O3 solution and stirred for 30 min followed by filtration. The solid was washed with water and saturated NaHCO$_3$ solution, dried in vacuo to afford 1001 as a yellow solid (14.6 g, 87%). LCMS: 247.0 [M+1]+. 1H NMR (400 MHz, DMSO-d$_6$): δ 8.22 (s, 1H), 11.40 (s, 1H), 11.51 (s, 1H).

Step 94b: 7-Bromo-2,4-dichlorothieno[3,2-d]pyrimidine (Compound 1002)

A mixture of compound 1001 (12.8 g, 51 mmol) in POCl$_3$ (150 mL) was heated to reflux for 12 h. The excess POCl$_3$ was removed in vacuo and the residue was poured into crush ice and filtered to afford the titled compound 1002 as a yellow solid. (11.8 g, 80.2%). LCMS: 284.8 [M+1]+. 1H NMR (400 MHz, DMSO-d$_6$): δ 8.86 (s, 1H).

Step 94c: 4-(7-Bromo-2chlorothieno[3,2-d]pyrimidin-4-yl)morpholine (Compound 1003)

Compound 1002 (11.8 g, 41.5 mmol) was suspended in methanol (150 mL) at room temperature. Morpholine (11.2 mL, 124.5 mmol) was added. The resulting mixture was stirred at room temperature for 2 h before it was filtered. The solid was washed with water, methanol and dried in vacuo to afford compound 1003 as a yellow solid. (11.5 g, 82.7%). LCMS: 336.0 [M+1]+. 1H NMR (400 MHz, DMSO-d$_6$): δ 3.77 (t, J=5.2 Hz, 4H), 3.92 (t, J=5.2 Hz, 4H), 8.52 (s, 1H).

Step 94d: 4-(7-Bromo-2chloro-6-nitrothieno[3,2-d] pyrimidin-4-yl)-morpholine (Compound 1004)

Compound 1003 (11.5 g, 34.3 mmol) was added portions to concentrated H$_2$SO$_4$ (35 mL) at 0° C. Then fuming HNO$_3$ (9 mL, 206 mmol) was added dropwise to above solution at 0° C. over 15-30 min. The resulting solution was stirred at 0° C. for 2 h before it was poured into crush ice. The resulting mixture was filtered, washed with water and dried in vacuo to afford 1004 as a yellow solid (12.0 g, 90.0%). LCMS: 371.0 [M+1]$^+$. $^1$H NMR (400 MHz, DMSO-$d_6$): δ 3.78 (t, J=5.2 Hz, 4H), 3.94 (t, J=5.2 Hz, 4H).

Step 94e: 2-Chloro-4-morpholinothieno[3,2-d]pyrimidin-6-amine (Compound 1005)

A mixture of compound 1004 (12.0 g, 31.5 mmol), Tin powder (11.0 g, 94.7 mmol) and concentrated HCl (31.6 mL) in methanol (350 mL) was stirred at 50° C. for 1 h until it became clear solution. More tin powder (7.6 g, 65.4 mmol) and concentrated hydrochloric acid (25 mL) were added to the solution and the resulting mixture was stirred at 50° C. overnight. The reaction mixture was cooled to room temperature and filtered to afford compound 1005 as a pale yellow solid (4.0 g, 47%). LCMS: 271.0 [M+1]$^+$. $^1$H NMR (400 MHz, DMSO-$d_6$): δ 3.69 (s, 8H), 5.94 (s, 1H), 7.15 (s, 2H).

Step 94f: (E)-Methyl 3-(4-(N-(2-chloro-4-morpholinothieno[3,2-d]pyrimidin-6-yl) sulfamoyl)phenyl) acrylate (Compound 1007-217)

To a mixture of 1006-217 (300 mg, 1.11 mmol) and 1005 (400 mg, 1.56 mmol) in THF (30 mL) was added NaH (300 mg, 12.5 mmol). The reaction mixture was stirred at room temperature for 3 h. The reaction mixture was concentrated. Water was added to the mixture and stirred for 30 min. The resulting mixture was neutralized with HOAc and filtered. The collected solid was dissolved in MeOH (20 mL), $H_2SO_4$ (5 drops) was added. The reaction mixture was refluxed for 3 h and concentrated. The residue was treated with water (20 mL) and filtered. The solid was washed with water and dried to afford the titled compound 1007-217 (250 mg, 46%). It was used for the next step reaction without further purification.

Step 94 g: (E)-Methyl 3-(4-(N-(2-(2-aminopyrimidin-5-yl)-4-morpholinothieno[3,2-d]pyrimidin-6-yl) sulfamoyl)phenyl)acrylate (Compound 1008-217)

A mixture of 1007-217 (250 mg, 0.516 mol), 5-(4,4,5,5-tetramethyl-1,3,2-dioxaborolan-2-yl)pyrimidin-2-amine (0602-217) (200 mg, 1.43 mmol), sat. $NaHCO_3$ (2 mL) and Pd(PPh$_3$)$_4$ (50 mg) in DMSO (15 mL) was stirred at 130° C. for 5 h under $N_2$. To the reaction mixture was added water and neutralized with HOAc. The precipitate was collected by filtration. The crude product was purified by column chromatography to afford the titled compound 1008-217 as a yellow solid (160 mg, 57.3%). $^1$HNMR (400 MHz, DMSO-$d_6$): δ 3.73 (s, 3H), 3.76 (s, 4H), 3.95 (s, 4H), 6.71 (d, J=16.0 Hz, 1H), 7.4 (br, 2H), 7.66 (d, J=16.0 Hz, 1H), 7.82 (br, 4H), 8.99 (s, 2H).

Step 94 h: (E)-3-(4-(N-(2-(2-aminopyrimidin-5-yl)-4-morpholinothieno[3,2-d]pyrimidin-6-yl)sulfamoyl)phenyl)-N-hydroxyacrylamide (Compound 217)

A mixture of 1008-217 (150 mg) and freshly prepared $NH_2OH$ (8 mL, 1.79 M in MeOH) in $CH_2Cl_2$ (5 mL) was stirred at 0° C. for 2 h. The reaction mixture was adjusted to pH=6-7 with 1.2 M aqueous HCl and filtered. The cake was purified by prep-HPLC to afford the titled compound 94 as a yellow solid (70 mg). M.p.>300° C. LCMS: 555 [M+1]$^+$. $^1$HNMR (400 MHz, DMSO-$d_6$): δ 3.75 (s, 3H), 3.92 (s, 4H), 6.30 (br, 1H), 6.51 (d, J=16.0 Hz, 1H), 7.30 (br, 1H), 7.45 (d, J=16.0 Hz, 2H), 7.66 (d, J=7.6 Hz, 2H), 7.81 (d, J=8.0 Hz, 2H), 8.99 (s, 2H), 9.08 (s, 1H), 10.82 (s, 1H).

Example 95: (E)-3-(3-(N-(2-(2-aminopyrimidin-5-yl)-4-morpholinothieno[3,2-d]pyrimidin-6-yl)sulfamoyl)phenyl)-N-hydroxyacrylamide (Compound 218)

Step 95a: (E)-Methyl 3-(3-(chlorosulfonyl)phenyl) acrylate (1006-218)

To a solution of 3-nitro-benzaldehyde (15 g, 0.1 mol), (dimethoxy-phosphoryl)-acetic acid methyl ester (27 g, 0.148 mol) in DMF (100 ml) was added NaOMe (10.7 g 0.198 mol). The reaction was monitored by TLC. After reaction was completed, the reaction mixture was adjusted to pH=1 with aqueous HCl solution and evaporated. The resulting solid was washed with water to afford (E)-methyl 3-(3-nitrophenyl)acrylate as a yellow solid (20.14 g, 98%).

A solution of (E)-methyl 3-(3-nitrophenyl)acrylate (20.14 g, 0.097 mol), Fe (32.5 g, 0.58 mol), concentrated HCl (3.5 ml) in 50% EtOH (100 ml) was refluxed for 2 h. Upon completion, the solution was filtered through Celite and washed with EtOH. The filtrate was concentrated and extracted with dichloromethane. The combined organic phase was dried over $MgSO_4$ and concentrated to afford (E)-methyl 3-(3-aminophenyl)acrylate as a yellow solid (9.73 g, 57%).

To a solution of (E)-methyl 3-(3-aminophenyl)acrylate (11.55 g, 0.065 mol) in AcOH (13 mL) was added conc. HCl (45 mL). The resulting mixture was cooled to −10° C. by EtOH/dry ice bath. $NaNO_2$ solution (5 g in 7.2 mL water) was added dropwise at such a rate that internal temperature did not exceed −5° C. to form diazotization reaction solution. $SO_2$ (g) was introduced below the surface of HOAc (65 mL) until saturation was evident. CuCl (1.7 g) was added to the solution and continued the introduction of $SO_2$ until the yellow green suspension became blue-green and cooled to 0° C. To the reaction mixture was added the diazotization solution in portions prepared above and continued reaction for 30 min. The reaction mixture was poured into ice and extracted with dichloromethane. The crude product was purified by column chromatography to afford 1006-218 as a yellow solid. $^1$HNMR (400 MHz, CDCl$_3$): δ 3.84 (s, 3H), 6.57 (d, J=16 Hz, 1H), 7.66 (t, J=8.0 Hz, 1H), 7.72 (d, J=16 Hz, 1H), 7.85 (d, J=7.6 Hz, 1H), 8.04 (d, J=8.0 Hz, 1H), 8.16 (s, 1H).

Step 95b: (E)-Methyl 3-(3-(N-(2-chloro-4-morpholinothieno[3,2-d]pyrimidin-6-yl) sulfamoyl)phenyl) acrylate (Compound 1007-218)

To a mixture of 1006-218 (300 mg, 1.11 mmol) and 1005 (400 mg, 1.56 mmol) in THF (30 mL) was added NaH (300 mg, 12.5 mmol). The reaction mixture was stirred at room temperature for 3 h. The reaction mixture was concentrated. Water was added to the mixture and stirred for 30 min. The resulting mixture was neutralized with HOAc and filtered. The collected solid was dissolved in MeOH (20 mL), $H_2SO_4$ (5 drops) was added. The reaction mixture was refluxed for 3 h and concentrated. The residue was treated with water (20 mL) and filtered. The solid was washed with water and dried to afford the titled compound 1007-218 as a yellow solid (320 mg, 58%).

¹HNMR (400 MHz, DMSO-d₆): δ 3.70-3.79 (m, 11H), 6.67 (s, 1H), 6.72 (d, 16.0 Hz, 1H), 7.66 (t, J=6.0 Hz, 1H), 7.74 (d, J=16.0 Hz, 1H), 7.88 (d, J=8.4 Hz, 1H), 8.04 (d, J=8.0 Hz, 1H), 8.17 (s, 1H).

Step 95c: (E)-Methyl 3-(3-(N-(2-(2-aminopyrimidin-5-yl)-4-morpholinothieno[3,2-d]pyrimidin-6-yl)sulfamoyl)phenyl)acrylate (Compound 1008-218)

The title compound 1008-218 was prepared as a yellow solid (200 mg, 60%) from 1007-218 (300 mg, 0.6 mol), 5-(4,4,5,5-tetramethyl-1,3,2-dioxaborolan-2-yl)pyrimidin-2-amine (0602-217) (300 mg, 2.16 mmol), sat. NaHCO₃ (2 mL) and Pd(PPh₃)₄ (50 mg) in DMSO (10 mL) using a procedure similar to that described for compound 1008-217 (Example 94): ¹HNMR (400 MHz, DMSO-d₆): δ 3.79-3.83 (m, 7H), 4.01 (s, 4H), 6.40 (br, 1H), 6.72 (d, J=16.0 Hz, 1H), 7.42 (br, 2H), 7.62 (t, J=7.6 Hz, 1H), 7.78 (d, J=16.0 Hz, 1H), 7.88-7.98 (m, 3H), 8.13 (s, 1H), 9.03 (s, 2H).

Step 95d: (E)-3-(3-(N-(2-(2-aminopyrimidin-5-yl)-4-morpholinothieno[3,2-d]pyrimidin-6-yl)sulfamoyl)phenyl)-N-hydroxyacrylamide (Compound 218)

The title compound 218 was prepared as a light yellow solid (83 mg) from 1008-218 (150 mg) and freshly prepared hydroxylamine methanol solution (10 mL) using a procedure similar to that described for compound 217 (Example 94): M.p.: >300° C. LCMS: 555[M+1]⁺. ¹HNMR: (400 MHz, DMSO-d₆): δ 3.75 (s, 4H), 3.95 (s, 4H), 6.13 (br, 1H), 6.55 (d, J=16.0 Hz, 1H), 7.47-7.55 (m, 3H), 7.70-7.79 (m, 2H), 7.98 (s, 1H), 9.00 (s, 2H), 9.15 (s, 1H), 10.15 (br, 1H), 10.81 (s, 1H), 13.4 (br, 1H).

Example 96: (E)-N-hydroxy-3-(3-(N-(2-(6-methoxypyridin-3-yl)-4-morpholinothieno[3,2-d]pyrimidin-6-yl)sulfamoyl)phenyl)acrylamide (Compound 221)

Step 96a: (E)-Methyl 3-(3-(N-(2-(6-methoxypyridin-3-yl)-4-morpholinothieno[3,2-d]pyrimidin-6-yl)sulfamoyl)phenyl)acrylate (Compound 1008-221)

To a stirred mixture of 1007-218 (300 mg, 0.61 mmol) and 0602-221 (287 mg, 1.22 mmol) in DMSO (20 mL) was added Pd(PPh₃)₄ (36.7 mg, 0.032 mmol) and saturated aq. NaHCO₃ (2 mL). The resulting mixture was heated at 120° C. for 4 h. To the reaction mixture was added water and adjusted to pH=6-7 with acetic acid. The precipitate was collected by filtration. The crude product was purified by column chromatography to afford the titled compound 1008-221 as a yellow solid (250 mg, yield 72%). ¹H NMR (400 MHz, DMSO-d₆): δ 3.71 (s, 3H), 3.76 (t, J=4.4 Hz, 4H), 3.92-3.98 (m, 7H), 6.68 (d, J=16.0 Hz, 1H), 6.97 (d, J=8.8 Hz, 1H), 7.52-7.60 (m, 2H), 7.73 (d, J=16.0 Hz, 1H), 7.85 (d, J=8.0 Hz, 1H), 7.94 (d, J=5.4 Hz, 1H), 8.10 (s, 1H), 8.43-8.46 (m, 1H), 9.02 (s, 1H).

Step 96b: (E)-N-hydroxy-3-(3-(N-(2-(6-methoxy-pyridin-3-yl)-4-morpholinothieno[3,2-d]pyrimidin-6-yl)sulfamoyl)phenyl)acrylamide (Compound 221)

The title compound was prepared as a white solid (70 mg, yield 46%) from 1008-221 (150 mg, 0.264 mmol) and freshly prepared hydroxylamine methanol solution (10 mL, 1.79 M in MeOH) using a procedure similar to that described for compound 217 (Example 94): M.p.: >300° C. LCMS: 569.2 [M+1]⁺. ¹H NMR (400 MHz, DMSO-d₆): δ 3.77 (s, 4H), 3.94 (s, 7H), 6.55 (d, J=16.0 Hz, 1H), 6.97 (d, J=8.4 Hz, 1H), 7.47-7.57 (m, 2H), 7.72-7.80 (m, 2H), 7.99 (s, 1H), 8.45 (d, J=8.0 Hz, 1H), 9.02 (s, 1H), 9.06 (br, 1H), 10.78 (s, 1H).

Example 97: N-Hydroxy-3-{4-[2-(6-methoxy-pyridin-3-yl)-4-morpholin-4-yl-thieno[3,2-d]pyrimidin-6-ylsulfamoyl]-phenyl}-acrylamide (Compound 222)

Step 97a: 3-{4-[2-(6-Methoxy-pyridin-3-yl)-4-morpholin-4-yl-thieno[3,2-d]pyrimidin-6-ylsulfamoyl]-phenyl}-acrylic acid methyl ester (Compound 1008-222)

The title compound 1008-222 was prepared as a yellow solid (200 mg, 58%) from 1007-217 (300 mg, 0.61 mol), 0602-221 (287 mg, 1.22 mmol), Pd(PPh₃)₄ (36.7 mg, 0.032 mmol) and sat. NaHCO₃ (2 mL) in DMSO (20 mL) using a procedure similar to that described for compound 1008-221 (Example 96): LCMS: 568.2 [M+1]⁺. ¹H NMR (400 MHz, DMSO-d₆): δ 3.72 (s, 3H), 3.76 (t, J=4.4 Hz, 4H), 3.93 (s, 7H), 5.75 (s, 1H), 6.71 (d, J=16 Hz, 1H), 6.96 (br, 1H), 7.67 (d, J=16 Hz, 1H), 7.81-7.85 (m, 4H), 8.45 (br, 1H), 9.02 (s, 1H).

Step 97b: N-Hydroxy-3-{4-[2-(6-methoxy-pyridin-3-yl)-4-morpholin-4-yl-thieno[3,2-d]pyrimidin-6-ylsulfamoyl]-phenyl}-acrylamide (Compound 222)

The title compound 222 was prepared as a white solid (32 mg, 21.%) from 1008-222 (150 mg, 0.264 mmol) and freshly prepared hydroxylamine methanol solution (5 mL, 1.79 M) using a procedure similar to that described for compound 217 (Example 94): M.p.: >300° C. LCMS: 569.2 [M+1]⁺. ¹H NMR (400 MHz, DMSO-d₆): δ 3.72 (s, 4H), 3.75 (s, 4H), 3.87 (s, 3H), 6.04 (s, 1H), 6.44 (d, J=16 Hz, 1H), 6.83 (d, J=8.8 Hz, 1H), 7.40 (d, J=16 Hz, 1H), 7.56 (d, J=8 Hz, 2H), 7.73 (d, J=7.6 Hz, 2H), 8.47 (d, J=8.4 Hz, 1H), 9.03 (m, 2H), 10.79 (s, 1H).

Example 98: 4-(2-(2-aminopyrimidin-5-yl)-4-morpholinothieno[3,2-d]pyrimidin-6-ylamino)-N-hydroxybutanamide (Compound 225)

Step 98a: tert-Butyl 2-chloro-4-morpholinothieno[3,2-d]pyrimidin-6-ylcarbamate (Compound 1101)

Compound 1005 (2.0 g, 7.4 mmol) and (Boc)₂O (1.95 g, 8.9 mmol) were taken into DMF (10 mL) followed by the addition of NaH (0.90 g, 22.2 mmol). The resulting mixture was stirred at 0° C. for 3 h. The reaction was monitored by TLC. After reaction completion, the mixture was partitioned between dichloromethane and water. The organic layer was washed with brine, dried over Na₂SO₄ and evaporated to give a crude product which was purified by column chromatography eluted with hexanes/ethyl acetate to afford the titled compound as a light yellow solid (1.3 g, 47.5%). LCMS: 371.0 [M+1]⁺. ¹H NMR (400 MHz, DMSO-d₆): δ 1.51 (s, 9H), 3.75 (t, J=4.8 Hz, 4H), 3.84 (t, J=4.8 Hz, 4H), 6.64 (s, 1H), 11.26 (s, 1H).

Step 98b: Ethyl 4-((2-(2-aminopyrimidin-5-yl)-4-morpholinothieno[3,2-d]pyrimidin-6-yl)(tert-butoxycarbonyl)amino)butanoate (Compound 1103-225)

A mixture of 1101 (300 mg, 0.81 mmol), ethyl 4-bromobutanoate (236 mg, 1.22 mmol) and Cs₂CO₃ (528 mg, 1.62 mmol) was taken into DMF (10 mL) and heated at 100° C. for 2 h. To the reaction mixture was added water and extracted with ethyl acetate. The ethyl acetate extract was concentrated to give a crude product 1102-225 which was used for the next step without further purification.

A mixture of compound 1102-225 (280 mg, 0.58 mmol), 5-(4,4,5,5-tetramethyl-1,3,2-dioxaborolan-2-yl)pyrimidin-2-amine (0602-217) (640 mg, 2.9 mmol), NaHCO$_3$ (150 mg, 1.5 mmol), and bis(triphenylphosphine)palladium(II) chloride (100 mg, 0.14 mmol) in a mixed solvents of toluene (23 mL), ethanol (14 mL) and water (6 mL) was flushed with nitrogen and heated at 130° C. for 3.5 h. The reaction mixture was concentrated and residue was partitioned between EtOAc and H$_2$O. The organic layer was washed with brine, dried over Na$_2$SO$_4$, and evaporated. The crude product was purified by column chromatography eluted with DCM/EtOAc to afford titled compound 1103-225 as a white solid (160 mg, 51%).

HNMR: (400 MHz, CDCl$_3$): δ 1.28 (t, J=7.2 Hz, 3H), 1.60 (s, 9H), 2.08-2.11 (m, 2H), 2.40-2.44 (m, 2H), 3.87 (t, J=4.4 Hz, 4H), 3.98-4.02 (m, 6H), 4.17 (q, J=7.2 Hz, 2H), 5.26 (s, 2H), 6.85 (s, 1H), 9.27 (s, 2H).

Step 98c: 4-(2-(2-Aminopyrimidin-5-yl)-4-morpholinothieno[3,2-d]pyrimidin-6-ylamino)-N-hydroxybutanamide (Compound 225)

A solution of compound 1103-225 (160 mg, 0.3 mmol) in TFA (2 mL) was stirred at room temperature for 5 h. Then the mixture was neutralized with sat. NaHCO$_3$ and extract with dichloromethane. Crude 1104-225 was obtained as white solid after concentration and used for next step reaction without further purification.

Crude 1104-225 (160 mg, 0.36 mmol) was taken into NH$_2$OH methanol solution (5 mL, 1.79 M) and DCM (2 mL) and stirred at room temperature overnight. The resulting mixture was adjusted to pH=6-7 with acetic acid and collected the solid. The crude product was purified by prep-HPLC to afford the title compound 225 as an off-white solid (40 mg). M.p.: 220-230° C. LCMS: 431.0[M+1]$^+$. $^1$H NMR (400 MHz, DMSO-d$_6$): δ 1.81-1.83 (m, 2H), 2.05-2.07 (m, 2H), 3.15-3.17 (m, 2H), 3.75-3.76 (m, 8H), 6.02 (s, 1H), 6.99 (s, 2H), 7.49 (t, J=5.2 Hz, 1H), 8.72 (s, 1H), 9.05 (s, 2H), 10.40 (s, 1H).

Example 99: 4-(2-(2-Aminopyrimidin-5-yl)-4-morpholinothieno[3,2-d]pyrimidin-6-yl)-amino)-N-hydroxybutanamide (Compound 226)

Step 99a: 5-[tert-Butoxycarbonyl-(2-chloro-4-morpholin-4-yl-thieno[3,2-d]pyrimidin-6-yl)-amino]-pentanoic acid ethyl ester (Compound 1102-226)

A mixture of compound 1101 (300 mg, 0.81 mmol), ethyl 5-bromopentanoate (314 mg, 1.62 mmol) and Cs$_2$CO$_3$ (0.53 g, 1.62 mmol) in DMF (23 mL) was stirred at 100° C. for 2 h. The reaction mixture was cooled to room temperature and partitioned between EtOAc (25 mL) and H$_2$O (25 mL). The organic layer was washed with brine, dried over Na$_2$SO$_4$, filtered, and evaporated. The crude product 1102-226 was obtained as a yellow solid after concentration and used for next step without further purification. $^1$H NMR (400 MHz, CDCl$_3$): δ 1.25 (J=7.2 Hz, t, 3H), 1.59 (s, 9H), 1.60-1.80 (m, 4H), 2.34 (t, J=7.2 Hz, 2H), 3.86 (t, J=4.4 Hz, 4H), 3.88 (t, J=7.6 Hz, 2H), 3.95 (t, J=4.4 Hz, 4H), 4.14 (t, J=7.2 Hz, q, 2H), 6.65 (s, 1H).

Step 99b: 5-{[2-(2-Amino-pyrimidin-5-yl)-4-morpholin-4-yl-thieno[3,2-d]pyrimidin-6-yl]-tert-butoxycarbonyl-amino}-pentanoic acid ethyl ester (Compound 1103-226)

A mixture of 1102-226 (280 mg, 0.56 mmol), 5-(4,4,5,5-tetramethyl-1,3,2-dioxaborolan-2-yl)pyrimidin-2-amine (0602-217) (620 mg, 2.8 mmol), NaHCO$_3$ (150 mg, 1.8 mmol), and bis(triphenylphosphine)palladium(II) chloride (100 mg, 0.14 mmol) in a mixed solvents of toluene (23 mL), ethanol (14 mL) and water (6 mL) was flushed with N$_2$ and heated at 130° C. for 3.5 h. Reaction mixture was concentrated and the residue was partitioned between EtOAc and water. The organic layer was washed with brine, dried over Na$_2$SO$_4$, and evaporated. The crude product was purified by column chromatography eluted with dichloromethane/EtOAc to afford 1103-226 as a white solid (160 mg, 51%). LCMS: 558 [M+1]$^+$. $^1$H NMR (400 MHz, CDCl$_3$): δ 1.25 (t, J=7.2 Hz, 3H), 1.59 (s, 9H), 1.76-1.90 (m, 4H), 2.36 (t, J=7.2 Hz, 2H), 3.86 (t, J=4.4 Hz, 4H), 3.92 (t, J=7.2 Hz, 2H), 4.00 (t, J=4.4 Hz, 4H), 4.14 (q, J=7.2 Hz, 2H), 5.30 (s, 2H), 6.76 (s, 1H), 9.26 (s, 2H).

Step 99c: 4-(2-(2-Aminopyrimidin-5-yl)-4-morpholinothieno[3,2-d]pyrimidin-6-yl amino)-N-hydroxybutanamide (Compound 226)

The title compound 226 was prepared as an off-white solid (25 mg) from 1103-226 (160 mg, 0.28 mmol) and TFA (2 mL), and followed by treatment with freshly prepared hydroxylamine methanol solution (5 mL, 1.79 M) using a procedure similar to that described for compound 1103-225 (Example 98): m.p: 175-180° C. LCMS: 445.0 [M+1]$^+$. $^1$HNMR (400 MHz, DMSO-d$_6$): δ 1.57 (br, 4H), 1.99 (t, J=6.4 Hz, 2H), 3.17 (s, 2H), 3.75 (s, 4H), 3.77 (s, 4H), 6.01 (s, 1H), 6.99 (br, 2H), 7.50 (br, 1H), 8.67 (s, 1H), 9.04 (s, 2H), 10.35 (s, 1H).

Example 100: N-Hydroxy-5-(2-(2-(methylamino)pyrimidin-5-yl)-4-morpholinothieno[3,2-d]pyrimidin-6-ylamino)pentanamide (Compound 227)

Step 100a: Ethyl 5-(tert-butoxycarbonyl(2-(2-(methylamino)pyrimidin-5-yl)-4-morpholinothieno[3,2-d]pyrimidin-6-yl)amino)pentanoate (Compound 1103-227)

A mixture of 1102-226 (300 mg, 0.6 mmol), N-methyl-5-(4,4,5,5-tetra methyl-1,3,2-dioxaborolan-2-yl)pyrimidin-2-amine (0602-227) (645 mg, 4.22 mmol) and Pd(PPh$_3$)$_2$Cl$_2$ (12.7 mg) in a mixed solvents of toluene (6 mL), ethanol (4 mL) and water (1 mL) was stirred at 90° C. for 3 h under N$_2$ atmosphere. After the completion of the reaction (monitored by TLC), the reaction mixture was concentrated and the residue was purified by column chromatography eluted with methanol in dichloromethane to afford title product as a colorless oil (150 mg, 43%). $^1$HNMR (400 MHz, DMSO-d$_6$): δ 1.16 (t, J=7.2 Hz, 3H), 1.53 (s, 9H), 1.60-1.80 (m, 4H), 2.36 (t, J=6.4 Hz, 2H), 2.87 (d, J=4.8 Hz, 3H), 3.78 (t, J=4.4 Hz, 4H), 3.90-3.96 (m, 6H), 4.04 (q, J=7.2 Hz, 2H), 6.99 (s, 1H), 7.52 (d, J=4.8 Hz, 1H), 9.14 (br, 2H).

Step 100b: Ethyl 5-(2-(2-(methylamino)pyrimidin-5-yl)-4-morpholinothieno[3,2-d]pyrimidin-6-ylamino)pentanoate (Compound 1104-227)

A mixture of 1103-227 (150 mg, 0.26 mmol) and TFA (7 ml) was stirred at room temperature for 1.5 h. Upon completion of reaction, water was added to the mixture at 10° C. The mixture was then adjusted to pH=10-12 with 30% NaOH and extracted with dichloromethane. The crude product was purified by column chromatography (dichloromethane/MeOH) to afford the title compound as a light-yellow solid (75 mg, 61%). $^1$HNMR (400 MHz, DMSO-$d_6$): δ 1.16 (t, J=7.2 Hz, 3H), 1.60-1.65 (m, 4H), 2.34 (m, 2H), 2.87 (d, J=4.8 Hz, 3H), 3.18-3.20 (m, 2H), 3.75-3.76 (m, 8H), 4.06 (q, J=7.2 Hz, 2H), 6.02 (s, 1H), 7.41-7.47 (m, 1H), 9.09 (br, 2H).

Step 100c: N-Hydroxy-5-(2-(2-(methylamino)pyrimidin-5-yl)-4-morpholinothieno[3,2-d]pyrimidin-6-ylamino)pentanamide (Compound 227)

The title compound 227 was prepared as a white solid (45 mg, 60%) from 1104-227 (75 mg, 0.16 mmol) and freshly prepared hydroxylamine methanol solution (1.79 M, 20 mL) using a procedure similar to that described for compound 217 (Example 94): m.p.: 206-210° C. LCMS: 459.0 [M+1]$^+$. $^1$HNMR (400 MHz, DMSO-$d_6$): δ 1.57-1.59 (m, 4H), 1.00 (t, J=6.4 Hz, 2H), 2.86 (d, J=4.8 Hz, 3H), 3.14-3.18 (m, 2H), 3.75-3.76 (m, 8H), 6.01 (s, 1H), 7.41-7.47 (m, 1H), 8.68 (s, 1H), 9.09 (br, 2H), 10.36 (s, 1H).

Example 101: N-Hydroxy-5-(2-(6-(methylamino)pyridin-3-yl)-4-morpholinothieno[3,2-d]pyrimidin-6-ylamino)pentanamide (Compound 228)

Step 101a: Ethyl 5-(tert-butoxycarbonyl(2-(6-(methylamino)pyridin-3-yl)-4-morpholino thieno[3,2-d]pyrimidin-6-yl)amino)pentanoate (Compound 1103-228)

A mixture of 1102-226 (500 mg, 1.11 mmole), methyl-[5-(4,4,5,5-tetramethyl-[1,3,2]dioxaborolan-2-yl)-pyridin-2-yl]-amine (0602-228) (920 mg, 6.01 mmole), NaHCO$_3$ (253 mg, 3.01 mmol) and Pd(PPh$_3$)$_2$Cl$_2$ (35 mg) in toluene/EtOH/H$_2$O (16 mL/10 mL/4 mL) was degassed with N$_2$ and heated at 110° C. overnight. TLC showed that the reaction was complete. The reaction mixture was concentrated. The residue was purified by column chromatography to afford 1103-228 as an off-white solid (370 mg, 65%). LCMS: [M+1]$^+$=571.

Step 101b: Ethyl 5-(2-(6-(methylamino)pyridin-3-yl)-4-morpholinothieno[3,2-d]pyrimidin-6-ylamino)pentanoate (Compound 1104-228)

The title compound 1104-228 was prepared as yellow solid (300 mg, 98%) from 1103-228 (370 mg, 0.65 mmole) and TFA (4 ml) using a procedure similar to that described for compound 1104-227 (Example 100): LCMS: [M+1]$^+$=471

Step 101c: N-hydroxy-5-(2-(6-(methylamino)pyridin-3-yl)-4-morpholinothieno[3,2-d]pyrimidin-6-ylamino)pentanamide (Compound 228)

The title compound 228 was prepared as a light yellow solid (80 mg, 51%) from 1104-228 (160 mg, 0.34 mmol) and a freshly prepared hydroxylamine methanol solution (10 mL, 1.79 M) using a procedure similar to that described for compound 217 (Example 94): M.p.:199-201° C. LCMS: 438 [M+1]$^+$. $^1$HNMR: (400 MHz, DMSO-$d_6$): δ 1.58 (s, 4H), 2.00 (s, 2H), 2.82 (d, J=4.4 Hz, 2H), 3.16 (d, J=4.0 Hz, 2H), 3.75 (s, 8H), 5.99 (s, 1H), 6.47 (d, J=8.8 Hz, 1H), 6.83 (d, J=4.0 Hz, 1H), 7.43 (s, 1H), 8.23 (d, J=8.4 Hz, 1H), 8.72 (s, 1H), 8.96 (s, 1H), 10.39 (s, 1H).

Example 102: N-Hydroxy-5-(2-(2-methylpyrimidin-5-yl)-4-morpholinothieno[3,2-d]pyrimidin-6-ylamino)pentanamide (Compound 229)

Step 102a: Ethyl 5-(tert-butoxycarbonyl(2-(2-methylpyrimidin-5-yl)-4-morpholino-thieno[3,2-d]pyrimidin-6-yl)amino)pentanoate (Compound 1103-229)

A mixture of 1102-226 (300 mg, 0.619 mmol), 2-methyl-5-(4,4,5,5-tetra methyl-1,3,2-dioxaborolan-2-yl)pyrimidine (0602-229) (681 mg, 3.10 mmol), NaHCO$_3$ (155 mg, 1.854 mmol) and Pd(PPh$_3$)$_2$Cl$_2$ (50 mg) in toluene/EtOH/H$_2$O (5.0 mL/3.2 mL/1.4 mL) was stirred at 120° C. for 5 h under N$_2$. The reaction mixture was concentrated. The residue was purified by column chromatography to afford the titled compound as an off-white solid (300 mg, yield 89.8%).

Step 102b: Ethyl 5-(2-(2-methylpyrimidin-5-yl)-4-morpholinothieno[3,2-d]pyrimidin-6-ylamino)pentanoate (Compound 1104-229)

The title compound 1104-229 was prepared as a white solid (130 mg) from 1103-229 (300 mg) and TFA (3 mL) using a procedure similar to that described for compound 1104-227 (Example 100).

Step 102c: N-Hydroxy-5-(2-(2-methylpyrimidin-5-yl)-4-morpholinothieno[3,2-d]pyrimidin-6-ylamino)pentanamide (Compound 229)

The title compound 229 was prepared as a white solid (55 mg) from 1104-229 (130 mg) and a freshly prepared hydroxylamine methanol solution (10 mL, 1.79 M) using a procedure similar to that described for compound 217 (Example 94): M.p.: 248-252° C. LCMS: 444.0 [M+1]$^+$. $^1$HNMR (400 MHz, DMSO-$d_6$): δ 1.58 (s, 4H), 2.00-2.01 (m, 2H), 2.69 (s, 3H), 3.18 (d, J=5.2 Hz, 2H), 3.76 (d, J=4.4 Hz, 4H), 3.80 (d, J=4.4 Hz, 4H), 6.09 (s, 1H), 7.60 (t, J=5.2 Hz, 1H), 8.71 (s, 1H), 9.44 (s, 2H), 10.28 (s, 1H).

Example 103: 6-[2-(2-Amino-pyrimidin-5-yl)-4-morpholin-4-yl-thieno[3,2-d]pyrimidin-6-ylamino]-hexanoic acid hydroxyamide (Compound 232)

Step 103a: 6-[tert-Butoxycarbonyl-(2-chloro-4-morpholin-4-yl-thieno[3,2-d]pyrimidin-6-yl)-amino]-hexanoic acid ethyl ester (Compound 1102-232)

The title compound 1102-232 was prepared as a yellow solid (480 mg, yield 100%) from 1101 (300 mg, 0.81 mmol), ethyl 6-bromohexanoate (360 mg, 1.62 mmol) and Cs$_2$CO$_3$ (0.53 g, 1.62 mmol) in DMF (23 mL) using a procedure similar to that described for compound 1102-226 (Example 99): $^1$HNMR (400 MHz, CDCl$_3$): δ 1.16 (t, J=7.2 Hz, 3H), 1.30-1.37 (m, 2H), 1.52 (s, 9H), 1.55-1.65 (m, 4H), 2.24-2.30 (m, 2H), 3.26 (t, 2H), 3.74 (t, J=4.8 Hz, 4H), 3.84 (t, J=4.4 Hz, 4H), 3.90 (t, J=7.2 Hz, 2H), 4.04 (q, J=7.2 Hz, 2H), 6.90 (s, 1H).

Step 103b: 6-{[2-(2-Amino-pyrimidin-5-yl)-4-morpholin-4-yl-thieno[3,2-d]pyrimidin-6-yl]-tert-butoxycarbonyl-amino}-hexanoic acid ethyl ester (Compound 1103-232)

The title compound 1103-232 was prepared as a white solid (300 mg, 67%) from 1102-232 (400 mg, 0.78 mmol), 5-(4,4,5,5-tetramethyl-1,3,2-dioxaborolan-2-yl)pyrimidin-2-amine (0602-217) (730 mg, 3.3 mmol), NaHCO$_3$ (200 mg, 2.4 mmol) and bis(triphenylphosphine)palladium(II) chloride (140 mg, 0.39 mmol) in toluene (32 mL), ethanol (20 mL) and water (8 mL) using a procedure similar to that described for compound 1103-226 (Example 99): LCMS: 572.2[M+1]$^+$. $^1$H NMR (400 MHz, CDCl$_3$): δ 1.25 (t, J=7.2 Hz, 3H), 1.39-1.45 (m, 2H), 1.59 (s, 9H), δ 1.67-1.80 (m, 4H), 2.32 (t, J=7.2 Hz, 2H), 3.85-3.91 (m, 6H), 4.00 (t, J=5.2 Hz, 4H), 4.14 (q, J=7.2 Hz, 2H), 6.75 (s, 1H), 9.27 (s, 2H).

Step 103c: 6-[2-(2-Amino-pyrimidin-5-yl)-4-morpholin-4-yl-thieno[3,2-d]pyrimidin-6-ylamino]-hexanoic acid ethyl ester (Compound 1104-232)

The title compound 1104-232 was prepared as a white solid (200 mg) from 1103-232 (300 mg, 0.5 mmol) and TFA (3 mL) using a procedure similar to that described for compound 1104-227 (Example 100): LCMS: 472.2[M+1]$^+$. $^1$H NMR (400 MHz, CDCl$_3$): δ 1.17 (t, J=7.2 Hz, 3H), 1.35-1.40 (m, 2H), 1.55-1.61 (m, 4H), 2.29 (t, J=7.2 Hz, 2H), 3.13-3.18 (m, 2H), 3.70-3.75 (m, 8H), δ 4.04 (q, J=7.2 Hz, 2H), 5.99 (s, 1H), δ 6.91 (s, 2H), δ 7.39 (t, J=5.6 Hz, 1H), 9.04 (s, 2H).

Step 103d: 6-[2-(2-Amino-pyrimidin-5-yl)-4-morpholin-4-yl-thieno[3,2-d]pyrimidin-6-ylamino]-hexanoic acid hydroxyamide (Compound 232)

The title compound 232 was prepared as an off-white solid (20 mg) from 1104-232 (100 mg, 0.21 mmol) and a freshly prepared hydroxylamine methanol solution (5 mL, 1.79 M) using a procedure similar to that described for compound 217 (Example 94): m.p: 220-225° C. LCMS: 459.0 [M+1]$^+$. $^1$HNMR (400 MHz, DMSO-d$_6$): δ 1.30-1.37 (m, 2H), 1.49-1.62 (m, 4H), 1.96 (t, J=7.2 Hz, 2H), 3.15-3.17 (m, 2H), 3.76-3.91 (m, 8H), 6.11 (s, 1H), 7.2 (br, 2H), 8.6 (br, 1H), 9.09 (s, 2H), 10.39 (s, 1H), 11.8 (br, 1H).

Example 104: 6-[2-(6-Methoxy-pyridin-3-yl)-4-morpholin-4-yl-thieno[3,2-d]pyrimidin-6-ylamino]-hexanoic acid hydroxyamide (Compound 233)

Step 104a: 6-{tert-Butoxycarbonyl-[2-(6-methoxy-pyridin-3-yl)-4-morpholin-4-yl-thieno[3,2-d]pyrimidin-6-yl]-amino}-hexanoic acid ethyl ester (Compound 1103-233)

A mixture of compound 1102-232 (200 mg, 0.39 mmol), 0602-221 (183 mg, 0.78 mmol), NaHCO$_3$ (98 mg, 1.17 mmol) and bis(triphenylphosphine)palladium(II) chloride (14 mg, 0.039 mmol) in toluene (14 mL), ethanol (8.8 mL) and water (3.5 mL) was flushed with nitrogen and heated at 120° C. overnight. The reaction mixture was concentrated and partitioned between EtOAc and water. The organic layer was washed with brine, dried over Na$_2$SO$_4$. The crude product was purified by column chromatography eluted with dichloromethan/EtOAc to afford the titled compound 1103-233 as a white solid (200 mg, 88%). LCMS: 586.2[M+1]$^+$.

Step 104b: Ethyl 6-(2-(6-methoxypyridin-3-yl)-4-morpholinothieno[3,2-d]pyrimidin-6-ylamino)hexanoate (Compound 1104-233)

The title compound 1104-233 was prepared as a white solid (160 mg, 96%) from 1103-233 (200 mg, 0.34 mmol) and TFA (3 mL) using a procedure similar to that described for compound 1104-227 (Example 100): LCMS: 486.5 [M+1]$^+$. $^1$H NMR (400 MHz, CDCl$_3$): δ 1.26 (t, J=7.2 Hz, 3H), 1.30-1.45 (m, 2H), 1.46-1.80 (m, 4H), 2.30-2.34 (m, 2H), 3.30-3.40 (m, 2H), 3.84-3.90 (m, 8H), 4.00 (s, 3H), 4.14 (m, 2H), 4.62 (br, 1H), 6.22 (s, 1H), 6.79 (d, J=8.8 Hz, 1H), 8.55 (dd, J=8.8 Hz, 2.4 Hz, 1H), 9.10 (s, 1H).

Step 104c: 6-[2-(6-Methoxy-pyridin-3-yl)-4-morpholin-4-yl-thieno[3,2-d]pyrimidin-6-ylamino]-hexanoic acid hydroxyamide (Compound 233)

The title compound 233 was prepared as an off-white solid (50 mg) from 1104-233 (160 mg, 0.33 mmol) and a freshly prepared hydroxylamine methanol solution (10 mL, 1.79 M) using a procedure similar to that described for compound 217 (Example 94): m.p: 125-130° C. LCMS: 473 [M+1]$^+$. $^1$H NMR (400 MHz, DMSO-d$_6$): δ 1.32-1.34 (m, 2H), 1.51-1.60 (m, 4H), 1.94-1.98 (m, 2H), 3.14-3.16 (m, 2H), 3.74-3.79 (m, 8H), 3.91 (s, 3H), 6.03 (s, 1H), 6.88 (d, J=8.8 Hz, 1H), 7.48 (t, J=5.2 Hz, 1H), 8.51 (dd, J=8.4 Hz, 2.4 Hz, 1H), 8.67 (s, 1H), 9.08 (s, 1H), 10.34 (s, 1H).

Example 105: 7-[2-(2-Amino-pyrimidin-5-yl)-4-morpholin-4-yl-thieno[3,2-d]pyrimidin-6-ylamino]-heptanoic acid hydroxyamide (Compound 234)

Step 105a: 7-[tert-Butoxycarbonyl-(2-chloro-4-morpholin-4-yl-thieno[3,2-d]pyrimidin-6-yl)-amino]-heptanoic acid ethyl ester (Compound 1102-234)

The title compound 1102-234 was prepared as a yellow solid (480 mg, 100%) from 1101 (300 mg, 0.81 mmol), ethyl 7-bromoheptanoate (383 mg, 1.62 mmol) and Cs$_2$CO$_3$ (0.53 g, 1.62 mmol) in DMF (23 mL) using a procedure similar to that described for compound 1102-226 (Example 99): LCMS: 527.2 [M+1]$^+$.

Step 105b: 7-{[2-(2-Amino-pyrimidin-5-yl)-4-morpholin-4-yl-thieno[3,2-d]pyrimidin-6-yl]-tert-butoxycarbonyl-amino}-heptanoic acid ethyl ester (Compound 1103-234)

The title compound 1103-234 was prepared as a white solid (220 mg, 49%) from 1102-234 (400 mg, 0.76 mmol), 5-(4,4,5,5-tetramethyl-1,3,2-dioxaborolan-2-yl)pyrimidin-2-amine (0602-217) (840 mg, 3.8 mmol), NaHCO$_3$ (200 mg, 2.4 mmol) and bis(triphenylphosphine)palladium(II) chloride (140 mg, 0.39 mmol) in toluene (32 mL), ethanol (20 mL) and water (8 mL) using a procedure similar to that described for compound 1103-226 (Example 99): LCMS: 586[M+1]$^+$. $^1$H NMR (400 MHz, CDCl$_3$): δ 1.25 (t, J=7.2 Hz, 3H), 1.40-1.41 (m, 2H), 1.59 (s, 9H), 1.63-1.76 (m, 2H), 2.30 (t, J=7.6 Hz, 2H), 3.85-3.90 (m, 6H), 4.00 (t, J=4.4 Hz, 4H), 4.13 (q, J=7.2 Hz, 2H), 5.38 (s, 2H), 6.76 (s, 1H), 9.26 (s, 2H).

Step 105c: 7-[2-(2-Amino-pyrimidin-5-yl)-4-morpholin-4-yl-thieno[3,2-d]pyrimidin-6-ylamino]-heptanoic acid ethyl ester (Compound 1104-234)

The title compound 1104-234 was prepared as a white solid (200 mg) from 1103-234 (220 mg, 0.38 mmol) and TFA (3 mL) using a procedure similar to that described for compound 1104-227 (Example 100): LCMS: 486.3[M+1]$^+$.

Step 105d: 7-[2-(2-Amino-pyrimidin-5-yl)-4-morpholin-4-yl-thieno[3,2-d]pyrimidin-6-ylamino]-heptanoic acid hydroxyamide (Compound 234)

The title compound 234 was prepared as an off-white solid (100 mg) from 1104-234 (100 mg, 0.21 mmol) and a freshly prepared hydroxylamine methanol solution (5 mL, 1.79 M) using a procedure similar to that described for compound 217 (Example 94): m.p: 235-240° C. LCMS: 473.0[M+1]$^+$. $^1$H NMR (400 MHz, DMSO-d$_6$): δ 1.23-1.35 (m, 4H), 1.48-1.59 (m, 4H), 1.95 (t, J=7.6 Hz, 2H), 3.12-3.19 (m, 2H), 3.74-3.75 (m, 8H), 5.99 (s, 1H), 6.97 (s, 2H), 7.43 (t, J=5.2 Hz, 1H), 8.64 (s, 1H), 9.04 (s, 2H), 10.32 (s, 1H).

Example 106: N-Hydroxy-2-(methyl((2-(6-(methylamino)pyridin-3-yl)-4-morpholinothieno[3,2-d]pyrimidin-6-yl)methyl)amino)pyrimidine-5-carboxamide (Compound 111)

Step 106a: (2-Chloro-4-morpholin-4-yl-thieno[3,2-d]pyrimidin-6-ylmethyl)-methylamine (Compound 0503)

To the solution of 0112 (20.0 g, 70.4 mmol) in methanol (125 mL) was added methylamine solution in methanol (27% v/v, 75 mL, 563.2 mmol) under nitrogen atmosphere. The reaction mixture was stirred at room temperature overnight and the solvent was removed in vacuo to give a crude solid product, which was dissolved in methanol (550 mL) and TH (220 mL) under nitrogen. Sodium borohydride (8 g, 211.2 mmol) was added in portions and reaction mixture was stirred at room temperature overnight. The reaction mixture was evaporated in vacuo and water (300 mL) was added. The aqueous mixture was extracted with methylene chloride and the combined extracts were dried over Na$_2$SO$_4$ and concentrated. The residue was dissolved in 6M HCl (230 mL) and stirred for 30 min. The aqueous solution was washed with methylene chloride for several times, and adjusted to pH=9-10 with NaOH (4N). The precipitated solid was collected by filtration and dried (60° C., 6 h) to give a light yellow solid (18 g, 85%).

LCMS: 299 [M+1]$^+$. $^1$H NMR (400 MHz, DMSO-d$_6$): δ 2.32 (s, 3H), 3.74 (t, J=5.2 Hz, 4H), 3.88 (t, J=5.2 Hz, 4H), 3.96 (s, 2H), 7.24 (s, 1H).

Step 106b: 2-[(2-Chloro-4-morpholin-4-yl-thieno[3,2-d]pyrimidin-6-ylmethyl)-methyl-amino]-pyrimidine-5-carboxylic acid ethyl ester (Compound 0504)

The mixture of 0503 (10 g, 33.6 mmol), CH$_3$CN (400 mL) and 0305 (6.8 g, 36.4 mmol) was stirred at room temperature. Diisopropylethylamine (DIPEA) (220 mL, 1.26 mol) was then added and the solution was stirred overnight and evaporated. After methylene chloride (300 mL) was added, the organic phase was washed with water, dried over Na$_2$SO$_4$ and concentrated in vacuo to leave a residue. To the residue was added ethyl acetate and the mixture was stirred in ice/water bath for 50 min. The titled product 0504 was collected as a white solid (10.6 g, 70%). LCMS: 449 [M+1]$^+$; $^1$HNMR (400 MHz, DMSO-d$_6$): δ 1.30 (t, J=7.2 Hz, 3H), 3.25 (s, 3H), 3.71 (t, J=5.2 Hz, 4H), 3.83 (t, J=4.8 Hz, 4H), 4.29 (m, 2H), 5.21 (s, 2H), 7.39 (s, 1H), 8.87 (s, 2H).

Step 106c: Ethyl 2-(methyl((2-(6-(methylamino)pyridin-3-yl)-4-morpholinothieno[3,2-d]pyrimidin-6-yl)methyl)amino)pyrimidine-5-carboxylate (Compound 0603-111)

A mixture of N-methyl-5-(4,4,5,5-tetramethyl-1,3,2-dioxaborolan-2-yl)pyridin-2-amine (0602-227) (351 mg, 1.5 mmol), 0504 (314 mg, 0.7 mmol), NaHCO$_3$ (176 mg, 2.1 mmol) and Pd(PPh$_3$)$_2$Cl$_2$ (24.6 mg, 0.035 mmol) were dissolved in Toluene/EtOH/H$_2$O (2.5 mL/1.6 mL/0.7 mL). Then the reaction was stirred at 120° C. in microwave for 2 h. Water (8 mL) was added to the mixture and extracted with ethyl acetate (15 mL×3). The organic layer was dried, concentrated, purified by column chromatography (methanol in dichloromethane, 5% v/v) to give the title compound 0603-111 (150 mg, 41%) as a white solid. LCMS: 521 [M+1]$^+$. $^1$H NMR (400 MHz, DMSO-d$_6$): δ 1.28 (t, J=7.2 Hz, 3H), 2.81 (d, J=4.4 Hz, 3H), 3.24 (s, 3H), 3.73 (d, J=4.4 Hz, 4H), 3.86 (d, J=4.4 Hz, 4H), 4.27 (q, J=7.2 Hz, 2H), 5.20 (s, 2H), 6.48 (d, J=8.4 Hz, 1H), 6.91 (d, J=4.4 Hz, 1H), 7.39 (s, 1H), 8.25 (d, J=8.4 Hz, 1H), 8.86 (s, 2H), 8.90 (s, 1H).

Step 106d: N-Hydroxy-2-(methyl((2-(6-(methylamino)pyridin-3-yl)-4-morpholinothieno[3,2-d]pyrimidin-6-yl)methyl)amino)pyrimidine-5-carboxamide (Compound 111)

The title compound 111 was prepared as a brown solid (21 mg, 14%) from 0603-236 (150 mg, 0.29 mmol) and a freshly prepared hydroxylamine methanol solution (6 mL) using a procedure similar to that described for compound 217 (Example 94): mp: 193-195° C. LCMS: 508 [M+1]$^+$. $^1$H NMR (400 MHz, DMSO-d$_6$): δ 2.83 (d, J=4.8 Hz, 3H), 3.23 (s, 3H), 3.74 (m, 4H), 3.89 (m, 4H), 5.20 (s, 2H), 6.50 (d, J=8.8 Hz, 1H), 6.92 (d, J=5.2 Hz, 1H), 7.39 (s, 1H), 8.27 (dd, J=8.8, 2.0 Hz, 1H), 8.75 (s, 2H), 9.01 (d, J=2.0 Hz, 1H), 9.07 (br, 1H).

Example 107: N-Hydroxy-2-(methyl(1-(2-(6-(methylamino)pyridin-3-yl)-4-morpholinothieno[3,2-d]pyrimidin-6-yl)ethyl)amino)pyrimidine-5-carboxamide (Compound 237)

Step 107a: 1-(2-Chloro-4-morpholinothieno[3,2-d]pyrimidin-6-yl)ethanone (Compound 1201)

To a solution of compound 0111 (5 g, 20 mmol) in THF (100 mL) at −78° C. was dropwise added a solution of nBuLi/THF (2.5 M, 11 mL). The reaction mixture was stirred at room temperature for about 30 minutes. DMA (7 g, 80 mmol) was added and the reaction mixture was allowed to slowly warm up to room temperature and stirred for 2 h. Reaction mixture was poured into a cold aqueous HCl solution. The crude product was precipitated from solution and collected by filtration to afford the title compound as a yellow solid (5 g, 86%).

Step 107b: 1-(2-Chloro-4-morpholinothieno[3,2-d]pyrimidin-6-yl)-N-methylethanamine (Compound 1202)

To a suspension of 1201 (2.36 g, 7.9 mmol) in MeOH (120 ml) was added MeNH$_2$/MeOH (7.3 g, 27%). The reaction mixture was stirred at 45° C. overnight. The reaction mixture was concentrated and the residue was dissolved in MeOH/THF (58 ml/23 ml). To the resulting solution was added MgSO$_4$ (2.4 g, 0.02 mol), NaBH$_4$ (897 mg, 23.7 mmol) and stirred at room temperature overnight. To the reaction mixture was added water. The mixture was adjusted to pH=5-6 with HCl and washed with dichloromethane. The aqueous layer was adjusted to pH=8-9 with aqueous NaOH and extracted with dichloromethane. The combine organic layers were dried and concentrated under reduced pressure to afford the crude product as a yellow solid (1.5 g, 60%). It was used for next step without further purification.

Step 107c: Ethyl 2-((1-(2-chloro-4-morpholinothieno[3,2-d]pyrimidin-6-yl)ethyl)(methyl) amino) pyrimidine-5-carboxylate (Compound 1203)

To a solution of 1202 (1.29 g, 4.12 mmol) in dioxane (40 mL) were added 0305 (962 mg, 5.15 mmol) and DIPEA (1.28 g, 9.9 mmol). The reaction mixture was refluxed overnight. The reaction mixture was concentrated and residue was purified by column chromatograph to afford titled compound as a white solid (1.9 g, 99%).
$^1$H NMR (400 MHz, DMSO-d$_6$): δ 1.31 (t, J=7.2 Hz, 3H), 1.71 (d, J=7.2 Hz, 3H), 3.01 (s, 3H), 3.70 (t, J=4.4 Hz, 4H), 3.82 (t, J=4.0 Hz, 4H), 4.29 (q, J=7.2 Hz, 2H), 6.50 (q, J=7.2 Hz, 1H), 7.38 (s, 1H), 8.88 (s, 2H).

Step 107d: Ethyl 2-(methyl(1-(2-(6-(methylamino) pyridin-3-yl)-4-morpholinothieno[3,2-d]pyrimidin-6-yl)ethyl)amino)pyrimidine-5-carboxylate (Compound 1204-237)

To a stirred mixture of compound 1203 (350 mg, 0.76 mmol) and compound 0602-237 (533 mg, 2.3 mmol) in toluene/EtOH/H$_2$O (20 mL/10 mL/2 ml) was added Pd(PPh$_3$)$_2$Cl$_2$ (28.7 mg, 0.038 mmol) and NaHCO$_3$ (191.52 mg, 2.28 mmol). The resulting mixture was heated to 120° C. and stirred for 5 h. The resulting mixture was concentrated to remove most of solvent. The residue was purified by column chromatography to afford the tiled compound 111-327-1 as a yellow solid (260 mg, 64%), $^1$H NMR (400 MHz, CDCl$_3$): δ 1.39 (t, J=7.2 Hz, 3H), 1.74 (s, 3H), 2.99 (d, J=5.2 Hz, 3H), 3.05 (s, 3H), 3.84 (t, J=4.8 Hz, 4H), 3.97 (t, J=4.4 Hz, 4H), 4.36 (q, J=7.2 Hz, 2H), 4.89 (d, J=4.0 Hz, 1H), 6.45 (d, J=8.8 Hz, 1H), 6.62 (q, J=6.4 Hz, 1H), 7.33 (s, 1H), 8.46 (dd, J=8.4 Hz, 2.0 Hz, 1H), 8.93 (s, 2H), 9.17 (s, 1H).

Step 107e: N-Hydroxy-2-(methyl(1-(2-(6-(methylamino)pyridin-3-yl)-4-morpholinothieno[3,2-d]pyrimidin-6-yl)ethyl)amino)pyrimidine-5-carboxamide (Compound 111-327)

A mixture of 1204-237 (150 mg, 0.28 mmol) and a freshly prepared NH$_2$OH in methanol (10 mL, 1.79 M in MeOH) was stirred at room temperature for 0.5 h. The mixture was adjusted to pH=5-6 with 2M aq. HCl and concentrated. The residue was purified by prep-HPLC to afford the titled compound 111-237 as a white solid (60 mg, 40%). M.p.: 270-275° C. LCMS: 522 [M+1]$^+$. $^1$HNMR (400 MHz, DMSO-d$_6$): δ 1.71 (s, 3H), 2.84 (d, J=4.0 Hz, 3H), 2.98 (s, 3H), 3.74 (s, 4H), 3.88 (s 4H), 6.45-6.25 (m, 2H), 6.90 (s, 1H), 7.39 (s, 1H), 8.27 (d, J=8.4 Hz, 1H), 8.76 (s, 2H), 9.02 (s, 1H), 9.06 (s, 1H), 11.13 (s, 1H).

Example 108: N-Hydroxy-2-(2-(2-(6-(methylamino) pyridin-3-yl)-4-morpholinothieno[3,2-d]pyrimidin-6-yl)propan-2-ylamino)pyrimidine-5-carboxamide (Compound 240)

Step 108a: 2-(2-Chloro-4-morpholinothieno[3,2-d] pyrimidin-6-yl)propan-2-ol (Compound 1205)

To a suspension of 0111 (5.10 g, 20.00 mmol) in THF (120 mL) at −70° C. was dropwise added a solution of n-BuLi/hexane (2.5 M, 22 mL, 55 mmol). The suspension was stirred at −20° C. for 45 min. The resulting red solution was re-cooled and dry acetone (5.8 g, 100 mmol) was then added at −70° C. and stirred at −20° C. for 5 h. The reaction mixture was quenched with ice water (125 mL) and extracted with ethyl acetate. The combined organic layers were dried over Na$_2$SO$_4$ and concentrated in vacuo to afford the crude product, which was purified by column chromatography (ethyl acetate in hexane) to afford the titled compound 1205 as a white solid (3.79 g, 60%). LC-MS: 314.1 [M+1]$^+$. $^1$H NMR (400 MHz, DMSO-d$_6$): δ 1.56 (s, 6H), 3.74 (m, 4H), 3.89 (m, 4H), 5.94 (s, 1H), 7.22 (s, 1H).

Step 108b: N-(2-(2-Chloro-4-morpholinothieno[3,2-d]pyrimidin-6-yl)propan-2-yl) formamide (Compound 1206)

To a suspension of 1205 (3.79 g, 12 mmol) in TMSCN (6 g, 60 mmol) was added conc. H$_2$SO$_4$ (13 g, 132 mmol) slowly at room temperature. The reaction mixture was stirred at room temperature for 5 h. The reaction mixture was quenched with ice water, basified with NH$_3$.H$_2$O and extracted with dichloromethane.
The crude product was purified by column chromatography (ethyl acetate/hexane) to afford the titled compound 1206 as an off-white solid (3.56 g, 87%). LC-MS: 341.1 [M+1]$^+$. $^1$H NMR (400 MHz, DMSO-d$_6$): δ 1.69 (s, 6H), 3.74 (m, 4H), 3.86 (m, 4H), 7.23 (s, 1H), 7.98 (s, 1H), 8.71 (s, 1H).

Step 108c: 2-(2-Chloro-4-morpholinothieno[3,2-d] pyrimidin-6-yl)propan-2-amine (Compound 1207)

A mixture of 1206 (3.55 g, 10.40 mmol) in MeOH (18 mL), H$_2$O (12 ml) and conc. HCl (47 mL) was stirred at room temperature overnight. Reaction mixture was concentrated and re-dissolved in water, neutralized with sat. NaHCO$_3$ and extracted with dichloromethane. The combined organic layers were dried over Na$_2$SO$_4$ and concentrated in vacuo to afford the crude product, which was purified by column chromatography (ethyl acetate/hexane) to afford the titled compound 1207 as a white solid (2.93 g, 90%).
LC-MS: 313 [M+1]$^+$. $^1$H NMR (400 MHz, DMSO-d$_6$): δ 1.49 (s, 6H), 2.40 (s, 2H), 3.74 (m, 4H), 3.89 (m, 4H), 7.23 (s, 1H).

Step 108d: Ethyl 2-(2-(2-chloro-4-morpholinothieno [3,2-d]pyrimidin-6-yl)propan-2-yl-amino)pyrimidine-5-carboxylate (Compound 1208)

A mixture of 1207 (1.50 g, 5 mmol), 0305 (1.85 g, 10 mmol) and DIPEA (1.92 g, 15 mmol) in dioxane (30 mL) was heated at 120° C. for 48 h. The reaction was then quenched with water and extracted with ethyl acetate. The combined organic layers were dried over Na$_2$SO$_4$ and concentrated in vacuo to afford the crude product, which was purified by column chromatography (ethyl acetate/hexane) to afford the title compound 1208 as an off-white solid (976 mg, 42%). LC-MS: 463.3 [M+1]$^+$. $^1$H NMR (400 MHz, DMSO-d$_6$): δ 1.25 (t, J=6.8 Hz, 3H), 1.82 (s, 6H), 3.70 (m, 4H), 3.81 (m, 4H), 4.23 (q, J=6.8 Hz, 2H), 7.20 (s, 1H), 8.71 (m, 3H).

Step 108e: Ethyl 2-(2-(2-(6-(methylamino)pyridin-3-yl)-4-morpholinothieno[3,2-d]pyrimidin-6-yl)propan-2-ylamino)pyrimidine-5-carboxylate (Compound 1210-240)

A mixture of 1208 (185 mg, 0.40 mmol), 0602-237 (187 mg, 0.80 mmol), NaHCO$_3$ (101 mg, 1.20 mmol) and PdCl$_2$ (PPh$_3$)$_2$ (28 mg, 0.04 mmol) in toluene (8 mL), EtOH (5 mL) and water (2 mL). The suspension was heated at 120° C. overnight. The reaction mixture was concentrated and the residue was purified by column chromatography (ethyl acetate/hexane) to afford the titled compound 1210-240 as a white solid (71 mg, 33%). LC-MS: 535 [M+1]$^+$. $^1$H NMR: (400 MHz, DMSO-d$_6$): δ 1.25 (t, J=7.2 Hz, 3H), 1.85 (s, 6H), 2.83 (d, J=0.8 Hz), 3.74 (m, 4H), 3.87 (m, 4H), 4.22 (q, J=7.2 Hz, 2H), 6.50 (d, J=8.8 Hz, 1H), 6.88 (d, J=4.8 Hz, 1H), 7.24 (s, 1H), 8.27 (dd, J=2.0 and 8.8 Hz, 1H), 8.69 (m, 3H), 9.01 (d, J=2.4 Hz, 1H).

Step 108f: N-Hydroxy-2-(2-(2-(6-(methylamino) pyridin-3-yl)-4-morpholinothieno[3,2-d]pyrimidin-6-yl)propan-2-ylamino)pyrimidine-5-carboxamide (Compound 240)

A mixture of 1210-240 (100 mg, 0.19 mmol) and a freshly prepared NH$_2$OH/MeOH solution (25 mL, 1.79M) in CH$_2$Cl$_2$ (4 mL) and stirred at room temperature for 1 h. The solution was filtrated and adjusted to pH=7 with acetic acid. To the mixture was added water (30 mL) and compound 240 (96 mg) was collected by filtration. m.p. 200-205° C. LC-MS: 522 [M+1]$^+$. $^1$H NMR (400 MHz, DMSO-d$_6$): δ 1.83 (s, 6H), 2.83 (d, J=4.8 Hz, 3H), 3.74 (m, 4H), 3.86 (m, 4H), 6.49 (d, J=8.8 Hz, 1H), 6.88 (s, 1H), 7.23 (s, 1H), 8.27 (dd, J=8.8 Hz, 2.4 Hz, 1H), 8.34 (s, 1H), 8.53 (br, 2H), 8.97 (s, 1H), 9.01 (d, J=2.4 Hz, 1H), 10.95 (s, 1H).

Example 109: N-Hydroxy-2-(methyl((2-(1-methyl-1H-pyrazol-4-yl)-4-morpholinothieno[3,2-d]pyrimidin-6-yl)methyl)amino)pyrimidine-5-carboxamide (Compound 246)

Step 109a: Ethyl 2-(methyl((2-(1-methyl-1H-pyrazol-4-yl)-4-morpholinothieno[3,2-d]pyrimidin-6-yl) methyl)amino)pyrimidine-5-carboxylate (Compound 0603-246)

The title compound 0603-246 was prepared as a yellow solid (196 mg, 35%) from 0504 (500 mg, 1.11 mmol), 1-methyl-4-(4,4,5,5-tetramethyl-1,3,2-dioxaborolan-2-yl)-1H-pyrazole (579 mg, 2.78 mmol) and Pd(PPh$_3$)$_2$Cl$_2$ (23 mg, 0.033 mmol) in toluene (11.2 mL), ethanol (7 mL) and water (2.3 mL) using a procedure similar to that described for compound 1103-226 (Example 99).

Step 109b: N-Hydroxy-2-(methyl((2-(1-methyl-1H-pyrazol-4-yl)-4-morpholinothieno[3,2-d]pyrimidin-6-yl)methyl)amino)pyrimidine-5-carboxamide (Compound 246)

The title compound 246 was prepared as a white solid (80 mg, 45%) from 0603-246 (190 mg, 0.38 mmol) and a freshly prepared hydroxylamine methanol solution (20 mL, 1.79 M in methanol) in dichloromethane (2 mL) using a procedure similar to that described for compound 217 (Example 94). m.p.:164-169° C. LCMS:482[M+1]$^+$. $^1$HNMR (400 MHz, DMSO-d$_6$): δ 3.22 (s, 3H), 3.73 (d, J=4.4 Hz, 4H), 3.86-3.90 (m, 7H), 5.18 (s, 2H), 7.35 (s, 1H), 7.97 (s, 1H), 8.31 (s, 1H), 8.75 (s, 2H), 9.09 (s, 1H), 11.15 (s, 1H).

Example 110: N-hydroxy-2-((1-(2-(6-methoxypyridin-3-yl)-4-morpholino-thieno[3,2-d]pyrimidin-6-yl) ethyl)(methyl)amino)pyrimidine-5-carboxamide (Compound 247)

Step 110a: Ethyl 2-((1-(2-(6-methoxypyridin-3-yl)-4-morpholinothieno[3,2-d]pyrimidin-6-yl)ethyl) (methyl)amino)pyrimidine-5-carboxylate (Compound 1210-247)

The title compound 1210-247 was prepared as a yellow solid (240 mg, 95%) from 1208 (200 mg, 0.43 mmol), 2-methoxy-5-(4,4,5,5-tetramethyl-1,3,2-dioxaborolan-2-yl) pyridine (153 mg, 0.65 mmol), NaHCO$_3$ (109 mg, 1.29 mmol) and bis(triphenylphosphine)palladium(II) chloride (15 mg, 0.02 mmol) in toluene (8 ml), ethanol (5 ml) and water (1 ml) using a procedure similar to that described for compound 1204-237 (Example 107): LCMS: 536.0 [M+1]$^+$. $^1$H NMR (400 MHz, DMSO-d$_6$): δ 1.31 (t, J=7.2 Hz, 3H), 1.74 (d, J=7.2 Hz, 3H), 3.03 (s, 3H), 3.75 (t, J=4.4 Hz, 4H), 3.913.93 (m, 7H), 4.30 (q, J=7.2 Hz, 2H), 6.50 (q, J=7.2 Hz, 1H), 6.92 (d, J=8.4 Hz, 1H), 7.48 (s, 1H), 7.57 (dd, J=8.4 Hz, 2.4 Hz, 1H), 8.89 (s, 2H), 9.15 (d, J=2.4 Hz, 1H).

Step 110b: N-Hydroxy-2-((1-(2-(6-methoxypyridin-3-yl)-4-morpholinothieno[3,2-d]pyrimidin-6-yl) ethyl)(methyl)amino)pyrimidine-5-carboxamide (Compound 247)

The title compound 247 was prepared as an light pink solid (120 mg, 56%) from 1210-247 (220 mg, 0.41 mmol) and a freshly prepared hydroxylamine methanol solution (30 mL, 1.79 M) using a procedure similar to that described for compound 237 (Example 107): LCMS: 523.0 [M+1]$^+$. $^1$H NMR (400 MHz, DMSO-d$_6$): δ 1.70 (d, J=6.8 Hz, 3H), 2.97 (s, 3H), 3.32 (m, 1H), 3.733.75 (m, 4H), 3.913.93 (m, 7H), 6.46 (d, J=6.8 Hz, 1H), 6.91 (d, J=8.8 Hz, 1H), 7.45 (s, 1H), 8.57 (dd, J=8.8 Hz, 2.0 Hz, 1H), 8.76 (s, 2H), 9.15 (d, J=2.4 Hz, 1H).

Example 111: N-Hydroxy-2-(2-(2-(6-methoxypyridin-3-yl)-4-morpholino-thieno[3,2-d]pyrimidin-6-yl) propan-2-ylamino)pyrimidine-5-carboxamide (Compound 250)

Step 11a: Ethyl 2-(2-(2-(6-methoxypyridin-3-yl)-4-morpholinothieno[3,2-d]pyrimidin-6-yl)propan-2-ylamino)pyrimidine-5-carboxylate (Compound 1210-250)

The title compound 1210-250 was prepared as a white solid (160 mg, 75%) from 1208 (185 mg, 0.40 mmol), 0602-222 (188 mg, 0.80 mmol), NaHCO$_3$ (101 mg, 1.20 mmol) and PdCl$_2$(PPh$_3$)$_2$ (28 mg, 0.04 mmol) was taken into toluene (8 mL), EtOH (5 mL) and water (2 mL) using a procedure similar to that described for compound 1204-237 (Example 107): LC-MS: 536.3 [M+1]$^+$. $^1$H NMR: (400 MHz, DMSO-d$_6$): δ 1.30 (t, J=6.8 Hz, 3H), 1.91 (s, 6H), 3.81 (m, 4H), 3.96 (m, 4H), 3.99 (s, 3H), 4.28 (q, J=6.8 Hz, 2H), 6.97 (d, J=8.8 Hz, 1H), 7.36 (s, 1H), 8.62 (dd, J=8.4 Hz, 2.4 Hz, 1H), 8.74 (m, 3H), 9.20 (d, J=2.0 Hz, 1H).

Step 111b: N-Hydroxy-2-(2-(2-(6-methoxypyridin-3-yl)-4-morpholinothieno[3,2-d]pyrimidin-6-yl)propan-2-ylamino)pyrimidine-5-carboxamide (Compound 250)

The title compound 247 was prepared as a white solid (140 mg) from 1210-250 (160 mg, 0.30 mmol) and a freshly prepared hydroxylamine methanol solution (30 mL, 1.79 M) in CH$_2$Cl$_2$ (4 mL) using a procedure similar to that described for compound 237 (Example 107): LC-MS: 523 [M+1]$^+$. $^1$H NMR (400 MHz, DMSO-d$_6$): δ 1.90 (s, 6H), 3.81 (m, 4H), 3.96 (m, 4H), 3.99 (s, 3H), 6.97 (d, J=8.4 Hz, 1H), 7.36 (s, 1H), 8.43 (s, 1H), 8.60 (m, 3H), 9.04 (s, 1H), 9.20 (d, J=2.0 Hz, 1H), 11.10 (s, 1H).

Example 112: N-Hydroxy-2-((2-(2-(6-methoxypyridin-3-yl)-4-morpholinothieno[3,2-d]pyrimidin-6-yl)propan-2-yl)(methyl)amino)pyrimidine-5-carboxamide (Compound 251)

Step 112a: Ethyl 2-((2-(2-chloro-4-morpholinothieno[3,2-d]pyrimidin-6-yl)propan-2-yl)(methyl)amino)pyrimidine-5-carboxylate (Compound 1209)

NaHDMS (2.0 M in THF, 1.5 mL) was added to a solution of compound 1208 (278 mg, 0.60 mmol) in dry THF (25 mL) at −70° C. followed by the addition of MeOTf (0.34 mL, 3 mmol). The resulting mixture was stirred at −70° C. for 0.5 h. The reaction was quenched with water, and extracted with EtOAc. The combined organic layers were dried with Na$_2$SO$_4$. The crude product was purified by column chromatography (Hexanes/EtOAc) to afford the titled compound 1209 as a white solid (52 mg, 18%). LCMS: 477.3[M+1]$^+$. $^1$H NMR: (400 MHz, DMSO-d$_6$): δ 1.24 (t, J=7.2 Hz, 3H), 1.89 (s, 6H), 3.48 (s, 3H), 3.69-3.71 (m, 4H), 3.78-3.80 (m, 4H), 4.21 (q, J=7.2 Hz, 2H), 7.16 (s, 1H), 8.65 (s, 2H).

Step 112b: Ethyl 2-((2-(2-(6-methoxypyridin-3-yl)-4-morpholinothieno[3,2-d]pyrimidin-6-yl)propan-2-yl)(methyl)amino)pyrimidine-5-carboxylate (Compound 1211-251)

A mixture of 1209 (52 mg, 0.11 mmol), 6-methoxypyridin-3-ylboronic acid (68 mg, 0.44 mmol), NaHCO$_3$ (27 mg, 0.32 mmol) and PdCl$_2$(PPh$_3$)$_2$ (7.8 mg, 0.011 mmol) in toluene (2.6 mL), EtOH (1.6 mL) and water (0.6 mL) was heated at 120° C. overnight. The reaction mixture was concentrated and purified by column chromatography (Hexanes/EtOAc) to afford the titled compound 1211-251 as a white solid (53 mg, 88%). LCMS: 550.4 [M+1]$^+$. $^1$H NMR: (400 MHz, DMSO-d$_6$): δ 1.23 (t, J=6.8 Hz, 3H), 1.93 (s, 6H), 3.50 (s, 3H), 3.74-3.76 (m, 4H), 3.88-3.90 (m, 4H), 3.92 (s, 3H), 4.20 (q, J=7.2 Hz, 2H), 6.90 (d, J=8.4 Hz, 1H), 7.25 (s, 1H), 8.55 (dd, J=2.0 Hz, 8.8 Hz, 1H), 8.65 (s, 2H), 9.12 (d, J=2.0 Hz, 1H).

Step 112c: N-Hydroxy-2-((2-(2-(6-methoxypyridin-3-yl)-4-morpholinothieno[3,2-d]pyrimidin-6-yl)propan-2-yl)(methyl)amino)pyrimidine-5-carboxamide (Compound 251)

The title compound 251 was prepared as a white solid (32 mg, 35%) from 1210-250 (95 mg, 0.17 mmol) and a freshly prepared hydroxylamine methanol solution (30 mL, 1.79 M) in CH$_2$Cl$_2$ (4 mL) using a procedure similar to that described for compound 237 (Example 107): m.p. 175-178° C. LCMS: 537.4 [M+1]$^+$. $^1$H NMR (400 MHz, DMSO-d$_6$): δ 1.91 (s, 6H), 3.46 (s, 3H), 3.73-3.74 (m, 4H), 3.86-3.90 (m, 4H), 3.92 (s, 3H), 6.90 (d, J=8.8 Hz, 1H), 7.24 (s, 1H), 8.53-8.57 (m, 3H), 8.91 (br, 1H), 9.12 (d, J=2.0 Hz, 1H), 10.91 (br, 1H).

Example 113: 2-[2-(6-Methoxy-pyridin-3-yl)-4-morpholin-4-yl-thieno[3,2-d]pyrimidine-6-sulfonylamino]-pyrimidine-5-carboxylic acid hydroxyamide (Compound 252)

Step 113a: 2-Chloro-4-morpholin-4-yl-thieno[3,2-d]pyrimidine-6-sulfonyl chloride (Compound 1301)

To a suspension of 0111 (10 g, 39.2 mmol) in THF (220 mL) at −78° C. was added slowly 2.5 M solution of n-BuLi in hexane (18.8 mL, 47.06 mmol) under nitrogen. The resulting slurry was allowed to warm up to −40° C. and a clear brown solution was observed. The solution was cooled to −50° C. and SO$_2$Cl$_2$ (6.3 mL, 78.43 mmol) was added slowly. The resulting solution was stirred at −40° C. for 2 h. The reaction mixture was concentrated and purified by column chromatography eluted with hexanes/ethyl acetate to afford compound 1301 as a yellow solid (3.7 g, 26.8%). LCMS: 353.8[M+1]$^+$. $^1$HNMR (400 MHz, DMSO-d$_6$): δ 3.75 (t, J=4.4 Hz, 4H), 3.89 (t, J=4.4 Hz, 4H), 7.27 (s, 1H).

Step 113b: 2-Chloro-4-morpholin-4-yl-thieno[3,2-d]pyrimidine-6-sulfonic acid amide (Compound 1302)

1301 (2 g, 5.67 mmol) was taken into a solution of NH$_3$ in methanol and stirred at room temperature overnight. The reaction mixture was concentrated and purified by column chromatography eluted with 2% methanol in dichloromethane to afford compound 1302 (0.97 g, 51%). LCMS: 335.0 [M+1]$^+$. $^1$HNMR (400 MHz, DMSO-d$_6$): δ 3.77 (t, J=4.4 Hz, 4H), 3.92 (t, J=4.4 Hz, 4H), 7.75 (s, 1H), 8.15 (s, 2H).

Step 113c: 2-(2-Chloro-4-morpholin-4-yl-thieno[3,2-d]pyrimidine-6-sulfonylamino)-pyrimidine-5-carboxylic acid ethyl ester (Compound 1303)

A mixture of 1302 (400 mg, 1.2 mmol), 0305 (335 mg, 1.8 mmol) and TEA in dichloromethane was stirred at reflux for 3 days. The reaction mixture was diluted by dichloromethane and washed with water. The crude product was purified by column chromatography to afford compound 1303 (210 mg, 36%).

LCMS: 485.0[M+1]$^+$. $^1$HNMR (400 MHz, DMSO-d$_6$): δ 1.27 (t, J=7.2 Hz, 3H), 3.79 (s, 4H), 3.94 (s, 4H), 4.27 (q, J=7.2 Hz, 2H), 7.64 (s, 1H), 8.71 (s, 2H).

Step 113d: 2-[2-(6-Methoxy-pyridin-3-yl)-4-morpholin-4-yl-thieno[3,2-d]pyrimidine-6-sulfonylamino]-pyrimidine-5-carboxylic acid ethyl ester (Compound 1304-252)

The title compound 1304-252 was prepared as a gray solid (100 mg, 38%) from 1303 (260 mg, 0.54 mmol), 6-methoxypyridin-3-ylboronic acid (246 mg, 1.61 mmol) and Pd(PPh$_3$)$_4$ (10 mg) in dioxane (9 mL) and sat. NaHCO$_3$ (3 mL) using a procedure similar to that described for compound 1211-251 (Example 112): $^1$HNMR (400 MHz, DMSO-d$_6$): δ 1.28 (t, J=7.2 Hz, 3H), 3.80 (t, J=4.4 Hz, 4H), 3.92 (s, 3H), 4.00 (t, J=4.4 Hz, 4H), 4.29 (q, J=7.2 Hz, 2H), 6.93 (d, J=8.4 Hz, 2H), 8.02 (s, 1H), 8.58 (dd, J=8.8 Hz, 2.4 Hz, 1H), 8.99 (s, 2H), 9.16 (s, 1H).

Step 113e: 2-[2-(6-Methoxy-pyridin-3-yl)-4-morpholin-4-yl-thieno[3,2-d]pyrimidine-sulfonylamino]-pyrimidine-5-carboxylic acid hydroxyamide (Compound 252)

The title compound 252 was prepared as a white solid (21 mg, 23%) from 1304-252 (100 mg) and a freshly prepared hydroxylamine methanol solution (16 mL, 1.79 M) using a procedure similar to that described for compound 237 (Example 107): m.p.: 259-265° C. LCMS: 545.3[M+1]⁺. ¹HNMR (400 MHz, DMSO-d₆): δ 3.81 (s, 4H), 3.96 (s, 3H), 4.00 (s, 4H), 6.93 (d, J=8.4 Hz, 2H), 7.99 (s, 1H), 8.58 (d, J=8.0 Hz, 1H), 8.84 (s, 2H), 9.16 (s, 1H), 9.18 (s, 1H), 11.23 (s, 1H).

Example 114: 2-(((2-(6-ethoxypyridin-3-yl)-4-morpholinothieno[3,2-d]pyrimidin-6-yl)methyl)(methyl)amino)-N-hydroxypyrimidine-5-carboxamide (Compound 255)

Step 114a: 5-Bromo-2-ethoxypyridine (Compound 0601-255)

A solution of freshly prepared sodium ethoxide in ethanol was treated with 2,5-Dibromo-pyridine and heated at reflux for 28 h. The mixture was concentrated and partitioned between dichloromethane and water, organic layer was washed with brine, dried over MgSO₄, filtered and evaporated in vacuum to get compound 0601-255 (3 g, 70%). LCMS: 202.0 [M+1]⁺.

Step 114b: 2-Ethoxy-5-(4,4,5,5-tetramethyl-1,3,2-dioxaborolan-2-yl)pyridine (Compound 0602-255)

A slurry of compound 0601-255 (3.0 g, 15.0 mmol), bis(pinacolatio)diboran (5.7 g, 22.0 mmol), PdCl₂(dppf) (327 mg, 0.45 mmol) and potassium acetate (4.4 g, 45.0 mmol) in anhydrous 1,4-dioxane (30 ml) was heated at 110° C. overnight. The reaction mixture was filtered and concentrated. The crude product was purified by column chromatography to afford titled compound (2.7 g, 73%) as a white solid. ¹HNMR (400 MHz, DMSO-d₆): δ 1.29 (s, 12H), 1.29 (t, J=7.2 Hz, 3H), 4.34 (q, J=7.2 Hz, 2H), 6.76 (d, J=8.4 Hz, 1H), 7.85 (dd, J=8.4 Hz, 1.6 Hz, 1H), 8.38 (d, J=1.6 Hz, 1H).

Step 114c: Ethyl 2-(((2-(6-ethoxypyridin-3-yl)-4-morpholinothieno[3,2-d]pyrimidin-6-yl) methyl)(methyl)amino)pyrimidine-5-carboxylate (Compound 0603-255)

The title compound 0603-255 was prepared as a white solid (335 mg, 94%) from 0504 (300 mg, 0.67 mmol), 0602-255 (333 mg, 1.34 mmol), NaHCO₃ (168 mg, 2 mmol) and bis(triphenylphosphine)palladium(II) chloride (23 mg, 0.03 mmol) in toluene (8 ml), ethanol (5 ml) and water (1 ml) using a procedure similar to that described for compound 1103-226 (Example 99): ¹HNMR (400 MHz, DMSO-d₆): δ 1.31-1.37 (m, 6H), 3.76 (t, J=4.4 Hz, 4H), 3.87 (3, 3H), 3.92 (t, J=4.4 Hz, 4H), 4.30 (q, J=7.2 Hz, 2H), 4.40 (q, J=7.2 Hz, 2H), 5.24 (s, 2H), 6.87 (d, J=8.8 Hz, 1H), 7.46 (s, 1H), 8.56 (dd, J=8.4 Hz, 1.2 Hz, 1H), 8.88 (s, 2H), 9.13 (s, 1H).

Step 114d: 2-(((2-(6-Ethoxypyridin-3-yl)-4-morpholinothieno[3,2-d]pyrimidin-6-yl)methyl)(methyl)amino)-N-hydroxypyrimidine-5-carboxamide (Compound 255)

The title compound 255 was prepared as a white solid (90 mg, 46%) from 0603-255 (200 mg, 0.37 mmol) and a freshly prepared hydroxylamine methanol solution (50 mL, 1.79 M) using a procedure similar to that described for compound 237 (Example 107): m.p.:162-165° C. LCMS: 523.0 [M+1]⁺. ¹HNMR (400 MHz, DMSO-d₆): δ 1.34 (t, J=7.2 Hz, 3H), 3.24 (s, 3H), 3.75 (t, J=4.0 Hz, 4H), 3.92 (t, J=4.0 Hz, 4H), 4.37 (q, J=7.2 Hz, 2H), 5.20 (s, 2H), 6.88 (d, J=8.4 Hz, 1H), 7.44 (s, 1H), 8.56 (dd, J=8.4 Hz, 1.2 Hz, 1H), 8.75 (s, 2H), 9.04 (s, 1H), 9.12 (s, 1H), 11.12 (s, 1H).

Example 115: N-Hydroxy-2-(((2-(6-(2-hydroxyethoxy)pyridin-3-yl)-4-morpholinothieno[3,2-d]pyrimidin-6-yl)methyl)(methyl)amino)pyrimidine-5-carboxamide (Compound 256)

Step 115a: 2-(5-Bromopyridin-2-yloxy)ethanol (Compound 0601-256)

To s stirred solution of 2,5-dibromopyridine (20 g, 85 mmol) in NMP (100 mL) was added NaH (17 g, 0.425 mol) portionwise at 0° C. The resulting mixture was stirred at 0° C. for 1 h. Ethylene glycol (26.4 g, 0.425 mol) was added. The resulting mixture was heated at 110° C. for 4 h. The reaction mixture was cooled to room temperature and partitioned between EtOAc and water. The organic layer was washed with water, dried over Na₂SO₄ and concentrated. The residue was purified by column chromatography eluted with hexanes/EtOAc to afford 0601-256 (7.2 g, yield 39%) as an off-white solid.

LCMS: 218.0 [M+1]⁺. ¹H NMR (400 MHz, CDCl₃): δ 3.45-3.48 (t, 1H, J=5.6 Hz), 3.92-3.95 (m, 2H), 4.39-4.42 (m, 2H), 6.70 (d, J=8.8 Hz, 1H), 7.66 (dd, J=8.8 Hz, 2.4 Hz, 1H), 8.16 (d, J=2.4 Hz, 1H).

Step 115b: 2-(5-(4,4,5,5-Tetramethyl-1,3,2-dioxaborolan-2-yl)pyridin-2-yloxy)ethanol (Compound 0602-256)

A mixture of 0601-256 (5 g, 0.023 mol), bis(pinacolato)diboron (7 g, 0.028 mol), KOAc (6.8 g, 0.069 mol) and Pd(dppf)Cl₂ (336.7 mg, 0.46 mmol) in dry dioxane (50 mL) was degassed with N₂ and heated at 90° C. for 4 h. The reaction mixture was concentrated. The residue was suspended in CH₂Cl₂ and stirred for 30 min and filtered. The filtrate was concentrated and purified by column chromatography eluted with hexanes/EtOAc to afford 0602-256 (9 g, containing Bis(pinacolato)diboron) as a yellow oil. LCMS: 266.0 [M+1]⁺. ¹H NMR (400 MHz, CDCl₃): δ 1.334 (s, 12H), 3.87 (m, 1H), 3.94 (m, 2H), 4.48-4.51 (m, 2H), 6.77 (d, J=8.4 Hz, 1H), 7.95 (dd, J=8.4 Hz, 2.0 Hz, 1H), 8.50 (d, 1H, J=1.2 Hz, 1H).

Step 115c: Ethyl 2-(((2-(6-(2-hydroxyethoxy)pyridin-3-yl)-4-morpholinothieno[3,2-d]pyrimidin-6-yl)methyl)(methyl)amino)pyrimidine-5-carboxylate (Compound 0603-256)

The title compound 0603-256 was prepared as an off-white solid (150 mg, 30%) from 0602-256 (708 mg, 2.67 mmole), 0504 (400 mg, 0.89 mmole), NaHCO₃ (224 mg, 2.67 mmole) and Pd(PPh₃)₂Cl₂ (31 mg, 0.05 mmole) in toluene/EtOH/H₂O (16 mL/10 mL/4 mL) using a procedure similar to that described for compound 1103-226 (Example 99): LCMS: 552 [M+1]⁺.

Step 115d: N-Hydroxy-2-(((2-(6-(2-hydroxyethoxy)pyridin-3-yl)-4-morpholinothieno[3,2-d]pyrimidin-6-yl)methyl)(methyl)amino)pyrimidine-5-carboxamide (Compound 256)

The title compound 256 was prepared as a light yellow solid (55 mg, 36%) from 0603-256 (150 mg, 0.27 mmol) and a freshly prepared hydroxylamine methanol solution (20 mL, 1.79 M) using a procedure similar to that described for compound 237 (Example 107): m.p.: 143-145° C. LCMS: 539.0 [M+1]$^+$. $^1$H NMR (400 MHz, DMSO-d$_6$): δ 3.24 (s, 3H), 3.75 (s, 6H), 3.92 (s, 4H), 4.35 (s, 2H), 4.84-4.87 (br, 1H), 5.20 (s, 2H), 6.90 (d, J=6.8 Hz, 1H), 7.44 (s, 1H), 8.57 (d, J=6.4 Hz, 1H), 8.76 (s, 2H), 9.06 (s, 1H), 9.12 (s, 1H), 11.26 (s, 1H).

Example 116: 2-(((2-(6-(2-(Dimethylamino)ethoxy) pyridin-3-yl)-4-morpholinothieno[3,2-d]pyrimidin-6-yl)methyl)(methyl)amino)-N-hydroxypyrimidine-5-carboxamide (Compound 257)

Step 116a: 2-(2-Bromoethoxy)-5-(4,4,5,5-tetramethyl-1,3,2-dioxaborolan-2-yl)pyridine (Compound 0601-257)

A mixture of 0602-256 (2.9 g, 0.01 mol) and PBr$_3$ (3 mL) in toluene (30 mL) was heated at 80° C. for 3 h. The reaction mixture was cooled to 0° C. and aq. NaHCO$_3$ was added slowly until pH=7-8 and extracted with EtOAc. The combined organic layers were washed with brine, dried over Na$_2$SO$_4$ and concentrated to afford crude 0601-257 (2 g, 61.2%) as a pink solid. LCMS: 328.1 [M+1]$^+$. $^1$H NMR (400 MHz, CDCl$_3$): δ 1.24 (s, 12H), 3.65 (t, J=6.4 Hz, 2H), 4.25 (t, J=6.4 Hz, 2H), 6.56 (d, J=8.8 Hz, 1H), 7.60 (dd, J=8.8 Hz, 1.6 Hz, 1H), 7.70 (d, J=1.6 Hz, 1H).

Step 116b: Ethyl 2-(((2-(6-(2-(dimethylamino) ethoxy)pyridin-3-yl)-4-morpholinothieno[3,2-d]pyrimidin-6-yl)methyl)(methyl)amino)pyrimidine-5-carboxylate (Compound 0603-257)

0601-257 (600 mg, 1.83 mmol) was taken into Me$_2$NH (20 mL in CH$_3$OH) and stirred at room temperature for 3 h. The reaction mixture was concentrated to give crude 0602-257 as a yellow solid (650 mg) which was used in the next step without further purification.

A mixture of 0602-257 (600 mg), 0504 (350 mg, 0.78 mmol), NaHCO$_3$ (196 mg, 2.33 mmol) and Pd(PPh$_3$)$_2$Cl$_2$ (27 mg) in toluene/EtOH/H$_2$O (16 mL/10 mL/4 mL) was degassed with N$_2$ and heated at 110° C. for 3 h. The reaction mixture was concentrated. The residue was suspended in CH$_2$Cl$_2$ (50 mL) and filtered. The filtrate was concentrated. The crude product was purified by column chromatography to afford 0603-257 as a white solid (200 mg, 44%).

Step 116c: 2-(((2-(6-(2-(Dimethylamino)ethoxy) pyridin-3-yl)-4-morpholinothieno[3,2-d]pyrimidin-6-yl)methyl)(methyl)amino)-N-hydroxypyrimidine-5-carboxamide (Compound 257)

The title compound 257 was prepared as a light yellow solid (30 mg, 30%) from 0603-257 (100 mg, 0.28 mmol) and a freshly prepared hydroxylamine methanol solution (10 mL, 1.79 M) in CH$_2$Cl$_2$ (2 mL) using a procedure similar to that described for compound 237 (Example 107). m.p.: 140-143° C. LCMS: 566 [M+1]$^+$. $^1$H NMR (400 MHz, DMSO-d$_6$): δ 2.21 (s, 6H), 2.56 (t, J=5.2 Hz, 2H), 3.23 (s, 3H), 3.75 (s, 4H), 3.90 (s, 4H), 4.12 (s, 2H), 5.16 (s, 2H), 6.46 (dd, J=8.8 Hz, 1.2 Hz, 1H), 7.40 (s, 1H), 8.17 (s, 1H), 8.30 (dd, J=8.4 Hz, 4.4 Hz, 1H), 8.63 (d, J=12 Hz, 1H), 8.80 (s, 2H), 11.11 (br, 1H).

Example 117: N-Hydroxy-2-(methyl((2-(6-(2-(methylamino)ethoxy)pyridin-3-yl)-4-morpholinothieno[3,2-d]pyrimidin-6-yl)methyl)amino)pyrimidine-5-carboxamide (Compound 258)

Step 117a: N-Methyl-2-(5-(4,4,5,5-tetramethyl-1,3,2-dioxaborolan-2-yl)-pyridin-2-yloxy) ethanamine (Compound 0602-258)

A mixture of 0601-257 (300 mg, 0.917 mmol) and MeNH$_2$ (20 mL, in alcohol) was stirred at room temperature for 3 h. The reaction mixture was concentrated to afford crude 0602-258 which was used in the next step without further purification. LCMS: 279.1 [M+1]$^+$. $^1$H NMR (400 MHz, CDCl$_3$): δ 1.24 (s, 12H), 3.13 (s, 3H), 4.06-4.08 (m, 2H), 4.60-4.64 (m, 2H), 6.84 (d, J=9.2 Hz, 1H), 7.92 (s, 1H), 8.04 (d, J=8.8 Hz, 1H).

Step 117b: Ethyl 2-(methyl((2-(6-(2-(methylamino) ethoxy)pyridin-3-yl)-4-morpholinothieno[3,2-d]pyrimidin-6-yl)methyl)amino)pyrimidine-5-carboxylate (Compound 0603-258)

The title compound 0603-258 was prepared as an grey solid (120 mg, 24%) from 0602-258 (prepared above), 0504 (400 mg, 0.89 mmol), NaHCO$_3$ (230 mg, 2.75 mmol) and Pd(PPh$_3$)$_2$Cl$_2$ (10 mg) in toluene/EtOH/H$_2$O (16 mL/10 mL/4 mL) using a procedure similar to that described for compound 1103-226 (Example 99): LCMS: 565 [M+1]$^+$. $^1$H NMR (400 MHz, CDCl$_3$): δ 1.38 (t, J=7.2 Hz, 3H), 3.19 (s, 3H), 3.32 (s, 3H), 3.87 (t, J=5.2 Hz, 4H), 3.99 (t, J=5.2 Hz, 4H), 4.15 (t, J=6.4 Hz, 2H), 4.37 (q, 2H, J=7.2 Hz), 4.76 (t, J=5.6 Hz, 2H), 5.20 (s, 2H), 6.93 (d, J=8.8 Hz, 1H), 7.32 (s, 1H), 8.71 (d, J=2.4 Hz, 1H), 8.78 (dd, J=9.2 Hz, 1.6 Hz, 1H), 8.93 (s, 2H).

Step 117c: N-Hydroxy-2-(methyl((2-(6-(2-(methylamino)ethoxy)pyridin-3-yl)-4-morpholinothieno[3,2-d]pyrimidin-6-yl)methyl)amino)pyrimidine-5-carboxamide (Compound 258)

The title compound 258 was prepared as a light yellow solid (55 mg, 47%) from 0603-258 (120 mg, 0.21 mmol) and a freshly prepared hydroxylamine methanol solution (10 mL, 1.79 M) in CH$_2$Cl$_2$ (2 mL) using a procedure similar to that described for compound 237 (Example 107). m.p.: 170-175° C. LCMS: 552.3 [M+1]$^+$. $^1$H NMR (400 MHz, DMSO-d$_6$): δ 2.98 (s, 3H), 3.23 (s, 3H), 3.71-3.77 (m, 6H), 3.90-3.92 (m, 4H), 4.32 (br, 2H), 5.19 (s, 2H), 6.94 (d, 1H, J=9.6 Hz), 7.39 (s, 1H), 8.42-8.45 (d, 2H), 8.68 (s, 1H), 8.71 (s, 2H).

Example 118: 2-(((2-(6-(2-Aminoethoxy)pyridin-3-yl)-4-morpholinothieno[3,2-d]pyrimidin-6-yl) methyl)(methyl)amino)-N-hydroxypyrimidine-5-carboxamide (Compound 259)

Step 118a: 2-(2-Azidoethoxy)-5-(4,4,5,5-tetramethyl-1,3,2-dioxaborolan-2-yl)pyridine (Compound 0602-259)

A mixture of 0601-257 (260 mg, 0.8 mmol) and NaN$_3$ (103.4 mg, 1.59 mmol) in DMF was heated at 60° C. for 2 h. The reaction mixture was partitioned between CH$_2$Cl$_2$ and water. The organic layer was washed with brine, dried over Na$_2$SO$_4$. The crude product was dissolved in toluene and was used in the next step directly.
LCMS: 291.1 [M+1]$^+$.

Step 118b: Ethyl 2-(((2-(6-(2-aminoethoxy)pyridin-3-yl)-4-morpholinothieno[3,2-d]pyrimidin-6-yl)methyl)(methyl)amino)pyrimidine-5-carboxylate (Compound 0603-259)

A mixture of 0602-259, 0504 (350 mg, 0.78 mmol), NaHCO$_3$ (200 mg, 2.4 mmol) and Pd(PPh$_3$)$_2$Cl$_2$ (10 mg) in toluene/EtOH/H$_2$O (16 mL/10 mL/4 mL) was degassed with N$_2$ and heated at 110° C. for 3 h. The reaction mixture was concentrated. The residue was purified by chromatography eluted with CH$_2$Cl$_2$/MeOH to afford the titled compound, ethyl 2-(((2-(6-(2-azidoethoxy)pyridin-3-yl)-4-morpholinothieno[3,2-d]pyrimidin-6-yl)methyl)(methyl)amino)pyrimidine-5-carboxylate. It was dissolved in methanol and can be used in the next step directly. LCMS: 577.3 [M+1]$^+$.

A mixture of ethyl 2-(((2-(6-(2-azidoethoxy)pyridin-3-yl)-4-morpholinothieno[3,2-d]pyrimidin-6-yl)methyl)(methyl)amino)pyrimidine-5-carboxylate (prepared above) and Pd/C (100 mg) in MeOH (10 mL) was stirred at room temperature under H$_2$ (1 atm) overnight. The reaction mixture was diluted with CH$_2$Cl$_2$ (10 mL) and filtered through celite. The filtrate was concentrated to afford the tiled compound 0603-259 as a light yellow solid (130 mg, 15.3%, 2 steps). LCMS: 551 [M+1]$^+$. $^1$H NMR (400 MHz, CDCl$_3$): δ 1.38 (t, J=7.2 Hz, 3H), 3.15 (q, J=5.6 Hz, 2H), 3.31 (s, 3H), 3.84-3.87 (m, 4H), 3.94-3.97 (m, 4H), 4.12 (t, J=6 Hz, 2H), 4.36 (q, 2H, J=7.2 Hz), 5.18 (s, 2H), 6.63 (d, J=9.2 Hz, 1H), 7.27 (s, 1H), 8.37 (dd, J=9.6 Hz, 2.4 Hz, 1H), 8.51 (d, J=2.4 Hz, 1H), 8.93 (s, 2H).

Step 118c: 2-(((2-(6-(2-Aminoethoxy)pyridin-3-yl)-4-morpholinothieno[3,2-d]pyrimidin-6-yl)methyl)(methyl)amino)-N-hydroxypyrimidine-5-carboxamide (Compound 259)

The title compound 259 was prepared as a light yellow solid (40 mg, 31%) from 0603-259 (130 mg, 0.24 mmol) and a freshly prepared hydroxylamine methanol solution (10 mL, 1.79 M) in CH$_2$Cl$_2$ (2 mL) using a procedure similar to that described for compound 237 (Example 107). m.p.: 110-115° C. LCMS: 538.3 [M+1]$^+$. $^1$H NMR (400 MHz, DMSO-d$_6$): δ 2.89 (q, J=6 Hz, 2H), 3.23 (s, 3H), 3.75 (t, J=4.8 Hz, 4H), 3.90 (t, J=4.4 Hz, 4H), 4.01 (t, J=6 Hz, 2H), 5.19 (s, 2H), 6.47 (d, J=9.2 Hz, 1H), 7.37 (s, 1H), 8.32 (dd, J=9.6 Hz, 2.4 Hz, 1H), 8.63 (d, J=2.4 Hz, 1H), 8.75 (s, 2H).

Example 119: N-Hydroxy-2-(((2-(2-methoxypyrimidin-5-yl)-4-morpholinothieno[3,2-d]pyrimidin-6-yl)methyl)(methyl)amino)pyrimidine-5-carboxamide (Compound 261)

Step 119a: 5-Bromo-2-methoxypyrimidine (Compound 0601-261)

5-Bromo-2-chloropyrimidine (10 g, 52 mmol) and sodium methoxide (8.42 g, 156 mmol) were taken in methanol (50 mL) and stirred at room temperature overnight. Reaction mixture was concentrated followed by the addition of water. The resulting mixture was extracted with ethyl acetate and dried over MgSO$_4$. The titled compound was obtained after concentration (8.07 g, 82.5%).

Step 119b: 2-Methoxy-5-(4,4,5,5-tetramethyl-1,3,2-dioxaborolan-2-yl)pyrimidine (Compound 0602-261)

A mixture of 0601-261 (0.5 g, 2.65 mmol), 4,4,4',4',5,5,5',5'-octamethyl-2,2'-bi(1,3,2-dioxaborolane) (1.35 g, 5.3 mmol), KOAc (780 mg, 7.95 mmol), Pd(dppf)Cl$_2$ (100 mg, 0.133 mmol) was taken into 1,4-dioxane (10 mL) in a pressure vessel was heated at 100° C. for 5 h. The reaction mixture was filtered through silica pad eluted with dichloromethane (50 mL). The titled compound was obtained as a white solid (0.5 g, 90%) after concentration.

Step 119c: Ethyl 2-(((2-(2-methoxypyrimidin-5-yl)-4-morpholinothieno[3,2-d]pyrimidin-6-yl)methyl)(methyl)amino)pyrimidine-5-carboxylate (Compound 0603-261)

The title compound 0603-261 was prepared as an grey solid (120 mg, 24%) from 0504 (450 mg, 1.0 mmol), 0602-261 (472 mg, 2.0 mmol), NaHCO$_3$ (252 mg, 3.0 mmol), bis(triphenylphosphine)palladium(II)chloride (120 mg, 0.15 mmol) was taken into ethanol (10 mL), water (6 mL), toluene (8 mL) using a procedure similar to that described for compound 1103-226 (Example 99).

Step 119d: N-Hydroxy-2-(((2-(2-methoxypyrimidin-5-yl)-4-morpholinothieno[3,2-d]pyrimidin-6-yl)methyl)(methyl)amino)pyrimidine-5-carboxamide (Compound 261)

The title compound 261 was prepared as a white solid (30 mg, 19.4%) from 0603-261 (160 mg, 0.31 mmol) and a freshly prepared hydroxylamine methanol solution (20 mL, 1.79 M) using a procedure similar to that described for compound 237 (Example 107). m.p.: 215-220° C. LCMS: 510.0[M+1]$^+$. $^1$HNMR (400 MHz, DMSO-d$_6$): δ 3.24 (s, 3H), 3.74-3.76 (m, 4H), 3.92-3.95 (m, 4H), 4.00 (s, 3H), 5.20 (s, 2H), 7.46 (s, 1H), 8.75 (s, 2H), 9.04 (s, 1H), 9.42 (s, 2H), 11.12 (s, 1H).

Example 120: N-Hydroxy-2-((1-(2-(2-methoxypyrimidin-5-yl)-4-morpholinothieno[3,2-d]pyrimidin-6-yl)ethyl)(methyl)amino)pyrimidine-5-carboxamide (Compound 262)

Step 120a: Ethyl 2-((1-(2-(2-methoxypyrimidin-5-yl)-4-morpholinothieno[3,2-d]pyrimidin-6-yl)ethyl)(methyl)amino)pyrimidine-5-carboxylate (Compound 1204-262)

The title compound 1204-262 was prepared as an grey solid (150 mg, 72%) from 1203 (180 mg, 0.388 mmol), 602 (183 mg, 0777 mmol), NaHCO$_3$ (98 mg, 1.17 mmol), bis(triphenylphosphine)Pdlladium(II)chloride (50 mg, 0.02 mmol), ethanol (5 mL), water (2 mL), toluene (8 mL) using a procedure similar to that described for compound 1204-237 (Example 107): LCMS: 537.2 [M+1]$^+$. $^1$H NMR (400 MHz, DMSO-d$_6$): δ 1.31 (t, J=7.2 Hz, 3H), 1.74 (d, J=6.8 Hz, 3H), 3.03 (s, 3H), 3.74 (s, 4H), 3.94 (s, 4H), 4.00 (s, 3H), 4.30 (q, J=7.2 Hz, 2H), 6.52 (s, 1H), 7.51 (s, 1H), 8.89 (s, 2H), 9.42 (s, 2H).

Step 120b: N-Hydroxy-2-((1-(2-(2-methoxypyrimidin-5-yl)-4-morpholinothieno[3,2-d]pyrimidin-6-yl)ethyl)(methyl)amino)pyrimidine-5-carboxamide (Compound 262)

The title compound 262 was prepared as a white solid (80 mg, 55%) from 1204-262 (150 mg, 0.28 mmol) and a freshly prepared hydroxylamine methanol solution (20 mL, 1.79 M) using a procedure similar to that described for compound 237 (Example 107). m.p.: 210-215° C. LCMS: 524.1

[M+1]⁺. ¹H NMR (400 MHz, DMSO-d₆): δ 1.72 (d, J=6.8 Hz, 3H), 2.98 (s, 3H), 3.74 (s, 4H), 3.92 (s, 4H), 4.00 (s, 3H), 6.48 (q, J=5.2 Hz, 1H), 7.48 (s, 1H), 8.76 (s, 2H), 9.41 (s, 2H).

Example 121: N-Hydroxy-2-(2-(2-(2-methoxypyrimidin-5-yl)-4-morpholinothieno[3,2-d]pyrimidin-6-yl)propan-2-ylamino)pyrimidine-5-carboxamide (Compound 263)

Step 121a: Ethyl 2-(2-(2-(2-methoxypyrimidin-5-yl)-4-morpholinothieno[3,2-d]pyrimidin-6-yl)propan-2-ylamino)pyrimidine-5-carboxylate (Compound 1210-263)

The title compound 1210-263 was prepared as a white solid (167 mg, 78%) from 1208 (185 mg, 0.40 mmol), boronate ester (189 mg, 0.80 mmol), NaHCO₃ (101 mg, 1.20 mmol) and PdCl₂(PPh₃)₂ (28 mg, 0.04 mmol) in toluene (8 mL), EtOH (5 mL) and water (2 mL) using a procedure similar to that described for compound 1204-237 (Example 107): LC-MS: 537.3 [M+1]⁺.

Step 121b: N-Hydroxy-2-(2-(2-(2-methoxypyrimidin-5-yl)-4-morpholinothieno[3,2-d]pyrimidin-6-yl) propan-2-ylamino)pyrimidine-5-carboxamide (Compound 263)

The title compound 263 was prepared as a white solid (30 mg) from 1210-263 (167 mg, 0.31 mmol) and a freshly prepared hydroxylamine methanol solution (20 mL, 1.79 M) in CH₂Cl₂ (4 mL) using a procedure similar to that described for compound 237 (Example 107). m.p. 202-207° C. LC-MS: 524.3 [M+1]⁺. ¹H NMR (400 MHz, DMSO-d₆): δ 1.84 (s, 6H), 3.74 (m, 4H), 3.92 (m, 4H), 4.00 (s, 3H), 7.31 (s, 1H), 8.38 (s, 1H), 8.43 (s, 1H), 8.52 (br, 2H), 8.98 (s, 1H), 9.41 (s, 2H), 10.95 (s, 1H).

Example 122: 2-(2-(2-(4-Aminophenyl)-4-morpholinothieno[3,2-d]pyrimidin-6-yl)propan-2-ylamino)-N-hydroxypyrimidine-5-carboxamide (Compound 269)

Step 122a: Ethyl 2-(2-(2-(4-aminophenyl)-4-morpholinothieno[3,2-d]pyrimidin-6-yl)pro-pan-2-ylamino)pyrimidine-5-carboxylate (Compound 1210-269)

The title compound 1210-269 was prepared as a white solid (100 mg, 48%) from 1208 (185 mg, 0.40 mmol), boronate ester (0602-217) (175 mg, 0.80 mmol), NaHCO₃ (101 mg, 1.20 mmol) and PdCl₂(PPh₃)₂ (28 mg, 0.04 mmol) in toluene (8 mL), EtOH (5 mL) and water (2 mL) using a procedure similar to that described for compound 1204-237 (Example 107): LC-MS: 520.4 [M+1]⁺.

Step 122b: 2-(2-(2-(4-Aminophenyl)-4-morpholinothieno[3,2-d]pyrimidin-6-yl) propan-2-ylamino)-N-hydroxypyrimidine-5-carboxamide (Compound 269)

The title compound 269 was prepared as a white solid (77 mg, 75%) from 1210-269 (100 mg, 0.19 mmol) and a freshly prepared hydroxylamine methanol solution (20 mL, 1.79 M) in CH₂Cl₂ (4 mL) using a procedure similar to that described for compound 237 (Example 107). LC-MS: 507.3 [M+1]⁺. ¹H NMR (400 MHz, DMSO-d₆): δ 1.82 (s, 6H), 3.28 (s, 1H), 3.74 (m, 4H), 3.85 (m, 4H), 5.48 (s, 2H), 6.60 (d, J=8.8 Hz, 2H), 7.19 (s, 1H), 8.07 (d, J=8.8 Hz, 2H), 8.33 (s, 1H), 8.53 (br, 2H), 8.96 (s, 1H), 10.94 (s, 1H).

Example 123: 2-[2-(4-Amino-phenyl)-4-morpholin-4-yl-thieno[3,2-d]pyrimidine-6-sulfonylamino]-pyrimidine-5-carboxylic acid hydroxyamide (Compound 271)

Step 123a: 2-[2-(4-Amino-phenyl)-4-morpholin-4-yl-thieno[3,2-d]pyrimidine-6-sulfonylamino]-pyrimidine-5-carboxylic acid ethyl ester (Compound 1304-271)

A mixture of 1303 (270 mg, 0.56 mmol), 4-(4,4,5,5-tetramethyl-1,3,2-dioxaborolan-2-yl)aniline (368 mg, 1.67 mmol) and Pd(PPh₃)₄ (200 mg, 0.3 mmol) in dioxane (9 mL) and sat. NaHCO₃ (3 mL) was stirred at 110° C. for 3 h under N₂ atmosphere. Upon completion, the reaction was concentrated and purified by column chromatography to afford compound 1304-271 (170 mg, 56%). LCMS: 542.3[M+1]⁺. ¹HNMR (400 MHz, DMSO-d₆): δ 1.28 (t, J=7.2 Hz, 3H), 3.79 (t, J=4.4 Hz, 4H), 3.96 (t, J=4.4 Hz, 4H), 4.27 (q, J=7.2 Hz, 2H), 6.62 (d, J=8.4 Hz, 2H), 7.85 (s, 1H), 8.08 (d, J=8.4 Hz, 2H), 8.89 (s, 2H).

Step 123b: 2-[2-(4-Amino-phenyl)-4-morpholin-4-yl-thieno[3,2-d]pyrimidine-6-sulfonylamino]-pyrimidine-5-carboxylic acid hydroxyamide (Compound 271)

The title compound 271 was prepared as a white solid (26 mg, 17%) from 1304-271 (160 mg) and a freshly prepared hydroxylamine methanol solution (20 mL, 1.79 M) using a procedure similar to that described for compound 237 (Example 107). m.p.: 197-205° C. LCMS: 529.2[M+1]⁺. ¹HNMR (400 MHz, DMSO-d₆): δ 3.79 (s, 4H), 3.94 (s, 4H), 6.60 (d, J=8.4 Hz, 2H), 7.83 (s, 1H), 8.08 (d, J=8.4 Hz, 2H), 8.76 (s, 2H), 9.16 (s, 1H), 11.18 (s, 1H).

Example 124: 2-(((2-(4-Amino-3-chlorophenyl)-4-morpholinothieno[3,2-d]pyrimidin-6-yl) methyl)(methyl)amino)-N-hydroxypyrimidine-5-carboxamide (Compound 275)

Step 124a: Ethyl 2-(((2-(4-amino-3-chlorophenyl)-4-morpholinothieno[3,2-d]pyrimidin-6-yl)methyl)(methyl)amino)pyrimidine-5-carboxylate (Compound 0603-275)

The mixture of 4-bromo-2-chloroaniline (516 mg, 2.5 mmol), bis(pinacolato)diboron (952 mg, 3.75 mmol), PdCl₂(dppf) (102 mg, 0.125 mmol) and KOAc (735 mg, 7.5 mmol) in anhydrous dioxane (10 mL) was heated at 100° C. for 3 h in a pressure vessel. The resulting solution was filtered and the solid was washed with CH₂Cl₂ (20 mL). The filtrate was concentrated in vacuo. The obtained deep brown solid was mixed with 0504 (505 mg, 1.125 mmol), NaHCO₃ (280 mg, 3.375 mmol) and PdCl₂(PPh₃)₂ (39 mg, 0.056 mmol) in toluene (11 mL), EtOH (7 mL) and water (2.8 mL). The suspension was heated at 130° C. overnight in a pressure vessel. After cooling to room temperature, CH₂Cl₂ (10 mL) and water (10 mL) were added and the mixture was filtered. The organic layer was separated, washed with brine, dried over MgSO₄, and evaporated. The crude compound was purified by column chromatography (Hexanes/ethyl acetate) to afford the titled compound as a light yellow solid.

(478 mg, 78%). LC-MS: 540.3 [M+1]$^+$. $^1$H NMR: (400 MHz, DMSO-d$_6$): δ 1.31 (t, J=6.8 Hz, 3H), 3.24 (s, 3H), 3.74 (t, J=4.4 Hz, 4H), 3.89 (t, J=4.0 Hz, 4H), 4.29 (q, J=6.8 Hz, 2H), 5.22 (s, 2H), 5.75 (s, 2H), 6.85 (d, 1H), 7.40 (s, 1H), 8.07 (dd, J=8.4 Hz, 1.6 Hz, 1H), 8.18 (d, J=2.0 Hz, 1H), 8.87 (s, 3H).

Step 124b: 2-(((2-(4-Amino-3-chlorophenyl)-4-morpholinothieno[3,2-d]pyrimidin-6-yl) methyl)(methyl)amino)-N-hydroxypyrimidine-5-carboxamide (Compound 275)

The title compound 275 was prepared as a light yellow solid (20 mg, 21%) from 0603-275 (100 mg, 0.185 mmol) and a freshly prepared hydroxylamine methanol solution (2.1 mL, 1.79 M)) in CH$_2$Cl$_2$ (2 mL) using a procedure similar to that described for compound 237 (Example 107). m.p. 241-246° C. LC-MS: 527.4 [M+1]$^+$. $^1$H NMR (300 MHz, DMSO-d$_6$): δ 3.21 (s, 3H), 3.74 (s, 4H), 3.87 (s, 4H), 5.16 (s, 2H), 5.74 (s, 2H), 6.85 (m, 1H), 7.36 (s, 1H), 8.07 (m, 1H), 8.17 (s, 1H), 8.72 (s, 2H).

Example 125: 2-(((2-(4-Amino-3-fluorophenyl)-4-morpholinothieno[3,2-d]pyrimidin-6-yl) methyl)(methyl)amino)-N-hydroxypyrimidine-5-carboxamide (Compound 276)

Step 125a: Ethyl 2-(((2-(4-amino-3-fluorophenyl)-4-morpholinothieno[3,2-d]pyrimidin-6-yl)methyl)(methyl)amino)pyrimidine-5-carboxylate (Compound 0603-276)

The title compound 0603-276 was prepared as a light yellow solid (503 mg, 85%) from 4-bromo-2-fluoroaniline (475 mg, 2.5 mmol), bis(pinacolato) diboron (952 mg, 3.75 mmol), PdCl$_2$(dppf) (102 mg, 0.125 mmol) and KOAc (735 mg, 7.5 mmol) in anhydrous dioxane (10 mL) followed by 0504 (505 mg, 1.125 mmol), NaHCO$_3$ (280 mg, 3.375 mmol) and PdCl$_2$(PPh$_3$)$_2$ (39 mg, 0.056 mmol) in toluene (11 mL), EtOH (7 mL) and water (2.8 mL) using a procedure similar to that described for compound 0603-275 (Example 124): LC-MS: 524.3 [M+1]$^+$. $^1$H NMR: (400 MHz, DMSO-d$_6$): δ 1.31 (t, J=7.2 Hz, 3H), 3.27 (s, 3H), 3.75 (t, J=4.8 Hz, 4H), 3.89 (t, J=4.8 Hz, 4H), 4.30 (q, J=7.2 Hz, 2H), 5.22 (s, 2H), 5.55 (s, 2H), 6.84-6.79 (m, 1H), 7.40 (s, 1H), 7.97-7.91 (m, 2H), 8.88 (s, 2H).

Step 125b: 2-(((2-(4-Amino-3-fluorophenyl)-4-morpholinothieno[3,2-d]pyrimidin-6-yl) methyl)(methyl)amino)-N-hydroxypyrimidine-5-carboxamide (Compound 276)

The title compound 276 was prepared as a light yellow solid (55 mg, 38%) from 0603-276 (150 mg, 0.286 mmol) and a freshly prepared hydroxylamine methanol solution (3.3 mL, 1.79 M in methanol) in CH$_2$Cl$_2$ (3 mL) using a procedure similar to that described for compound 237 (Example 107). m.p. 203-206° C. LC-MS: 511 [M+1]$^+$. $^1$H NMR (300 MHz, DMSO-d$_6$): δ 3.23 (s, 3H), 3.82 (m, 4H), 3.88 (m, 4H), 5.18 (s, 2H), 5.53 (s, 2H), 6.79-6.83 (m, 1H), 7.37 (s, 1H), 7.91-7.96 (m, 2H), 8.74 (s, 2H), 9.02 (br, 1H), 11.08 (br, 1H).

Example 126: 2-(((2-(4-Amino-3-nitrophenyl)-4-morpholinothieno[3,2-d]pyrimidin-6-yl)methyl)(methyl)amino)-N-hydroxypyrimidine-5-carboxamide (Compound 278)

Step 126a: Ethyl 2-(((2-(4-amino-3-nitrophenyl)-4-morpholinothieno[3,2-d]pyrimidin-6-yl)methyl)(methyl)amino)pyrimidine-5-carboxylate (Compound 0603-278)

The title compound 0603-278 was prepared as an orange solid (538 mg, 86%) from 4-bromo-2-nitroaniline (543 mg, 2.5 mmol), bis(pinacolato) diboron (952 mg, 3.75 mmol), PdCl$_2$(dppf) (102 mg, 0.125 mmol) and KOAc (735 mg, 7.5 mmol) in anhydrous dioxane (10 mL) followed by 0504 (505 mg, 1.125 mmol), NaHCO$_3$ (280 mg, 3.375 mmol) and PdCl$_2$(PPh$_3$)$_2$ (39 mg, 0.056 mmol) in toluene (11 mL), EtOH (7 mL) and water (2.8 mL) using a procedure similar to that described for compound 0603-275 (Example 124).

Step 126b: 2-(((2-(4-Amino-3-nitrophenyl)-4-morpholinothieno[3,2-d]pyrimidin-6-yl)methyl)(methyl)amino)-N-hydroxypyrimidine-5-carboxamide (Compound 278)

The title compound 278 was prepared as a light pink solid (35 mg, 23%) from 111-243-2 (150 mg, 0.272 mmol) and a freshly prepared hydroxylamine methanol solution (3.3 mL, 1.79 M in methanol) in CH$_2$Cl$_2$ (3 mL) using a procedure similar to that described for compound 237 (Example 107). m.p. 202-206° C. LCMS: 538.5 [M+1]$^+$. $^1$H NMR (400 MHz, DMSO-d$_6$): δ 3.24 (s, 3H), 3.77 (m, 4H), 3.91 (m, 4H), 5.19 (s, 2H), 7.10 (d, J=6.6 Hz, 1H), 7.44 (s, 1H), 7.69 (s, 2H), 8.37 (dd, J=6.6, 1.5 Hz, 1H), 8.74 (s, 2H), 9.00 (d, J=1.5 Hz, 2H).

Example 127: 2-(((2-(4-Amino-3-hydroxyphenyl)-4-morpholinothieno[3,2-d]pyrimidin-6-yl)methyl)(methyl)amino)-N-hydroxypyrimidine-5-carboxamide (Compound 279)

Step 127a: Ethyl 2-(((2-(4-amino-3-hydroxyphenyl)-4-morpholinothieno[3,2-d]pyrimidin-6-yl)methyl)(methyl)amino)pyrimidine-5-carboxylate (Compound 0603-279)

The title compound 0603-279 was prepared as a yellow solid (200 mg) from 2-amino-5-bromophenol (1 g, 5.3 mmol), 4,4,4',4,5,5,5',5'-octamethyl-2,2'-bi(1,3,2-dioxaborolane) (2.7 g, 10.6 mmol), KOAc (1.5 g, 15.9 mmol) and Pd(dppf)Cl$_2$ (200 mg) in DMSO (15 mL) followed by 0504 (500 mg, 2.12 mmol), 2-amino-5-(4,4,5,5-tetramethyl-1,3,2-dioxaborolan-2-yl)phenol (a solution in DMSO prepared in previous step, sat. NaHCO$_3$ (2 mL) and Pd(PPh$_3$)$_4$ (100 mg) in DMSO (50 mL) using a procedure similar to that described for compound 0603-275 (Example 124).

Step 127b: 2-(((2-(4-Amino-3-hydroxyphenyl)-4-morpholinothieno[3,2-d]pyrimidin-6-yl)methyl)(methyl)amino)-N-hydroxypyrimidine-5-carboxamide (Compound 279)

The title compound 279 was prepared as a yellow solid (50 mg, 25%) from 111-247-3 (200 mg) and a freshly prepared hydroxylamine methanol solution (8 mL, 1.79 M in methanol) in CH$_2$Cl$_2$ (3 mL) using a procedure similar to that described for compound 237 (Example 107). m.p.:

214-218° C. LCMS: 509 [M+1]⁺. ¹HNMR (400 MHz, DMSO-d₆): δ 3.20 (s, 3H), 3.76 (t, J=4.4 Hz, 4H), 3.88 (t, J=4.0 Hz, 4H), 5.17 (s, 2H), 6.49 (s, 2H), 6.58-6.64 (m, 2H), 7.44 (s, 1H), 7.73 (s, 1H), 8.69 (s, 2H).

Example 128: 2-(((2-(4-Amino-3-cyanophenyl)-4-morpholinothieno[3,2-d]pyrimidin-6-yl)methyl)(methyl)amino)-N-hydroxypyrimidine-5-carboxamide (Compound 280)

Step 128a: 2-Amino-5-bromobenzonitrile (Compound 0601-280)

2-Aminobenzonitrile (5.0 g, 42.3 mmol) was taken into dichloromethane (60 mL). NBS (7.54 g, 42.3 mmol) was added and stirred at 0° C. for 3 h. The reaction mixture was diluted with dichloromethane and washed with brine, dried over MgSO₄. The crude product was purified by column chromatography (hexane/ethyl acetate=10/1) to afford the titled compound (7.20 g, 87%). ¹HNMR (400 MHz, DMSO-d₆): δ 6.22 (s, 2H), 6.75 (d, J=9.2 Hz, 1H), 7.42 (dd, J=8.8 Hz, 2.4 Hz, 1H), 7.58 (s, 1H).

Step 128b: Ethyl 2-(((2-(4-amino-3-cyanophenyl)-4-morpholinothieno[3,2-d]pyrimidin-6-yl)methyl)(methyl)amino)pyrimidine-5-carboxylate (Compound 0603-280)

A mixture of 0601-280 (500 mg, 2.54 mmol), 4,4,4',4',5,5,5',5'-octamethyl-2,2'-bi(1,3,2-dioxaborolane) (775 mg, 3.04 mmol), KOAc (742 mg, 7.62 mmol), PdCl₂(dppf) (66 mg) in anhydrous 1,4-dioxane (20 mL) was heated to 90° C. for 12 h. The reaction mixture was filtered and concentrated to afford crude product 0602-280 as a brown solid (550 mg) which was used for the next step reaction without further purification.

A mixture of 0602-280 (500 mg, prepared above), 0504 (500 mg, 1.11 mmol), NaHCO₃ (269 mg, 3.2 mmol), PdCl₂(Ph₃P)₂ (60 mg), in toluene/ethanol/water (17.1 mL/10.5 mL/4.5 mL) was stirred at 140° C. overnight. The reaction mixture was filtered and concentrated in vacuo. The crude product was purified by column chromatography to afford 0603-280 (140 mg, 24%) as a white solid. LCMS: 531.4 [M+1]⁺. ¹HNMR, (400 MHz, DMSO-d₆): δ 1.31 (t, J=7.2 Hz, 3H), 3.27 (s, 3H), 3.75 (s, 4H), 3.91 (s, 4H), 4.29 (q, J=7.2 Hz, 2H), 5.22 (s, 2H), 6.44 (s, 2H), 6.87 (d, J=8.8 Hz, 1H), 7.41 (s, 1H), 8.29-8.34 (m, 2H), 8.88 (s, 1H).

Step 128c: 2-(((2-(4-Amino-3-cyanophenyl)-4-morpholinothieno[3,2-d]pyrimidin-6-yl)methyl)(methyl)amino)-N-hydroxypyrimidine-5-carboxamide (Compound 280)

The title compound 280 was prepared as a yellow solid (20 mg, 14%) from 0603-280 (150 mg, 0.28 mmol) and a freshly prepared hydroxylamine methanol solution (6 mL, 1.79 M in methanol) in CH₂Cl₂ (2 mL) using a procedure similar to that described for compound 237 (Example 107). m.p.:237-240° C. LCMS: 518.0 [M+1]⁺. ¹HNMR, (400 MHz, DMSO-d₆): δ 3.23 (s, 3H), 3.75 (s, 4H), 3.89 (s, 4H), 5.18 (s, 2H), 6.86 (s, 2H), 6.87 (d, J=8.4 Hz, 1H), 7.38 (s, 1H), 8.29-8.33 (m, 2H), 8.74 (s, 1H).

Example 129: 2-{[2-(3-Acetyl-4-amino-phenyl)-4-morpholin-4-yl-thieno[3,2-d]pyrimidin-6-yl methyl]-methyl-amino}-pyrimidine-5-carboxylic acid hydroxyamide (Compound 281)

Step 129a: 1-(2-Amino-5-bromo-phenyl)-ethanone (Compound 0601-281)

To a mixture of 1-(2-aminophenyl)ethanone (5.0 g, 0.037 mol) in dichloromethane (60 mL) was added NBS (7.3 g, 0.04 mol). The resulting mixture was cooled to 0° C. followed by the addition of H₂SO₄ (0.05 mL). It was allowed to warm to room temperature and stirred overnight. To the reaction mixture was added water and extracted with dichloromethane, dried over MgSO₄. The crude product was purified by column chromatography eluted with ethyl acetate/hexanes to afford the titled compound (4.6 g, 58%) as a yellow solid. m.p 87-89° C. ¹H NMR (400 MHz, CDCl₃): δ 2.56 (s, 3H), 6.31 (s, 2H), 7.56 (d, J=8.8 Hz, 1H), 7.33 (dd, J=2.4 Hz, 1H), 7.80 (d, J=2.4 Hz, 1H).

Step 129b: 1-[2-Amino-5-(4,4,5,5-tetramethyl-[1,3,2]dioxaborolan-2-yl)-phenyl]-ethanone (Compound 0602-281)

A mixture of 0601-281 (1 g, 4.7 mmol), bis(pinacolato)diboron (1.66 g, 6.5 mmol), PdCl₂(dppf) (230 mg, 0.28 mmol) and KOAc (1.48 g, 15 mmol) in anhydrous dioxane (30 mL) was heated at 100° C. for 4 h in a pressure vessel. The reaction mixture was filtered and the solid was washed with CH₂Cl₂. The filtrate was concentrated in vacuo and purified by column chromatography (3% ethyl acetate/hexanes) to afford 0602-281 (1 g, 83%) as an off-white solid. m.p 45-48° C. ¹H NMR (400 MHz, CDCl₃): δ 1.33 (s, 12H), 2.62 (s, 3H), 6.49 (s, 2H), 6.60 (d, J=8.4 Hz, 1H), 7.66 (d, J=8.0 Hz, 1H), 8.18 (s, 1H).

Step 129c: 2-{[2-(3-Acetyl-4-amino-phenyl)-4-morpholin-4-yl-thieno[3,2-d]pyrimidin-6-ylmethyl]-methyl-amino}-pyrimidine-5-carboxylic acid ethyl ester (Compound 0603-281)

The title compound 0603-281 was prepared as a light yellow solid (450 mg, 92%) from 0602-281 (720 mg, 2.7 mmol), 0504 (412 mg, 0.9 mmol), NaHCO₃ (232 mg, 2.7 mmol) and PdCl₂(PPh₃)₂ (107 mg) in toluene (7.5 mL), EtOH (4.8 mL) and water (2.1 mL) using a procedure similar to that described for compound 1103-226 (Example 99): LCMS: 548.4 [M+1]⁺.

Step 129d: 2-{[2-(3-Acetyl-4-amino-phenyl)-4-morpholin-4-yl-thieno[3,2-d]pyrimidin-6-yl methyl]-methyl-amino}-pyrimidine-5-carboxylic acid hydroxyamide (Compound 281)

The title compound 281 was prepared as a pale yellow solid (40 mg) from 0603-281 (500 mg) and a freshly prepared hydroxylamine methanol solution (12 mL, 1.79 M in methanol) in CH₂Cl₂ (5 mL) using a procedure similar to that described for compound 237 (Example 107). m.p.:156-158° C. LC-MS: 535 [M+1]⁺. ¹H NMR (400 MHz, DMSO-d₆): δ 2.61 (s, 3H), 3.23 (s, 3H), 3.76 (s, 4H), 3.90 (s, 4H), 5.19 (s, 2H), 6.84 (m, 1H), 7.40 (s, 1H), 7.53 (s, 2H), 8.27 (m, 1H), 8.78 (d, J=23.2 Hz, 3H), 9.02 (s, 1H), 11.09 (s, 1H).

Example 130: 2-(((2-(4-Amino-3,5-difluorophenyl)-4-morpholinothieno[3,2-d]pyrimidin-6-yl) methyl)(methyl)amino)-N-hydroxypyrimidine-5-carboxamide (Compound 282)

Step 130a: 2,6-Difluoro-4-(4,4,5,5-tetramethyl-1,3,2-dioxaborolan-2-yl)aniline (Compound 0602-282)

The title compound 0602-282 was prepared as an off-white solid (3 g) from 4-bromo-2,6-difluoroaniline (2.08 g, 10 mmol), 4,4,4',4',5,5,5',5'-octamethyl-2,2'-bi(1,3,2-dioxaborolane (3.79 g, 15 mmol), KOAc (3 g, 30 mmol) and Pd(dppf)Cl$_2$ (400 mg, 0.5 mmol) in dioxane (50 mL) using a procedure similar to that described for compound 0602-281 (Example 129). $^1$H NMR (400 MHz, CDCl$_3$): δ 1.31 (s, 12H), 3.91 (br, 2H), 7.22-7.25 (m, 2H).

Step 130b: Ethyl 2-(((2-(4-amino-3,5-difluorophenyl)-4-morpholinothieno[3,2-d]pyrimidin-6-yl)methyl)(methyl)amino)pyrimidine-5-carboxylate (Compound 0603-282)

The title compound 0603-282 was prepared as a yellow solid (200 mg, 55%) from 0602-282 (500 mg, 2 mmol), 0504 (300 mg, 0.669 mmol), NaHCO$_3$ (168 mg, 2 mmol) and Pd(PPh$_3$)$_2$Cl$_2$ (50 mg) in toluene/EtOH/H$_2$O (5 mL/3.2 mL/1.4 mL) using a procedure similar to that described for compound 1103-226 (Example 99): $^1$HNMR: (400 MHz, CDCl$_3$): δ 1.31 (t, J=7.2 Hz, 3H), 3.28 (s, 3H), 3.76-3.77 (m, 4H), 3.89-3.91 (m, 4H), 4.30 (q, J=7.2 Hz, 2H), 5.23 (s, 2H), 5.59 (s, 2H), 7.42 (s, 1H), 7.86 (d, J=9.6 Hz, 2H), 8.88 (s, 2H).

Step 130c: 2-(((2-(4-Amino-3,5-difluorophenyl)-4-morpholinothieno[3,2-d]pyrimidin-6-yl) methyl)(methyl)amino)-N-hydroxypyrimidine-5-carboxamide (Compound 282)

The title compound 282 was prepared as a white solid (95 mg, 63%) from 0603-282 (150 mg, 0.277 mmol) and a freshly prepared hydroxylamine methanol solution (4 mL, 1.79 M in methanol) in CH$_2$Cl$_2$ (2 mL) using a procedure similar to that described for compound 237 (Example 107). m.p.: 190-193° C. LCMS: 529 [M+1]$^+$. $^1$HNMR: (400 MHz, CDCl$_3$): δ 3.23 (s, 3H), 3.75 (br, 4H), 3.89 (br, 4H), 5.18 (s, 2H), 5.62 (s, 2H), 7.39 (s, 1H), 7.85 (d, J=8.4 Hz, 2H), 8.74 (s, 2H), 9.02 (br, 1H), 11.08 (s, 1H).

Example 131: 2-{[2-(4-Amino-2-fluoro-phenyl)-4-morpholin-4-yl-thieno[3,2-d]pyrimidin-6-ylmethyl]-methyl-amino}-pyrimidine-5-carboxylic acid hydroxyamide (Compound 283)

Step 131a: 4-Bromo-3-fluoro-phenylamine (Compound 0601-283)

3-fluoroaniline (4.44 g, 40 mmol), NBS (7.11 g, 40 mmol) were taken into dichloromethane (30 mL). Conc. H$_2$SO$_4$ (2 drops) was added. The resulting mixture was stirred at 0° C. for 4 h. The reaction mixture was diluted with water and extracted with ethyl acetate. The combined extract was washed with aq. NaHCO$_3$, dried over Na$_2$SO$_4$. The crude product was purified by column chromatography (hexanes/ethyl acetate=10/1) to afford the titled compound (5.00 g, 66%) as a light yellow solid. LCMS: 190 [M+1]$^+$.

$^1$H NMR (400 MHz, DMSO-d$_6$): δ 5.53 (s, 2H), 6.34 (dd, J=8.8 Hz, 3.2 Hz, 1H), 6.45 (dd, J=11.6 Hz, 2.4 Hz, 1H), 7.18 (t, 1H).

Step 131b: 2-{[2-(4-Amino-2-fluoro-phenyl)-4-morpholin-4-yl-thieno[3,2-d]pyrimidin-6-ylmethyl]-methyl-amino}-pyrimidine-5-carboxylic acid ethyl ester (Compound 0603-283)

The title compound 0603-283 was prepared as a light yellow solid (250 mg, 28%) from 0601-283 (500 mg, 3.44 mmol), 4,4,4',4',5,5,5',5'-octamethyl-2,2'-bi(1,3,2-dioxaborolane) (1.74 g, 6.87 mmol), KOAc (842 mg, 8.60 mmol), PdCl$_2$(dppf) (50 mg) in anhydrous 1,4-dioxane (5 mL) followed by 3-Fluoro-4-(4,4,5,5-tetramethyl-[1,3,2]dioxaborolan-2-yl)-phenylamine, 0504 (772 mg, 1.72 mmol), NaHCO$_3$ (433 mg, 5.16 mmol), PdCl$_2$(Ph$_3$P)$_2$ (75 mg) in toluene/ethanol/water (8 mL/4 mL/2 mL) using a procedure similar to that described for compound 0603-275 (Example 124). LCMS: 524 [M+1]$^+$. $^1$H NMR (400 MHz, DMSO-d$_6$): δ 1.31 (t, J=6.8 Hz, 3H), 3.25 (s, 3H), 3.72 (m, 4H), 3.85 (m, 4H), 3.88 (m, 2H), 4.28 (q, J=7.2 Hz, 2H), 5.20 (s, 2H), 6.34 (d, J=12.8 Hz, 1H), 6.43 (d, J=8.4 Hz, 1H), 7.38 (s, 1H), 7.83-7.90 (m, 1H), 8.86 (s, 2H).

Step 131c: 2-{[2-(4-Amino-2-fluoro-phenyl)-4-morpholin-4-yl-thieno[3,2-d]pyrimidin-6-ylmethyl]-methyl-amino}-pyrimidine-5-carboxylic acid hydroxyamide (Compound 283)

The title compound 283 was prepared as a white solid (50 mg, 20%) from 0603-283 (250 mg, 0.4 8 mmol) and a freshly prepared hydroxylamine methanol solution (8 mL, 1.79 M in methanol) in CH$_2$Cl$_2$ (2 mL) using a procedure similar to that described for compound 237 (Example 107). m.p:195~197° C. LCMS: 511 [M+1]$^+$. $^1$HNMR (400 MHz, DMSO-d$_6$): δ 3.22 (s, 3H), 3.71-3.74 (m, 4H), 3.84-3.87 (m, 4Hm), 5.18 (s, 2H), 5.74 (s, 2H), 6.34 (dd, J=13.6 Hz, 1.6 Hz, 1H), 6.43 (dd, J=8.4 Hz, 1.6 Hz, 1H), 7.36 (s, 1H), 7.85 (t, J=8.4 Hz, 1H), 8.74 (2H, s), 9.02 (br, 1H), 11.01 (br, 1H).

Example 132: 2-(((2-(4-Amino-2-chlorophenyl)-4-morpholinothieno[3,2-d]pyrimidin-6-yl)methyl)(methyl)amino)-N-hydroxypyrimidine-5-carboxamide (Compound 284)

Step 132a: 3-Chloro-4-(4,4,5,5-tetramethyl-1,3,2-dioxaborolan-2-yl)aniline (Compound 0602-284)

The title compound 0602-284 was prepared as a light yellow solid (1 g, 66.7%) from 4-bromo-3-chloroaniline (1.23 g, 5.9 mmol), 4,4,4',4',5,5,5',5'-octamethyl-2,2'-bi(1,3,2-dioxaborolane) (2.2 g, 8.9 mmol), KOAc (1.7 g, 17.7 mmol) and Pd(dppf)Cl$_2$ (200 mg, 0.24 mmol) in dioxane using a procedure similar to that described for compound 0602-281 (Example 129). $^1$HNMR (400 MHz, CDCl$_3$): δ 3.84 (br, 2H), 1.33 (s, 12H), 6.49 (d, J=8.0 Hz, 1H), 6.44 (s, 1H), 7.51 (d, J=8.0 Hz, 1H).

Step 132b: Ethyl 2-(((2-(4-amino-2-chlorophenyl)-4-morpholinothieno[3,2-d]pyrimidin-6-yl)methyl)(methyl)amino)pyrimidine-5-carboxylate (Compound 0603-284)

The title compound 0603-284 was prepared as a yellow solid (200 mg, 55%) from 0602-284 (220 mg, 0.869 mmol), 0504 (300 mg, 0.66 mmol), NaHCO$_3$ (166 mg, 2 mmol) and Pd(PPh$_3$)$_2$Cl$_2$ (50 mg) in toluene/EtOH/H$_2$O (5 mL/3.2 mL/1.4 mL) using a procedure similar to that described for compound 1103-226 (Example 99): $^1$HNMR (400 MHz, DMSO-d$_6$): δ 1.31 (t, J=7.2 Hz, 2H), 3.72 (t, J=4.0 Hz, 4H), 3.87 (t, J=4.0 Hz, 4H), 4.29 (q, J=7.2 Hz, 2H), 5.23 (s, 2H), 5.61 (br, 2H), 6.57 (d, J=8.4 Hz, 1H), 6.67 (s, 1H), 7.41 (s, 1H), 7.60 (d, J=8.0 Hz, 2H), 8.88 (s, 2H).

Step 132c: 2-(((2-(4-Amino-2-chlorophenyl)-4-morpholinothieno[3,2-d]pyrimidin-6-yl)methyl)(methyl)amino)-N-hydroxypyrimidine-5-carboxamide (Compound 284)

The title compound 284 was prepared as a light tan solid (31 mg, 15%) from 0603-284 (200 mg, 0.37 mmol) and a freshly prepared hydroxylamine methanol solution (4 mL, 1.79 M in methanol) in CH$_2$Cl$_2$ (2 mL) using a procedure similar to that described for compound 237 (Example 107). m.p.:179-183° C. LCMS: 527.0[M+1]$^+$. $^1$HNMR (400 MHz, DMSO-d$_6$): δ 3.22 (s, 3H), 3.72 (t, J=4.8 Hz, 4H), 3.87 (t, J=4.0 Hz, 4H), 5.19 (s, 2H), 5.61 (s, 2H), 6.57 (dd, J=8.4 Hz, 2 Hz, 1H), 6.67 (s, 1H), 7.39 (s, 1H), 7.60 (d, J=8.4 Hz, 2H), 8.73 (s, 2H).

Example 133: 2-(((2-(4-Amino-3-(hydroxymethyl)phenyl)-4-morpholinothieno[3,2-d]pyrimidin-6-yl)methyl)(methyl)amino)-N-hydroxypyrimidine-5-carboxamide (Compound 285)

Step 133a: (2-Amino-5-bromophenyl)methanol (Compound 0601-285)

A solution of 2-Amino-5-bromo-benzoic acid (5.0 g, 23.15 mmol) in anhydrous THF was added dropwise to the mixture of LiAlH$_4$ (2.2 g, 58 mmol) in THF under N$_2$ protection at 0° C. The resulting mixture was warmed to room temperature and stirred for 2 h. The reaction was quenched by adding Na$_2$SO$_4$ 10H$_2$O to the reaction mixture at 0° C. The resulting mixture was filtered and the filtrate was concentrated to afford the titled compound 0601-285 (2.05 g, 43%) as an off-white solid, m.p.103-106° C. The crude product was used for next step reaction without further purification. $^1$H NMR (400 MHz, CDCl$_3$): δ 4.61 (s, 2H); 6.56 (d, J=8.0 Hz, 2H); 7.19-7.26 (m, 2H).

Step 133b: (2-Amino-5-(4,4,5,5-tetramethyl-1,3,2-dioxaborolan-2-yl)phenyl) methanol (Compound 0602-285)

The title compound 0602-285 was prepared as a yellow solid (900 mg, 77%) from 0601-285 (950 mg, 4.7 mmol), bis(pinacolato)diboron (1.8 g, 7.08 mmol), AcOK (1.38 g, 14 mmol) PdCl$_2$(dppf)$_2$ (390 mg, 0.478 mmol) in anhydrous dioxane using a procedure similar to that described for compound 0602-281 (Example 129). LCMS: 250.3 [M+1]$^+$. $^1$HNMR (400 MHz, CDCl$_3$): δ 1.31 (s, 12H); 4.40 (br, 2H); 4.66 (s, 2H); 6.66 (d, J=8.0 Hz, 1H); 7.51 (s, 1H); 7.58 (dd, J=8.0 Hz, 1.2 Hz, 1H).

Step 133c: Ethyl 2-(((2-(4-amino-3-(hydroxymethyl)phenyl)-4-morpholinothieno[3,2-d]pyrimidin-6-yl)methyl)(methyl)amino)pyrimidine-5-carboxylate (Compound 0603-285)

The title compound 0603-285 was prepared as a light yellow solid (239 mg, 55.8%) from 0602-285 (450 mg, 1.8 mmol), 0504 (360 mg 0.8 mmol) NaHCO$_3$ (202 mg, 2.4 mmol), Pd(PPh$_3$)$_2$Cl$_2$ (60 mg, 0.085 mmol) in toluene (12 mL), ethanol (7 ml) and water (3 ml) using a procedure similar to that described for compound 1103-226 (Example 99): mp 215-217° C. LCMS, 536.3 [M+1]$^+$; $^1$HNMR (400 MHz, DMSO-d$_6$): δ 1.33, (m, 3H), 3.77 (m, 4H), 3.92 (m, 4H), 3.30 (m, 3H), 4.32 (m, 2H), 4.50 (m, 2H), 5.04 (m, 1H), 5.22 (m, 2H), 5.33 (m, 2H), 6.70 (m, 1H), 7.40 (m, 1H), 8.07 (m, 1H), 8.19 (m, 1H), 8.92 (s, 2H).

Step 133d: 2-(((2-(4-Amino-3-(hydroxymethyl)phenyl)-4-morpholinothieno[3,2-d]pyrimidin-6-yl)methyl)(methyl)amino)-N-hydroxypyrimidine-5-carboxamide (Compound 285)

The title compound 285 was prepared as a light yellow solid (97 mg) from 0603-285 (115 mg, 0.2147 mmol) and a freshly prepared hydroxylamine methanol solution (30 mL, 1.79 M in methanol) in CH$_2$Cl$_2$ (2 mL) using a procedure similar to that described for compound 237 (Example 107). m.p.: 195-200° C. LCMS: 523.0 [M+1]$^+$. $^1$HNMR (400 MHz, DMSO-d$_6$): δ 3.17 (s, 3H); 3.76 (s, 4H); 3.89 (s, 4H); 4.46 (s, 2H); 5.18 (s, 2H); 5.33 (s, 2H); 8.67 (t, J=3.6 Hz, 1H); 7.37 (s, 1H); 8.04 (d, J=7.2 Hz, 1H); 8.16 (s, 1H), 8.74 (s, 2H).

Example 134: 2-({2-[3-(2-Hydroxy-ethoxy)-phenyl]-4-morpholin-4-yl-thieno[3,2-d]pyrimidin-6-ylmethyl}-methyl-amino)-pyrimidine-5-carboxylic acid hydroxyamide (Compound 289)

Step 134a: [2-(3-Bromo-phenoxy)-ethoxy]-t-butyl-dimethyl-silane (Compound 0601-289)

To a solution of 2-(3-Bromo-phenoxy)-ethanol (2.0 g, 9.2 mol) in dichloromethane (15 mL) at ice water bath temperature was added (1.25 g, 1.84 mmol) imidazole followed by the addition of TBSCl (1.67 g, 11 mmol) under nitrogen protection. TLC showed reaction was complete in 1 h. The reaction mixture was filtered. The filtrate was washed with water and dried over Na$_2$SO$_4$. The crude product was purified by column chromatography eluted with hexanes/ethyl acetate to afford titled product as a light color oil (2.65 g, 87%).

Step 134b: 2-{3-[2-(tert-Butyl-dimethyl-silanyloxy)-ethoxy]-phenyl}-4,4,5,5-tetramethyl-[1,3,2]dioxaborolane (Compound 0602-289)

The title compound 0602-289 was prepared as an off-white solid (1.94 g, 64%) from 0601-289 (2.65 g, 8 mmol), bis (pinacolato) diboron, KOAc (2.36 g, 24 mmol) and Pd(dppf)Cl$_2$ (0.117 g, 2 mmol) in anhydrous dioxane (30 mL) using a procedure similar to that described for compound 0602-281 (Example 129).

Step 134c: 2-({2-[3-(2-Hydroxy-ethoxy)-phenyl]-4-morpholin-4-yl-thieno[3,2-d]pyrimidin-6-ylmethyl}-methyl-amino)-pyrimidine-5-carboxylic acid ethyl ester (Compound 0603-289)

A mixture of 0602-289 (1.94 g, 5.1 mmol), 0504 (0.5079 g, 1.3 mmol) and NaHCO$_3$ (0.323 g, 3.8 mmol) were taken into 10 ml toluene (10 mL), ethanol (6.4 mL) and water (2.8 mL) followed the addition of Pd(PPh$_3$)$_2$Cl$_2$ (54 mg). The resulting mixture was heated at 120° C. overnight. TLC showed the reaction complete. The reaction mixture was filtered through celite and washed with dichloromethane.

The crude product was purified by column chromatography eluted with hexanes/ethyl acetate to afford 2-[(2-{3-[2-(tert-Butyl-dimethyl-silanyloxy)-ethoxy]-phenyl}-4-morpholin-4-yl-thieno[3,2-d]pyrimidin-6-ylmethyl)-methyl-amino]-pyrimidine-5-carboxylic acid ethyl ester (0.71 g, 83%) as an off-white solid. LC-MS: 665[m+1]$^+$.

Step 134d: 2-[(2-{3-[2-(tert-Butyl-dimethyl-silanyloxy)-ethoxy]-phenyl}-4-morpholin-4-yl-thieno[3,2-d]pyrimidin-6-ylmethyl)-methyl-amino]-pyrimidine-5-carboxylic acid ethyl ester (680 mg, 1.02 mmol) was taken into THF (20 mL) followed by the addition of tetrabutyl ammonium fluoride (533 mg, 2.04 mmol). The resulting mixture was stirred at room temperature for 30 min. TLC showed reaction complete. Reaction mixture was diluted with ethyl acetate, washed with water and dried with $Na_2SO_4$. The crude product was purified by column chromatography eluted with hexanes/ethyl acetate to afford titled compound as an off-white solid (540 mg, 96%). m.p.: 216-220° C. LC-MS: 551.3 [M+1]$^+$. $^1$H NMR (400 MHz, CDCl$_3$): δ 1.38 (t, J=6.8 Hz, 3H), 3.31 (s, 3H), 3.86 (t, J=5.2 Hz, 4H), 3.99-4.02 (m, 6H), 4.20 (t, J=4.4 Hz, 2H), 4.37 (q, J=7.2 Hz, 2H), 5.19 (s, 2H). 7.01 (dd, J=8 Hz, 2 Hz, 1H), 7.35-7.39 (m, 2H). 8.01-8.05 (m, 2H), 8.92 (s, 2H).

Step 134e: 2-({2-[3-(2-Hydroxy-ethoxy)-phenyl]-4-morpholin-4-yl-thieno[3,2-d]pyrimidin-6-ylmethyl}-methyl-amino)-pyrimidine-5-carboxylic acid hydroxyamide (Compound 289)

The title compound 289 was prepared as a white solid solid (70 mg, 71.7%) from 0603-289 (100 mg) and a freshly prepared hydroxylamine methanol solution (3 mL, 1.79 M in methanol) in $CH_2Cl_2$ (1 mL) using a procedure similar to that described for compound 237 (Example 107). m.p.: 148-152° C. LC-MS: 538.0 [M+1]$^+$. $^1$H NMR (400 MHz, DMSO-d$_6$): δ 3.24 (S, 3H), 3.75-3.78 (m, 6H), 3.92 (t, J=4.8 Hz, 4H), 4.06 (t, J=5.2 Hz, 2H). 4.85 (t, J=4.4 Hz, 1H), 5.20 (s, 2H), 7.05 (dd, J=8.0 Hz, 2 Hz, 1H). 7.38 (t, J=8 Hz, 1H), 7.46 (s, 1H). 7.92 (s, 1H), 7.97 (d, J=3.6 Hz, 1H), 8.75 (s, 2H), 9.02 (s, 1H), 11.09 (s, 1H).

Example 135: N-Hydroxy-2-(((2-(3-(2-hydroxyethylthio)phenyl)-4-morpholinothieno[3,2-d]pyrimidin-6-yl)methyl)(methyl)amino)pyrimidine-5-carboxamide (Compound 290)

Step 135a: 2-(3-Bromophenylthio)ethanol (Compound 0601-290)

A mixture of 3-bromobenzenethiol (1.5 g, 7.93 mmol), 2-bromoethanol (1.19 g, 9.52 mmol) and $Cs_2CO_3$ (5.16 g, 15.8 mmol) in DMF (10 ml) was heated to 50° C. overnight. The reaction mixture was diluted with ethyl acetate and filtered. The filtrate was washed with water and dried. The crude product was purified by column chromatography to afford the titled compound (1.5 g, 81%). $^1$HNMR (400 MHz, CDCl$_3$): δ 3.12 (t, J=6.0 Hz, 2H), 3.77 (t, J=6.4 Hz, 2H), 7.14 (t, J=8.0 Hz, 1H), 7.26-7.34 (m, 2H), 7.51 (s, 1H).

Step 135b: Ethyl 2-(((2-(3-(2-hydroxyethylthio)phenyl)-4-morpholinothieno[3,2-d]pyrimidin-6-yl)methyl)(methyl)amino)pyrimidine-5-carboxylate (Compound 0603-290)

The title compound 0603-290 was prepared as a yellow solid (525 mg, 70%) from 0601-290 (487 mg, 2.1 mmol), bis(pinacolato)diboron (0.8 g, 3.15 mmol), AcOK (720 mg 7.35 mmol) and PdCl$_2$(dppf)$_2$ (190 mg, 0.26 mmol) in dioxane followed by 0504 (600 mg, 1.33 mmol), 0602-290, NaHCO$_3$ (400 mg, 4.76 mmol), Pd(PPh$_3$)$_2$Cl$_2$ (60 mg, 0.086 mmol) in toluene (12 ml), ethanol (8 ml), water (6 ml) using a procedure similar to that described for compound 0603-275 (Example 124). m.p.: 144-147° C. LCMS: 567.2[M+1]$^+$. $^1$HNMR (400 MHz, DMSO-d$_6$): δ 1.30 (t, J=6.8 Hz, 3H), 3.10 (t, J=6.8 Hz, 2H), 3.59-3.64 (m, 2H), 3.76 (br, 4H), 3.93 (br, 4H), 4.29 (q, J=6.8 Hz, 2H), 4.91 (t, J=4.2 Hz, 1H), 5.24 (s, 2H), 7.43-7.45 (br, 2H); 8.19 (d, J=7.2 Hz, 1H), 8.33 (s, 1H); 8.87 (s, 2H).

Step 135c: N-Hydroxy-2-(((2-(3-(2-hydroxyethylthio)phenyl)-4-morpholinothieno[3,2-d]pyrimidin-6-yl)methyl)(methyl)amino)pyrimidine-5-carboxamide (Compound 290)

The title compound 290 was prepared as a white solid (97 mg) from 0603-290 (260 mg, 0.46 mmol) and a freshly prepared hydroxylamine methanol solution (30 mL, 1.79 M in methanol) using a procedure similar to that described for compound 237 (Example 107). m.p.: 188-192° C. LCMS: 554.0[M+1]$^+$. $^1$H NMR (400 MHz, DMSO-d$_6$): δ 3.10 (t, J=6.8 Hz, 2H), 3.24 (s, 3H), 3.58-3.63 (m, 2H), 3.76 (br, 4H), 3.92 (br, 4H), 4.99 (t, J=5.2 Hz, 1H), 5.20 (s, 2H), 7.43-7.49 (br, 3H), 8.18 (d, J=6.8 Hz, 1H), 8.32 (s, 1H), 8.75 (s, 2H), 9.08 (br, 1H), 11.15 (s, 1H).

Example 136: 2-(((2-(2-Fluoro-5-hydroxyphenyl)-4-morpholinothieno[3,2-d]pyrimidin-6-yl)methyl)(methyl)amino)-N-hydroxypyrimidine-5-carboxamide (Compound 292)

Step 136a: Ethyl 2-(((2-(2-fluoro-5-hydroxyphenyl)-4-morpholinothieno[3,2-d]pyrimidin-6-yl)methyl)(methyl)amino)pyrimidine-5-carboxylate (Compound 0603-292)

The title compound 0603-292 was prepared as a grey solid (1.32 g 74.9%) from 3-bromo-4-fluorophenol (1.425 g, 7.5 mmol), bis(pinacolato) diboron (2.86 g, 11.25 mmol), PdCl$_2$(dppf) (306 mg, 0.375 mmol), and KOAc (2.205 g, 22.5 mmol) in anhydrous dioxane (20 mL) followed by 0504 (1.5 g, 3.375 mmol), NaHCO$_3$ (850 mg, 10.13 mmol) and PdCl$_2$(PPh$_3$)$_2$ (118 mg, 0.168 mmol) in toluene (11 mL), EtOH (7 mL) and water (2.8 mL) using a procedure similar to that described for compound 0603-275 (Example 124). LCMS: 525.2 [M+1]$^+$. $^1$H NMR (400 MHz, DMSO-d$_6$): δ 1.30 (m, 3H), 3.27 (s, 3H), 3.74 (m, 4H), 3.88 (m, 4H), 4.29 (m, 2H), 5.24 (s, 2H), 6.83 (m, 1H), 7.07 (m, 1H), 7.42 (m, 2H), 8.88 (s, 2H), 9.48 (s, 1H).

Step 136b: 2-(((2-(2-Fluoro-5-hydroxyphenyl)-4-morpholinothieno[3,2-d]pyrimidin-6-yl)methyl)(methyl)amino)-N-hydroxypyrimidine-5-carboxamide (Compound 292)

The title compound 292 was prepared as a tan solid (380 mg) from 0603-292 (560 mg, 1.07 mmol) and a freshly prepared hydroxylamine methanol solution (30 mL, 1.79 M in methanol) using a procedure similar to that described for compound 237 (Example 107). m.p. 250-255° C. LCMS: 512 [M+1]$^+$. $^1$H NMR (400 MHz, DMSO-d$_6$): δ 3.24 (s, 3H), 3.73 (m, 4H), 3.88 (m, 4H), 5.21 (s, 2H), 6.83 (m, 1H), 7.06 (m, 1H), 7.42 (m, 1H), 7.45 (s, 1H), 8.75 (s, 2H), 9.04 (s, 1H), 9.45 (s, 1H), 11.11 (s, 1H).

Example 137: N-Hydroxy-2-(((2-(3-hydroxy-4-nitrophenyl)-4-morpholinothieno[3,2-d]pyrimidin-6-yl)methyl)(methyl)amino)pyrimidine-5-carboxamide (Compound 293)

Step 137a: 2-Nitro-5-(4,4,5,5-tetramethyl-1,3,2-dioxaborolan-2-yl)phenol (Compound 0602-293)

The title compound 0602-293 was prepared as yellow solid (2.9 g, 80%) from 5-bromo-2-nitrophenol (3 g, 13.76 mmol), 4,4,4',4',5,5,5',5'-octamethyl-2,2'-bi(1,3,2-dioxaborolane) (5.25 g, 20.69 mmol), KOAc (3.75 g, 41.28 mmol) and Pd(dppf)Cl$_2$ (300 mg) in dioxane (100 mL) using a procedure similar to that described for compound 0602-281 (Example 129). LCMS: 266.2[M+1]$^+$. $^1$HNMR (400 MHz, CDCl$_3$): δ 1.44 (s, 12H), 6.80 (d, J=8.8 Hz, 1H), 6.84 (s, 1H), 8.04 (d, J=8.8 Hz, 1H).

Step 137b: Ethyl 2-(((2-(3-hydroxy-4-nitrophenyl)-4-morpholinothieno[3,2-d]pyrimidin-6-yl)methyl)(methyl)amino)pyrimidine-5-carboxylate (Compound 0603-293)

The title compound 0603-293 was prepared as a yellow solid (100 mg, 27%) from 0602-293 (350 mg, 1.337 mmol), 0504 (300 g, 0.668 mmol), sat. NaHCO$_3$ (4 mL) and Pd(PPh$_3$)$_4$ (100 mg) in dioxane (12 mL) using a procedure similar to that described for compound 1103-226 (Example 99): LCMS: 552.3[M+1]$^+$. $^1$HNMR: (400 MHz, DMSO-d$_6$): δ 1.36 (t, J=6.8 Hz, 3H), 3.76 (s, 4H), 3.86 (s, 4H), 4.35 (d, J=6.4 Hz, 2H), 5.30 (s, 2H), 7.00 (d, J=7.6 Hz, 1H), 7.33 (s, 1H), 7.52 (s, 1H), 7.85 (d, J=8.8 Hz, 1H), 8.94 (s, 2H).

Step 137c: N-Hydroxy-2-(((2-(3-hydroxy-4-nitrophenyl)-4-morpholinothieno[3,2-d]pyrimidin-6-yl)methyl)(methyl)amino)pyrimidine-5-carboxamide (Compound 293)

The title compound 293 was prepared as a yellow solid (40 mg, 30%) from 0603-293 (130 mg) and a freshly prepared hydroxylamine methanol solution (3 mL, 1.79 M in methanol) using a procedure similar to that described for compound 237 (Example 107). m.p.: 258-261° C. LCMS: 559[M+1]$^+$. $^1$HNMR: (400 MHz, DMSO-d$_6$): δ 3.23 (s, 3H), 3.69 (s, 4H), 3.79 (s, 4H), 5.20 (s, 2H), 6.90 (s, 1H), 7.20 (s, 1H), 7.44 (s, 1H), 7.79 (s, 1H), 8.74 (s, 2H).

Example 138: N-Hydroxy-2-(((2-(3-(1-hydroxyethyl)phenyl)-4-morpholinothieno[3,2-d]pyrimidin-6-yl)methyl)(methyl)amino)pyrimidine-5-carboxamide (Compound 294)

Step 138a: Ethyl 2-(((2-(3-(1-hydroxyethyl)phenyl)-4-morpholinothieno[3,2-d]pyrimidin-6-yl)methyl)(methyl)amino)pyrimidine-5-carboxylate (Compound 0603-294)

1-(3-bromophenyl) ethanone (1.00 g, 5.02 mmol), 4,4,4',4',5,5,5',5'-octamethyl-2,2'-bi(1,3,2-dioxaborolane) (2.55 g, 10.05 mmol), KOAc (1.23 g, 12.55 mmol), PdCl$_2$(dppf) (100 mg) were taken into anhydrous 1,4-dioxane (10 mL) and heated to 100° C. for 3 h. After cooling to room temperature the reaction mixture was filtered and concentrated. The crude product was isolated as brown solid (1.2 g) and was used for the next step reaction without further purification.

A mixture of 0602-294 (1.2 g, prepared above), 0504 (563 mg, 1.26 mmol), NaHCO$_3$ (318 mg, 3.78 mmol), PdCl$_2$(Ph$_3$P)$_2$ (55 mg), in toluene/ethanol/water (4 mL/2 mL/1 mL) was stirred at 130° C. overnight. The reaction mixture was filtered and concentrated. The crude product was purified by column chromatography to afford ethyl 2-(((2-(3-acetylphenyl)-4-morpholinothieno[3,2-d]pyrimidin-6-yl)methyl)(methyl)amino)pyrimidine-5-carboxylate as an off-white solid (350 mg, 52%). LCMS 533.3 [M+1]$^+$. $^1$HNMR (400 MHz, DMSO-d$_6$): δ 1.31 (t, J=7.2 Hz, 3H), 2.66 (s, 3H), 3.30 (s, 3H), 3.76-3.80 (m, 4H), 3.92-3.97 (m, 4H), 4.29 (q, J=7.2 Hz, 2H), 4.79-4.84 (m, 1H), 5.24 (s, 2H), 7.40-7.49 (m, 2H), 7.49 (s, 1H), 8.07 (dd, J=6.4 Hz, 1.6 Hz, 1H), 8.63 (d, J=7.6 Hz, 1H), 8.88 (s, 2H), 8.90 (s, 1H).

A mixture of ethyl 2-(((2-(3-acetylphenyl)-4-morpholinothieno[3,2-d]pyrimidin-6-yl) methyl) (methyl)amino)pyrimidine-5-carboxylate (350 mg, 0.66 mmol), NaBH$_4$ (124 mg, 3.29 mmol) in anhydrous THF was stirred at room temperature for 0.5 h. The mixture was quenched with water and extracted with dichloromethane. The combined organic layers were washed brine and dried over MgSO$_4$. Crude product 0603-294 was obtained as a white solid (200 mg, 57%) after filtration and was used directly for next step reaction without further purification. LCMS: 535.4 [M+1$^+$. $^1$HNMR (400 MHz, DMSO-d$_6$): δ 1.31 (t, J=7.2 Hz, 3H), 1.38 (d, J=6.4 Hz, 3H), 3.28 (s, 3H), 3.76-3.80 (m, 4H), 3.92-3.97 (m, 4H), 4.29 (q, J=7.2 Hz, 2H), 4.79-4.84 (m, 1H), 5.24 (s, 2H), 7.40-7.49 (m, 2H), 7.49 (s, 1H), 8.23-8.26 (m, 1H), 8.39 (s, 1H), 8.88 (s, 2H).

Step 138b: N-Hydroxy-2-(((2-(3-(1-hydroxyethyl)phenyl)-4-morpholinothieno[3,2-d]pyrimidin-6-yl)methyl)(methyl)amino)pyrimidine-5-carboxamide (Compound 294)

The title compound 294 was prepared as a light yellow solid (70 mg, 36% yield) from 0603-294 (200 mg, 0.37 mmol) and a freshly prepared hydroxylamine methanol solution (8 mL, 1.79 M in methanol) in dichloromethane (2 mL) using a procedure similar to that described for compound 237 (Example 107). m.p.:168-171° C. LCMS: 522.0 [M+1]$^+$. $^1$H-NMR, (400 MHz, DMSO-d$_6$): δ (ppm) 1.37 (d, J=6.0 Hz, 3H), 3.24 (s, 3H), 3.77 (s, 4H), 3.93 (s, 4H), 4.81 (br, 1H), 5.20 (s, 3H), 7.39-7.47 (3H, m), 8.25 (d, J=6.0 Hz, 1H), 8.38 (s, 1H), 8.75 (s, 2H), 9.02 (s, 1H), 11.09 (s, 1H).

Example 139: 2-(((2-(2-Fluoro-5-(1-hydroxyethyl)phenyl)-4-morpholinothieno[3,2-d]pyrimidin-6-yl)methyl)(methyl)amino)-N-hydroxypyrimidine-5-carboxamide (Compound 295)

Step 139a: Ethyl 2-(((2-(5-acetyl-2-fluorophenyl)-4-morpholinothieno[3,2-d]pyrimidin-6-yl)methyl)(methyl)amino)pyrimidine-5-carboxylate (Compound 0603-295)

The title compound 0603-295 was prepared as a light yellow solid (500 mg, 79%) from 1-(3-bromo-4-fluorophenyl)ethanone (500 mg, 2.3 mmol), 4,4,4',4',5,5,5',5'-octamethyl-2,2'-bi(1,3,2-dioxaborolane (1.17 g, 4.6 mmol), KOAc (1.35 g, 6.9 mmol), Pd(dppf)Cl$_2$ (84 mg, 0.115 mmol) in 1,4-dioxane (10 mL) followed by 0504 (516 mg, 1.15 mmol), NaHCO$_3$ (290 mg, 3.45 mmol), bis(triphenylphosphine)palladium(II)chloride (40 mg, 0.06 mmol) in ethanol (5 mL), water (10 mL), toluene (2.5 mL) using a procedure similar to that described for compound 0603-275 (Example 124).

Step 139b: 2-(((2-(2-Fluoro-5-(1-hydroxyethyl)phenyl)-4-morpholinothieno[3,2-d]pyrimidin-6-yl)methyl)(methyl)amino)-N-hydroxypyrimidine-5-carboxamide (Compound 295)

A mixture of 0603-295 (180 mg, 0.33 mmol), NaBH$_4$ (110 mg, 1.3 mmol), and THF (10 mL) was stirred at room temperature for 2 h. To the reaction was added water and extracted with dichloromethane. The combined organic layers were washed with brine and dried with MgSO$_4$. The crude product was obtained as an off-white solid (180 mg) after concentration and was used for the next step reaction without further purification. The hydroxyethyl intermediate (160 mg, 0.29 mmol) was taken into NH$_2$OH methanol solution (20 mL, 1.79M in methanol) and stirred for 1 h. The reaction mixture was adjusted pH to 6 with acetic acid followed by concentration. The residue was triturated with water and filtered. The crude product was purified by prep-HPLC to afford the titled compound 295 as a white solid (45 mg, 29%). m.p.:230-235° C. LCMS: 540.0 [M+1]$^+$. $^1$HNMR (400 MHz, DMSO-d$_6$): δ 1.34 (d, J=6.4 Hz, 3H), 3.23 (s, 3H), 3.72-3.75 (m, 4H), 3.87-3.90 (m, 4H), 4.78 (q, J=6.4 Hz, 1H), 5.21 (s, 2H), 7.21 (dd, J=10.8 Hz, 8.4 Hz, 1H), 7.43 (d, J=1.2 Hz, 1H), 7.48 (s, 1H), 7.96 (dd, J=7.6 Hz, 2.4 Hz, 1H), 8.74 (s, 2H), 9.15 (br, 1H), 11.13 (s, 1H).

Example 140: (S)—N-Hydroxy-2-(((2-(3-(1-hydroxyethyl)phenyl)-4-morpholinothieno[3,2-d]pyrimidin-6-yl)methyl)(methyl)amino)pyrimidine-5-carboxamide (Compound 296)

Step 140a: (S)-Ethyl 2-(((2-(3-(1-hydroxyethyl)phenyl)-4-morpholinothieno[3,2-d]pyrimidin-6-yl)methyl)(methyl)amino)pyrimidine-5-carboxylate (Compound 0603-296)

The title compound 0603-296 was prepared as an off-white solid (400 mg, 82%) from (S)-1-(3-bromophenyl)ethanol (500 mg, 2.49 mmol), 4,4,4',4',5,5,5',5'-octamethyl-2,2'-bi(1,3,2-dioxaborolane) (1.26 g, 4.98 mmol), KOAc (6.1 g, 6.22 mmol), PdCl$_2$(dppf) (50 mg) in DMSO (10 mL) followed by 0504 (400 mg, 0.89 mmol), NaHCO$_3$ (150 mg, 1.78 mmol), PdCl$_2$(Ph$_3$P)$_2$ (40 mg) in toluene/ethanol/water (12 mL/6 mL/3 mL) using a procedure similar to that described for compound 0603-275 (Example 124). LCMS: 535.0 [M+1]$^+$. $^1$H-NMR, (400 MHz, DMSO-d$_6$): δ (ppm) 1.31 (t, J=6.8 Hz, 3H), 1.37 (d, J=6.4 Hz, 3H), 3.28 (s, 3H), 3.76-3.78 (m, 4H), 3.92-3.95 (m, 4H), 4.28 (q, J=6.8 Hz, 2H), 4.78-4.84 (m, 1H), 5.17 (d, J=4.4 Hz, 1H), 5.24 (s, 2H), 5.24 (1H, s), 7.39-7.44 (m, 2H), 7.45 (s, 1H), 8.22-8.26 (m, 1H), 8.39 (s, 1H), 8.90 (s, 2H).

Step 140b: (S)—N-Hydroxy-2-(((2-(3-(1-hydroxyethyl)phenyl)-4-morpholinothieno[3,2-d]pyrimidin-6-yl)methyl)(methyl)amino)pyrimidine-5-carboxamide (Compound 296)

The title compound 296 was prepared as a white solid (110 mg, 57%) from 0603-296 (200 mg, 0.37 mmol) and a freshly prepared hydroxylamine methanol solution (10 mL, 1.79 M in methanol) in dichloromethane (4 mL) using a procedure similar to that described for compound 237 (Example 107). m.p.:168-172° C. LCMS: 522.0 [M+1]$^+$. $^1$H-NMR, (400 MHz, DMSO-d$_6$): δ (ppm) 1.37 (d, J=6.4 Hz, 3H), 3.22 (s, 3H), 3.77 (m, 4H), 3.93 (m, 4H), 4.81 (br, 1H), 5.20 (s, 2H), 5.24 (1H, s), 7.41-7.48 (m, 3H), 8.25 (d, J=6.4 Hz, 1H), 8.39 (s, 1H), 8.75 (s, 2H).

Example 141: (R)—N-Hydroxy-2-(((2-(3-(1-hydroxyethyl)phenyl)-4-morpholinothieno[3,2-d]pyrimidin-6-yl)methyl)(methyl)amino)pyrimidine-5-carboxamide (Compound 297)

Step 141a: (R)-Ethyl 2-(((2-(3-(1-hydroxyethyl)phenyl)-4-morpholinothieno[3,2-d]pyrimidin-6-yl)methyl)(methyl)amino)pyrimidine-5-carboxylate (Compound 0603-297)

The title compound 0603-297 was prepared as an off-white solid (350 mg, 74%) from (R)-1-(3-bromophenyl)ethanol (500 mg, 2.49 mmol), 4,4,4',4',5,5,5',5'-octamethyl-2,2'-bi(1,3,2-dioxaborolane) (1.26 g, 4.98 mmol), KOAc (6.10 g, 6.22 mmol), PdCl$_2$(dppf) (50 mg) in DMSO (10 mL) followed by 0504 (400 mg, 0.89 mmol), NaHCO$_3$ (150 mg, 1.78 mmol), PdCl$_2$(Ph$_3$P)$_2$ (40 mg) in toluene/ethanol/water (12 mL/6 mL/3 mL) using a procedure similar to that described for compound 0603-275 (Example 124). LCMS: 535.0 [M+1]$^+$. $^1$H-NMR (400 MHz, DMSO-d$_6$): δ 1.30 (t, J=7.2 Hz, 3H), 1.37 (d, J=6.4 Hz, 3H), 3.28 (s, 3H), 3.75-3.78 (m, 4H), 3.92-3.95 (m, 4H), 4.28 (q, J=7.2 Hz, 2H), 4.78-4.84 (m, 1H), 5.17 (d, J=4.4 Hz, 1H), 5.24 (s, 2H), 5.24 (1H, s), 7.39-7.44 (m, 2H), 7.45 (s, 1H), 8.22-8.26 (m, 1H), 8.39 (s, 1H), 8.90 (s, 2H).

Step 141b: (R)—N-Hydroxy-2-(((2-(3-(1-hydroxyethyl)phenyl)-4-morpholinothieno[3,2-d]pyrimidin-6-yl)methyl)(methyl)amino)pyrimidine-5-carboxamide (Compound 297)

The title compound 297 was prepared as a white solid (130 mg, 67%) from 0603-297 (200 mg, 0.37 mmol) and a freshly prepared hydroxylamine methanol solution (10 mL, 1.79 M in methanol) in dichloromethane (4 mL) using a procedure similar to that described for compound 237 (Example 107). m.p.:169-173° C. LCMS: 522.0 [M+1]$^+$. $^1$H-NMR (400 MHz, DMSO-d$_6$): δ 1.37 (d, J=6.4 Hz, 3H), 3.25 (s, 3H), 3.77 (m, 4H), 3.93 (m, 4H), 4.80-4.84 (m, 1H), 5.21 (s, 2H), 5.22 (1H, s), 7.40-7.48 (m, 3H), 8.25 (d, J=6.8 Hz, 1H), 8.39 (s, 1H), 8.75 (s, 2H), 9.05 (br, 1H), 11.14 (br, 1H).

Example 142: 2-(4-Aminophenyl)-N-((1-(5-(hydroxycarbamoyl)pyrimidin-2-yl) piperidin-4-yl)methyl)-4-morpholinothieno[3,2-d]pyrimidine-6-carboxamide (Compound 307)

Step 142a: 2-Chloro-4-morpholinothieno[3,2-d]pyrimidine-6-carboxylic acid (Compound 1401)

0112 (5 g, 17.67 mmol) was suspended in dichloromethane (100 mL) followed the addition of mCPBA (75%, 4 g, 22.97 mmol). The resulting mixture was heated to reflux for 24 h. Upon completion, the mixture was cooled to room temperature and concentrated to 2 volume. The mixture was filtered to afford a crude yellow solid which was re-crystallized from Hexanes/Ethyl acetate=1/1 to give the titled compound as a light yellow solid (3.2 g, 61%). $^1$HNMR (400 MHz, DMSO-d$_6$): δ 3.74-3.3.78 (m, 4H), 3.92-3.95 (m, 4H), 7.86 (s, 1H).

Step 142b: Ethyl 2-(4-((2-chloro-4-morpholinothieno[3,2-d]pyrimidine-6-carboxamido)methyl)piperidin-1-yl)pyrimidine-5-carboxylate (Compound 1402)

To a suspension of 1401 (400 mg, 1.34 mmol), 0401 (384 mg, 1.47 mmol) and TBTU (644 mg, 2.07 mmol) in dichloromethane (80 mL) was added DIPEA (518 mg, 4.02 mmol) at 0° C. The resulting mixture was stirred at room temperature for 1 h. The reaction mixture was diluted with dichloromethane and washed with water. The crude product was triturated with water and filtered to afford titled compound as a white solid (473 mg, 65%). $^1$HNMR (400 MHz, DMSO-$d_6$): δ 1.15-1.43 (m, 7H), 1.78-1.82 (m, 2H), 1.82-1.84 (m, 1H), 2.98-3.15 (m, 2H), 3.77 (br, 4H); 3.93 (br, 4H), 4.25-4.28 (m, 2H), 4.75-4.78 (m, 2H), 8.02 (s, 1H), 8.78 (s, 2H), 9.02-9.06 (m, 1H).

Step 142c: Ethyl 2-(4-((2-(4-aminophenyl)-4-morpholinothieno[3,2-d]pyrimidine-6-carboxamido)methyl)piperidin-1-yl)pyrimidine-5-carboxylate. (Compound 1403-307)

1402 (300 mg, 0.55 mmol), 4-(4,4,5,5-tetramethyl-1,3,2-dioxaborolan-2-yl) aniline (180 mg, 0.82 mmol) and Pd(PPh$_3$)$_2$Cl$_2$ (12 mg) were taken into toluene (6 mL), ethanol (3.6 mL) and water (1.2 mL) and stirred at 120° C. for 2 h under N$_2$ atmosphere. Upon completion the reaction was cooled with ice-water bath, followed by the addition of water (50 mL). After stirring for 1 h, the solid was collected by filtration and purified by column chromatography to afford titled compound as a white solid (200 mg, 60%). $^1$HNMR (400 MHz, DMSO-$d_6$): δ 1.10-1.40 (m, 7H), 1.80-2.00 (m, 3H), 2.98-3.10 (m, 2H), 3.21-3.25 (m, 2H), 3.80 (br, 4H); 3.99 (br, 4H), 4.26 (t, J=6.8 Hz, 2H), 4.75-4.79 (m, 2H), 5.55 (s, 2H), 6.62 (d, J=8.4 Hz, 2H), 8.06 (s, 1H), 8.10 (d, J=8.8 Hz, 2H), 8.77 (s, 2H), 8.95 (br, 1H).

Step 142d: 2-(4-Aminophenyl)-N-((1-(5-(hydroxycarbamoyl)pyrimidin-2-yl)piperidin-4-yl) methyl)-4-morpholinothieno[3,2-d]pyrimidine-6-carboxamide (Compound 307)

1403-307 (190 mg, 0.32 mmol) was taken into freshly prepared NH$_2$OH methanol solution (20 mL, 1.79 M in methanol) and dichloromethane (3 mL). The resulting mixture was sealed and stirred at room temperature for 4 h. Upon completion, the reaction solution was adjusted to pH 7-8 with HCl aqueous solution (1.2 M). Water was added followed by filtration to afford product as a yellow solid (130 mg, 70%). m.p:232-238° C. LCMS:590.0[M+1]$^+$. $^1$HNMR (400 MHz, DMSO-$d_6$): δ1.09 (m, 2H), 1.79 (d, J=11.6 Hz, 2H), 1.93 (m, 1H), 2.93-2.99 (m, 2H), 3.21-3.31 (m, 2H), 3.80 (br, 4H), 3.96 (br, 4H), 4.72 (d, J=13.2 Hz, 2H), 5.55 (s, 2H), 6.62 (d, J=8.4 Hz, 2H), 8.07-8.12 (m, 3H), 8.66 (s, 2H), 8.95 (d, J=10.0 Hz, 2H), 11.03 (s, 1H).

Example 143: N-((1-(5-(Hydroxycarbamoyl)pyrimidin-2-yl)piperidin-4-yl) methyl)-2-(6-(methylamino)pyridin-3-yl)-4-morpholinothieno[3,2-d]pyrimidine-6-carboxamide (Compound 308)

Step 143a: Ethyl 2-(4-((2-(6-(methylamino)pyridin-3-yl)-4-morpholinothieno[3,2-d]pyrimidine-6-carboxamido)methyl)piperidin-1-yl)pyrimidine-5-carboxylate (Compound 1403-308)

The title compound 0403-308 was prepared as a yellow solid (110 mg, 41%) from 1402 (240 mg, 0.44 mmol), N-methyl-5-(4,4,5,5-tetramethyl-1,3,2-dioxaborolan-2-yl)pyridin-2-amine (154 mg, 0.66 mmol), NaHCO$_3$ (111 mg, 1.3 mmol) and Pd(PPh$_3$)$_2$Cl$_2$ (9.6 mg) in toluene (8 mL), ethanol (4.8 mL) and water (1.6 mL) using a procedure similar to that described for compound 1403-307 (Example 142). $^1$HNMR (400 MHz, DMSO-$d_6$): δ 1.16-1.20 (m, 2H), 1.29 (t, J=7.2 Hz, 3H), 1.78-1.82 (m, 2H), 1.95-2.00 (m, 1H), 2.84 (d, J=4.4 Hz, 3H), 3.01 (t, J=11.6 Hz, 2H), 3.21-3.24 (m, 2H), 3.79 (t, J=5.2 Hz, 4H), 3.98 (t, J=4.8 Hz, 4H), 4.26 (q, J=6.8 Hz, 2H), 4.76 (d, J=12.6 Hz, 2H), 6.52 (d, J=8.8 Hz, 2H), 6.91 (d, J=4.8 Hz, 1H), 8.11 (s, 1H), 8.27 (dd, J=8.8 Hz, 2 Hz, 1H), 8.76 (s, 2H), 8.91 (t, J=4.2 Hz, 1H), 9.04 (s, 1H).

Step 143b: N-((1-(5-(Hydroxycarbamoyl)pyrimidin-2-yl)piperidin-4-yl)methyl)-2-(6-(methylamino)pyridin-3-yl)-4-morpholinothieno[3,2-d]pyrimidine-6-carboxamide (Compound 308)

The title compound 308 was prepared as a white solid (55 mg, 51%) from 1403-308 (110 mg, 0.18 mmol) and a freshly prepared hydroxylamine methanol solution (20 mL, 1.79 M in methanol) in dichloromethane (3 mL) using a procedure similar to that described for compound 307 (Example 142). m.p:215-218° C. LCMS:605.0[M+1]$^+$. $^1$HNMR (400 MHz, DMSO-$d_6$): δ 1.16-1.23 (m, 2H), 1.78-1.82 (m, 2H), 1.90-1.94 (m, 1H), 2.84 (d, J=4.8 Hz, 3H), 2.93 (t, J=4.8 Hz, 2H), 3.21-3.24 (m, 2H), 3.80 (t, J=5.2 Hz, 4H), 3.98 (t, J=4.8 Hz, 4H), 4.72 (d, J=13.2 Hz, 2H), 6.51 (d, J=8.8 Hz, 2H), 6.96 (d, J=4.8 Hz, 1H), 8.11 (s, 1H), 8.27 (dd, J=8.8 Hz, 2 Hz, 1H), 8.66 (s, 2H), 8.96 (d, J=13.2 Hz, 2H), 9.04 (s, 1H), 11.05 (s, 1H).

Example 144: N-Hydroxy-2-(4-((2-(6-(methylamino)pyridin-3-yl)-4-morpholinothieno[3,2-d]pyrimidine-6-sulfonamido)methyl)piperidin-1-yl)pyrimidine-5-carboxamide (Compound 310)

Step 144a: Ethyl 2-(4-((2-(6-(methylamino)pyridin-3-yl)-4-morpholinothieno[3,2-d]pyrimidine-6-sulfonamido)methyl)piperidin-1-yl)pyrimidine-5-carboxylate (Compound 1405-310)

The title compound 0405-310 was prepared as a yellow solid (350 mg, 78%) from 1404 (400 mg, 0.704 mmol), N-methyl-5-(4,4,5,5-tetramethyl-1,3,2-dioxaborolan-2-yl)pyridin-2-amine (247 mg, 1.06 mmol), NaHCO$_3$ (177 mg, 2.11 mmol) and (PPh$_3$)$_4$Pd (40 mg, 0.035 mmol) were taken into toluene (8 mL), ethanol (16 mL) and water (4 mL) using a procedure similar to that described for compound 1403-307 (Example 142). LCMS: 654.0 [M+1]$^+$. $^1$H NMR (400 MHz, DMSO-$d_6$): δ 1.07-1.13 (m, 2H), 1.28 (t, J=7.2 Hz, 3H), 1.76-1.79 (m, 3H), 2.78-3.00 (m, 7H), 3.80 (t, J=4.4 Hz, 4H), 3.97 (t, J=4.4 Hz, 4H), 4.25 (q, J=6.8 Hz, 2H), 4.72 (d, J=12.4 Hz, 2H), 6.52 (d, J=8.8 Hz, 1H), 6.97 (d, J=4.4 Hz, 1H), 7.60 (d, J=6.4 Hz, 1H), 7.82 (s, 1H), 8.29 (d, J=4.4 Hz, 1H), 8.34 (s, 1H), 8.75 (s, 2H), 9.04 (s, 1H).

Step 144b: N-Hydroxy-2-(4-((2-(6-(methylamino)pyridin-3-yl)-4-morpholinothieno[3,2-d]pyrimidine-6-sulfonamido)methyl)piperidin-1-yl)pyrimidine-5-carboxamide (Compound 310)

The title compound 310 was prepared as a white solid (183 mg, 94%) from 1405-310 (200 mg, 0.306 mmol) and a freshly prepared hydroxylamine methanol solution (25 mL, 1.79 M in methanol) in dichloromethane (3 mL) using a procedure similar to that described for compound 307 (Example 142). M.p.:190-197° C. LCMS: 641.0 [M+1]⁺.

¹H NMR (400 MHz, DMSO-d₆): δ 1.021.11 (m, 2H), 1.74-1.77 (m, 3H), 2.832.94 (m, 7H), 3.79 (t, J=4.4 Hz, 4H), 3.97 (t, J=4.4 Hz, 4H), 4.67 (d, J=12.8 Hz, 2H), 6.52 (d, J=8.8 Hz, 1H), 6.99 (d, J=4.8 Hz, 1H), 7.82 (s, 1H), 8.28 (dd, J=8.8 Hz, 2 Hz, 1H), 8.63 (s, 2H), 9.03 (d, J=2.4 Hz, 1H).

Example 145: N-Hydroxy-2-(methyl((7-morpholino-5-(2-(trifluoromethyl)-1H-benzo[d]imidazol-5-yl)benzo[b]thiophen-2-yl)methyl)amino)pyrimidine-5-carboxamide (Compound 318)

Step 145a: 5-Bromo-2-(trifluoromethyl)-1H-benzo[d]imidazole (Compound 0601-318)

A mixture of 4-bromobenzene-1,2-diamine (3.0 g, 16.0 mmol), TFA (9.5 mL, 128.3 mmol) and aq. HCl (3 M, 32 mL) was heated to reflux overnight. The reaction mixture was concentrated and purified by column chromatography to afford the titled compound (2.60 g, 60%). LCMS: 265.0[M+1]⁺. ¹HNMR (400 MHz, DMSO-d₆): δ 7.52 (dd, J=8.8 Hz, 1.2 Hz, 1H), 7.69 (d, J=8.4 Hz, 1H), 7.95 (s, 1H), 14.20 (br, 1H).

Step 145b: Ethyl 2-(methyl((7-morpholino-5-(2-(trifluoromethyl)-1H-benzo[d]imidazol-5-yl)benzo[b]thiophen-2-yl)methyl)amino)pyrimidine-5-carboxylate (Compound 0603-318)

A mixture of 0601-318 (100 mg, 0.38 mmol), 4,4,4',4',5,5,5',5'-octamethyl-2,2'-bi(1,3,2-dioxaborolane)(107 mg, 0.42 mmol), PdCl₂(dppf) (10 mg), KOAc (74 mg, 0.76 mmol) in anhydrous 1,4-dioxane (2 mL) was stirred at 100° C. overnight. The reaction mixture was filtered and concentrated. The crude product was obtained as a brown solid (150 mg) which was used for next step without further purification.

A mixture of above crude boronate, 0504 (119 mg, 0.27 mmol), PdCl₂(Ph₃P)₂ (10 mg), NaHCO₃ (68 mg, 0.81 mmol) were taken into toluene/ethanol/water (4 mL/2 mL/1 mL) and stirred at 130° C. for 3 h. The reaction mixture was filtered and concentrated. The residue was purified by column chromatography to afford titled compound as an off-white solid (129 mg, 80%). ¹HNMR, (400 MHz, DMSO-d₆): δ 1.30 (t, J=6.8 Hz, 3H), 3.28 (s, 3H), 3.77-3.81 (m, 4H), 3.95-3.97 (m, 4H), 4.28 (q, J=6.4 Hz, 2H), 5.24 (s, 2H), 7.50 (s, 1H), 7.75 (br, 1H), 8.48 (br, 1H), 8.48 (d, J=7.6 Hz, 1H), 8.73 (s, 1H), 8.87 (s, 2H).

Step 145c: N-Hydroxy-2-(methyl((7-morpholino-5-(2-(trifluoromethyl)-1H-benzo[d]imidazol-5-yl)benzo[b]thiophen-2-yl)methyl)amino)pyrimidine-5-carboxamide (Compound 318)

The title compound 318 was prepared as an off-white solid (15 mg, 15%) from 0603-318 (100 mg, 0.167 mmol) and a freshly prepared hydroxylamine methanol solution (2 mL, 1.79 M in methanol) using a procedure similar to that described for compound 307 (Example 142). m.p.>300° C. LCMS: 586 [M+1]⁺. ¹HNMR (400 MHz, DMSO-d₆): δ 3.25 (s, 3H), 3.77-3.80 (m, 4H), 3.95-3.97 (m, 4H), 5.22 (s, 2H), 7.50 (s, 1H), 7.70 (d, J=8.4 Hz, 0.5H), 7.88 (d, J=8.4 Hz, 0.5H), 8.44 (d, J=8.4 Hz, 0.5H), 8.52 (d, J=8.4 Hz, 0.5H), 8.65 (s, 0.5H), 8.81 (s, 0.5H), 8.76 (s, 2H), 9.02 (s, 1H), 11.09 (s, 1H), 14.03 (s, 1H).

Example 146: N-Hydroxy-5-(4-(6-((4-(methylsulfonyl)piperazin-1-yl)methyl)-4-morpholinothieno[3,2-d]pyrimidin-2-yl)phenoxy)pentanamide (Compound 319)

Step 146a: 5-(4-Bromo-phenoxy)-pentanoic acid ethyl ester (Compound 1502-319)

A mixture of 4-Bromo-phenol (12 g, 68.0 mmol), Cs₂CO₃ (44.0 g, 0.136 mmol), 5-bromo-pentanoic acid ethyl ester (16.9 g, 82.0 mmol) in DMF was heated to 80° C. for 4 h. The reaction mixture was diluted with water and extracted ethyl acetate. The combined organic layers were washed with water, brine and dried with Na₂SO₄. The crude product was purified by column chromatography to afford the titled compound 1502-319 as an oil (16.0 g). ¹HNMR (400 MHz, CDCl₃): δ 1.25 (t, J=7.2 Hz, 3H); 1.81 (m, 4H); 2.35-2.39 (m, 2H), 3.93 (t, J=6.0 Hz, 2H), 4.13 (q, J=7.2 Hz, 2H), 6.76 (d, J=8.8 Hz, 2H), 7.35 (d, J=8.8 Hz, 2H).

Step 146b: Ethyl 5-(4-(4,4,5,5-tetramethyl-1,3,2-dioxaborolan-2-yl)phenoxy) pentanoate (Compound 1503-319)

A mixture of 1502-319 (5.0 g, 0.0167 mmol), bis(pinacolato)diboron (6.4 g, 0.025 mol), PdCl₂(dppf)₂ (610 mg, 0.835 mmol), KOAc (5 g, 0.05 mol) in anhydrous dioxane was heated to reflux overnight. The reaction mixture was diluted with EtOAc/hexanes and stirred for 30 min. It was filtered to remove solid and concentrated to afford the titled compound 1503-319 as a brown solid (3.5 g, 60%). ¹HNMR: (400 MHz, CDCl₃): δ 1.28 (t, J=7.2 Hz, 3H), 1.33 (s, 12H), 1.82 (br, 4H), 2.37 (m, 2H), 3.99 (m, 2H), 4.13 (q, J=7.2 Hz, 2H), 6.87 (d, J=8.8 Hz, 2H), 7.73 (d, J=8.4 Hz, 2H).

Step 146c: Ethyl 5-(4-(6-((4-(methylsulfonyl)piperazin-1-yl)methyl)-4-morpholino thieno[3,2-d]pyrimidin-2-yl)phenoxy)pentanoate (Compound 1504-319)

A mixture of 1503-319 (350 mg, 1 mmol), 0113 (300 mg, 0.486 mmol), NaHCO₃ (126 mg, 1.5 mmol) and bis(triphenylphosphine)palladium(II) chloride (40 mg, 0.057 mmol) in toluene (12 ml), ethanol (8.0 ml) and water (3.0 ml) was heated at 108° C. for 4 h under N₂ atmosphere. The reaction mixture was partitioned between water and EtOAc and separated. The crude product was purified by column chromatography to afford the title compound as a light yellow solid (180 mg, 60%). m.p.: 110-114° C. LCMS: 618.4 [M+1]⁺. ¹H NMR: (400 MHz, CDCl₃): δ1.26 (t, J=7.2 Hz, 3H), 1.85 (m, 4H), 2.39 (t, J=6.8 Hz, 2H), 2.67 (t, J=4.8 Hz, 4H), 2.80 (s, 3H), 3.29 (t, J=4.8 Hz, 4H), 3.86-3.90 (m, 6H), 4.03-4.05 (m, 6H), 4.14 (q, J=6.8 Hz, 2H), 6.95 (d, J=8.8 Hz, 2H), 7.31 (s, 1H), 8.37 (d, J=8.8 Hz, 2H).

Step 146d: N-Hydroxy-5-(4-(6-((4-(methylsulfonyl)piperazin-1-yl)methyl)-4-morpholinothieno[3,2-d]pyrimidin-2-yl)phenoxy)pentanamide (Compound 319)

The title compound 319 was prepared as a white solid (100 mg, 66%) from 1504-319 (150 mg, 0.243 mmol) and a freshly prepared hydroxylamine methanol solution (30 mL, 1.79 M in methanol) using a procedure similar to that described for compound 307 (Example 142). m.p. 140-144° C. LC-MS: 605.2[M+1]⁺. ¹H NMR: (400 MHz, DMSO-d₆):

δ 1.66-1.72 (br, 4H), 2.01-2.04 (m, 2H), 2.59 (m, 4H), 2.90 (s, 3H), 3.16 (d, J=3.6 Hz, 4H); 3.80 (t, J=4.0 Hz, 4H), 3.95-4.05 (m, 8H), 7.01 (d, J=8.8 Hz, 2H), 7.38 (s, 1H), 8.33 (d, J=8.8 Hz, 2H), 10.39 (br, 1H).

Example 147: N-Hydroxy-6-(4-(6-((4-(methylsulfonyl)piperazin-1-yl)methyl)-4-morpholino thieno[3,2-d]pyrimidin-2-yl)phenoxy)hexanamide (Compound 320)

Step 147a: Ethyl 6-(4-bromophenoxy)hexanoate (Compound 1502-320)

The title compound 1502-320 was prepared as an oil (4.0 g, 74%) from 4-Bromo-phenol (3.0 g, 17.34 mmol), $Cs_2CO_3$ (11.3 g, 34.68 mmol), ethyl 6-bromohexanoate (16.9 g, 82 mmol) in DMF using a procedure similar to that described for compound 1502-319 (Example 146). $^1$HNMR (400 MHz, $CDCl_3$): δ 1.25 (t, J=7.2 Hz, 3H), 1.54 (q, J=8.4 Hz, 2H), 1.66-1.73 (m, 2H); 1.74-1.82 (m, 2H), 2.32 (t, J=7.6 Hz, 2H), 3.91 (t, J=6.4 Hz, 2H), 4.13 (q, J=7.2 Hz, 2H), 6.75 (d, J=9.2 Hz, 2H), 7.35 (d, J=8.8 Hz, 2H).

Step 147b: Ethyl 6-(4-(4,4,5,5-tetramethyl-1,3,2-dioxaborolan-2-yl)phenoxy) hexanoate (Compound 1503-320)

The title compound 1503-320 was prepared as a brown oil (1.5 g, 67%) from 1502-320 (2.0 g, 6.35 mmol), bis(pinacolato)diboron (2.42 g, 9.5 mmol), $PdCl_2(dppf)_2$ (300 mg, 0.41 mmol), KOAc (1.86 g, 19.0 mmol) in anhydrous dioxane using a procedure similar to that described for compound 1503-319 (Example 146). $^1$HNMR (400 MHz, $CDCl_3$): δ 1.25 (t, J=7.2 Hz, 3H), 1.33 (s, 12H), 1.46-1.54 (m, 2H), 1.63-1.73 (m, 2H), 1.77-1.84 (m, 2H), 2.32 (t, J=7.2 Hz, 2H), 3.98 (t, J=6.4 Hz, 2H); 4.13 (q, J=7.2 Hz, 2H), 6.87 (d, J=8.8 Hz, 2H), 7.73 (d, J=8.8 Hz, 2H).

Step 147c: Ethyl 6-(4-(6-((4-(methylsulfonyl)piperazin-1-yl)methyl)-4-morpholino thieno[3,2-d]pyrimidin-2-yl)phenoxy)hexanoate (Compound 1504-320)

The title compound 1504-320 was prepared as an off-white solid (185 mg, 50%) from 1503-320 (420 mg, 1.16 mmol), 0113 (250 mg, 0.58 mmol), $NaHCO_3$ (150 mg, 1.74 mmol) and bis(triphenylphosphine)palladium(II) chloride (50 mg, 0.071 mmol) in toluene (10 mL), ethanol (8 mL) and water (3 mL) using a procedure similar to that described for compound 1504-319 (Example 146). m.p.: 125-129° C. LCMS: 632.4 [M+1]$^+$. $^1$HNMR: (400 MHz, $CDCl_3$): δ 1.26 (t, J=7.2 Hz, 3H), 1.50-1.57 (br, 2H), 1.68-1.74 (m, 2H), 1.80-1.87 (m, 2H), 2.34 (t, J=7.2 Hz, 2H), 2.67 (m, 4H), 2.80 (s, 3H), 3.29 (m, 4H), 3.82-3.90 (m, 6H), 4.01-4.04 (m, 6H), 4.14 (q, J=7.2 Hz, 2H), 6.95 (d, J=8.8 Hz, 2H), 7.31 (s, 1H), 8.37 (d, J=8.8 Hz, 2H).

Step 147d: N-Hydroxy-6-(4-(6-((4-(methylsulfonyl)piperazin-1-yl)methyl)-4-morpholino thieno[3,2-d]pyrimidin-2-yl)phenoxy)hexanamide (Compound 320)

The title compound 320 was prepared as a white solid (70 mg, 36%) from 1504-320 (200 mg, 0.316 mmol) and a freshly prepared hydroxylamine methanol solution (30 mL, 1.79 M in methanol) using a procedure similar to that described for compound 307 (Example 142). m.p. 140-142° C. LCMS: 619.2[M+1]$^+$. $^1$HNMR: (400 MHz, DMSO-$d_6$): δ 1.42-1.44 (m, 2H), 1.54-1.58 (m, 2H), 1.72-1.754 (m, 2H), 1.98 (t, J=7.2 Hz, 2H), 2.59 (br, 4H), 2.90 (s, 3H), 3.15 (br, 4H), 3.79 (t, J=4.0 Hz, 4H), 3.81-4.04 (m, 8H), 7.01 (d, J=8.8 Hz, 2H), 7.37 (s, 1H), 8.32 (d, J=8.8 Hz, 2H), 8.67 (s, 1H), 10.35 (s, 1H).

Example 148: N-Hydroxy-7-(4-(6-((4-(methylsulfonyl)piperazin-1-yl)methyl)-4-morpholinothieno[3,2-d]pyrimidin-2-yl)phenoxy)heptanamide (Compound 321)

Step 148a: Ethyl 7-(4-bromophenoxy)heptanoate (Compound 1502-321)

The title compound 1502-321 was prepared as an oil (1.6 g, 80%) from 4-Bromo-phenol (1.1 g, 6.5 mmol), $Cs_2CO_3$ (4.0 g, 13 mmol), ethyl 7-bromoheptanoate (1.7 g, 7.2 mmol) in DMF using a procedure similar to that described for compound 1502-319 (Example 146). $^1$HNMR: (400 MHz, $CDCl_3$): δ 1.25 (t, J=7.2 Hz, 3H), 1.35-1.51 (m, 4H), 1.617-1.69 (m, 2H), 1.75-1.78 (m, 2H), 2.30 (t, J=7.2 Hz, 2H), 3.90 (t, J=6.4 Hz, 2H), 4.12 (q, J=7.2 Hz, 2H), 6.76 (d, J=8.8 Hz, 2H), 7.35 (d, J=8.8 Hz, 2H).

Step 148b: Ethyl 7-(4-(4,4,5,5-tetramethyl-1,3,2-dioxaborolan-2-yl)phenoxy) heptanoate (Compound 1503-321)

The title compound 1503-321 was prepared as an oil (1.7 g, 60%) from 1502-321 (1.9 g, 5.8 mmol), bis(pinacolato)diboron (2.2 g, 8.7 mmol), $PdCl_2(dppf)_2$ (212 mg, 0.29 mmol), KOAc (1.8 g, 17.4 mmol) in anhydrous dioxane using a procedure similar to that described for compound 1503-319 (Example 146). $^1$HNMR: (400 MHz, $CDCl_3$): δ 1.25 (t, J=7.2 Hz, 3H), 1.33 (s, 12H), 1.37-1.43 (m, 2H), 1.46-1.50 (m, 2H), 1.62-1.70 (m, 2H); 1.75-1.80 (m, 2H), 2.30 (d, J=7.6 Hz, 2H), 3.97 (t, J=6.8 Hz, 2H), 4.12 (q, J=7.2 Hz, 2H), 6.87 (d, J=8.8 Hz, 2H), 7.73 (d, J=8.8 Hz, 2H).

Step 148c: N-Hydroxy-7-(4-(6-((4-(methylsulfonyl)piperazin-1-yl)methyl)-4-morpholinothieno[3,2-d]pyrimidin-2-yl)phenoxy)heptanamide (Compound 1504-321)

The title compound 1504-321 was prepared as a pale yellow solid (260 mg, 50%) from 1503-321 (600 mg, 1.60 mmol), 0113 (350 mg, 0.81 mmol), $NaHCO_3$ (200 mg, 2.4 mmol) and bis(triphenylphosphine)palladium(II) chloride (60 mg, 0.085 mmol) in toluene (12 mL), ethanol (9 mL) and water (4 mL) using a procedure similar to that described for compound 1504-319 (Example 146). m.p.: 154-157° C. LCMS: 646.4 [M+1]$^+$. $^1$HNMR: (400 MHz, $CDCl_3$): δ 1.25 (t, J=7.2 Hz, 3H), 1.47-1.54 (m, 2H), 1.54-1.60 (m, 2H), 1.66-1.68 (m, 2H), 1.78-1.85 (m, 2H), 2.31 (d, J=7.6 Hz, 2H), 2.67 (m, 4H), 2.79 (s, 3H), 3.29 (m, 4H), 3.85-3.89 (m, 6H), 4.00-4.03 (m, 6H), 4.13 (q, J=7.2 Hz, 2H), 6.96 (d, J=8.8 Hz, 2H), 7.31 (s, 1H), 8.37 (d, J=8.8 Hz, 2H).

Step 148d: N-Hydroxy-7-(4-(6-((4-(methylsulfonyl)piperazin-1-yl)methyl)-4-morpholinothieno[3,2-d]pyrimidin-2-yl)phenoxy)heptanamide (Compound 321)

The title compound 321 was prepared as a white solid (130 mg, 54.5%) from 1504-321 (220 mg, 0.34 mmol) and a freshly prepared hydroxylamine methanol solution (30 mL, 1.79 M in methanol) using a procedure similar to that described for compound 307 (Example 142). m.p. 143-145° C. LC-MS: 633.2[M+1]+. ¹HNMR: (400 MHz, DMSO-d$_6$): δ 1.30-1.56 (m, 6H), 1.73 (t, J=6.4 Hz, 2H), 1.96 (t, J=7.6 Hz, 2H), 2.59 (br, 4H), 2.89 (s, 3H), 3.15 (br, 4H), 3.80 (m, 4H), 3.80-4.04 (m, 8H), 7.01 (d, J=8.8 Hz, 2H), 7.38 (s, 1H), 8.32 (d, J=8.8 Hz, 2H), 8.66 (s, 1H), 10.33 (s, 1H).

Example 149: N-Hydroxy-2-(((2-(6-methoxypyridin-3-yl)-4-morpholinothieno[3,2-d]pyrimidin-6-yl)methyl)(methyl)amino)pyrimidine-5-carboxamide (Compound 236)

Step 149a: 5-Bromo-2-methoxypyridine (Compound 0601-236)

A solution of 2-methoxy-pyridine (100 g, 0.92 mole), NBS (180 g, 1.0 mole) in acetonitrile (1.OL) was stirred at reflux for 21 h. TLC showed reaction complete. The reaction mixture was cooled to room temperature and concentrated. ~900 ml solvent was collected. The resulting suspension was filtered and washed with n-hexane (~400 mL). The filtrate was concentrated again to afford crude product. The crude product was distilled at reduced pressure (30° C./~0.3 mmHg) to afford the title compound as clear oil (146 g, 84%). LCMS (m/z): 190.0 [M+1]+. ¹H NMR (400 MHz, CDCl$_3$): δ 3.90 (s, 3H), 6.65 (d, J=8.8 Hz, 1H), 7.62 (dd, J=8.8 Hz, 2.4 Hz, 1H), 8.19 (s, 1H).

Step 149b: 6-Methoxypyridin-3-ylboronic acid (Compound 1601-236)

To a solution of compound 0601-236 (20 g, 0.11 mole) in anhydrous THF (180 ml) was added dropwise n-BuLi (59 mL, 2M in THF) at −78° C., the resulting mixture was stirred for 1 h. Triisopropyl borate (37 mL) was added at −78° C. and the reaction mixture was warmed to room temperature and continued to stir overnight. TLC (hexanes/ethyl acetate=5:1) showed reaction complete. The mixture was adjusted pH to 3-4 with 4N HCl (90 ml). The precipitate was collected by filtration to afford crude compound 1601-236 (21 g, 128%). The crude compound 1601-236 (21 g) was dissolved in water (200 ml) and the solution was adjusted pH to 8-9 with concentrated ammonia solution, the precipitate was collected by filtration to afford the pure title compound 1601-236 as a white solid. (11 g, 67%). LCMS (m/z): 154.1 [M+1]+. ¹H NMR (400 MHz, DMSO-d$_6$): δ 3.86 (s, 3H), 6.76 (d, J=8.4 Hz, 1H), 7.99 (dd, J=8.4 Hz, 2.0 Hz, 1H), 8.05 (br, 2H), 8.52 (d, J=2.0 Hz, 1H).

Step 149c: 2-Methoxy-5-(4,4,5,5-tetramethyl-1,3,2-dioxaborolan-2-yl)pyridine (Compound 0602-236)

A mixture of compound 0601-236 (55 g, 0.29 mol), 4,4,4',4',5,5,5',5'-octamethyl-2,2'-bi(1,3,2-dioxaborolane) (90 g, 0.35 mol), potassium acetate (57 g, 0.58 mol) and bis(triphenylphosphine)palladium(II) chloride (2.2 g, 3 mmol) in anhydrous dioxane (500 mL) was heated at 108° C. under N$_2$ atmosphere overnight. The reaction mixture was concentrated and purified by column chromatography eluted with hexanes/ethyl acetate to afford titled compound 0602-236 (58 g, 84%). ¹H NMR (400 MHz, DMSO-d$_6$): δ 1.30 (s, 12H), 3.88 (s, 3H), 6.81 (d, J=8.0 Hz, 1H), 7.88 (dd, J=8.0 Hz, 2.0 Hz, 1H), 8.41 (d, J=2.0 Hz, 1H).

Step 149d: Ethyl-2-(((2-(6-methoxypyridin-3-yl)-4-morpholinothieno[3,2-d]pyrimidin-6-yl) methyl)(methyl)amino)pyrimidine-5-carboxylate (Compound 0603-236)

Method A: A mixture of compound 0504 (12 g, 26.7 mmol), 1601-236 (4.9 g, 32 mmol), NaHCO$_3$ (6.7 g, 80.1 mmol) and bis(triphenylphosphine)palladium(II) chloride (188 mg, 0.267 mmol) in a mixed solvents of toluene (80 ml), ethanol (50 ml) and water (10 ml) was heated at 108° C. for 4.5 h under N$_2$ atmosphere. TLC showed reaction was complete. The reaction mixture was then cooled to room temperature and water (20 ml) was added. The resulting solid was collected by filtration and was then suspended in ethanol (100 mL). The suspension was stirred at room temperature for 30 minutes and filtered. The collected solid was washed with ethanol and dried in vacuo to afford titled compound 0603-236 as a white solid (10 g, 72%).

Method B: A mixture of compound 0504 (1.5 g, 3.34 mmol), 0602-236 (1.6 g, 6.68 mmol), NaHCO$_3$ (0.84 g, 10.0 mmol) and bis(triphenylphosphine)palladium(II) chloride (118 mg, 0.167 mmol) in a mixed solvents of toluene (24 ml), ethanol (15 ml), and water (3 ml) was heated at 108° C. under N$_2$ atmosphere overnight. The reaction mixture was partitioned between dichloromethane and water. The organic layer was separated and was washed with brine, dried over Na$_2$SO$_4$, filtered and evaporated in vacuo to give a residue which was purified by column chromatography eluted with hexanes/ethyl acetate to afford compound 0603-236 as a white solid (1.7 g, 98%).

M.p.198-202° C. LCMS: 522.30 [M+1]+. ¹H NMR (400 MHz, DMSO-d$_6$): δ 1.31 (t, J=7.2 Hz, 3H), 3.28 (s, 3H), 3.76 (t, J=4.4 Hz, 4H), 3.93 (t, J=4.4 Hz, 4H), 3.94 (s, 3H), 4.30 (q, J=7.2 Hz, 2H), 5.24 (s, 2H), 6.92 (d, J=8.8 Hz, 1H), 7.47 (s, 1H), 8.57 (dd, J=8.8 Hz, 2.0 Hz, 1H), 8.88 (s, 2H), 9.15 (d, J=2.0 Hz, 1H).

Step 149e: 2-[(2-Chloro-4-morpholin-4-yl-thieno[3,2-d]pyrimidin-6-ylmethyl)-methyl-amino]-pyrimidine-5-carboxylic acid methyl ester (Compound 1602-236)

A mixture of compound 0503 (25 g, 84 mmol), CH$_3$CN (500 mL) and methyl 2-chloropyrimidine-5-carboxylate (16 g, 92 mmol) was stirred at room temperature. Diisopropylethylamine (DIPEA) (500 mL, 2.9 mol) was added. The solution was stirred overnight and evaporated. After methylene chloride (500 mL) was added, the organic phase was washed with water, dried with Na$_2$SO$_4$ and concentrated in vacuo. To the residue was added ethyl acetate (200 mL) and the mixture was stirred in ice/water bath for 50 min. The title product was collected as a white solid (29.4 g, 81%). LCMS (m/z): 435.2 [M+1]+. ¹HNMR (400 MHz, DMSO-d$_6$): 3.25 (s, 3H), 3.71 (t, J=5.2 Hz, 4H), 3.82-3.84 (m, 7H), 5.21 (s, 2H), 7.39 (s, 1H), 8.87 (s, 2H).

Step 149f: Methyl-2-(((2-(6-methoxypyridin-3-yl)-4-morpholinothieno[3,2-d]pyrimidin-6-yl) methyl)(methyl)amino)pyrimidine-5-carboxylate (Compound 1603-236)

A mixture of compound 1602-236 (29.4 g, 67.7 mmol), 1601-236 (12.4 g, 81.3 mmol), NaHCO$_3$ (17.1 g, 203 mmol) and bis(triphenylphosphine)palladium(II) chloride (475 mg, 0.68 mmol) in toluene (480 ml), ethanol (300 ml) and water (60 ml) was heated at 108° C. for 6.5 h under N$_2$ atmosphere. TLC showed reaction complete. The reaction mixture was cooled to room temperature and filtered to remove any insoluble solid, then water/EtOH (150 ml/150 mL) was added. The resulting precipitate was collected by filtration. The solid was suspended in ethanol (200 mL) and stirred at room temperature for 30 min. It was filtered and washed with ethanol and dried in vacuo to afford titled compound 1603-236 (25 g, 73%). LCMS (m/z): 508.30 [M+1]$^+$. $^1$H NMR (400 MHz, DMSO-d$_6$): δ 3.27 (s, 3H), 3.75 (t, J=4.4 Hz, 4H), 3.82 (s, 3H), 3.93 (t, J=4.4 Hz, 4H), 3.90-3.93 (m, 7H), 5.23 (s, 2H), 6.90 (d, J=8.8 Hz, 1H), 7.47 (s, 1H), 8.57 (dd, J=8.4 Hz, 2.0 Hz, 1H), 8.88 (s, 2H), 9.15 (d, J=2.0 Hz, 1H).

Step 149 g: N-Hydroxy-2-(((2-(6-methoxypyridin-3-yl)-4-morpholinothieno[3,2-d]pyrimidin-6-yl)methyl)(methyl)amino)pyrimidine-5-carboxamide (Compound 236)

Preparation of Hydroxylamine Methanol Solution

A mixture of NH$_2$OH.HCl (80 g, 1.12 mol) in MeOH (400 mL) was heated at 60-65° C. for 1 h to form a clear solution. It was then cooled in an ice-water bath. To the cold mixture was added a solution of KOH (96 g, 1.68 mol) in MeOH (240 mL) dropwise while maintaining the reaction temperature at 0-10° C. The resulting mixture was stirred at 0° C. for 30 minutes and then filtered through a constant pressure funnel filled with anhydrous Na$_2$SO$_4$ (700 g). The filtrate was collected under an ice-bath and stored in refrigerator for future use.

Preparation of Compound 236 from Compound 0603-236

Compound 0603-236 (10 g, 19 mmol) was suspended in the above freshly prepared hydroxylamine methanol solution (1.79M, 350 ml). To this mixture was added dichloromethane (100 mL). The reaction flask was sealed and the mixture was stirred at room temperature for 5 h before it turned into clear solution. Reaction was stirred for additional 9 h. and was filtered to remove any insoluble solid. The filtrate was adjusted to pH 6-7 with the addition of acetic acid to form solid precipitate. The solid was collected by filtration and washed with water and minimum amount of methanol, dried in vacuo at 60° C. for 5 h to afford compound 236 as a white solid (9.2 g, 96%). m.p. 177-180° C. LCMS: 509.3 [M+1]$^+$. $^1$H NMR (400 MHz, DMSO-d$_6$): δ 3.24 (s, 3H), 3.76 (t, J=5 Hz, 4H), 3.92 (t, J=5 Hz, 4H), 3.92 (s, 3H), 5.20 (s, 2H), 6.90 (d, J=8.8 Hz, 1H), 7.44 (s, 1H), 8.57 (dd, J=8.8 Hz, 2.4 Hz, 1H), 8.75 (s, 2H), 9.01 (s, 1H), 9.14 (d, J=2.0 Hz, 1H), 11.08 (s, 1H).

Preparation of Compound 236 from Compound 1603-236

Compound 1603-236 (500 mg, 0.98 mmol) was suspended in above hydroxylamine methanol solution (1.79M, 12 ml). Dichloromethane (5 mL) was added. The reaction flask was sealed and stirred at room temperature for 5 h before it turned into clear solution. Reaction solution was filtered to remove any insoluble solid and added water (5 mL). Acetic acid was added to adjust pH to 9 and added water (10 mL) dropwise. The resulting reaction mixture was filtered and washed with water and minimum amount of methanol. The white solid was collected and dried in vacuo at 60° C. for 5 h to afford compound 236 as a white solid (388 mg, 77%). LCMS (m/z): 509.4 [M+1]$^+$. $^1$H NMR (400 MHz, DMSO-d$_6$): δ 3.24 (s, 3H), 3.76 (t, J=5 Hz, 4H), 3.92 (t, J=5 Hz, 4H), 3.93 (s, 3H), 5.20 (s, 2H), 6.91 (d, J=8.8 Hz, 1H), 7.45 (s, 1H), 8.57 (dd, J=8.8 Hz, 2.0 Hz, 1H), 8.75 (s, 2H), 9.01 (s, 1H), 9.15 (d, J=2.0 Hz, 1H), 11.09 (s, 1H).

Biological Assays:

The following assays are used to determine the IC$_{50}$ of compounds of the present invention as it identifies inhibitors of PI3 kinases:

(a) An In Vitro Assay which Determines the Ability of a Test Compound to Inhibit PI3Kα.

Activity of PI3Kα was measured using fluorescence polarization assay. PI3Kα, a complex of N-terminal histidine-tagged recombinant full-length human p110α and untagged recombinant full length human p85α were coexpressed in a Baculovirus infected Sf9 cell expression system. (GenBank Accession No. for p110α, U79143; for p85α, XM_043865). The proteins are purified by one-step affinity chromatography using glutathione-agarose. A competition assay was performed to measure the amount of PIP3 generated from PIP2 in the presence of purified recombinant PI3Kα (p110α/p85α). PI3K a was incubated with 10 μM PIP2 substrate in the reaction buffer (20 mM HEPES, pH 7.5, 10 mM NaCl, 4 mM MgCl2, 2 mM DTT, 10 μM ATP and 1% DMSO) for 1 hour at 30° C. The reaction product was then mixed with a PIP3 detector protein and the fluorescent PIP3 probe. Polarization (mP) values decrease as fluorescent probe binding to the PIP3 detector is displaced by PIP3 produced by enzymatic activity and the amount of unbound fluorescent probe in the mixture increases. Polarization degrees (mP) value was determined using microplate reader with background subtraction.

(b) An In Vitro Assay which Determines the Ability of a Test Compound to Inhibit PI3Kβ.

Activity of PI3Kβ was measured using time-resolved fluorescence resonance energy transfer (TR-FRET) assay utilizing homogenous time resolved fluorescence (HTRF) technology. PI3Kβ, a complex of N-terminal histidine-tagged recombinant full-length human p110β and untagged recombinant full length human p85α were coexpressed in a Baculovirus infected Sf21 cell expression system. (GenBank Accession No. for p110β, NM_006219; for p85α, XM_043865). The proteins are purified by one-step affinity chromatography using glutathione-agarose. A competition assay was performed to measure the amount of PIP3 generated from PIP2 in the presence of purified recombinant PI3Kbeta (p110β/p85α). PI3Kβ was incubated with 10 M PIP2 substrate in the reaction buffer (20 mM HEPES, pH 7.5, 10 mM NaCl, 4 mM MgCl2, 2 mM DTT, 10 M ATP and 1% DMSO) for 30 minutes at 30° C. The reaction product was then mixed with a PIP3 detector protein, europium-labeled antibody, biotin-labeled PIP3 probe and allophycocyanin-labeled Streptavidin. A sensor complex is formed to generate a stable TR-FRET signal in the reaction mixture. This signal intensity decrease as biotin-labeled probe binding to the PIP3 detector is displaced by PIP3 produced by enzymatic activity and the amount of unbound biotin-labeled PIP3 probe in the mixture increases. TR-FRET signal was determined using microplate reader with background subtraction.

(c) An In Vitro Assay which Determines the Ability of a Test Compound to Inhibit PI3Kδ.

Activity of PI3Kδ was measured using fluorescence polarization assay. PI3Kδ, a complex of N-terminal histidine-tagged recombinant full-length human p110δ and untagged recombinant full length human p85α were coexpressed in a Baculovirus infected Sf9 cell expression system. (GenBank Accession No. for p110δ, NM_005026). The proteins are purified by one-step affinity chromatography using glutathione-agarose. A competition assay was performed to measure the amount of PIP3 generated from PIP2 in the presence of purified recombinant PI3Kδ (p110δ/p85α). PI3Kδ was incubated with 10 M PIP2 substrate in the reaction buffer (20 mM HEPES (pH 7.5), 10 mM NaCl, 4 mM MgCl2, 2 mM DTT, 10 μM ATP and 1% DMSO) for 1 hour at 30° C. The reaction product was then mixed with a PIP3 detector protein and the fluorescent PIP3 probe. Polarization (mP) values decrease as fluorescent probe binding to the PIP3 detector is displaced by PIP3 produced by enzymatic activity and the amount of unbound fluorescent probe in the mixture increases. Polarization degrees (mP) value was determined using microplate reader with background subtraction.

(d) An In Vitro Assay which Determines the Ability of a Test Compound to Inhibit PI3Kγ.

Activity of PI3Kγ was measured using time-resolved fluorescence resonance energy transfer (TR-FRET) assay utilizing homogenous time resolved fluorescence (HTRF) technology. N-terminal histidine tagged human PI3Kδ was expressed in a Baculovirus infected Sf9 cell expression system. (GenBank Accession AF327656). The proteins are purified by one-step affinity chromatography using glutathione-agarose. A competition assay was performed to measure the amount of PIP3 generated from PIP2 in the presence of purified recombinant PI3Kγ (p120γ). PI3Kγ (2 nM) was incubated with 10 M PIP2 substrate in the reaction buffer (20 mM HEPES, pH 7.5, 10 mM NaCl, 4 mM MgCl2, 2 mM DTT, 10 M ATP and 1% DMSO) for 30 minutes at 30° C. The reaction product was then mixed with a PIP3 detector protein, europium-labeled antibody, biotin-labeled PIP3 probe and allophycocyanin-labeled Streptavidin. A sensor complex is formed to generate a stable TR-FRET signal in the reaction mixture. This signal intensity decrease as biotin-labeled probe binding to the PIP3 detector is displaced by PIP3 produced by enzymatic activity and the amount of unbound biotin-labeled PIP3 probe in the mixture increases. TR-FRET signal was determined using microplate reader with background subtraction.

(e) An In Vitro Assay which Determines the Ability of a Test Compound to Inhibit HDAC Enzymatic Activity.

HDAC inhibitory activity was assessed using the Biomol Color de Lys system (AK-500, Biomol, Plymouth Meeting, Pa.). Briefly, HeLa cell nuclear extracts were used as a source of HDAC8. Different concentrations of test compounds were serially diluted in dimethylsulphoxide (DMSO) and added to HeLa cell nuclear extracts in the presence of a colorimetric artificial substrate. Final assay condition contained 50 mM Tris/Cl, pH 8.0, 137 mM NaCl, 2.7 mM KCl and 1 mM MgCl2. Reactions were carried in room temperature (25° C.) for 1 hour before addition of developer for termination. Relative enzyme activity was measured in the WALLAC Victor 111420 microplate reader as floorescence intensity (excitation: 350-380 nm; emission: 440-460 nm). Data were analyzed using GraphPad Prism (v4.0a) with a sigmoidal dose response curve fitting for IC50 calculation.

(f) An In Vitro Assay which-Determines the Ability of a Test Compound to Inhibit mTor Serine/Threonine Protein Kinase.

The ability of compounds to inhibit mTor activity was assayed using standard radioisotope assay for kinase. Briefly, FLAG-tagged, recombinant full-length human mTor (GenBank accession No. NM_004958) was expressed using baculovirus expression system in Sf21 cells and purified using antibody affinity column. Purified enzyme was incubated with c-terminal fragment of p70S6K as it's substrate in the presence of ATP. p33 ATP tracers were included in the assay to monitor the enzyme activity. Final assay condition was with 50 mM HEPES pH 7.5, 1 mM EGTA, 0.01% Tween 20, 2 mg/ml substrate, 3 mM Manganese Chloride and 70 uM of ATP and was carried out at room temperature for 40 minutes. The reaction was then stopped by the addition of 3% phosphoric acid solution. 10 ul of the reaction was spotted onto a P30 filtermat and washed three times for 5 minutes in 75 mM phosphoric acid and once in methanol prior to drying and scintillation counting. Different concentrations of compounds were added to reaction to assess the activity of compounds to inhibit mTor kinase. IC50 was calculated using Prism software with sigmoidal dose-response curve fitting.

The following TABLE B lists compounds representative of the invention and their activity in HDAC, P3K and m-TOR assays. In these assays, the following grading was used: I>10 μM, 10 μM≥II≥1 μM, 1 μM≥III≥0.1 μM, and IV≤0.1 μM for IC$_{50}$.

TABLE B

| Compound No. | HDAC | PI3Kα | PI3Kβ | PI3Kγ | PI3Kδ | m-TOR |
| --- | --- | --- | --- | --- | --- | --- |
| 3 | IV | I | | | | |
| 4 | IV | I | | | | |
| 5 | IV | I | | | | |
| 7 | III | III | | | | |
| 8 | IV | I | | | | |
| 9 | IV | I | | | | |
| 11 | II | | | | | |
| 12 | III | IV | | | | |
| 13 | III | III | | | | |
| 14 | IV | IV | IV | IV | III | II |
| 15 | IV | III | | | | I |
| 16 | III | IV | | | | II |
| 18 | IV | III | | | | |
| 19 | IV | III | | | | |
| 20 | IV | III | | | | |
| 30 | III | I | | | | |
| 31 | III | I | | | | |
| 32 | III | I | | | | |
| 34 | III | I | | | | |
| 35 | IV | I | | | | |
| 36 | IV | I | | | | |
| 41 | IV | III | | | | |
| 42 | IV | II | | | | |
| 43 | IV | II | | | | II |
| 44 | III | IV | | | | |
| 45 | I | IV | | | | |
| 46 | II | III | | | | |
| 48 | IV | IV | | | | |
| 49 | III | IV | | | | |
| 50 | IV | IV | | | | |
| 51 | III | IV | | | | |
| 53 | IV | IV | IV | IV | IV | |
| 54 | IV | IV | IV | IV | IV | |
| 60 | IV | I | | | | |
| 61 | IV | I | | | | |
| 62 | IV | I | | | | |
| 63 | IV | I | | | | |
| 65 | IV | III | | | | |
| 66 | IV | III | | | | |
| 67 | IV | III | | | | |
| 68 | IV | III | | | | |
| 69 | IV | IV | | | | II |
| 70 | IV | IV | | | | III |
| 71 | IV | III | | | | |
| 73 | IV | III | | | | |
| 74 | IV | III | | | | |
| 75 | III | IV | | | | |
| 76 | IV | IV | | | | |
| 78 | IV | III | | | | |
| 79 | IV | IV | | | | |
| 80 | III | IV | | | | |
| 81 | II | IV | | | | |
| 83 | II | III | | | | |
| 84 | IV | IV | | | | |
| 85 | IV | III | | | | |
| 86 | IV | IV | IV | | | |
| 87 | IV | IV | | | | II |
| 88 | III | IV | | | | |

TABLE B-continued

| Compound No. | HDAC | PI3Kα | PI3Kβ | PI3Kγ | PI3Kδ | m-TOR |
|---|---|---|---|---|---|---|
| 89 | IV | IV | | | | II |
| 90 | IV | IV | | | | |
| 91 | IV | IV | | | | |
| 92 | IV | IV | | | | |
| 93 | III | III | | | | |
| 94 | IV | IV | | | | |
| 95 | III | IV | | | | |
| 96 | IV | IV | | | | |
| 97 | IV | IV | | | | |
| 98 | IV | IV | | | | |
| 99 | IV | IV | | | | III |
| 101 | I | III | | | | III |
| 102 | III | III | | | | III |
| 103 | IV | III | | | | |
| 104 | III | IV | | | | |
| 105 | III | I | | | | |
| 106 | II | IV | | | | |
| 107 | IV | II | | | | |
| 108 | IV | II | | | | |
| 109 | IV | IV | | | | III |
| 110 | IV | IV | | | | IV |
| 111 | IV | IV | III | III | IV | IV |
| 112 | IV | IV | | | | |
| 114 | IV | III | | | | |
| 115 | IV | IV | | | | IV |
| 116 | IV | IV | | | | IV |
| 117 | IV | IV | | | | II |
| 119 | IV | IV | | | | |
| 120 | IV | IV | | | | III |
| 121 | IV | IV | | | | II |
| 122 | IV | IV | | | | |
| 124 | IV | IV | | | | |
| 125 | IV | IV | | | | |
| 129 | IV | I | | | | |
| 130 | IV | III | | | | |
| 131 | IV | I | | | | |
| 132 | IV | IV | | | | IV |
| 133 | IV | III | | | | |
| 134 | IV | III | | | | |
| 135 | IV | III | | | | |
| 136 | | I | | | | I |
| 137 | IV | II | | | | |
| 138 | IV | IV | | | | IV |
| 139 | IV | III | | | | |
| 140 | IV | III | | | | |
| 141 | IV | III | | | | |
| 142 | IV | III | | | | III |
| 143 | IV | III | | | | |
| 144 | IV | II | | | | |
| 146 | IV | I | | | | |
| 147 | IV | I | | | | |
| 148 | IV | I | | | | |
| 149 | IV | I | | | | |
| 150 | IV | IV | IV | III | IV | IV |
| 151 | IV | I | | | | |
| 152 | IV | I | | | | |
| 153 | IV | I | | | | |
| 154 | IV | I | | | | |
| 155 | IV | I | | | | |
| 156 | IV | III | | | | |
| 157 | IV | IV | | | | IV |
| 158 | IV | I | | | | |
| 159 | IV | II | | | | |
| 160 | IV | I | | | | |
| 161 | IV | III | | | | |
| 162 | IV | II | | | | |
| 163 | IV | III | | | | |
| 164 | IV | IV | | | | |
| 165 | IV | I | | | | |
| 166 | IV | I | | | | |
| 167 | IV | III | | | | |
| 168 | IV | II | | | | |
| 176 | IV | III | | | | |
| 177 | IV | I | | | | |
| 178 | IV | I | | | | I |
| 181 | IV | II | | | | I |
| 182 | IV | II | | | | |
| 183 | IV | I | | | | I |
| 184 | IV | II | | | | III |
| 186 | IV | I | | | | |
| 187 | IV | IV | | | | |
| 191 | IV | | | | | |
| 192 | IV | III | | | | |
| 193 | IV | I | | | | |
| 194 | IV | I | | | | |
| 196 | IV | III | | | | |
| 197 | IV | IV | | | | |
| 199 | IV | IV | | | | |
| 200 | IV | I | | | | |
| 201 | IV | III | | | | |
| 202 | IV | III | | | | |
| 203 | III | III | | | | |
| 204 | III | III | | | | |
| 206 | IV | III | | | | |
| 207 | IV | III | | | | |
| 209 | IV | I | | | | |
| 210 | III | III | | | | |
| 211 | IV | III | | | | |
| 214 | IV | | | | | |
| 215 | IV | III | | | | |
| 216 | IV | IV | | | | |
| 217 | IV | IV | | | | |
| 218 | IV | IV | | | | |
| 219 | IV | IV | | | | |
| 220 | IV | IV | | | | |
| 221 | IV | IV | | | | |
| 222 | IV | III | | | | |
| 223 | IV | IV | | | | |
| 224 | IV | IV | | | | |
| 225 | II | IV | | | | |
| 226 | IV | IV | | | | |
| 227 | IV | IV | | | | |
| 228 | IV | IV | | | | |
| 229 | IV | IV | | | | |
| 230 | IV | IV | | | | |
| 231 | IV | IV | | | | |
| 232 | IV | IV | | | | |
| 233 | IV | IV | | | | |
| 234 | IV | IV | | | | |
| 235 | IV | IV | | | | |
| 236 | IV | IV | III | III | IV | II |
| 237 | IV | IV | | | | |
| 240 | IV | IV | | | | |
| 241 | IV | III | | | | |
| 243 | III | IV | | | | |
| 245 | IV | IV | | | | |
| 246 | IV | III | | | | I |
| 247 | IV | IV | | | | |
| 250 | IV | IV | | | | |
| 251 | IV | II | | | | |
| 252 | IV | IV | | | | |
| 253 | III | IV | | | | |
| 254 | IV | III | | | | |
| 255 | IV | IV | | | | |
| 256 | IV | IV | | | | I |
| 257 | IV | I | | | | |
| 258 | IV | I | | | | |
| 259 | IV | I | | | | |
| 260 | IV | I | | | | |
| 261 | IV | IV | | | | |
| 262 | IV | IV | | | | |
| 263 | IV | IV | | | | |
| 264 | IV | III | | | | |
| 265 | IV | IV | | | | I |
| 266 | IV | III | | | | |
| 269 | IV | II | | | | |
| 270 | IV | | | | | |
| 271 | IV | IV | | | | |
| 272 | IV | IV | | | | |
| 273 | III | IV | | | | |
| 274 | IV | IV | | | | III |
| 275 | IV | III | | | | |
| 276 | IV | IV | | | | |
| 277 | IV | IV | | | | |
| 278 | IV | IV | | | | |
| 279 | IV | IV | | | | |

TABLE B-continued

| Compound No. | HDAC | PI3Kα | PI3Kβ | PI3Kγ | PI3Kδ | m-TOR |
|---|---|---|---|---|---|---|
| 280 | IV | III | | | | |
| 281 | IV | III | | | | |
| 282 | IV | III | | | | |
| 283 | IV | III | | | | |
| 284 | IV | IV | | | | |
| 285 | IV | IV | | | | IV |
| 286 | IV | III | | | | |
| 287 | IV | I | | | | |
| 288 | IV | I | | | | |
| 289 | IV | IV | | | | |
| 290 | IV | III | | | | |
| 291 | IV | I | | | | |
| 292 | IV | IV | | | | IV |
| 293 | IV | IV | | | | I |
| 294 | IV | IV | | | | III |
| 295 | IV | III | | | | |
| 296 | IV | III | | | | I |
| 297 | IV | III | | | | III |
| 298 | IV | III | | | | |
| 299 | IV | III | | | | |
| 300 | IV | III | | | | |
| 301 | IV | II | | | | I |
| 302 | IV | I | | | | |
| 303 | IV | III | | | | |
| 304 | IV | II | | | | |
| 305 | IV | III | | | | |
| 306 | IV | III | | | | |
| 307 | IV | III | | | | |
| 308 | IV | IV | | | | |
| 309 | III | III | | | | |
| 310 | IV | IV | | | | |
| 311 | IV | III | | | | I |
| 312 | IV | III | | | | |
| 313 | IV | III | | | | I |
| 314 | IV | III | | | | I |
| 315 | IV | IV | | | | |
| 316 | IV | IV | | | | |
| 317 | IV | IV | | | | |
| 318 | IV | IV | | | | III |
| 319 | III | III | | | | |
| 320 | III | III | | | | |
| 321 | III | III | | | | |
| 322 | III | III | | | | |
| 323 | III | IV | | | | |
| 324 | III | III | | | | |
| 325 | III | II | | | | |
| 326 | III | III | | | | |
| 327 | III | II | | | | |
| 328 | III | IV | | | | |
| 329 | III | IV | | | | |

Cell Proliferation Assay: Method A

Cancer cell lines were plated at 5,000 to 10,000 per well in 96-well flat bottomed plates with various concentration of compounds. The cells were incubated with compounds for 72 hours in the presence of 0.5% of fetal bovine serum. Growth inhibition was accessed by adenosine triphosphate (ATP) content assay using Perkin Elmer ATPlite kit. ATPlite is an ATP monitoring system based on firefly luciferase. Briefly, 25 µl of mammalian cell lysis solution was added to 50 µl of phenol red-free culture medium per well to lyse the cells and stabilize the ATP. 25 µl of substrate solution was then added to the well and subsequently the luminescence was measured.

The following TABLE C lists compounds representative of the invention and their antiproliferative activity in these cell-based assays. In these assays, the following grading was used: I>10 µM, 10 µM≥II≥1 µM, 1 µM≥III≥0.1 µM, and IV<0.1 µM for $IC_{50}$.

TABLE C

| Compound No. | HCT-118 | BT-474 | Sk-Mel-28 | H1993 |
|---|---|---|---|---|
| 53 | III | IV | III | III |
| 54 | IV | IV | IV | IV |
| 69 | IV | IV | IV | IV |
| 70 | IV | IV | IV | IV |
| 75 | III | III | III | III |
| 76 | III | III | III | III |
| 86 | III | III | II | |
| 87 | III | II | III | II |
| 90 | IV | III | | II |
| 91 | II | II | | I |
| 92 | IV | IV | III | |
| 99 | I | III | III | I |
| 109 | IV | IV | | IV |
| 110 | IV | IV | IV | IV |
| 115 | IV | IV | IV | IV |
| 116 | IV | IV | IV | IV |
| 117 | IV | IV | IV | IV |
| 125 | IV | IV | III | III |
| 132 | IV | IV | IV | IV |
| 138 | IV | IV | IV | IV |
| 150 | IV | IV | IV | IV |

Cell Proliferation Assay: Method B

Cancer cell lines were plated at 5,000 to 10,000 per well in 96-well flat bottomed plates with various concentration of compounds. The cells were incubated with compounds for 72 hours in the presence of 0.5% of fetal bovine serum. Growth inhibition was accessed by adenosine triphosphate (ATP) content assay using Promega CellTiter-Glo kit. Promega CellTiter-Glo kit is an ATP monitoring system based on firefly luciferase. Briefly, 16 µl of mammalian cell lysis and substrate solution was added to 84 µl of culture medium per well to lyse the cells and stabilize the ATP. The mixture was shaken and incubated for 30 minutes and subsequently the luminescence was measured.

The following TABLEs D and E list compounds representative of the invention and their antiproliferative activity in these cell-based assays. In these assays, the following grading was used: I>10,000 nM, 10,000 nM≥II≥1000 nM, 1000 nM≥III≥100 nM, 100 nM≥IV≥10 nM, and V<10 nm for $IC_{50}$.

TABLE D

| Cancer Type | Cell Line | SAHA | GDC-0941 | SAHA/GDC-0941 | 150 | 236 | 111 | 261 | 70 | 116 | 120 | 138 | 292 |
|---|---|---|---|---|---|---|---|---|---|---|---|---|---|
| Colon | WiDr | II | I | III | IV | IV | IV | | IV | IV | IV | IV | |
| | HCT116 | II | II | III | V | V | V | | | | | IV | |
| | SW403 | II | I | II | V | V | V | | | | | | |
| | SW620 | II | I | III | V | V | V | | | | | | |
| | SWI-116 | II | I | II | V | V | V | IV | | | | | |
| | T-84 | II | II | III | IV | IV | IV | | | | | | |
| NSCLC | H358 | II | II | II | V | V | V | | | | | IV | |
| | H292 | II | II | III | V | V | V | | | | | | |
| | H2122 | II | II | III | V | V | V | | | | | IV | |
| | H460 | I | I | II | IV | IV | IV | | | | | IV | |

TABLE D-continued

| Cancer Type | Cell Line | SAHA | GDC-0941 | SAHA/GDC-0941 | 150 | 236 | 111 | 261 | 70 | 116 | 120 | 138 | 292 |
|---|---|---|---|---|---|---|---|---|---|---|---|---|---|
| | A549 | II | II | II | V | IV | IV | | | | | | III |
| | Calu6 | II | I | II | V | IV | IV | | | IV | IV | IV | |
| | H1975 | II | III | | V | | | | | IV | IV | IV | |
| | H1993 | II | II | | V | | | | | IV | IV | IV | |
| Pancreas | MiaPaca1 | II | I | II | V | IV | V | | | | | | IV |
| | CaPan2 | II | I | III | V | IV | IV | | | | | | |
| | CFPAC-1 | II | I | II | IV | IV | IV | | | | | | |
| | PANC-1 | II | II | II | IV | IV | IV | | | | | | |
| | SW1990 | II | I | II | V | V | V | | | | | | |
| Breast | MDA-MB-231 | II | I | II | V | | | | | | | | |
| Prostate | PC-3 | II | II | II | IV | | | | | | | | |
| | LN-Cap | III | III | IV | V | | | | | | | | |
| Ovarian | OVCAR-5 | II | III | III | V | | | | | | | | |
| Breast | HCC1500 | II | I | II | V | V | | V | | | | | |
| | HCC1806 | II | I | II | IV | IV | IV | V | | | | | |
| | MDA-MB-231 | II | I | II | IV | IV | | IV | | IV | IV | IV | |
| | SKBr3 | II | I | II | IV | IV | IV | IV | | | | | |
| | BT474 | II | III | III | V | V | V | V | V | IV | IV | V | |
| | MDA-MB-361 | II | III | IV | V | V | V | V | | | | | |
| | UACC-893 | II | II | III | V | IV | | | | | | | |
| | MDA-MB-453 | III | III | III | V | V | V | | | | | | |
| | MCF-7 | II | III | III | V | V | V | V | | | | | |
| | T47D | II | I | III | V | IV | V | V | | | | | |
| | ZR-75-1 | II | III | II | IV | IV | IV | V | | IV | IV | IV | |
| | MDA-MB-468 | III | | II | IV | IV | | | | IV | IV | IV | |
| | HCC1937 | II | III | | V | | | | | IV | IV | IV | |
| | MDA-MB-436 | II | II | | V | | | | | IV | IV | IV | |
| Glioblastoma | U87MG | II | III | | V | | | | | IV | IV | V | |
| HNC | Cal27 | II | III | | V | | | | | IV | IV | IV | |
| Melanoma | Sk-Mel-28 | II | IV | | V | | | | III | V | IV | IV | |
| | A375 | II | II | | V | | | | | IV | IV | IV | V |
| ALL | MOLT-4 | III | III | | V | V | V | | | | | | |
| | SUP-B15 | III | | | V | V | | | | | | | |
| AML | HL-60 | III | III | | V | V | V | | | | | | |
| | U937 | III | II | | V | V | V | | | | | | |
| | THP-1 | I | II | | V | IV | IV | | | | | | |
| | MV-4-11 | III | II | | V | V | V | | | | | | |
| NHL | Pfeiffer | I | III | | V | V | V | | | | | | |
| | Raji | III | I | | V | IV | IV | | | | | | |
| | Daudi | I | I | | V | IV | V | | | | | | |
| CML | K562 | I | I | | IV | III | IV | | | | | | |
| | MEG-01 | I | I | | IV | IV | | | | | | | |
| Multiple Myeloma | RPMI-8226 | III | I | | V | V | V | | | V | V | | |
| | OPM-2 | III | III | | V | V | V | | | | | V | |
| | ARH77 | II | I | | V | IV | V | | | | | | |
| Mouse LL | L1210 | I | I | | V | IV | V | | | | | | |
| Mouse Lymphoma | P388 D1 | I | II | | V | IV | V | | | | | | |

TABLE E

| Cancer Type | Cell Line | 125 | 284 | 289 | 157 | 294 | 115 | 110 | 132 | 54 | 296 | 308 |
|---|---|---|---|---|---|---|---|---|---|---|---|---|
| Colon | WiDr | | IV | V | III | IV | III | IV | III | | V | III |
| | HCT116 | IV | V | V | | V | | | V | V | III | |
| NSCLC | H358 | | V | V | | V | | | | | IV | III |
| | H292 | | | V | | IV | | | | | IV | III |
| | H2122 | | V | V | | V | | | | | IV | III |
| | H460 | | IV | IV | | IV | | | | III | IV | III |
| | A549 | | IV | IV | | IV | IV | | | | IV | III |
| | Calu6 | | | | IV | | IV | IV | IV | IV | IV | |

TABLE E-continued

| Cancer Type | Cell Line | 125 | 284 | 289 | 157 | 294 | 115 | 110 | 132 | 54 | 296 | 308 |
|---|---|---|---|---|---|---|---|---|---|---|---|---|
| | H1975 | | | | IV | | IV | IV | IV | IV | | |
| | H1993 | III | | | IV | | | IV | IV | IV | | |
| Pancreas | MiaPaca1 | | IV | V | | V | | | | | IV | III |
| | MDA-MB-231 | | | | IV | | | IV | IV | | | |
| | BT474 | IV | | | V | | IV | V | V | V | | |
| | MDA-MB-468 | | | | IV | | III | IV | III | V | | |
| | HCC1937 | | | | | | IV | IV | III | IV | | |
| | MDA-MB-436 | | | | IV | | III | IV | IV | | | |
| Glioblastoma | U87MG | | | | IV | | IV | V | IV | IV | | |
| HNC | Cal27 | | | | IV | | IV | IV | IV | | | |
| Melanoma | Sk-Mel-28 | III | | V | IV | V | IV | IV | IV | IV | | |
| | A375 | | | | IV | | IV | IV | IV | | | |
| Multiple Myeloma | RPMI-8226 | | V | V | IV | V | | | V | | V | III |
| | OPM-2 | | | | | | IV | V | | | | |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (X) or Formula (XI),

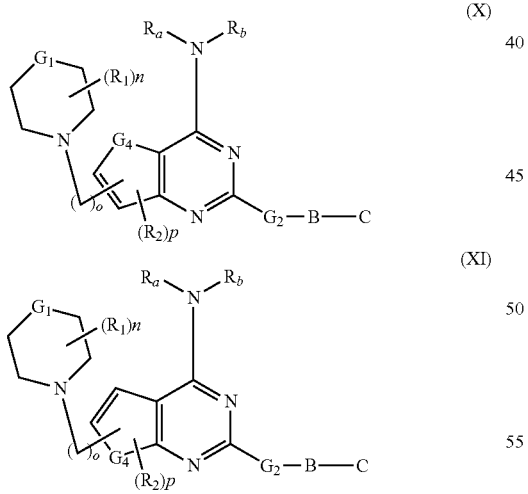

or a pharmaceutically acceptable salt thereof, wherein
$G_1$ is $CR_1$, S, O, $NR_{10}$ or $NS(O)_2R_{10}$;
$G_2$ is substituted or unsubstituted aryl, substituted or unsubstituted heteroaryl or, substituted or unsubstituted heterocyclic;
$G_4$ is $NR_8$, S or O;
each $R_1$ and $R_2$ is independently selected from absent, hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic;
$R_{10}$ is selected from hydrogen, hydroxy, amino, alkoxy, alkylamino, dialkylamino, sulfonyl, acyl, aliphatic, substituted aliphatic, aryl, substituted aryl, heteroaryl, substituted heteroaryl, heterocyclic, and substituted heterocyclic;
$R_a$ and $R_b$, together with the nitrogen atom to which they are attached, form an optionally substituted heterocyclic group;
$R_8$ is hydrogen, acyl, aliphatic or substitute aliphatic;
B is a direct bond or a linker;
C is

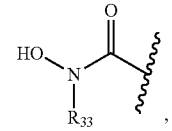

where $R_{33}$ is hydrogen;
n is 0, 1, 2, 3 or 4;
o is 1, 2, 3, or 4; and
p is 0 or 1.

2. The compound of claim 1, wherein B is selected from the group consisting of a direct bond, straight chain $C_1$-$C_{10}$ alkyl, $C_1$-$C_{10}$ alkenyl, $C_1$-$C_{10}$ alkynyl, $C_1$-$C_{10}$ alkoxy, alkoxy$C_1$-$C_{10}$alkoxy, $C_1$-$C_{10}$ alkylamino, alkoxy$C_1$-$C_{10}$alkylamino, $C_1$-$C_{10}$ alkylcarbonylamino, $C_1$-$C_{10}$ alkylaminocarbonyl, aryloxy$C_1$-$C_{10}$alkoxy, aryloxy$C_1$-$C_{10}$alkylamino, aryloxy$C_1$-$C_{10}$alkylamino carbonyl, $C_1$-$C_{10}$-alkylaminoalkylaminocarbonyl, $C_1$-$C_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxy$C_1$-$C_{10}$alkoxy, alkenylarylamino$C_1$-$C_{10}$alkoxy, alkenylaryllalkylamino$C_1$-$C_{10}$alkoxy, alkenylaryloxy$C_1$-$C_{10}$alkylamino, alkenylaryloxy$C_1$-$C_{10}$alkylaminocarbonyl, piperazinoalkylaryl, heteroaryl$C_1$-$C_{10}$alkyl, heteroaryl$C_2$-$C_{10}$alkenyl, heteroaryl$C_2$-$C_{10}$alkynyl, heteroaryl$C_1$-$C_{10}$alkylamino, heteroaryl$C_1$-$C_{10}$alkoxy, heteroaryloxy$C_1$-$C_{10}$alkyl, heteroaryloxy$C_2$-$C_{10}$alkenyl, heteroaryloxy$C_2$-$C_{10}$alkynyl, heteroaryloxy$C_1$-$C_{10}$alkylamino and heteroaryloxy$C_1$-$C_{10}$alkoxy.

3. The compound of claim 1, wherein $G_2$ is optionally substituted phenyl, pyridyl, pyrimidyl, indazolyl, pyrrolyl or benzimidazolyl.

4. The compound of claim 1, wherein B is selected from:

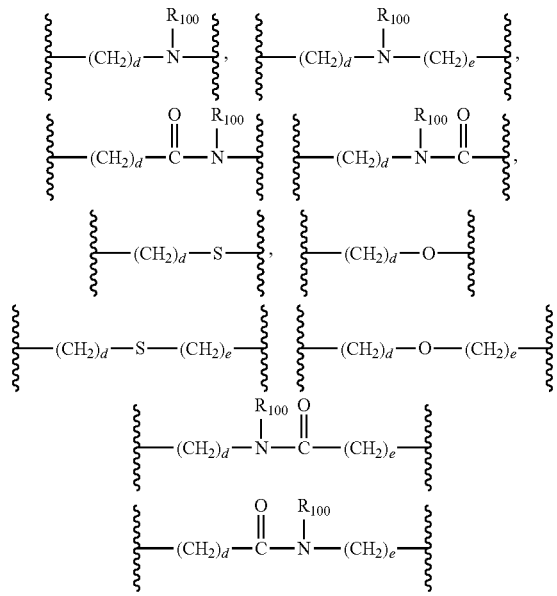
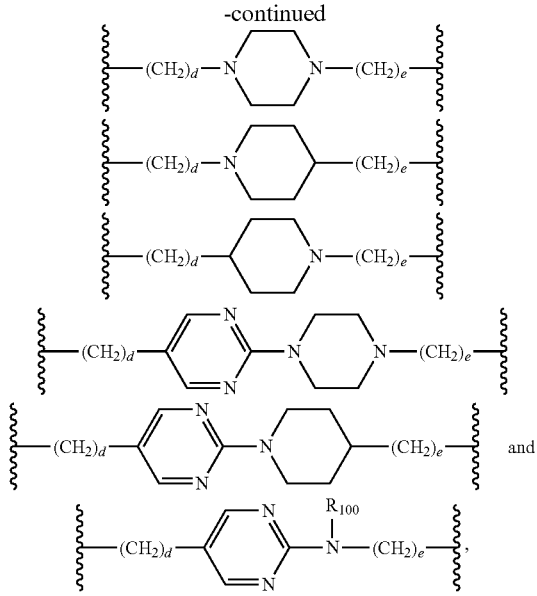

wherein d and e are independently 0, 1, 2, 3, 4, 5, 6, 7 or 8; and $R_{100}$ is selected from hydrogen, $C_1$-$C_8$ alkyl, $C_2$-$C_8$ alkenyl, $C_2$-$C_8$ alkynyl and $C_3$-$C_8$ cycloalkyl.

5. The compound according to claim 1 selected from the compounds delineated in Table A or a pharmaceutically accept

TABLE A

| Compound No. | Structure |
|---|---|
| 1 | 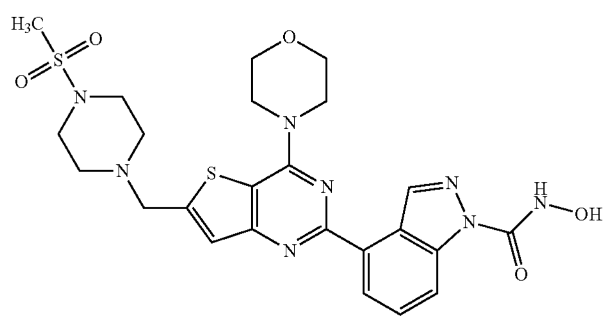 [SMILES: CS(=O)(=O)N1CCN(Cc2cc3nc(-c4cccc5c4cnn5C(=O)NO)nc(N4CCOCC4)c3s2)CC1] |
| 2 | 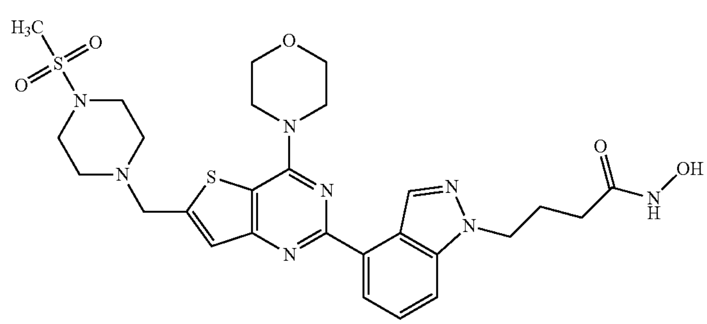 [SMILES: CS(=O)(=O)N1CCN(Cc2cc3nc(-c4cccc5c4cnn5CCCC(=O)NO)nc(N4CCOCC4)c3s2)CC1] |

TABLE A-continued

| Compound No. | Structure |
| --- | --- |
| 3 | (structure) |
| 4 | (structure) |
| 5 | (structure) |
| 6 | (structure) |
| 7 | (structure) |

TABLE A-continued

| Compound No. | Structure |
|---|---|
| 8 | (structure) |
| 9 | (structure) |
| 35 | (structure) |
| 37 | (structure) |

TABLE A-continued

| Compound No. | Structure |
|---|---|
| 38 | 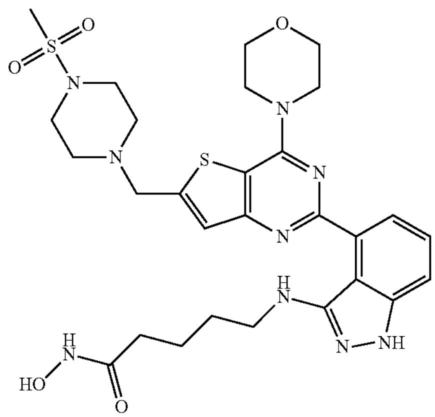 [SMILES: CS(=O)(=O)N1CCN(Cc2cc3nc(-c4cccc5[nH]nc(NCCCCC(=O)NO)c45)nc(N4CCOCC4)c3s2)CC1] |
| 39 | 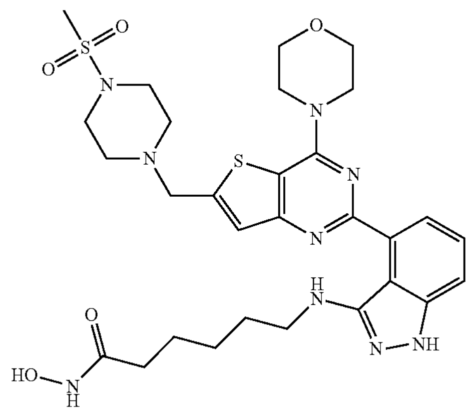 [SMILES: CS(=O)(=O)N1CCN(Cc2cc3nc(-c4cccc5[nH]nc(NCCCCCC(=O)NO)c45)nc(N4CCOCC4)c3s2)CC1] |
| 40 | 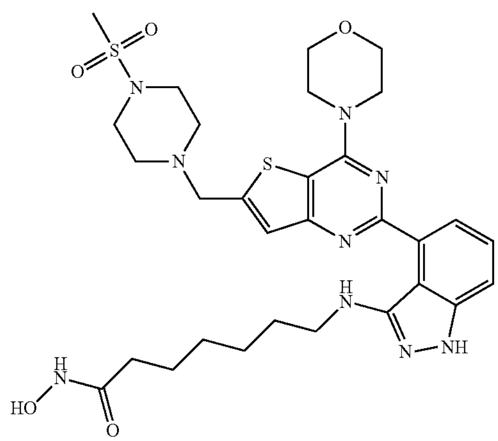 |

6. A pharmaceutical composition comprising as an active ingredient a compound of claim 1 and a pharmaceutical acceptable carrier.

7. A method of treating a PI3K related disease or disorder in a subject in need thereof, the method comprising administering to the subject a therapeutically effective amount of the pharmaceutical composition of claim 6.

8. A method of treating an HDAC-mediated disease comprising administering to a subject in need thereof a pharmaceutical composition of claim 6.

* * * * *

UNITED STATES PATENT AND TRADEMARK OFFICE
CERTIFICATE OF CORRECTION

PATENT NO. : 10,894,795 B2
APPLICATION NO. : 15/930103
DATED : January 19, 2021
INVENTOR(S) : Xiong Cai et al.

Page 1 of 1

It is certified that error appears in the above-identified patent and that said Letters Patent is hereby corrected as shown below:

In the Claims

Column 372, Claim 5, Line 30: please replace "accept" and insert -- acceptable salt thereof: --

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*